(12) United States Patent
Kelsey et al.

(10) Patent No.: US 10,619,211 B2
(45) Date of Patent: Apr. 14, 2020

(54) METHODS USING DNA METHYLATION FOR IDENTIFYING A CELL OR A MIXTURE OF CELLS FOR PROGNOSIS AND DIAGNOSIS OF DISEASES, AND FOR CELL REMEDIATION THERAPIES

(71) Applicants: Brown University, Providence, RI (US); The Regents of the University of California, Oakland, CA (US)

(72) Inventors: Karl Kelsey, Brookline, MA (US); Eugene Andres Houseman, Albany, OR (US); John Wiencke, San Francisco, CA (US); William P. Accomando, Jr., Providence, RI (US); Carmen Marsit, Enfield, NH (US)

( * ) Notice: Subject to any disclaimer, the term of this patent is extended or adjusted under 35 U.S.C. 154(b) by 254 days.

(21) Appl. No.: 15/271,909

(22) Filed: Sep. 21, 2016

(65) Prior Publication Data

US 2017/0067121 A1    Mar. 9, 2017

Related U.S. Application Data

(63) Continuation of application No. 14/089,398, filed on Nov. 25, 2013, now abandoned, which is a continuation-in-part of application No. PCT/US2012/039699, filed on May 25, 2012.

(60) Provisional application No. 61/489,883, filed on May 25, 2011, provisional application No. 61/509,644, filed on Jul. 20, 2011, provisional application No. 61/585,892, filed on Jan. 12, 2012, provisional application No. 61/619,663, filed on Apr. 3, 2012, provisional application No. 61/865,479, filed on Aug. 13, 2013.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/118* (2013.01); *C12Q 2600/154* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 6,582,908 B2 | 6/2003 | Fodor et al. | |
| 2007/0243161 A1 | 10/2007 | Olek et al. | |
| 2007/0269823 A1 | 11/2007 | Huehn et al. | |

FOREIGN PATENT DOCUMENTS

| | | |
|---|---|---|
| EP | 1826278 A1 | 8/2007 |
| WO | 2010069499 A2 | 6/2010 |

OTHER PUBLICATIONS

Koestler, Devin C., et al. "Peripheral blood immune cell methylation profiles are associated with non-hematopoietic cancers." Cancer Epidemiology and Prevention Biomarkers (2012): cebp-0361.*
Houseman et al. (2012) "DNA methylation arrays as surrogate measures of cell mixture distribution", BMC Bioinformatics 13:86 (16 pgs.).
Houseman et al. (2008) "Model-based clustering of DNA methylation array data: a recursive-partitioning algorithm for high-dimensional data arising a mixture of beta distributions", BMC Bioinformatics 9:365 (15 pgs.).
Houwen (2001) "The Differential Cell Count" Laboratory Hematology 7: 89-100.
Huber et al. (2008) "Fgd2, a cdc42-specitic exchange factor expressed by antigen-presenting cells, localizes to early endosomes and active membrane ruffles", J Bioi Chern 283:34002-34012.
Ishigami et al. (2000) "Prognostic value of intratumoral natural killer cells in gastric carcinoma", Cancer, 88:577-83.
Jaenisch (1997) "DNA methylation and imprinting: Why bother?", Trends in genetics 13(8): 323-329.
Janson et al. (2009) "At the crossroads of T helper lineage commitment—Epigenetics points the way", Biochim Biophys Acta 1790: 906-919.
Karagas et al. (1998) "Design of an epidemiologic study of drinking water arsenic exposure and skin and bladder cancer risk in a US population", Environ Health Perspect 106:1047-1050.
Kerkel etal. (2010) "Altered DNA methylation in leukocytes with Trisomy 21" PLoS Genet 6(11): e1001212 (13 pgs.).
Khavari et al. (2010) "DNA methylation and epigenetic control of cellular differentiation", Cell Cycle 9, 3880-3883.
Kim et al. (2007) "Cancer immunoediting from immune surveillance to immune escape", Immunology, 121: 1-14.
Kleihues et al. (1993) "The new WHO classification of brain tumours", Brain Pathol 3(3): 255-68. (Abstract 1 page.).
Koestler et al. (2010) "Semi-supervised recursively partitioned mixture models for identifying cancer subtypes", Bioinformatics 26: 2578-2585.
Kondo et al. (2003) "Preoperative natural killer cell activity as a prognostic factor for distant metastasis following surgery for colon cancer", Dig Surg, 20: 445-51.
Kossenkov et al. (2011) "Resection of non-small cell lung cancers reverses tumor-induced gene expression changes in the peripheral immune system", Clin Cancer Res 17(18): 5867-77.
Kumanogoh et al. (2001) "The cd100-cd72 interaction: a novel mechanism of immune regulation", Trends Immunol 22: 670-676.
Kuss et al. (2004) "Decreased absolute counts of T lymphocyte subsets and their relation to disease in squamous cell carcinoma of the head and neck", Clin Cancer Res, 10(11), 3755-62.

(Continued)

*Primary Examiner* — G Steven Vanni
(74) *Attorney, Agent, or Firm* — Adler Pollock & Sheehan P.C.

(57) ABSTRACT

Methods using DNA Methylation arrays are provided for identifying a cell or mixture of cells and for quantification of alterations in distribution of cells in blood or in tissues, and for diagnosing, prognosing and treating disease conditions, particularly cancer. The methods use fresh and archival samples.

8 Claims, 119 Drawing Sheets

Specification includes a Sequence Listing.

(56) References Cited

OTHER PUBLICATIONS

Kuss et al. (2005) "Imbalance in absolute counts of T lymphocyte subsets in patients with head and neck cancer and its relation to disease", Adv Otorhinolaryngol, 62:161-72.
Langevin et al. (2012) "Peripheral blood DNA methylation profiles are indicative of head and neck squamous cell carcinoma: an epigenome-wide association study", Epigenetics 7(3): 291-9.
Lanier (2006) "Viral immunoreceptor tyrosine-based activation motif (ITAM)-mediated signaling in cell transformation and cancer", Trends Cell Bioi 16(8): 388-90.
Li et al.(2007) "On surrogate dimension reduction for measurement error regression: An invariance law", The Annals of Statistics 35(5): 2143-72.
Louis et al. (2007) "The 2007 WHO classification of tumours of the central nervous system", Acta Neuropathol 114(2):97-109.
Lynch et al. (2009) "Are natural killer cells protecting the metabolically healthy obese patient?", Obesity 17(3): 601-5.
Marsit et al. (2006) "Examination of a CpG island methylator phenotype and implications of methylation profiles in solid tumors", Cancer Res 66:10621-10629.
Marsit et al. (2011) "DNA Methylation Array Analysis Identifies Profiles of Blood-Derived DNA Methylation Associated With Bladder Cancer", Journal of Clinical Oncology 29(9):1133-1139.
Mazzoccoli et al. (1999) "Lymphocyte subpopulations anomalies in lung cancer patients and relationship to the stage of disease", In Vivo 13(3): 205-9. (Abstract 1 pg).
McVicar et al. (1992) "In vitro analysis of the proliferative potential of T cells from patients with brain tumor: glioma-associated immunosuppression unrelated to intrinsic cellular defect", J Neurosurg 76(2): 251-60.
Mehta et al. (2008) "Cigarette smoking and innate immunity", Inflammation research 57:497-503.
Meissner (2010) "Epigenetic modifications in pluripotent and differentiated cells", Nature biotechnology 28, 1079-1088.
Mold et al. (2010) "Fetal and adult hematopoietic stem cells give rise to distinct T cell lineages in humans", Science 330(6011): 1695-9.
Molling et al. (2007) "Low levels of circulating invariant natural killer T cells predict poor clinical outcome in patients with head and neck squamous cell carcinoma", J Clin Oncol 25: 862-8.
Nishikawa et al. (2010) "Regulatory T cells in tumor immunity", Int J Cancer 127(4): 759-67.
Ohgaki et al. (2005) "Epidemiology and etiology of gliomas", Acta Neuropathol109(1): 93-108.
Ohgaki et al. (2007) "Genetic pathways to primary and secondary glioblastoma", Am J Pathol 170(5): 1445-53.
Ostrand-Rosenberg (2008) "Immune surveillance: a balance between protumor and antitumor immunity", Curr Opin Genet Dev 18: 11-18.
Palmer et al. (2006) "Cell-type specific gene expression profiles of leukocytes in human peripheral blood", BMC Genomics 7: 115 (15 pgs.).
Parnes et al. (2000) "Cd72, a negative regulator of b-cell responsiveness", Immunol Rev 176: 75-85.
Pedersen et al. (2011) "Leukocyte DNA methylation signature differentiates pancreatic cancer patients from healthy controls", PLoS ONE 6, e18223.
Peters et al. (2005) "The ADH1C polymorphism modifies the risk of squamous cell carcinoma of the head and neck associated with alcohol and tobacco use", Cancer Epidemiol Biomarkers Prev, 14(2): 476-82.
Polansky et al. (2008) "DNA methylation controls Foxp3 gene expression", Eur J Immunol 38(6): 1654-63.
Pries et al. (2006) "Cytokines in head and neck cancer", Cytokine Growth Factor Rev, 17:141-6.
Ram et al. (2011) "Infections and immunodeficiency in Down syndrome", Clin Exp Immunol 164: 9-16.
Rui et al. (2011) "Malignant pirates of the immune system", Nat Immunol 12:933-940.
Sato et al. (2005) "Intraepithelial CD8+ tumor-infiltrating lymphocytes and a high CD8+/regulatory T cell ratio are associated with favorable prognosis in ovarian cancer", Proc Natl Acad Sci 102: 18538-18543.
Schmidl et al. (2009) "Lineage-specific DNA methylation in T cells correlates with histone methylation and enhancer activity", Genome Res 19: 1165-1174.
Schwartzbaum et al. (2010) "Inherited variation in immune genes and pathways and glioblastoma risk", Carcinogenesis 31(10): 1770-7.
Schwartzbaum et al. (2011) "A DNA methylation microarraybased study identifies ERG as a gene commonly methylated in prostate cancer", Epigenetics 6:1248-1256.
Sehouli et al. (2011) "Epigenetic quantification of tumor-infiltrating T-lymphocytes", Epigenetics 6: 236-246.
Shen-Orr et al. (2010) "Cell type-specific gene expression differences in complex tissues", Nature Methods vol. 7:4, 287-289.
Shimizu et al. (1999) "Induction of tumor immunity by removing CD25+CD4+ T cells: a common basis between tumor immunity and autoimmunity", J Immunol163(10): 5211-5218.
Abbas et al. (2009) "Deconvolution of Blood Microarray Data Identifies Cellular Activation Patterns in Systemic Lupus Erythematosus", PLoS One 4(7) e6098.
Accomando et al. (2012) "Decreased NK cells in patients with head and neck cancer determined in archival DNA", Clin Cancer Res 18: 6147-6154.
Alcon et al. (2009) "B-cell co-receptor cd72 is expressed on nk cells and inhibits ifn-gamma production but not cytotoxicity", Eur J Immunol 39: 826-832.
Alhamarneh et al. (2008) "Regulatory T cells: what role do they play in antitumor immunity in patients with head and neck cancer", Head Neck 30: 251-261.
Anderson et al. (2011) "Adipose tissue recruitment of leukocytes", Curr Opin Lipidol, 21(3): 172-177.
Applebaum et al. (2007) "Lack of association of alcohol and tobacco with HPV16-associated head and neck cancer", Journal of the National Cancer Institute 99:1801-10.
Applebaum et al. (2009) "Smoking modifies the relationship between XRCC1 haplotypes and HPV6-negative head and neck squamous cell carcinoma", Int J Cancer 124: 2690-2696.
Ashkenazi et al. (1997) "A selective impairment of the IL-2 system in lymphocytes of patients with glioblastomas: increased level of soluble IL-2R and reduced protein tyrosine phosphorylation", Neuroimmunomodulation 4(1 ): 49-56.
Baron et al. (2007) "DNA demethylation in the human FOXP3 locus discriminates regulatory T cells from activated FOXP3(+) conventional T cells" Eur J Immunol 37(9): 2378-89.
Baron et al. (2006) "DNA methylation analysis as a tool for cell typing", Epigenetics 1: 55-60.
Beyer et al. "Regulatory T cells in cancer" (2006) Blood 108(3): 804-11.
Bird (2002) "DNA methylation patterns and epigenetic memory", Genes Dev 16(1): 6-21.
Bishara et al. (2008) "Pre-treatment white blood cell subtypes as prognostic indicators in ovarian cancer", Reprod Biol 138: 71-75.
Bocker et al. (2011) "Genome-wide promoter DNA methylation dynamics of human hematopoietic progenitor cells during differentiation and aging", Blood 117(19): e182-189.
Brandsma et al. (2008) "Heme oxygenase-1 prevents smoke induced B-cell infiltrates: a role for regulatory T cells?" Respir Res 9:17.
Bui et al. (2007) "Cancer immunosurveillance, immunoediting and inflammation: independent or interdependent processes?" Curr Opin Immunol 19: 203-208.
Camilleri-Brot et al. (2004) "Her-2 overexpression is an independent marker of poor prognosis of advanced primary ovarian carcinoma: a multicenter study of the gineco group", Ann Oncol 15:104-112.
Campan et al. (2009) "Methylight", Methods Mol Biol 507: 325-337.
Cesana et al. (2006) "Characterization of CD4+CD25+ regulatory T cells in patients treated with high-dose interleukin-2 for metastatic melanoma or renal cell carcinoma", J Clin On col. 24, 1169-1177.

(56) References Cited

OTHER PUBLICATIONS

Cho et al. (2009) "Localized expression of GITR-L in the tumor microenvironment promotes CD8+ T cell dependent anti-tumor immunity", Cancer Immunol Immunother, 58(7): 1057-69.
Christensen et al. (2009) "Epigenetic profiles distinguish pleural mesothelioma from normal pleura and predict lung asbestos burden and clinical outcome", Cancer Res 69: 227-234.
Christensen et al. (2009) "Aging and environmental exposures alter tissue-specific DNA methylation dependent upon CpG island context", PLoS Genet 5:e1000602.
Christensen et al. (2011) "DNA methylation, isocitrate dehydrogenase mutation, and survival in glioma", J Natl Cancer Inst 10 3(2): 143-53.
Chua et al. (2011) "Neutrophil/lymphocyte ratio predicts chemotherapy outcomes in patients with advanced colorectal cancer", Brit J Cancer 104: 1288-1295.
Cui (2007) "Loss of imprinting of IGF2 as an epigenetic marker for the risk of human cancer", Dis Markers 23: 105-112.
Curiel et al. (2004) "Specific recruitment of regulatory T cells in ovarian carcinoma fosters immune privilege and predicts reduced survival", Nat Med 10: 942-949.
Davies et al. (2012) "Functional annotation of the human brain methylome identifies tissue-specific epigenetic variation across brain and blood", Genome Biol13(6): R43.
Den Ouden et al. (1997) "Whole blood cell counts and leucocyte differentials in patients with benign or malignant ovarian tumours", Eur J Obstet Gynecol Reprod Biol 72: 73-77.
Dieye et al. (2011) "Evaluation of a flow cytometry method for CD4 T cell enumeration based on volumetric primary CD4 gating using thermoresistant reagents", Journal of immunological methods 372: 7-13.
Doi et al. (2009) "Differential methylation of tissue- and cancer-specific CpG island shores distinguishes human induced pluripotent stem cells, embryonic stem cells and fibroblasts", Nat Genet 41(12): 1350-3.
Du et al. (2006) "Genomic profiles for human peripheral blood T cells, B cells, natural killer cells, monocytes, and polymorphonuclear cells: comparisons to ischemic stroke, migraine, and Tourette syndrome", Genomics 87: 693-703.
Dunn et al. (2002) "Cancer immunoediting: from immunosurveillance to tumor escape", Nat Immunol 3(11): 991-998.
Duray et al. (2010) "Immune suppression in head and neck cancers: a review", Clinical & developmental immunology 701657.
El Andaloussi et al. (2006) "An increase in CD4+CD25+FOXP3+ regulatory T cells in tumor-infiltrating lymphocytes of human glioblastoma multiforme", Neuro Oncol 8(3): 234-43.
El Andaloussi et al. (2007) "CD4+CD25+FoxP3+ T-cell infiltration and heme oxygenase-1 expression correlate with tumor grade in human gliomas", J Neurooncol 83(2): 145-52.
Supplementary European Search Report in EP12789375, dated Nov. 4, 2014 (5 pgs.).
Fecci et al. "Increased regulatory T-cell fraction amidst a diminished CD4 compartment explains cellular immune defects in patients with malignant glioma", (2006) Cancer Res 66(6): 3294-302.
Felini et al. (2009) "Reproductive factors and hormone use and risk of adult gliomas", Cancer Causes Control 20(1): 87-96.
Floess et al. (2007) "Epigenetic control of the foxp3 locus in regulatory T cells", PLoS Biol 5(2): e38.
Furniss et al. (2009) "Human papillomavirus 6 seropositivity is associated with risk of head and neck squamous cell carcinoma, independent of tobacco and alcohol use", Annals of oncology: official journal of the European Society for Medical Oncology/ESMO 20: 534-41.
Gao et al. (2011) "Innate immunity in alcoholic liver disease", American journal of physiology Gastrointestinal and liver physiology 300: G516-25.
Ginns et al. (1982) "T-lymphocyte subsets in smoking and lung cancer", Am Rev Respir Dis 126(2): 265-9.
Goldfarb et al. (1983) "A numerically stable dual method for solving strictly convex quadratic programs", Mathematical Programming 27:1-33.
Grauer et al. (2007) "CD4+FoxP3+regulatory T cells gradually accumulate in gliomas during tumor growth and efficiently suppress antiglioma immune responses in vivo", Int J Cancer 121(1): 95-105.
Hanahan et al. (2011) "Hallmarks of cancer: the next generation", Cell144(5): 646-74.
Hashimoto et al. (2003) "Gene expression profile in human leukocytes", Blood 101: 3509-3513.
Hawkins et al. (2010) "Distinct epigenomic landscapes of pluripotent and lineage-committed human cells", Cell Stem Cell 6: 479-491.
Heimberger et al. (2008) "Incidence and prognostic impact of FoxP3+ regulatory T cells in human gliomas", Clin Cancer Res 14(16): 5166-72.
Heimberger et al. (2008) "Immunological responses in a patient with glioblastoma multiforme treated with sequential courses of temozolomide and immunotherapy: case study", Neuro Oncol 10(1): 98-103.
Hinoue T et al. (2012) "Genome-scale analysis of aberrant DNA methylation in colorectal cancer", Genome Res. 22(2):271-82.
Carroll et al., "Measurement Error in Nonlinear Models", A Modern Perspective, Second Edition, Chapman & Hall, Jun. 21, 2006, 484 pages.
Eads et al., "Methylight: A High-Throughput Assay to Measure DNA Methylation", Nucleic Acids Research, vol. 28, Issue 8, e32, Apr. 15, 2000, 9 pages.
Laird, "The Power and the Promise of DNA Methylation Markers", Nature Reviews Cancer, vol. 3, 2003, pp. 253-266.
Little et al., "Statistical Analysis with Missing Data", 2nd Edition, ISBN: 978-0-471-18386-0, Sep. 2002, 408 pages.
Mittag et al., "Recent Advances in Cytometry Applications: Preclinical, Clinical, and Cell Biology", Methods in Cell Biology, vol. 103, Jan. 1, 2011, pp. 1-20.
Parham, "The Immune System/Peter Parham", Second Edition, Garland Science, 2005, 62 pages.
Pollard et al., "Cell Biology", 2nd Edition, Apr. 18, 2007, 928 pages.
Roussel et al., "Refining the White Blood Cell Differential: The First Flow Cytometry Routine Application", Cytometry Part A : The Journal of the International Society for Analytical Cytology, vol. 77, No. 6, Jun. 1, 2010, pp. 552-563.
Schouten, "Blood: Principles and Practice of Hematology", 2nd edition, Annals of Oncology, vol. 15, Issue 8, Aug. 2004, 1301 pages.
Shen et al., "Genome-Wide Profiling of DNA Methylation Reveals a Class of Normally Methylated CpG Island Promoters", PLoS Genetics, vol. 3, Issue 10, e181, Oct. 2007, pp. 2023-2036.
Whiteside, "The Role of Immune Cells in the Tumor Microenvironment", Cancer Treat Res., vol. 130, 2006, pp. 103-124.
International Search Report and Written Opinion of the International Searching Authority for PCT/US2012/039699 dated Jan. 2, 2013 (11 pgs.).
Martin-Subero et al. (2009) "A comprehensive microarray-based DNA methylation study of 367 hematological neoplasms", PLos One 4(9): e6986 (11 pgs.).
Showe et al. (2009) "Gene expression profiles in peripheral blood mononuclear cells can distinguish patients with non-small cell lung cancer from patients with nonmalignant lung disease", Cancer Res 69(24): 9202-10.
Sincic et al. (2011) "DNA methylation and cancer: ghosts and angels above thegenes", Curr Opin Oncol 23:69-76.
Smyth et al. (2007) "CD4-regulatory cells in COPD patients", Chest 132(1): 156-63.
Smyth (2004) "Linear models and empirical Bayes methods for assessing differential expression in microarray experiments", Stat Appl Genet and Mol Biol, 3(1): 3 (28 pgs.).
Sonabend et al. (2008) "The role of regulatory T cells in malignant glioma", Anticancer Res 28(2B): 1143-50.
Tan et al. (2009) "Pituitary adenylyl cyclase-activating polypeptide is an intrinsic regulator of treg abundance and protects against experimental autoimmune encephalomyelitis", Proc Natl Acad Sci 106:2012-2017.

(56) References Cited

OTHER PUBLICATIONS

Teschendorff et al. (2009) "An epigenetic signature in peripheral blood predicts active ovarian cancer", PLoS One 4:e8274 (12 pgs.).
Teschendorff et al. (2011) "Independent surrogate variable analysis to deconvolve confounding factors in large-scale microarray profiling studies", Bioinformatics 27(11): 1496-505.
Thurston et al. (2003) "Equivalence of regression calibration methods for main study/external validation study designs", J Stat Plan Inf 113: 527-34.
Tomsova et al. (2008) "Prognostic significance of CD3+ tumor-infiltrating lymphocytes in ovarian carcinoma", Gynecol Oncol 108:415-420.
Trellakis et al. (2010) "Polymorphonuclear granulocytes in human head and neck cancer: enhanced inflammatory activity, modulation by cancer cells and expansion in advanced disease", Int J Cancer 129:2183-2193.
Varley et al. (2013) "Dynamic DNA methylation across diverse human cell lines and tissues", Genome Res 23:555-567.
Verschuere et al. (2011) "Cigarette smoking alters epithelial apoptosis and immune composition in murine GALT", Lab Invest. 91(7):1056-67.
Verstegen et al. (2010) "Down syndrome B-lymphocyte subpopulations, intrinsic defect or decreased T-lymphocyte help", Pediatr Res 67: 563-9.
Villegas et al. (2002) "Prognostic significance of tumor infiltrating natural killer cells subset CD57 in patients with squamous cell lung cancer", Lung Cancer 2002; 35:23-8.
Wang et al. (2010) "Obesity related methylation changes in DNA of peripheral blood leukocytes", BMC Med 8(87) (8pgs.).
Wang et al. (2005) "Protein expression and prognostic value of genes in the erb-b signaling pathway in advanced ovarian carcinomas", Am J Clin Pathol 124:392-401.
Wansom et al. (2010) "Correlation of cellular immunity with human papillomavirus 16 status and outcome in patients with advanced oropharyngeal cancer", Archives of otolaryngology—head & neck surgery 136:1267-73.
Watkins et al. (2009) "A HaemAtlas: characterizing gene expression in differentiated human blood cells", Blood 113(19): e1-e9.
Weisenberger et al. (2008) "DNA methylation analysis by digital bisulfite genomic sequencing and digital Methylight", Nucleic Acids Res 36(14): 4689-98.
Wieczorek et al. (2009) "Quantitative DNA methylation analysis of FOXP3 as a new method for counting regulatory T cells in peripheral blood and solid tissue", Cancer Res 69: 599-608.
Wiemels et al. (2009) "IgE, allergy, and risk of glioma: Update from the San Francisco Bay Area Adult Glioma Study in the Temozolomide era", Int J Cancer. 125(3): 680-7.
Wiencke et al. (2012) "Epigenetic biomarkers of T-cells in human glioma", Epigenetics 7(12): 1391-1402.
Wilhelm-Benartzi et al. (2010) "DNA methylation profiles delineate etiologic heterogeneity and clinically important subgroups of bladder cancer", Carcinogenesis 31: 1972-1976.
Wrensch et al. (2005) "History of chickenpox and shingles and prevalence of antibodies to varicella-zoster virus and three other herpesviruses among adults with glioma and controls", Am J Epidemiol 161 (10): 929-38.
Wrensch et al. (2007) "Nonsynonymous coding single-nucleotide polymorph isms spanning the genome in relation to glioblastoma survival and age at diagnosis", Clin Cancer Res 13(1): 197-205.
Wrensch et al. (2009) "Variants in the CDKN2B and RTEL 1 regions are associated with high-grade glioma susceptibility", Nat Genet 41(8): 905-8.
Wulff et al. (2009) "Decreased levels of circulating regulatory NK cells in patients with head and neck cancer throughout all tumor stages", Anticancer research 29: 3053-7.
Yang et al. (2010) "CD8+ T-cell infiltrate in newly diagnosed glioblastoma is associated with long-term survival", J Clin Neurosci 17(11): 1381-5.
Zaidi et al. (2011) "Bookmarking the genome: maintenance of epigenetic information", The Journal of biological chemistry 286: 18355-18361.
Zhang et al. (2003) "Intratumoral T cells, recurrence, and survival in epithelial ovarian cancer", N Engl J Med 348:203-213.
Zhang et al. (2007) "TCRzetadim lymphocytes define populations of circulating effector cells that migrate to inflamed tissues", Blood 109: 4328-4335.
Zheng et al. (2011) "DNA hypermethylation profiles associated with glioma subtypes and EZH2 and IGFBP2 mRNA expression", Neuro Oncol13(3): 280-9.
Zou (2006) "Regulatory T cells, tumour immunity and immunotherapy", Nat Rev Immunol 6: 295-307.
Goldfarb et al. (1982) Dual and Primal-Dual Methods for Solving Strictly Convex Quadratic Programs. In: Hennart JP, ed. Numerical Analysis. Berlin: Springer-Verlag pp. 226-239.
Wu et al. "Bayesian modeling of Chip-chip data using latent variables" BMC Bioinformatics, vol. 10, 352, 2009 (13 pgs.).
Bibikova et al. (2009) "Genome-wide DNA methylation profiling using Infinium® assay", Epigenomics 1:177-200.
Bibikova et al; Genome Research, vol. 916, pp. 383-393, 2006.
Bibikova et al; Genomics, vol. 98, pp. 288-295, 2011.
Wallace et al. (2009) "Selenium and risk of bladder cancer: a population-based case-control study", Cancer Prev Res 2:70-73.

\* cited by examiner

Expected

| | | | | | | | | | | | | |
|---|---|---|---|---|---|---|---|---|---|---|---|---|
| Monocyte | 90 | 80 | 60 | 40 | 20 | 10 | 0 | 0 | 0 | 0 | 0 | 0 |
| B Cell | 10 | 20 | 40 | 60 | 80 | 90 | 0 | 0 | 0 | 0 | 0 | 0 |
| NK | 0 | 0 | 0 | 0 | 0 | 0 | 0 | 0 | 0 | 0 | 0 | 0 |
| T Cell | 0 | 0 | 0 | 0 | 0 | 0 | 10 | 20 | 40 | 60 | 80 | 90 |
| Granulocyte | 0 | 0 | 0 | 0 | 0 | 0 | 90 | 80 | 60 | 40 | 20 | 10 |

Observed

| | | | | | | | | | | | | |
|---|---|---|---|---|---|---|---|---|---|---|---|---|
| Monocyte | 86 | 77 | 57 | 37 | 18 | 9 | 0.5 | 0 | 0 | 0 | 0 | 2 |
| B Cell | 10 | 20 | 37 | 56 | 74 | 86 | 0 | 0 | 0 | 0 | 0 | 0 |
| NK | 2 | 2 | 2 | 0 | 0 | 0 | 1 | 3 | 6 | 5 | 5 | 2 |
| T (CD8+) | 0 | 0 | 0 | 0 | 0 | 0 | 2 | 0 | 0 | 1 | 9 | 2 |
| T (CD4+) | 0 | 0 | 0 | 0 | 0 | 0 | 13 | 23 | 40 | 56 | 66 | 83 |
| Granulocyte | 3 | 4 | 7 | 10 | 10 | 7 | 82 | 73 | 54 | 38 | 20 | 10 |

FIG. 2

Heatmap of HNSCC data ($S_1$)

Heatmap of Ovarian cancer data ($S_1$)

Heatmap of Down Syndrome data ($S_1$)

Heatmap of Obesity data ($S_1$)

FOXP3, CD3Z and C-Less Primer Sequences.
Underlined letters are "C" within CpG motifs.

| Primer name | Chromosome location | Wildtype Sequence 5'-3' | Bisulfite sequence | Amplicon bp |
|---|---|---|---|---|
| FOXP3 qMSP Forward | chrX:49004142-49004170 | CATCTGGGCCCTGTTGTCACAGCCCCG (SEQ ID NO: 108) | TATTTGGGTTTTGTTGTTATAGTTTTTG (SEQ ID NO: 106) | 109 (Lower Strand) |
| FOXP3 qMSP Reverse | chrX:49004227-49004250 | CGACACCACGGAGGAAGAGAAGAG (SEQ ID NO: 109) | CTCTTCTCTTCCTCCATAATATCA (SEQ ID NO: 107) | (Lower Strand) |
| FOXP3 qMSP Probe-Deme | chrX:49004200-49004218 | ATGGCGGCCGGATGCGCCG (SEQ ID NO: 110) | CAACACATCCAACCACCAT (SEQ ID NO: 105) | (Lower Strand) |
| Reference: Examples 13-21 | | | | |
| CD3ZU5 Forward | chr1:165754293-165754313 | GGATGGCCGCGGTGAAAAGCG (SEQ ID NO: 111) | GGATGGTTGTGGTGAAAAGTG (SEQ ID NO: 100) | 117 (Lower Strand) |
| CD3ZU3 Reverse | chr1:165754386-165754409 | CGGTTAGGAGAAAAGGAGTCTCTG (SEQ ID NO: 112) | CAAAAACTCCTTTTCTCCTAACCA (SEQ ID NO: 101) | (Lower Strand) |
| CD3ZUProbe | chr1:165754365-165754383 | CTGAGGCAGCGGTGGCCGG (SEQ ID NO: 113) | CCAACCACCACTACCTCAA (SEQ ID NO: 102) | (Lower Strand) |
| Reference: Examples 13-21 | | | | |
| C-Less Forward | chr20:19199387-19199412 | TTGTATGTATGTGAGTGTGGGAGAGA (SEQ ID NO: 97) | TTGTATGTATGTGAGTGTGGGAGAGA (SEQ ID NO: 97) | 69 (Lower Strand) |
| C-Less Reverse | chr20:19199434-19199455 | GGAAGAGAAGGGGTGGAAGAAA (SEQ ID NO: 114) | TTTCTTCCACCCCTTCTCTTCC (SEQ ID NO: 98) | (Lower Strand) |
| C-Less Probe | chr20:19199414-19199431 | ATAGAGTTAGAGGGGGAG (SEQ ID NO: 115) | CTCCCCCTCTAACTCTAT (SEQ ID NO: 99) | (Lower Strand) |
| Reference: Daniel J. Weisenberger, Mihaela Campan, et al., Nucleic Acids Research 2005, 33:6823-36. | | | | |

FIG. 12

| CpG Name | Chromosome | MapInfo | Entrez ID | Gene Symbol |
|---|---|---|---|---|
| cg00974864 | 1 | 159867677 | 2215 | FCGR3B |
| cg01980222 | 6 | 41238895 | 54209 | TREM2 |
| cg08368934 | 16 | 56258956 | 222487 | GPR97 |
| cg08399444 | 12 | 13139815 | 83445 | GSG1 |
| cg24211388 | 6 | 31690816 | 199 | AIF1 |
| cg25634666 | 11 | 71524436 | 2352 | FOLR3 |
| cg27461196 | 19 | 40321946 | 5348 | FXYD1 |

AUC: 0.871 (0.819-0.922)
AUC: 0.841 (0.785-0.896)

— Unadjusted ROC
— Adjusted ROC

Heatmap of demethylation status of gene NKp46 obtained by MS-rPCR

Heatmap of demethylation status of gene *NKp46* obtained by bisulfite pyrosequencing SEQ ID NO: 1
Chromosome: 1
Coordinate: 170894886
Source: NCBI
Gene: FASLG
Accession Id.: NM_000639.1
GCCAGCCCCAGCAAACGGTTTTACTTCTTCTCAGTCCTGTAGAGGCTGAGGTGTCAAGGA
[CG] GGACCCTGTTGCTGACTGCTCAAGAGGAGGCAAGCTGGATCTCTCTTATAGAGTTTC
CAT SEQ ID NO: 2
Chromosome: 6
Coordinate: 37080005
Source: NCBI
Gene: FGD2
Accession Id.: NM_173558.2
TCTCCACTGAACCTGGTCTGTGTCCTGGAGTGCAGGGCCTGAGCCTCGGTGCTCTTGGTA
[CG] TGAAGTGCCTGGAACAGCTTCACGCTCCAGTAACTGTGAACCCCTGGGGCCTCACAT
GCC SEQ ID NO: 3
Chromosome: 12
Coordinate: 14930292
Source: NCBI
Gene: MGP
Accession Id.: NM_000900.2
GATCATGTGTTTGTGGCAACTTCCTCTGTGGGCTTTTGCCCAGGTCTGTCCCCAAGCATA
[CG] ATGGCAAAACTTCTGCACCAGAGCAGCATCCTGTGTAACACAGTCAGGTCCAGCAG
TTA SEQ ID NO: 4
Chromosome: 1
Coordinate: 110108114
Source: NCBI
Gene: EPS8L3
Accession Id.: NM_024526.2
AGCTTCTCTGCTAGTGGCCACAGGCAGAGCCTGCCTTTGATGAGGTTACAGAGGCAGCCA
[CG] CCTGTGCTCTTTGGACTCTGGTGGGTGGGAGGCTTCCTGGTCACTAACCGCTCAAC
ATC SEQ ID NO: 5
Chromosome: 21
Coordinate: 44056660
Source: NCBI
Gene: LOC284837
Accession Id.: NM_194310.1
CACCCACGGGGCCAGGCTGGCACAACGCCCCAACGCTGCAATCCTGGGAAGAGTCACACG
[CG] CCCTCCCGGGACCCACGTGACCATCAAGGGAGTGTGGAGGACACATCCCTCGGGGT
GAC

SEQ ID NO: 6
Chromosome: 11
Coordinate: 47237946
Source: NCBI
Gene: NR1H3
Accession Id.: NM_005693.1
TGGCTTCCTCTCTGAGGATGCAGCTGCTGCCTCCCTGGGCCTGGCTGCTTGCATCCTGTG
[CG] CCTGGCTTCCACAGCTCCACCGCAGAGTCTGAGCTCCAAAAGAGAGGCACAAGGGGG
TCT SEQ ID NO: 7
Chromosome: 9
Coordinate: 126992712
Source: NCBI
Gene: PPP6C
Accession Id.: NM_002721.3
TTTTTGTAGCTACAGATAGAATAGAGATCTTTGTCTATTTTGTTCACGAAGTACTGCAAG
[CG] CCTTGAGCTGTACCTGGCACATCTTTGTTGCTCAGCAAAGAGTGGTTGGATAAACGA
ACG SEQ ID NO: 8
Chromosome: 21
Coordinate: 36458793
Source: NCBI
Gene: DOPEY2
Accession Id.: NM_005128.2
ACCAAATGAGAGAGCCATTTGGGGATACAAATCATTCCCAACCCAGAGCTACAGAAGACA
[CG] TGTCCACAAACACAACTGTGCACAAACTCACTGGGCAATCCTGTTCAAATATTTAGC
AAG SEQ ID NO: 9
Chromosome: 19
Coordinate: 40727715
Source: NCBI
Gene: NIFIE14
Accession Id.: NM_032635.2
TCTCTACGGACTTCCTCGGTGATACCCACTCGTCCATCTTCGATGCTAAGGCCGGCATTG
[CG] CTCAATGACAATTTCGTGAAGCTCATTTCATGGTAAGGGGAAGGAGCTGGAGACTT
AGA SEQ ID NO: 10
Chromosome: 2
Coordinate: 242450682
Source: NCBI
Gene: PDCD1
Accession Id.: NM_005018.1
CGCGCCAGCTGTCAGGCGGTTTCTAGCCTCGCTTCGGTTATTTTAAGCTGATGAGCCTGA
[CG] CATCTCATCACTAATATCAGCAGTTTCATTTCTCCTGTTTTCCATTCGCTGTAATAA
AAT

SEQ ID NO: 11
Chromosome: 10
Coordinate: 44815977
Source: NCBI
Gene: ZNF22
Accession Id.: NM_006963.3
CATTTACAGGAAAGGAACCAAGGCTCAGAGAAGAAATGTGCTCCGTTCACCGTGTGTAAG
[CG] GACGACCCAGAATTGGAATGGTTCTTTGTGGCTCCAAAGTCTGATTTCAACACACCC
CTT SEQ ID NO: 12
Chromosome: 1
Coordinate: 26728010
Source: NCBI
Gene: RPS6KA1
Accession Id.: NM_001006665.1
GGGAGACCTGACCTGAAAGGACCCCCTTCAAGTGATAGGGCAGAGCACAGATTGCAAAAA
[CG] CATATTAAGAAATCACTCTTGGCCGGGCGCGGTGGCTCATGCCTGTAATCCCAGCAC
TTT SEQ ID NO: 13
Chromosome: 2
Coordinate: 108971950
Source: NCBI
Gene: EDAR
Accession Id.: NM_022336.1
TCCCAGGCAGCCCTGCTGGCCCCTAAGGACATAGAGTACCTGCTTCTGAGAGGGCTGCCA
[CG] GTGGCCACCTGTGAAGCCTGTCACCCAGAACTGGATGGTACCTGACTTTCTTCATAG
ACC SEQ ID NO: 14
Chromosome: 1
Coordinate: 54293020
Source: NCBI
Gene: TMEM59
Accession Id.: NM_004872.3
TTTAACATTCCTAACAGACTACATTTTGCAAAAGAATAACAACGAAGGGGACTTGTCCTA
[CG] AGCTAGCACACATGGTGTAAACCGGAGTAATTACAAGGGTGTAGCAGGGGTGTGCAG
AAA SEQ ID NO: 15
Chromosome: 5
Coordinate: 176869969
Source: NCBI
Gene: DOK3
Accession Id.: NM_024872.1
GGCCTCCCTTGACCACTCCACGCTGTCCGAGAGCTCAAAGGCCCTCACGGTATACACTCA
[CG] CTGGGCATCCAGTCCACATGGGACCCACAGCCCTGAATGGCCCCAACCACGTGAGTG
TGG

SEQ ID NO: 16
Chromosome: 6
Coordinate: 43720625
Source: NCBI
Gene: C6orf206
Accession Id.: NM_152732.2
CCTCCTCCCCACGGAGGCCTAGGCATCAGCCCCTCCCTCATCCTTTCCAGAGTTTGGGA
[CG]GGATGTCTTCAGTTGCCACGGCCACAGTATGGCTTCCCCTACAGTTAGGCTACAGTT
GGG SEQ ID NO: 17
Chromosome: 22
Coordinate: 37044362
Source: NCBI
Gene: CSNK1E
Accession Id.: NM_001894.4
AGGGAAGATACGGCTATTATAGAAGTGACTCCTCCCAGGAACTGTGCTTCCGGGATTGGA
[CG]CAGGGCCTCAGGCATTTTGCGTGTCCACAGTCACAACTGTGTGAATATAGGTGTGTC
ATA SEQ ID NO: 18
Chromosome: 5
Coordinate: 139705861
Source: NCBI
Gene: HBEGF
Accession Id.: NM_001945.1
GTCGGCATCGGTGCGTGTTGGTCAGGGGTCTGGGCGGGTGTCTGATGCGGCCTGGCCTCT
[CG]CCCGCAGTTCTCTCGGCACTGGTGACTGGCGAGAGCCTGGAGCGGCTTCGGAGAGGG
CTA SEQ ID NO: 19
Chromosome: 10
Coordinate: 44815441
Source: NCBI
Gene: ZNF22
Accession Id.: NM_006963.3
TGGCTTGGTGGTTATAGCAGTGGAAGTGTTGAAAGTGGCTTGATAATGAATATATTTTAA
[CG]ATGAAGCCGACAGAATTTGTGGATAAATCACAGGTGAATTTTGGATGAAAAAAGAA
GAG SEQ ID NO: 20
Chromosome: 20
Coordinate: 57016289
Source: NCBI
Gene: CTSZ
Accession Id.: NM_001336.2
CCCAAAGGAAGATTCCACTTGGCGCAGGCATCAGGAGTTATCCAATGTGACTTCCAAAGA
[CG]CCTTGAAAAGGTTTTCTGCTAACGAAACTCTTCTTAGTCAAATGAGGAACCAAAAGC
AGA

SEQ ID NO: 21
Chromosome: 14
Coordinate: 22658002
Source: NCBI
Gene: CEBPE
Accession Id.: NM_001805.2
GCCCGGGGAGCTAGGGGACATGTGTGAGCATGAGGCCTCCATTGACCTCTCCGCCTACAT
[CG] AGTCTGGGGAAGAGCAGCTTCTCTCCGATCTCTTTGCCGTGAAGCCAGCGCCTGAGG
CCA SEQ ID NO: 22
Chromosome: 12
Coordinate: 8167985
Source: NCBI
Gene: CLEC4A
Accession Id.: NM_016184.2
TGAGTATGTCTGGGAAACACAAGAGTCCCAGAAGATTGAGTGGCCTGCAGATACGCATTA
[CG] GGGTGTACATTTGTATTGTGGAGAAGAAAGATTTTGTGCCACTCTCTTCAGCCTCC
ACT SEQ ID NO: 23
Chromosome: 6
Coordinate: 6534074
Source: NCBI
Gene: LY86
Accession Id.: NM_004271.3
CAGCTGCAGTGGAGGCGGCGGTGGGAAAGCCTGGCCCACACACGTGGTCTGTAGCGACAG
[CG] GCTTGGAAGTGCTCTACCAGAGTTGCGGTAAGCCCTTGCAGTACACCCATGTGTGTT
TAT SEQ ID NO: 24
Chromosome: 16
Coordinate: 66120919
Source: NCBI
Gene: FAM65A
Accession Id.: NM_024519.2
CAGCCCCTTGCCCAAACCAGTTCTGCAGAGAGCCCAGGCCCGGCTGTTGCAGGAACCTTG
[CG] CCAACCTCCATTTCCAGGGAAAAGCTCCGTTCCCCGACAAGGACGATCCTCTCCGGC
TTC SEQ ID NO: 25
Chromosome: 15
Coordinate: 38388759
Source: NCBI
Gene: PLCB2
Accession Id.: NM_004573.1
TTTCTGTGCTGGGAATTCCCTTAGCTCCAGCCTCCACTGGGCAGTTTATTATCTTAATTC
[CG] CATGAAGAGTGTCCTCCCTCACCCTCCACCCTGCCCTGGACCAGACCTCCAGCCGCG
ACA

SEQ ID NO: 26
Chromosome: 15
Coordinate: 48345209
Source: NCBI
Gene: HDC
Accession Id.: NM_002112.1
GAGCTAAGGTCAAAGAAAGAACCCTTTAAATAAAGGGCCCACACTGGCTGCCAGGGAGTG
[CG] CAGGACTGGCAAGAGGGAAGCCGGGCTGCTCCACGCCTTTCACGCCTTCCACCTCCT
GCG SEQ ID NO: 27
Chromosome: 17
Coordinate: 77868065
Source: NCBI
Gene: CD7
Accession Id.: NM_006137.6
CCGTCCTCGTAGTAAATGATGTCTTGGGGCTGTGGCCCGAGCTGCCTCAGGTAGATCCCA
[CG] CAGGCCCCGCTGGTGGAGCAGGTGATGTTGACGGAGGCTCCACGGGACAGTCGT
GCA SEQ ID NO: 28
Chromosome: 16
Coordinate: 21572639
Source: NCBI
Gene: IGSF6
Accession Id.: NM_005849.1
GGAGAGACACAAGGCCTGGGAGCCGCTTTCCTGGCCTGCCGTGCAGCTGAGGCACTGGCA
[CG] CAGCCTAAGCCAGGCACACTTGCCCATGCCCTGGAATGGAGAGCCAGTGACCCAGAG
TAG SEQ ID NO: 29
Chromosome: 7
Coordinate: 100667471
Source: NCBI
Gene: CLDN15
Accession Id.: NM_138429.1
GCTGATGCTGGGGGTGACTCTGCCAAACAGCTACTGGCGAGTGTCCACTGTGCACGGGAA
[CG] TCATCACCACCAACACCATCTTCGAGAACCTCTGGTTTAGCTGTGCCACCGACTCCC
TGG SEQ ID NO: 30
Chromosome: 4
Coordinate: 47830991
Source: NCBI
Gene: TXK
Accession Id.: NM_003328.1
GAGGAAAGGATCATGGTAGCCCCTTCTGCGGGGAGCACACAACAGTCTTCAGTTCTTCTG
[CG] GTGCTCTACTCACAAAAACACATCTTTCAACTGAAATCATAGTTCGCTCAAGATGTT
TCT

SEQ ID NO: 31
Chromosome: 4
Coordinate: 8251449
Source: NCBI
Gene: SH3TC1
Accession Id.: NM_018986.2
TGGCCCGGAGGGCACCCGGGCAGAGACGGAAGAAATTGCACGTGAGCGTTTGTGTGCATA
[CG] TGTGCCTGTCCATGTGTGCACACACTTGTGCTTGTGAGTCTCTGTGTGCCCATGCAT
ATG SEQ ID NO: 32
Chromosome: 3
Coordinate: 139810060
Source: NCBI
Gene: FAIM
Accession Id.: NM_018147.2
AAGTGTGGGTAGGAGCCGGCCGCTGGCCCCGCTCTGGGCTAGACGGTGGGGACATACTGG
[CG] GGCAAAAACAGCCCTGTGCCTGCTCTGCAGCTATGGGGAAGGAATATCTGTTCATGG
CAG SEQ ID NO: 33
Chromosome: 1
Coordinate: 111848223
Source: NCBI
Gene: ADORA3
Accession Id.: NM_020683.5
TTGGTGGCAGCCTCCTAACCTTAGCCAGAACTATTCCTGCTAAGTTCTTGCACGAGTTGA
[CG] CTTTGCTGAGCACAGCCGATACCCAGCCTTTGCAGCAAAGATCCTTGGTCAAAGGGA
TAA SEQ ID NO: 34
Chromosome: 12
Coordinate: 121753810
Source: NCBI
Gene: GPR109A
Accession Id.: NM_177551.3
CCAGAAAGTGATCCTGCAGATGGTGCCGATTCATGAGTGCGGCTAGTGAGTCCGATGGAG
[CG] CCTCGCCTAGTGAATGCTCCAGCAAGGAGGTGTGTGTCTGTGGTGAACGTGTGGT
TCC SEQ ID NO: 35
Chromosome: 17
Coordinate: 72827828
Source: NCBI
Gene: 39333
Accession Id.: NM_006640.2
GACAATGCTACTTCAGTTTGGAGCACAAACATATGATCAGCACATGGAAATGTGGTAATT
[CG] GATGCATTCGTGATTGCAACAGATTGAAGAAATTAGACCAGACAAAGAGTGTTTTA
GAG

SEQ ID NO: 36
Chromosome: 4
Coordinate: 16509831
Source: NCBI
Gene: LDB2
Accession Id.: NM_001290.2
CTCCAGCCAGGACCCTTCACAACCTGATTGCTAAGCTTGTTAGCATAGAGGTGGTCTAAC
[CG] CTACATGAGCCGCTCACCCCTGACAACCACACTGTTGTAATGTATCAGAAATGTTGA
TTA SEQ ID NO: 37
Chromosome: 19
Coordinate: 40512021
Source: NCBI
Gene: CD22
Accession Id.: NM_001771.1
CACGCGGAAACAGGTAAAAATCATTTTGCTTTTATTTTGCATTCAACAAGCAAGTTATTA
[CG] GAACAGCAGTTATGGGCCAGGCATACCTCCCAGAGCTGGGAACACAGTGGGGACCTC
CCT SEQ ID NO: 38
Chromosome: 19
Coordinate: 59739533
Source: NCBI
Gene: FLJ00060
Accession Id.: NM_033206.1
ACCTTGTGATCCGCCCACGTCAGCCTCCCAAAGTGCTGGGATTACAGGCGTAAGCCACAG
[CG] CCCAGCCTCGCTGTTCTTATCTTGGCAGCAGATTCCGAATGTCGGCTGGTGCCCCTG
TCA SEQ ID NO: 39
Chromosome: 9
Coordinate: 134926722
Source: NCBI
Gene: CEL
Accession Id.: NM_001807.2
AGGCTGGATGGTGACACTTCCACACCCTTGAGTGGGACTGCCTTGTGCTGCTCTGGGATT
[CG] CACCCAGCTTGGACTACCCGCTCCACGGGCCCCAGGAAAGCTCGTACAGATAAGGT
CAG SEQ ID NO: 40
Chromosome: 8
Coordinate: 11388980
Source: NCBI
Gene: BLK
Accession Id.: NM_001715.2
CAGAGTTAGCAAACCTCCATGCTGACTCTACAAGGTAATTTGCCCTGCCGTGTGGACAAA
[CG] CTGCAGATCTCATGGAGAGGGCTTGGGCTCTGCCATGTGCCATCTGTGTGCACCAGG
GCA

SEQ ID NO: 41
Chromosome: 6
Coordinate: 41230059
Source: NCBI
Gene: TREML1
Accession Id.: NM_178174.2
GCCCATGGCTGGGCAGAGAAATGTCAACTCCTGGGCTTGCCTGGGCACTGATGCAGCATT
[CG] CCTGAGGGCAGGAAACATCTGCCTCAGAAAGTCACTTGGGGTGGGAGAAAGGAAATG
ATG SEQ ID NO: 42
Chromosome 3
Coordinate: 48240150
Source: NCBI
Gene: CAMP
Accession Id.: NM_004345.3
ATTGCCCAGGTCCTCAGCTACAAGGAAGCTGTGCTTCGTGCTATAGATGGCATCAACCAG
[CG] GTCCTCGGATGCTAACCTCTACCGCCTCCTGGACCTGGACCCCAGGCCCACGATGGT
GAG SEQ ID NO: 43
Chromosome: 6
Coordinate: 32892233
Source: NCBI
Gene: HLA-DOB
Accession Id.: NM_002120.2
GAGAAACAACCTGCAGTAGGCTGGGTCACAGAGGCAATCTGTGATTTTTTGGTCAGGACA
[CG] GAAACAAATCTCAGTTGGGGTATATGTGGACAAATGAAACTGGAAACAAAGGTTGCT
CCT SEQ ID NO: 44
Chromosome: 20
Coordinate: 34707347
Source: NCBI
Gene: SLA2
Accession Id.: NM_032214.2
ACGCCCGTCCTAGTCCCATCTCAGGTGCGCACTTGCTGTGTGACTTTGGGCCCCTCTCTG
[CG] CTGCAGTCAGACTCCAAAGTCAGGAACGTGAGGGCTACCATCTCTCAAGACATTTCA
GCT SEQ ID NO: 45
Chromosome: 19
Coordinate: 6621390
Source: NCBI
Gene: TNFSF14
Accession Id.: NM_003807.2
GTGACTCAGGTGGCAAGTGCAGTGGGGAGCCCCAGCTTTCCCTTCTTGGATGCTTCATT
[CG] CTTGGGGCCACCAAATATCGACTGAGGACTTTCTGCCCATGCCAGGCTCTGCTCTCG
GTG

SEQ ID NO: 46
Chromosome: 3
Coordinate: 189379299
Source: NCBI
Gene: FLJ42393
Accession Id.: NM_207488.1
CTAGGAAACTTCTTCCATATATCATAAACAGAGACCAGTATTACAATACTTCACCCACTG
[CG] CCAATTTGGCTTTCATGTCTGTTTCCTGTGTCGATCACAACATCCTAGACAGCCCAA
ACA SEQ ID NO: 47
Chromosome: 17
Coordinate: 43861946
Source: NCBI
Gene: SCAP1
Accession Id.: NM_003726.2
GCTCTCCAGGGGGCTGCGAGGGGCTCATGGGATCCCCATGGGCCAAGGCCAGGTGGTTGA
[CG] TGAGTTTTTGTCAGTGCGAAAACCCCAGCCCTCCCTTTATCACCCTGCAGACGTCTA
GGG SEQ ID NO: 48
Chromosome: 17
Coordinate: 22823100
Source: NCBI
Gene: KSR1
Accession Id.: NM_014238.1
TGCCCCCAAGCAGGCCGGGACTGCCAGGCTTTACATCAGAGAACTGAGTTTCAGTTACCA
[CG] GTGAAGGCTGACAGCACAGAGCACAGTTCCGTGCAAATCAAGACACATTTCCCAAGT
CCC SEQ ID NO: 49
Chromosome: 15
Coordinate: 66285305
Source: NCBI
Gene: CALML4
Accession Id.: NM_033429.1
CCACCCTTAAAGTCCTCAGAAGGTGGGAACTGAACTGGCACAGGATGGGAACCGGCTGTG
[CG] CTGGCCACTTGATTTTGCCAGCTGCCCTGTAATTCAGCTGGTGAGGAAACTGAGGCA
CAG SEQ ID NO: 50
Chromosome: 9
Coordinate: 130007893
Source: NCBI
Gene: CIZ1
Accession Id.: NM_012127.2
TGATAGCCAATTAGGCTTGGGGACCTGCATGCCCAGCCCCTGCCTTCCTGGAGCCCATGA
[CG] CAGGGGCCATCCCTGACCACAGCAGATTTCATCGAGTACTTGCTTGTTGAGTGGTGG
AGC

SEQ ID NO: 51
Chromosome: 8
Coordinate: 71479423
Source: NCBI
Gene: NCOA2
Accession Id.: NM_006540.2
CTCCAGAGGGGATGGAGAGGCGCGACTGTGGGAGCTGGAAGGGGCACCACCCGGCAATTG
[CG] GGATAAAGCAAATGCTGCACACAGAGTGTGAAACTTAACCTGGTTGAGAATTTTCGG
CAC SEQ ID NO: 52
Chromosome: 17
Coordinate: 24393906
Source: NCBI
Gene: PIPOX
Accession Id.: NM_016518.2
CTGACCTCACCACCCACCAGGGAGGTGGGTCTTATTCTGGGCATCGTGCCAAGTTCTTAG
[CG] GGGCCCTCTAGAATCTCTAAAGCAAATCAGGCTGAAGAGGGGAAAACCAGCAGGGGG
AGG SEQ ID NO: 53
Chromosome: 9
Coordinate: 136949449
Source: NCBI
Gene: FCN1
Accession Id.: NM_002003.2
GGGTTGTTACCAGCTTTTAGGGACCAGAAAACCCAGGTCTGTCTCACCTGGACATGTGTC
[CG] CAGCCTGGGCAGGCAGGTTCTTGATATGCAGGAACAAGACTAGCAGGACAGCGAGCC
CCC SEQ ID NO: 54
Chromosome: 19
Coordinate: 43995615
Source: NCBI
Gene: LGALS4
Accession Id.: NM_006149.2
TCCCTTGCCAGCTTCCCTGGTGACCAGCCAGGACCCAAATCACCTGGGTCCCCTCCCCTA
[CG] CCCTCCTGCAAAGAGGAAGTGCTCATGAACTTCGGCCCTGCCAGGGCCTTATCAGAG
CCC SEQ ID NO: 55
Chromosome: 17
Coordinate: 70039110
Source: NCBI
Gene: CD300LB
Accession Id.: NM_174892.1
AGGCTGAGAAGGAGCAGAGCAGGGGGCAGCCACATGGCTCTGCCTTCCCGGCTCCTCGTC
[CG] CCTGATCTGCAACCAGTGGCAAATGCAGATCCCAGATGCACTCTGGAAGTTCTGCCT
GAG

SEQ ID NO: 56
Chromosome: 12
Coordinate: 6423750
Source: NCBI
Gene: TNFRSF7
Accession Id.: NM_001242.3
ACCAACTGGGAGGAAGCTTAAATAGCCTTGTCTCAATTGAGGTCTGGTTTGATGGCCAAA
[CG]AGTTTGCTACAGAATGCTCAGAATTGCAAGCAAGGGGTGTAGAGCTGCCTCTCTTCT
GTC SEQ ID NO: 57
Chromosome: 11
Coordinate: 59979867
Source: NCBI
Gene: MS4A1
Accession Id.: NM_152866.2
AGTTTGTTTCTCAAGCACACTGGGAGGGTGAGTGGTGTAGTCCAGGCCTGAAGATGAAAT
[CG]CTGATAGACATCAGGTGACAGGAAATCAGTAGCTTCTGCTACCTTGGGCTTCGCTCC
AAT SEQ ID NO: 58
Chromosome: 22
Coordinate: 43451388
Source: NCBI
Gene: PRR5
Accession Id.: NM_015366.3
AAGCCCAGCTGCTGGCTGATAAATATTTTATCACTGCTCACAGAGCAGTCCCCAGGAAGG
[CG]CCTGCATCCTCCAAGCCCACAGAGCACCCCTTCCTGCCCGGACAGAAGGAACTGGCC
AGG SEQ ID NO: 59
Chromosome: 5
Coordinate: 118718932
Source: NCBI
Gene: TNFAIP8
Accession Id.: NM_014350.1
AAGGCCCTTTGGAGTAACTGCAGCAATGAGTGCCCGGGCTGTGCTTGGAGTACCAGTGCT
[CG]CCCGGGGCTATACTGAATGAGTAAGCAGCCCCGTCTGCTTTTGCTGTGCAAAGGTAA
GGG SEQ ID NO: 60
Chromosome: 17
Coordinate: 25729371
Source: NCBI
Gene: CPD
Accession Id.: NM_001304.3
GAAATCTGCCTAATGAGGGTCGAGGCCAGCACACACAGGGACCTATTTGCAGTAAAACAA
[CG]TGGGGTGACGCCTAAGAAATAGACAACATTAACACAAAGGGAGCCTACTACGTAGCA
CAT

SEQ ID NO: 61
Chromosome: 19
Coordinate: 15451532
Source: NCBI
Gene: PGLYRP2
Accession Id.: NM_052890.2
TGGCCAGCAGCGGCTACAGAGCCGTCACTATGGGGAGGGACAGGACTTGAGGGGTTGCCT
[CG] GTCCACCTCACTGGAGAATGGGCAGAGTTTATGGAGTCTGAACCACCTGGTCTCCAG
GCC SEQ ID NO: 62
Chromosome: 1
Coordinate: 24386999
Source: NCBI
Gene: IL28RA
Accession Id.: NM_170743.2
TTTCTGACCCCGAAGGCTGTGGTGTTCACCTGGACAGCAGTAGCTTCCCAGTAAGGCACA
[CG] CCACGACGCGCAATATTATGCGGCCCTTTAGGAGGACGTTGCCGAATGGTGTGTATC
GAC SEQ ID NO: 63
Chromosome: 11
Coordinate: 67534528
Source: NCBI
Gene: ALDH3B1
Accession Id.: NM_000694.2
AGTGGGCCAGCAGTCGGGCCAGAGTCCAGCTCAGCAACTCCGGGTTACAGGCAGCCCAGG
[CG] GGCCTAGCCACCGGCAGCTGCACTCAGAGGCCACTGTGTCCTGGCTGAGCTCATCTG
CCT SEQ ID NO: 64
Chromosome: 11
Coordinate: 3077976
Source: NCBI
Gene: OSBPL5
Accession Id.: NT_009237.17
CGGCAAAGCCACGCTCACCTTCCTGAACCGAGCCGAGGATTACACCCTTACCATGCCCTA
[CG] CCCACTGCAAAGGTGAGAGGCTCAGCCACACTCCGAGGGCAGAGCCAGGCTCTGT
GAG SEQ ID NO: 65
Chromosome: 19
Coordinate: 15252927
Source: NCBI
Gene: BRD4
Accession Id.: NM_058243.1
GAGCTGCCTCGGCGCACGGCCACTGGCCCGGCTCCAGGCGGCGCAGTCTGGCTGATGACA
[CG] AGCGCTGTTCTCACCAGCTGCCTGAGCCAGTCAGATGGAAAAGTAATCCTATTTGTG
CTT

SEQ ID NO: 66
Chromosome: 16
Coordinate: 56258956
Source: NCBI
Gene: GPR97
Accession Id.: NM_170776.3
TAAAGACAACAATTTCACAGCTCTGATGATCAGAAATGATGTAATGGCCACAGGCGGCTC
[CG] CCTGCGTCATCCATGATTTCATCACACCTCGGGAGGCTCAGGGTGACAGACAGTG
CAT SEQ ID NO: 67
Chromosome: 12
Coordinate: 13139815
Source: NCBI
Gene: GSG1
Accession Id.: NM_031289.1
AAACCAAAGGGACTTGGAGTGCAGATGGCATCCTTCGGTTCTTCCAGACAAGCTGCAAGA
[CG] CTGACCATGGCCAAGGTAACCGGCTTCCCCTCCTATTGCTCAAAGGATGCAGTCTAC
AGC SEQ ID NO: 68
Chromosome: 10
Coordinate: 81699171
Source: NCBI
Gene: SFTPD
Accession Id.: NM_003019.4
AGAAGTGGACACAGCAGGTCTTGGCTCTTAAGATCTGCAGTTGTGAGTTCCTTTTGCAAT
[CG] CTGTAGGTCATTGTGCAACCTGCTGGTCTCTGGACTCCTGATTTCTAGACATCTATA
AAA SEQ ID NO: 69
Chromosome: 20
Coordinate: 58063710
Source: NCBI
Gene: FLJ33860
Accession Id.: NM_173644.1
CCCTTCAAAGCCCGCCTTCTTGCCGTGTGATGCTGCCTGGGCCAGCAGGGCAGGTCACCA
[CG] CTGTCTCTTCAAAGCAGCTCGCTCATGCCCACAGCGCTGGGCACAAGGGCAGCCACG
AGC SEQ ID NO: 70
Chromosome: 2
Coordinate: 73723682
Source: NCBI
Gene: NAT8
Accession Id.: NM_003960.2
TCGGGTACAAGAGCATGAATTTGGGCCTCCCCAACATCTGCAGTGCAAAATATTTAACAA
[CG] GGTGTGGCACAGCCTCTGACCAACAGCCAGAACACACAAGCCACACACAGCCATG
CCT

SEQ ID NO: 71
Chromosome: 14
Coordinate: 22375620
Source: NCBI
Gene: MMP14
Accession Id.: NM_004995.2
TTTTCCGGTTTTTGATCTTTCTTCTGCTTAGTCGGCGAACTGGGGTCTGGTTCCCTCTCT
[CG] CTCTCTCCTCTGGTCCCTCCCTTCTCCCACAGCCTCTCCTCCGTCCCGCCCCAGTG
CCC SEQ ID NO: 72
Chromosome: 17
Coordinate: 43977490
Source: NCBI
Gene: HOXB2
Accession Id.: NM_002145.2
CCAGGCCCAGACGAGCGATTGGCGGAGGCCGGTCCCGTGACCACGAATTCCCTGTAATTT
[CG] CTGGAGTCCTGGGTTTAATAGAGAGTCCCCATACGCTTGTATTTATCAGCAATAT
ACA SEQ ID NO: 73
Chromosome: 11
Coordinate: 33870664
Source: NCBI
Gene: LMO2
Accession Id.: NM_005574.2
CTCACATGACCTGGATTGGAACTTGGCTCAGCCACTGACTAGCCAGACAAACTCAAATAA
[CG] TACACAGCTTCTCAGCACCTCACCCCCTCATTCATAAAAACAGGGACAATGGTACC
CAC SEQ ID NO: 74
Chromosome: 10
Coordinate: 124729456
Source: NCBI
Gene: C10orf89
Accession Id.: NM_153336.1
CTGTCTGCATGCACTGGAATTGAGGTCTGTGGATGTGCCTTTCCTGACAATATTTCTTCA
[CG] CTTGCTGCCCACTGGTGCTGTGAGGGCACAATAACGAATGTTTACTTTGCCCTTGCA
CTC SEQ ID NO: 75
Chromosome: 9
Coordinate: 128925551
Source: NCBI
Gene: ANGPTL2
Accession Id.: NM_012098.2
TGAGCTAATTAATACTAGTAATCTACCTGCAACAGCTGCAGCGAGGACTCTGTGAGGTCA
[CG] TGGGAAGGAGCTTGGCACAGTGTCAAGGACGCCTCCTTGAACTGAGCTTAGGACTCT
GGA

SEQ ID NO: 76
Chromosome: 22
Coordinate: 35586846
Source: NCBI
Gene: NCF4
Accession Id.: NM_013416.2
GGAAGTGGACCCTCGGGTGCCAGGTTTGCAGGAATCCACTTCCTTGATGTCAGTCCTTGG
[CG] CCAAGCCTCAGTTGGGTATCAGAAGCCTTGCTCCATCAGAGATGGGGTCCCAGCCAT
CAG SEQ ID NO: 77
Chromosome: 20
Coordinate: 61962518
Source: NCBI
Gene: C20orf135
Accession Id.: NM_080622.2
CTGCCAGCAACAGCAGTGACCTTCTGGGGCGGGTCCTGCCTGGCTGGGGTTCCTCTTTCT
[CG] CTCCTGGGTCGAGCCCCCACTCCCAGGCTGCGCCTCCCTCTTTTCTGGAGAGGTATC
TTT SEQ ID NO: 78
Chromosome: 20
Coordinate: 23419693
Source: NCBI
Gene: CST8
Accession Id.: NM_005492.2
TGTGGGTCCTGGTCTGCGGTCTCTCTTGCCCCTCTGAGTCCACGCCCTGCAGGGAGGTTA
[CG] CTTTGTGATGTAATTCAGCACCTGTGTCTTGTCCCAGTGAGGACATCTCCCACTTGC
CAG SEQ ID NO: 79
Chromosome: 13
Coordinate: 98028005
Source: NCBI
Gene: STK24
Accession Id.: NM_003576.2
CTTTGGTTACCGAAAACAGCCCGGCTGGGACTGCTGGGCTGGGAACTTAGCTAAGCAGTG
[CG] GAGGCTGAACCCCACCATCTCTGGGATCCGCAGCAAATCAGAAGCCCCACCCACGA
TAA SEQ ID NO: 80
Chromosome: 1
Coordinate: 54786297
Source: NCBI
Gene: ACOT11
Accession Id.: NM_015547.2
TGGGGGTGCCTGGAGTTTGGCTGGGCTGGGTGCCCAGTGGGCGGGCACAGGCCCCTTGA
[CG] TGGCTGTGGCCTAGCTGGCAGCCTCGTCCTTCCTCTCCGCTAGGCGGGCACTGGAGC
TTT

SEQ ID NO: 81
Chromosome: 17
Coordinate: 59437937
Source: NCBI
Gene: ICAM2
Accession Id.: NM_000873.2
CTTCCCAGCTTCCTCTGCCTGGATTCTTAGAGGCCTGGGGTCCTAGAACGAGCTGGTGCA
[CG] TGGCTTCCCAAAGATCTCTCAGATAATGAGAGGAAATGCAGTCATCAGTTTGCAGAA
GGC SEQ ID NO: 82
Chromosome: 11
Coordinate: 72606702
Source: NCBI
Gene: P2RY2
Accession Id.: NM_002564.2
AGGGGCGGGACAGGGGTAGGGTGGCGCGGTGGCTGGGCGCAAAGGTCCCGCAGTGGGCCA
[CG] CAGGCACCGGGCTGACCTGGCAAAACTTTGGCGTCTCTGAAAACCTCTGGTAACCAG
CTC SEQ ID NO: 83
Chromosome: 7
Coordinate: 100077108
Source: NCBI
Gene: TFR2
Accession Id.: NM_003227.2
TGCCTGCCAGGACTGATAAGGGGCCCTCCTAGGGCTCCCACAAACGGTTTATCGGTTTAT
[CG] CTGGGGACAGCCTGCAGGCTTCAGGAGGGGACACAAGCATGGAGCGGCTTTGGGGT
CTA SEQ ID NO: 84
Chromosome: 16
Coordinate: 11256179
Source: NCBI
Gene: SOCS1
Accession Id.: NT_010393.15
CCTCCGCGACTACCTGAGCTCCTTCCCCTTCCAGATTTGACCGGCAGCGCCCGCCGTGCA
[CG] CAGCATTAACTGGGATGCCGTGTTATTTGTTATTACTTGCCTGGAACCATGTGGGT
ACC SEQ ID NO: 85
Chromosome: 11
Coordinate: 122214681
Source: NCBI
Gene: CRTAM
Accession Id.: NM_019604.2
GACACACACTATAATGATCCTTTCTATACTCCTTAGCCATTGAACGAGAGATCAAATAAA
[CG] CAGTAACATCCCTCAGATGCATGATTTGAGCATGGCTTGGAAAGTATTAGCAGTTAC
CTG

SEQ ID NO: 86
Chromosome: 2
Coordinate: 106047843
Source: NCBI
Gene: ECRG4
Accession Id.: NM_032411.1
GTTGAACAGGCCAGTTACTGGGATGCAGTTCTGCGTTTCCCTTGGGTCTCACCTTAACAT
[CG] CTCGCTGAAGTGTGCCCAGATTACAGAGCGGGCAAAGGGAAGCAGTGGTTTTGCTCA
CAG SEQ ID NO: 87
Chromosome: 15
Coordinate: 56217683
Source: NCBI
Gene: AQP9
Accession Id.: NM_020980.2
TTGGTTTTTTTCAAGAGATGAGAAAAGAGATGTGCCAGTTGTGTTGCCAAATCACAGTGA
[CG] GGCCCTGGTCCAGAAAAGATTTTCATGTTACACAATTGCAGGCTTCTGATTTTTTTT
TCT SEQ ID NO: 88
Chromosome: 7
Coordinate: 94374723
Source: NCBI
Gene: PPP1R9A
Accession Id.: XM_371933.2
CCTGGGGCAAGGCCCCTTCCTGTTCGGGTGTTGGCTCCGGAACTTGGTTCTGGGGCTGAC
[CG] CTGCTGGGGCCCCACTTAGTCTGAGTCTGCAGTTAACTCCGTGACCCCAAGGCATCC
AAG SEQ ID NO: 89
Chromosome: 2
Coordinate: 128174869
Source: NCBI
Gene: SFT2D3
Accession Id.: NM_032740.3
TGCTTCTCTATTCTGTTCTCAGTTTCGGCCACAGGCCTGGCAACATCCTTGACTCCTTCG
[CG] CCCCTTGTCCAAGACTCGGTGCTGCTGTCCATGTGTTTGGTGTCACTCTCGTGCTC
TGG SEQ ID NO: 90
Chromosome: 1
Coordinate: 27822930
Source: NCBI
Gene: FGR
Accession Id.: NM_005248.1
ATTGGAGCCGGTGGCCACGGCCAAGGAGGATGCTGGCCTGGAAGGGACTTCAGAAGCTA
[CG] GGGCAGCAGACCACTATGGGCCTGACCCACTAAGGCCCGGCCTGCATCCTCATTTG
CCC

SEQ ID NO: 91
Chromosome: 19
Coordinate: 60109459
Source: NCBI
Gene: NCR1
Accession Id.: NM_004829.3
TGAAGGAAGGACTCACGCTGCTGGGCGCTGATCCTCTGACTCAGACACAGCCCTGGAAGA
[CG] GGAGTAATGAGACCTGTTGCCTCCAGGCACACCGTGATCCCATTCCCCTTCCACGC
CAG SEQ ID NO: 92
Chromosome: 11
Coordinate: 117720322
Source: NCBI
Gene: CD3G
Accession Id.: NM_000073.1
TGGAGCCAGTCTAGCTGCTGCACAGGCTGGCTGGCTGGCTGGCTGCTAAGGGCTGCTCCA
[CG] CTTTTGCCGGAGGACAGAGACTGACATGGAACAGGGGAAGGGCCTGGCTGTCCTCAT
CCT SEQ ID NO: 93
Chromosome: 11
Coordinate: 117718540
Source: NCBI
Gene: CD3D
Accession Id.: NM_000732.3
AGGGCAGCTCTCACCCAGGCTGATAGTTCGGTGACCTGGCTTTATCTACTGGATGAGTTC
[CG] CTGGGAGATGGAACATAGCACGTTTCTCTCTGGCCTGGTACTGGCTACCCTTCTCTC
GCA SEQ ID NO: 94
Chromosome: 1
Coordinate:
Source: NCBI
Gene: CD3Z
Accession Id.: NM_000734.2
CTGCCTCCCAGCCTCTTTCTGAGGGAAAGGACAAGATGAAGTGGAAGGCGCTTTTCACCG
[CG] GCCATCCTGCAGGCACAGTTGCCGATTACAGGTAGGGCCGACGTGTCGACGGCAGGG
AAC SEQ ID NO: 95
Chromosome: X
Coordinate:
Source: NCBI
Gene: FOXP3
Accession Id.: NM_014009.2
TTGGATTATTAGAAGAGAGAGGTCTGCGGCTTCCACACCGTACAGCGTGGTTTTTCTTCT
[CG] GTATAAAGCAAAGTTGTTTTTGATACGTGACAGTTTCCCACAAGCCAGGCTGATCC
TTT

FIG. 40

(cont.)
SEQ ID NO: 96
Chromosome: X
Coordinate:
Source: NCBI
Gene: FOXP3
Accession Id.: NM_014009.2
TCGATGAAGCCCGGCGCATCCGGCCGCCATGACGTCAATGGCGGAAAAATCTGGGCAAGT
[CG]GGGGCTGTGACAACAGGGCCCAGATGCAGACCCCGATATGAAAACATAATCTGTGTC
CCA

FIG. 40

Different sources of effects on measured DNA methylation

Different sources of effects on measured DNA methylation

NKp46 Demethylation Assay
NK-cell and Methylated Control DNA

| Sample | Restriction Enzyme Digestion | C-less (FAM) conc. (copies/ul) | NKp46 (FAM) conc. (copies/ul) | NKp46 / C-less |
|---|---|---|---|---|
| NK2510 | None | 524 | 403 | 0.769 |
| NK2510 | Mock | 506 | 352 | 0.696 |
| NK2510 | MseI | 467 | 353 | 0.756 |
| Methylated Control | None | 432 | 0.769 | 0.002 |
| Methylated Control | Mock | 320 | 1.04 | 0.003 |
| Methylated Control | Mse I | 466 | 4.76 | 0.010 |
| 50/50 (NK/Meth) | None | 515 | 181 | 0.351 |
| 50/50 (NK/Meth) | Mock | 339 | 146 | 0.431 |
| 50/50 (NK/Meth) | MseI | 432 | 134 | 0.310 |
| NTC | None | 0 | 0 | N/A |

FIG. 45B

| Sample | NKp46 (FAM) copies/ul | C-less (FAM) copies/ul | NKp46 / C-less |
|---|---|---|---|
| Whole Blood DNA [30ng/20ul] | 150 | 724 | 0.207 |
| Whole Blood DNA [60ng/20ul] | 268 | 1450 | 0.185 |
| Whole Blood DNA [120ng/20ul] | 463 | 3070 | 0.151 |
| Neutrophil DNA | 325 | 858 | 0.379 |
| CD16$^+$CD56$^{dim}$ NK cell Cell DNA | 720 | 779 | 0.924 |
| CD16$^-$CD56$^{bright}$ NK cell Cell DNA | 523 | 776 | 0.674 |

FIG. 46B

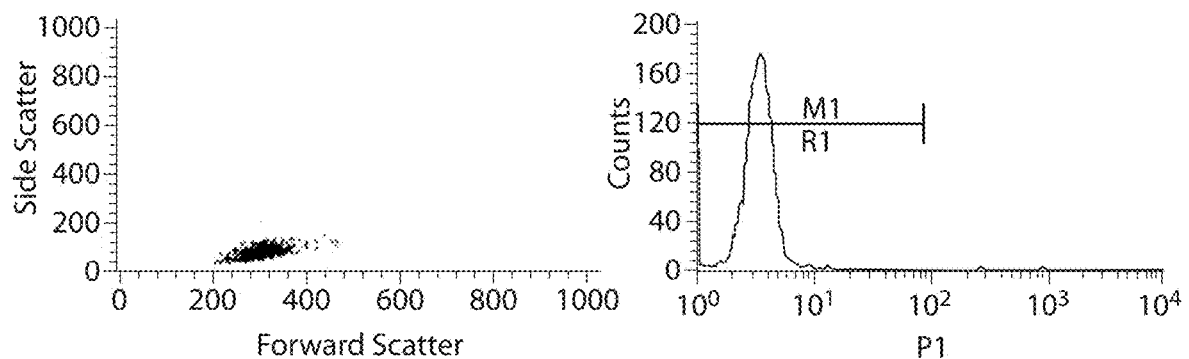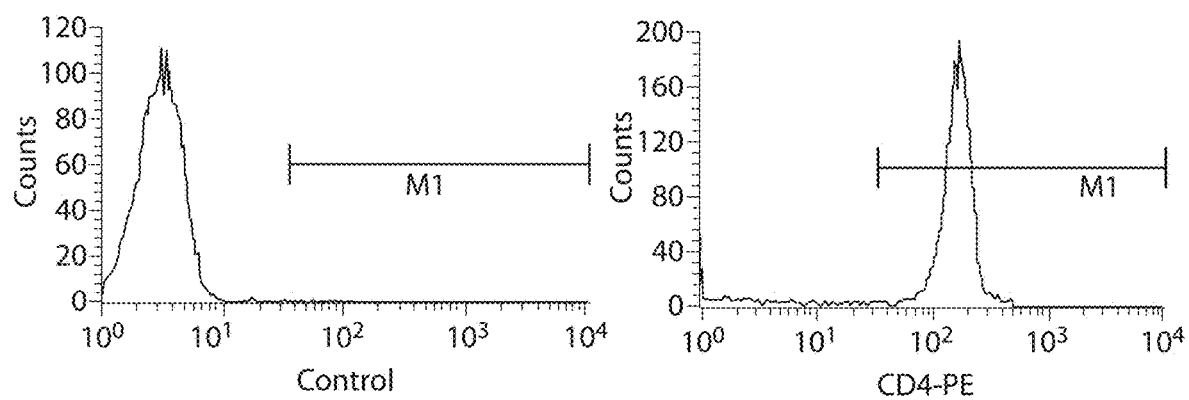
FIG. 48B

CD3+CD56+ Natural killer T lymphocytes
"NKT cells"
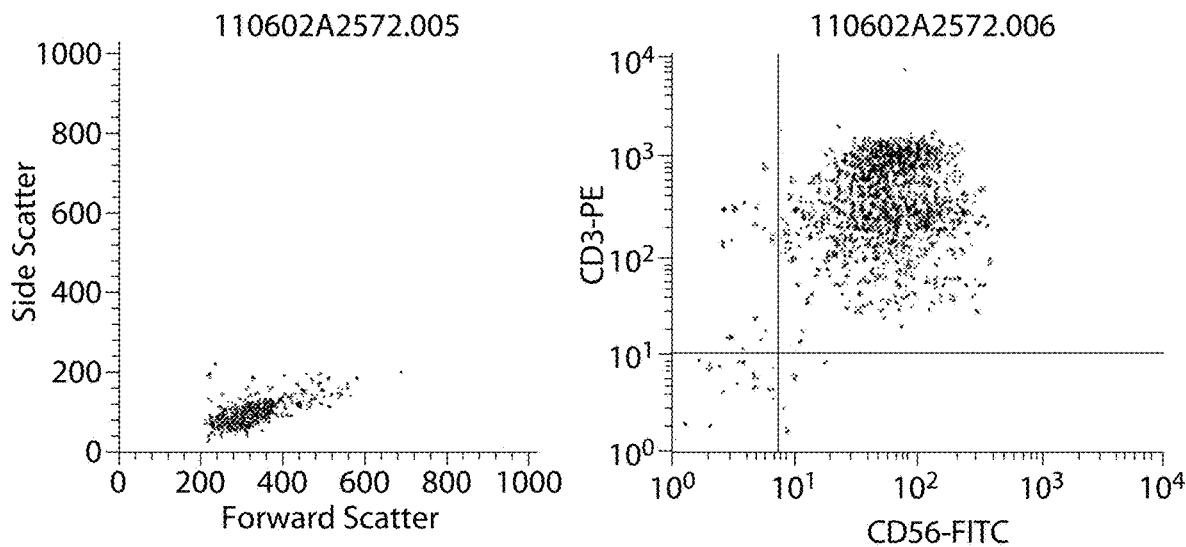
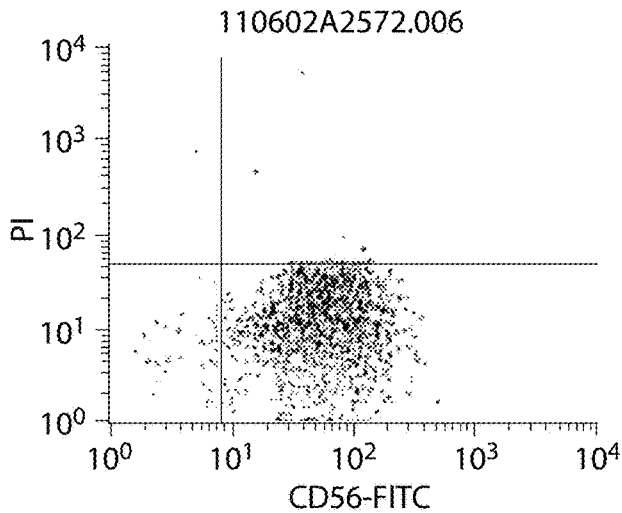
Sample ID: BM3000 CD34
Quad Location: 7, 10
| Quad | Events | % Gated |
|------|--------|---------|
| UL   | 116    | 1.15    |
| UR   | 9747   | 97.47   |
| LL   | 100    | 1.00    |
| LR   | 37     | 0.37    |
Sample ID: BM3000 CD34
Quad Location: 8, 51
| Quad | Events | % Gated |
|------|--------|---------|
| UL   | 1      | 0.01    |
| UR   | 77     | 0.77    |
| LL   | 242    | 2.42    |
| LR   | 9580   | 96.80   |
FIG. 48E

CD56+CD56$^{dim}$ Natural killer cells
"Effector NK cells"
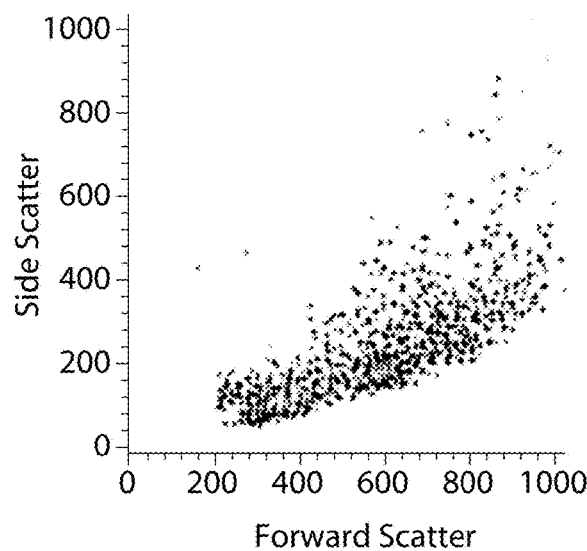
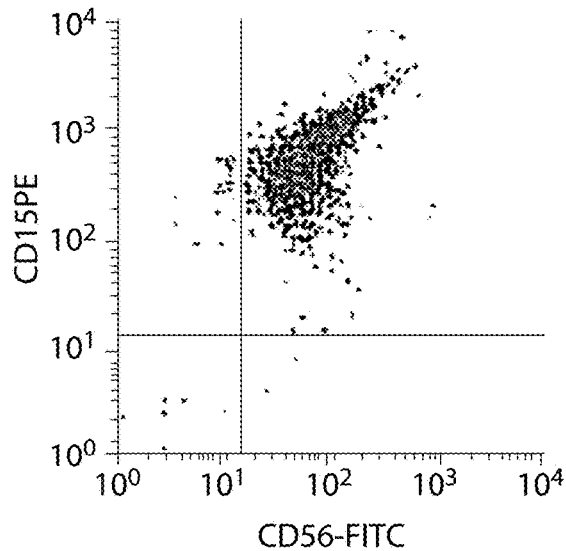
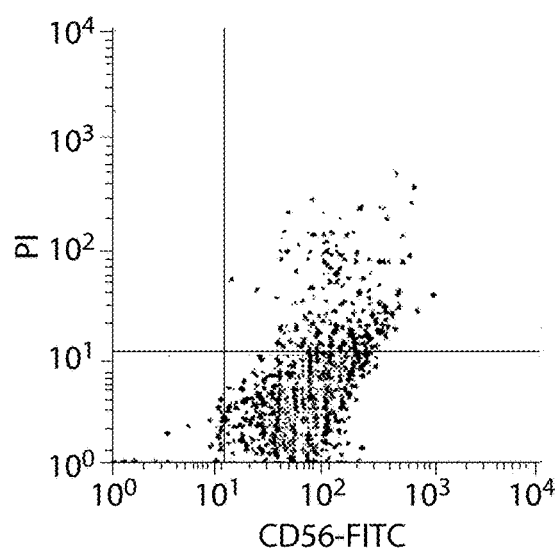
Patient ID: A2594
Sample ID: Untouched NK cells
Quad Location: 14, 12
| Quad | Events | % Gated |
|------|--------|---------|
| UL | 28 | 0.28 |
| UR | 9959 | 99.59 |
| LL | 11 | 0.11 |
| LR | 2 | 0.02 |
Patient ID: A2594
Sample ID: Untouched NK cells
Quad Location: 11, 10
| Quad | Events | % Gated |
|------|--------|---------|
| UL | 0 | 0 |
| UR | 501 | 1 |
| LL | 21 | 0.1 |
| LR | 9478 | 94.78 |
FIG. 48H

CD8+CD56+ Natural killer cells
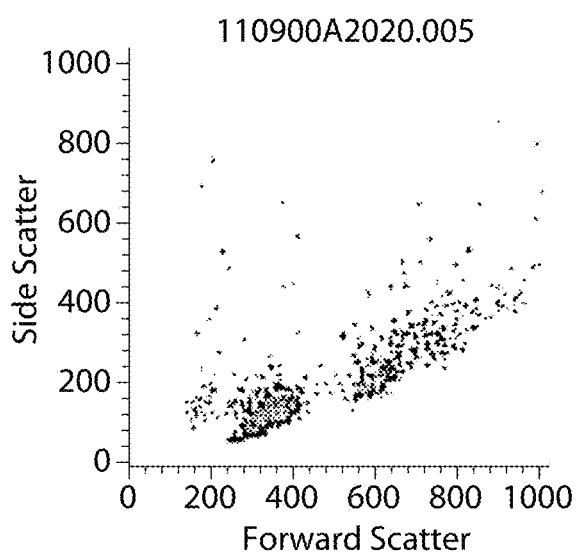
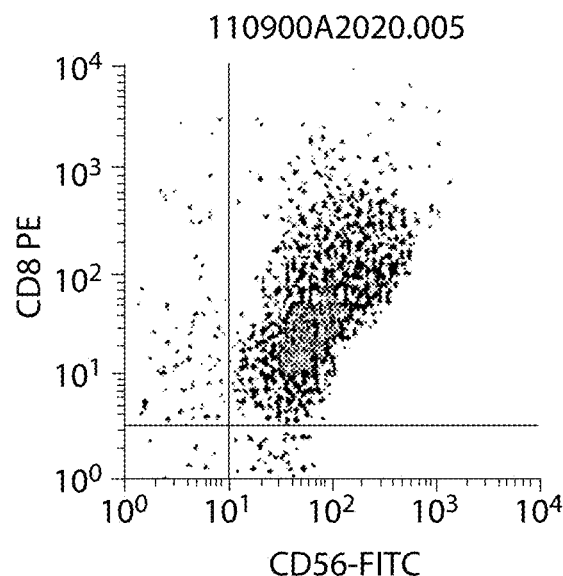
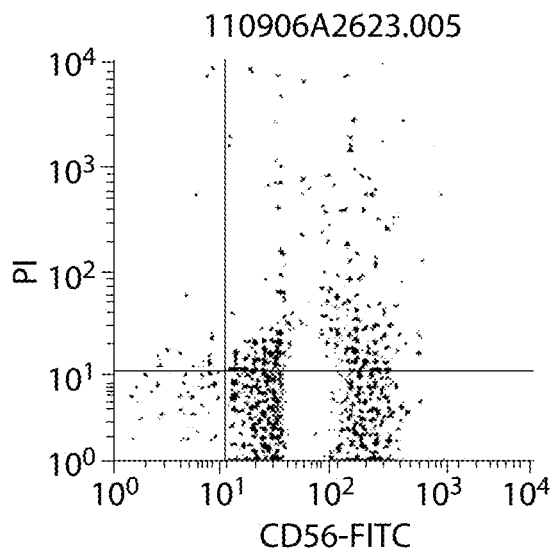
Sample ID: Untouched NK cells
Quad Location: 10, 3
| Quad | Events | % Gated |
|------|--------|---------|
| UL | 97 | 0.97 |
| UR | 9820 | 98.20 |
| LL | 15 | 0.15 |
| LR | 67 | 0.67 |
Sample ID: Unabstructed NK cells
Quad Location: 11, 10
| Quad | Events | % Gated |
|------|--------|---------|
| UL | 35 | 0.35 |
| UR | 1949 | 19.49 |
| LL | 82 | 0.82 |
| LR | 7934 | 79.34 |
FIG. 48J

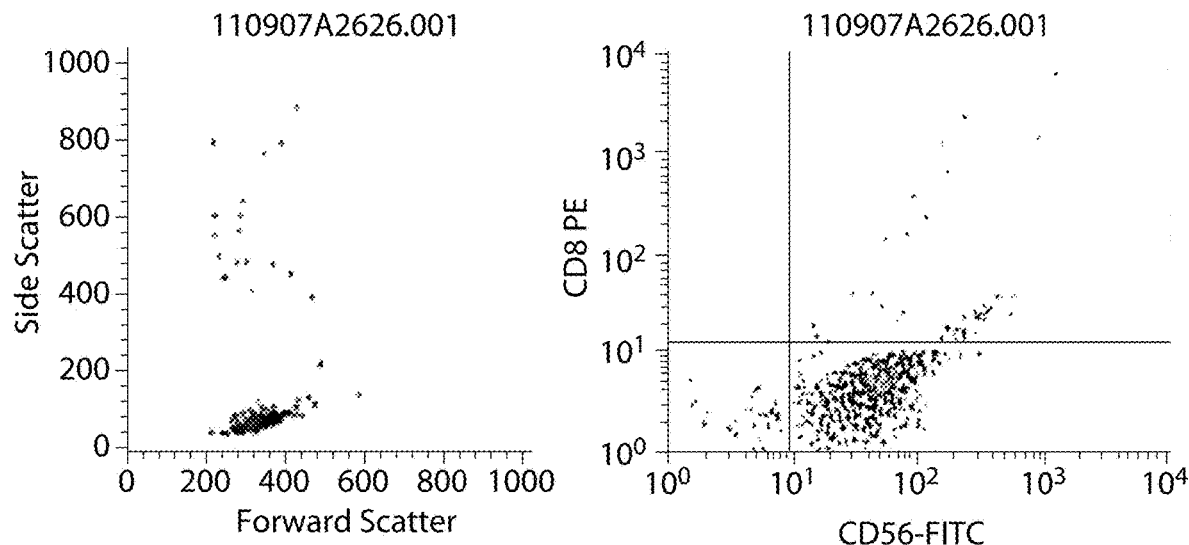
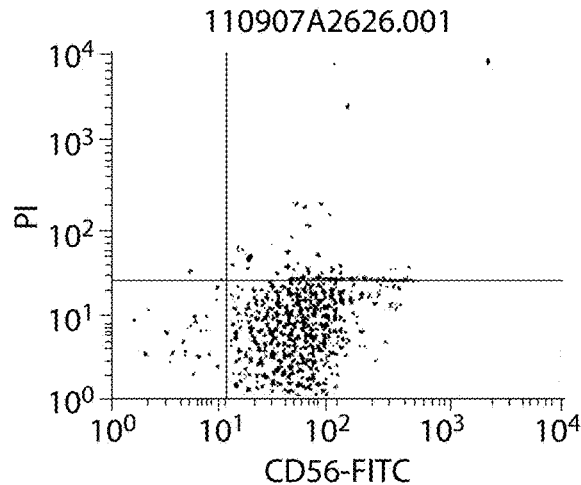
FIG. 48K

METHODS USING DNA METHYLATION FOR IDENTIFYING A CELL OR A MIXTURE OF CELLS FOR PROGNOSIS AND DIAGNOSIS OF DISEASES, AND FOR CELL REMEDIATION THERAPIES

RELATED APPLICATIONS

This application is a continuation of U.S. utility application Ser. No. 14/089,398 filed Nov. 25, 2013, entitled, "Methods using DNA methylation for identifying a cell or a mixture of cells for prognosis and diagnosis of diseases, and for cell remediation therapies", which claims the benefit of U.S. provisional application Ser. No. 61/865,479 filed Aug. 13, 2013, entitled, "Methods using DNA methylation for identifying a cell or a mixture of cells for prognosis and diagnosis of diseases, and for cell remediation therapies", and is a continuation-in-part of international application number PCT/US2012/39699 filed May 25, 2012, entitled, "Methods using DNA Methylation for identifying a cell or a mixture of cells for prognosis and diagnosis of diseases, and for cell remediation therapies" which claims the benefit of provisional applications having Ser. Nos. 61/489,883 filed May 25, 2011 entitled, "Methods of Immunodiagnostics using DNA Methylation arrays as surrogate measures of the identity of a cell or a mixture of cells"; 61/509,644 filed Jul. 20, 2011 entitled, "Methods of Immunodiagnostics using DNA Methylation arrays as surrogate measures of the identity of a cell or a mixture of cells for prognosis and diagnosis of diseases"; 61/585,892 filed Jan. 12, 2012 entitled, "Methods of Immunodiagnostics using DNA Methylation arrays as surrogate measures of the identity of a cell or a mixture of cells for prognosis and diagnosis of diseases"; and 61/619,663, filed Apr. 3, 2012 entitled, "Methods using DNA Methylation arrays for identifying a cell or a mixture of cells for prognosis and diagnosis of diseases, and for cell remediation therapies", inventors Karl Kelsey, Eugene Andres Houseman, John Wiencke, William P. Accomando, Jr. and Carmen Marsit, of which each patent application is hereby incorporated by reference herein in its entirety.

GOVERNMENT SUPPORT

This invention was made with government support under grants CA126831, R01 CA052689, CA126939, CA121147, CA100679, CA078609, ES006717, MH094609 and P50 CA097257 awarded by the National Institutes of Health. The government has certain rights in the invention.

TECHNICAL FIELD

Methods of determining altered immune cell distribution to diagnose or prognose a disease condition based on determining DNA methylation signatures of specific immune cell type of or mixture of immune cells types are provided.

BACKGROUND

Leukocytes, commonly called white blood cells, are cells that are primarily responsible for mounting an immune response by a host to pathogens and to foreign antigens. Leukocyte distribution is currently determined by simple histologic or flow cytometric assessments. These methods have significant limitations. In particular, flow cytometry is limited by the following: availability of fluorescent antibody tags, laborious nature of the antibody tagging process, and needs for separation of cells requiring large volumes of fresh cells, expensive technology as well as equipment for detection of cells, and maintaining the integrity of the outer membrane of the cells to preserve labile protein epitopes. Further limitation of methods requiring fresh cells is that the methods are not useful in situations in which prospective studies are impractical, such as in the case of rare diseases, in which large numbers of disease subjects are not available. In these cases retrospective studies are needed to correlate disease outcome with disease parameters. However, retrospective studies can be performed only if archival samples derived from archived cohort populations could be used to analyze the disease parameters. Currently there are no known methods in which archived samples from patients and normal subjects could be used to provide a quantitative estimate of leukocyte distributions in disease conditions.

Thus there is a need for methods that provide quantification of alterations in distribution of leukocytes in blood or tissues in disease conditions that do not rely upon fresh samples, that are not labor intensive and that do not use expensive technology or equipment.

SUMMARY

In diverse medical conditions such as in disease or in instances of immune-toxic exposure, the leukocyte distribution in blood or tissues contains information about the underlying immune-biology of the medical condition which is useful for diagnosis, prognosis or treatment of the medical condition, or for monitoring response to therapy. Accordingly, an embodiment of the invention provides a method a method for assessing a disease condition in a subject, including: measuring a CD3Z positive T lymphocyte cell number in a sample from the subject by analyzing methylation in the sample of at least one CpG dinucleotide (CpG) in gene CD3Z or in an orthologous or a paralogous gene thereof, such that an amount of a demethylated C of the at least one CpG in the sample is a measure of CD3+ T lymphocyte cell number; and comparing the amount of the demethylated C in the sample from the subject with that in positive control samples from patients with the disease condition, and with that in negative control samples from healthy subjects, such that the disease condition is selected from: an autoimmune disease, an allergy, a transplant rejection, obesity, an inherited disease, immunosuppression and a cancer. As used herein "subject" refers to any animal, for example, a mammal that is healthy or that has a disease condition for example a human, or a high value agricultural animal or a zoo animal. A "patient" is a subject that either has a disease condition or is in need of obtaining a diagnosis of a disease condition.

A related embodiment of the method includes at least one of: monitoring, diagnosing, prognosing, and measuring response to therapy by comparing the measured CD3+ T lymphocyte cell numbers in the subject after therapy to that in the patients with the disease condition and in the healthy subjects.

An embodiment of the method provides that the inherited disease is an aneuploidy. For example, aneuploidy is selected from trisomy 21, Turner's syndrome, and Klinefelter's syndrome.

The sample used in the method is a fresh sample. For example, the fresh sample is freshly drawn blood, a tumor infiltrate or cells obtained from a lymph node puncture. Alternatively, the sample is an archival sample. For example, the archival sample is archival blood collected and stored on filter paper cards such as a Guthrie card, frozen blood specimens or frozen tissue. Demethylation of DNA is a stable chemical modification of DNA, and archival samples are used to measure cell numbers. Flow cytometry in contrast, requires fresh cells, for detection of cells depends on the availability of protein epitopes, which are labile and not well preserved in archival samples.

In a related embodiment of the method the amount of the demethylated C of the at least one CpG in the CD3Z gene in the sample is at least about 80%, at least about 90%, or at least about 95% of the total amount of the CpG in CD3Z genes in the sample.

An embodiment of the method further involves analyzing the methylation of the CD3Z gene further by amplifying by Polymerase Chain Reaction (PCR) using primer pairs specific for amplification of specific demethylated CpG loci. For example, amplification by PCR involves monitoring quantitative PCR in real time using a MethyLight assay or using digital PCR. In various embodiments, the CpG loci are listed herein. For at least one gene or locus is selected from the group of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO: 14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO: 34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO: 54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO: 74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO: 94, SEQ ID NO:95, SEQ ID NO:96, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, and SEQ ID NO: 140. In various embodiments, at least one locus is selected from the group consisting of: FGD2, HLA-DOB, BLK, IGSF6, CLDN15, SFT2D3, ZNF22, CEL, HDC, GSG1, FCN1, OSBPL5, LDB2, NCR1, EPS8L3, CD3D, PPP6C, CD3G, TXK, and FAIM. In various embodiments, at least one locus is selected from the group consisting of: CLEC9A (2 loci), INPP5D, INHBE, UNQ473, SLC7A11, ZNF22, XYLB, HDC, RGR, SLCO2B1, C1orf54, TM4SF19, IGSF6, KRTHA6, CCL21, SLC11A1, FGD2, TCL1A, MGMT, CD19, LILRB4, VPREB3, FLJ10379, HLA-DOB, EPS8L3, SHANK1, CD3D (2 loci), CHRNA3, CD3G (2 loci), RARA, and GRASP. The nucleotide sequence and corresponding amino acid sequence of each of the genes or loci herein are listed and characterized in genome or protein databases such as GenBank, European Nucleotide Archive, European Bioinformatics Institute, GenomeNet, or The National Center for Biotechnology Information (NCBI) Protein database. The nucleotide sequences of the loci in computer readable form as an ASCII text file (114 kilobytes) created Nov. 25, 2013 entitled "SEQ_ID_11252013" containing sequence listings numbers 1-140 has been electronically filed herewith and is incorporated by reference herein in its entirety. In various embodiments, each locus includes a portion of any of the sequences described herein.

An embodiment of the method further involves analyzing the methylation of the CD3Z gene by a method selected from the group of: Pyrosequencing, Methylation-sensitive single-nucleotide primer extension (Ms-SNuPE), Methylation-sensitive single stranded conformation analysis (MS-SSCA), and High resolution melting analysis (HRM) and digital PCR methods comprising emulsion and nanofluidic partitioning. According to a related embodiment, Methylation-sensitive single-nucleotide primer extension further includes: chemically converting the lymphocyte derived whole genomic DNA with bisulfite; amplifying chemically converted whole genomic DNA; enzymatically fragmenting resulting amplified DNA; hybridizing fragmented DNA to methylation sensitive CpG locus specific DNA oligomers; and labeling by single-base extension using fluorescently labeled nucleotides.

Another embodiment of the method further provides steps for analyzing methylation of differentially methylated regions (DMRs) of gene FOXP3, using primer pairs for amplification of specific loci of demethylated CpG in the FOXP3 gene. Within a gene "loci" as used herein refers to locations of CpG dinucleotide containing sequences present in that gene, and only one or a few may be differentially demethylated in a specific cell.

A related embodiment of the method further includes: determining a ratio of CpG demethylation of FOXP3 gene DMR to the CpG demethylation of CD3Z gene DMR, in a sample of tumor infiltrate, such that the ratio involves an index of T regulatory cell number to the total T cell number in the infiltrate; and the method further involves diagnosing of a pathological grade of the cancer, so that the index of T regulatory cell number to the total T cell number in the tumor infiltrate correlates with the grade of the cancer. In a related embodiment, the cancer is selected from: a glioma; an ovarian cancer; a head and neck squamous cell cancer (HNSCC), breast cancer, lung cancer, prostate cancer, colon cancer, pancreatic cancer, bladder cancer, cervical cancer and liver cancer.

In a related embodiment the method further includes prognosing survival of a patient having or needing a diagnosis of glioma or HNSCC, in which amount of demethylation of CD3Z gene DMR in the patient as a percent of total DNA greater than a median value in a sample population of subjects correlates with a prognosis of poor survival.

An embodiment of the invention provides a kit for measuring CD3+ T lymphocyte and FOXP3+ T regulatory cell numbers by analyzing methylation of CpG positions in CD3Z and FOXP3 genes, the kit having sequencing and PCR primers specific for the CD3Z and the FOXP3 gene DMRs and instructions for analyzing and comparing the CpG methylation between healthy subjects and a patient.

An embodiment provides a method for assessing a disease condition by estimating an alteration in proportions of types of leukocytes in a sample from a subject, the method including the steps of: measuring a DNA methylation profile for each type of leukocyte and for unfractionated cells, such that DNA methylation profiles are obtained for a pluralitany of CpG loci, and obtaining the status of an individual CpG locus by amplifying DNA from each of the types of leukocyte and from the unfractionated cells, such that amplifying comprises hybridizing methylation sensitive locus-specific DNA oligomers corresponding to each CpG locus; ordering CpG loci by ability to distinguish types of leukocytes, such that the ordering of the CpG loci determines differentially methylated DNA regions (DMRs), such that obtaining DMRs comprises statistically minimizing introduction of bias in amount of total methylation status of a large number of CpG loci obtained from the unfractionated cells by employing a Bayesian treatment of prior probabilities of the methylation status at each individual locus, thereby identifying a plurality of CpG loci to include in the measurement, such that an amount of CpG loci distinguishes DMR signatures among the types of leukocytes and minimizes bias; obtaining DNA methylation profiles comprising DMRs from the types of leukocytes, such that the DNA methylation profiles comprise validating measures of relative amounts of the types of leukocytes, and obtaining DNA methylation profiles of the unfractionated cells as surrogate measures of relative amounts of each leukocyte type in the unfractionated cells; employing an analog of a measurement error model wherein a DNA methylation surrogate y is reverse formulated with respect to the disease outcome z, as $$y=f(z),$$

such that y denotes a multivariate random variable representing a methylation profile, z denotes a disease outcome or state, and $f$ denotes a probability distribution; y, z, and leukocyte distribution, ω are related by the estimator equations, $$E(y|\omega)=g(\omega), \text{ and}$$

under an assumption $E(z|\omega,y)=E(z|\omega)$, such that, E denotes an expectation of a random variable and ω denotes a subject specific distribution of leukocytes; and, comparing relative amounts of each type of leukocyte in the sample from the subject with those in a control sample, thereby providing an assessment of the disease condition. In related embodiments, the locus-specific DNA oligomers are linked to an array selected from the group of: a glass slide array; a quartz slide array; a fiber optic bundle array, a planar slide array, a micro-well array; a multi-well dish array; a digital PCR array; and a bead array having beads located at known addressable locations on the array. A related embodiment of the method further provides at least one of steps of: monitoring, diagnosing, prognosing and measuring response to therapy of the disease condition.

The method in a related embodiment further includes analyzing sensitivity for correcting bias, such that correcting bias is unrelated to measurement error and is related to errors arising from unprofiled cell types and non-cell mediated profile differences. In related embodiments of the method, fractionated leukocyte types include at least one selected from: CD19+ B lymphocytes, CD15+ granulocytes, CD14+ monocytes, CD56+ Natural Killer cells, and CD3+ T lymphocytes.

In an embodiment of the method the disease condition is Head and Neck Squamous Cell Carcinoma (HNSCC).

An embodiment of the method provides that the inherited disease is an aneuploidy. For example, aneuploidy is selected from trisomy 21, Turner's syndrome, and Klinefelter's syndrome.

According to another embodiment of the method the control sample is taken from the subject at a different point in time for prognosis of the course of the disease condition in the subject. In another related embodiment, the method of assessing disease condition further includes after employing the measurement model, comparing the distribution of leukocytes to the relative amounts in the control sample as a normal standard, such that the normal standard is a statistical measure obtained from a plurality of disease-free subjects.

In a related embodiment the method provides a diagnosis of immunosuppression due to smoking in a currently smoking subject by: determining a ratio of CpG demethylation of FOXP3 gene DMR to the CpG demethylation of CD3Z gene DMR in blood in the currently smoking subject, such that the ratio is an index of T regulatory cell number to the total T cell number; and providing a diagnosis of immunosuppression in the currently smoking subject, such that the value of the index of T regulatory cell number to the total T cell number in the currently smoking subject, greater than the average value in a sample population of currently non-smoking subjects correlates with immunosuppression due to smoking. In a related embodiment of the method the subject with the currently-smoking or currently non-smoking status is a patient having a cancer, an infection or in need of a transplant.

An embodiment provides a method of predicting a methylation class membership in a bodily fluid sample of a subject for assessing disease status of the subject, in which the methylation class membership corresponds to an epigenetic signature of a plurality of leukocyte types, the method including: measuring amounts of DNA methylation in each of a plurality of leukocyte type populations to determine differentially methylated regions (DMRs); ranking leukocyte DMRs for each leukocyte type according to statistical strength of association of the DMR with each leukocyte type; randomly dividing a data set of control subjects and subjects with a disease into groups having substantially the same numbers of control subjects and subjects with the disease to obtain a training set and a testing set; clustering samples in the training set using a defined number of highest ranked leukocyte DMRs to determine clustering solutions, in which a clustering solution corresponds to the methylation class membership; and predicting methylation class membership for subjects within the testing set by applying the clustering solutions obtained from the training set to the highest ranked leukocyte DMRs in the testing set, such that clinical utility of the predicted methylation class membership is determined by testing association of the predicted methylation class membership with the disease status of the subject.

According to an embodiment of the method, the highest ranked leukocyte DMRs are as shown in Table 21, in which each DMR is identified by chromosomal location and gene name, and the defined number of highest ranked leukocyte DMRs is selected from: least 10, at least 20, at least 30, at least 40 and is 50.

The methylation class membership of the subject in the testing set is predicted for example using a naïve Bayes classifier. Testing the association of the predicted methylation class with disease status includes for example using receiver operating characteristic curves (ROC) and the corresponding area under each curve.

The bodily fluid sample in some embodiments is a fresh sample, for example freshly collected blood or a blood derivative. Alternatively, the bodily fluid is an archival sample, for example stored frozen blood or archival blood collected and stored on a filter paper card such as a Guthrie card.

The method in a related embodiment includes at least one of: diagnosing, monitoring, prognosing and measuring response to therapy of the disease status.

In related embodiments the leukocyte types are selected from the group of: natural killer cells, B Cells, CD4+ T cells, CD8+ T cells, granulocytes and monocytes. The disease according to an embodiment of the method is exemplified by one of: head and neck squamous cell carcinoma (HNSCC), ovarian cancer, and bladder cancer.

An array is provided as another embodiment for estimating proportions of leukocyte types in a sample from a mammal for assessing a disease condition of the mammal by analyzing differential methylation of CpG dinucleotides in a plurality of genes of the sample, the array including: a plurality of DNA probes attached to a plurality of surfaces at known addressable locations on the array, such that the surface at each location is attached to a DNA probe having a specific nucleotide sequence, such that the DNA probe having the specific nucleotide sequence hybridizes to a nucleotide sequence of a methylated form or an ummethylated form of a CpG dinucleotide in a sequence of a gene of the plurality of genes in the sample, such that the array is selected from having: at least 16 probes, at least 64 probes, at least 96 probes, and at least 384 probes.

The plurality of probes, in a related embodiment of the array, have nucleotide sequences that hybridize with a respective plurality of 118 different nucleotide sequences which are found in nature occurring in the plurality of genes. In another related embodiment, the plurality of probes include at least one of SEQ ID NO: 1 to SEQ ID NO: 96. In various embodiments of the array, the plurality of probes have nucleotide sequences that hybridize with at least one gene or locus described herein. For example, the at least one gene or locus is any of SEQ ID NO: 1-140. In various embodiments, the at least one gene or locus is selected from the group of: SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 1, SEQ ID NO:12, SEQ ID NO:13, SEQ ID NO: 14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO: 34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO: 54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO: 74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO: 94, SEQ ID NO:95, SEQ ID NO:96, SEQ ID NO:119, SEQ ID NO:120, SEQ ID NO:121, SEQ ID NO:122, SEQ ID NO:123, SEQ ID NO:124, SEQ ID NO:125, SEQ ID NO: 126, SEQ ID NO:127, SEQ ID NO:128, SEQ ID NO:129, SEQ ID NO: 130, SEQ ID NO:131, SEQ ID NO:132, SEQ ID NO:133, SEQ ID NO:134, SEQ ID NO:135, SEQ ID NO: 136, SEQ ID NO:137, SEQ ID NO:138, SEQ ID NO:139, and SEQ ID NO:140.

In a related embodiment of the array, the addressable locations are wells of a substrate, such that the substrate is selected from: glass slide; quartz slide; fiber optic bundle and planar silica slides. In another related embodiment the surfaces included in the array are particles added to the wells.

In alternative embodiments the addressable locations of the array are defined spots on a glass slide or are microbeads or particles labeled with a code. For example, the particles are microbeads in the form of glass cylinders identifiable with inscribed holographic code.

In various embodiments the disease condition is selected from: an autoimmune disease, an allergy, a transplant rejection, obesity, an inherited disease, immunosuppression and a cancer.

Another embodiment provides a method for estimating proportions of types of leukocytes in a sample from a subject for assessing a disease condition of the subject by analyzing differential methylation of CpG dinucleotides in a plurality of genes of the sample, the method including: providing an array having a plurality of DNA probes attached to a plurality of surfaces at known addressable locations on the array, such that the surface at each location is attached to a DNA probe having a specific nucleotide sequence; reacting genomic DNA in the sample with a bisulfite reagent to convert unmethylated cytosine residues to uracil; hybridizing resulting bisulfite treated genomic DNA with the array to obtain resulting hybridized probes on the array, such that the DNA probes hybridize to a DNA sequence of each of a methylated form and an ummethylated form of a sequence having a CpG dinucleotide in a gene for each of the plurality of genes; and detecting the methylation status of each of the CpG dinucleotides in each sequence, thereby estimating proportions of types of leukocyte in the sample from the subject for assessing the disease condition of the subject.

In a related embodiment, detecting the methylation status of the CpG dinucleotide sequence includes: extending each hybridized probe of the resulting hybridized probes on the array by primer extension to obtain a resulting primer extension product; ligating the resulting primer extension product to an oligonucleotide complementary to the DNA sequence of a 3' region of the gene to obtain a resulting template for PCR on the array; and amplifying by PCR and measuring amount of resulting PCR product, thereby detecting the methylation status of the CpG dinucleotide containing nucleotide sequence.

In another related embodiment amplifying by PCR further includes: amplifying the resulting template on the array using primers pairs including a 5' primer specific to each of the methylated or the unmethylated form of the CpG dinucleotide containing gene, and a 3'primer specific to the gene containing the CpG dinucleotide, thereby resulting in a first PCR product; amplifying the resulting first PCR product with differentially labeled 5' primers that specifically amplify either the methylated or the unmethylated form of the CpG dinucleotide containing nucleotide sequence containing gene, and a common 3' primer, resulting in a differentially labeled second PCR product, and hybridizing the second PCR product to the CpG dinucleotide containing gene for measuring amount of the second PCR product, thereby detecting the methylation status of the CpG dinucleotide sequence.

Detecting the methylation status of the CpG dinucleotide sequence, in another related embodiment of the method, includes extending the resulting hybridized probes on the array by single base primer extension with a labeled nucleotide.

The array used in the method, in a related embodiment, includes at least 16 probes, at least 64, at least 96 probes or at least 384 probes. In another related embodiment of the method the plurality of probes on the array hybridizes with a plurality of 118 different nucleotide sequences occurring in the plurality of genes. In yet another related embodiment of the method each probe on the array is complementary to nucleotide sequences having SEQ ID NO: 1 to SEQ ID NO: 96.

In various embodiments of the method, at least one probe on the array is complementary to a nucleotide sequence described herein, for example the nucleotide sequence corresponds to a gene or locus described herein. In various embodiments, the gene or the locus is found herein in an example, a figure, or a table. In various embodiments, the gene or locus is selected from the group of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO: 14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO: 34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO: 54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO: 74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO: 94, SEQ ID NO:95, SEQ ID NO:96, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO: 127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO: 136, SEQ ID NO:137, SEQ ID NO:138, SEQ ID NO:139, and SEQ ID NO:140.

In various embodiments of the method, the disease condition assessed is selected from: an autoimmune disease, an allergy, a transplant rejection, obesity, an inherited disease, and a cancer. Assessing the disease condition using the array, in related embodiments of the method, includes at least one of: monitoring, diagnosing, prognosing, and measuring response to therapy by comparing estimated proportions of types of leukocytes of the subject after therapy to proportions of leukocytes from a healthy subject.

In a related embodiment of the method the sample containing the genomic DNA used to hybridize with the probes on the array is fresh i.e., obtained in real time prior to performing the method. In another related embodiment of the method the sample is archival.

In various embodiments of the method for estimating proportions of leukocytes using the array, the leukocyte types include at least one selected from: CD19+ B lymphocytes, CD15+ granulocytes, CD14+ monocytes, CD56+ natural Killer cells, and CD3+ T lymphocytes.

Another related embodiment provides a kit for estimating proportions of leukocyte types in a sample by analyzing differential methylation of CpG dinucleotides in a plurality of genes of the sample, the kit including: an array having: a plurality of DNA probes attached to a plurality of surfaces at known addressable locations on the array, such that the surface at each location is attached to a DNA probe having a specific nucleotide sequence, such that the DNA probe having the specific nucleotide sequence hybridizes to a DNA sequence of a methylated form or an ummethylated form of a CpG dinucleotide in a sequence of a gene of the plurality of genes in the sample, such that the array is selected from having: at least 16 probes, at least 64 probes, at least 96 probes, and at least 384 probes; primers and reagents for detecting the hybridized probes and for detecting the reaction products derived from the hybridized probes; and instructions for using the array with a bisulfite reagent, thereby providing an estimation of proportions of leukocyte types in the sample.

In a related embodiment of the kit, the probes hybridize with a respective plurality of 118 different DNA sequences occurring in the plurality of genes. In yet another related embodiment of the kit the probes have nucleotide sequences complementary to 96 nucleotide sequences having SEQ ID NO: 1 to SEQ ID NO: 96.

In various embodiments of the kit, at least one probe is complementary to a nucleotide sequence described herein, for example at least one nucleotide sequence corresponds to a gene or locus described herein. For example, the gene or locus is shown or listed in an example, a figure, or a table herein. In various embodiments, the gene or locus is at least one selected from the group of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO: 14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO: 34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO: 54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO: 74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO: 94, SEQ ID NO:95, SEQ ID NO:96, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO: 136, SEQ ID NO:137, SEQ ID NO:138, SEQ ID NO:139, and SEQ ID NO:140.

The instructions in a related embodiment of the kit include methods for: reacting genomic DNA in the sample with the bisulfite reagent to convert unmethylated cytosine residues to uracil; hybridizing resulting bisulfite treated genomic DNA with probes immobilized to the surfaces to obtain resulting hybridized probes on the array, such that the DNA probes hybridize to a DNA sequence of each of a methylated form and an unmethylated form of a CpG dinucleotide sequence in a gene of the plurality of genes; and detecting the methylation status of the CpG dinucleotide sequence, thereby estimating proportions of leukocyte types in the sample from the subject for assessing the disease condition of the subject.

In a related embodiment of the kit the instructions for detecting the methylation status of the CpG dinucleotide sequence include methods for: extending each hybridized probe of the resulting hybridized probes on the array by primer extension to obtain a resulting primer extension product; ligating the resulting primer extension product to an oligonucleotide complementary to the DNA sequence of a 3' region of the gene to obtain a resulting template for PCR on the array; and amplifying by PCR and measuring amount of resulting PCR product, thereby detecting the methylation status of the CpG dinucleotide sequence.

In another related embodiment of the instructions for kit amplifying by PCR include methods for: amplifying the resulting template on the array using primers pairs having a 5' primer specific to each of the methylated or the unmethylated form of the CpG dinucleotide containing gene, and a 3'primer specific to the gene containing the CpG dinucleotide, thereby resulting in a first PCR product; amplifying the resulting first PCR product with differentially labeled 5' primers that specifically amplify each of the methylated and unmethylated form of the CpG dinucleotide sequence containing gene, and a common 3' primer, resulting in a differentially labeled second PCR product, and hybridizing the second PCR product to the CpG dinucleotide containing gene for measuring amount of the second PCR product, to detect the methylation status of the CpG dinucleotide sequence.

Instructions for detecting the methylation status of the CpG dinucleotide sequence, in another related embodiment of the kit, include methods for extending the resulting hybridized probes on the array by single base primer extension with a labeled nucleotide.

Another embodiment of the invention is a method of treating a subject for a disease condition, such that the subject is a human patient and, such that the disease condition is a cancer, the method comprising: obtaining signatures comprising differentially methylated regions (DMRs) from types of leukocytes in a blood sample of the patient, the types of leukocytes comprising at least one selected from: CD19+ B lymphocyte, CD15+ granulocyte, CD14+ monocyte, $CD56^{dim}$ Natural Killer cell, $CD56^{bright}$ Natural Killer cell, and CD3+ T lymphocyte, and from a healthy control human subject not having the cancer; comparing a signature specific for the type of leukocyte in the patient with that in the healthy subject, such that the type of leukocyte specific signature is an indication of amount of cells of the type of leukocyte circulating in blood, and such that a decreased amount of the cells of the type of leukocyte circulating in the blood of the patient compared to the healthy subject is an indicium of the cancer; and, administering a composition comprising the cells of the type of leukocyte to the patient, thereby increasing the amount of the cells of the type of leukocyte in the patient and treating the cancer.

In various embodiments of the method the leukocyte type cell is the $CD56^{dim}$ Natural Killer cell.

The cancer in related embodiments of the method is head and neck squamous cell carcinoma (HNSCC). In embodiments of the method the DMR signature specific for $CD56^{dim}$ Natural Killer cells includes at least one CpG dinucleotide in a region near the promoter of gene NKp46. In other embodiments of the method the DMR signature specific for $CD56^{dim}$ Natural Killer cells is a CpG dinucleotide in a region near the promoter of the gene NKp46, such the methylation status of the CpG dinucleotide is quantified by methylation specific quantitative polymerase chain reaction (MS-qPCR) using primers and probes having SEQ ID NOs: 116-118 and 97-99. According to other embodiments of the method, the DMR signature specific for $CD56^{dim}$ Natural Killer cells is a CpG dinucleotide in a region near the promoter of the gene NKp46, such that the methylation status of the CpG dinucleotide is quantified by digital PCR involving emulsion and nanofluidic partitioning using primers and probes having SEQ ID NOs: 116-118 and 97-99.

In related embodiments of the method the blood sample is archival. Alternatively the blood sample is fresh.

In various embodiments of the method, the signature comprises at least one gene or locus described or shown in examples herein, for example SEQ ID NO: 1-96 and 119-140. In various embodiments of the method, the at least one gene or locus is selected from the group consisting of: FGD2, HLA-DOB, BLK, IGSF6, CLDN15, SFT2D3, ZNF22, CEL, HDC, GSG1, FCN1, OSBPL5, LDB2, NCR1, EPS8L3, CD3D, PPP6C, CD3G, TXK, and FAIM. In various embodiments of the method, the at least one gene or locus is selected from the group consisting of: CLEC9A (2 loci), INPP5D, INHBE, UNQ473, SLC7A11, ZNF22, XYLB, HDC, RGR, SLCO2B1, C1orf54, TM4SF19, IGSF6, KRTHA6, CCL21, SLC11A1, FGD2, TCL1A, MGMT, CD19, LILRB4, VPREB3, FLJ10379, HLA-DOB, EPS8L3, SHANK1, CD3D (2 loci), CHRNA3, CD3G (2 loci), RARA, and GRASP.

BRIEF DESCRIPTION OF THE DRAWINGS

FIG. 2 is a chart of the results of cell mixture reconstruction experiments validating prediction of individual sample profiles. The reconstruction experiments involved six known mixtures of monocytes and B cells and six known mixtures of granulocytes and T cells. Known fractions (Expected) and resulting predictions from Infinium 27K profiles (Observed) percentages of each cell type are shown by shade (dark=100, white=0).

FIG. 5A shows convergence by correlating the Hessian Matrix with the number of CpG sites included in the measurement. The dotted line shows the tangent at low values of m.

FIG. 5B shows the Rate of convergence which was calculated by smoothing the first differences of $\log_{10}(\text{trH}_m)$. The dotted line (red) in (B) corresponds to linear convergence.

FIG. 10 A shows DNA methylation status of a region in CD3E that was identified from the DNA methylation array analysis (the results of which are shown in FIG. 9) as one of the two candidate DMRs with specificity towards CD3+ T cells. The DNA methylation status was measured by pyrosequencing bisulfite converted DNA from different sorted, human, peripheral blood leukocytes.

FIG. 10 B shows DNA methylation status of a region in CD3Z gene that was identified from the DNA methylation array analysis (the results of which are shown in FIG. 9) as one of the two candidate DMRs with specificity towards CD3+ T cells. The DNA methylation status of the region in CD3Z gene in different sorted, human, peripheral blood leukocytes was measured by MethyLight® qPCR.

FIG. 12 is a list of genomic regions used for measuring methylation of CD3Z and FOXP3 gene, for quantitating genome copy numbers, and a list of the corresponding primer and probe sequences. Underlined letters are "C" in CpG motifs.

FIG. 13 A.

FIG. 13B shows dilution of isolated normal PanT cells (N=seven replicates).

FIG. 13C shows dilution and calibration curve for isolated CD3+CD25+ T cells (N=8 eight replicates). Calibration curves (FIG. 13A-C) were used to estimate total input copies, CD3+ T cell and Tregs copies, respectively.

FIG. 14A is a schematic diagram showing methylation specific primers and probe targeting six CpGs (lollipops) in a region of the CD3Z gene identified herein as demethylated in CD3+ T cells.

FIG. 14B shows results of real time PCR. The real time PCR Ct values decreased linearly with a ten-fold increase in bisulfite converted CD3+ T cell DNA concentration. Bisulfite converted universal methylated DNA was used to keep total amount of DNA in samples constant. At least five replicates of each sample were plotted.

FIG. 14C shows correlation between T cell levels determined by flow cytometry and CD3Z MS-qPCR. Evaluation of CD3+ T cell level by flow cytometry was observed to be highly correlated with T cell quantification by CD3Z MS-qPCR in whole blood specimens from glioma patients and healthy donors.

FIG. 14D shows correlation between T cell counts obtained using by immunohistochemical staining and CD3Z MS-qPCR. CD3+ T cell count by immunohistochemical staining correlates with T cell quantification by CD3Z MS-qPCR in excised tumors across histological subtypes. Pearson correlations and F-test p-values are shown in FIG. 14B-D.

FIG. 15 A, FIG. 15B and FIG. 15C (FIG. 15A-C) are graphical representations showing T cells and Tregs in the peripheral blood of glioblastoma multiform (GBM) patients and healthy donors determined by MS-qPCR for demethylation of specific CpG loci.

FIG. 16 A, FIG. 16B and FIG. 16 C (FIG. 16A-C) are graphical representations showing association between cigarette smoking and peripheral blood T cells and Tregs in glioma patients and healthy donors determined by MS-qPCR for demethylation of specific CpG loci.

FIG. 17A shows T cell levels, determined by CD3Z demethylation, in solid glioma samples stratified by tumor grade.

FIG. 17B shows Treg levels, determined by FOXP3 demethylation, in solid glioma samples stratified by tumor grade.

FIG. 17C shows Treg percent of T cells, determined by ratio of FOXP3 to CD3Z demethylation, in solid glioma samples stratified by tumor grade. Wilcoxon rank sum p-values are shown.

FIG. 18A shows a forward and side scatter plot of a representative blood sample showing gating for lymphocytes and counting beads.

FIG. 18B shows lymphocyte subpopulation observed using gating for CD3 expression.

FIG. 18C shows CD45 gating on non-bead events. CD45+ low and high cells were added in order to count total CD45+ cells.

FIG. 19A shows CD3 staining. Average number of cells positive for staining was 418.

FIG. 19 B shows CD8 staining. Average number of cells positive for staining was 296.

FIG. 19 C shows correlation of CD3 and CD8 staining, Pearson r=0.992

FIG. 20A is a heatmap of DNA methylation in FOXP3 and CD3Z gene regions assessed by MS-qPCR.

FIG. 20B is a heatmap of DNA methylation at three CpG loci in the CD3Z gene assessed by bisulfite pyrosequencing.

FIG. 21A shows T cell levels determined by CD3Z demethylation in solid glioma samples stratified by tumor histology.

FIG. 21B shows Treg levels determined by FOXP3 demethylation in solid glioma samples stratified by tumor histology.

FIG. 21C shows Treg percent of T cells, determined by ratio of FOXP3 to CD3Z demethylation in solid glioma samples stratified by histology.

FIG. 22A shows survival (ordinate) of glioma patients as a function of time (abscissa) in relation to T cell levels as determined by CD3Z demethylation.

FIG. 22B shows survival of glioma patients in relation to Treg levels as determined by FOXP3 demethylation.

FIG. 22C shows survival of glioma patients in relation to Treg percent of T cells as determined by ratio of FOXP3 to CD3Z demethylation.

FIG. 23A shows a heat map of the methylation status for the highest ranked 50 leukocyte DMRs by leukocyte subtype.

FIG. 23B shows a Plot depicting the $-\log_{10}$ (P-values) for the highest ranked 50 leukocyte DMRs across three cancer data sets (HNSCC; Ovarian; Bladder). P-values (ordinate) show methylation differences between cancer cases and non-cancer controls and were obtained from individual unconditional logistic regression models fit to each of the 50 leukocyte DMRs. For the HNSCC data set, logistic regression models were adjusted for patient age, gender, smoking status (never, former, current), smoking pack years, weekly alcohol consumption, and HPV serology status. The bladder cancer data set was adjusted for patient age, gender, smoking status, smoking pack years, and family history of bladder cancer. The ovarian cancer data set was adjusted for patient age group (55-60, 60-65, 65-70, 70-75 and >75 years). The horizontal dashed line represents $-\log_{10}$ (p=0.05).

FIG. 24A left column shows a heat map of the HNSCC testing data set. Rows represent subjects, which are grouped by predicted methylation class membership. Columns represent the highest ranked 50 leukocyte DMRs that were used to generate the methylation classes for the HNSCC testing set. FIG. 24 A right column is a bar-plot depicting the percent cancer case/control across the predicted methylation classes in the HNSCC testing set.

FIG. 24B shows receiver operating characteristic (ROC) curves based on the predicted methylation classes only in the HNSCC testing set and methylation classes including patient age, gender, smoking status (never, former, current), smoking pack years, weekly alcohol consumption, and HPV serostatus.

FIG. 25A is a heat map of the ovarian testing data set. Rows represent subjects which are grouped by predicted methylation class membership. Columns represent the highest ranked ten leukocyte DMRs that were used to generate the methylation classes for the ovarian testing set. FIG. 25 A right column is a bar-plot depicting the percent cancer case/control across the predicted methylation classes in the ovarian testing set.

FIG. 25B shows ROC curves based on the predicted methylation classes alone in the ovarian testing set and methylation classes plus patient age group (55-60, 60-65, 65-70, 70-75 and >75 years).

FIG. 26A is a heat map of the bladder testing data set. Rows represent subjects, which are grouped by predicted methylation class membership. Columns represent the highest ranked 56 leukocyte DMRs that were used to generate the methylation classes for the bladder testing set. FIG. 26 A right column represents a bar-plot depicting the percent cancer case/control across the predicted methylation classes in the bladder testing set.

FIG. 26B shows ROC curves based on the predicted methylation classes alone in the bladder testing set and methylation classes plus patient age, gender, smoking status (never, former, current), smoking pack years, and family history of bladder cancer.

FIG. 27A shows the six CpG loci identified by HNSCC analysis (Langevin S M et al., Epigenetics. 2012 March; 7(3):291-9) and the highest ranked 50 leukocyte DMRs used in the present analysis.

FIG. 27B shows the seven CpG loci identified by the alternative ovarian analysis and the highest ranked ten leukocyte DMRs used in the present analysis, and (c) the nine CpG loci identified by the bladder analysis reported in (Laird P W, 2003 Nat Rev Cancer 3:253-266) and the highest ranked 56 leukocyte DMRs used in the present analysis.

FIG. 27C shows the nine CpG loci identified by the bladder analysis reported in (Shen L et al., 2007 PLoS genetics 3:2023-2036) and the highest ranked 56 leukocyte DMRs used in the present analysis.

FIG. 33A is a heatmap of the testing set obtained by predicted methylation class using the SS-RPMM procedure. Rows represent subjects and columns represent the seven CpG loci identified by this analysis.

FIG. 33B represents percentage of cases/controls obtained by predicted methylation class membership in the testing set.

FIG. 33C sows information regarding the seven CpG loci identified by the SS-RPMM analysis.

FIG. 33D shows a ROC/AUC (area under the curve) analysis based on the predicted methylation class memberships in the testing set. Dark represents the ROC/AUC based on the predicted methylation classes along and light represents the ROC/AUC using the predicted methylation classes and patient age group.

Linear mixed effects modeling of DNA methylation microarray data from MACS isolated human leukocytes generated a coefficient estimating differential methylation in NK cells relative to other cell subtypes, shown on the avscissa. Linear modeling of mRNA microarray data from the same isolated cells determined log-fold change in expression between NK cells and each of the following subtypes: T cells, B cells, granulocytes and monocytes. The average of these four log-fold change values is shown on the ordinate. Significance for a particular gene region was achieved when q<0.1 for four mRNA expression linear models as well as the DNA methylation mixed effects model. Candidates for NK cell-specific DNA methylation biomarkers were limited to significant gene loci exhibiting decreased methylation in NK cells (methylation estimate <0) and within genes that exhibited increased RNA expression (log fold change >1). The candidate loci are marked with asterisks in the top left quadrant, and NKp46 loci are marked with grey asterisks.

Figure 35:
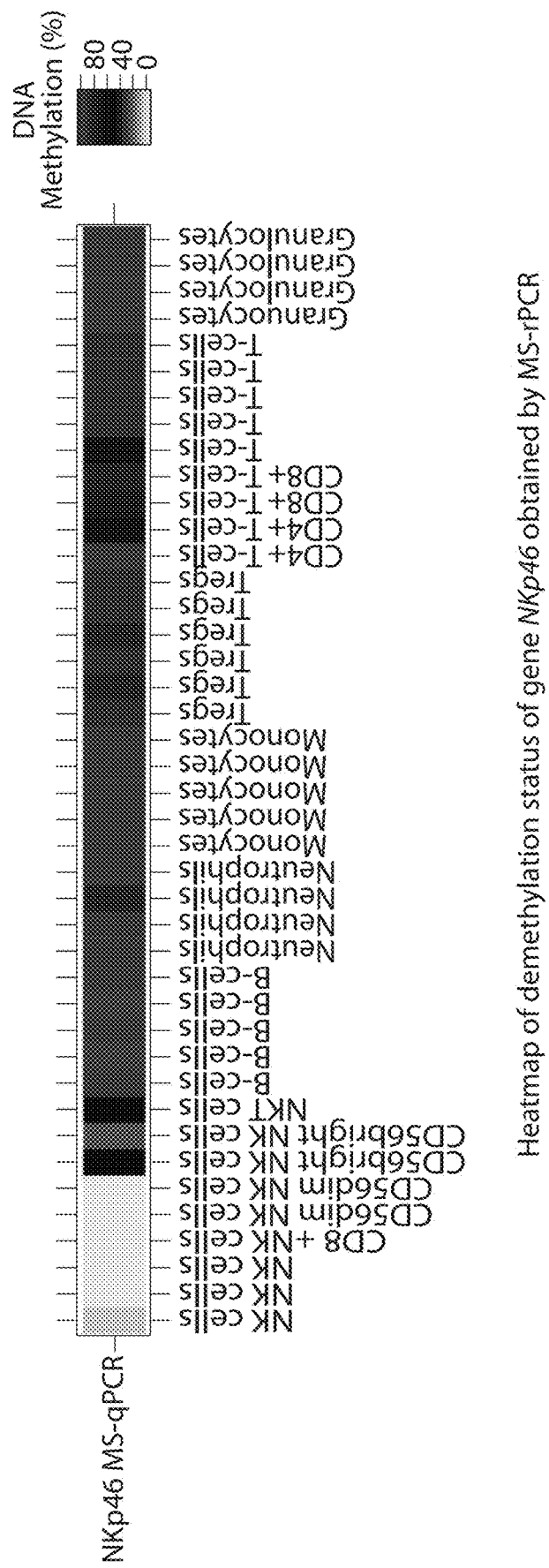

FIG. 35 is a heatmap showing demethylation status of NKp46 determined by methylation specific quantitative PCR (MS-qPCR) of isolated human leukocyte populations. Individual samples of (MACS) purified white blood cell subtypes were subjected to a MS-qPCR assay that detects demethylated copies of NKp46 DNA. Extent of NKp46 methylation is illustrated in this heatmap in which light indicates that copies of DNA in particular sample were demethylated in the targeted region of NKp46, and dark indicates that copies were methylated.

Figure 36:
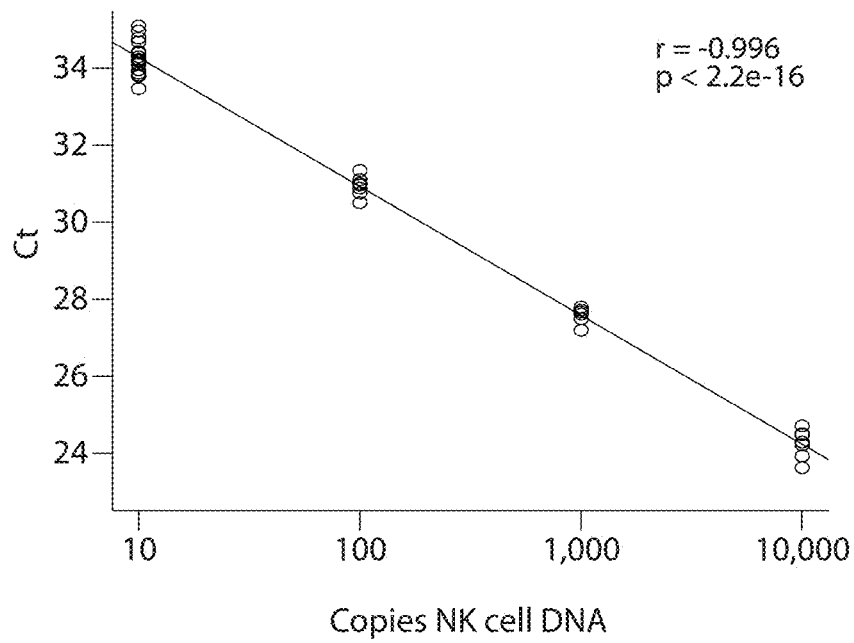

FIG. 36 is a line graph showing linearity of NKp46 MS-qPCR calibration. Bisulfite converted universal methylated DNA was used to standardize total amount of DNA in samples at a constant amount. At least three replicates of each standard are plotted. Real time PCR Ct values decrease linearly with ten-fold increase in bisulfite converted NK cell DNA concentration.

Figure 37:
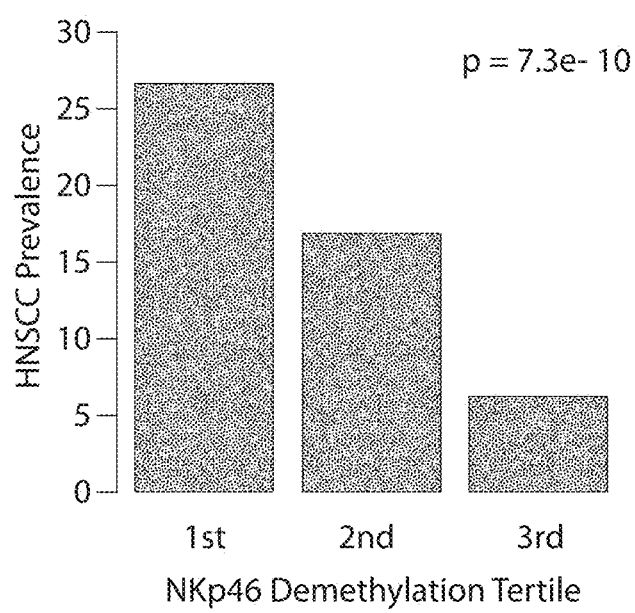

FIG. 37 is a bar graph showing prevalence of HNSCC by normal NKp46 demethylation tertile. Normal NKp46 demethylation tertile cutoffs were determined from control blood samples only. Higher tertiles indicate higher NK cell levels. HNSCC prevalence (ordinate) refers to the percent of total cases in this example whose NKp46 demethylation measurements fell within the control derived tertile range. Displayed p-value is from a chi-squared test for trend in proportions.

Figure 38:
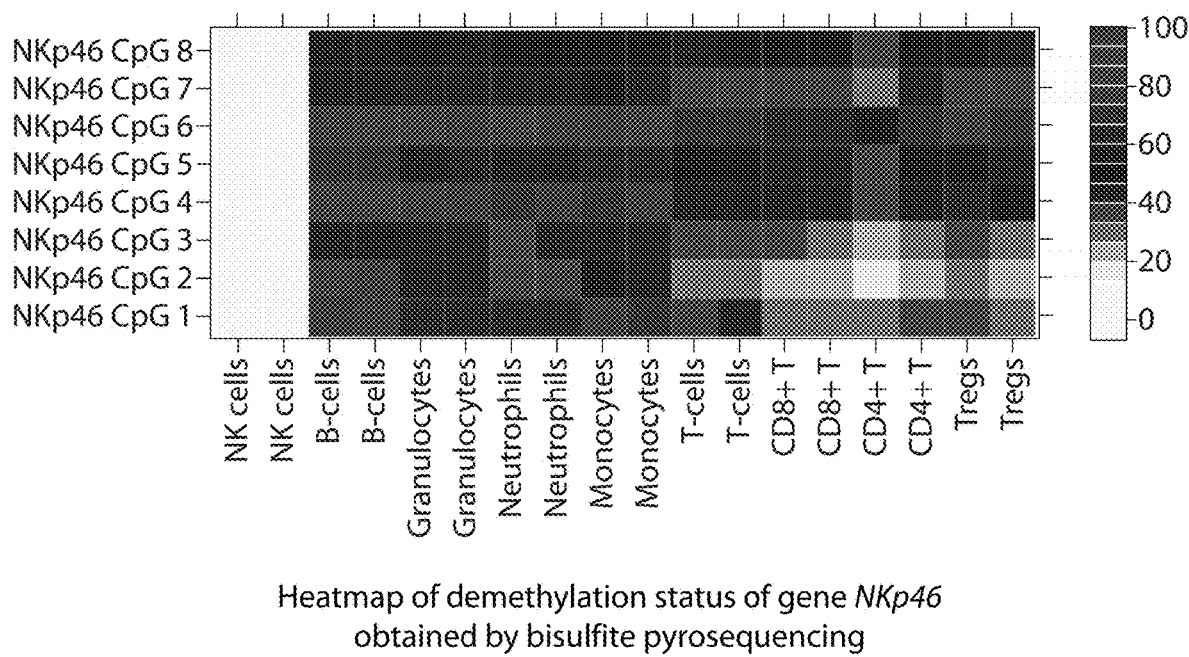

FIG. 38 is a heatmap showing methylation status of selected NKp46 CpG loci measured by bisulfite pyrosequencing of isolated human leukocytes. The methylation status of eight individual CpG loci near the promoter region of NKp46 were interrogated by pyrosequencing of bisulfite converted DNA extracted from Magnetic activated cell sorting (MACS) isolated human leukocyte populations. CpG numbers 2 through 7 represent the six loci targeted in the MS-qPCR assay. This heatmap displays methylation levels at each locus ranging from unmethylated (light) to methylated (dark).

Figure 39:
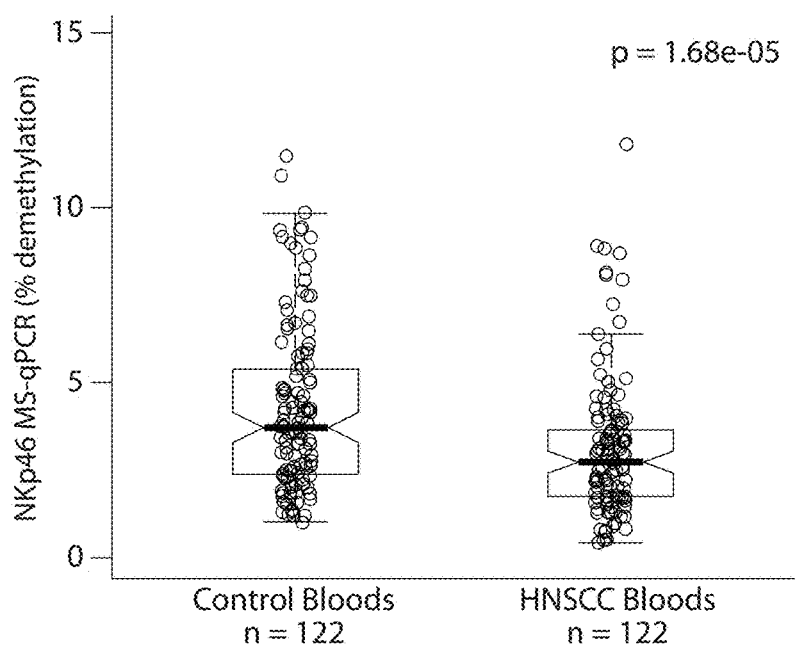

FIG. 39 is a graph showing percent demethylation (ordinate) of a DNA region in NKp46 in control and HNSCC patient blood samples (abscissa) assessed by MS-qPCR. The NKp46 MS-qPCR assay measures the extent of DNA demethylation. A higher level of demethylation indicates a higher level of NK cells within a sample. Wilcoxon rank sum p-value is displayed.

FIG. 40 is a listing of DNA sequences of regions in 96 different genes, each sequence having one CpG dinucleotide shown within square brackets and used to determine methylation status of the gene. The DNA sequence surrounding the CpG dinucleotides was used to design probes for the array and for primers for performing the methods for analyzing differential methylation. Also included are the names of the genes, chromosome number indicating the chromosome in which genes are located, the source of the DNA sequences, Genebank accession numbers, and the coordinate of the CpG dinucleotide in respective genes.

Figure 41A:
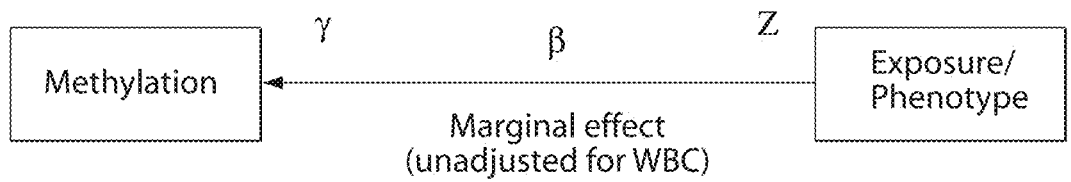
Figure 41B:
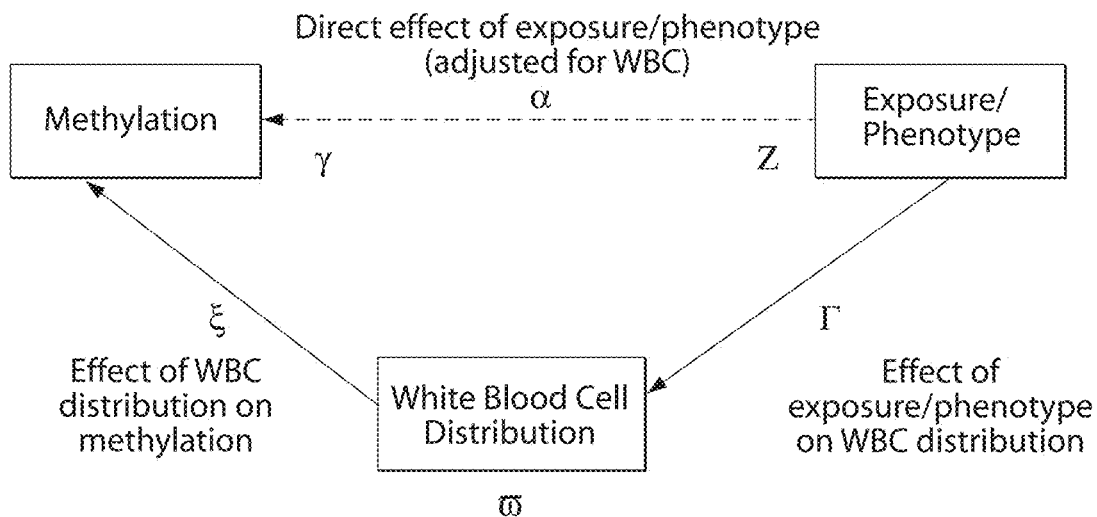

FIG. 41A-B are schematic diagrams showing different ways of representing effects on measured DNA methylation due to an exposure or a specific phenotype.

FIG. 41A depicts the marginal effects ($\beta$) on measured DNA methylation. The marginal effects are effects which are not adjusted for white blood cell (WBC) distribution.

FIG. 41B depicts the effects on measured DNA methylation adjusted for WBC distribution resulting from exposure or a specific phenotype.

Figure 42:
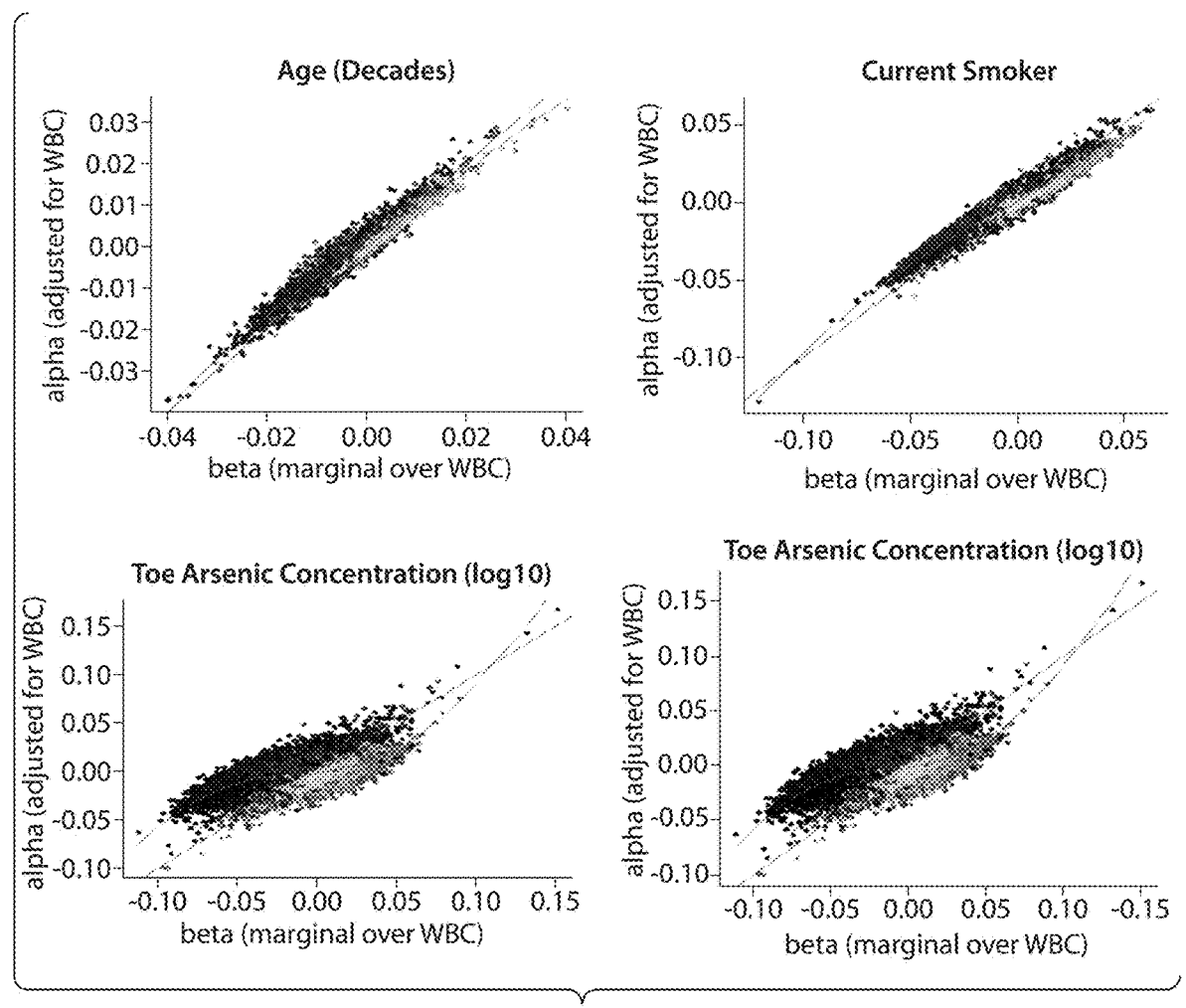

FIG. 42 is a set of graphical representations showing the relationship between $\alpha$ and $\hat{\beta}$, the effect on measured DNA methylation not adjusted or adjusted for WBC distribution, for the covariate (e.g. age, current smoker status, toe Arsenic concentration and Dye use) of interest over autosomal CpGs. Dots represents overall methylation as indicated by the first component of the coefficient vector $\hat{\beta}$, corresponding to the intercept (Example 38), light=low, black=moderate, dark=high. The diagonal straight line represents identity ($\hat{\alpha}=\hat{\beta}$). The curve depicts a loess fit to the scatter plot.

Figure 43A:
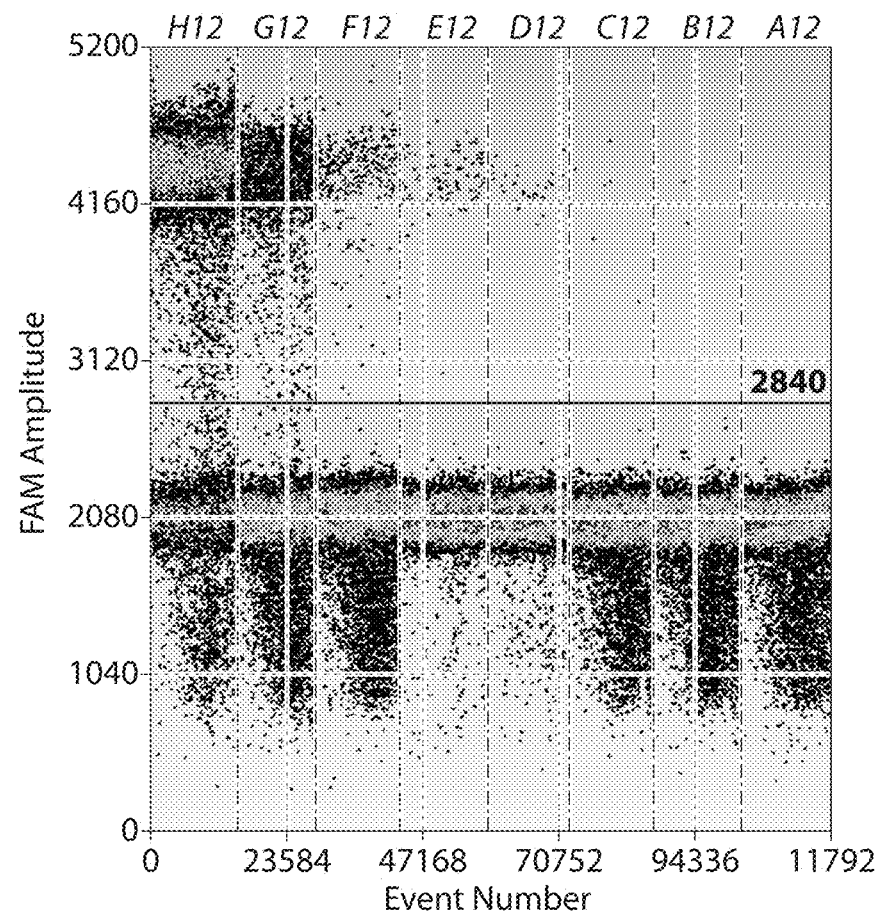
Figure 43B:
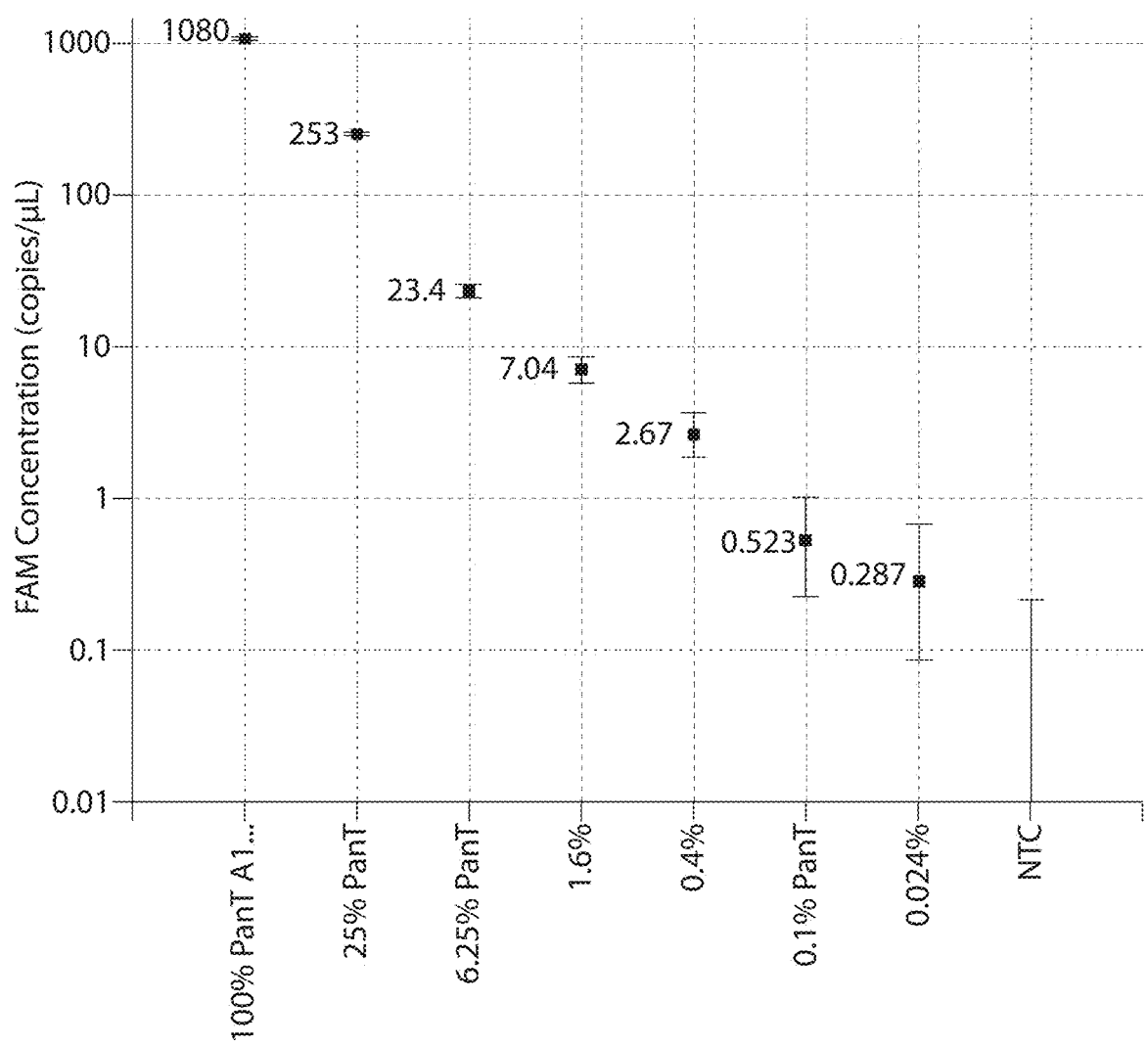

FIG. 43A-B are a graphical representation showing fluorescence intensities of CD3Z gene amplified by digital droplet PCR, and a graphical representation showing concentration of CD3Z gene in PCR samples.

FIG. 43A shows a fluorescence intensity dot plot for amplification of CD3Z gene by detection of intensities of 6 FAM (6-Carboxyfluorescein). Positive and negative droplets are distinguished by a horizontal line.

FIG. 43B shows a correlation of the concentration of copy numbers of CD3Z gene obtained by measuring 6 FAM fluorescence intensities and the expected copy numbers of CD3Z gene obtained by dilution of a known amount of DNA from CD3+ T cells.

Figure 44A:
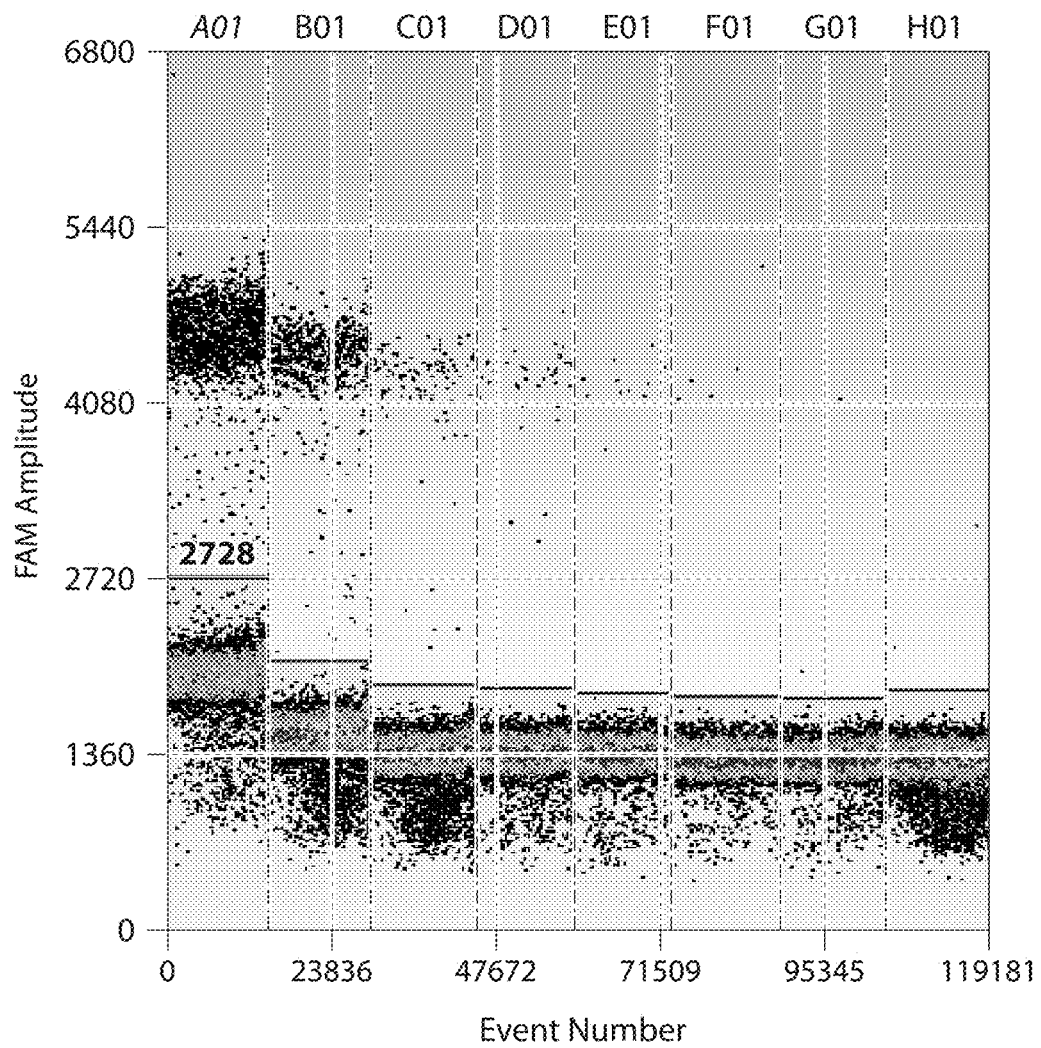
Figure 44B:
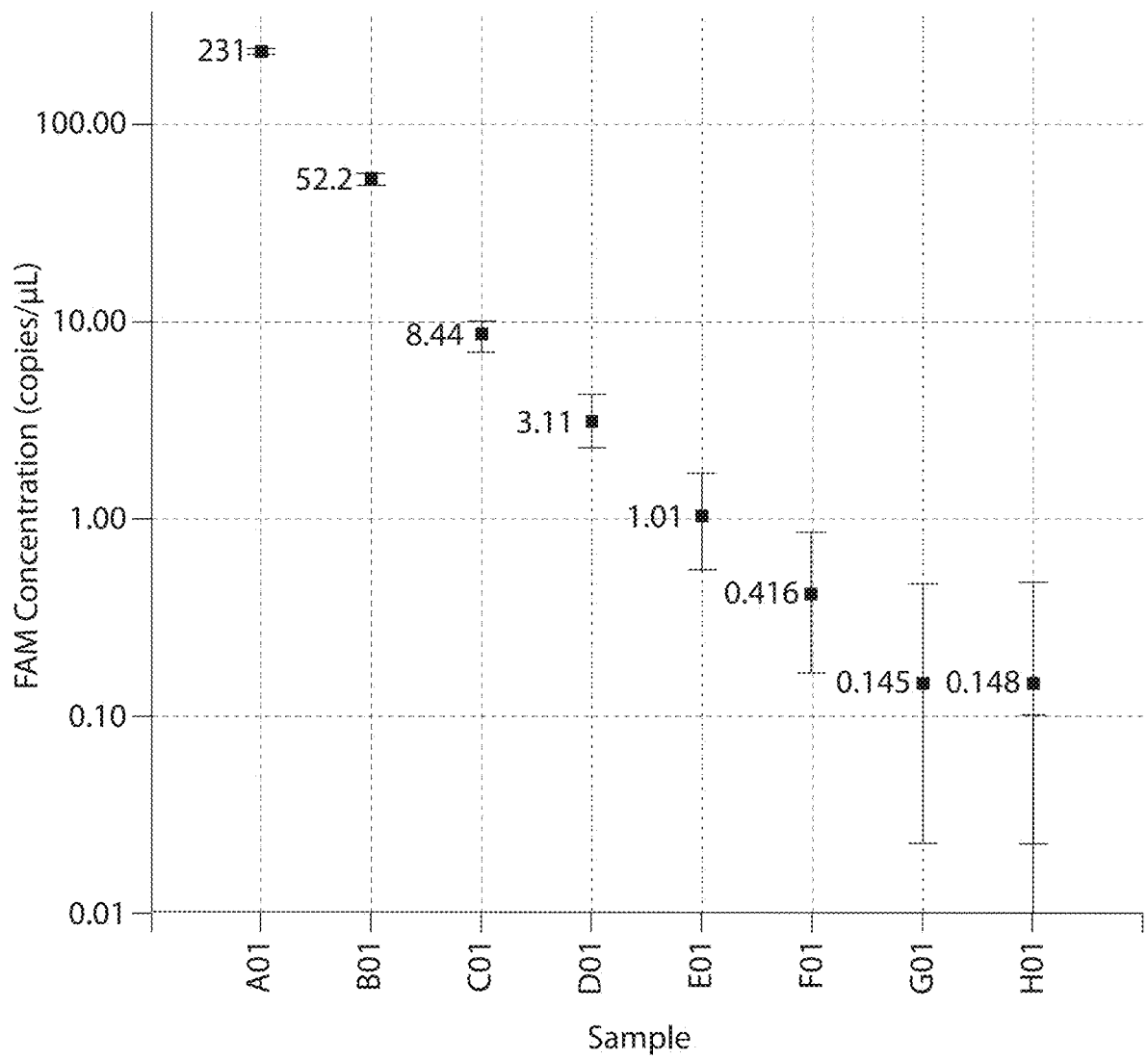

FIG. 44A-B are a graphical representation showing fluorescence intensities of FoxP3 gene amplified by digital droplet PCR, and a graphical representation showing concentration of FoxP3 gene in PCR samples.

FIG. 44A shows a fluorescence intensity dot plot for amplification of FoxP3 gene by detection of intensities of 6 FAM (6-Carboxyfluorescein). Positive and negative droplets are distinguished by a horizontal line.

FIG. 44B shows a correlation of the concentration of copy numbers of FoxP3 gene obtained by measuring 6 FAM fluorescence intensities and the expected copy numbers of FoxP3 gene obtained by dilution of a known amount of DNA from CD3+ T cells.

Figure 45A:
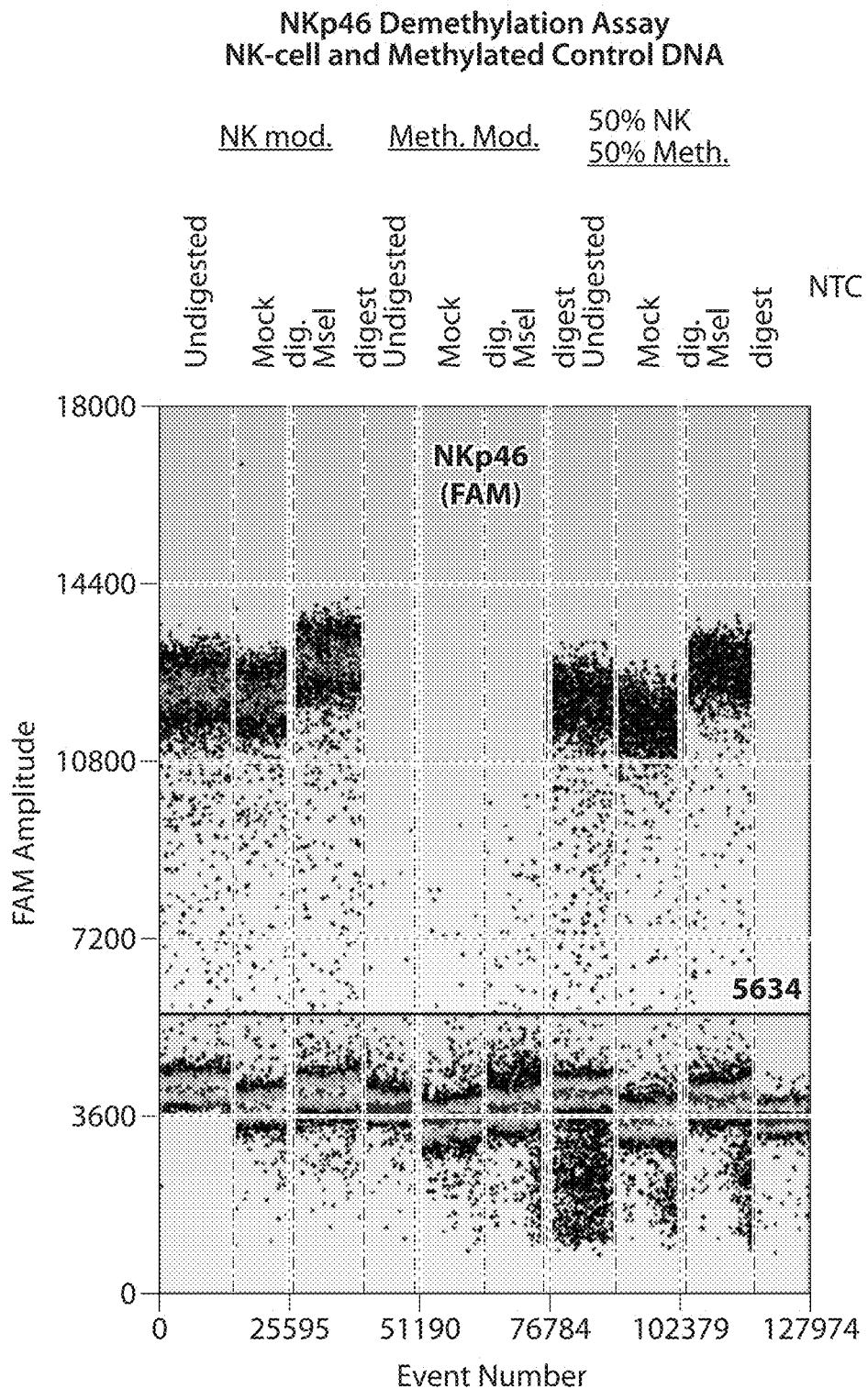

FIG. 45A-B are a graphical representation showing fluorescence intensities of NKp46 gene amplified by digital droplet PCR, and a table showing concentration of NKp46 gene in the PCR samples amplified under different conditions.

FIG. 45A shows a fluorescence intensity dot plot for amplification of NKp46 gene under different conditions by detection of intensities of 6 FAM (6-Carboxyfluorescein). Positive and negative droplets are distinguished by a horizontal line.

FIG. 45B is a table showing concentration of NKp46 gene in copies/μl determined under different PCR conditions as fractions of methylated control DNA.

Figure 46A:
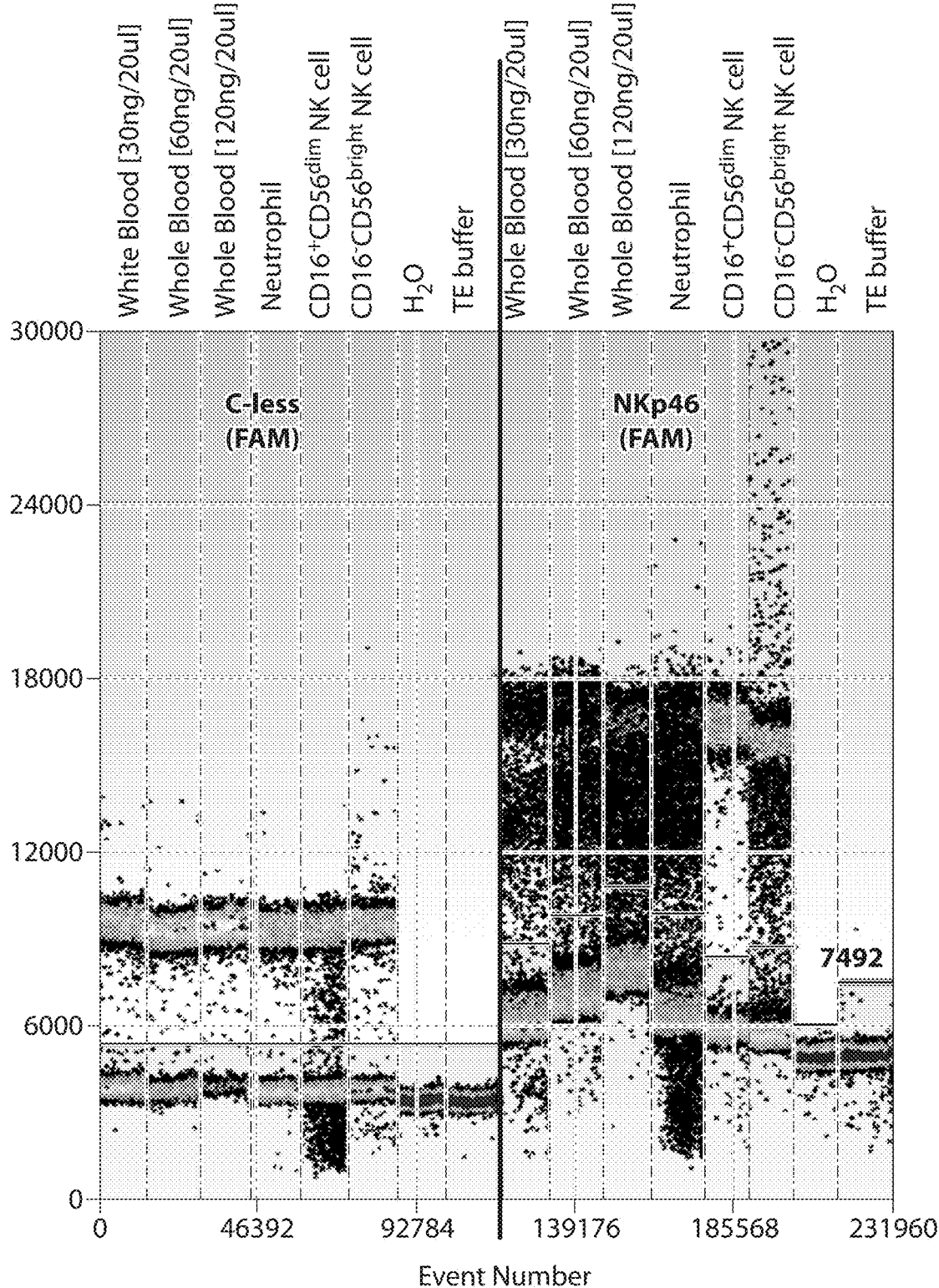

FIG. 46A-B are a graphical representation showing fluorescence intensities of NKp46 gene amplified by digital droplet PCR, and a table showing concentration of NKp46 gene in the PCR samples amplified under different conditions.

FIG. 46A shows a fluorescence intensity dot plot for amplification of NKp46 gene by detection of intensities of 6 FAM (6-Carboxyfluorescein). The amplification of demethylated NKp46 locus was performed using C-less and NKp46 DMR specific primers and probes, and results compared. Positive and negative droplets are distinguished by a horizontal line.

FIG. 46B is a table showing concentration of NKp46 gene in copies/μl determined with whole blood DNA, Neutrophil DNA, CD16+CD56$^{dim}$ NK cell DNA and CD16+CD56$^{bright}$ NK cell DNA.

Figure 47:
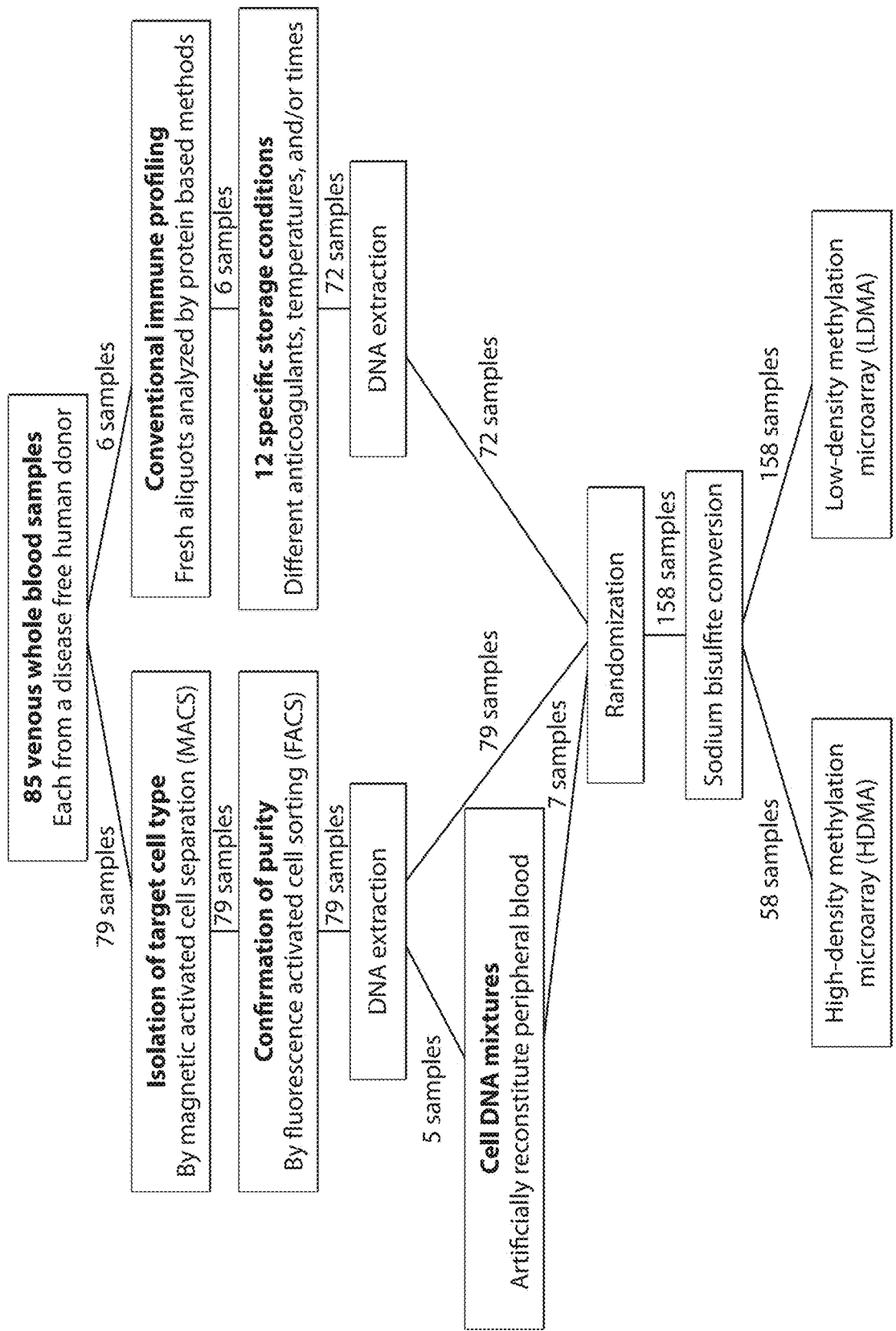

FIG. 47 is a drawing of processing and workflow of 85 venous whole blood samples analyzed in Examples herein. Eighty five venous whole blood samples were collected from disease free human donors. Of these samples 79 samples were used for isolation of target cell type by magnetic activated cell separation (MACS) and six samples were subjected to conventional immune profiling in which fresh aliquots were analyzed by protein based methods. Purity was confirmed by fluorescence activated cell sorting (FACS) in 79 samples isolated by MACS. The six samples analyzed by conventional immune profiling were placed in 12 specific different storage conditions that differ by presence of coagulants, temperature, and/or duration.

DNA was extracted from each of the 79 samples analyzed by FACS and the 72 samples in the 12 specific storage conditions. Aliquots of the genomic DNA from five of the FACS purified, DNA extracted 79 samples samples were combined in quantities that mimicked human blood as determined by artificially reconstituting peripheral blood. Aliquots of each of seven of the cell DNA mixtures, the FACS purified DNA extracted 79 samples, and the 72 samples stored according to the 12 specific storage conditions were randomized. Aliquots of each of the resulting 158 samples were contacted with sodium bisulfate, for analysis of methylation status of cytosines in DNA. Aliquots of 58 of these samples were analyzed using a high-density methylation microarray (HDMA) and aliquots of 158 samples were analyzed using a low-density methylation microarray (LDMA).

Figure 48A:
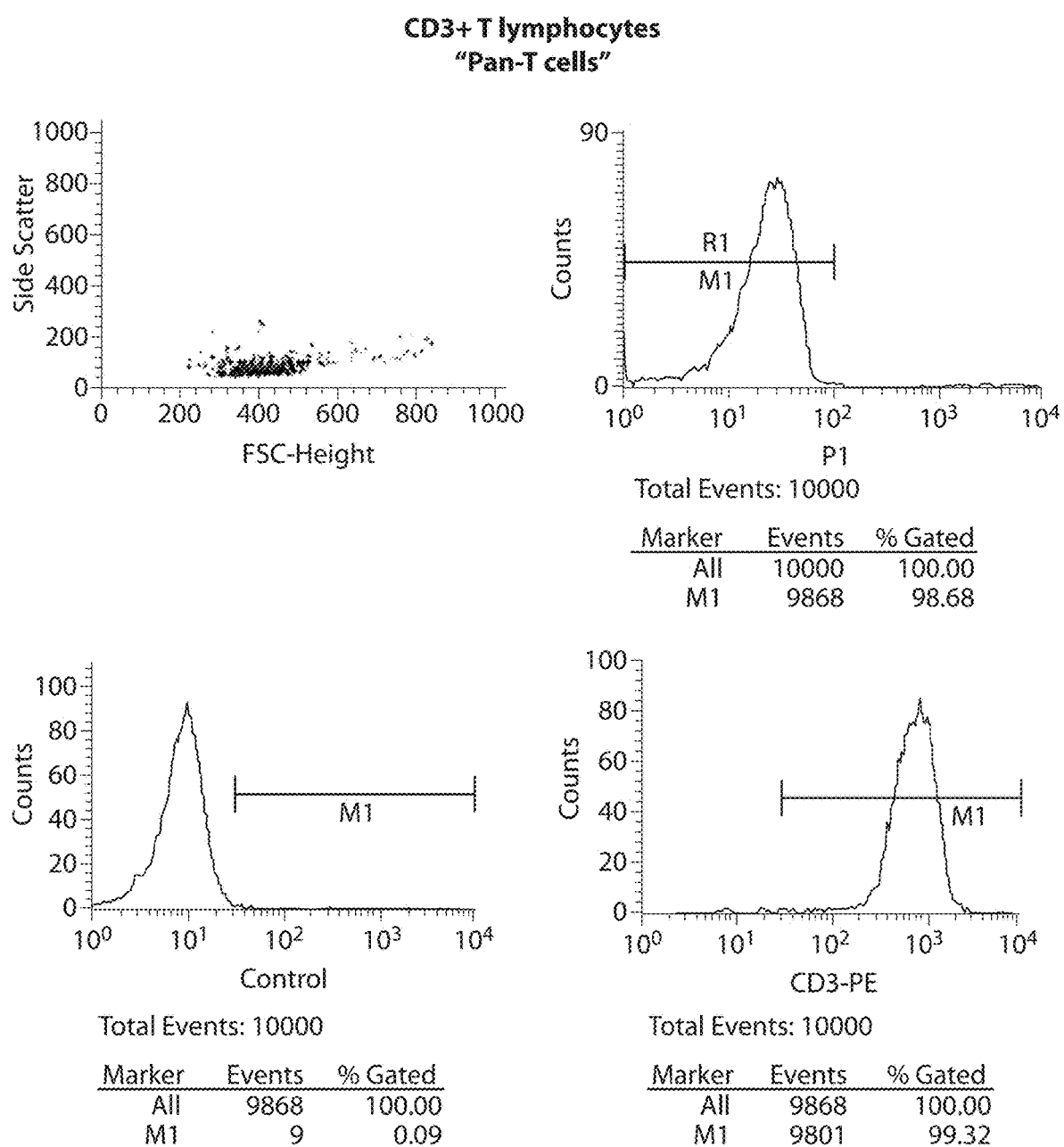
Figure 48C:
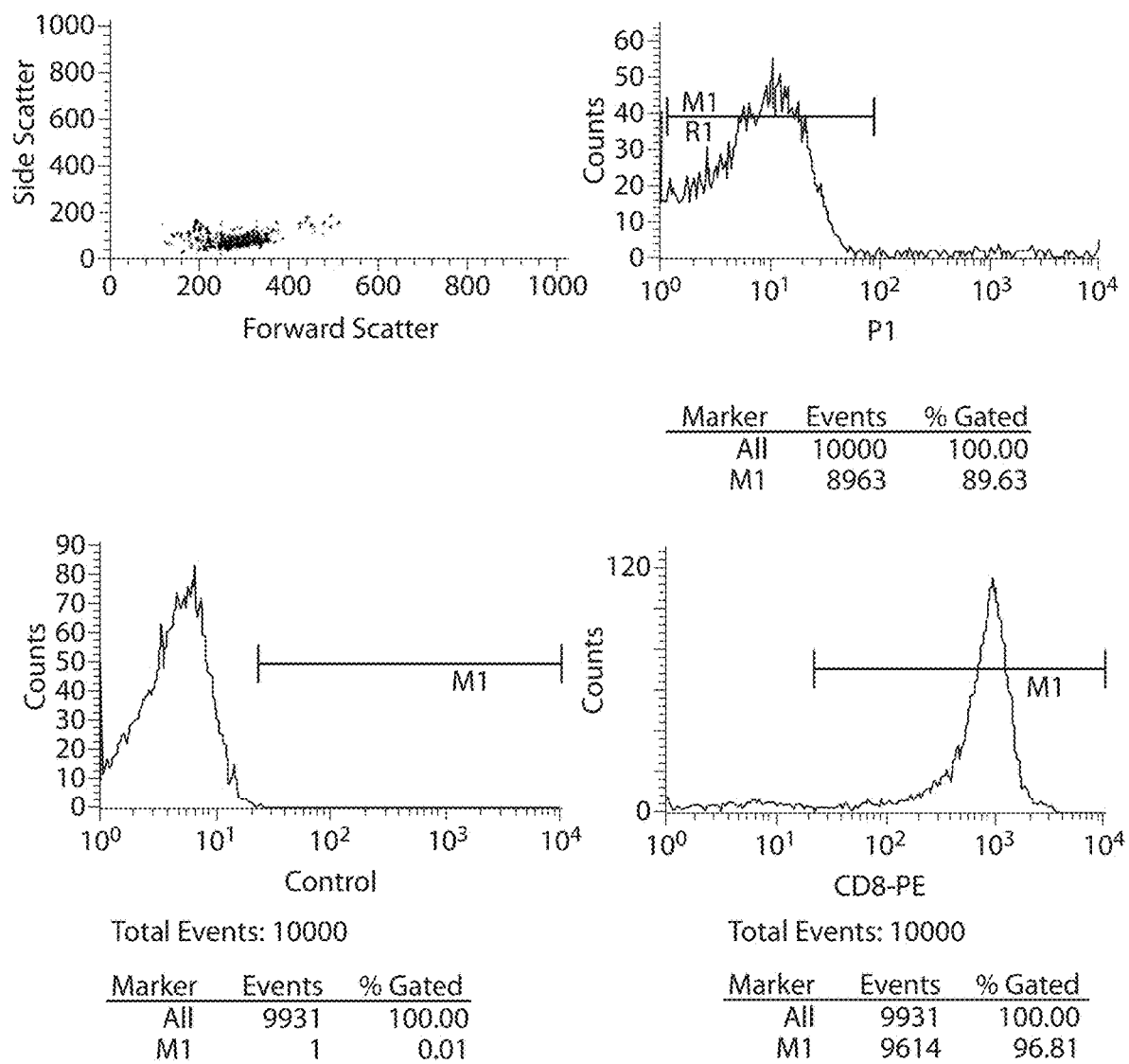
Figure 48D:
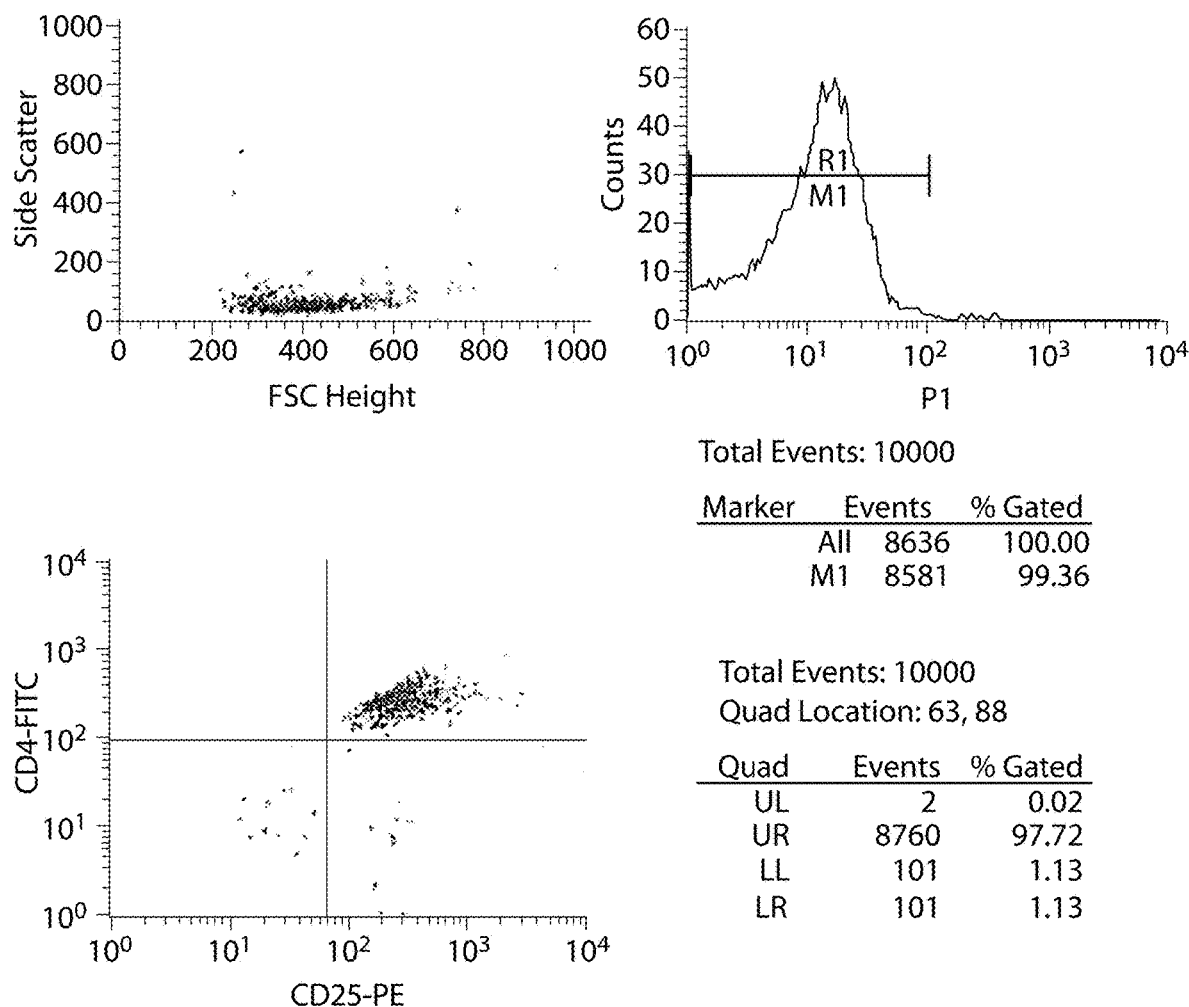
Figure 48F:
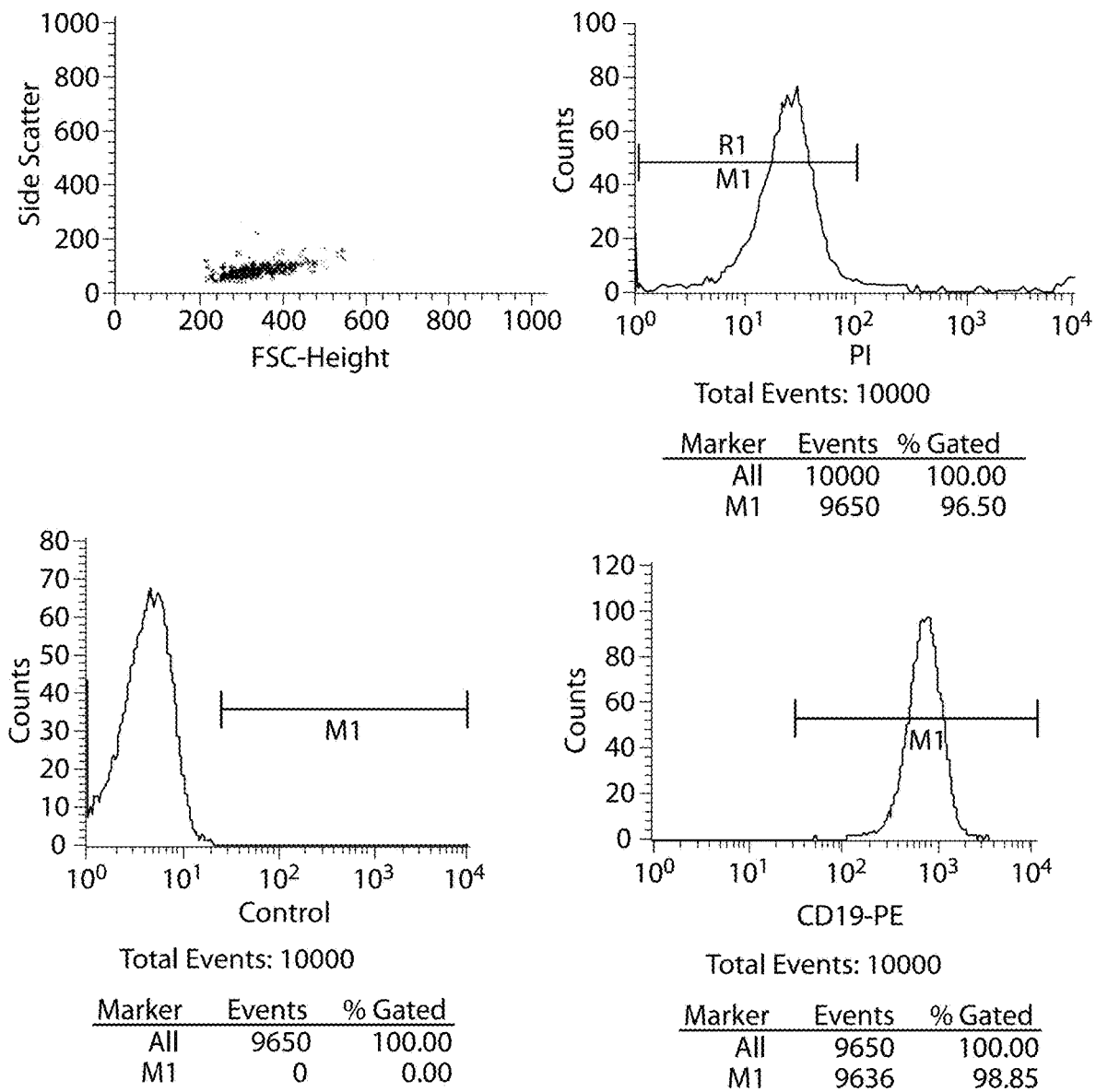
Figure 48G:
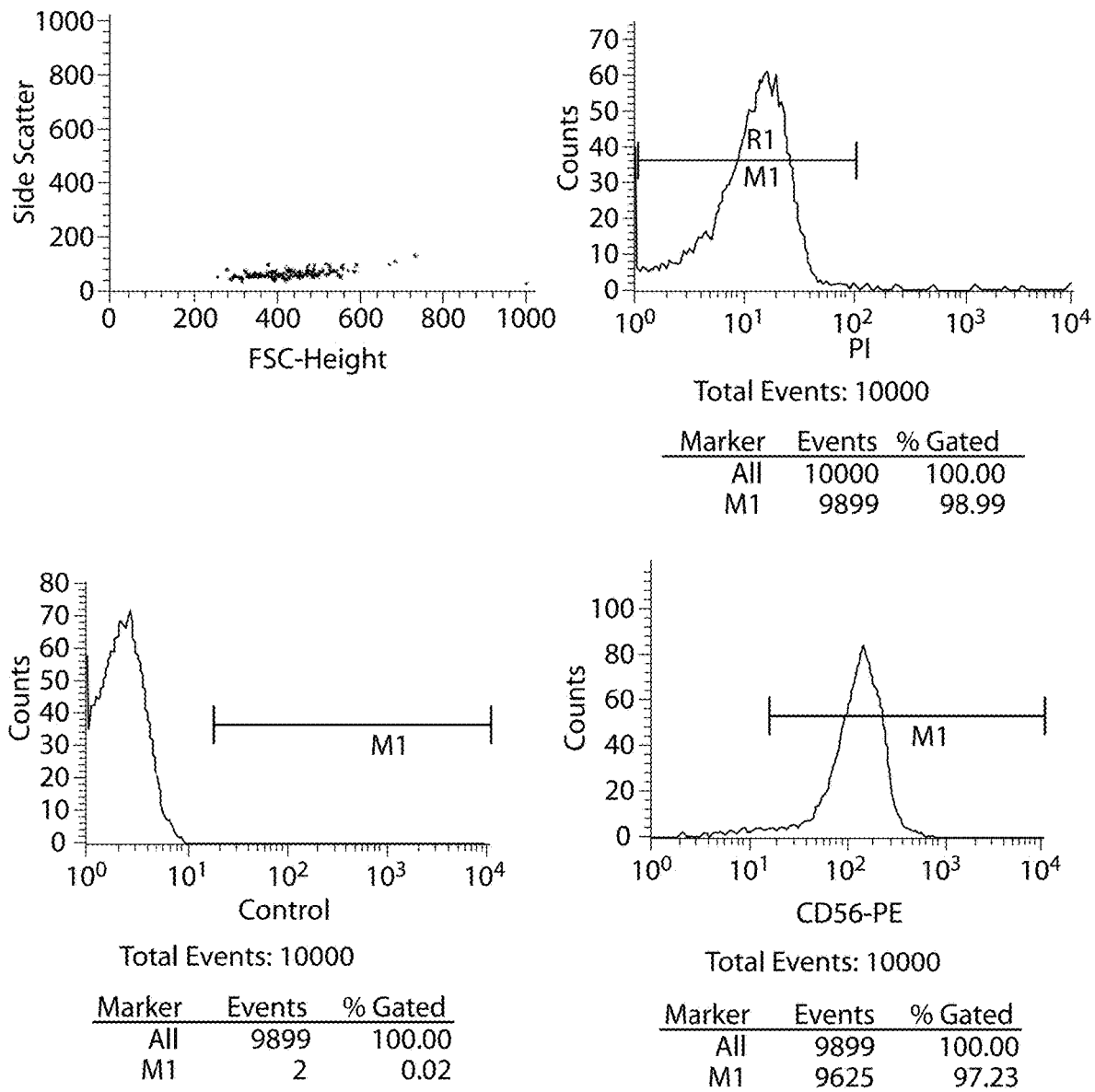
Figure 48I:
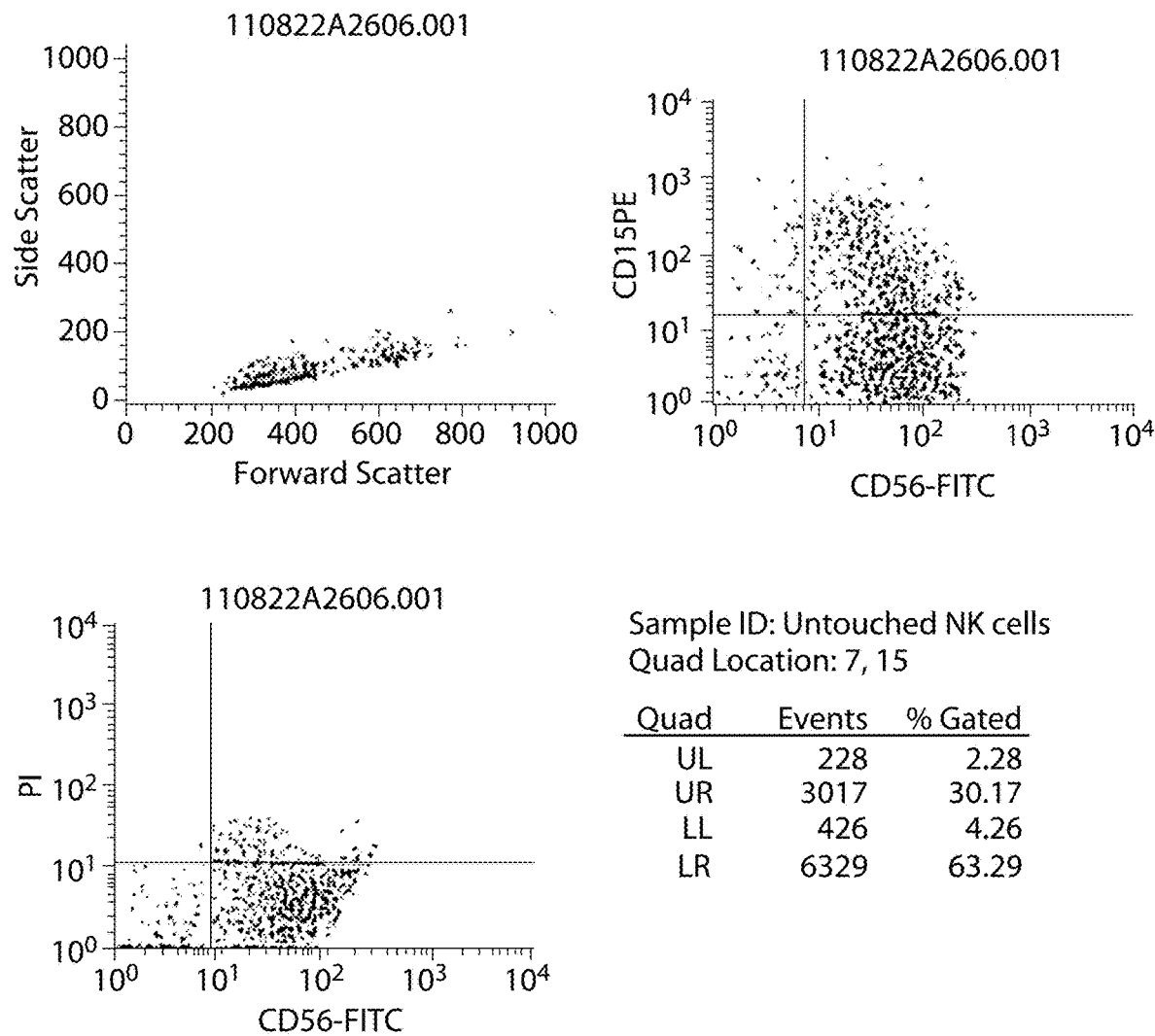
Figure 48L:
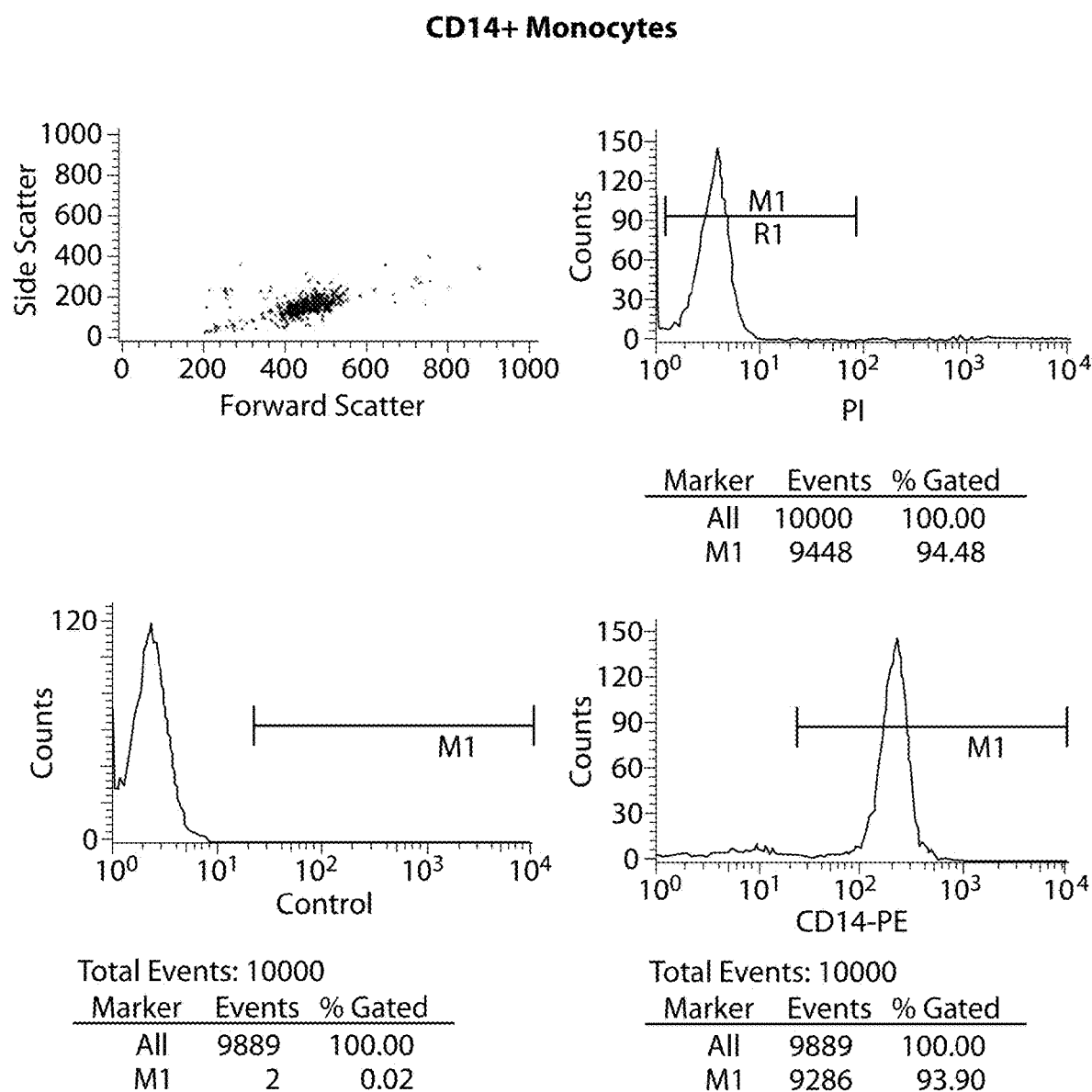
Figure 48M:
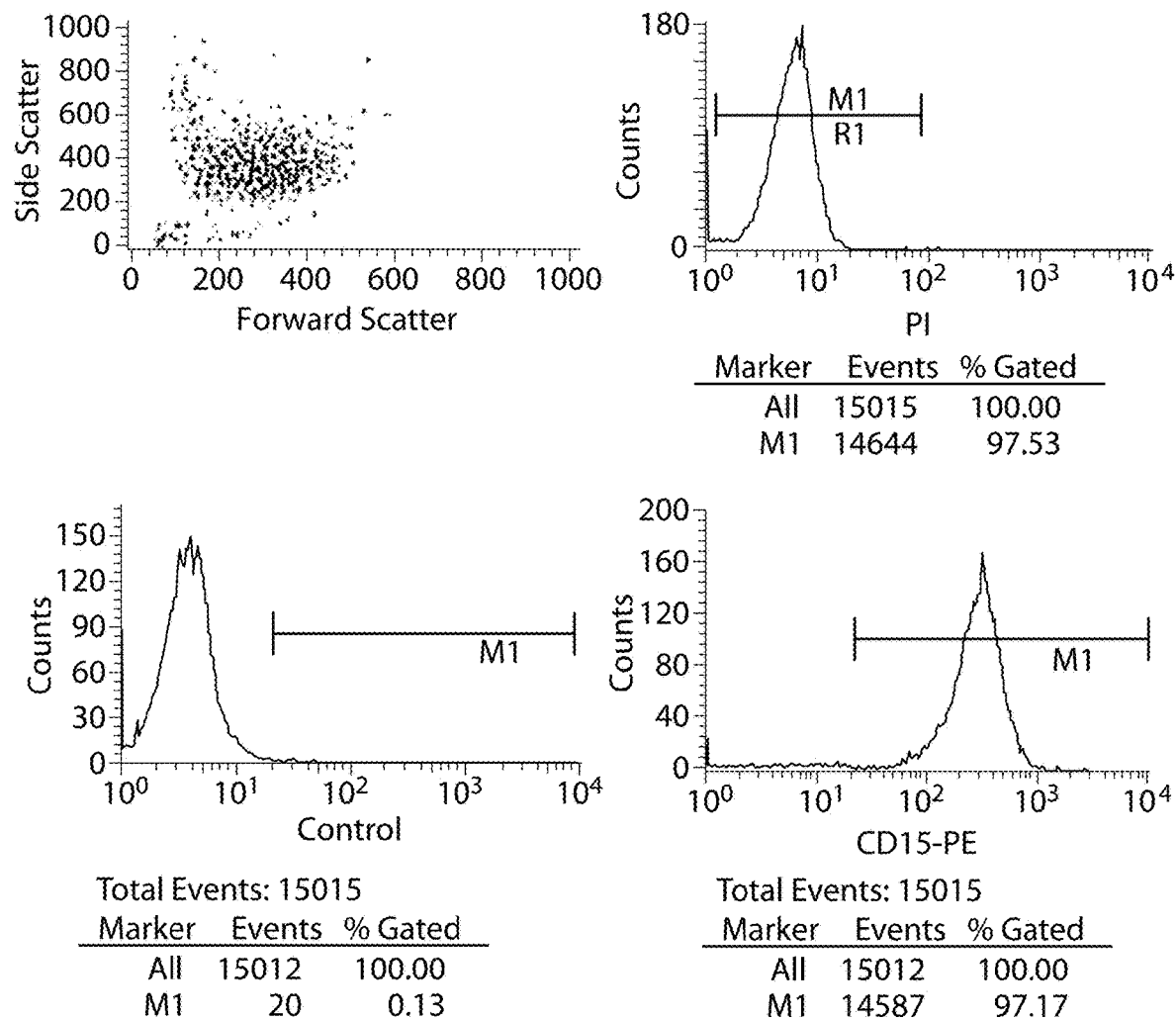
Figure 48N:
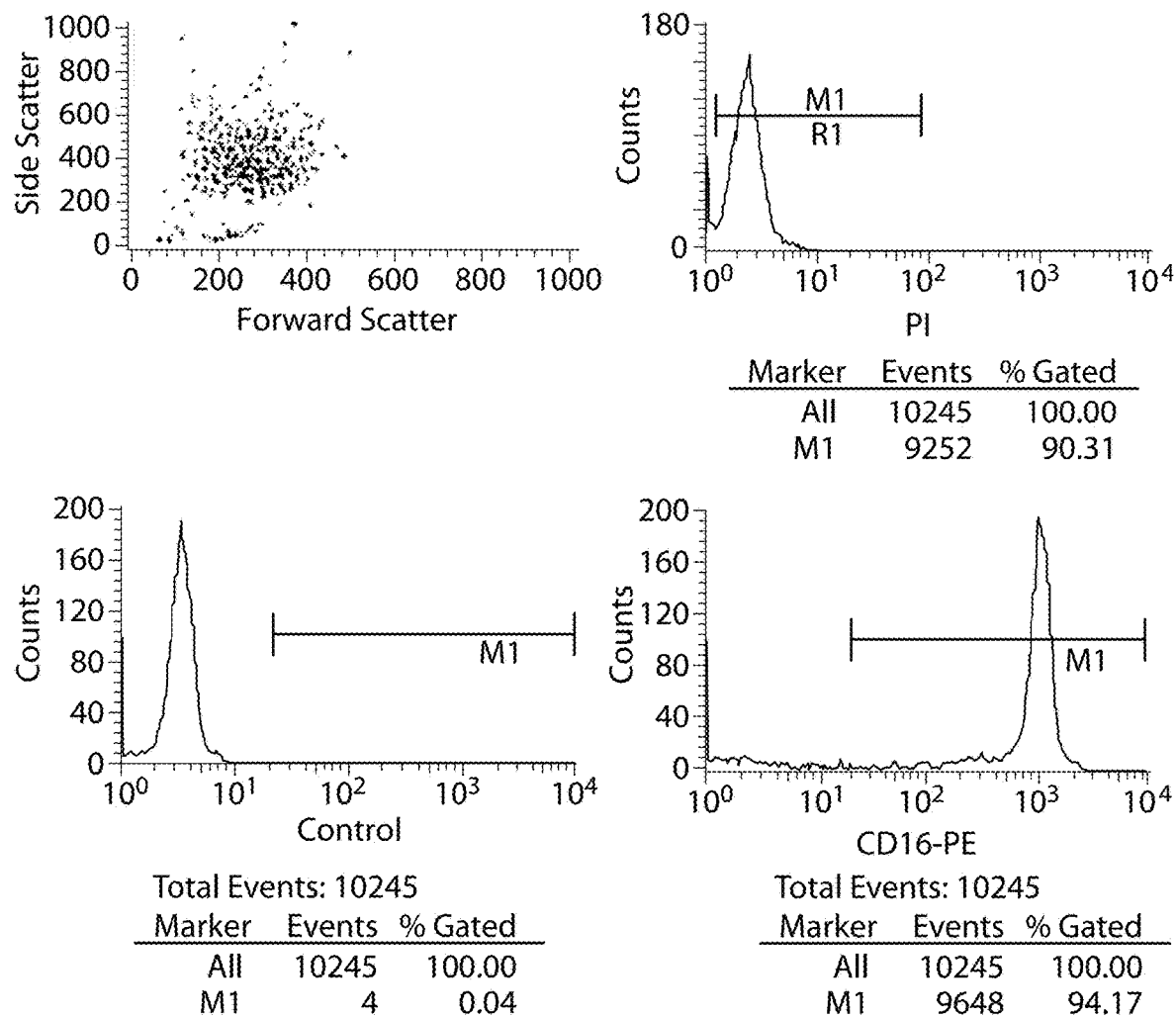
Figure 48O:
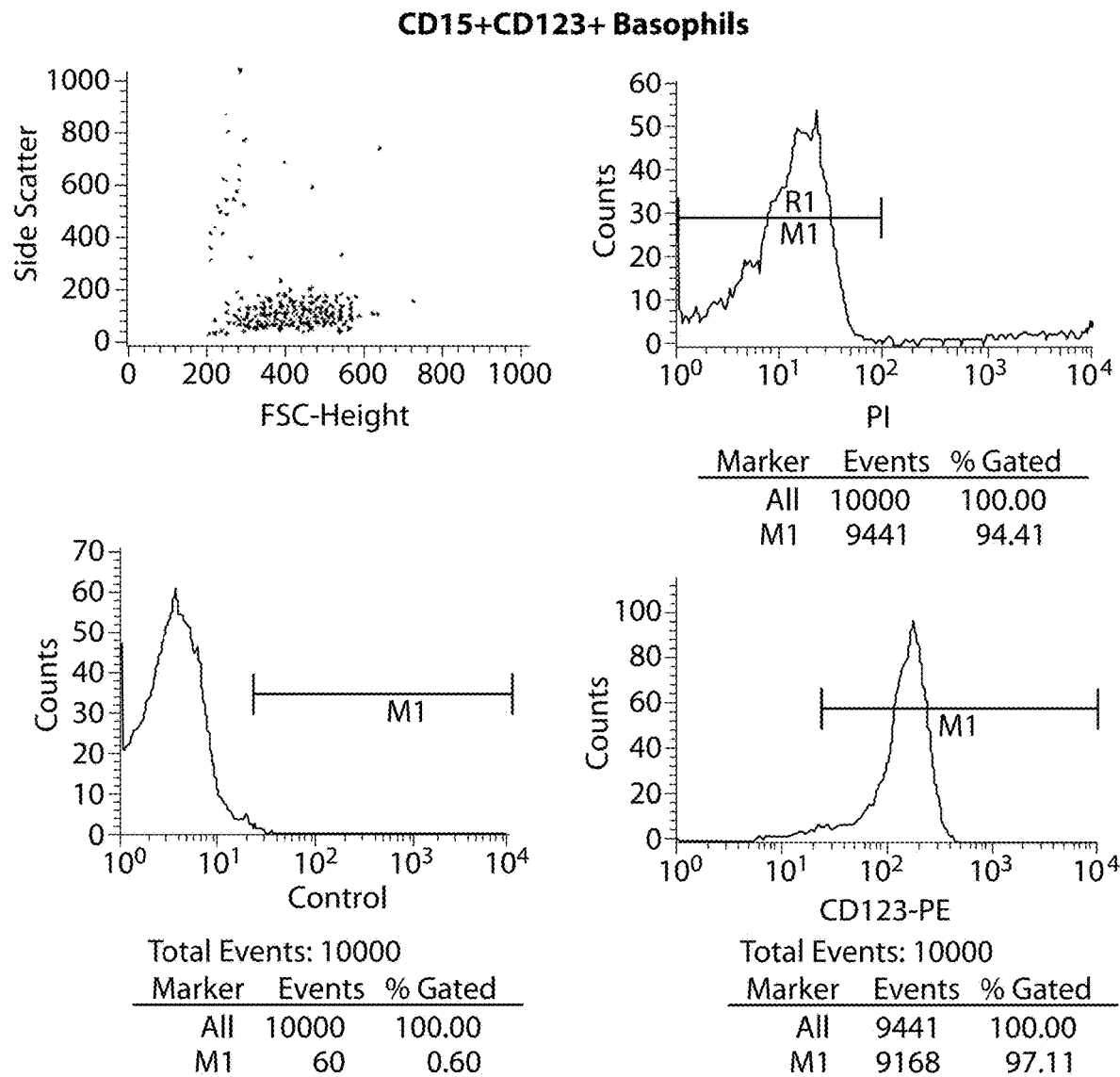
Figure 48P:
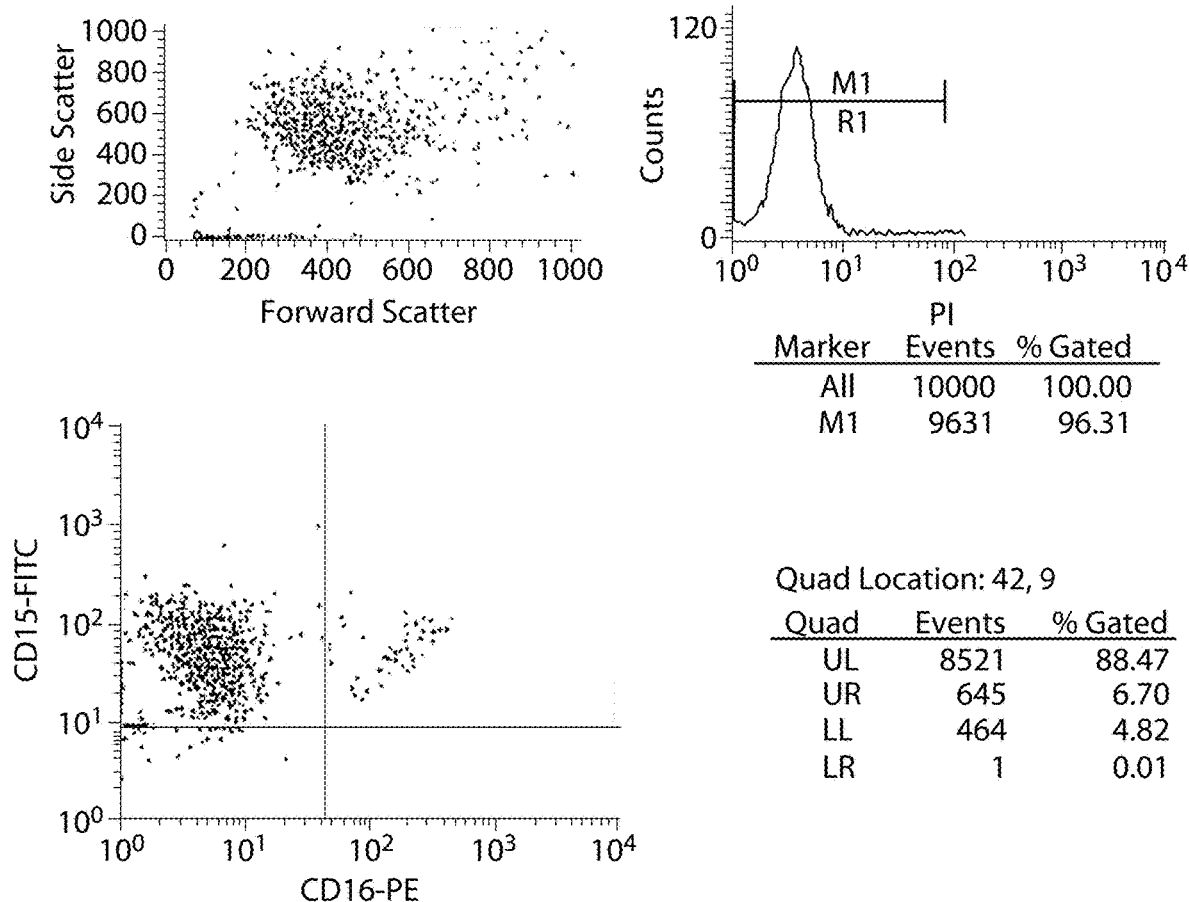

FIG. 48A-48P are a set of graphs of representative FACS results for purified WBC subsets used in examples herein. The lower right quadrant of each panel indicates sample purity. The upper right quadrant of each panel indicates the viability of the cells in the sample.

FIG. 48A is a graph of representative FACS results for purified CD3+ T lymphocytes (Pan-T cells) used in examples herein.

FIG. 48B is a graph of representative FACS results for purified CD3+CD4+ Helper T lymphocytes (Th cells) used in examples herein.

FIG. 48C is a graph of representative FACS results for purified CD3+CD8+ Cytotoxic T lymphocytes (Tc cells) used in examples herein.

FIG. 48D is a graph of representative FACS results for purified CD3+CD4+CD25+ Regulatory T-cells (Tregs) used in examples herein.

FIG. 48E is a graph of representative FACS results for purified CD3+CD56+ Natural killer T lymphocytes (NKT cells) used in examples herein.

FIG. 48F is a graph of representative FACS results for purified CD19+ B lymphocytes (B-cells) used in examples herein.

FIG. 48G is a graph of representative FACS results for purified CD56+ Natural killer cells (Pan NK cells) used in examples herein.

FIG. 48H is a graph of representative FACS results for purified CD56+CD56$^{dim}$ Natural killer cells (Effector NK cells) used in examples herein.

FIG. 48I is a graph of representative FACS results for purified CD16-CD56$^{bright}$ Natural killer cells (Regulatory NK cells) used in examples herein.

FIG. 48J is a graph of representative FACS results for purified CD8+CD56+ Natural killer cells used in examples herein.

FIG. 48K is a graph of representative FACS results for purified CD8-CD56+ Natural killer cells used in examples herein.

FIG. 48L is a graph of representative FACS results for purified CD14+ Monocytes used in examples herein.

FIG. 48M is a graph of representative FACS results for purified CD15+ Granulocytes used in examples herein.

FIG. 48N is a graph of representative FACS results for purified CD15+CD16+ Neutrophils used in examples herein.

FIG. 48O is a graph of representative FACS results for purified CD15+CD123+ Basophils used in examples herein.

FIG. 48P is a graph of representative FACS results for purified CD15+CD16− Eosinophils used in examples herein.

Figure 49:
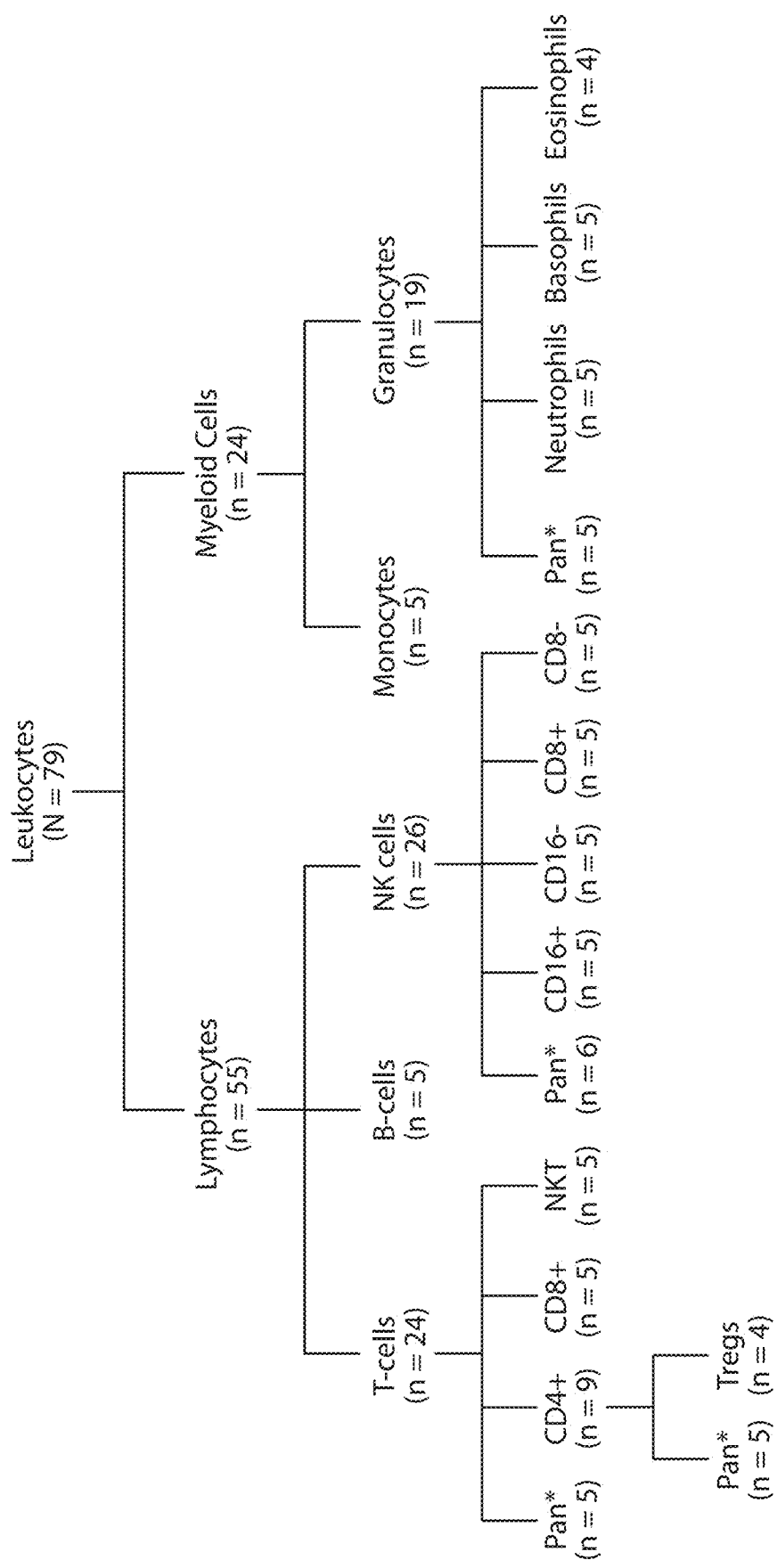

FIG. 49 is a diagram representing MACS purified WBC subset samples used to establish reference libraries of DNA methylation signatures. Terminal nodes represent the final sample cell types, which were each purified from a specimen of disease-free human blood. The tree diagram indicates the hierarchical relationship of sample cell lineages. Pan* samples were not subsequently selected in the MACS separation process, and therefore contained a biological mixture of subsets within the cell type immediately above them in the tree.

Figure 50:
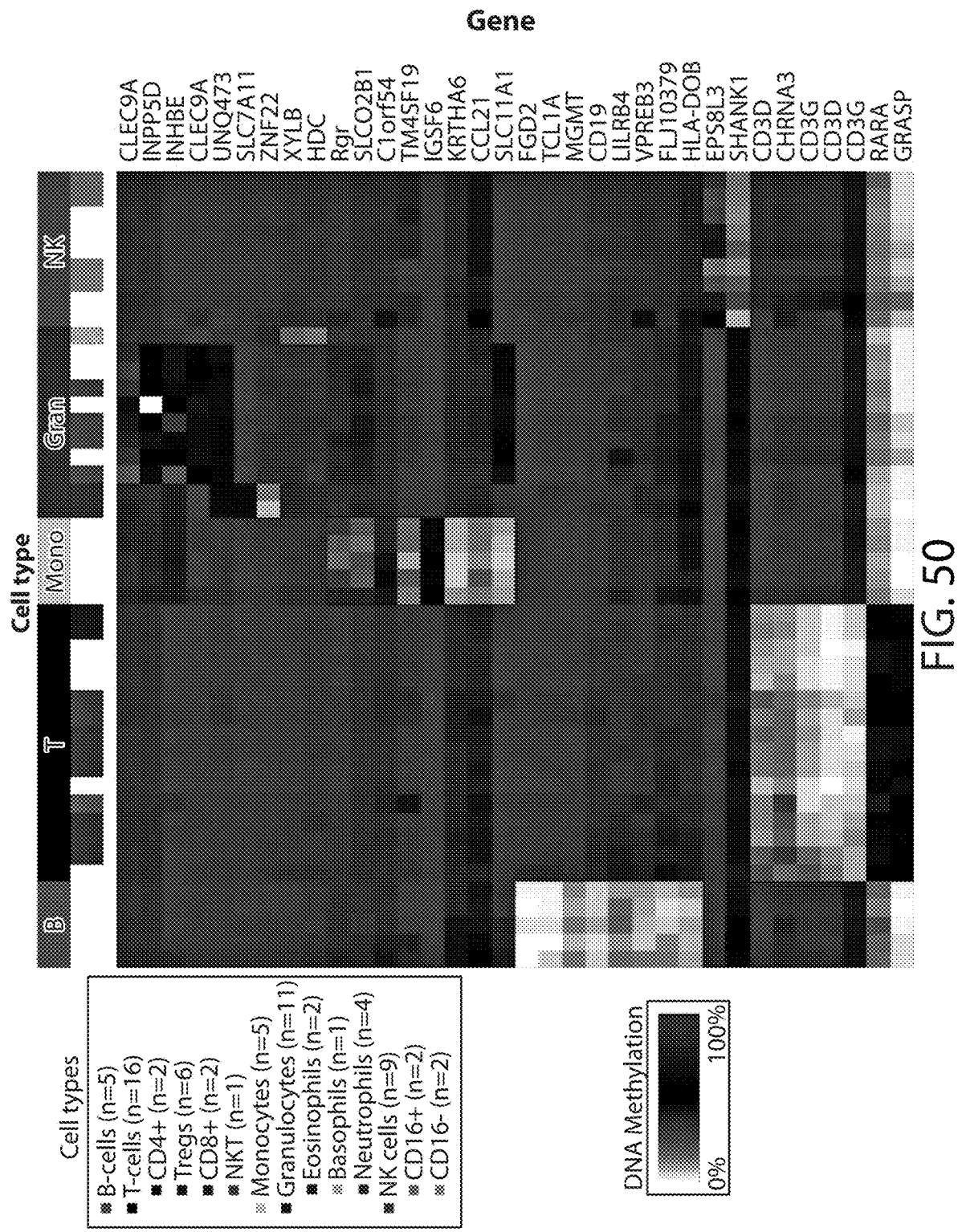

FIG. 50 is a photograph of a clustering heatmap for WBC lineage-specific DNA methylation. DNA methylation signatures distinguishing normal human leukocyte subtypes were obtained using a high-density DNA methylation microarray. Purified WBC subset samples are displayed in FIG. 50 in columns with cell type indicated at the bottom on the x-axis. Individual CpG loci are displayed in rows with the gene containing each locus indicated to the right on the y-axis. Methylation values from completely unmethylated (represented by gray areas) to completely methylated (represented by dark areas) are indicated in the key at the bottom left. Samples and loci were organized according to unsupervised hierarchical clustering.

Figure 51:
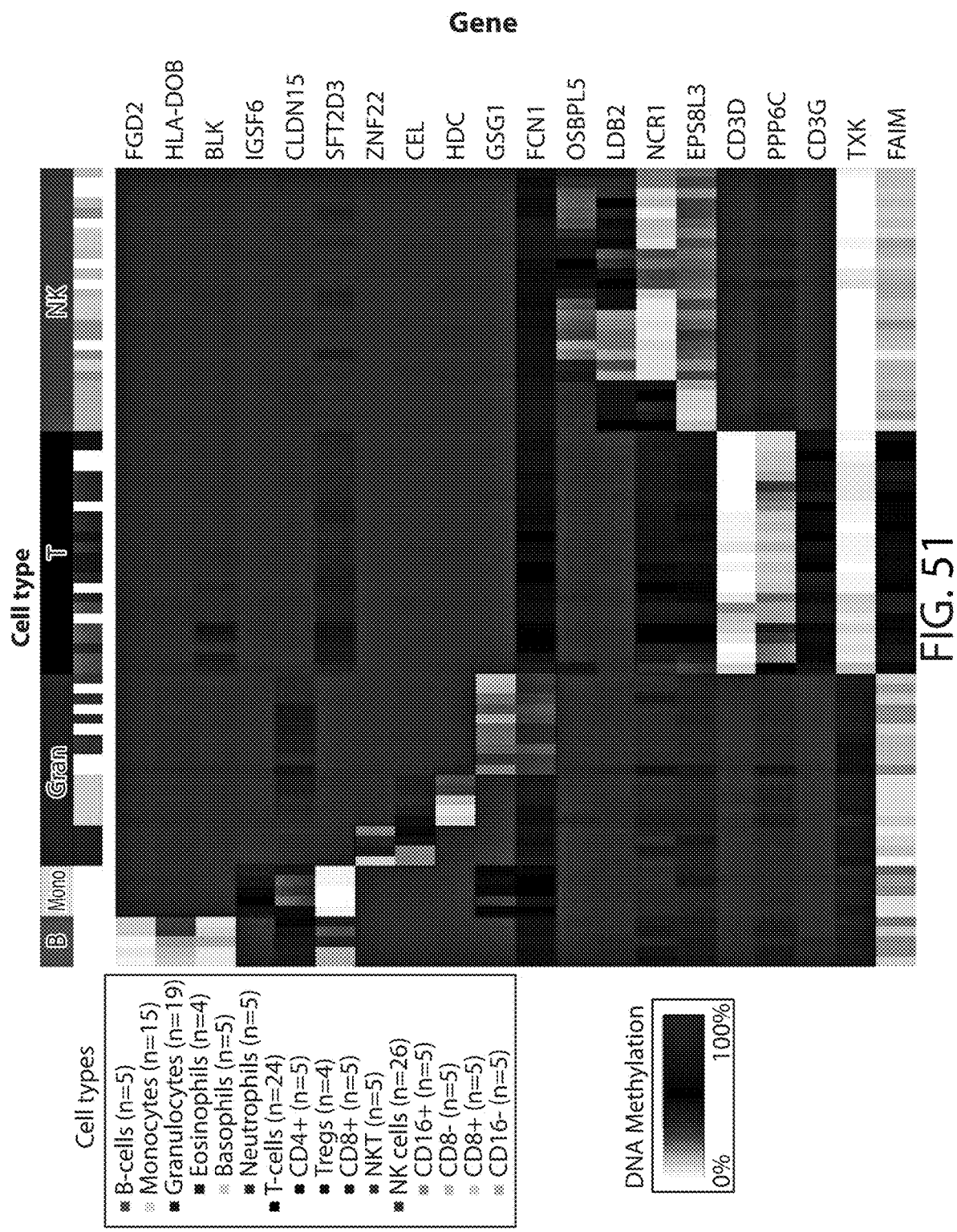

FIG. 51 is a photograph of DNA methylation signatures distinguishing normal human leukocyte subtypes that was obtained using custom, low-density DNA methylation microarray. Purified WBC subset samples are displayed in FIG. 51 in columns with cell type indicated at the bottom on the x-axis. Individual CpG loci are displayed in rows with the gene containing each locus indicated to the right on the y-axis. Methylation values from completely unmethylated (represented by gray areas) to completely methylated (represented by dark areas) are indicated in the key at the bottom left. Samples and loci were organized according to unsupervised, hierarchical clustering.

Figure 52:
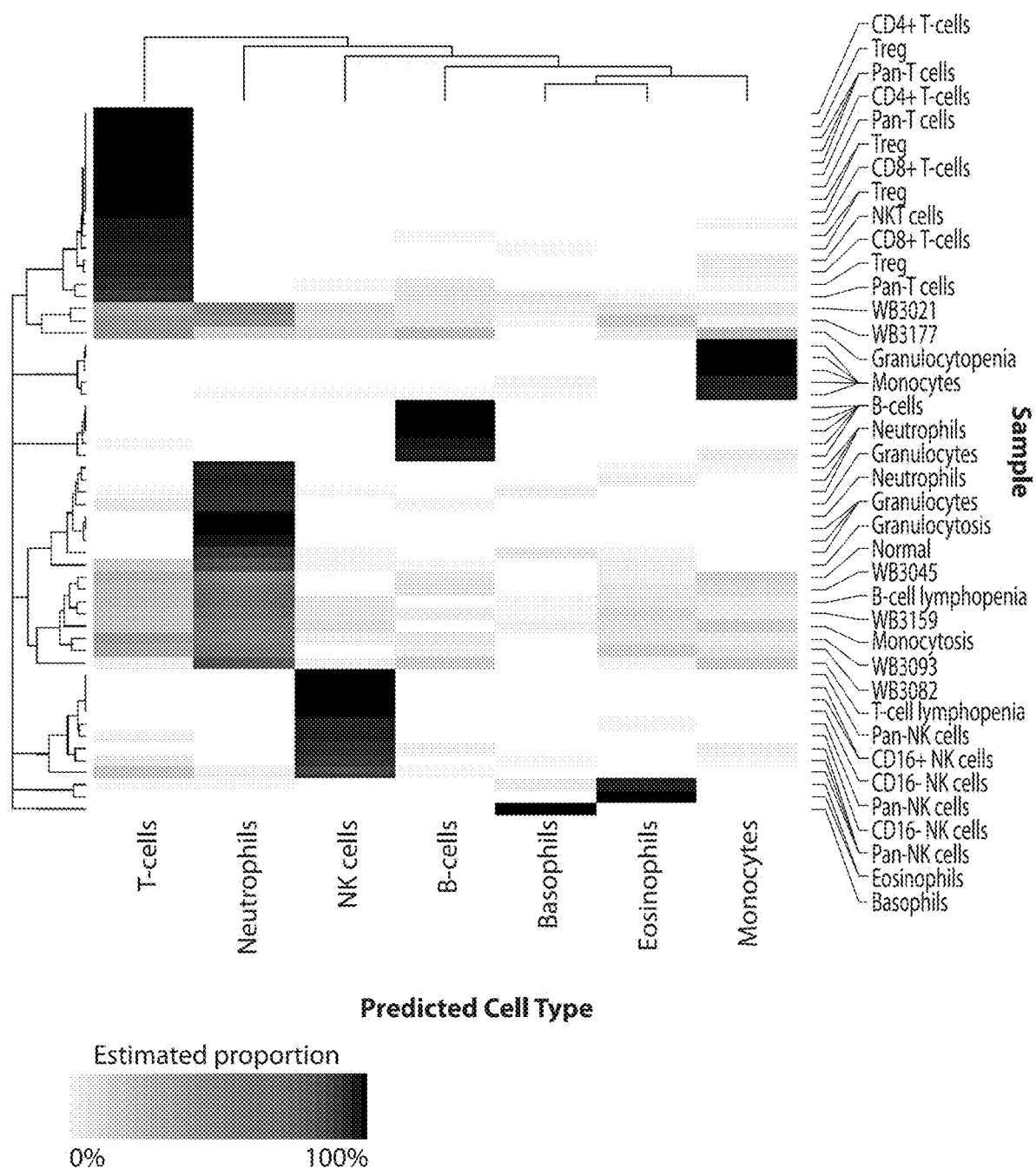

FIG. 52 is a photograph of a crosscheck of purified WBC subset samples that was obtained using on a high density DNA methylation microarray. The quantity of each of seven WBC subsets (displayed on the abscissa) was predicted in the purified WBC subset samples using DNA methylation. The true identity of each purified WBC subset sample is shown on the ordinate, as indicated to the right. Saturation of the interior bins indicate the estimated proportions of WBC subsets, determined using DNA methylation, in purified WBC subset samples, as shown in the key at the bottom right.

Figure 53:
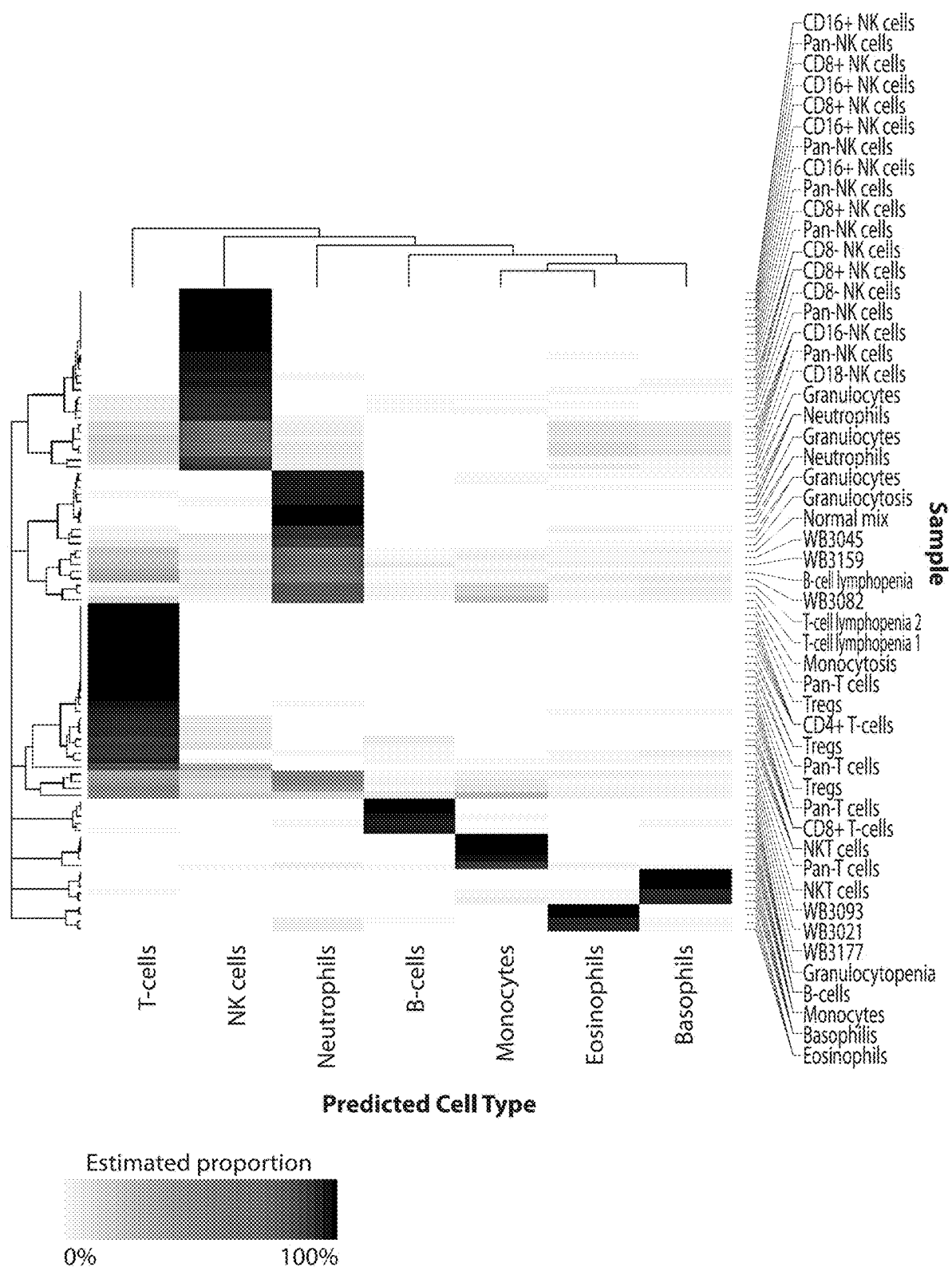

FIG. 53 is a photograph of a crosscheck of purified WBC subset samples that was obtained using a custom, low-density DNA methylation microarray. The quantity of each of seven WBC subsets (displayed on the abscissa) was predicted in the purified WBC subset samples using DNA methylation. The true identity of each purified WBC subset sample is shown on the ordinate, as indicated to the right. Saturation of the interior bins indicate the estimated proportions of WBC subsets, determined using DNA methylation, in purified WBC subset samples, as shown in the key at the bottom right.

Figure 54A:
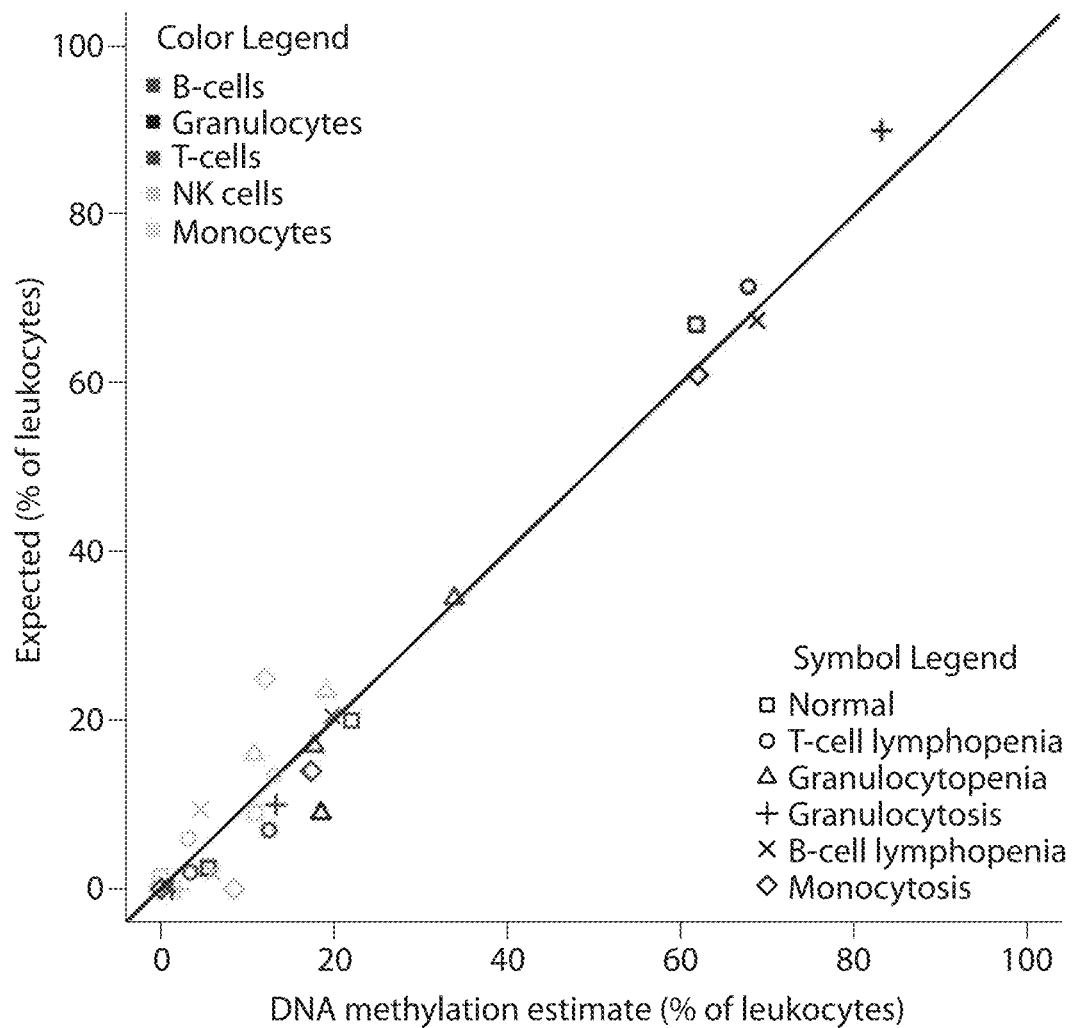
Figure 54B:
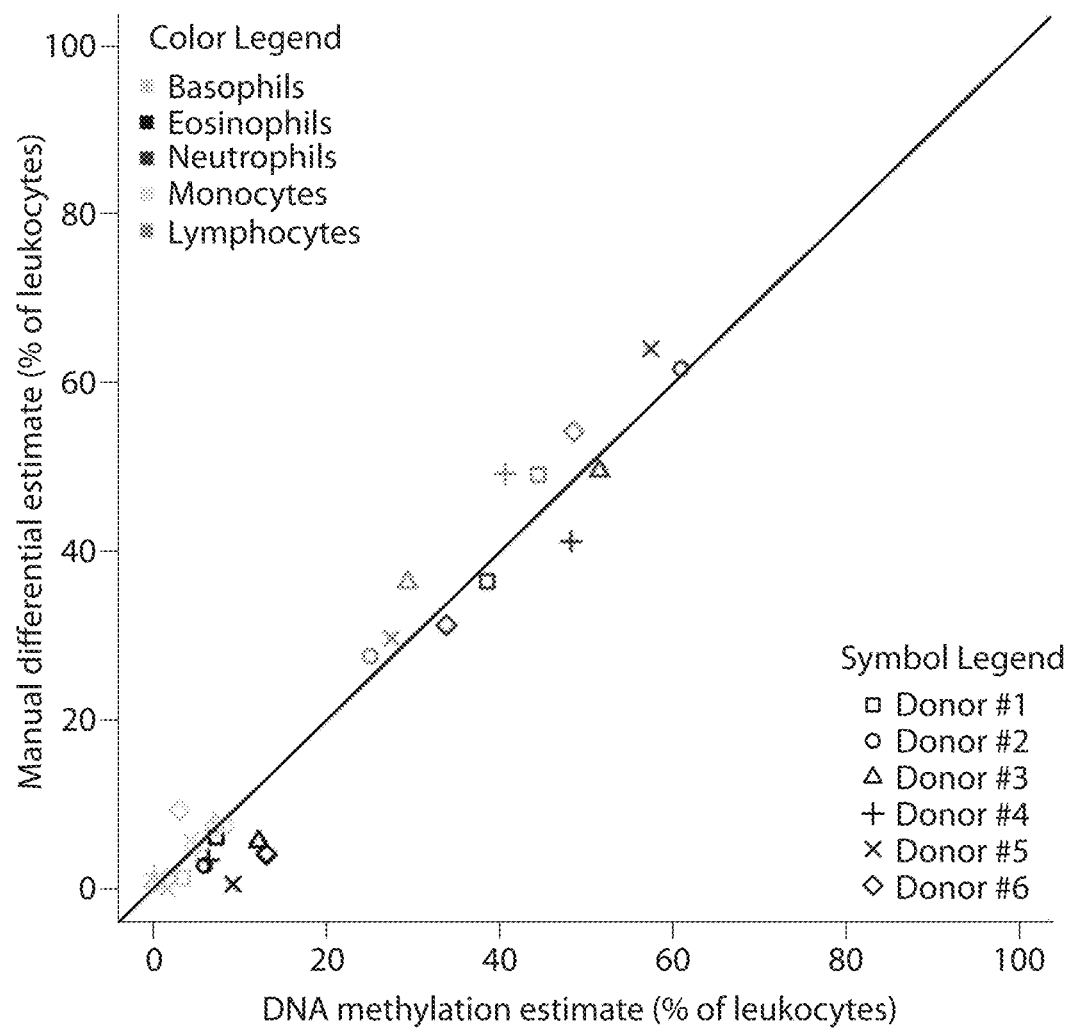
Figure 54C:
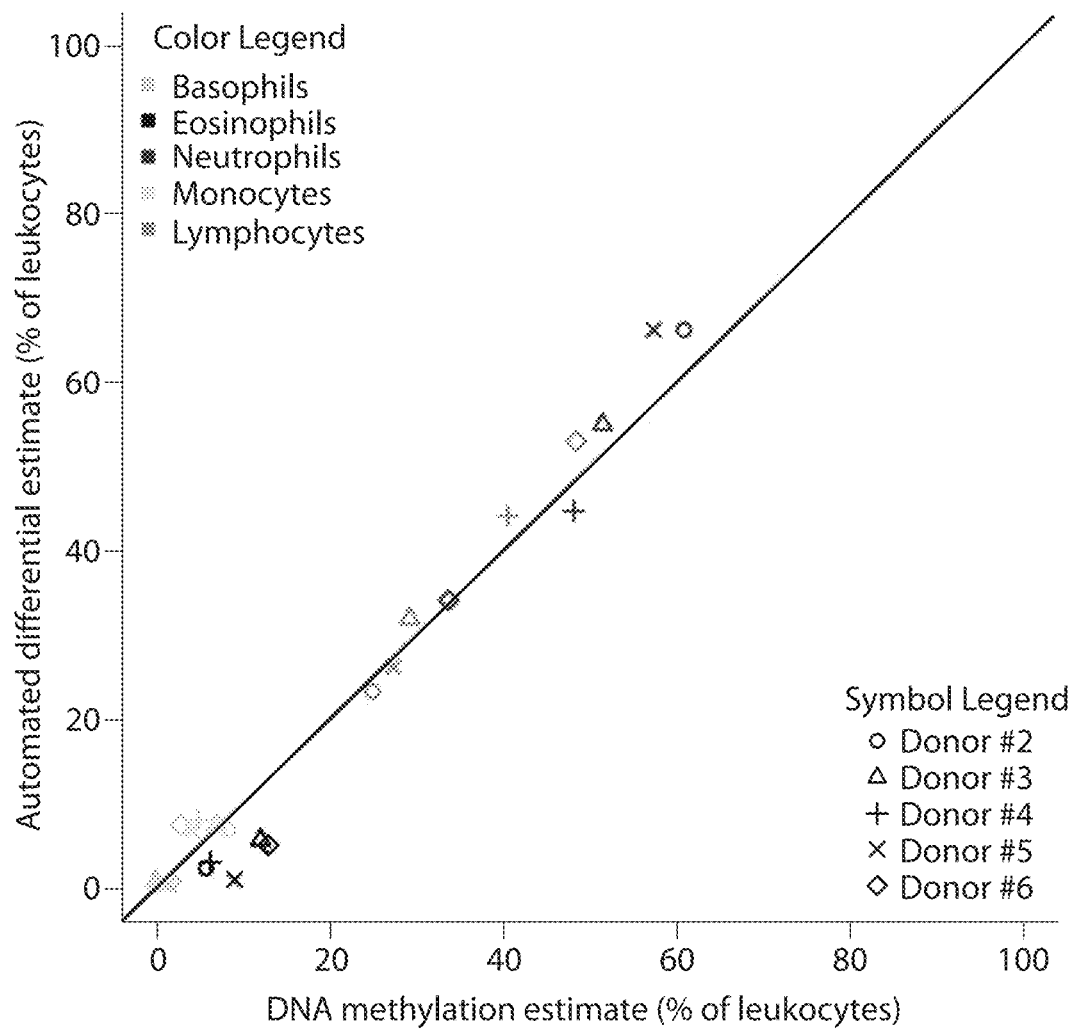
Figure 54D:
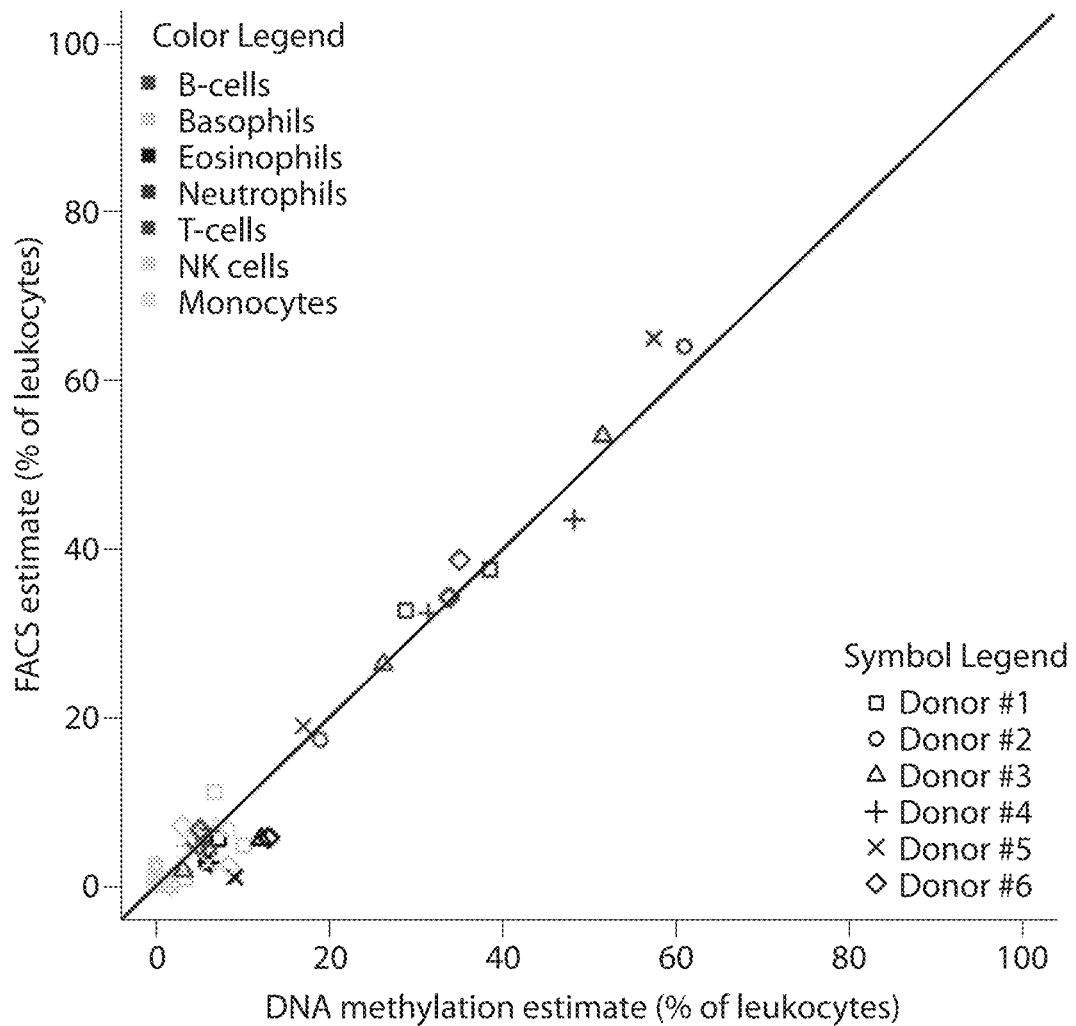

FIG. 54A-D are graphs showing quantitative reconstructions of leukocyte subsets that were obtained using a high density DNA methylation microarray. In FIG. 54A-D, the abscissa displays quantities of specific WBC subsets determined using DNA methylation. Cell type is indicated by color (light and dark grays) and sample type is indicated by shapes listed in the insets. Lines are from the origin having a slope of one indicating ideal correspondence between the displayed values in each panel. FIG. 54A contains data for DNA from purified WBC subsets that were combined in quantities mimicking human blood under clinical conditions. The expected quantity of each cell type is plotted on the ordinate. Whole blood samples from disease-free human donors were subjected to WBC subset quantification by the described methods. The granulocytes were observed to be the highest percentage of the leukocytes (50-60%) compared to B-cells, T cells, NK cells and monocytes (less than about 40%). FIG. 54B-D are graphs of data for whole blood samples from disease-free human donors subjected to WBC subset quantification by established methods: manual 5-part differential (FIG. 54A); automated 5-part differential (FIG. 54B); and FACS (FIG. 54D). It was observed that the five WBC quantitations measured using DNA methylation were very close to the values expected by other methods. In FIG. 54B-D, the neutrophils had the highest percentage of leukocytes (50-60%) compared to cell types lymphocytes, monocytes, and B cells. The methods herein detected specific, clinically relevant modulations in peripheral blood immune cell composition.

Figure 55A:
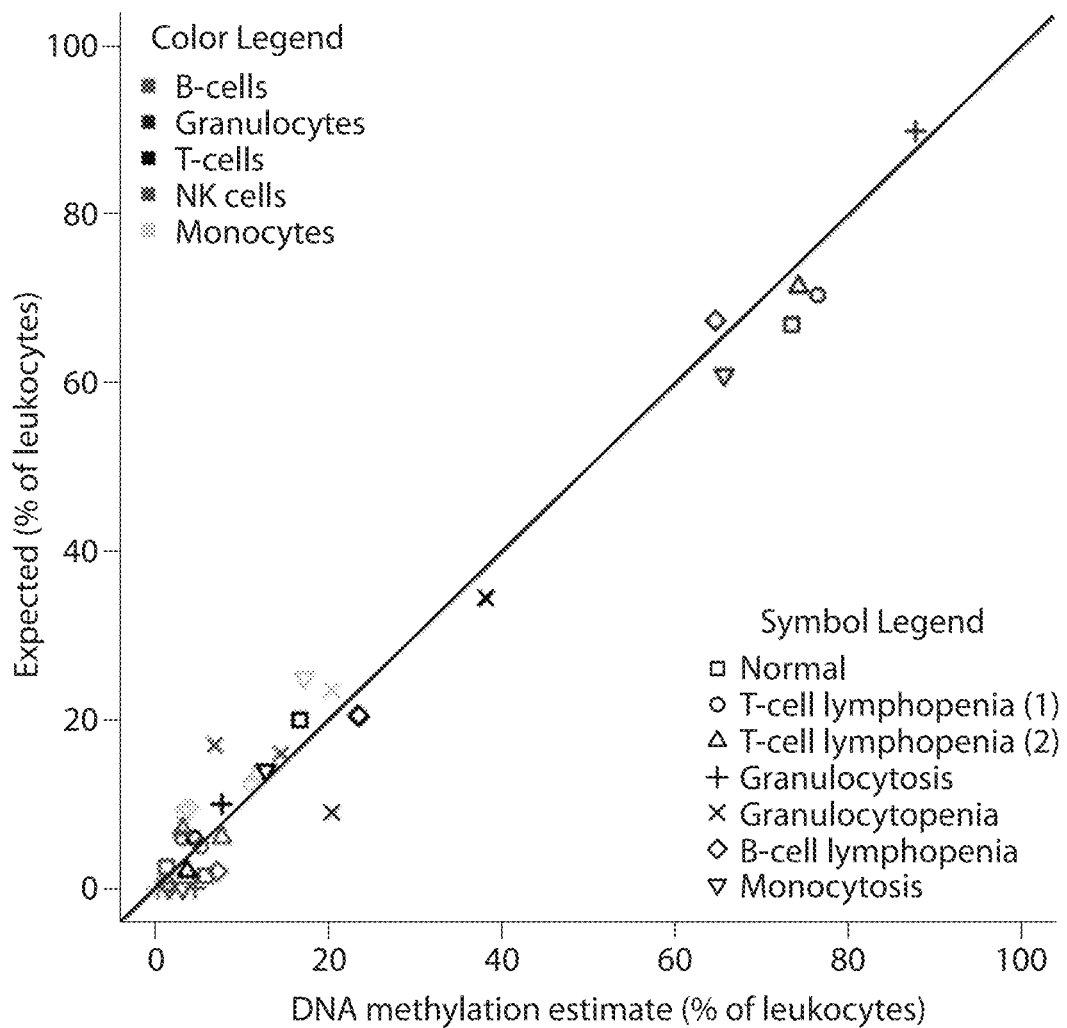
Figure 55B:
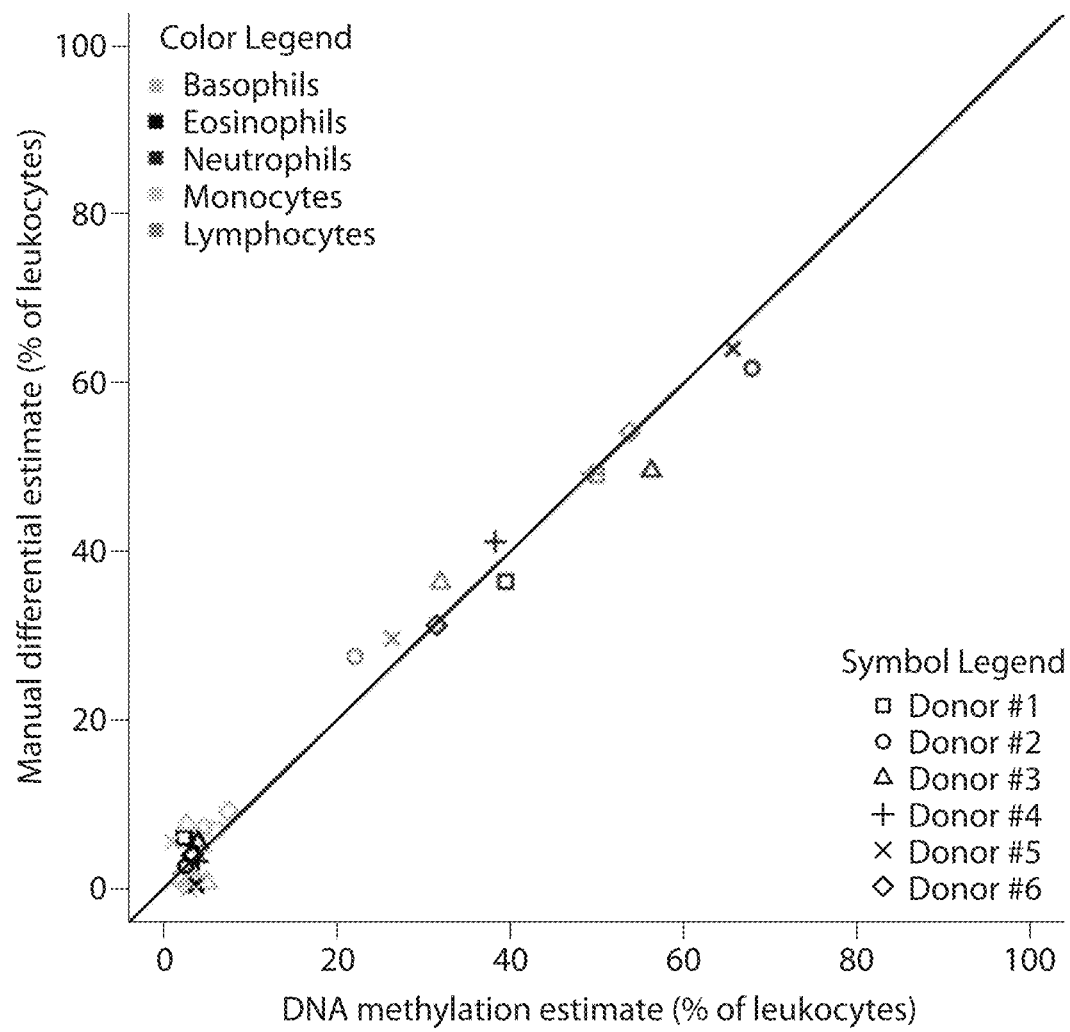
Figure 55C:
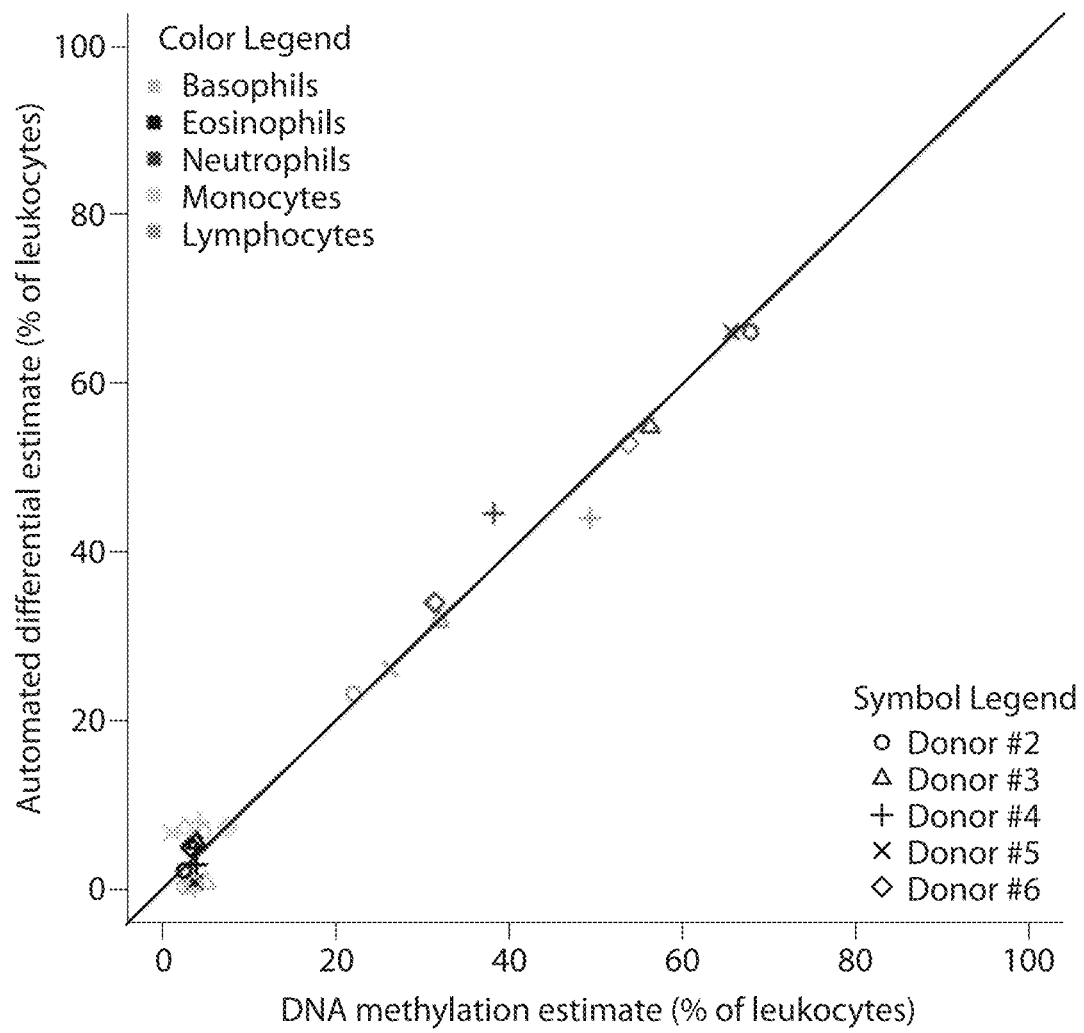
Figure 55D:
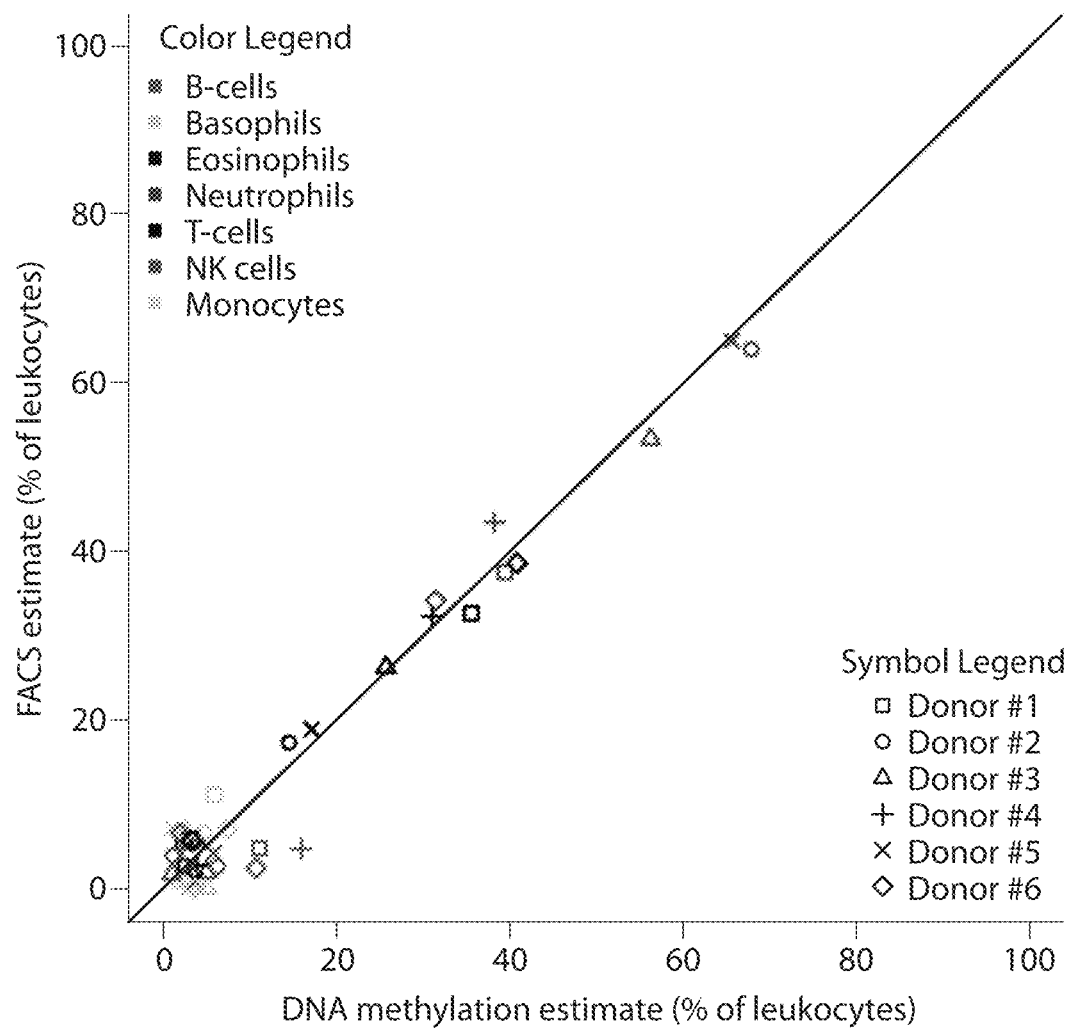

FIG. 55A-D are a set of graphs of quantitative reconstruction of leukocyte subsets using a custom, low density DNA methylation microarray. The abscissa indicates the quantities of specific WBC subsets determined using DNA methylation. Cell type is indicated by shading and sample type is indicated by shape of the datum point, as described in the inset legends. Lines are drawn from the origin with a slope of one indicating ideal correspondence between the displayed values in each panel. The expected quantity of each cell type is indicated by the ordinate. FIG. 55A is a graph of DNA from purified WBC subsets that were combined in quantities mimicking human blood under 19 clinical conditions. In FIG. 55 A the granulocytes contained the highest percentage of leukocytes (50-60%) compared to B-cells, T cells, NK cells and monocytes (less than about 20%). FIG. 55B-D are graphs of data for whole blood samples from disease-free human donors subjected to WBC subset quantification by the following methods: manual 5-part differential (FIG. 55A); automated 5-part differential (FIG. 55B); and FACS (FIG. 55D). In FIG. 54B-D, the neutrophils were observed to have the highest percentage of leukocytes (about 60%) compared to other cell types including lymphocytes, monocytes, eosinophils, basophils, T cells, NK cells, and B cells.

Figure 56A:
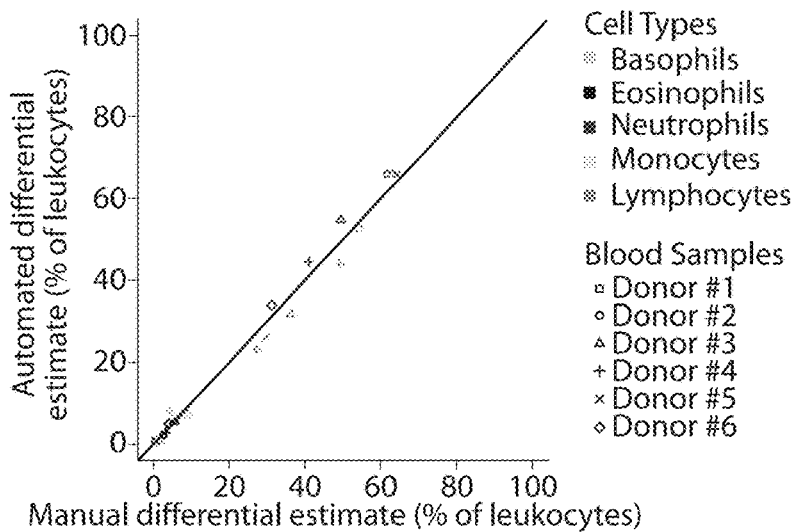
Figure 56B:
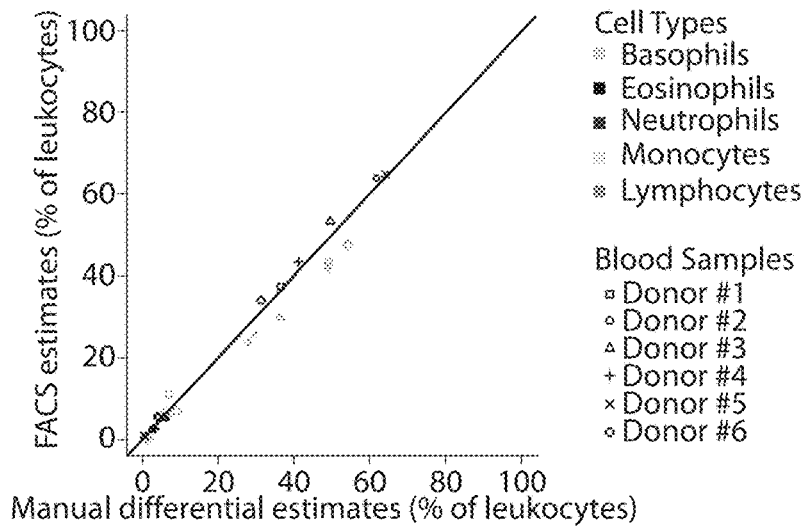
Figure 56C:
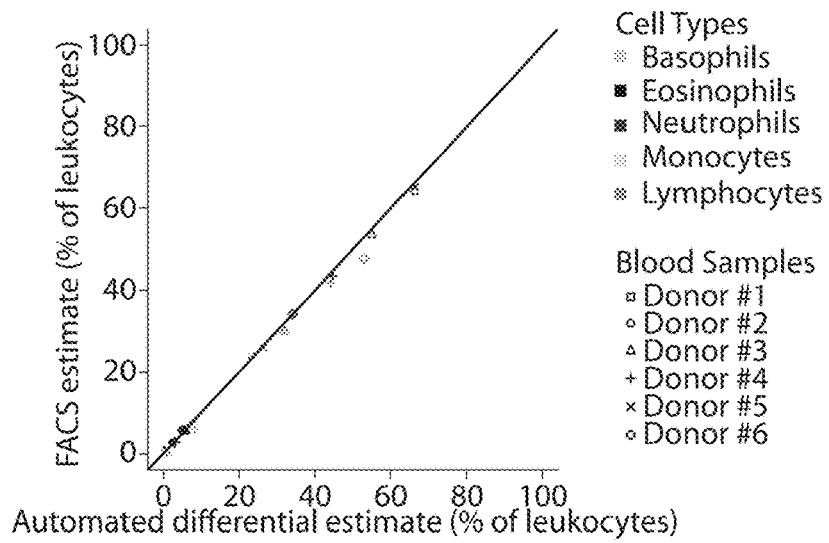

FIG. 56A-C are a set of graphs of comparisons of conventional immune cell quantification methods. Cell type is indicated by shading and disease-free human blood donor is indicated by shape of the point, as described in the legends to the right. Lines are drawn from the origin. A slope of one indicates ideal correspondence between the displayed values in each panel. The following methods were compared: manual 5-part differential and CBC with automated 5-part differential (FIG. 56A); manual 5-part differential and FACS (FIG. 56B); and CBC with automated 5-part differential and FACS (FIG. 56C).

Figure 57A:
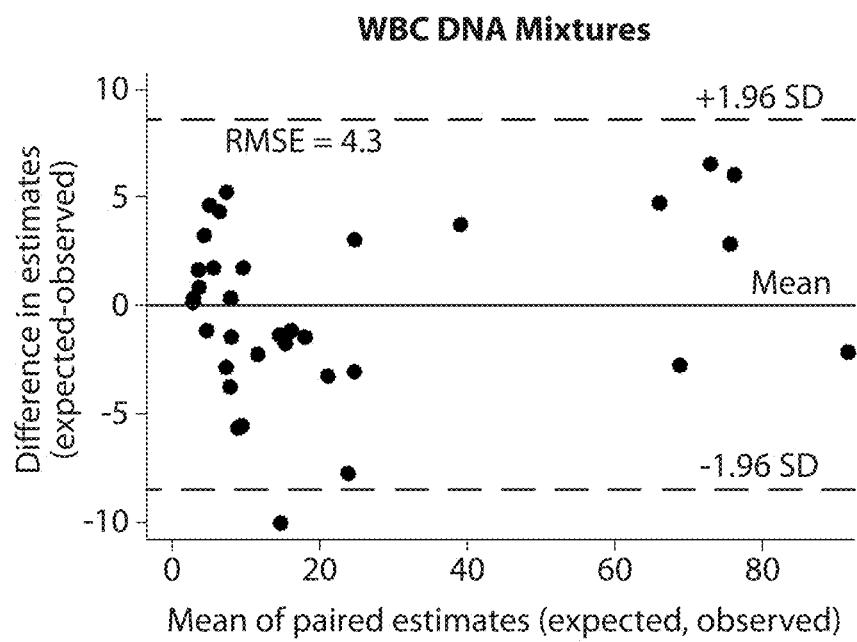
Figure 57B:
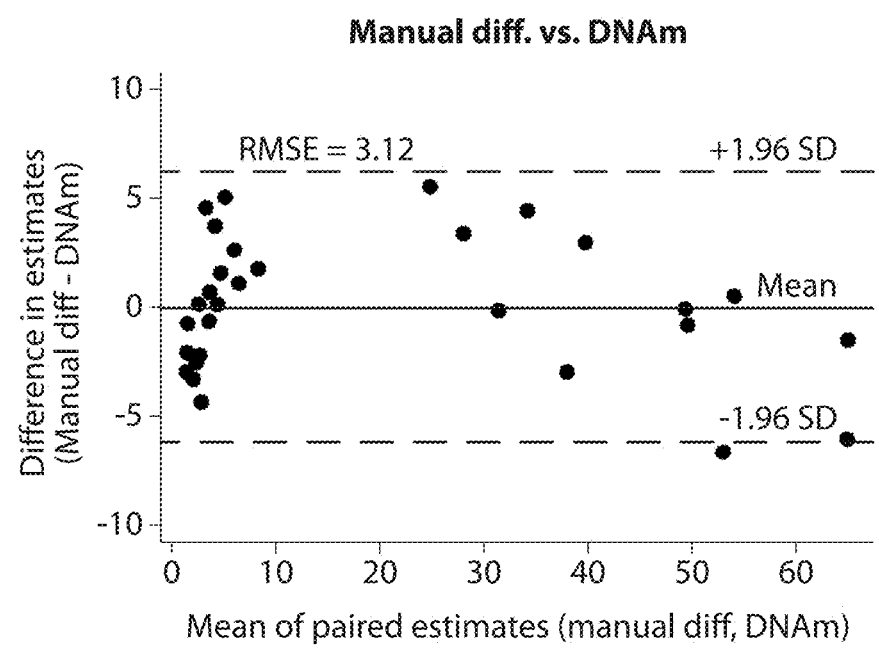
Figure 57C:
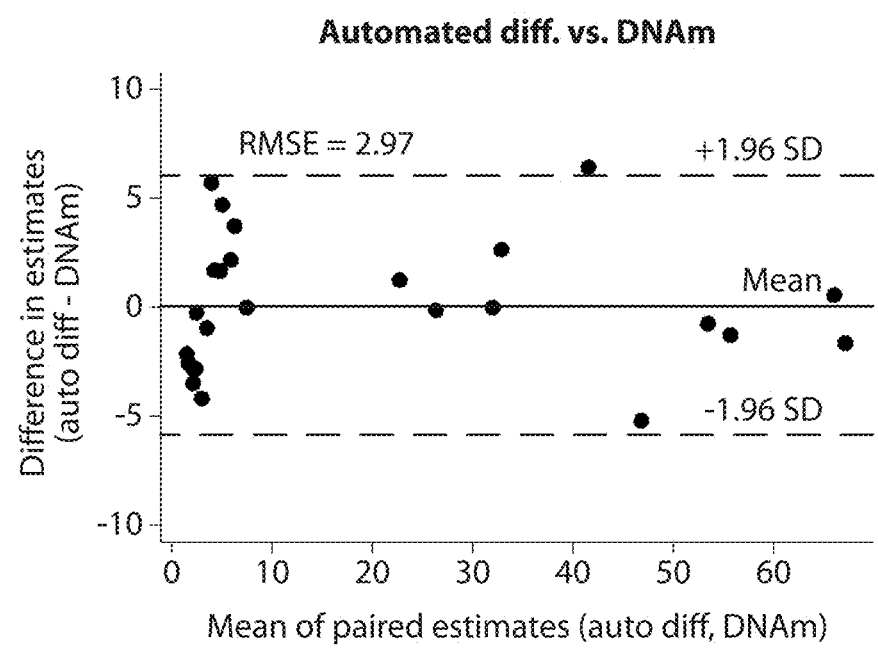
Figure 57D:
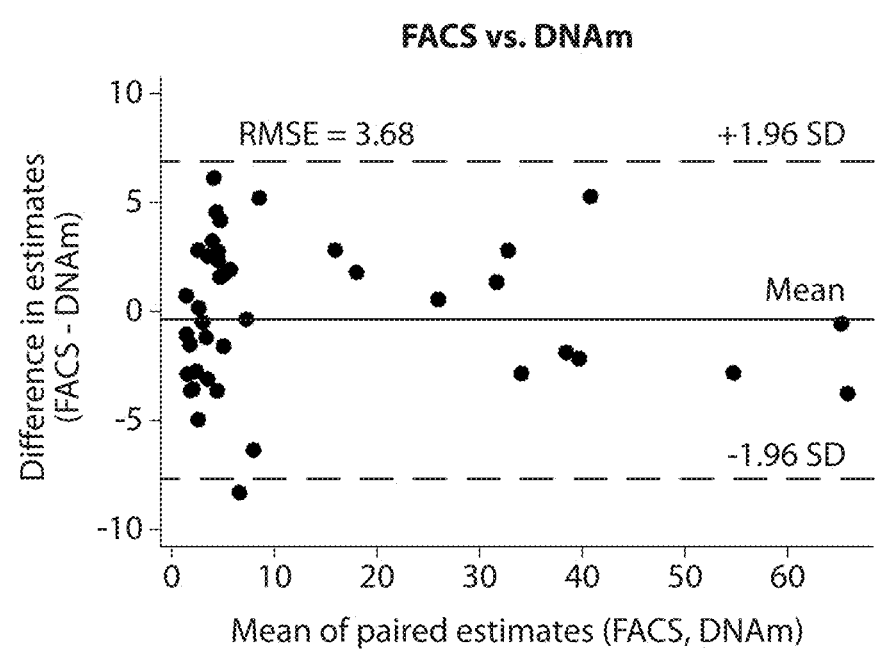
Figure 57E:
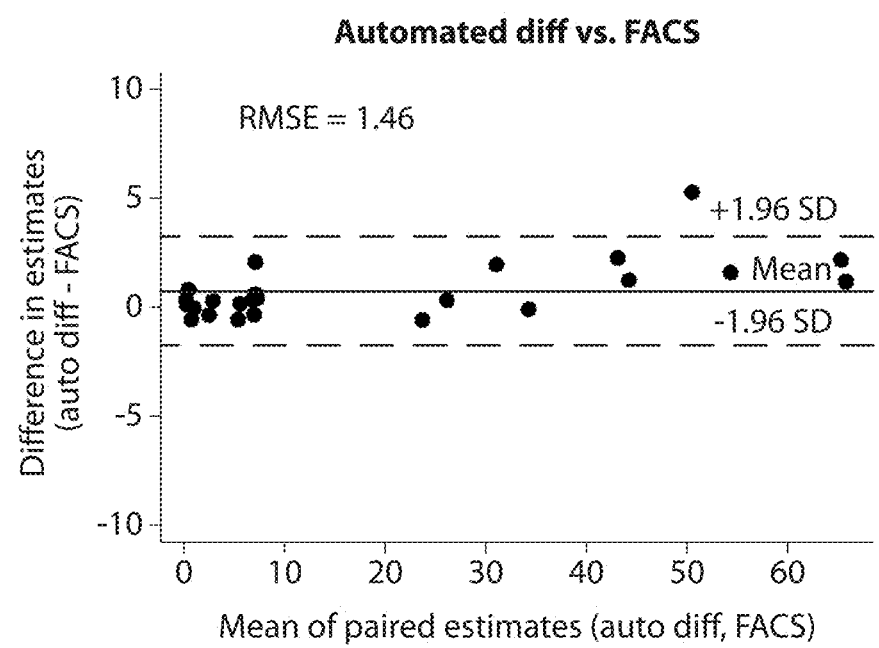
Figure 57F:
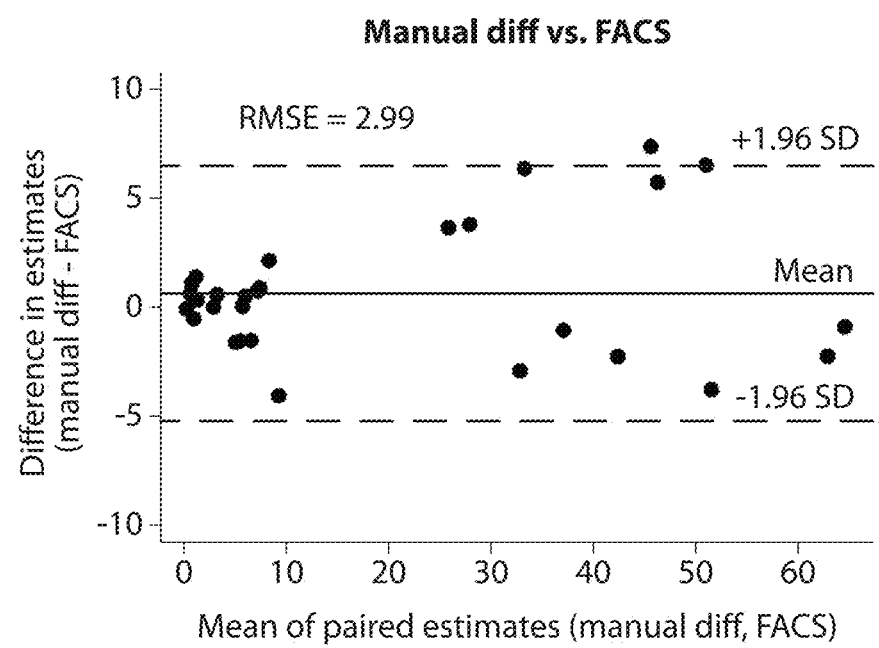
Figure 57G:
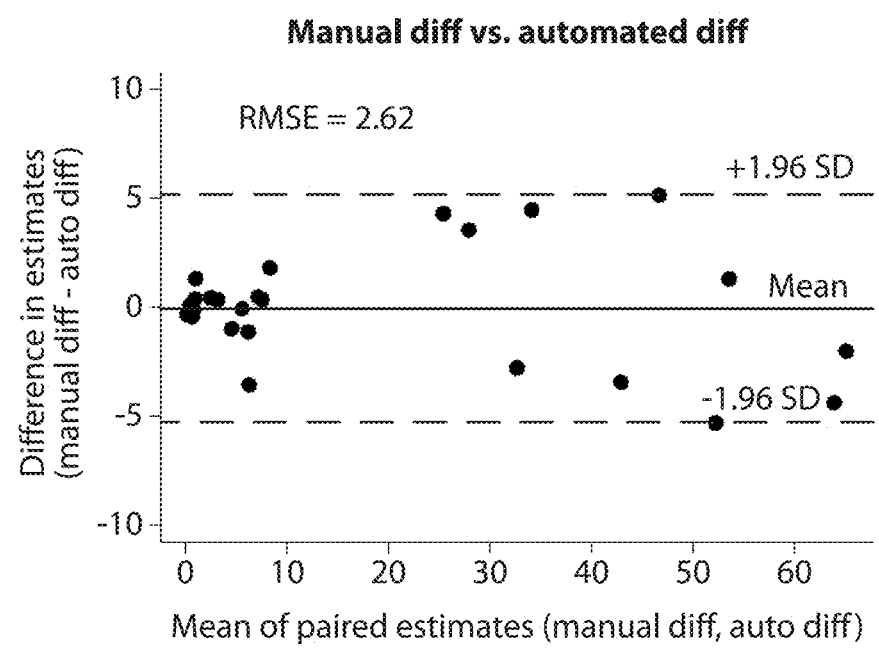

FIG. 57A-F are a set of graphs showing Bland-Altman agreement of immune cell quantification methods/assays applied to whole blood samples from disease free human donors. Each data point corresponds to one WBC subset in one blood sample. The mean WBC subset quantity (percent)

determined by the two methods is indicated by the abscissa and the difference between the WBC subset quantities (percent) determined by the two given methods is indicated by the ordinate. The root-mean-square-error (RMSE) value between the two given methods is shown at the top left, in units of WBC subset quantity (percent). The data in FIG. 57A show agreement between measurements obtained from the Low Density Methylation Microarray (LDMA) DNA methylation and known amounts of each of the cell types in laboratory constructed DNA mixtures. FIG. 57B-D contain data that indicate agreement between immune cell quantification using DNA methylation (DNAm) from the custom, low-density DNA methylation microarray and either: manual 5-part differential (FIG. 57B); CBC with automated 5-part differential (FIG. 57C), and FACS (FIG. 57D). FIG. 57E-G contain data that indicate agreement among the following immune cell quantification methods: CBC with automated 5-part differential and FACS (FIG. 57E); manual 5-part differential and FACS (FIG. 57F); and manual 5-part differential and CBC with automated 5-part differential (FIG. 57G).

Figure 58:
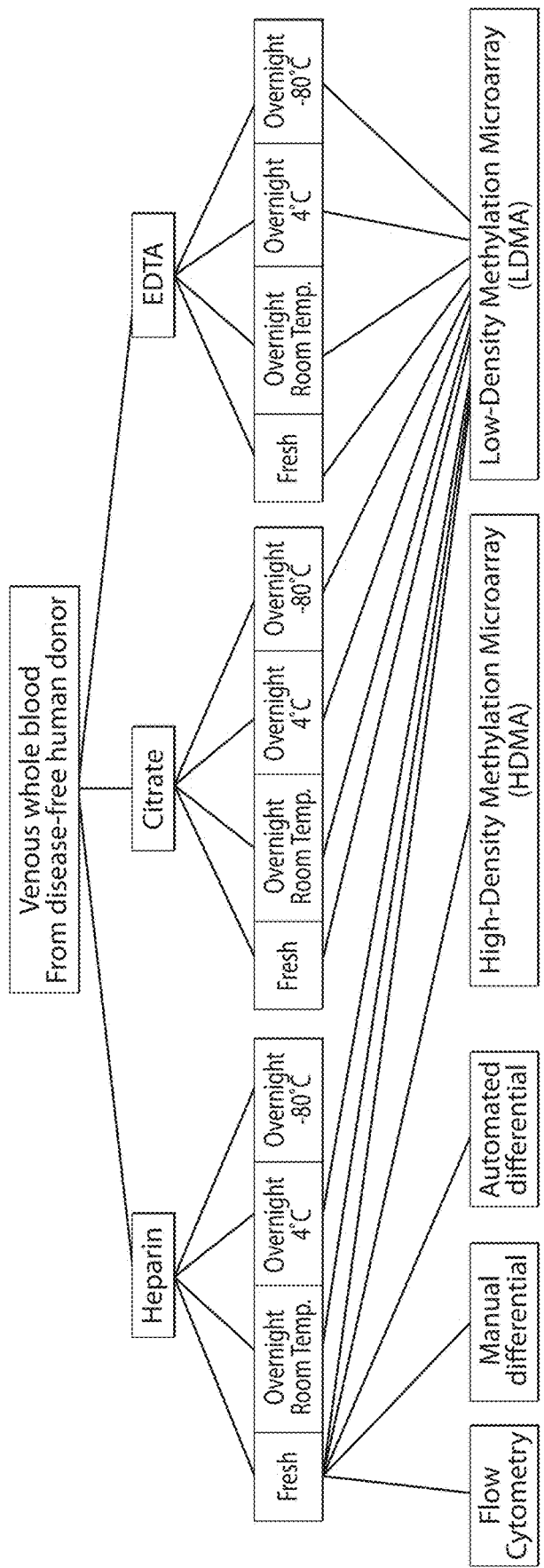

FIG. 58 is a diagram showing details of workflow followed in methods herein for whole blood samples from disease-free human donors. The samples were subjected to following methods of WBC subset quantification to compare to quantitative reconstruction of WBC subsets using DNA methylation by the methods herein. Venous whole blood was collected from a disease free human donor and aliquots of the sample were contacted with heparin, citrate, or EDTA. Each of the heparin, citrate, or EDTA samples was maintained either as a fresh sample or as a sample stored overnight at room temperature, 4° C., or at −80° C. The heparin fresh sample was analyzed for WBC subsets by using flow cytometry, manual differential WBC counting, automated differential WBC counting, a high density methylation microarray (HDMA), or a low-density methylation microarray (LDMA). The other samples including the citrate and EDTA fresh samples or as samples stored overnight at one of room temperature, 4° C., or −80° C., and the heparin samples stored overnight at room temperature, 4° C., or −80° C. were each analyzed for WBC subsets using the HDMA and LDMA.

Figure 59A:
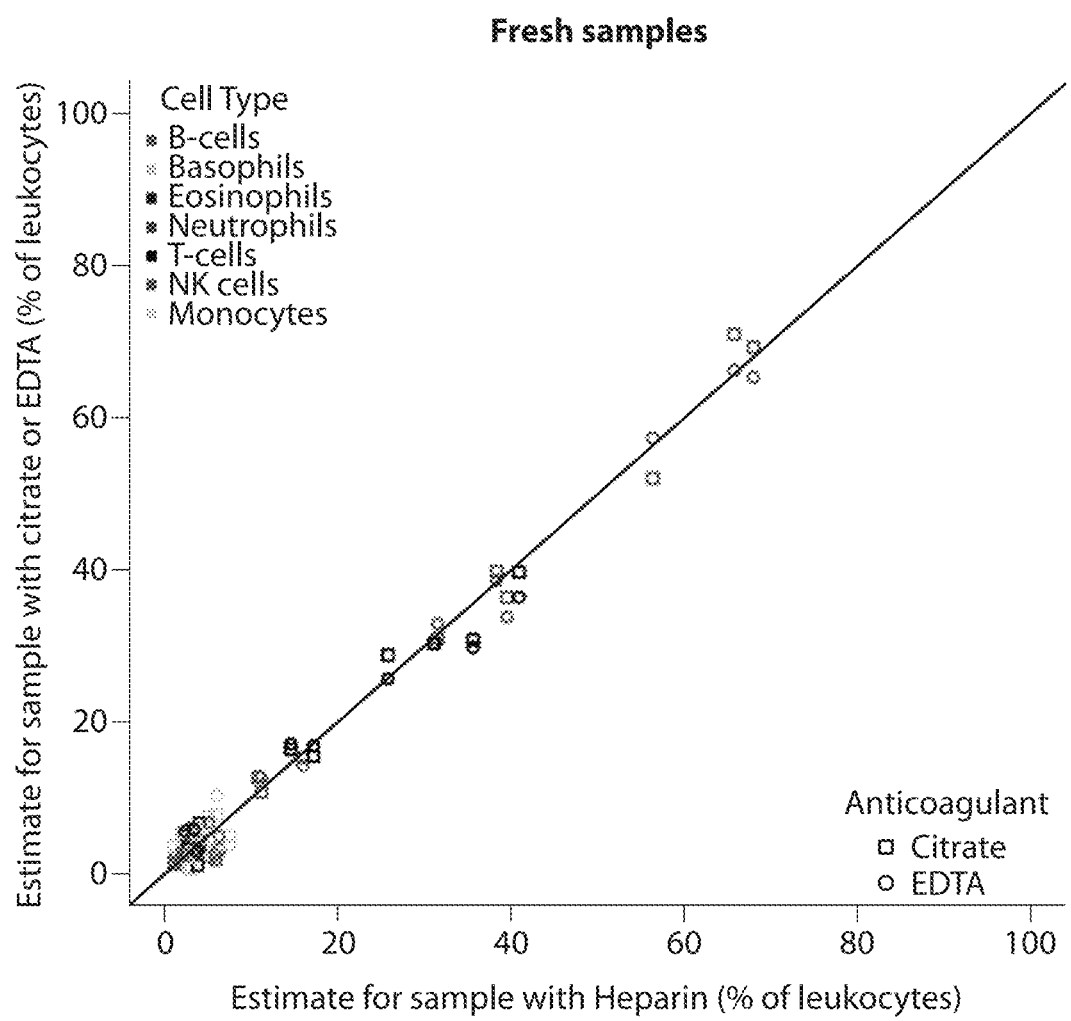
Figure 59B:
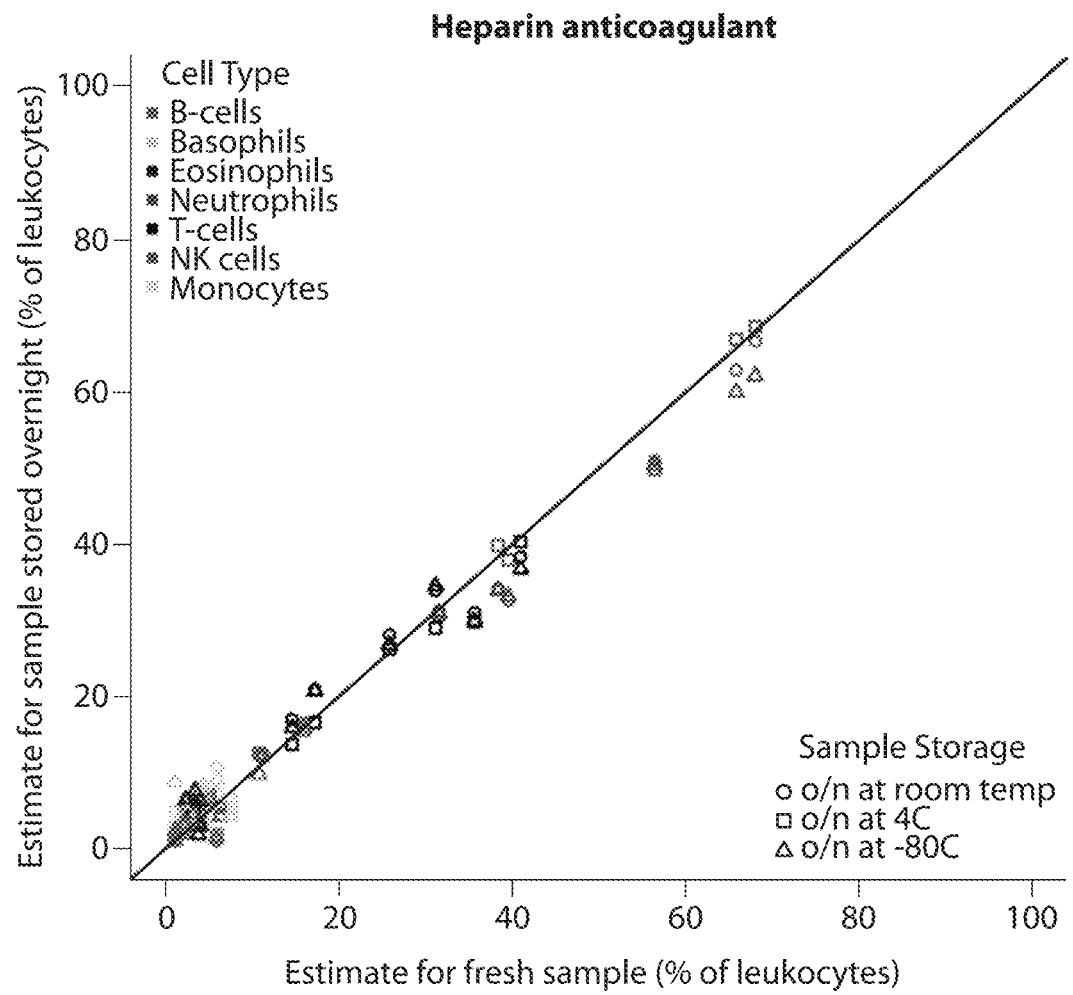
Figure 59C:
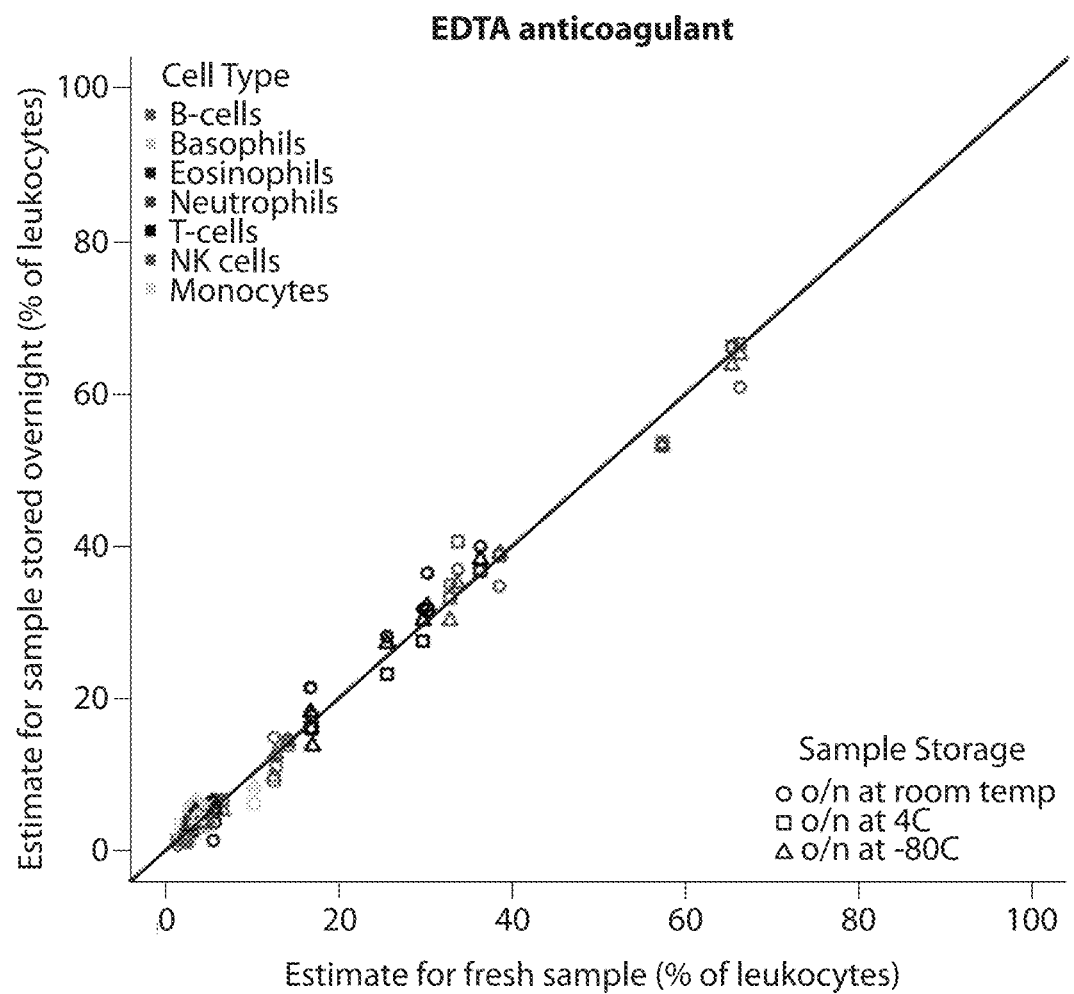
Figure 59D:
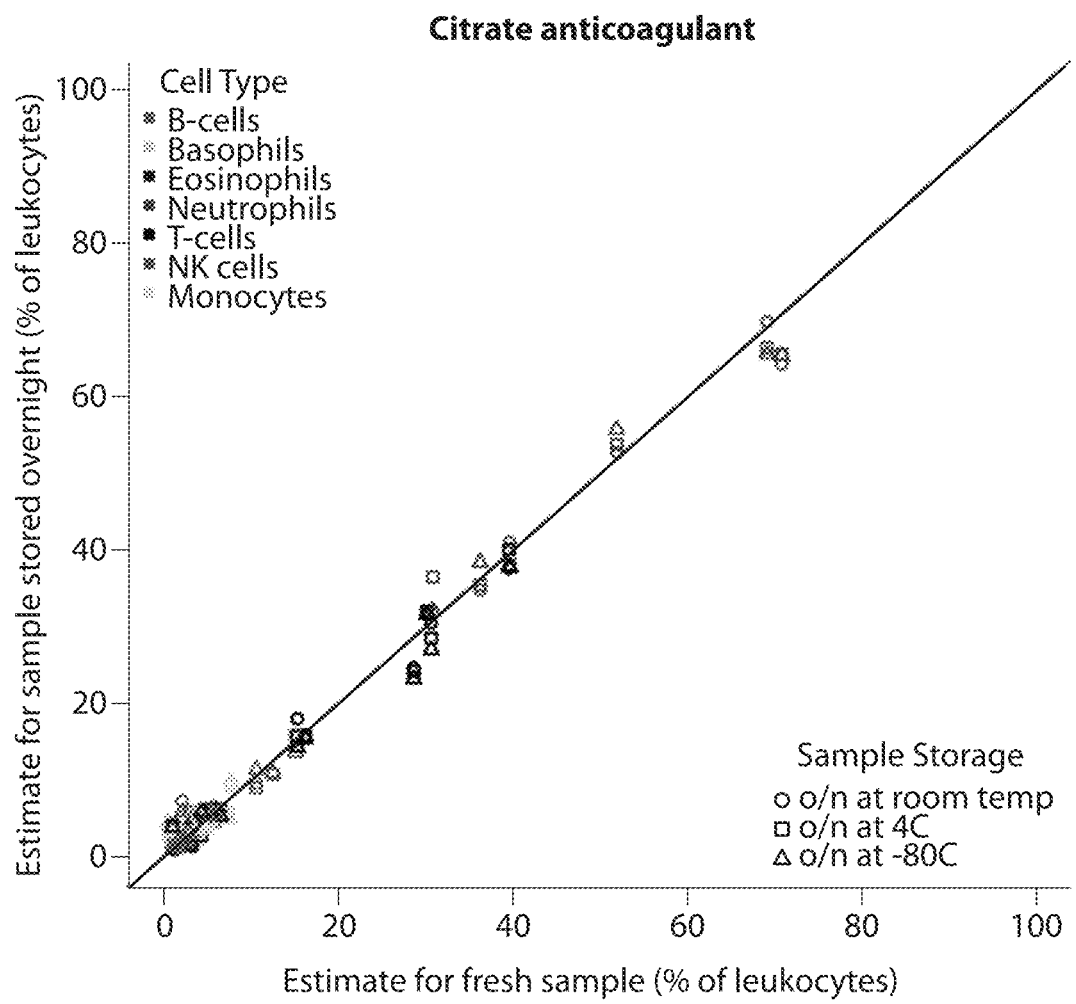

FIG. 59A-59D are a set of graphs showing comparisons of immune cell quantification by DNA methylation for samples treated with different blood anticoagulants and storage conditions. Blood samples were from disease-free human donors. Lines are drawn from the origin with a slope of one indicating ideal correspondence between the displayed values in each panel. Cell type is indicated by shading and shape of the datum point. FIG. 59A shows data for DNA methylation for blood samples treated with citrate (open square) or EDTA (open circle) as an anti-coagulant. FIG. 59B-59D show data for DNA methylation for blood samples treated with: heparin (FIG. 59B); EDTA (FIG. 59C); or citrate (FIG. 59D) as an anti-coagulant and stored at different conditions. The cells were stored at room temperature (open circle), at 4° C. (open square), or at −80° C. (open triangle). Comparable WBC subset data were observed for fresh samples compared to samples treated with different coagulants. Further, the WBC subset data for samples stored at room temperature compared to samples stored at 4° C. and −80° C. were observed to be comparable.

DETAILED DESCRIPTION OF THE INVENTION

A model of hematopoiesis includes an early restriction point at which multipotent progenitor cells become committed to either lymphoid or myeloid lineages. The standard methods of distinguishing immune cell lineages are inadequate for fully distinguishing lineage commitment and the process of hematopoiesis.

Epigenetics refers to heritable control of gene expression that occurs without changing the sequence of DNA. Chromatin packaging is a mechanism of epigenetic gene regulation which has been implicated in cell lineage commitment and lineage-specific gene expression. Transcriptionally inactive, or silenced, heterochromatin is more tightly packaged around histone proteins than transcriptionally active euchromatin due to differences in DNA methylation patterns and post-translational histone modifications. Due to its accessibility for measurement, DNA methylation is a marker of chromatin packaging. DNA methylation is largely confined to cytosine residues in CpG dinucleotides which, though underrepresented in the genome, are frequently found in high concentrations called CpG islands. Less methylated CpG islands are highly associated with transcriptional activity and subsequent gene expression, and more methylated CpG islands are highly associated with transcriptional inactivity and gene silencing. Methylation of CpG dinucleotides causes chromatin to become more compact and inaccessible to transcription machinery by moving histones and altering the organization of chromatin and nucleosomes. (Christensen, B. C., et al. 2009, *PLoS Genet* 5, e1000602; Schmidl, C., et al. 2009, *Genome Res* 19, 1165-1174).

In some instances, the overall balance of leukocyte subclasses in circulation or in tissue most prominently influences pathogenesis. For example, incipient cancer cells are recognized and eliminated by cytotoxic T cells (CTLs) and natural killer (NK) cells, and tumorigenesis is also promoted by certain other inflammatory cells, including B-lymphocytes, mast cells, neutrophils, regulatory T cells (Tregs), and others. These cells have been shown to promote angiogenesis, tumor cell proliferation, tissue invasion and metastasis (Hanahan and Weinberg 2011, *Cell*, 144, 646-74; Ostrand-Rosenberg, 2008, *Curr Opin Genet Dev*, 18, 11-18). Likewise, higher levels of NK cells and CTLs circulating in the blood and residing in adipose tissues are associated with lower incidence of metabolic diseases such as type II diabetes (Lynch et al., 2009, *Obesity*, 17, 601-5), and higher levels of M1 macrophages in adipose tissue can induce inflammation and insulin resistance (Anderson et al., 2011, *Curr Opin Lipidol.* 21, 172-177). Methods of quantifying the composition of lymphocyte populations can be informative regarding the underlying immuno-biology of disease states as well as the immune response to chronic medical conditions. (Chua et al., 2011, *Brit J Cancer* 104, 1288-1295).

The methods described herein provide a measurement of individual human or animal immune cell numbers or immune cell ratios and in diverse biologic media without the requirement for viable cells or cell sorting or the use of any antibodies or protein markers. The methods are applicable to blood including samples of unsorted blood that is fresh, or is frozen or unfrozen anticoagulant treated peripheral whole blood, finger stick blood, non-anticoagulant treated whole blood, blood clots, isolated mononuclear cells, buffy coat, archival Guthrie card neonatal blood, and to a sample that is a spot, fresh, frozen or is from a tumor such as a formalin-fixed tumor biopsy, and to urine sediment, CNS fluid, fat or other tissue biopsy.

In one embodiment the methods described herein are provided as diagnostic kits for testing laboratories in the form of immune cell specific detection reagents, premixed and optimized plate formatted multiplex assays for immune profiling compatible with specific instrument platforms, applications for in vitro diagnostics of blood, CNS, urine or bronchoalveolar lavage and point of care blood sampling kits for mail-in immune testing and immune monitoring.

The simplified DNA based immuno-diagnostic approach provided herein uses samples that are much smaller volumes of blood than required for earlier methods and that require no processing. These samples can be simply 'spotted' onto a solid phase carrier and transported through the mail or delivered using courier.

In another embodiment, the methods described include development of software that can process the output data of immune specific methylation assays to create immune parameter reports by comparison to different reference and control values.

In an alternate embodiment the methods herein describe a discovery platform which is a bioinformatic integration of empirically derived genome wide methylation analyses with publically available differential gene expression analyses. The merged datasets are then sorted to produce candidates for further examination. The discovery platform is useful to discover clinically useful gene biomarkers.

The methods described herein include a proof-of-principal test of the discovery platform. For the test the goal set was to discover a gene or gene set that provides a marker of CD3+ T cells. The method is applicable to finding a biomarker for any cell. Specifically, the platform identifies gene regions that are 'demethylated' within the target cell population (CD3+ T cell) and completely methylated in non-target cells.

To accomplish this discovery phase for the set goal, normal immune cells from the peripheral blood of different individuals was isolated using flow cytometry antibody based cell sorting. Following purification each of the immune cell subtypes was subjected to methylation discovery analysis using the Infinium genome-wide methylation platform. (Infinium® HumanMethylation27 Beadchip Microarray, developed by Illumina®, Inc., San Diego, Calif.). The DNA methylation data was then merged with existing gene expression data. Candidates that have high potential to discriminate CD3+ T cells from non-T cells were then further analyzed with two different methylation validation methods (pyrosequencing and quantitative methylation specific PCR i.e. MethylLight). Finally, a quantitative calibration curve was developed by diluting known and measured numbers of CD3+ T cells into a background matrix of fully methylated lymphocyte DNA. The latter procedure reconstructs the conditions of detection that are present in differentiating CD3+ T cells from a mixture of cells in a complex biological sample.

The methods described herein use individual samples of sorted, normal, human, peripheral blood leukocytes shown in Table 15, Example 13, purchased from AllCells®, LLC (Emeryville, Calif.). These leukocytes were sorted in a column containing antibody-conjugated magnetic beads through a combination of positive and negative selection. DNA from the leukocytes was extracted according to manufacturer's protocol using the DNeasy Blood & Tissue kit (Qiagen), and subjected to Bisulfite conversion by treatment with sodium bisulfite using the EZ DNA Methylation Kit (Zymo) following the manufacturer's protocol, thereby converting unmethylated cytosine residues to uracil and leaving methylated cytosine residues intact. DNA methylation is measured using a DNA methylation microarray as described in Example 13.

Huehn et al. (U.S. patent publication number 2007/0269823 A1) describes a method for identifying FoxP3-positive regulatory T cells by analyzing the methylation status of CpG positions in the FOXP3 gene, and further describes a method for diagnosing immune status of a mammal by measuring amounts of regulatory T cells thus identified. CpG methylation analysis of FoxP3 gene is also used to determine the quality of in vitro generated T regulatory cells and for identifying chemical or biological substances that modulate the expression of the FOXP3 gene in T cells. Specific CpG positions in the mouse FoxP3 gene are identified for analyzing methylation status and primers for amplifying mouse and human CpG dense regions in FOXP3 gene are described.

Olek (U.S. patent publication number 2007/0243161 A1) describes a method for pan-cancer diagnostics involving identification of an amount and/or proportion of stable regulatory T cells in a patient suspected of having cancer by analyzing methylation status of CpG positions in the FOXP3 and/or camtal genes. Increased amount/proportion of stable regulatory T cells in the patient is indicative of an unspecified cancerous disease. A method of treating cancer by reducing the amount or proportion of stable regulatory T cells and a method for diagnosing survival of a cancer patient by measuring T regulatory cell amounts and/or proportions in patients suspected of having cancer using CpG methylation analysis of FoxP3 and/or camtal genes are described. Increased amounts and/or proportions of stable regulatory T cells in the cancer patient is indicative of a shorter survival.

Olek et al. (International publication number WO 2010/069499 A2) describes a method of identifying T-lymphocytes, in particular CD3+CD4+ and/or CD3+CD8+ cells by analyzing the methylation status of CpG positions in one or more of genes for CD3 multi-protein complex CD3 γ, -δ and -ε, or in other genes. Demethylation is indicative of a CD3+ cell. Olek further describes methods for methylation analysis of CpG positions in CD4+ and/or CD8+ genes, in particular CD8 beta gene, or in other genes, and for determining immune status based on T-lymphocytes identified by methylation analyses, and for monitoring amounts of T-lymphocytes in response to chemical and/or biological substance exposure, in particular CD4+ or CD8+ T lymphocytes.

Shen-Orr et al. 2010, Nature Methods Vol. 7:4, 287-289 describes a cell-type specific significance analysis of microarrays for analyzing differential gene expression for each cell type in a biological sample from microarray data and relative cell type frequencies. In Shen-Orr's method relative abundance of each cell type in a mix tissue sample is first quantified, and this information is used in combination with microarray gene expression data to deconvolve and compare cell type-specific average expression profiles for groups of mixed tissue samples.

Abbas et al. 2009, PLoS One Vol. 4:7 e6098 describes deconvolution of microarray gene expression data to characterize proportions of cells in a tissue, and further identifies cellular activation patterns in Systematic Lupus Erythematosus.

A method similar to regression calibration is provided herein for determining changes in the distribution of white blood cells between different subpopulations (e.g. cases and controls) using DNA methylation signatures ro DNA methylation profiles, in combination with an external validation set having methylation signatures from purified leukocyte samples. The method is demonstrated with Head and Neck Squamous Cell Carcinoma (HNSCC) cases and matched controls, showing that DNA methylation signatures register known changes in CD4+ and granulocyte populations.

Use of DMRs as markers of immune cell identity is employed herein with a high density methylation platform, and a set of analytical tools for estimating the proportions of immune cells in unfractionated whole blood to determine the DNA methylation signature of each of the principal immune components of whole blood (B cells, granulocytes, monocytes, NK cells, and T cells subsets). A form of regression calibration was determined that considers a methylation signature as a high-dimensional multivariate surrogate for the distribution of white blood cells. This distribution was used to predict or model disease states. As a surrogate, the DNA methylation signature was assumed to be a highly correlated measure of leukocyte distribution, and thus fits into the framework of measurement error models, in which the use of a noisy surrogate marker to investigate an association with a disease outcome of interest results in biased estimates, unless internal or external validation data are obtained to "calibrate" the model and correct the bias (Carroll et al., 2006, *Measurement error in nonlinear models*. Chapman & Hall, Boca Raton, Fla., $2^{nd}$ edition).

In this case, the problem was complicated by the extremely high dimension of the surrogate. Measurement error problems are formulated as a set of relationships between z, the disease outcome (e.g. case/control status), ω, the gold standard (e.g. leukocyte distribution), and y, the surrogate (e.g. DNA methylation). The concept $E(z|\omega)$, was difficult to estimate due to the cost or logistical complications involved in obtaining ω in a large number of samples. Sufficient data for modeling $E(z|y)=f(y)$ were collected, which provides information about $E(z|\omega)$ through the (often imperfect) association $E(y|\omega)=g(\omega)$, which is inferred from an external validation sample (Thurston et al., 2003, *J Stat Plan Inf*, 113, 527-34; Carroll et al., 2006, *Measurement error in nonlinear models*. Chapman & Hall, Boca Raton, Fla., $2^{nd}$ edition). An additional assumption was that $E(z|\omega, y)=E(z|\omega)$, i.e. the surrogate provides no information about disease above and beyond the standard for which it serves as a surrogate. The high-dimensional nature of y renders $f(y)$ difficult to formulate. Although multivariate methods of measurement error correction exist, even in a high-dimensional context (e.g. Li and Yin, 2007, *Ann Stat*, 35, 2143-72) an explicit specification of $f(y)$ is important, which becomes unwieldy as each component of y contributes a small amount of information about z, and both dimension-reduction strategies and constrained regression strategies entail substantial loss of information. In the present context, specification of $y=f(z)$ is natural and straightforward. Consequently, a reversal of the modeling equation is here provided, formulating $y=f(z)$ as part of the modeling strategy, and linking the linear functions $f$ and $g$ in a manner that admits the estimation of ω. In methods herein several major sources of possible bias were identified and methods provided for control and subjection to sensitivity analysis of the sources of the bias.

Examples herein include methods for an estimation technique, theoretical treatment of bias, and a demonstration of the approach through an application to whole blood specimens collected in an example of head and neck squamous cell carcinoma (HNSCC). See FIG. 3. Also provided are methods for a sensitivity analysis, demonstrating the impact of possible biases. Simulation study results are shown in examples herein based on the biology in the samples used.

Examples 1-3 herein show a method for determining changes in distribution of white blood cells between different subpopulations (e.g. cases and controls) from DNA methylation signatures, assuming an external validation set consisting of methylation signatures from purified white blood cell (WBC) samples exists. Examples 4, 10 and 11 herein demonstrate the methodology using a data set of HNSCC cases and matched controls, inferring from DNA methylation assays alone known changes in CD4+ and granulocyte populations between cases and controls and change in CD4+ populations due to aging. Using previous methods flow cytometry would have been necessary to obtain the same results. A method for assessing the sensitivity of the magnitude estimates to possible biases is also provided. Example 12 validates the method through simulation.

Methods are provide herein for determining changes in the distribution of white blood cell types between different human populations (e.g. cases and controls) using DNA methylation signatures; by using an external validation set having methylation profiles from purified white blood cell components. DNA methylation in peripheral blood was accordingly shown to be a biomarker for clinical and epidemiological investigation. Studies have attempted to distinguish cancer cases from controls using whole peripheral blood assayed with DNA methylation arrays, including ovarian (Teschendorff et al., 2009, *PLoS ONE* 4, e8274), bladder (Marsit et al., 2011, *J Clin Oncol* 29, 1133-1139), and pancreatic (Pedersen et al., 2011, *PLoS ONE* 6, e18223) cancers. Although these studies have demonstrated discrimination of cases from controls, sound evidence for a biological mechanism has been elusive. Presumably, disease associated alterations in blood methylation have several etiological components driven by endogenous genetic, environmental and disease specific factors. From known developmental associated differences in DNA methylation among specific blood cell types, changes in the distributions of blood cell types alone could account for disease associated DNA methylation. The many diverse types of immune cells in blood make this issue highly complex and problematic to tackle using single cell type assays. Therefore, it is important for the development of this new avenue of biomarker research to delineate effects due to the immune cell distribution itself from other "non cell type" alterations in DNA methylation. The differences among human populations attributed to cell distributions are termed "immunologically mediated".

Immunological explanations for differences in mRNA profiles between cases and controls have been proposed, e.g. Showe et al., 2009, Cancer Res 69: 9202-10 and Kossenkov et al., 2011, Clin Cancer Res 17: 5867-77. The statistical principles described in the method herein apply to mRNA expression profiles and an appropriate validation set $S_0$ based on mRNA expression arrays. Little to no modification of mathematical expressions and computer code is necessary to apply the statistical principles described in the method herein to analysis of mRNA expression profiles. Under the assumption that the upstream epigenetic control mechanisms are more biologically stable, less variability in measurement of DNA methylation is expected compared with measurement of mRNA expression.

In the methods herein, a solution to partition this component of variation in methylation from other determinants employs multivariate analytic tools including regression coefficients, associated inference, and coefficients of determination measures. These tools were used to evaluate whether the observed DNA methylation differences were due to an immunologically mediated response. Prior measurement error formulations (Thurston et al., 2003, *J Stat Plan Inf*, 113, 527-34; Li and Yin, 2007, *Ann Stat*, 35, 2143-2172) require specification of a logistic regression model for case/control status, conditional on DNA methylation signature, a computationally difficult task that is vulnerable to model mis-specifications. A reverse formulation was used herein that naturally models the relationship of DNA methylation conditional on known phenotypes. The formulation respects the protocol (DNA methylation assay data collected after sampling from phenotype groups). Other strategies to formulate errors were found to be unsuccessful. For example, the strategy utilizing Expectation-Maxinlization (EM) algorithm to integrate over the missing data ω (Little and Rubin, 2002, *Statistical Analysis with Missing Data*. Wiley, Hoboken, N.J., 2$^{nd}$ edition) is outside the measurement error literature and within the larger missing-data literature. However, by design, the distribution of ω varied substantially between the data sets $S_0$ and $S_1$, severely complicating the approach, with side-effect of introducing feedback from $S_1$ to $S_0$, contaminating the gold-standard status of $S_0$. Another alternative that was found to be unsuccessful was the simpler approach of an empirical Bayes procedure, similar to existing mixture-model approaches (Koestler et al., 2010, *Bioinformatics*, 26, 2578-2585). However, difficulty in specifying the distribution of ξ rendered this approach untenable, and in a separate simulation, attempts to impute ω among $S_1$ samples using parameters obtained from $S_0$ samples resulted in extremely biased estimates of ω.

Examples herein show that group level comparisons of blood cell DNA methylation revealed significant immune alterations. Methods for individual level immune cell profiling are applicable also, since methods herein are useful also to clinical and detailed analytical epidemiologic applications that examine individual risk factor information. When $z_{1i}$ involves an orthogonal (e.g. one-way ANOVA) parameterization and ordinary least squares (OLS) is used to obtain $B_1$, then equation 5 (Example 3) herein reduces to simple expressions involving the projected quantities $\omega_i = y_{1i} B_0 (B_0 B_0)^{-1}$. For exploratory purposes, projections $\omega_i$ serve as estimates of individual profiles. There is interest in minor immune cell fractions and their role in disease, though the signal strength of cell types comprising <5% of the total white cell compartment is difficult to quantitate. Examples of such cell types include the regulatory T cell or NK cell fractions, which are implicated in autoimmune and malignant diseases. Optimization of platforms for technical sensitivity to minor subtypes combined with statistical optimization of signature recognition are needed to enhance the approach for testing highly targeted immune hypotheses.

In addition to group level comparisons of blood cell DNA methylation, immune cell profiling at the individual level is important for examining individual risk factors in clinical and detailed analytical epidemiologic applications. As shown in Examples herein, individual immune profiles are theoretically achievable and require extensive validation with a wide array of mixture combinations.

The methods herein have potentially far reaching implications for rapid, simple and complete assessment of the composition of human white blood cell populations, i.e. the immune profile. Currently, assessment of the cellular composition of peripheral blood cannot be accomplished without the use of freshly drawn venous blood that is immediately prepared in a specially equipped laboratory. A complete assessment of the entire immune profile requires extensive flow cytometric measurements based on protein epitopes on leukocyte membranes that distinguishes subtypes of immune cells that are either too rare or too similar in appearance to be distinguished using simple microscopic approaches. In particular, flow cytometry is limited by the following: cells must be separated, requiring large volumes of fresh cells; detection can be accomplished only by the fluorescent antibody tags available, which require expensive technology to read; the outer cell membrane must be intact, mandating limited utility in many instances.

In contrast, using the methods herein, the application of labor-intensive or expensive steps is required only in the construction of the validation set $S_0$, which need only be developed once. Once $S_0$ is available, subsequent interrogation is based on the chemically stable CpG methylation of DNA. Thus the methods herein obviate the need for fresh blood and the preservation of labile protein epitopes. The methods herein are able to also simultaneously assess the individual components of the peripheral blood using a highly multiplexed molecular platform and therefore logistically straightforward. Furthermore, the statistical methodology used here is implemented easily with the instrumental output of the methylation arrays, which simplifies the interpretation of the immune profile data from the operator's point of view. The methods herein are immediately deployed in a research framework to cost effectively assess human immune profiles (in fresh or archival samples), to explore the potential of the immune profiles to function as biomarkers, and to address key questions regarding disease pathogenesis. Furthermore, the approach used in the methods herein is readily suited for rapid translation to a broad base of clinical applications such as disease monitoring, diagnosis, prognosis, and response to therapy.

The methods herein are applied to tumor biopsies for immune characterization of cancer patients. Other notable applications exist including the application of the test to urine sediments in patients with autoimmune and diabetic kidney disease or in patients undergoing kidney transplantation. Positive detection of T cells in urine sediment is indicative of immune activation and potential kidney disease progression or acute rejection in the context of kidney transplantation.

Populations of blood lymphocytes can be distinguished morphologically on the basis of size and the presence of a granular cytoplasm.

Small lymphocytes, including subsets of T- and B cells, are responsible for adaptive immune responses. Sublineages of small lymphocytes are morphologically indistinguishable and are distinguished by cell surface receptors and cellular function. B cells are typically distinguished by expression of the surface molecule CD19. They express immunoglobulins, which are surface receptors for pathogens. In addition, B cells are capable of further differentiating into effector cells called plasma cells. (Parham, P. *The Immune System*, Garland Science, New York, N.Y., 2005). Differentiated T cells exhibit a complex of surface molecules which function as antigen receptors, referred to as the T cell receptor (TCR) complex. This complex includes the TCR α plus β, or γ plus δ antigen recognition chains, which are associated with invariant chain subunits CD3γ, δ, ε, and ζ. (Zhang, Z., et al. 2007, *Blood* 109, 4328-4335). In general, T cells are distinguished from other cell lineages by expression of CD3 molecules on the cell surface. The genes that encode CD3 γ, δ, ε, and ζ subunits are CD3G, CD3D, CD3E and CD3Z respectively. The former three genes are tightly clustered on chromosome 11, whereas CD3Z is located on chromosome 1. Differentiated T cells are further divided into two lineages depending on their expression of either CD4 or CD8. The main function of CD8+ T cells, also known as cytotoxic T cells, is to kill infected and transformed cells. The main function of CD4+ T cells is to help other immune cells respond appropriately to sources of infection or malignancy. There are several subsets of CD4+ T cells, including Th1, Th2, Th17 and regulatory T cells. (Parham, P. *The Immune System*, Garland Science, New York, N.Y., 2005). Regulatory T cells suppress an immune response by influencing the activity of other cell types. They act primarily in the periphery on mature lymphocytes that have exited the main lymphoid tissues and serve as a means of preventing autoimmunity during protective immune responses. Exemplary regulatory T cells are thymus-derived CD4+CD25+ Foxp3+ T cells, commonly referred to as Tregs. (Zou, W. 2006, *Nat Rev Immunol* 6, 295-307). These cells primarily function to maintain peripheral self-tolerance. (Cesana, G. C., et al., 2006, *J Clin Oncol* 24, 1169-1177). Forkhead Box P3 (FOXP3), a transcription factor expressed by Tregs, is an important developmental and functional factor that regulates Treg immunosuppressive functions. (Janson, P. C., Winerdal, M. E. & Winqvist, O. 2009, *Biochim Biophys Acta* 1790, 906-919; Zou, W. 2006, *Nat Rev Immunol* 6, 295-307).

Natural killer (NK) cells are large CD56+ lymphocytes with a granular cytoplasm. They enter infected or malignant tissue to kill damaged cells and secrete cytokines aimed at preventing the spread of disease to other cells or tissues. Thus, NK cells act as effector cells of innate immunity. A subset of CD56+ NK cells that express CD3 surface molecules are NKT cells.

To determine if distinct methylation profiles are indeed associated with leukocyte lineages, statistical clustering of methylation patterns was performed using a modified model-based form of unsupervised clustering known as recursively partitioned mixture modeling (RPMM). (Houseman, E. A., et al. 2008, *BMC Bioinformatics*, 2008, 9, 365).

A locus by locus comparison was performed in which putative leukocyte DMRs were identified from Infinium data in SAS version 9.1 using a macro for locus-by-locus linear modeling that adjusts for control probe and beadchip plate. Infinium beta values for Group 1 leukocyte samples were compared to Infinium beta values for Group 2 leukocyte samples, in which group membership for each phase of the comparison is shown in Table 1.

TABLE 1

Locus by locus comparison groups

| | Group 1 Leukocytes | Group 2 Leukocytes |
| --- | --- | --- |
| Phase I | CD3+, Pan-T, CD4, Treg, CD8 | NK, B, Mono, Gran, Neut |
| Phase II | NK | Pan-T, CD4, Treg, CD8, B, Mono, Gran, Neut |
| Phase III | CD8 | CD4, Treg, NK, B, Mono, Gran, Neut |

Resultant t-values from each comparison were converted to p-values in R version 2.11.1 of Illumina's software which provides convenient mechanisms for loading and analyzing the results of methylation status, and for quality control and basic visualization tasks.

False discovery rate estimation and Q-values were computed by the Q-value package in R to adjust for multiple comparisons. (Significance was characterized as Q≤0.05.)

For significant CpG loci (Q≤0.05), a negative t-value indicates the locus putatively represents a DMR that is unmethylated in group 1 leukocyte lineage(s) and methylated in group 2 leukocyte lineage(s). Conversely, a positive t-value indicates that the locus putatively represents a DMR that is methylated in group 1 leukocyte lineages and unmethylated in group 2 leukocyte lineages. A DMR that is unmethylated in the leukocyte lineage(s) of interest and methylated in other leukocyte lineages would make the best epigenetic biomarker, since unmethylation is associated with transcriptional activity whereas methylation is associated with transcriptional silencing. Therefore, significant CpG loci exhibiting negative t-values are preferred.

In the methods herein, results of locus by locus comparisons were merged with cell type specific gene expression data. (Palmer et al., 2006, *BMC Genomics* 7, 115; Du et al., 2006, *Genomics* 87, 693-703; and Hashimoto et al., 2003, *Blood* 101, 3509-3513) to identify putative DMRs that are in genes associated with altered expression by Group 1 leukocyte lineages compared to Group 2 leukocyte lineages. An exemplary candidate epigenetic biomarker of a specific leukocyte lineage is an unmethylated region of a gene that is highly expressed by the leukocyte lineage, and not expressed by other cell types such as lineage-specific surface molecules, obligate differentiation proteins, and secreted factors. A further candidate is a methylated region of a gene that is not expressed by the leukocyte lineage and is expressed by other cell types. Without being limited by any theory or mechanism of action scenarios correlate with chromatin packaging, so that differential DNA methylation plays a large role in regulating leukocyte lineage specific expression of the gene. If no leukocyte lineage specific difference in expression of the gene containing a putative DMR were observed, other modes of gene regulation such as activators, repressors, and enhancers overshadow the role of chromatin packaging in regulating expression of the gene. Alternatively, such a gene is expressed in a temporally or environmentally specific manner that was not elucidated by the gene expression candidate data. Such a putative DMR would not be an ideal target to explore as an epigenetic biomarker of that leukocyte lineage.

In the methods described herein DMR validation is performed for each putative DMR identified from array data using bisulfite pyrosequencing and/or MethyLight quantitative real time PCR assays that measure DNA methylation of the gene region in sorted human leukocyte samples shown in Table 15, Example 13. Bisulfite pyrosequencing assays were designed using Pyromark Assay Design 2.0 (Qiagen), and carried out on a Pyromark MD pyrosequencer running Pyromark qCpG software (Qiagen). Oligonucleotide primers were obtained from Invitrogen™ by Life Technologies™. The gene region of interest were PCR amplified from bisulfite converted DNA using a biotinylated reverse primer and an unlabelled forward primer. The biotinylated PCR product was complexed with sequencing primers that anneal upstream from the target region, and was then incubated with enzymes and substrates. Then, dNTPs were dispensed in a specific order and light emitted with the incorporation of each nucleotide is measured with a CCD camera. Methylation was quantified by calculating the ratio of cytosine (methylated) to thymine (unmethylated) at each CpG locus.

In the methods described herein methylation status of specific gene regions was calculated using MethyLight according to the protocol described by Campan et al. 2009, *Methods Mol Biol* 507, 325-337, with the following modifications: C-less primers and probe were used to determine total DNA input for each sample and control reference rather than ALU-C4 primers and probe. To measure unmethylation, control unmethylated DNA was used as a reference, generating a percent unmethylated reference value which is subsequently converted into percent methylation. Real time PCR primers and fluorescent (major groove binding) MGB probes were obtained from Applied Biosystems (Foster City, Calif.). TaqMan® Universal PCR Mastermix, no AmpErase® UNG was obtained from Applied Biosystems, manufactured by Roche (Branchburg, N.J.). Quantitative, real time PCR reactions were performed with Applied Biosystems 7300 Real Time PCR System using Applied Biosystems 7300 system sequence detection software version 1.4.0.25 ©2001-2006.

In the methods herein, a putative DMR identified as being unmethylated in group 1 leukocytes based on Infinium methylation data was shown using bisulfite pyrosequencing or MethyLight® qPCR to be unmethylated in group 1 leukocytes and methylated in group 2 leukocytes and the DMR was confirmed as an unmethylated epigenetic biomarker specific to the group 1 leukocyte lineage(s). A putative DMR shown using bisulfite pyrosequencing or MethyLight® qPCR to be unmethylated in group 1 leukocytes and in some group 2 leukocytes, was not confirmed as an epigenetic biomarker specific to the group 1 leukocyte lineage(s). Instead that DMR represents an epigenetic biomarker of several different human leukocyte lineages including the group 1 lineage(s). A DMR that is partially unmethylated by bisulfite pyrosequencing or MethyLight® qPCR in group 1 leukocytes and methylated in group 2 leukocytes, is a weak epigenetic biomarker of the group 1 leukocyte lineage(s). That DMR is heterogeneously unmethylated in group 1 leukocytes and is homogeneously methylated in group 2 leukocytes and is therefore not useful for distinguishing group 1 from group 2 leukocyte lineages.

If Infinium data suggested that a CpG locus represents a DMR specific to group 1 leukocytes, and bisulfite pyrosequencing or MethyLight qPCR did not find a difference in DNA methylation in that region between group 1 and group 2 leukocyte samples, the region was not considered a DMR that would serve as an epigenetic biomarker of the group 1 leukocyte lineage(s).

Figure 10A:
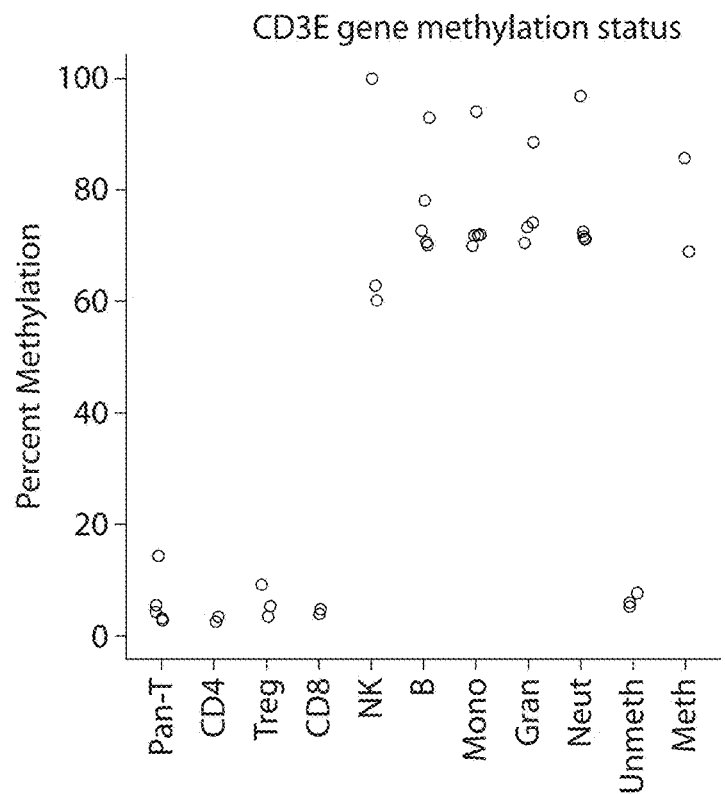
FIG. 10A and FIG. 10B are graphical representations of the DNA methylation status of regions in CD3E and CD3Z genes.
Figure 10B:
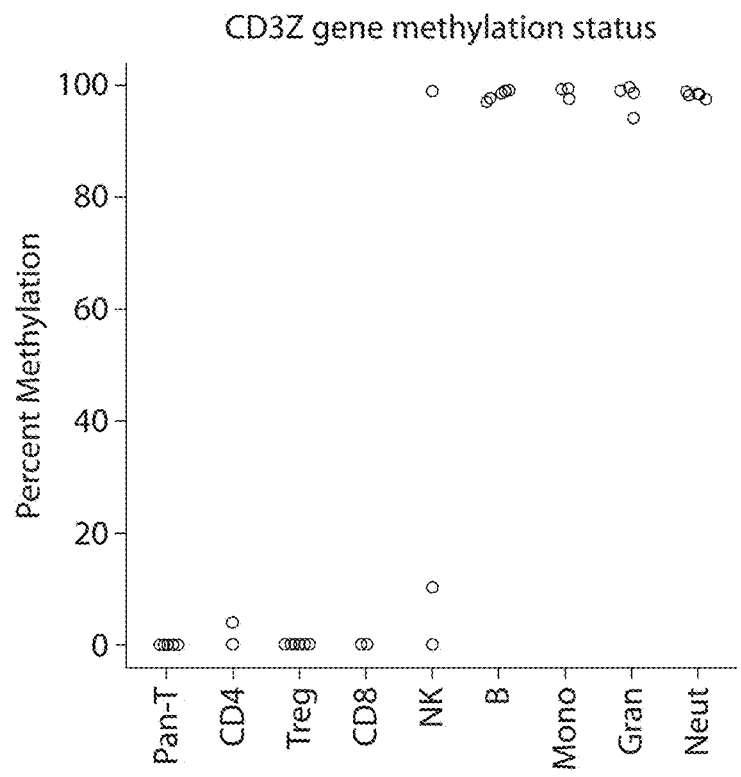

These discovery platform criteria successfully identified a unique heretofore unknown sequence of genomic DNA that is specifically marked by CpG demethylation in CD3 positive T cells, not in other hematopoietic peripheral blood cells (FIG. 10B). In examples herein it is further shown the DNA methylation status of this region in the promoter of CD3Z gene in sorted human peripheral blood leukocytes measured by MethyLight® qPCR confirms that the identified genomic sequence is an immune cell type specific differentially methylated region that is a useful marker to quantify CD3+ T cells in biological specimens such as whole or separated blood and other tissues.

Gliomas are a histologically diverse cancer with few established risk factors and poor prognoses (Kleihues et al. 1993, Brain Pathol 3(3): 255-68; Ohgaki and Kleihues 2005, Acta Neuropathol 109(1): 93-108; Louis et al. 2007, Acta Neuropathol 114(2): 97-109; Ohgaki, and Kleihues 2007, Am J Pathol 170(5): 1445-53). However, immune factors are associated with increased glioma risk and are also thought to play a role in patient outcomes (Wiemels et al. 2009, Int J Cancer. 2009 Aug. 1; 125(3):680-7; Yang et al. 2010, J Clin Neurosci 17(11): 1381-5). Patients with glioblastoma multiforme (GBM) exhibit abnormalities (McVicar et al., 1992, J Neurosurg 76(2): 251-60; Ashkenazi et al. 1997, Neuroimmunomodulation 4(1): 49-56) of T cell response associated with pronounced reductions in T cell numbers in peripheral blood including the suppressive regulatory T cells (Tregs) (Fecci, et al., 2006, Cancer Res 66(6): 3294-302). Despite low T cell and Treg counts, the ratio of Tregs to T cells is clinically relevant in immunosuppression. Currently there is no validated method to quantify this ratio. The quantification of immunosuppression is envisioned herein to help also in characterizing patient tumors. An immunosuppressive environment in glioma is also suggested by the accumulation of tumor infiltrating lymphocytes (TILs) displaying markers of Tregs, (i.e. cell membrane CD4 and CD25 and intracellular staining of the FOXP3 protein).

Epigenetic markers involving the demethylation of the FOXP3 gene have been determined to be the most specific marker of stable Tregs. (Baron et al., 2007, Eur J Immunol 37(9): 2378-89; Floess et al., 2007 PLoS Biol 5(2): e38; Polansky et al., 2008, Eur J Immunol 38(6): 1654-63). As described in examples herein, by combining information about the FOXP3 differentially methylated region (DMR) with methylation specific quantitative PCR (MS-qPCR) highly sensitive and accurate counts of Tregs in blood and tissues were obtained. Such DNA-based methods to interrogate specific populations of T cell subsets are far less expensive than flow-cytometry and can be applied to archival specimens. Examples herein show that the DMR marker for CD3+ T cells identified herein is used alone or in conjunction with the previously described Treg DMR marker.

A quantitative assay for CD3+ T cells based on the demethylation of the promoter of a component of the T cell receptor complex: CD3Z (CD247) is also described herein. Examples herein show the validity of CD3Z demethylation as a CD3+ T cell marker and illustrate its application in patients with glioma that demonstrate the high discriminating value of CD3Z demethylation in glioma case-control subject comparisons, histopathological characterization of tumors and patient prognosis.

An understanding of the role played by an altered immune response in etiology facilitates development of more effective therapies and prognostic indicators. Epidemiological studies implicate atopic immune alterations in glioma risk (Wrensch et al., 2005, Am J Epidemiol 161(10): 929-38; Schwartzbaum et al., 2010, Carcinogenesis 31(10): 1770-7). Immune suppression and abnormalities in T cells in glioma patients may prevent antitumor immunity and poses barriers to effective immunotherapeutic strategies (Grauer et al., 2007, Int J Cancer 121(1): 95-105; Sonabend et al., 2008, Anticancer Res 28(2B): 1143-50). Data obtained using novel T cell epigenetic assays described in examples herein demonstrate dramatic decreases in CD3+ T cells and Tregs in peripheral blood from GBM patients. The copy numbers of demethylated CD3Z and FOXP3, as a percent of total leukocyte copies, were observed to be reduced about two-fold in GBM patients, which was highly statistically significant.

Validation studies herein support the notion that the CD3Z MS-qPCR assay using unprocessed archival whole blood is an accurate reflection of T cells as measured by conventional flow cytometry. Previous studies have validated the FOXP3 demethylation assay as a measure of Tregs in blood and tissues (Baron et al., 2007, Eur J Immunol 37(9): 2378-89). Current steroid use (dexamethasone), temozolomide and radiation exposures as possible factors in these effects among cases were investigated but no significant associations of any factor with these T cell alterations was found. The methods described in examples herein that delineate T cell subsets from DNA facilitate immune cell analyses using blood specimens that have been archived in cohort populations with long-term glioma follow-up data. Nested case control studies within large epidemiologic cohorts are now feasible as a result, allowing for the first time, to test whether T cell and Treg abnormalities precede the diagnosis of glioma.

Figure 16A:
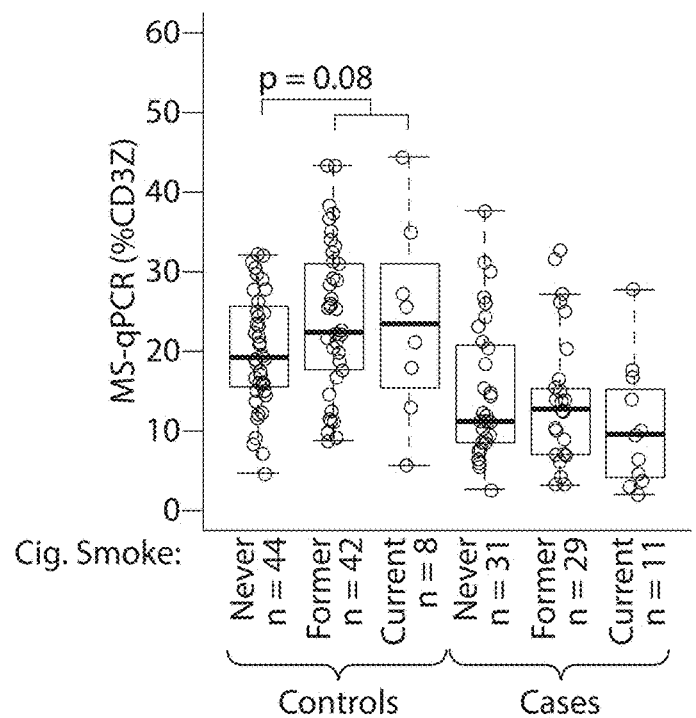
FIG. 16A shows a comparison of peripheral blood T cell levels, determined by CD3Z demethylation, among never, former and current cigarette smokers stratified by glioma case status (indicated "cases" on the abscissa).

The balance of suppressive Tregs to total T cells in peripheral blood has been reported to be shifted towards greater suppression in GBM patients and other types of cancer (Beyer and Schultze, 2006, Blood 108(3): 804-11). Ratio of Tregs/T cells in association with cigarette smoking was examined herein. An association of current smoking with higher Treg/T cell ratios was observed. There is strong evidence that cigarette smoke exposure leads to the accumulation of Tregs in respiratory airways in mice (Brandsma et al., 2008, Respir Res 9: 17) and humans (Smyth et al., 2007, Chest 132(1): 156-63) as well as in the gut epithelium of exposed mice (Verschuere et al., 2011 Lab Invest. 91(7): 1056-67). Treg/T cell ratios were herein observed to be higher in current smokers versus former smokers (FIG. 16). It was subsequently confirmed in an independent population that current but not former cigarette smoking exhibit higher Treg/T cell ratios. Results herein illustrate the need for examination of patient characteristics to include cigarette smoking in diseases that affect Treg levels. New epigenetic methods described herein are useful in promoting these types of studies.

Similar to many types of cancer CD4+ T helper cells and Tregs have been shown to infiltrate the human glioma tumor microenvironment (Nishikawa and Sakaguchi, 2010, Int J Cancer 127(4): 759-67). In glioma studies using IHC to quantify T cells in FFPE preparations CD4+ T cell numbers were reported to increase with tumor grade, whereas CD8+ T cells appear in equal frequencies across glioma grades (Heimberger et al., 2008, Clin Cancer Res 14(16): 5166-72). Results herein indicate increased CD3Z demethylated cells according to grade (FIG. 17). Immmunohistochemical IHC analysis herein showed that mostly these cells were CD8+ cells with very few CD4+ cells. Examples herein also show that ependymal tumor cells and some significant fraction of grade II Oligodendrogliomas (OD) and Astrocytomas (AS) tumors contain significant numbers of T cells and Tregs (FIG. 21). As progression of lower grade to higher grade brain tumors is a common and serious clinical problem results herein show that epigenetic analyses are useful for characterizing low grade OD and AS tumors as well as Ependymomas (EP). Compared to previous reports (El Andaloussi and Lesniak, 2006, Neuro Oncol 8(3): 234-43; El Andaloussi and Lesniak, 2007, J Neurooncol 83(2): 145-52; Heimberger et al., 2008, Clin Cancer Res 14(16): 5166-72; Heimberger et al., 2008, Neuro Oncol 10(1): 98-103) analysis herein using the MS-qPCR showed significantly increased ratio of Treg/CD3+ Tcells within glioma tumor tissues of different pathological grade (FIG. 17). Results herein showed also how the ratio of Tregs/CD3+ Tcells increases with tumor grade in comparison to blood. Thus, until the present results, there was no evidence of a specific accumulation of Tregs in human brain tumors. The survival data in examples herein show significant associations of immune parameters with patient survival (FIG. 22).

Without being limited by any theory or mechanism of action, observations herein of a close linear relationship between flow cytometry of CD3+ T cells and CD3Z demethylation that was identical among glioma cases and controls argues against a cancer related effect on CD3Z demethylation such as downregulation of CD3Z through a posttranslational effect on CD3Z proteins mediated by up regulation of lysosomal or proteasomal degradation pathways. Another issue concerning the validity of CD3Z demethylation as a CD3+ T cell marker in cancer tissues is that DNA demethylation may take place in transformed cells and thus 'mimic' a lymphocyte signal. To ascertain that the observed CD3Z demethylation was taking place in CD3+ T cells and not due to DNA demethylation taking place in transformed cells CD3Z and FOXP3 demethylation in brain tumor cells lines and in human GBM xenografts which cannot contain human T cells was assessed. These samples contained non-detectable levels of CD3Z or FOXP3 demethylation. Normal brain tissue was also uniformly devoid of T cell signals, consistent with the specificity of the MS-qPCR in tumor as reflecting infiltration of immune cells. Some subtypes of NK cells ($CD56^{dim}CD16^{bright}$) utilize CD3Z in NK receptor signaling (Lanier, 2006, Trends Cell Biol 16(8): 388-90). The contribution of CD3Z expressing and demethylated NK cells to the overall CD3Z demethylated signal in peripheral white blood cells is estimated to be very small. Furthermore, NK cells have not been observed in glioma tissues.

The fundamental innovation in the epigenetic analyses described herein is a shift in immunodiagnostics away from proteomic-based approaches to one that is based on quantifying cell type specific DNA methylation events. This new approach produces gains in versatility, sensitivity, feasibility and throughput compared with conventional flow cytometry or IHC and does so at a lower cost. The high chemical stability of cytosine methylation marks within genomic DNA and the fact that differentiation within the immune system is tightly linked with gene specific DNA methylation events makes quantification of immune cells through epigenetic analyses a unique approach. The method combines the intrinsic chemical stability of DNA with the high sensitivity of qPCR methods. Automation and liquid robotic handling in processing and analysis add further to the power of the methodology and open avenues for investigations in the immunoepidemiology of glioma and many other diseases.

Methods herein show that blood-based DNA methylation signatures across a complex cellular mixture of WBCs are useful for distinguishing solid tumor cancer cases in which there are well-defined immune-mediated responses and controls. As tumorigenesis elicits a distinct immune response (Camilleri-Brot S et al., 2004, Ann Oncol 15:104-112; Wang Y et al., 2005, Am J Clin Pathol 124:392-401; Rui L et al., 2011 Nat Immunol 12:933-940), the result is a hematopoietic shift in WBC populations, which can be precisely discerned by applying the unique epigenetic signature of differing lineages. The aggregate methylation signature in blood that distinguishes cancer cases from controls corresponds to the epigenetic signatures that define leukocyte subtypes.

To understand the role of immune-mediated responses to tumorigenesis in defining distinct signatures of blood-based DNA methylation between cancer cases and cancer-free controls in examples herein, the epigenetic landscape of WBCs was obtained by identifying DMRs among leukocyte subtypes. This analysis revealed that the majority of the highest ranking 50 leukocyte DMRs (Example 25) were differentially methylated between disease cases and normal controls for HNSCC and ovarian cancers, with a smaller fraction differentially methylation between bladder cancer cases and controls. Among the eight overlapping CpG loci that were found to be significantly differentially methylated between cancer cases and controls across the three data sets, the direction of the relationships was similar for HNSCC and ovarian cancer cases compared to controls. These findings show that HNSCC and ovarian cancer elicit similar shifts in leukocyte compositions in the hematopoietic system.

Of the seven overlapping DMRs (CD72, PACAP, FGD2, SLC22A18, GSTP1, NFE2, ASGR2) several are located within genes with either established or alleged involvement in immune differentiation or function, viz., CD72, PACAP and FGD2 (Kumanogoh and Kikutani, 2001, Trends Immunol 22:670-676; Parnes and Pan, 2000, Immunol Rev 176: 75-85; Tan et al., 2009, Proc Natl Acad Sci 106:2012-2017; Huber C et al., 2008, J Biol Chem 283:34002-34012). CD72, a member of the C-type lectin superfamily, negatively regulates B cell coreceptor signaling (Kumanogoh and Kikutani, 2001) and has been shown to act as a unique inhibitory receptor on NK cells regulating cytokine production (Alcon V L et al., 2009, Eur J Immunol 39:826-832). Moreover, PACAP has been implicated as an intrinsic regulator of regulatory T cell abundance after inflammation 36 and FGD2 has been shown to play a role in leukocyte signaling and vesicle trafficking in cells specialized to present antigen in the immune system (Huber C et al., 2008, J Biol Chem 283:34002-34012).

In the model described herein containing the DNA methylation profile for the highest ranking 50 leukocyte DMRs, patient age, gender, smoking status, smoking pack years, weekly alcohol consumption, and HPV serological status (Table 19, Example 13), HNSCC cancer was predicted with high degree of sensitivity and specificity. Similarly high prediction performance was obtained for ovarian cancer using the DNA methylation profile for the highest ranking ten leukocyte DMRs and patient age group. Prediction performance for bladder cancer, based on the methylation profile of the highest ranking 56 DMRs, patient age, gender, smoking status, smoking pack years, and family history of bladder cancer, was lower than that observed for HNSCC and ovarian cancer. One explanation for the differences in magnitude for discriminating cancer cases and controls among cancer types is underlying differences in the magnitude of shift in leukocyte subtypes. Cancers characterized by a pronounced immunologic response such as HNSCC and ovarian cancer (Alhamarneh O et al., 2008, Head Neck 30:251-261; Zhang L et al., 2003, N Engl J Med 348:203-213; Tomsova M et al., 2008, Gynecol Oncol 108:415-420; Sato E et al., 2005, Proc Natl Acad Sci 102:18538-18543; Curiel T J et al., 2004, Nat Med 10:942-949), correspond to more discernable shifts in leukocyte sub-population, thus resulting in greater discrimination of blood-derived DNA methylation using leukocyte DMRs for these cancers compared to bladder cancer.

Figure 32:
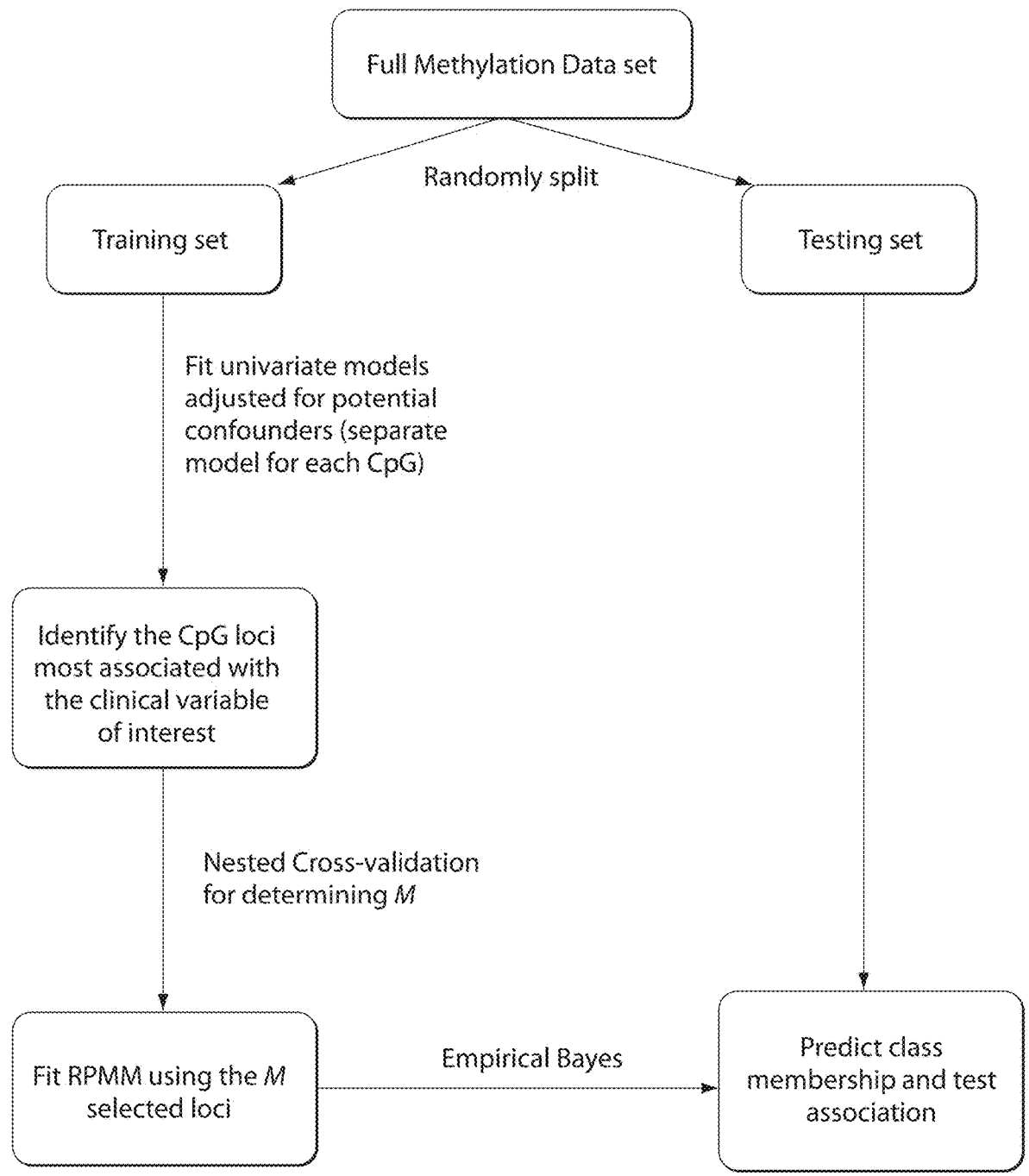
FIG. 32 is a diagram illustrating Semi-Supervised Recursively Partitioned Mixture Models (SS-RPMM) for predicting methylation class membership. The full methylation dataset was randomly divided into training and testing sets. Using the training data only, univariate models (adjusted for potential confounders) were used to identify CpG loci whose methylation is most strongly associated with the clinical variable of interest (i.e., case/control status). RPMM is then fit to the training data using the M CpGs that are most associated with the clinical variable of interest (M is determined using a nested cross-validation procedure) CpGs. The resulting solution is then used in conjunction with an empirical Bayes classifier to predict methylation class membership for the observations in the testing data.

Substantial correlation was also obtained in methylation of the loci identified via the semi-supervised recursively partitioned mixture model (SS-RPMM) analyses and the leukocyte DMRs that defined the methylation classes discovered for the HNSCC and ovarian data sets. A diagram illustrating the analytic framework for SS-RPMM is provided in FIG. 32. The SS-RPMM25 procedure is specifically designed to construct methylation classes that are based on an optimal number of informative features (loci whose methylation is most strongly associated with cancer case/control status). The results demonstrate that the methylation classes identified through SS-RPMM for the HNSCC and ovarian data sets are in large part due to systematic hematopoietic changes in WBC populations in response to tumorigenesis. The 56 leukocyte DMRs used in the bladder profile analysis were less correlated with the nine CpG loci identified via the previously reported SSRPMM analysis of this data set (Marsit C J et al., 2011, J Clin Oncol 29:1133-1139). Alternative biological epigenetic mechanisms may be operative in bladder cancer in addition to the epigenetic signatures characteristic of leukocyte subtypes, and contribute independently to the blood-derived differences in DNA methylation between bladder cancer cases and controls.

Examples herein provide evidence that observed differences in blood-derived DNA methylation in cancer cases are largely explained by systematic differences in the methylation signatures of leukocyte sub-populations. These findings signify that different cancers elicit a discernible, unique immune response evident in peripheral blood. These results have important implications for research into the immunology of cancer. Further, the approach of observing differences in blood derived DNA methylation provides a completely novel tool for the study of the immune profiles of diseases where only DNA can be accessed; that is, this approach has utility not only in cancer diagnostics and risk-prediction, but can also be applied to future research (including stored specimens) for any disease where the immune profile holds medical information. The approach represents an extremely simple, yet truly powerful and important new tool for medical research and may serve as a catalyst for future non-invasive disease diagnostics.

Natural killer (NK) cells are a key element of the innate immune system implicated in human cancer. To examine NK cell levels in archived blood samples from a study of human head and neck squamous cell carcinoma (HNSCC), a DNA-based quantification method described in methods herein was developed (Examples 27-36).

Head and neck squamous cell carcinoma (HNSCC) is strongly associated with alterations in the immune system and it is postulated that progression of HNSCC tumors is linked to immune evasion or failure of the immune system to fight the cancer (Duray A, et al., 2010, Clinical & developmental immunology, 2010:701657; Pries R, and Wollenberg B, 2006, Cytokine Growth Factor Rev, 17:141-6; Wulff S et al., 2009, Anticancer research, 29:3053-7; Kuss I et al., 2004. Clin Cancer Res, 10:3755-62; Kuss I et al., 2005, Adv Otorhinolaryngol, 62:161-72). Natural killer (NK) cells are of particular interest in the context of HNSCC and other cancers, since they are able to recognize and destroy pre-cancerous and malignant cells (Kim R et al., 2007, Immunology, 121:1-14; Ostrand-Rosenberg S. 2008, Curr Opin Genet Dev, 18:11-8; Whiteside T L, 2006, Cancer Treat Res, 130:103-24; Parham P. The Immune System. 2nd ed. New York, N.Y.: Garland Science; 2005). Natural killer cell infiltration into solid tumor tissue has been associated with improved survival in studies of many different types of cancer (Ishigami S et al., 2000 Cancer, 88:577-83; Kondo E et al., 2003, Dig Surg, 20:445-51; Villegas F R et al., 2002, Lung Cancer 2002; 35:23-8). Immune suppression is frequently seen in patients with head and neck cancer (Duray A, et al., 2010, Clinical & developmental immunology, 2010:701657; Pries R, and Wollenberg B, 2006, Cytokine Growth Factor Rev, 17:141-6; Wulff S et al., 2009, Anticancer research, 29:3053-7; Kuss I et al., 2004. Clin Cancer Res, 10:3755-62; Kuss I et al., 2005, Adv Otorhinolaryngol, 62:161-72). Diminished NK cell and natural killer T (NKT) cell activity and number have been observed in the peripheral blood of patients with HNSCC (Wulff S et al., 2009, Anticancer research, 29:3053-7; Molling J W et al., 2007, J Clin Oncol, 25:862-8).

A novel DMR is identified herein that distinguishes NK cells from other leukocytes to facilitate the quantification of NK cells in archived blood samples from a case control study of HNSCC. Many chemical exposures, such as tobacco and alcohol, as well as viral factors, such as human papilloma virus (HPV), are known or suspected to be causal factors in HNSCC (Furniss C S et al., 2009 Annals of oncology: official journal of the European Society for Medical Oncology/ESMO, 20:534-41; Applebaum K M et al., 2007, Journal of the National Cancer Institute, 99:1801-10) and may independently affect immune profiles (Mehta H et al., 2008, Inflammation research, 57:497-503; Wansom D et al., 2010, Archives of otorhinolaryngology—head & neck surgery 2010; 136:1267-73; Gao B et al., 2011 American journal of physiology Gastrointestinal and liver physiology 300:G516-25). Unlike previous studies, data shown herein evaluates the effects of these factors on the depression in NK immune profile. Patient risk factors and disease characteristics (e.g. tumor location) are evaluated herein in relationship to NK cells to determine the independent associations of HNSCC with innate immune parameters.

NK cell-specific DNA methylation was identified by analyzing DNA methylation and mRNA array data from purified blood leukocyte subtypes (NK, T, B, monocytes, granulocytes), and confirmed via pyrosequencing and methylation specific quantitative PCR (MS-qPCR). NK cell levels in archived whole blood DNA from 122 HNSCC patients and 122 controls from a study population were assessed by MS-qPCR. Details of this study population have been previously described (Applebaum K M et al., 2007, Journal of the National Cancer Institute, 99:1801-10). Briefly, peripheral blood from 122 control donors and 122 HNSCC patients was collected between December 1999 and December 2003 in the greater Boston area. Population based control subjects with no prior history of cancer were from the same region as cases, and were frequency matched on age and gender. Study approval was obtained from the Brown University Institutional Review Board. Subjects provided written informed consent for participation in this study. Venous anticoagulated whole blood was drawn into sodium citrate and stored at −20° C. prior to DNA isolation.

Pyrosequencing and MS-qPCR (FIG. 39) confirmed that a demethylated DNA region in NKp46 distinguishes NK cells from other leukocytes, and serves as a quantitative NK cell marker. Demethylation of NKp46 was significantly lower in HNSCC patient blood samples compared with controls ($p<0.001$). Individuals in the lowest NK tertile had over 5-fold risk of being a HNSCC case, controlling for age, gender, HPV16 status, cigarette smoking, alcohol consumption, and BMI (OR=5.6, 95% CI: 2.0, 17.4) (FIG. 37). Cases did not show differences in NKp46 demethylation based on disease treatment or tumor site.

The results of this study indicate a significant depression in NK cells in HNSCC patients that is unrelated to exposures associated with the disease. DNA methylation biomarkers of NK cells represent an alternative to conventional flow cytometry that can be applied in a wide variety of clinical and epidemiologic settings including archival blood specimens.

Understanding of immune cell level alterations associated with cancer and other diseases has, until now, been restricted by the limitations of immunodiagnostic methods. Described herein is a new method for measuring NK cell levels in human blood and tissue based on cell-lineage specific DNA methylation that can be applied to samples regardless of handling and storage procedures. This is a step forward in immune cell detection and quantification that is applicable to many types of clinical samples. Applying the method to a case-control study of HNSCC (Examples 27-36) revealed a case-associated decrease in circulating NK cells that is independent of known risk factors and treatments. This shows that it is important to monitor NK cell levels in patients with HNSCC, and that it may be worthwhile to pursue future immune therapies may be designed aimed at restoring circulating NK cells in patients with HNSCC.

A variety of methods are available as bases for methodology used to analyze CpG methylation states. These methods can be divided roughly into two types: gene-specific and global methylation analysis. A large number of techniques have been developed for gene-specific CpG methylation analysis. Early studies used methylation sensitive restriction enzymes to digest DNA followed by Southern detection or PCR amplification. Bisulfite reaction based methods such as methylation specific PCR (MSP) and bisulfite genomic sequencing PCR are commonly used currently. Global methylation analysis measures the overall level of methyl cytosines in genome by methods such as chromatography or methyl accepting capacity assay. Further, methylation hotspots or methylated CpG islands in the genome may also be identified by several of the recently developed genome-wide screen methods such as Restriction Landmark Genomic Scanning for Methylation (RLGS-M), and CpG island microarray.

The gene-specific method MethyLight is a highly sensitive high-throughput quantitative methylation assay, capable of detecting methylated alleles in the presence of a 10000-fold excess of unmethylated alleles using fluorescence-based real-time PCR technology that requires few or minor further manipulations after the PCR step. Eads C A et al., Nucl. Acids Res. (2000) 28 (8): e32-00. For example, a MethyLight assay is commercially available from QIAGEN, Inc. Valencia, Calif.

In another embodiment of the method, analyzing the methylation of any gene, e.g., the CD3Z gene through amplification by Polymerase Chain Reaction (PCR) is performed using digital PCR. Digital PCR is an improved method of PCR useful to overcome difficulties associated with conventional PCR. Conventional PCR assumes that amplification of nucleic acid is exponential and nucleic acids are quantified by comparing the number of amplification cycles and amount of PCR end-product to those of a reference sample. In practice however, several factors interfere with this calculation, making measurements uncertainties and inaccurate and hence unsuitable for highly sensitive measurements.

In digital PCR, a sample is partitioned so that individual nucleic acid molecules within the sample are localized and concentrated within many separate regions. Molecules can be counted by estimating by using a Poisson distribution. Each partition contains "0" or "1" molecules, or a negative or positive reaction, respectively. After PCR amplification, nucleic acids are quantified by counting the regions that contain PCR end-product, which is a count of positive reactions. A system for digital PCR based on integrated fluidic circuits (chips) having integrated chambers and valves for partitioning samples is commercially available. For example a digital PCR system is available from Life Technologies (Grand Island, N.Y. 14072USA) and QuantaLife QuantaLife Pleasanton, Calif. USA).

This application relates to international application PCT/US2012/039669 filed May 25, 2012 (published as international publication number WO/2012/162660 published Nov. 29, 2012), which claims the benefit of provisional applications having Ser. Nos. 61/489,883 filed May 25, 2011 entitled, "Methods of Immunodiagnostics using DNA Methylation arrays as surrogate measures of the identity of a cell or a mixture of cells"; 61/509,644, filed Jul. 20, 2011 entitled "Methods of Immunodiagnostics using DNA Methylation arrays as surrogate measures of the identity of a cell or a mixture of cells for prognosis and diagnosis of diseases"; 61/585,892 filed Jan. 12, 2012 entitled, "Methods of Immunodiagnostics using DNA Methylation arrays as surrogate measures of the identity of a cell or a mixture of cells for prognosis and diagnosis of diseases"; and 61/619,663, filed Apr. 3, 2012 entitled "Methods using DNA Methylation arrays for identifying a cell or a mixture of cells for prognosis and diagnosis of diseases, and for cell remediation therapies" inventors Karl Kelsey, Eugene Andres Houseman, John Wiencke, William P. Accomando, Jr. and Carmen Marsit, each of which applications including the sequence listings is hereby incorporated herein by reference in its entirety. A portion of the examples and figures herein have been submitted as an appendix to provisional application Ser. No. 61/865,479 filed Aug. 13, 2013, entitled, "Methods using DNA methylation for identifying a cell or a mixture of cells for prognosis and diagnosis of diseases, and for cell remediation therapies", and is an unpublished manuscript submitted to the journal Genome Biology entitled, "Quantitative reconstruction of leukocyte subsets using DNA methylation" by William P. Accomando, Jr., John Wiencke, Eugene Andres Houseman, Heather H. Nelson, and Karl Kelsey.

The invention having been fully described is further illustrated by the following claims and examples herein. Data in Example herein show that cell mixture distributions within peripheral blood were assessed accurately and reliably using DNA methylation. DNA methylation was measured and analyzed in leukocyte subsets purified from whole blood, and a library of lineage specific DNA methylation signatures that distinguish human T-cells, B-cells, NK cells, monocytes, eosinophils, basophils and neutrophils were included that list these signatures. The library was used as a reference to quantify simultaneously these cell types in DNA from adult human blood. The methods described were successful in detecting clinically relevant shifts in leukocyte populations. The methods, compositions and kits herein more accurately analyzed human whole blood samples compared to established methods of immune cell quantification. Data obtained by these methods using DNA methylation were found to be unaffected by duration of storage of blood. Data show that it was possible, using only DNA rather than whole cells by the methods herein, to reconstruct precise immune cell differential numbers. Methods in various embodiments used a library including signatures comprising differentially methylated regions (DMRs) from types of leukocytes in a blood sample of the patient. In various embodiments, the library includes at least one gene or locus selected from the group consisting of: FGD2, HLA-DOB, BLK, IGSF6, CLDN15, SFT2D3, ZNF22, CEL, HDC, GSG1, FCN1, OSBPL5, LDB2, NCR1, EPS8L3, CD3D, PPP6C, CD3G, TXK, and FAIM. In various embodiments, the library includes at least one selected from the group consisting of: CLEC9A (2 loci), INPP5D, INHBE, UNQ473, SLC7A11, ZNF22, XYLB, HDC, RGR, SLCO2B1, C1orf54, TM4SF19, IGSF6, KRTHA6, CCL21, SLC11A1, FGD2, TCL1A, MGMT, CD19, LILRB4, VPREB3, FLJ10379, HLA-DOB, EPS8L3, SHANK1, CD3D (2 loci), CHRNA3, CD3G (2 loci), RARA, and GRASP. The nucleotide sequence and corresponding amino acid sequence of each of the genes or loci are listed in genome or protein databases such as GenBank, European Nucleotide Archive, European Bioinformatics Institute, GenomeNet, or The National Center for Biotechnology Information (NCBI) Protein database.

Examples herein accurately assessed cell mixture distributions within peripheral blood using DNA methylation. DNA methylation was measured in leukocyte subsets purified from whole blood and was used to establish a library of lineage specific DNA methylation signatures that distinguished human T-cells, B-cells, NK cells, monocytes, eosinophils, basophils, and neutrophils. This library was used as a reference to simultaneously quantify these cell types in DNA from adult human blood. Methods, compositions and kits described herein more effectively detected clinically relevant shifts in leukocyte populations that established methods of immune cell quantification performed on human whole blood samples. Unlike established methods, methods described herein were not affected by type and duration of storage of blood samples. Data show that precise immune cell differential estimates were reconstructed using only DNA rather than whole cells.

Different human cell types, defined by function and morphology, are shown in Examples herein in complex mixtures using a variety of physical, optical and proteomic characteristics. (Pollard, T. D. et al. 2007 Cell Biology second edition Saunders Elsevier publishing, Philadelphia, Pa.).

Lineage-specific DNA methylation has been investigated to distinguish different types of cells (Baron, U. et al. 2006 Epigenetics 1: 55-60; Wieczorek, G. et al. 2009 Cancer Res 69: 599-608; Sehouli, J. et al. 2011 Epigenetics 6: 236-246; Wiencke, J. K. et al. 2012 Epigenetics 7: 1391-1402; Accomando, W. P. et al. 2012 Clin Cancer Res 18: 6147-6154; Christensen, B. C. et al. 2009 PLoS Genet 5, e1000602, doi:10.1371/journal.pgen.1000602). Patterns of DNA methylation, occurring at cytosine residues in the context of cytosine-guanine (CpG) dinucleotides, are tightly associated with chromatin conformation, which coordinates gene expression and reflects transcriptional programming of gene expression. (Bird, A. 2002 Genes & development 16: 6-21; and Zaidi, S. K. et al. 2011 The Journal of biological chemistry 286: 18355-18361). During differentiation, somatic cell lineages undergo de novo DNA methylation followed by maintenance methylation (Jaenisch, R. 1997 Trends in genetics: TIG 13: 323-329), thereby establishing mitotically heritable, cell lineage specific methylation signatures (Khavari, D. A., et al. 2010 Cell Cycle 9, 3880-3883; Bocker, M. T. et al. 2011 Blood 117, e182-189; Meissner, A. 2010 Nature biotechnology 28, 1079-1088; Hawkins, R. D. et al. 2010 Cell Stem Cell 6: 479-491). Patterns of DNA methylation served as reliable indicators of cell lineage and were used as sensitive and specific biomarkers for diverse cell types (Baron, U. et al. 2006 Epigenetics 1: 55-60; Accomando, W. P. et al. 2012 Clin Cancer Res 18: 6147-6154; Meissner, A. 2010 Nature biotechnology 28, 1079-1088; Davies, M. N. et al. 2012 Genome Biol 13: R43, doi:10.1186/gb-2012-13-6-r43; and Varley, K. E. et al. 2013 Genome Res 23: 555-567).

The immune system is a powerful model for investigating, developing and implementing new approaches to human cell detection and quantification. Blood is a complex mixture of many different specialized cell types and the composition of white blood cell (WBC, or leukocyte) populations reflects disease states and toxicant exposures (Bui, J. D. et al. 2007 Curr Opin Immunol 19: 203-208; Kim, R. et al. 2007 Immunology 121: 1-14; Ostrand-Rosenberg, S. 2008 Curr Opin Genet Dev 18: 11-18; Dunn, G. P. et al. 2002 Nat Immunol 3: 991-998; Shimizu, J. et al. 1999 J Immunol 163, 5211-5218; Zou, W. 2006 Nat Rev Immunol 6: 295-307). Thus, the ability to detect an improper balance of immune cells is valuable both in a clinical and research setting. However, research aimed at further understanding immune cell level alterations is restricted by the limitations of immunodiagnostic methods. Routine blood leukocyte differentiation is achieved using physical cell isolation and the electrical impedance or optical light scattering properties of the cells (Handin, R. I., Lux, S. E. & Stossel, T. P. 2003 *Blood*: Principles and Practice of Hematology second edition, 2304, Lippincott Williams & Wilkins). Fluorescently labeled antibodies and flow cytometry are used to identify specialized cell subtypes, e.g. CD4+ T-cells (Sehouli, J. et al.

2011 Epigenetics 6: 236-246; Dieye, T. N. et al. 2011 Journal of immunological methods 372: 7-13). These methods rely upon intact cells, and therefore require fresh samples and cannot be applied to older, archived blood samples.

Human leukocytes derive from pluripotent hematopoietic stem cells through a developmental process called hematopoiesis, resulting in a hierarchy of leukocyte lineages each with unique functions and gene expression patterns (Parham, P. 2005 The Immune System second edition, Garland Science, New York, N.Y.). Epigenetic regulation of gene expression is important to hematopoiesis; cellular fates are largely determined by patterns of DNA packaging into chromatin (Janson, P. C. et al. 2009 Biochim Biophys Acta 1790: 906-919).

Examples herein shown that human leukocyte lineages were distinguished with very high sensitivity and specificity by epigenetic marks such as patterns of DNA methylation occurring in differentially methylated regions, DMRs. The identification of DMRs that are biomarkers of specific human leukocyte lineages resulted in the development of sensitive assays for monitoring these leukocytes in the peripheral blood by measuring DNA methylation. While some immune cell lineage-specific DMRs have been used in assays to detect and quantify a single type of leukocyte in human blood and tissue (Wieczorek, G. et al. 2009 Cancer Res 69: 599-608; Sehouli, J. et al. 2011 Epigenetics 6: 236-246; Wiencke, J. K. et al. 2012 Epigenetics 7: 1391-1402; Accomando, W. P. et al. 2012 Clin Cancer Res 18: 6147-6154). Examples herein elucidate a different approach to simultaneously quantify the entire distribution of WBC types in human blood using methylation profiles assessed in archived DNA.

The compositions, methods and kits herein are useful for assessing immune modulations including gimmune profiling to be performed in a wide variety of archival blood samples from large epidemiological studies of human disease and exposure and clinical trials of drug efficacy and biomonitoring. Examples herein include a novel platform for expansion of the nascent field of human immunotoxicology. Compositions, methods and kits herein provide an effective improvement in a vast number of novel diagnostic and therapeutic procedures, by serving as a reliable alternative to the accepted reference standard of manual differential as well as the automated differential and even FACS based analysis. Thus, compositions, methods and kits herein are useful in clinical applications as well as population studies; aiding in diagnostic follow-up, toxicologic assessment and in numerous new approaches being developed in translational medical research. Furthermore, Examples herein provide new approaches to clinicalprofiling of immune response to therapy for chronic diseases.

Without being limited by any particular theory or mechanism of action, it is envisioned that the compositions, methods and kits herein provide can be used to identify, characterize and enumerate any type of lineage stable human cells within complex mixtures. This presents an unprecedented opportunity for the development of a new generation of methods for cellular quantification that exploits the human methylome; supporting the feasibility of "molecular" histology. Using the immune system as a model, Examples herein created a paradigm for the mapping of cell-specific DNA methylation signatures in order to generate reference libraries of efficacious biomarkers that distinguish different cell types. During mitosis, patterns of DNA methylation are replicated at the time of DNA synthesis such that daughter cells inhert both genetic material and epigenetic information contained within the parental cell (Khavari, D. A. et al. 2010 Cell Cycle 9, 3880-3883).

Examples herein include established powerful computational tools to quantitatively reconstruct the precise makeup of cellular mixtures. In the past, simultaneous quantification of normal or disease-associated changes in cell population composition has been accomplished using flow cytometry, electrical impedance, light scatter and/or immunohistochemistry. This approach required large volumes of fresh blood or tissue, and, for flow cytometry, can involve laborious antibody tagging (Roussel, M., et al. 2010 Cytometry. Part A: the journal of the International Society for Analytical Cytology 77: 552-563; Mittag, A. et al. 2011 Methods in cell biology 103: 1-20). In contrast, Examples herein use high-throughput techniqyes which entail simple, convenient DNA analysis methods that can easily be automated to facilitate rapid quantitative reconstruction of cell subsets. Moreover, the assays and arrays (e.g., LDMA) employed use different chemistry than the HDMA, highlighting the crossplatform applicability of the approach described herein.

Further examples of the inventions are found in a manuscript (48 pages) submitted to the journal Genome Biology entitled, "Quantitative reconstruction of leukocyte subsets using DNA methylation" by William P. Accomando, Jr., John K. Wiencke, E. Andres Houseman, Heather H. Nelson, and Karl T. Kelsey, which is incorporated by reference herein in its entirety.

A skilled person will recognize that many suitable variations of the methods may be substituted for or used in addition to those described above and in the claims. It should be understood that the implementation of other variations and modifications of the embodiment of the invention and its various aspects will be apparent to one skilled in the art, and that the invention is not limited by the specific embodiments described herein and in the claims. The present application mentions various patents, scientific articles, and other publications, each of which is hereby incorporated herein in its entirety by reference.

The invention having now been fully described, it is exemplified by the following examples and claims which are for illustrative purposes only and are not meant to be further limiting.

EXAMPLES

Example 1

Statistical Methods for Using DNA Methylation Arrays as Surrogate Measures of Cell Mixture Distribution In the framework for measurement of methylation status of CpG sites in cell mixtures $Y_{0h}$ represents an m×1 vector of methylation assay values, e.g. average beta values from an Infinium bead-array product corresponding to a purified blood sample consisting of a homogenous cellular population (e.g. monocytes or granulocytes), with the qualitative characterization of the cell type indicated by a $d_0 \times 1$ covariate vector $w_h$. Here, $h \in \{1, \ldots, n_0\}$, and the m individual values correspond to CpG sites on a DNA methylation microarray, possibly pre-selected to correspond to putative DMRs for distinguishing different cellular types. Correspondingly, $Y_{1i}$ represents an m×1 vector of methylation assay values for the same CpG sites (in the same order) as $Y_{0h}$, but corresponding to a heterogeneous mixture of cells (e.g. peripheral whole blood) from a human subject. Here, i∈{1, ..., $n_1$}, $n_1$ is the number of target specimens, and $z_{1i}$ is a $d_1 \times 1$ covariate vector representing an intercept as well as phenotypes or exposures corresponding to the subject, e.g. $d_1=2$ for a simple case/control study without confounders. Here the goal is to understand the associations between $Y_{1i}$ and $z_{1i}$ in terms of associations between $Y_{0h}$ and $w_{0h}$, i.e. to infer changes in mixtures of cell types associated with phenotypes or exposures, using DNA methylation as a surrogate measure of cell mixture. Thus, there are two data sets, $S_0=\{(Y_{01}, w_1), \ldots, (Y_{0n_0}, w_{n_0})\}$, the set of data from "purified" cell samples effectively representing external validation or gold-standard data and $S_1=\{(Y_{1i}, z_1), \ldots, (Y_{1n_1}, z_{n_1})\}$, representing surrogate data collected from a target population. To this end following linear models are provided:

$$Y_{0h} = B_0 w_{0h} + e_{0h}$$

$$Y_{1i} = \mu_1 + B_1 z_{1i} + e_{1i}, \quad (1)$$

where $B_0$ and $B_1$ are, respectively, $m \times d_0$ and, $m \times d_1$ matrices and $e_0$ and $e_1$ are error vectors. For simplicity a one-way ANOVA parameterization for w is assumed. Slight generalizations to account for design complications met in practice is described in Example 2.

A reasonable regression parameterization for z is also assumed, including an intercept, and for convenience, the first column of $B_0$ is denoted as $\mu_1$, the $m \times 1$ intercept. The error vectors $e_0$ and $e_1$ may reflect independence among arrays h and i, or else may have more complex random effects structure accounting for technical effects or biological replication; however, their substructures are incidental to this analysis, with the exception of the fine details of the bootstrap procedure proposed below.

To implement a surrogacy relation, the following linking regression model is proposed:

$$B_1 = 1_m \gamma_0^T + B_0 \Gamma + U, \quad (2)$$

where $\Gamma$ is a $d_0 \times d_1$ matrix that summarizes associations between the rows of $B_{0j}$ and $B_{1i}$ and U is a matrix of errors. Substituting equation (2) into (1), writing $B_0=(b_{01}, \ldots, b_{0d_0})$ explicitly in terms of its columns and writing $\Gamma^T=(\gamma_1, \ldots, \gamma_{d_0})$, it follows that $$Y_{1i} = \sum_{l=0}^{d_0} b_{0l}(\gamma_l^T z_{1i}) + (1_m \gamma_0^T + U) z_{1i} + e_{1i}. \quad (3)$$

To impart a biological interpretation, it is assumed assume that the DNA assayed in $S_1$ arises as a mixture of DNA from cell types profiled in $S_0$, with mixture coefficients whose population average, conditional on z, are $\{\omega_1^{(z)}, \ldots, \omega_{d_0}^{(z)}\}$, so that $$E(Y_{1i} \mid z_{1i} = z) = \xi^{(z)} + \sum_{l=1}^{d_0} b_{0l} \omega_l^{(z)}, \quad (4)$$

where the $m \times 1$ vector $\xi^{(z)}$ represents cell types excluded from consideration among the purified samples in $S_0$, or else non-cell specific methylation, including alterations at the molecular level in the maintenance of DNA methylation patterns themselves (possibly exposure related, age, or disease related). It follows from (3) and (4) that the mixture coefficients are recoverable from $\Gamma$, $\omega_l^{(z)} = \gamma_l^T z_{1i}$, provided $\xi^{(z)}$ is orthogonal to the column space of $B_0$. As discussed in detail in the Example 3 bias can arise if differences in $\xi^{(z)}$ between distinct values of z have nonzero projection onto the column space of $B_0$, although the magnitude of anticipated biases can be assessed through sensitivity analysis as shown in Example 11.

It is possible to assign interpretations to the components of variation in (3). $SS_o$ represents overall variability in $Y_{1i}$, i.e.

$$SS_o = \sum_{i=1}^{n_1} \|Y_{1i} - \mu_1\|^2, \text{ where } \mu_1 = E(Y_{1i}).$$

From multivariate probability theory it is straightforward to show that $$SS_o = SS_e + SS_v + SS_u, \text{ where}$$

$$SS_e = \sum_{i=1}^{n_1} \|e_{1i}\|^2,$$

$$SS_v = \sum_{i=1}^{n_1} (z_{1i} - \bar{z}_1)^T \Gamma^T B_0^T B_0 \Gamma (z_{1i} - \bar{z}_1), \text{ and}$$

$$SS_u = \sum_{i=1}^{n_1} \{(z_{1i} - \bar{z}_1)^T U^T U (z_{1i} - \bar{z}_1) + m(z_{1i} - \bar{z}_1)^T \gamma_0 \gamma_0^T (z_{1i} - \bar{z}_1)\}.$$

$SS_e$ measures variation unexplained by the covariates $z_{1i}$, presumed to represent a combination of technical noise and unsystematic biological heterogeneity. $SS_v$ measures variability explained by mixtures of profiles in the set $S_0$, and $SS_u$ measures variability in systematic biological heterogeneity that nevertheless remains unexplained by mixtures of profiles in $S_0$, presumably due to some process other than differences in mixtures of cell types. Thus two partial coefficient of determination measures are proposed: $R_{1,0}^2 = SS_v/SS_o$, which represents the proportion of total variation in $S_1$ explained by $S_0$, and $R_{1,1}^2 = SS_v/(SS_o - SS_e)$, which represents the proportion of systematic variation in $S_1$ explained by $S_0$. It is noted that $R_{1,1}^2$ is poorly defined when $SS_o \approx SS_e$.

Estimation proceeds by applying an appropriate linear model, e.g. ordinary least squares, linear mixed effects models (Wang and Petronis, 2008, DNA Methylation Microarrays: Experimental Design and Statistical Analysis. Chapman & Hall, Boca Raton, Fla.), limma (Smyth, 2004, Stat Appl Genet and Mol Biol, 3(1), 3), or surrogate variable analysis (Teschendorff et al., 2011, Bioinformatics, 27(11), 1496-505), to obtain estimates $\hat{B}_0$ and $\hat{B}_1$. Estimates of $\gamma_0$ and $\Gamma$ are then obtained by projecting $\hat{B}_1$ onto the column space of $\tilde{B}_0 = (1_m, B_0)$, as described in detail in the Example 3. Standard errors can be obtained in one of three ways. The simplest estimator, $SE_0$, is the "naive" estimator from simple least squares theory, ignoring the fact that $\hat{B}_0$ and $\hat{B}_1$ are estimates, i.e. potentially variable. To account for variation in estimating $\hat{B}_1$, a simple alternative is to use a nonparametric bootstrap procedure.

For each bootstrap iteration t, sampling is performed with replacement from $S_1$ (or sample errors in a manner consistent with a hierarchical experimental design) to obtain $S_1^{(t)}$, producing bootstrap estimates $\hat{B}_1^{(t)}$ from which "single-bootstrap" standard errors $SE_1$ are computed. Finally, it is possible to account for variation in estimating $B_0$ by also bootstrapping $S_0$; because of potentially small sample sizes $n_0$, using a parametric bootstrap is proposed herein. A "double-bootstrap" standard error estimator, $SE_2$, is computed from these two sets of bootstraps. The double-bootstrap has the additional benefit over the single-bootstrap, in that it can be used to assess bias due to measurement error (variability) in $\hat{B}_0$. Estimation details are provided in Example 3.

Beyond bias due to measurement error, which is easily corrected using the double-bootstrap procedure, there are additional sources of potential bias. For example, a univariate $z_{1i}$ representing case/control status is considered, where $\delta \equiv \xi^{(1)} - \xi^{(0)} = B_0 \alpha$ for some $d_0 \times 1$ vector $\alpha \neq 0$. In such a situation, there will be a bias equal to $\alpha$ in estimating the mixture differences. Example 2 provides a detailed analysis of such biases, and proposes a sensitivity analysis procedure for assessing the magnitude of possible bias in a given data set.

In the examples herein the method for inferring changes in the distribution of white blood cells between different subpopulations is used for analysis of population data. It is possible to use $S_0$ to predict distribution of leukocytes in a single sample having DNA methylation profile $Y^*$. Equating the intercept term of $B_1$ in (1) with $Y^*$ and applying (2), mixing proportion estimates $\Gamma^* = (\tilde{B}_0^T \tilde{B}_0)^{-1} \tilde{B}_0^T Y$ is obtained. Estimates can be further refined with the use of quadratic programming techniques (Goldfarb and Idnani, 1983, Math Prog, 27, 1-33), restricting the components of $\Gamma^*$, $\gamma_i^* \geq 0$ in minimizing $\|Y^* - B_0 \Gamma^*\|^2$ with respect to $\Gamma^*$. Such individual projections of methylation profiles on the column space spanned by $S_0$ facilitate the application of the fundamental ideas proposed above to individual, clinically-based diagnostic procedures.

It is noted that DNA methylation arrays are typically focused on the comparison of methylated to unmethylated CpG dinucleotides, not quantifying actual amounts of DNA. Therefore, information on cell mixtures from DNA methylation is limited to distributions, not actual counts, as one might obtain from flow cytometry. In addition, it is possible to model $z_{1i}$ directly as a function of mixture coefficients $\Gamma^*$ obtained individually via the constraint $\gamma_1^* \geq 0$.

Example 2

General Designs for the Treatment of Methylation Assay Data Obtained from Purified Cells $S_0$ Because the cell types assembled in $S_0$ potentially involve hierarchical relationships corresponding to cell lineage, designs that are more general than a one-way ANOVA parameterization may be necessary for w. If cell-type interpretations can be extracted from $S_0$ via a $d_0 \times d^*_0$ contrast matrix L (i.e. $B_0 L$ identifies the mean methylation for $d^*_0$ cell types), then interpretations can be obtained by simply replacing $\hat{B}_0$ with $\hat{B}L$ in the projection used to estimate $\gamma_0$ and $\Gamma$ and their standard errors. The case of CD4+ and CD8+ T cells, both of which are the primary components of the T-lymphocyte group is considered as an example. In this example one sample is purified CD4+ T cells, another sample is purified CD8+ T cells, and yet another sample is T-lymphocyte cells that have not been purified to more specific lineages. Such was the case for $S_0$ in the examples. The CD4+ sample may be identified as $w_{0h} = (1,1,0)^T$, the CD8+ sample as $w_{0h} = (1,0,1)^T$, and the latter, less specific sample as $w_{0h} = (1,0,0)^T$. Then an appropriate contrast L for identifying CD4+ and CD8+ samples would be constructed as a 3×2 matrix with columns $(1,1,0)^T$ and $(1,0,1)^T$. This approach was used in the examples 6-9 below, and was also employed in the simulations.

Example 3

Estimation Details and Bias

Estimation:

A two-stage estimation procedure is here introduced. The first stage of analysis involves estimation of $B_0$ and $B_1$ by appropriate linear models, e.g. ordinary least squares (OLS) regression estimator $$\hat{B}_0^T = \left[ \sum_{h=1}^{n_0} z_{0h} z_{0h}^T \right]^{-1} \left[ \sum_{h=1}^{n_0} z_{0h}^T Y_{0h}^T \right]$$

and a similar estimator for $(\hat{\mu}_1, \hat{B}_1)^T$; a procedure such as limma; or else locus-by-locus linear mixed effects models that adjust for technical (e.g. chip) effects. The second stage of analysis, estimation of $\Box\gamma_0$ and $\Box\Gamma$, proceeds as follows:

$$(\hat{\gamma}_0, \hat{\Gamma}^T)^T = \tilde{B}_1^T \tilde{B}_0 (\tilde{B}_0^T \tilde{B}_0)^{-1}, \tag{5}$$

where $\tilde{B}_0 = (1_m, \hat{B}_0)$. Let $\hat{r}_y = \hat{B}_1 - 1_m \hat{\gamma}_0 - \hat{B}_0 \hat{\Gamma}$, $\hat{\Sigma}_y \equiv (\hat{\sigma}_{rs}^{(Y)})_{rs} = (m - d_0 - 1)^{-1} \hat{r}_y^T \hat{r}_y$, $V_0 = m(\tilde{B}_0^T \tilde{B}_0)^{-1}$, and $V_0 = (v_{rs}^{(0)})_{rs}$. Naive standard error estimates for the $(r,s)^{th}$ element of $(\hat{\gamma}_0, \hat{\Gamma}^T)$ can be obtained by computing $(m^{-1} v_{ss}^{(0)} \hat{\sigma}_{rr}^{(Y)})^{1/2}$. The naive standard error estimates fail to account for the variability in estimating $\hat{B}_0$ and $\hat{B}_1$, and are consequently biased, as demonstrated in the simulations, Example 12.

A nonparametric bootstrap procedure is used as an alternative. For each bootstrap iteration t, with replacement from $S_1$ is sampled, (or sample errors in a manner consistent with a hierarchical experimental design, e.g. taking into account chip effects), to obtain $S_1^{(t)}$. From $S_1^{(t)}$ an estimate of $\hat{B}_1^{(t)}$ is obtained, and then $\hat{\gamma}_0^{(t)}$ and $\hat{\Gamma}^{(t)}$ are computed by replacing $\hat{B}_1$ with $\hat{B}_1^{(t)}$ in (S1). After resampling a large number T times, standard errors are obtained empirically from the bootstrap sets $\{\hat{\gamma}_0^{(t)}\}_{t=1, \ldots, T}$ and $\{\hat{\Gamma}^{(t)}\}_{t=1, \ldots, T}$. This method of estimation is called the "single bootstrap" to distinguish it from an alternative that accounts for variability in estimation of $\hat{B}_0$ as well.

Because $S_0$ will typically consist of small sample sizes per cell type, a nonparametric bootstrap procedure for estimating variation in $\hat{B}_0$ may not perform well. Therefore a parametric bootstrap is used. Let $\Omega_j$ be the variance-covariance matrix for the $j^{th}$ row of $\hat{B}_0$. A resampled matrix $\hat{B}_0^{(t)}$ is formed by adding, to each row j of $\hat{B}_0$, a zero-mean multivariate normal vector with variance-covariance $\Omega_j$, or a corresponding multivariate t-distribution with $n_0-d_0$ degrees of freedom. Then $\hat{\gamma}_0^{(t)}$ and $\hat{\Gamma}^{(t)}$ are computed from (S1) by replacing $\hat{\beta}_0$ with $\hat{B}_0^{(t)}$ (in addition to the previously mentioned replacement). This method is referred to as the "double bootstrap". The double bootstrap ignores correlation between CpG sites within a single validation sample, and given the relative purity assumed for these samples and adequate correction for technical effects, this is reasonable to first order. As is demonstrated in Examples 6-9 and simulations (Example 10), there is negligible difference between the single and double bootstrap, so the incorporation of additional complexity to model cross-CpG correlations is unlikely to produce much benefit. However, the double-bootstrap has the additional benefit over the single-bootstrap, in that it can be used to assess bias due to measurement error (variability) in $\hat{B}_0$.

Bias:

There are several potential sources of bias in this analysis. The first arises from measurement error in $B_0$, and the others arise from biological non-orthogonality.

It can be shown that first form of bias, from measurement error, manifests as a multiple of $\Gamma$ on the order of $V_0 \bar{\Omega}$, where $$\bar{\Omega} = m^{-1} \sum_{j=1}^{m} \Omega_j.$$

However, it is easily assessed using the double-bootstrap procedure described above, by subtracting $$\hat{\gamma}_0 \text{ from } T^{-1} \sum_{t=1}^{T} \hat{\gamma}_0^{(t)} \text{ and } \hat{\Gamma} \text{ from } T^{-1} \sum_{t=1}^{T} \hat{\Gamma}^{(t)},$$

and bias correction can be implemented by subtracting this term from the estimate.

Biases induced by biological non-orthogonality are more insidious. For example, a univariate $z_{1i}$ is considered representing case/control status, where $\delta \equiv \xi^{(1)} - \xi^{(0)} = B_0 \alpha$ for some $d_0 \times 1$ vector $\alpha \neq 0$. In such a situation, there will be a bias equal to $\alpha$ in estimating the mixture differences. Non-orthogonal $\delta$ may arise from two distinct sources. One occurs when some cell types have not been profiled in $S_0$, so that $$\sum_{l=0}^{d_0} \omega_l^{(z)} < 1.$$

The other may arise when some non-cell-mediated biological process (i.e. distinct from a change in cellular mixtures) nevertheless results in methylation profiles that appear similar to those that distinguish cell types profiled in $S_0$. To this end, model represented by equation (4) is elaborated follows:

$$E(Y_{1i} \mid z_{1i1} = z) = \sum_{l=1}^{d_0} (B_0 \varepsilon_l + \lambda_l^{(z)}) \omega_l^{(z)} + \sum_{q=1}^{Q} (\tilde{\mu}_q + \tilde{\lambda}_q^{(z)}) \tilde{\omega}_q^{(z)}, \quad (6)$$

where $q \in \{1, \ldots, Q\}$ indexes unprofiled cell types (or free DNA), each with methylation profile $\tilde{\mu}_q$, and in mixture proportions $\omega_l^{(z)}$ and $\tilde{\omega}_q^{(z)}$, $$\sum_{l=1}^{d_0} \omega_l^{(z)} + \sum_{q=1}^{Q} \tilde{\omega}_q^{(z)} = 1.$$

Here $\lambda^{(z)}$ denotes an "abnormal", or at least non-functional, non-cell-mediated process that is specific to disease status (and may affect different cell types in different degrees of intensity).

Let $P = (\tilde{B}_0^T \tilde{B}_0)^{-1} \tilde{B}_0^T$, and denote difference between case and control parameters using $\Delta$, e.g. $\Delta \omega_l = \omega_l^{(1)} - \omega_l^{(0)}$ and $\Delta E(Y_{1i}) = E(Y_{1i} | z_{1i1} = 1) - E(Y_{1i} | z_{1i1} = 0)$. It follows from equation (6) that $$P \Delta E(Y_{1i}) = \sum_{l=1}^{d_0} \varepsilon_l \Delta \omega_l + \sum_{q=1}^{Q} P \mu_q \Delta \tilde{\omega}_q + \sum_{l=1}^{d_0} P \Delta(\lambda_l \omega_l) + \sum_{q=1}^{Q} P \Delta(\tilde{\lambda}_q \tilde{\omega}_q). \quad (7)$$

The values $\Delta \tilde{\omega}_q$ may need to shift in order to accommodate any shifts in $\Delta \omega_l$, since the model constrains $$\sum_{l=1}^{d_0} \Delta \omega_l + \sum_{q=1}^{Q} \Delta \tilde{\omega}_q = 0.$$

The first term on the right hand side of (6) is the target quantity, identifying the desired mixture weights. The second term will be negligible if the profiles $\tilde{\mu}_q$ are approximately orthogonal to the columns of $B_0$, or else the differences $\Delta \tilde{\omega}_q$ are small. This condition will be satisfied if $S_0$ is exhaustive in the sense that $$1 - \sum_{l=1}^{d_0} \omega_l^{(z)}$$

is negligible.

Mathematically, it is difficult to further characterize the latter two terms, without specifying what kinds of non-cell-mediated processes are likely. For example, even if $\Delta \tilde{\lambda}_q = 0$ for a particular value of q, it may nevertheless still produce a bias if $\Delta \tilde{\omega}_q \neq 0$. Conversely, even if $\Delta \omega_l = 0$, bias can result from a nonzero difference $\Delta \lambda_l$ (e.g. different methylation intensities at island shores due to distinct risk profiles) if $\Delta \lambda_l$ is not annihilated by P. Only processes that are equal in intensity in both cases and controls and across cell types will be differenced out of equation (7). Thus, a key consideration is whether P annihilates the methylation signature corresponding to a given non-cell-mediated biological process. In order to examine this issue more carefully, a Bayesian view is adopted to characterize a prior expectation of bias as a function of prior probabilities for individual CpG sites. The goal, in part, is to understand the potential for bias, given the number m of CpG sites chosen to be measured in $S_0$, with the goal of selecting m in a manner consistent with minimizing bias.

Assuming that the CpGs under consideration are ordered in advance (e.g. randomly or by F-statistic $F_j = d_0^{-1} \hat{B}_{0j} \Omega_j^{-1} \hat{B}_{0j}^T$, and that the dependence of $\text{trH}_m = \tilde{B}_0^T \tilde{B}_0$ is explicitly written on m. If the CpGs are randomly ordered, then $\text{trH}_m = O(m)$, otherwise it is possible that $\text{trH}_m = O(m^{1-\zeta})$, $\zeta > 0$ reflecting a diminishing rate of return by adding additional non-informative CpG sites. Then $$\delta = \sum_{l=1}^{d_0} P \Delta(\lambda_l \omega_l) + \sum_{q=1}^{Q} P \Delta(\tilde{\lambda}_q \tilde{\omega}_q)$$

is decomposed by the number k of CpG sites affected by alterations that distinguish cases from controls. k is fixed, $k \in J_m = \{1, \ldots, m\}$; each of the $C(m,k) = m!/[k!(m-k)!]$ subsets $J_{kl} \subset J_m$ of k indices corresponds to a vector $\delta_{kl}$ representing the mean methylation difference between case and control over systematic biological processes that result in changes at the k specific CpG sites represented by the k indices, and only those k CpG sites. Thus $\delta_{kl}$ has at most k nonzero values. The bias resulting from such processes is $H_m^{-1}\check{B}_0^T\delta_{kl}=O(km^{\xi-1})$. A prior probability $\pi_{kl}$ is assumed that the subset $J_{kl}$ could correspond to one or more biological processes that distinguish cases from controls. It follows from this view that the prior expectation of $\delta$ is $$E[\delta \mid (\pi_{kl})_{kl}] = \sum_{k=1}^{m}\sum_{l=1}^{C(m,k)}\pi_{kl}\delta_{kl} = O\left(\sum_{k=1}^{m}\sum_{l=1}^{C(m,k)}\pi_{kl}km^{\xi-1}\right). \quad (8)$$

If a prior probability over sets of CpG sites in the genome is constructed so that CpG sites are considered independent, and each CpG site is assigned a uniform prior probability of $\pi_0$, then $\pi_{kl} \equiv \pi_0^k(1-\pi_0)^{m-k}$ and, from (8), $$E(\delta \mid \pi_0) = O\left(m^{\xi}\sum_{k=1}^{m}C(m-1,k-1)\pi_0^k(1-\pi_0)^{m-k}\right) = \pi_0(1-\pi_0)O(m^{\xi}). \quad (9)$$

The bias does not depend on m if $trH_m=O(m)$, i.e. random ordering. Random ordering renders the size of $E(\delta|\pi_0)$ theoretically independent of m, it does so at the cost of including many potentially noninformative CpGs, early on at low values of m, and these may be possible sources of bias in practice, without offering any modeling benefit in return. If the CpG sites are ordered by level of informativeness, then potentially $H_m=O(m^{1-\zeta})$, and there will be a small increasing prior expectation of bias, motivating judicious choice of m. The key, then, is to order the CpGs in terms of their ability to distinguish different types profiled in $S_0$, choosing m large enough to distinguish the signatures from one another, but small enough that the $E(\delta|\pi_0)$ is reasonably low, in a relative sense. Naturally, different choices of prior $\pi_{kl}$ in (8) will lead to different conclusions about the magnitude of bias. If the set $J_m$ of CpG sites used in $S_0$ and $S_1$ oversample those known to have less modifiable methylation states, e.g. away from so-called shore regions (Doi A et al., 2009, Nat Genet 41: 1350-3), then $\pi_0$ is effectively lowered, and so will be the corresponding expected prior bias. It is worth emphasizing that this analysis concerns only a Bayesian prior, not the actual biological truth. In choosing CpG sites among those assayed in $S_0$ and $S_1$, a potentially negative outcome would be to have included a number of sites that also happen to represent systematic, non-cell-mediated biological differences between cases and controls in $S_1$, in which case biased estimates will be inevitable. In summary, bias in the proposed estimation procedure is controlled by selecting a sufficiently exhaustive list of cell types to profile in $S_0$, and by choosing m judiciously.

Example 4

Figure 1:
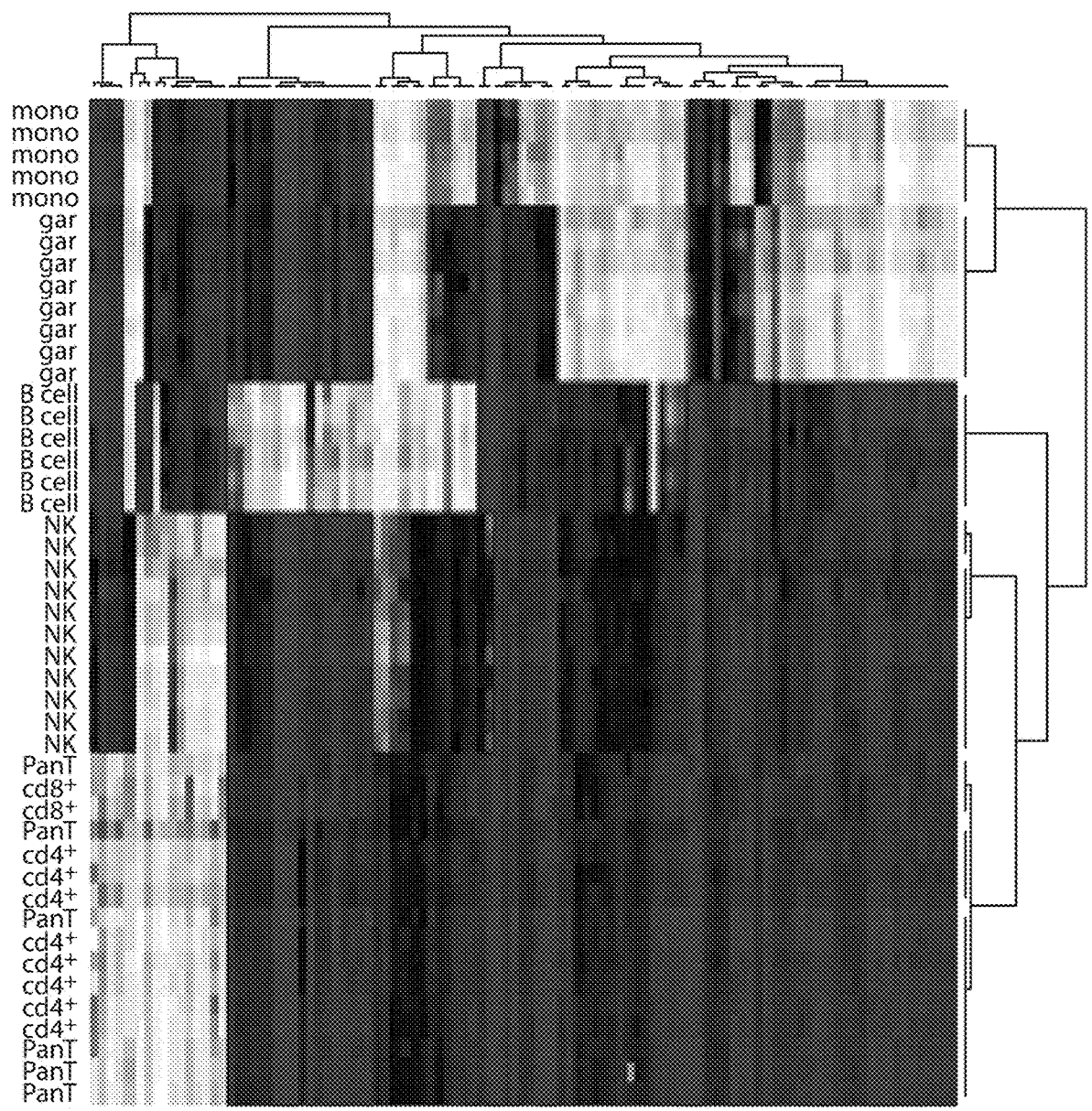
FIG. 1 is a photograph of a clustering heatmap for External Validation White Blood Cell Data ($S_0$). The data were obtained by applying the measurement error formulation described in Examples 1-3. The method delineates effects resulting from immune cell distribution as compared to those resulting from other "non-cell type" alterations in DNA methylation. Methylation array procedure was carried out using Infinium HumanMethylation27 Beadchip Microarrays from Illumina, Inc. (San Diego, Calif.). The White Blood Cell data were gathered from a set of 46 samples of purified white blood leukocyte subtypes obtained commercially. Light=unmethylated ($Y_{hj}=0$), black=partially methylated ($Y_{hj}=0$:5), dark=methylated ($Y_{hj}=1$).

Proof of Concept of Measurement Error Model for Determining Changes in Distribution of White Blood Cells Between Different Subpopulations In this example, general features of the method herein are described that can be used with existing methylation data sets as benchmarks for validating the proposed method to demonstrate its clinical or epidemiological utility. Examples 6-9 that follow show application of the method to specific data sets. The data analyses involve DNA methylation data obtained by the Infinium HumanMethylation27 Beadchip Microarrays from Illumina, Inc. (San Diego, Calif.). A subset of m=100 CpG sites on the array was used and the subset was selected as described below. In Examples 6-9, $S_0$ consisted of 46 white blood cell samples; the sorted, normal, human, peripheral blood leukocyte subtypes were purchased from AllCells®, LLC (Emeryville, Calif.) and were isolated from whole blood using a combination of negative and positive selection with highly specific cell surface antibodies conjugated to magnetic beads; materials and protocols were obtained from Miltenyi Biotec, Inc. (Auburn, Calif.). These 46 samples are summarized in Table 2 and depicted by the clustering heatmap in FIG. 1. T lymphocytes that express CD4 or CD8 constitute over 95% of the T cell class. The pan-T cell type was further refined to CD4+, CD8+, and "other" Pan-T cells subtypes.

In summary, the covariate vector $w_h$ consisted of indicators for five cell types and another two indicators for CD4+ and CD8+ T cell subtypes. A generalization of the one-way ANOVA parameterization assumed above for $w_h$ (Example 2) was necessary to account for the ambiguous status of some Pan-T cells. For each CpG site, a linear mixed effects model with a random intercept for bead chip was used to estimate $B_0$; 27 additional whole blood control samples (replicates from the same individual) were used to assist in estimating chip effects, since otherwise the data set would have been sufficiently sparse to risk confounding between cell type and chip. These "array controls" were indicated with an additional term in $w_{0h}$. For each CpG site, a linear mixed effects model with a random intercept for bead chip was used to estimate the corresponding row of $B_0$ and $B_1$.

Figure 5A:
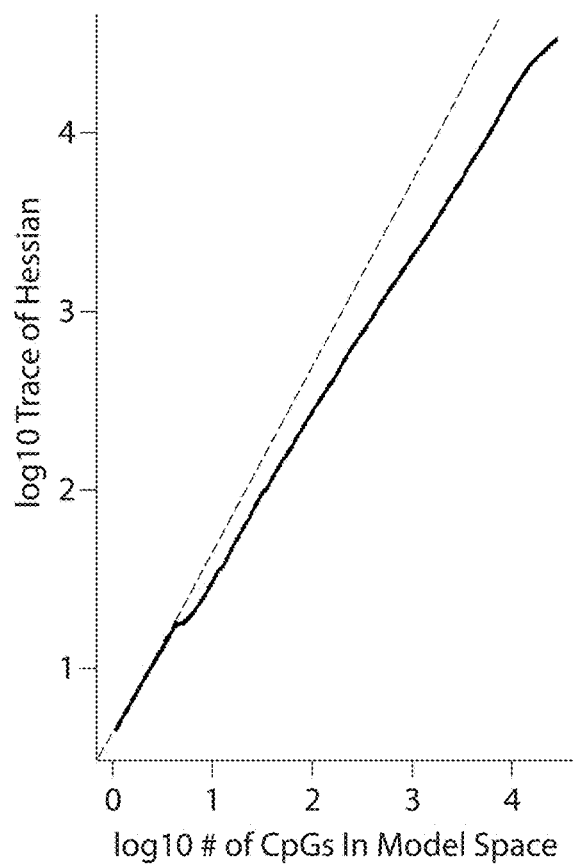
FIG. 5A and FIG. 5B are graphs of Rate-of-Convergence of the Hessian matrix $H_m$ which allows the determination of the optimal number of CpG sites whose combined methylation status measurements most accurately reflect the exact distribution of different cells in a mixture. The x-axis represents increasing m, the number of CpG sites (ordered by F-statistic) included in the model space, on a logarithmic scale.
Figure 5B:
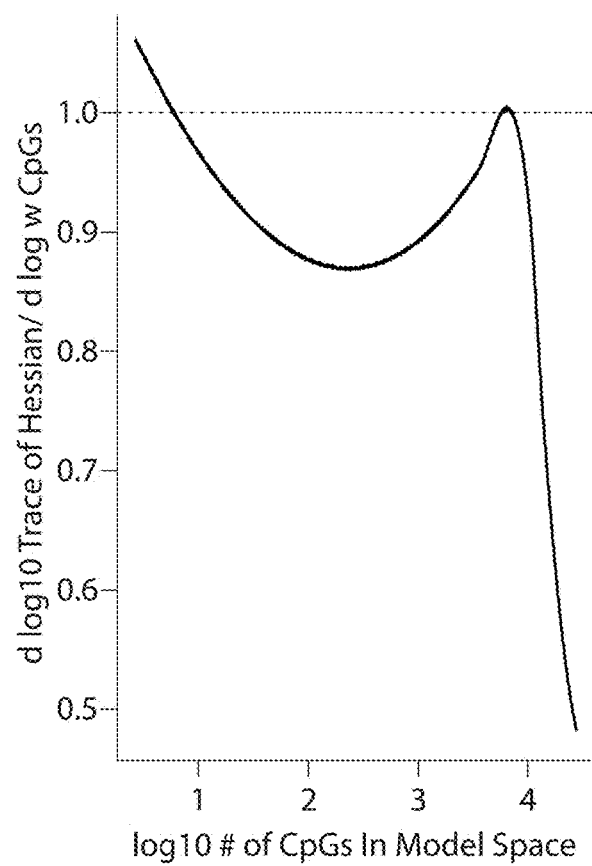

From $S_0$, F statistics were computed and used to order each of the 26,486 autosomal CpGs by decreasing level of informativeness with respect to blood cell types. FIG. 5A depicts the relationship $\log_{10} trH_m$ by $\log_{10}(m)$ for increasing array sizes. FIG. 5B depicts the relationship $\partial \log_{10} tr(H_m)/\partial \log(m)$ by $\log_{10}(m)$ for increasing array sizes, obtained by smoothing the first differences of the curve depicted in FIG. 5A via loess smoother. FIG. 5A also shows the tangent (obtained from the loess curve) at low values of m. For O(m) convergence, FIG. 5A should show a linear association with slope equal to one, and the curve in FIG. 5B should show a curve close to the value of 1.0. Neither is the case, i.e. convergence is sub-linear in m. It is noted that the rate of convergence dropped precipitously after about 6,000 CpG sites, but was notably slower than O(m) even after m=10. In the range of 1-1000 CpG sites the convergence rate appeared parabolic with a minimum of about 0.85, starting to stabilize in the m=100-300 range. Thus, maximum informativeness was provided by the highest ranking m=100-300 CpG sites, with m>300 reflecting diminishing returns from adding additional CpGs. Therefore, a moderately low value of m in this range, m=100, consistent with the size of a small custom microarray chip was chosen.

TABLE 2

Sorted white blood cells in $S_0$

| Short Name | Description | Number |
| --- | --- | --- |
| B cells | CD19+ B-lymphocytes | 6 |
| Granulocytes | CD15+ granulocytes | 8 |
| Monocytes | CD14+ monocytes | 5 |
| NK | CD56+ Natural Killer (NK) cells | 11 |
| T cells (CD4+)[1,2] | CD3+CD4+ T-lymphocytes | 8 |
| T cells (CD8+)[1,3] | CD3+CD8+ T-lymphocytes | 2 |

TABLE 2-continued

Sorted white blood cells in $S_0$

| Short Name | Description | Number |
|---|---|---|
| T cells (NKT)[1] | CD3+CD56+ natural killer | 1 |
| T cells (other)[1] | CD3+ T-lymphocytes | 5 |

[1]Considered as a member of the "pan-T cell" group.
[2]Pan-T cell further refined as also belonging to the "CD4+" group.
[3]Pan-T cell further refined as also belonging to the "CD8+" group.

Example 5

Cell Mixture Experiment for Validating the Method for Determining Changes in Distribution of White Blood Cells Between Different Subpopulations In this example is described a laboratory reconstruction experiment, which validates the concept on which the method herein is based that DNA methylation retains substantial information about cell mixtures. The results of applying the method herein to several different target data sets $S_1$ is described in Examples 6-9.

For the HNSCC and ovarian cancer data sets, from which bead chip data were available, a linear mixed effects model with a random intercept for bead chip was used to estimate the corresponding row of B1. For the remaining data sets, no bead chip data were available; consequently, ordinary least squares was used. 250 bootstrap iterations were used for each example and each of the two bootstrap methods of standard error estimation.

An experiment was conducted which involved six known mixtures of monocytes and B cells and six known mixtures of granulocytes and T cells. FIG. 2 presents both the known fractions ("Expected") and the resulting predictions ("Observed") from Infinium 27K profiles, as described above. As FIG. 2 shows, accuracy of prediction is within 10%, and often less than 5%, with the largest errors occurring for granulocytes, as shown in Table 3. It is noted that the sum of the individual observed predictions for each individual profile ranged from 98.9% to 102.7% even though the constraints of the projection do not explicitly constrain the sum to 100%; this provides additional evidence that the DNA methylation profile captures information about cell mixtures.

TABLE 3

Summary statistics for errors in cell mixture reconstruction Results*

|  | B cell | Granulocyte | Monocyte | NK | T cell |
|---|---|---|---|---|---|
| minimum | 0.0 | 0.3 | 0.0 | 0.0 | 0.0 |
| median | 0.1 | 6.5 | 1.1 | 2.1 | 0.3 |
| maximum | 5.5 | 10.0 | 4.1 | 6.4 | 5.3 |

*|Observed % − Expected %|

Example 6

Figure 3:
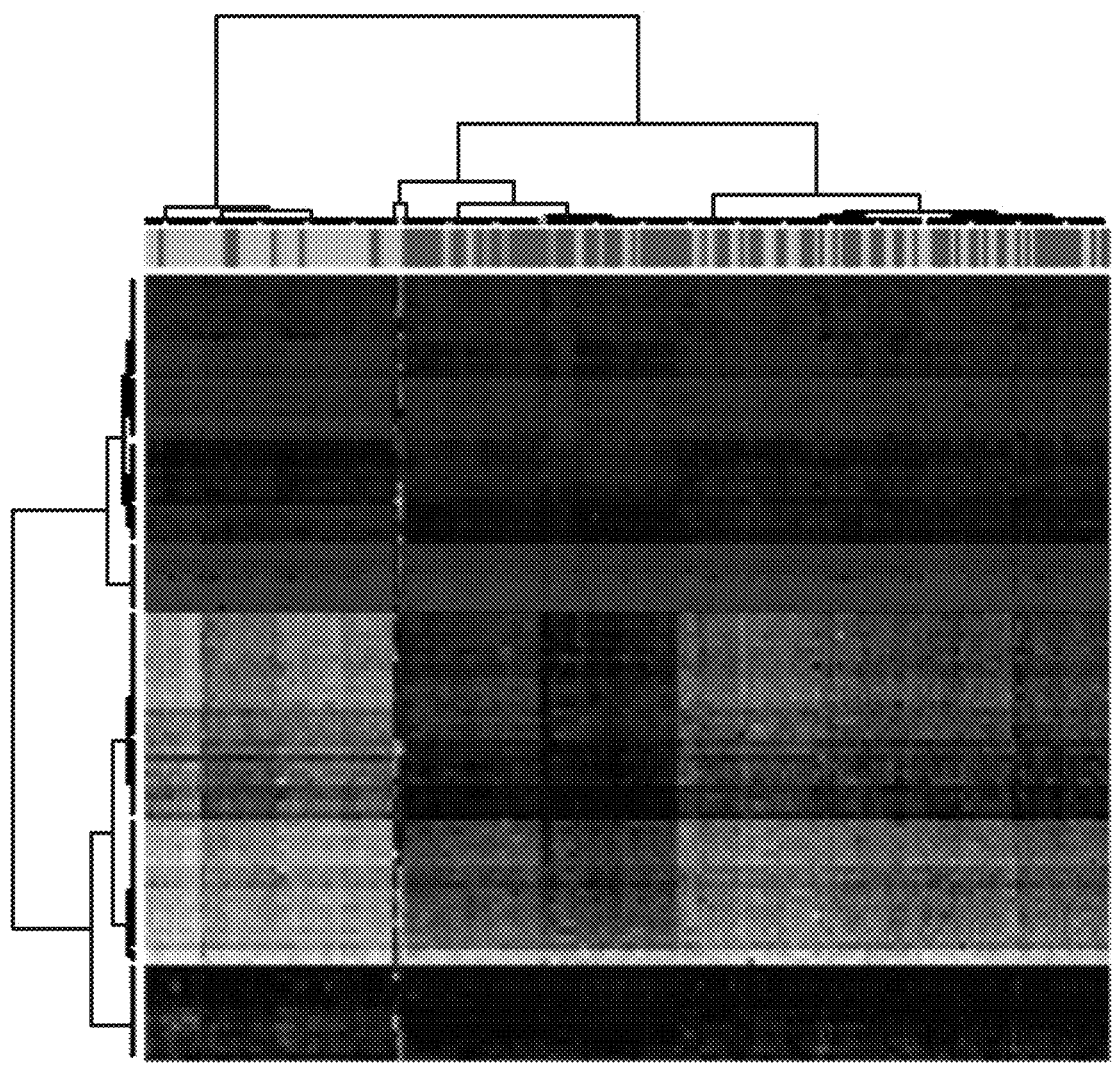
FIG. 3 is a photograph of a clustering heatmap for Target HNSCC data ($S_1$). The target data set $S_1$ consisted of arrays applied to whole blood specimens collected in a random subset of individuals involved in an ongoing population-based case-control study (Peters et al., 2005) of head and neck cancer (HNSCC): 92 cases and 92 age and sex matched controls. Blood was drawn at enrollment (prior to treatment in 85% of the cases). Yellow or light areas represent unmethylated ($Y_{hj}=0$), black areas represent partially methylated ($Y_{hj}=0:5$), gray areas represent methylated ($Y_{hj}=1$). The annotation track above the heatmap indicates case-control status.

Application of the Methods Herein to the Subpopulations of Head and Neck Cancer Patients and Controls This example describes the application of the method herein for determining changes in the distribution of white blood cells between different subpopulations to patients having head and neck squamous cell carcinoma (HNSCC). The target data set $S_1$ was obtained from arrays applied to whole blood specimens collected in a random subset of individuals involved in an ongoing population-based case-control study (Peters et al., 2005, Cancer Epidemiol Biomarkers Prev, 14(2), 476-82) of head and neck cancer (HNSCC): 92 cases and 92 age and sex matched controls. Blood was drawn at enrollment (prior to treatment in 85% of the cases). Mean age among the subjects arrayed in this study was 60 years, and there were 56 females and 128 males, consistent with the higher incidence of the disease in men. Thus, the covariate vector z consisted of an indicator for case/control status, an indicator for male sex, and age (in decades) centered at the mean. The clustering heatmap in FIG. 3 depicts the raw DNA methylation data in $S_1$. Table 4 presents coefficient case status, double-bootstrap bias estimates (estimates of bias arising from measurement error), as well as naive, single-bootstrap, and double-bootstrap standard error estimates. Each of these quantities is measured in percentage points (%). Estimates of bias arising from measurement error (i.e. substituting estimated quantities for known ones in a two-stage statistical procedure) were almost always less than half a percentage point, and for significant coefficient estimates, always towards the null.

The proportion of CD4+ T-lymphocytes decreased in cases compared with controls, with a bias-corrected estimate of −10:4 percentage points and approximate 95% confidence interval (−13:1%; −3:3%); the proportion of NK cells decreased, with a bias-corrected estimate of −1.5 percentage points and 95% confidence interval (−2:2%; −0:75%); and the proportion of granulocytes increased, with a bias-corrected estimate of 7.6 percentage points and 95% confidence interval (4:2%; 10:9%). There was also some evidence of an increase in CD8+ T-lymphocytes, with an estimate of 4.5 percentage points and 95% confidence interval (4:5%; 7:0%). As shown in Table 5 the proportion of CD4+ T-lymphocytes decreased by 3.3 percentage points (−4:4%; −2:2%) per decade of age, and CD8+ T-lymphocytes increased by 2.0 percentage point (1:0%; 3:0%) per decade. The other coefficients were insignificant.

For this analysis, $R_{1,0}^2$ was estimated at 14.2%, and $R_{1,1}^2$ was estimated at 93:9%. Thus, a small but non-negligible proportion of total variation (systematic variation+unexplained biological heterogeneity+technical noise) appeared to have been driven by changes in cell population between cases and controls and as a result of aging. The $SS_e$ comprised 85% of total variation, so a substantial portion of variability in DNA methylation appeared to remain unexplained (presumably due, in large part, to technical noise). However, the systematic variation was explained by changes in cell population.

These results were consistent with previous studies, as HNSCC patients are known to display an absolute and relative increase in myeloid derived granulocytes (Trellakis et al., 2011, Int J Cancer, Epub ahead of print, DOI: 10.1002/ijc.25892) and also displayed an alteration in lymphoid T cell homeostasis that leads to decreases in CD4+ T cells (Kuss et al., 2004, Clin Cancer Res, 10(11), 3755-62; Kuss et al., 2005, Adv Otorhinolaryngol, 62, 161-72). In addition, the proportion of Treg cells (a subclass of CD4+ T cells) is known to decrease from infancy to adulthood (Mold et al., 2010, Science, 330(6011), 1695-9). The bias estimates obtained from the double-bootstrap procedure allow the correction of bias arising from measurement error. However, there is no statistical procedure for correcting the other possible sources of bias, those arising from changes in distribution among unprofiled cell types as well as non-immune-mediated methylation differences. Example 7 presents a detailed sensitivity analysis which shows that the magnitude of the resulting bias is likely to be small, less than a percentage point.

TABLE 4

Estimates for HNSCC analysis (case vs. control)

|  | Est | Bias$_2$ | SE$_0$ | SE$_1$ | SE$_2$ | P-value |
|---|---|---|---|---|---|---|
| (Intercept, $\gamma_0$) | −0.62 | −0.02 | 0.41 | 0.52 | 0.52 | 0.23 |
| B Cell | −0.45 | 0.04 | 0.30 | 0.77 | 0.76 | 0.55 |
| Granulocyte | 7.51 | −0.07 | 0.50 | 1.73 | 1.71 | <0.0001 |
| Monocyte | 0.49 | 0.10 | 0.50 | 0.47 | 0.48 | 0.31 |
| NK | −1.43 | 0.06 | 0.56 | 0.37 | 0.38 | 0.00017 |
| T Cell (cd4+) | −9.08 | 1.32 | 1.95 | 1.15 | 1.39 | <0.0001 |
| T Cell (cd8+) | 3.06 | −1.46 | 1.96 | 0.98 | 1.27 | 0.016 |

Est = Regression coefficient estimate (×100%).
Bias$_2$ = Double-bootstrap bias estimate (×100%).
SE$_0$ = Naive standard error (×100%).
SE$_1$ = Single-bootstrap standard error (×100%).
SE$_2$ = Double-bootstrap standard error (×100%).
P-values were computed using SE$_2$.

TABLE 5

Estimated Regression Coefficients for Sex and Age in HNSCC Data Set

|  |  | Est | Bias$_2$ | SE$_0$ | SE$_1$ | SE$_2$ | P-value |
|---|---|---|---|---|---|---|---|
| Sex | (Intercept, $\gamma_0$) | 0.12 | 0.00 | 0.24 | 0.57 | 0.57 | 0.83 |
|  | B Cell | 0.38 | 0.01 | 0.17 | 0.85 | 0.84 | 0.65 |
|  | Granulocyte | −0.29 | −0.08 | 0.28 | 1.82 | 1.81 | 0.87 |
|  | Monocyte | 0.13 | 0.01 | 0.29 | 0.47 | 0.47 | 0.78 |
|  | NK | 0.49 | 0.05 | 0.32 | 0.40 | 0.40 | 0.22 |
|  | T Cell (cd4+) | −1.80 | 0.45 | 1.12 | 1.25 | 1.20 | 0.13 |
|  | T Cell (cd8+) | 0.82 | −0.44 | 1.12 | 1.03 | 1.04 | 0.43 |
| (Age − 60)/10 | (Intercept, $\gamma_0$) | −0.20 | −0.02 | 0.15 | 0.24 | 0.24 | 0.40 |
|  | B Cell | 0.24 | 0.01 | 0.11 | 0.34 | 0.33 | 0.47 |
|  | Granulocyte | 1.12 | −0.01 | 0.19 | 0.67 | 0.67 | 0.096 |
|  | Monocyte | 0.13 | 0.02 | 0.19 | 0.20 | 0.20 | 0.54 |
|  | NK | −0.22 | 0.02 | 0.21 | 0.15 | 0.15 | 0.14 |
|  | T Cell (cd4+) | −2.75 | 0.56 | 0.73 | 0.53 | 0.57 | <0.0001 |
|  | T Cell (cd8+) | 1.44 | −0.56 | 0.73 | 0.46 | 0.50 | 0.0038 |

Est = Regression coefficient estimate (×100%)
Bias$_2$ = Double-bootstrap bias estimate (×100%).
SE$_0$ = Naive standard error (×100%).
SE$_1$ = Single-bootstrap standard error (×100%).
SE$_2$ = Double-bootstrap standard error (×100%).
P-values were computed using SE$_2$.

Example 7

Figure 6:
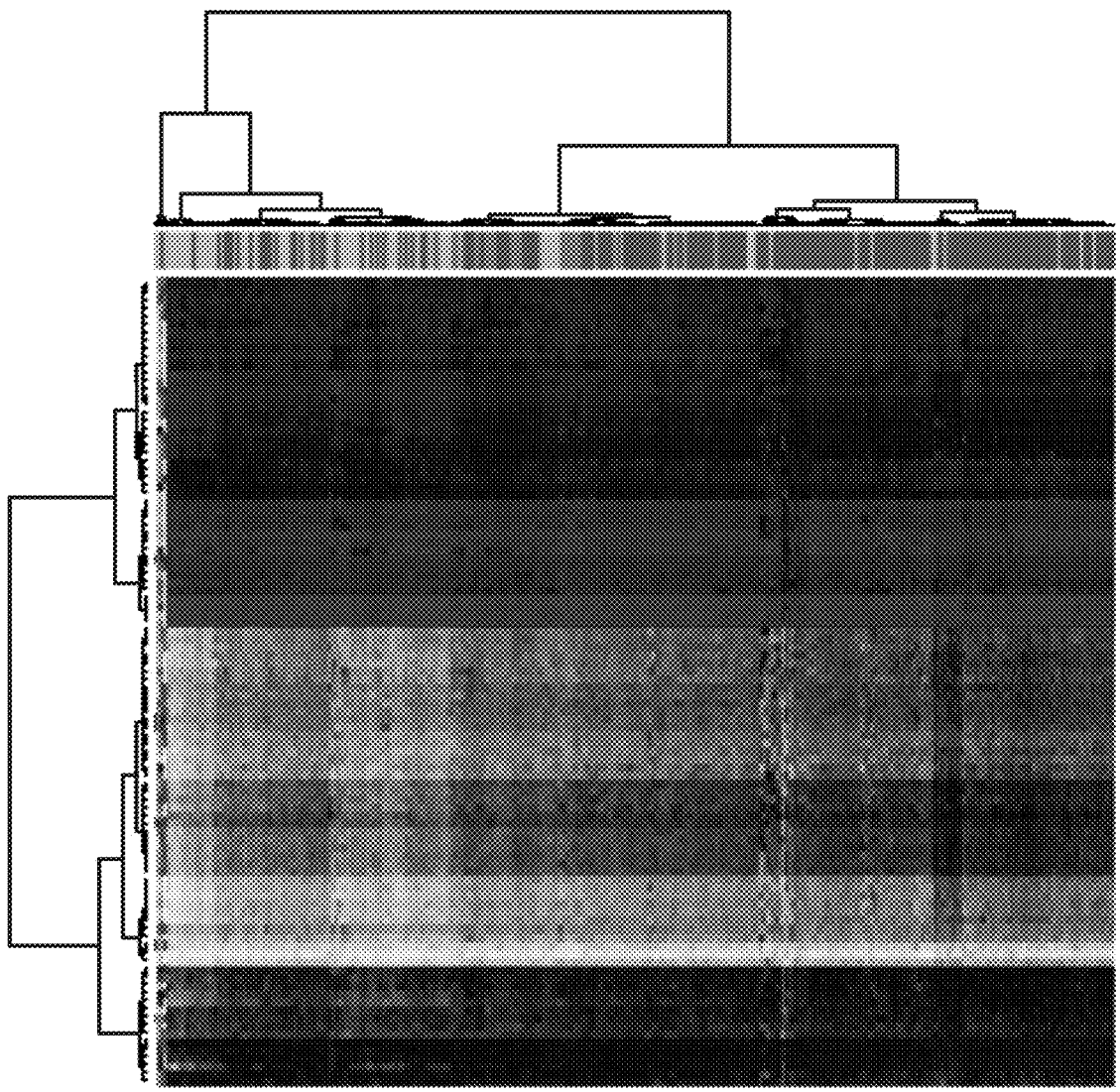
FIG. 6 is a photograph of a clustering heatmap for Target Ovarian Cancer data ($S_1$) (Teschendorff et al., 2009, *PLoS ONE* 4, e8274). Only those cases were included in which blood was collected pre-treatment. After removing four arrays with a preponderance of missing values, the data set consisted of 272 controls and 129 cases having blood drawn prior to treatment. Light=unmethylated ($Y_{hj}=0$), black=partially methylated ($Y_{hj}=0:5$), dark=methylated ($Y_{hj}=1$). The annotation track above the heatmap indicates case-control status (cancer case or control).

Application of the Methods Herein to Subpopulations of Ovarian Cancer Cases and Controls In this example the method herein for inferring changes in the distribution of white blood cells between different subpopulations (e.g. cases and controls) was applied to an ovarian cancer data set (Teschendorff et al., 2009, PLoS ONE, 4(12), e8274). DNA methylation data for blood samples were obtained from Gene Expression Omnibus (Accession number GSE19711). Only those cases in which blood was collected pre-treatment were used ere. After removing four arrays with a preponderance of missing values, the data set consisted of 272 controls and 129 cases in which blood was collected prior to treatment. A clustering heatmap displaying the DNA methylation data is shown in FIG. 6. In this analysis, z consisted of case-control status, age (categorized in five-year increments), and two bisulfite conversion efficiency measures. Tables 6-8 presents result for case-control status and estimated regression coefficients for age in ovarian cancer data set. $R_{1,0}^2$ was estimated at 17.8%, and $R_{1,1}^2$ was estimated at 86:1%.

TABLE 6

Estimates for Ovarian Cancer Analysis (Case vs. Control)

|  | Est | Bias$_2$ | SE$_0$ | SE$_1$ | SE$_2$ | P-value |
|---|---|---|---|---|---|---|
| (Intercept, $\gamma_0$) | −0.05 | −0.05 | 0.41 | 0.19 | 0.20 | 0.81 |
| B Cell | −1.36 | 0.02 | 0.29 | 0.22 | 0.23 | <0.0001 |
| Granulocyte | 8.97 | −0.04 | 0.49 | 1.02 | 1.00 | <0.0001 |
| Monocyte | 0.55 | 0.06 | 0.49 | 0.29 | 0.30 | 0.066 |
| NK | −2.09 | 0.01 | 0.55 | 0.31 | 0.34 | <0.0001 |
| T Cell (cd4+) | 5.64 | 0.18 | 1.93 | 1.06 | 1.34 | <0.0001 |
| T Cell (cd8+) | −0.35 | −0.17 | 1.93 | 0.95 | 1.19 | 0.77 |

Est = Regression coefficient estimate (×100%).
Bias$_2$ = Double-bootstrap bias estimate (×100%).
SE$_0$ = Naive standard error (×100%)
SE$_1$ = Single-bootstrap standard error (×100%).
SE$_2$ = Double-bootstrap standard error (×100%).
P-values were computed using SE2.

TABLE 7

Estimated Regression Coefficients for Age in Ovarian Cancer Data Set

|  |  | Est | Bias$_2$ | SE$_0$ | SE$_1$ | SE$_2$ | P-value |
|---|---|---|---|---|---|---|---|
| Age 55-60 | (Intercept, $\gamma_0$) | −1.24 | −0.05 | 0.37 | 0.41 | 0.40 | 0.0021 |
|  | B Cell | 0.40 | 0.04 | 0.27 | 0.50 | 0.49 | 0.42 |
|  | Granulocyte | 0.91 | 0.04 | 0.45 | 2.04 | 2.02 | 0.65 |
|  | Monocyte | 0.85 | 0.12 | 0.45 | 0.59 | 0.58 | 0.15 |
|  | NK | −0.25 | 0.10 | 0.50 | 0.55 | 0.55 | 0.65 |
|  | T Cell (cd4+) | −2.79 | 0.63 | 1.76 | 2.13 | 1.96 | 0.15 |
|  | T Cell (cd8+) | 2.22 | −0.84 | 1.77 | 1.81 | 1.59 | 0.16 |
| Age 60-65 | (Intercept, $\gamma_0$) | −0.72 | −0.07 | 0.35 | 0.39 | 0.39 | 0.070 |
|  | B Cell | 0.54 | 0.07 | 0.25 | 0.49 | 0.49 | 0.27 |
|  | Granulocyte | 0.71 | 0.06 | 0.42 | 1.99 | 1.98 | 0.72 |
|  | Monocyte | 0.27 | 0.08 | 0.42 | 0.58 | 0.58 | 0.64 |
|  | NK | −0.24 | 0.06 | 0.47 | 0.55 | 0.55 | 0.65 |
|  | T Cell (cd4+) | −3.54 | 0.80 | 1.66 | 2.02 | 1.97 | 0.072 |
|  | T Cell (cd8+) | 2.84 | −0.97 | 1.66 | 1.85 | 1.64 | 0.084 |
| Age 65-70 | (Intercept, $\gamma_0$) | −0.53 | −0.08 | 0.40 | 0.41 | 0.41 | 0.19 |
|  | B Cell | −0.03 | 0.07 | 0.29 | 0.51 | 0.51 | 0.96 |
|  | Granulocyte | 2.46 | 0.02 | 0.48 | 2.17 | 2.17 | 0.26 |
|  | Monocyte | 0.85 | 0.12 | 0.48 | 0.64 | 0.64 | 0.18 |
|  | NK | −0.89 | 0.07 | 0.54 | 0.59 | 0.60 | 0.14 |
|  | T Cell (cd4+) | −6.12 | 1.48 | 1.89 | 2.18 | 2.12 | 0.0038 |
|  | T Cell (cd8+) | 4.37 | −1.64 | 1.89 | 1.87 | 1.71 | 0.011 |
| Age 70-75 | (Intercept, $\gamma_0$) | −1.20 | −0.07 | 0.40 | 0.41 | 0.41 | 0.0037 |
|  | B Cell | 0.29 | 0.07 | 0.29 | 0.48 | 0.48 | 0.55 |
|  | Granulocyte | 2.13 | −0.05 | 0.48 | 2.05 | 2.04 | 0.30 |
|  | Monocyte | 0.76 | 0.12 | 0.48 | 0.60 | 0.60 | 0.21 |
|  | NK | −0.51 | 0.19 | 0.54 | 0.56 | 0.55 | 0.36 |
|  | T Cell (cd4+) | −6.82 | 1.97 | 1.89 | 2.16 | 2.12 | 0.0013 |
|  | T Cell (cd8+) | 5.35 | −2.20 | 1.90 | 1.89 | 1.79 | 0.0028 |
| Age 75+ | (Intercept, $\gamma_0$) | −0.31 | −0.09 | 0.49 | 0.46 | 0.45 | 0.49 |
|  | B Cell | 0.13 | 0.08 | 0.35 | 0.54 | 0.53 | 0.81 |
|  | Granulocyte | 1.10 | −0.15 | 0.58 | 2.12 | 2.11 | 0.60 |
|  | Monocyte | 1.73 | 0.12 | 0.59 | 0.64 | 0.63 | 0.0065 |

TABLE 7-continued

Estimated Regression Coefficients
for Age in Ovarian Cancer Data Set

|  | Est | Bias$_2$ | SE$_0$ | SE$_1$ | SE$_2$ | P-value |
|---|---|---|---|---|---|---|
| NK | −0.30 | 0.13 | 0.66 | 0.60 | 0.59 | 0.61 |
| T Cell (cd4+) | −6.54 | 1.31 | 2.30 | 2.29 | 2.18 | 0.0027 |
| T Cell (cd8+) | 2.73 | −1.37 | 2.31 | 2.06 | 1.86 | 0.14 |

Est = Regression coefficient estimate (×100%)
Bias$_2$ = Double-bootstrap bias estimate (×100%).
SE$_0$ = Naive standard error (×100%).
SE$_1$ = Single-bootstrap standard error (×100%).
SE$_2$ = Double-bootstrap standard error (×100%).
P-values were computed using SE$_2$

TABLE 8

Estimated Regression Coefficients for Bisulfite
Conversion in Ovarian Cancer Data Set

| | | Est | Bias$_2$ | SE$_0$ | SE$_1$ | SE$_2$ | P-value |
|---|---|---|---|---|---|---|---|
| BSC1 | (Intercept, γ$_0$) | −0.08 | 0.00 | 0.14 | 0.09 | 0.10 | 0.39 |
| (Green/ | B Cell | −0.10 | 0.00 | 0.10 | 0.10 | 0.10 | 0.30 |
| 1000) | Granulocyte | 0.13 | 0.04 | 0.17 | 0.40 | 0.40 | 0.74 |
| | Monocyte | 0.13 | −0.01 | 0.17 | 0.12 | 0.12 | 0.26 |
| | NK | −0.09 | 0.00 | 0.19 | 0.14 | 0.14 | 0.53 |
| | T Cell (cd4+) | 0.51 | −0.14 | 0.65 | 0.48 | 0.51 | 0.32 |
| | T Cell (cd8+) | −0.23 | 0.11 | 0.66 | 0.40 | 0.47 | 0.62 |
| BSC2 | (Intercept, γ$_0$) | 0.25 | 0.00 | 0.14 | 0.08 | 0.08 | 0.0027 |
| (Green/ | B Cell | 0.07 | 0.00 | 0.10 | 0.08 | 0.08 | 0.40 |
| 1000) | Granulocyte | 0.07 | 0.01 | 0.17 | 0.38 | 0.37 | 0.84 |
| | Monocyte | −0.18 | 0.01 | 0.17 | 0.10 | 0.10 | 0.075 |
| | NK | 0.10 | 0.00 | 0.19 | 0.12 | 0.12 | 0.41 |
| | T Cell (cd4+) | −0.65 | 0.20 | 0.67 | 0.41 | 0.50 | 0.20 |
| | T Cell (cd8+) | 0.63 | −0.21 | 0.68 | 0.34 | 0.45 | 0.16 |

Est = Regression coefficient estimate (×100%)
Bias$_2$ = Double-bootstrap bias estimate (×100%).
SE$_0$ = Naive standard error (×100%).
SE$_1$ = Single-bootstrap standard error (×100%).
SE$_2$ = Double-bootstrap standard error (×100%).
P-values were computed using SE$_2$.
It is noted that coefficients are given as %/1000 units fluorescence, and that standard deviations for BSC1 and BSC2 were 1950 and 2169, respectively.

Compared with controls, data obtained from cases showed significant increases in granulocytes and significant decreases in B cells, NK cells, and CD4+ T cells. Cases also showed marginally significant increases in monocytes. These results are consistent with previous literature, in which it has been demonstrated that ovarian cancer patients experience decreases in B and T lymphocytes (den Ouden et al., 1997, Eur J Obstet Gynecol Reprod Biol, 72, 73-77; Bishara et al., 2008, Reprod Biol, 138, 7175; Cho et al., 2009, Cancer Immunol Immunother, 58, 1523), increases in monocytes (den Ouden et al., 1997, Eur J Obstet Gynecol Reprod Biol, 72, 73-77; Bishara et al., 2008, Reprod Biol, 138, 7175) and (somewhat equivocally) increases in eosinophil granulocytes (Bishara et al., 2008, Reprod Biol, 138, 7175). Additionally, there were significant systematic decreases in CD4+ T cells with increasing age, with a gradient consistent in direction and somewhat consistent in magnitude with the corresponding effect found in the HNSCC data set. The CD8+ T cell coefficients for were positive, with gradient consistent in direction and somewhat consistent in magnitude with the corresponding effect found in the HNSCC data set. No bisulfite conversion coefficient was significant, and coefficients were of small magnitude (Table 8; generally less than 1 percentage point per standard deviation).

Example 8

Figure 7:
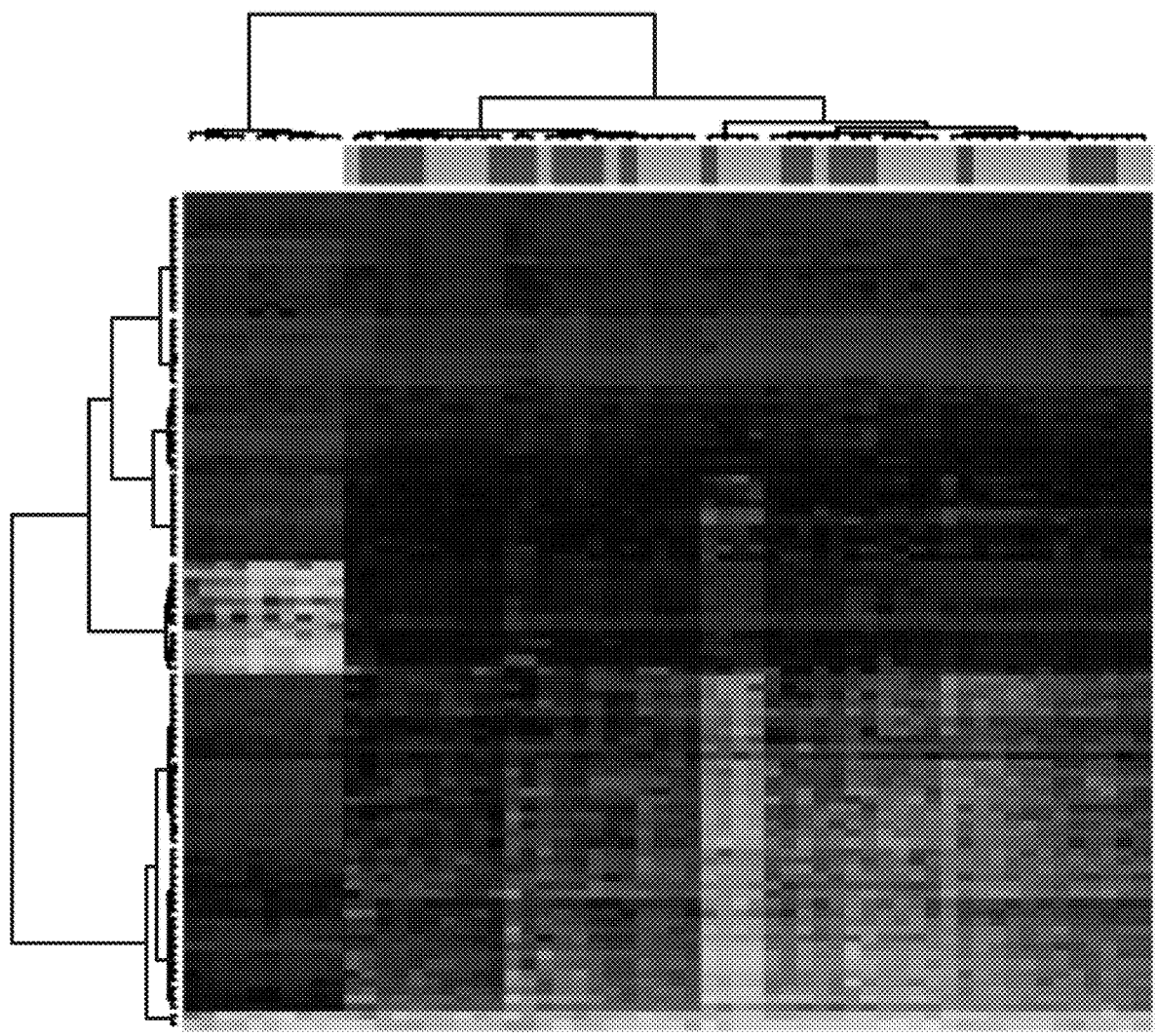
FIG. 7 is a photograph of a clustering heatmap for Target Down Syndrome Data. The method herein was applied to a trisomy 21 (Down syndrome) data set (Kerkel et al., *PLoS Genet* 2010, 6(11):e1001212) consisting of 29 total peripheral blood leukocyte samples from Down syndrome cases and 21 controls, as well as six T cell samples from cases and four T cell samples from controls (GEO Accession number GSE25395). Light=unmethylated ($Y_{hj}=0$), black=partially methylated ($Y_{hj}=0:5$), dark=methylated ($Y_{hj}=1$). The annotation track above the heatmap indicates case-control and cell type status [Down syndrome case (whole blood), control (whole blood), T cell (pooled cases and controls)].

Application of the Methods Herein to Subpopulations of Down Syndrome Patients and Controls The method herein was applied to trisomy 21 (Down syndrome) data set (Kerkel et al., PLoS Genet 2010, 6(11): e1001212) consisting of 29 total peripheral blood leukocyte samples from Down syndrome cases and 21 controls, as well as six T cell samples from cases and four T cell samples from controls (GEO Accession number GSE25395). Because of the potential for bias induced by copy number amplification four CpG sites on Chromosome 21 were excluded, resulting in m=96 CpG sites that were used for analysis. A clustering heatmap displaying the DNA methylation data is shown in FIG. 7. In one analysis data from cases and controls were compared using the total leukocyte samples only, and in another total leukocytes to T cells were compared, pooling cases and controls. Coefficient estimates are provided in Table 9. The only significant difference between cases and controls was in B cell distribution, with bias-corrected estimated decrease of 4.8%, 95% confidence interval (−6: 2%; −3:5%). This result is consistent with known immune characteristics of Down Syndrome, including deficiencies in both B and T cells (Verstegen et al., 2010, Pediatr Res, 67, 563-9; Ram and Chinen, 2011, Clin Exp Immunol, 164, 9-16). However, in the comparison between total leukocytes and T cells, the coefficients except B Cell and NK were highly significant, in directions consistent with comparison of a sample of purified T cells to a generic whole blood sample. In fact, an estimate of the cellular composition of the T cell samples can be obtained by a simple linear transformation of F estimates (adding intercept terms with the T cell coefficients); this operation produces values that are not significantly distinct from zero for the cell types except CD4+ and CD8+, whose bias-corrected estimates were, respectively, 75.9%, 95% confidence interval (67%; 85%) and 8.6%, 95% confidence interval (0%; 17%), for cases and controls consistent with the known distribution of these T cells. For the analysis of case vs. control within total leukocytes, $R_{1,0}^2$ was estimated at 4.5%, and $R_{1,1}^2$ was estimated at 67:6%. For the analysis of total leukocyte vs. T cell with pooled cases and controls, $R_{1,0}^2$ was estimated at 81.4%, and $R_{1,1}^2$ was estimated at 98:9%. The latter set of coefficients of determination indicates that a substantial portion of variation is explained by composition of leukocytes, which is the expected result for such an analysis.

TABLE 9

Estimates for Down syndrome analysis (case
vs. control, total leukocyte vs. T Cell)

| | | Est | Bias$_2$ | SE$_0$ | SE$_1$ | SE$_2$ | P-value |
|---|---|---|---|---|---|---|---|
| Case | Intercept, γ$_0$ | 2.02 | −0.10 | 0.86 | 1.17 | 1.17 | 0.084 |
| Status | B Cell | −4.87 | −0.03 | 0.62 | 0.70 | 0.69 | <0.0001 |
| (total | Granulocyte | 3.85 | 0.15 | 1.02 | 3.01 | 2.98 | 0.20 |
| leuko- | Monocyte | 0.12 | 0.11 | 1.03 | 0.97 | 0.96 | 0.90 |
| cytes) | NK | −0.63 | −0.06 | 1.16 | 0.83 | 0.82 | 0.44 |
| | T Cell (cd4+) | −0.30 | −0.37 | 4.02 | 2.49 | 2.66 | 0.91 |
| | T Cell (cd8+) | −1.89 | 0.35 | 4.03 | 2.47 | 2.42 | 0.43 |
| T Cell | Intercept, γ$_0$ | −0.97 | 0.07 | 1.7 | 1.4 | 1.6 | 0.54 |
| (cases + | B Cell | −0.51 | 0.02 | 1.2 | 1.2 | 1.2 | 0.67 |
| controls) | Granulocyte | −56.21 | 0.49 | 2.1 | 3.4 | 3.4 | <0.0001 |
| | Monocyte | −5.13 | −0.37 | 2.1 | 1.1 | 1.3 | <0.0001 |

TABLE 9-continued

Estimates for Down syndrome analysis (case vs. control, total leukocyte vs. T Cell)

|  | Est | Bias$_2$ | SE$_0$ | SE$_1$ | SE$_2$ | P-value |
|---|---|---|---|---|---|---|
| NK | 0.07 | 0.34 | 2.3 | 1.5 | 1.7 | 0.97 |
| T Cell (cd4+) | 60.18 | −2.89 | 8.1 | 3.2 | 5.2 | <0.0001 |
| T Cell (cd8+) | 3.00 | 2.34 | 8.2 | 3.3 | 5.4 | 0.58 |

Est = Regression coefficient estimate (×100%).
Bias$_2$ = Double-bootstrap bias estimate (×100%).
SE$_0$ = Naive standard error (×100%).
SE$_1$ = Single-bootstrap standard error (×100%).
SE$_2$ = Double-bootstrap standard error (×100%).
P-values were computed using SE$_2$.

Example 9

Application of the Methods Herein to Obesity in an African American Population

Figure 8:
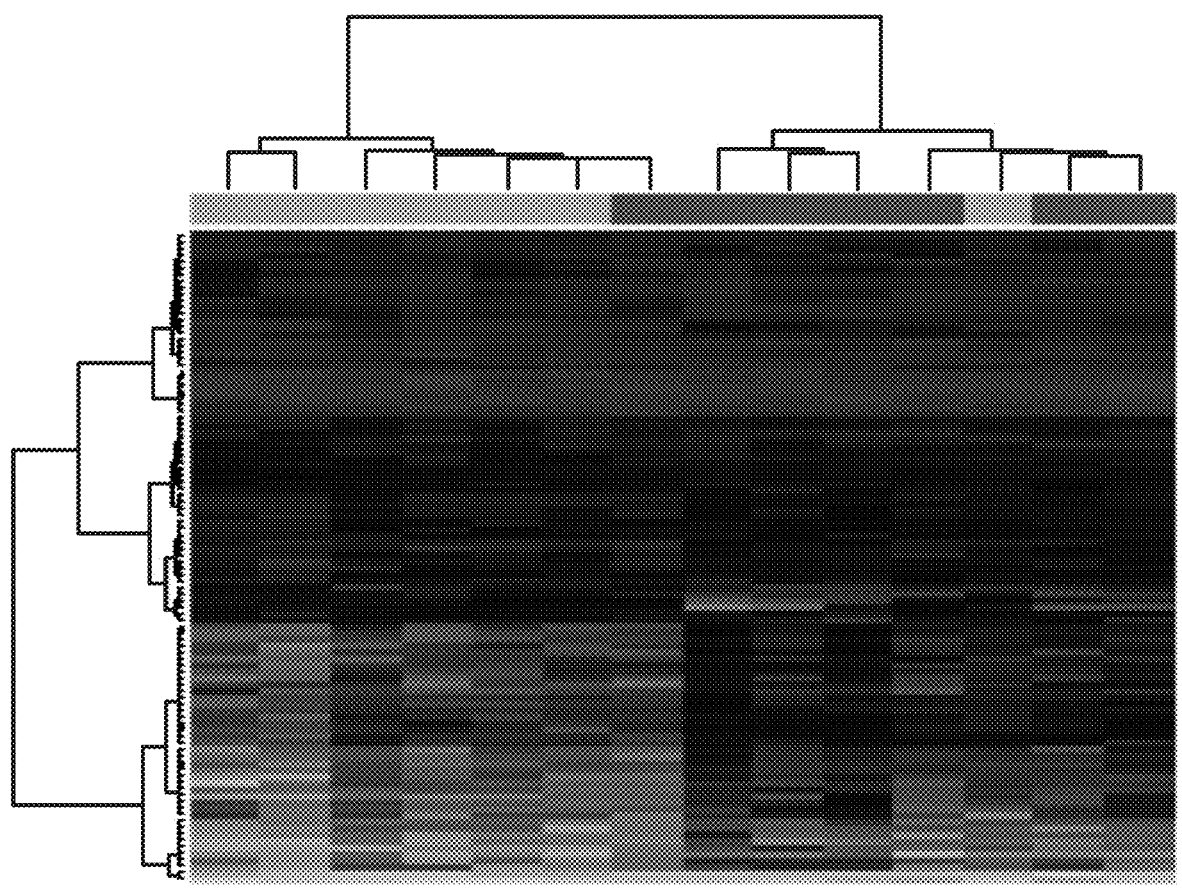
FIG. 8 is a photograph of a clustering heatmap for Target Obesity Data obtained from applying the methods herein to an obesity data set (Wang et al., BMC Med 2010, 8:87) having 7 lean African-Americans and 7 Obese African-Americans (GEO Accession number GSE25301). Light areas represent unmethylated ($Y_{hj}=0$), black areas represent partially methylated ($Y_{hj}=0:5$), grey areas represent methylated ($Y_{hj}=1$). The annotation track above the heatmap indicates case-control status (obese and lean).

The method herein was also applied to an obesity data set (Wang et al., 2010) consisting of seven lean African-Americans and seven Obese African-Americans (GEO Accession number GSE25301). FIG. 8 shows a clustering heatmap displaying the DNA methylation data. In this analysis, z consisted of obesity status. Obese subjects had an estimated increase of 12 percentage points in granulocytes, bias-corrected 95% confidence interval (3:4%; 20%) and an estimated decrease of 4 percentage points in NK cells, bias-corrected 95% confidence interval (−7:7%; −0:9%) (Table 10). No significant differences were found for other blood cell types. The specific immunological differences estimated by the method herein are consistent with known immunological perturbations associated with type II diabetes (Lynch et al., 2009, Obesity, 17(3), 601-5; Anderson et al., 2011, Curr Opin Lipidol, 21(3), 172-7.).

TABLE 10

Estimated Regression Coefficients for Data Set concerning Obesity in African Americans

|  |  | Est | Bias$_2$ | SE$_0$ | SE$_1$ | SE$_2$ | P-value |
|---|---|---|---|---|---|---|---|
| Obese | Intercept, γ$_0$ | 0.96 | −0.09 | 1.08 | 0.85 | 0.84 | 0.25 |
|  | B Cell | 0.70 | −0.03 | 0.78 | 1.16 | 1.14 | 0.54 |
|  | Granulocyte | 12.25 | 0.51 | 1.30 | 4.27 | 4.27 | 0.0041 |
|  | Monocyte | −0.70 | −0.01 | 1.31 | 1.57 | 1.54 | 0.65 |
|  | NK | −4.42 | −0.13 | 1.46 | 1.75 | 1.73 | 0.011 |
|  | T Cell (cd4+) | −6.97 | −0.29 | 5.11 | 6.27 | 5.49 | 0.20 |
|  | T Cell (cd8+) | −2.29 | 0.22 | 5.13 | 4.97 | 4.36 | 0.60 |

Est = Regression coefficient estimate (×100%).
Bias$_2$ = Double-bootstrap bias estimate (×100%).
SE$_0$ = Naive standard error (×100%).
SE$_1$ = Single-bootstrap standard error (×100%).
SE$_2$ = Double-bootstrap standard error (×100%).
P-values were computed using SE$_2$.

Example 10

Additional Analyses

In this example a special case was considered in which subject population was such that for this population z=0 and the population was sufficiently homogeneous with respect to blood cell distribution to admit sensible characterization of that distribution. In such case it is possible to recover estimates from $\hat{\Gamma}$. The results of such an analysis applied to the HNSCC case/control data set is shown in Table 11 below.

TABLE 11

White Blood Cell Distribution in HNSCC Controls

|  | Est | SE$_2$ | Bias$_2$ | BC-Est | 95% Conf. Int. |
|---|---|---|---|---|---|
| B Cell | 7.9 | 0.5 | 0.1 | 7.8 | (6.8, 8.9,) |
| Granulocyte | 42.2 | 1.2 | −0.1 | 42.3 | (39.9, 44.6) |
| Monocyte | 9.9 | 0.7 | 0.3 | 9.6 | (8.3, 10.9) |
| NK | 7.9 | 0.7 | 0.2 | 7.7 | (6.3, 9.1) |
| T Cell (cd4+) | 15.2 | 3.0 | −0.1 | 15.3 | (9.5, 21.2) |
| T Cell (cd8+) | 7.6 | 3.0 | 0.4 | 7.2 | (1.4, 13.0) |

Est = Regression coefficient estimate (×100%), normalized so that estimates sum to 90%.
SE$_2$ = Double-bootstrap standard error (×100%).
Bias$_2$ = Double-bootstrap bias estimate (×100%).
BC-Est = bias-corrected estimate.

If the coefficients represented a complete profiling of blood cell types, the estimates should sum approximately to one, even though the model does not explicitly constrain them so. In this case, the original bias corrected estimates (of leukocyte distribution in HNSCC controls) summed to 133%. The table shows the values re-normalized to 90%, the anticipated proportion of the cell types. The resulting estimated distribution of leukocytes is consistent with the literature (Alberts B et al., 2008, Molecular Biology of the cell. New York, N.Y.: Taylor and Francis, 5$^{th}$ edition)

An additional analysis was also conducted in which S$_0$ consisted of only samples with pure CD4+ or CD8+ cells and S$_1$ to consisted only of samples having the less purified T-lymphocytes. For such S$_1$, there were no covariates, so z consisted only of an intercept. The following unnormalized bias-corrected estimates: 69.0% CD4+, 95% confidence interval (54%; 84%), and 32.5% CD8+, 95% confidence interval (19%; 46%). This is consistent with known proportions of these specific cell types among T lymphocytes.

Example 11

Sensitivity Analysis

The bias estimates evident from the double-bootstrap procedure admit the possibility of correcting the bias arising from measurement error. There is no statistical procedure for correcting the other possible sources of bias, those arising from unprofiled cell types and non-cell-mediated profile differences, i.e. methylation difference signatures δ with nonzero projection onto the space spanned by the WBC signatures. It is possible to conduct a sensitivity analysis using the theory presented under "Bias" (equations 6-9). It is shown that the magnitude of the bias is likely to be small, less than a percentage point.
Detailed Analysis
A method of sensitivity analysis to estimate the magnitude of bias arising from unprofiled cell types and non-cell-mediated profile differences is described below for the HNSCC data set presented in Example 6 and FIG. 4.

Figure 4:
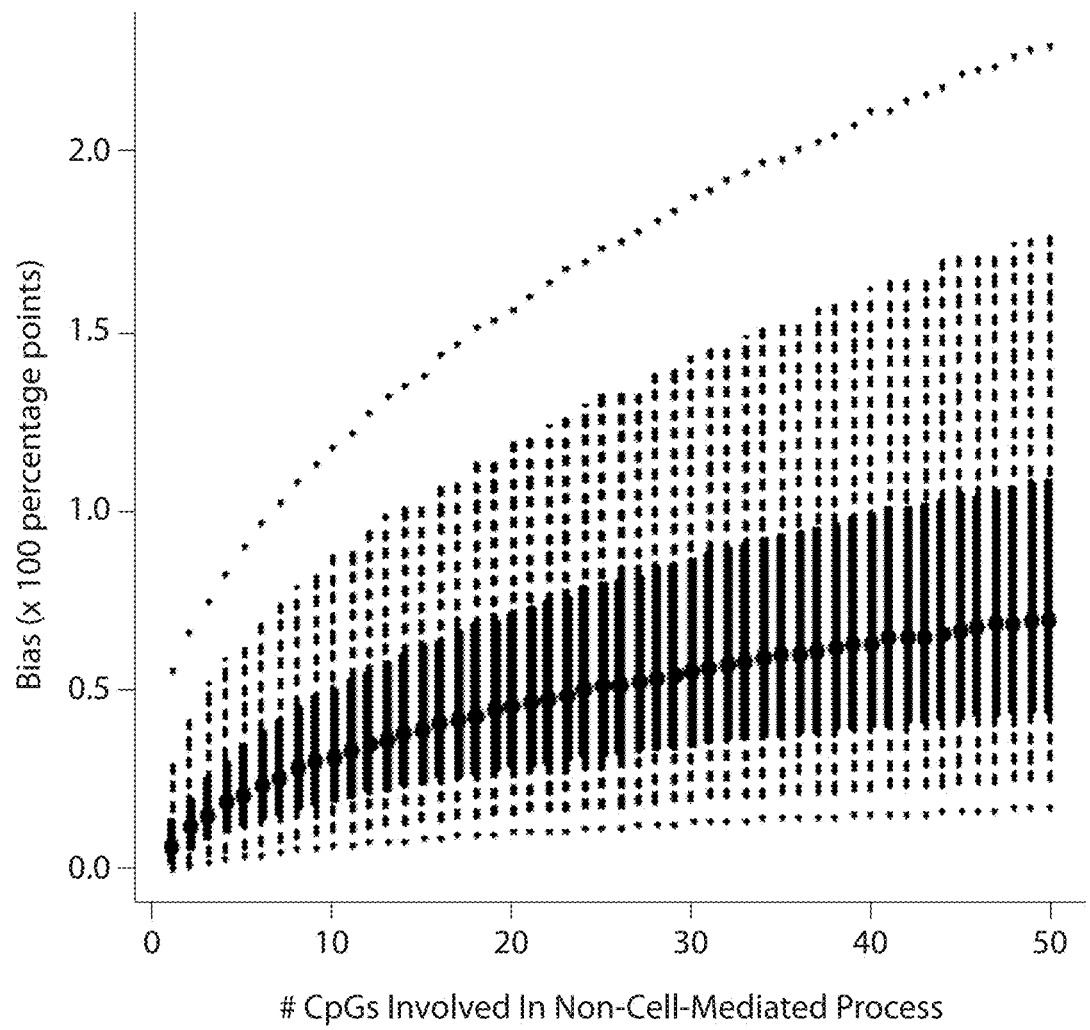
FIG. 4 is a graphical representation of bias sensitivity analysis for HNSCC Data. Bias was assessed by resampling the case coefficients of $B_1$, a procedure that assumes maximum bias. The abscissa shows the number of assumed non-zero alterations. The knob-shaped central portions of each thick vertical lines (red) indicate median value, the thick vertical lines (blue) indicate interquartile range, the thin lines (blue) represent 95% probability ranges, and the upper dots (black) represent 99% probability ranges.

For each value of k∈$\mathbb{J}_m$, k elements are randomly sampled, $\mathbb{J}_k \subset \mathbb{J}_m$ without replacement, then k rows of B$_1$ are sampled without replacement, δ* is set equal to the m×d$_1$ zero matrix, and the rows indicated by $\mathbb{J}_k$ are substituted by the k rows selected from B$_1$. The matrix δ* served as a representative of the sum of processes having systematic methylation changes at k locations, of total magnitude consistent with the observed data (under the conservative assumption that no systematic methylation difference is cell mediated), and $\alpha^* = (B_0 B_0)^{-1} B_0 \delta^*$ represented the corresponding bias in $\Gamma$. If, as in this situation, the goal was to assess the sensitivity to bias in column of $B_1$ (i.e. Case Status), the uninteresting columns of $\delta^*$ or $\alpha^*$ could be simply deleted. Replicating this resampling procedure 100,000 times, an approximation to the distribution of possible biases corresponding to processes involving exactly k CpG sites was generated. FIG. 4 displays the results of such an analysis, showing the distribution of $(\alpha^{*T}\alpha^*)^{-1/2}$ for various values of k. It is noted that the relationship of median values to m was consistent with the theory presented in Example 12 under the subheading "Additional simulations." The median values of $(\alpha^{*T}\alpha^*)$ had an almost perfect linear relationship with m. The magnitude of the bias was small: for the more likely low values of k, the bias was 0.1 to 0.25 of a percentage point. In addition, this analysis was conservative in that it assumed the effect in $B_1$ was due to non-cell-mediated processes, a strongly conservative assumption. In addition, for various choices of $\pi_0$ over a range of small magnitudes, the expected bias over the uniform posterior implied by $\pi_0$ was computed by iterated expectation, first by computing the mean bias for each choice of k, then forming the expectation over the binomial distribution Bin(100, $\pi_0$), As noted in details described under "Bias" in Example 3 the result scaled linearly with $\pi_0$. The constant of proportionality was estimated to be 2.08 percentage points. In summary, if the prior expectation is of even moderate size (~0.1) that any one CpG among the 100 selected for this application will show systematic differentiation between cases and controls, then the implied bias would be expected to be less than a percentage point.

Example 12

Simulations

To verify the properties of the proposed methodology, extensive simulation studies were conducted. Simulation parameters were obtained from the HNSCC data set, and most simulations assumed no sources of biological bias (DNA methylation changes arising from processes not mediated by the profiled leukocytes, including shifts in distribution within cell types not profiled). In every simulation, $S_0$ was specified to consist of five B cell samples, ten granulocyte samples, five monocyte samples, 15 NK samples, five general T cell samples, eight specific CD4+ T cell samples, and two specific CD8+ T cell samples. Estimates from the external validation set $S_0$, described above, were used for mean methylation profiles among WBC types, using the m=100 most informative CpG sites.

$n_1/2$ cases and $n_0/2$ controls, were specified, $n_0 \in \{100, 200, 500\}$. Among the controls, methylation profiles were generated by a white blood cell population of 7% B cells, 62% granulocytes, 6% monocytes, 2% NK cells, and 13% were T cells, of which 65% were CD4+ cells and 35% were CD8+ cells, and the remaining 5% were unspecified (and assumed to have mean equal to the unsorted T-lymphocytes). Among cases, one of the following scenarios was specified: a 4% reduction in CD4+ cells, a 2% reduction in CD8+ cells, and an 8% increase in granulocytes (alternative with changes in both CD4+ and CD8+, "Strong Alternative I"); a 6% reduction in CD4+ cells, and an 8% increase in granulocytes (alternative with changes in CD4+ and not CD8+, "Strong Alternative II"); a weaker alternative with half the effects of Strong Alternative I ("Mixed Alternative" elaborated upon below); and two null scenarios with no changes in cell population, each with a different assumption about $\delta$. It is noted that these changes reflect absolute changes in percentage points, not relative changes. It is also noted that these values were actually used to generate Dirichlet-distributed mixture weights for each simulated subject, with Dirichlet parameters equal to a precision parameter (10 corresponding to "noisy", and 100 corresponding to "precise") times the mean weight described above.

Residual effects $\xi_i^{(0)}$ for controls were set equal to 0.1 times estimated intercept $\mu_1$ and residual effects $\xi_i^{(1)}$ for cases were set equal to 0.08 or 0.09 times $\mu_1$ plus multiples 10$\theta$ of the column of U corresponding to case. The constants of proportionality 0.1, 0.08, and 0.09 were chosen to correspond to assumed contributions of $\xi$ to an overall methylation signature presumed to be dominated by profiled populations of white blood cells in specified proportions, with 0.08 used for the strong alternatives and 0.09 used for the Mixed Alternative. The constant 10 was used to amplify the scale of $\delta$ so that its effect could be detected in simulation; it is noted that U was orthogonal to the white blood cell profiles, by construction.

It is noted also that the individual, Dirichlet-generated subject weights did not necessarily sum to one, and the difference from 1 was not applied as a multiplier; thus the resulting $\xi$ corresponded to the situation $P\mu_q$=0, where $P=(B_0 B_0)^{-1} B_0$ along with orthogonal contributions from the $\lambda$ terms of (6). The multiplier $\theta$=0 was used for strong alternatives, and the "Strong Null" case (i.e. no methylation differences between cases and controls) and $\theta$=0.5 was used for the Mixed Alternative, and $\theta$=1 was used for the "Mixed Null" with case/control differences not mediated by cellular population differences.

A simple normal error structure for $e_{oh}$ and $e_{oi}$ was specified, with no chip effects, and with variance equal to the sum of chip and residual variance estimated (individually for each CpG) for the HNSCC data. For each simulation, 50 bootstraps were used to estimate standard errors. 1000 simulations were run for each scenario. Table 12 presents results for $n_1$=200 with precise mixture weights (small within-status heterogeneity in distribution), and Table 13 presents results for $n_1$=200 with noisy mixture weights (larger within-status heterogeneity). The tables show mean estimate, simulation standard deviation, median estimates for the three types of proposed standard errors, and proportion of p-values (obtained from z-scores constructed using the double-bootstrap standard error) falling below $\alpha$=0.05 and $\alpha$=0.01.

In these cases, the bias in estimation was minimal. Both types of bootstrap produced similar standard error estimates, which were close to the simulation standard deviation and often quite different from the naive standard error estimate. Under null scenarios, the rejection probabilities were tolerably close to their nominal values, and for alternatives, power could be quite high, even with this modest design.

Results for Coefficients of Determination

Results for the coefficients of determination are provided in Table 14. $R_{1,0}^2$ decreased with decreasing strength of the alternative, falling to zero under both null scenarios. For strong alternatives, $R_{1,1}^2$ was frequently close to 1.0. For the Mixed Alternative, $R_{1,1}^2$ had a lower, and still high values ranging from about 0.85 to 0.90. For the mixed null result, $R_{1,1}^2$ typically had lower values, from about 0.05 to 0.20. In the Strong Null case, $R_{1,1}^2$ covered a broader range among moderately low values; note, however, that this scenario effectively represents 0/0, i.e. a poorly defined value. Scenarios with $n_1 \in \{100, 500\}$ produced similar results, with simulation standard deviations and power adjusted accordingly, and still having practical utility.

Additional Simulations

Additional simulations, were conducted which assumed bias arising from processes not profiled by the profiled leukocytes. For these scenarios, $\xi^0$ was set to $\hat{\mu}_1$, and $\xi^1 = \xi^0$ except for a set of CpG sites randomly selected among the m dimensions of the array (once and for all before 1000 simulations); among those dimensions j, $\xi_j^1$ was set to $1 - \hat{\mu}_{1j}$, reflecting a "reversal" of methylation state. Estimates were biased towards the null, on the order of about a percentage point.

TABLE 12

Simulation results (precise mixtures, $n_1 = 200$)

| | Truth | Est | SD | SE$_0$ | SE$_1$ | SE$_2$ | pow(0.05) | pow(0.01) |
|---|---|---|---|---|---|---|---|---|
| Strong Alternative I ($\theta = 0$) | | | | | | | | |
| B Cell | 0.0 | 0.07 | 1.00 | 0.92 | 0.97 | 0.98 | 0.057 | 0.018 |
| Granulocyte | 8.0 | 8.02 | 0.73 | 0.39 | 0.73 | 0.73 | 1.000 | 1.000 |
| Monocyte | 0.0 | 0.01 | 0.48 | 0.43 | 0.47 | 0.47 | 0.055 | 0.013 |
| NK | 0.0 | −0.09 | 1.08 | 1.02 | 1.02 | 1.05 | 0.066 | 0.015 |
| T Cell (cd4+) | −4.0 | −4.06 | 0.81 | 0.80 | 0.78 | 0.81 | 0.999 | 0.989 |
| T Cell (cd8+) | −2.0 | −1.93 | 0.83 | 0.81 | 0.78 | 0.81 | 0.653 | 0.419 |
| Strong Alternative II ($\theta = 0$) | | | | | | | | |
| B Cell | 0.0 | 0.00 | 0.97 | 0.92 | 0.97 | 0.99 | 0.048 | 0.016 |
| Granulocyte | 8.0 | 8.00 | 0.71 | 0.39 | 0.72 | 0.72 | 1.000 | 1.000 |
| Monocyte | 0.0 | 0.03 | 0.48 | 0.42 | 0.47 | 0.47 | 0.063 | 0.016 |
| NK | 0.0 | 0.03 | 1.04 | 1.02 | 1.01 | 1.05 | 0.052 | 0.014 |
| T Cell (cd4+) | −6.0 | −5.83 | 0.76 | 0.80 | 0.77 | 0.80 | 1.000 | 1.000 |
| T Cell (cd8+) | 0.0 | −0.22 | 0.81 | 0.81 | 0.80 | 0.81 | 0.064 | 0.014 |
| Mixed Alternative ($\theta = 0.5$) | | | | | | | | |
| B Cell | 0.0 | −0.02 | 1.02 | 1.10 | 0.96 | 0.98 | 0.065 | 0.011 |
| Granulocyte | 4.0 | 3.99 | 0.75 | 0.47 | 0.73 | 0.73 | 1.000 | 0.995 |
| Monocyte | 0.0 | 0.02 | 0.49 | 0.51 | 0.47 | 0.47 | 0.060 | 0.015 |
| NK | 0.0 | 0.04 | 1.05 | 1.22 | 1.01 | 1.04 | 0.054 | 0.009 |
| T Cell (cd4+) | −2.0 | −2.07 | 0.82 | 0.96 | 0.79 | 0.83 | 0.695 | 0.471 |
| T Cell (cd8+) | −1.0 | −0.95 | 0.82 | 0.96 | 0.78 | 0.82 | 0.203 | 0.082 |
| Mixed Null ($\theta = 1$) | | | | | | | | |
| B Cell | 0.0 | 0.00 | 1.04 | 1.58 | 0.96 | 1.02 | 0.066 | 0.017 |
| Granulocyte | 0.0 | 0.03 | 0.73 | 0.67 | 0.74 | 0.74 | 0.055 | 0.014 |
| Monocyte | 0.0 | −0.01 | 0.47 | 0.73 | 0.47 | 0.48 | 0.054 | 0.013 |
| NK | 0.0 | −0.01 | 1.12 | 1.76 | 1.01 | 1.09 | 0.063 | 0.014 |
| T Cell (cd4+) | 0.0 | 0.01 | 0.87 | 1.38 | 0.80 | 0.90 | 0.054 | 0.013 |
| T Cell (cd8+) | 0.0 | −0.02 | 0.88 | 1.39 | 0.79 | 0.89 | 0.057 | 0.015 |
| Strong Null ($\theta = 0$) | | | | | | | | |
| B Cell | 0.0 | −0.01 | 0.99 | 0.90 | 0.96 | 0.96 | 0.068 | 0.014 |
| Granulocyte | 0.0 | 0.03 | 0.72 | 0.38 | 0.74 | 0.73 | 0.052 | 0.013 |
| Monocyte | 0.0 | −0.01 | 0.47 | 0.42 | 0.47 | 0.47 | 0.055 | 0.013 |
| NK | 0.0 | −0.01 | 1.06 | 1.00 | 1.01 | 1.02 | 0.059 | 0.020 |
| T Cell (cd4+) | 0.0 | 0.00 | 0.81 | 0.78 | 0.80 | 0.82 | 0.054 | 0.013 |
| T Cell (cd8+) | 0.0 | −0.01 | 0.81 | 0.79 | 0.79 | 0.80 | 0.054 | 0.015 |

Est = Mean regression coefficient estimate (×100%);
SD = SD regression coefficient estimate (×100%).
SE$_0$ = Naive standard error (×100%);
SE$_1$ = Single-bootstrap standard error (×100%).
SE$_2$ = Double-bootstrap standard error (×100%).
pow($\alpha$) = Pr$\{P_2 < \alpha\}$, where $P_2$ is the p-value computed from SE$_2$.

TABLE 13

Simulation Results (Noisy Mixtures, $n_1 = 200$)

| | Truth | Est | SD | SE$_0$ | SE$_1$ | SE$_2$ | pow(0.05) | pow(0.01) |
|---|---|---|---|---|---|---|---|---|
| Strong Alternative I ($\theta = 0$) | | | | | | | | |
| B Cell | 0.0 | −0.06 | 1.39 | 0.92 | 1.36 | 1.34 | 0.065 | 0.019 |
| Granulocyte | 8.0 | 7.87 | 2.02 | 0.39 | 2.00 | 1.99 | 0.974 | 0.897 |
| Monocyte | 0.0 | 0.05 | 1.03 | 0.42 | 1.04 | 1.02 | 0.049 | 0.012 |
| NK | 0.0 | −0.02 | 1.21 | 1.02 | 1.16 | 1.18 | 0.061 | 0.010 |
| T Cell (cd4+) | −4.0 | −4.00 | 1.23 | 0.79 | 1.21 | 1.22 | 0.903 | 0.739 |
| T Cell (cd8+) | −2.0 | −1.97 | 1.05 | 0.80 | 1.02 | 0.98 | 0.517 | 0.298 |

TABLE 13-continued

Simulation Results (Noisy Mixtures, $n_1 = 200$)

| | Truth | Est | SD | SE$_0$ | SE$_1$ | SE$_2$ | pow(0.05) | pow(0.01) |
|---|---|---|---|---|---|---|---|---|
| Strong Alternative II ($\theta = 0$) | | | | | | | | |
| B Cell | 0.0 | −0.08 | 1.38 | 0.92 | 1.36 | 1.34 | 0.063 | 0.017 |
| Granulocyte | 8.0 | 7.90 | 2.03 | 0.39 | 1.99 | 1.98 | 0.973 | 0.905 |
| Monocyte | 0.0 | 0.10 | 1.07 | 0.42 | 1.04 | 1.02 | 0.054 | 0.019 |
| NK | 0.0 | 0.02 | 1.17 | 1.02 | 1.14 | 1.18 | 0.053 | 0.009 |
| T Cell (cd4+) | −6.0 | −5.70 | 1.19 | 0.80 | 1.13 | 1.16 | 0.999 | 0.986 |
| T Cell (cd8+) | 0.0 | −0.23 | 1.08 | 0.81 | 1.10 | 1.04 | 0.066 | 0.015 |
| Mixed Alternative ($\theta = 0.5$) | | | | | | | | |
| B Cell | 0.0 | 0.05 | 1.42 | 1.10 | 1.34 | 1.34 | 0.066 | 0.016 |
| Granulocyte | 4.0 | 4.00 | 2.01 | 0.47 | 2.02 | 2.01 | 0.500 | 0.291 |
| Monocyte | 0.0 | 0.01 | 1.06 | 0.51 | 1.03 | 1.02 | 0.072 | 0.020 |
| NK | 0.0 | −0.02 | 1.24 | 1.22 | 1.13 | 1.16 | 0.064 | 0.013 |
| T Cell (cd4+) | −2.0 | −2.11 | 1.30 | 0.95 | 1.26 | 1.28 | 0.391 | 0.191 |
| T Cell (cd8+) | −1.0 | −0.94 | 1.08 | 0.96 | 1.05 | 1.02 | 0.163 | 0.052 |
| Mixed Null ($\theta = 1$) | | | | | | | | |
| B Cell | 0.0 | 0.06 | 1.41 | 1.59 | 1.36 | 1.37 | 0.062 | 0.016 |
| Granulocyte | 0.0 | 0.04 | 2.08 | 0.67 | 2.06 | 2.05 | 0.056 | 0.008 |
| Monocyte | 0.0 | −0.02 | 1.05 | 0.73 | 1.03 | 1.03 | 0.058 | 0.020 |
| NK | 0.0 | 0.01 | 1.26 | 1.76 | 1.14 | 1.22 | 0.066 | 0.011 |
| T Cell (cd4+) | 0.0 | −0.01 | 1.42 | 1.38 | 1.31 | 1.36 | 0.067 | 0.016 |
| T Cell (cd8+) | 0.0 | 0.00 | 1.19 | 1.39 | 1.08 | 1.10 | 0.073 | 0.011 |
| Strong Null ($\theta = 0$) | | | | | | | | |
| B Cell | 0.0 | 0.06 | 1.37 | 0.91 | 1.36 | 1.32 | 0.065 | 0.017 |
| Granulocyte | 0.0 | 0.03 | 2.07 | 0.38 | 2.06 | 2.05 | 0.055 | 0.009 |
| Monocyte | 0.0 | −0.02 | 1.04 | 0.42 | 1.03 | 1.02 | 0.057 | 0.021 |
| NK | 0.0 | 0.01 | 1.19 | 1.01 | 1.14 | 1.16 | 0.053 | 0.018 |
| T Cell (cd4+) | 0.0 | −0.04 | 1.38 | 0.79 | 1.31 | 1.31 | 0.069 | 0.015 |
| T Cell (cd8+) | 0.0 | 0.01 | 1.11 | 0.79 | 1.08 | 1.03 | 0.065 | 0.016 |

Est = Mean regression coefficient estimate (×100%);
SD = SD regression coefficient estimate (×100%).
SE$_0$ = Naive standard error (×100%);
SE$_1$ = Single-bootstrap standard error (×100%).
SE$_2$ = Double-bootstrap standard error (×100%).
pow($\alpha$) = Pr{P$_2$ < $\alpha$}, where P$_2$ is the p-value computed from SE$_2$.

TABLE 14

Results for coefficients of determination

| | | Median $R_{1,0}^2$ (Interquartile Range) | Median $R_{1,1}^2$ (Interquartile Range) |
|---|---|---|---|
| Precise Mixtures $n_1 = 200$ | Strong Alternative I ($\theta = 0$) | 0.13 (0.12-0.15) | 0.98 (0.97-0.98) |
| | Strong Alternative II ($\theta = 0$) | 0.13 (0.12-0.15) | 0.98 (0.97-0.98) |
| | Mixed Alternative ($\theta = 0.5$) | 0.04 (0.03-0.05) | 0.88 (0.85-0.91) |
| | Mixed Null ($\theta = 1$) | 0.00 (0.00-0.00) | 0.10 (0.05-0.17) |
| | Strong Null ($\theta = 0$) | 0.00 (0.00-0.00) | 0.25 (0.15-0.38) |
| Noisy Mixtures $n_1 = 200$ | Strong Alternative I ($\theta = 0$) | 0.05 (0.03-0.06) | 0.98 (0.97-0.98) |
| | Strong Alternative II ($\theta = 0$) | 0.05 (0.03-0.06) | 0.98 (0.97-0.98) |
| | Mixed Alternative ($\theta = 0.5$) | 0.01 (0.01-0.02) | 0.89 (0.81-0.94) |
| | Mixed Null ($\theta = 1$) | 0.00 (0.00-0.01) | 0.46 (0.28-0.64) |
| | Strong Null ($\theta = 0$) | 0.00 (0.00-0.01) | 0.72 (0.55-0.85) |

Example 13

Identification of a Unique DMR in CD3Z Gene

Individual samples of sorted, normal, human, peripheral blood leukocytes as shown in Table 15, were purchased from AllCells®, LLC (Emeryville, Calif.). These leukocytes were sorted in a column with antibody-conjugated magnetic beads using a combination of positive and negative selection. Genomic DNA from the leukocytes was extracted according to manufacturer's protocol using the DNeasy Blood & Tissue kit (Qiagen) or the AllPrep DNA/RNA/Protein Mini Kit according to manufacturer's protocol (Cat. No. 8004, QIAGEN, Valencia, Calif.), then quantified by NanoDrop ND-1000 Spectrophotometer (NanoDrop Technologies, Inc., Wilmington, Del.) and stored at −20° C. The extracted genomic DNA was subjected to Bisulfite conversion by treatment with sodium bisulfite using the EZ DNA Methylation Kit (Zymo) following the manufacturer's protocol, thereby converting unmethylated cytosine residues to uracil and leaving methylated cytosine residues intact.

TABLE 15

Sorted leukocytes from AllCells®, LLC

| Cell Lineage | Abbreviation | N |
|---|---|---|
| CD3+ T Lymphocytes | Pan-T | 5 |
| CD3+CD4+ T Lymphocytes | CD4 | 2 |
| CD3+CD4+CD25+ Regulatory T Lymphocytes | Treg | 6 |
| CD3+CD8+ T Lymphocytes | CD8 | 2 |
| CD56+ Natural Killer Cells (Large Granular Lymphocytes) | NK | 3 |

TABLE 15-continued

Sorted leukocytes from AllCells ®, LLC

| Cell Lineage | Abbreviation | N |
| --- | --- | --- |
| CD19+ B Lymphocytes | B | 5 |
| CD14+ Monocytes | Mono | 4 |
| CD15+ Granulocytes | Gran | 5 |
| CD16+ Neutrophils | Neut | 4 |

Analysis of the methylation status of the bisulfate converted DNA was performed using DNA methylation microarray, Infinium® HumanMethylation27 Beadchip Microarray, (Illumina®, Inc., San Diego, Calif.). This microarray quantifies the methylation status of 27,578 CpG loci from 14,495 genes, with a redundancy of 15-18-fold. Bisulfite converted, genomic DNA from sorted human peripheral blood leukocytes was subjected to whole genome amplification. The purified whole genome amplified DNA was hybridized to locus-specific DNA oligomers linked to individual bead types corresponding to each CpG locus, unmethylated or methylated. Allele-specific primer annealing was followed by specific single-base extension using labeled ddNTPs. Extension only occurs if the bead type matches the methylation status of the genomic DNA.

The array was fluorescently stained, scanned, and fluorescent intensities of each of the unmethylated and methylated bead types were measured. The ratio of fluorescent signals is computed from both alleles using the following equation: $\beta=(\max(M,0))/(|U|+|M|)+100$. The β-value is a continuous variable ranging from 0 (unmethylated) to 1 (completely methylated) that represents the methylation at each CpG site and is used in subsequent statistical analyses. Data were assembled with BeadStudio methylation software from Illumina, Inc. (San Diego, Calif.). Bibikova, M., et al., *Epigenomics* 1, 177-200 (2009).

Figure 9:
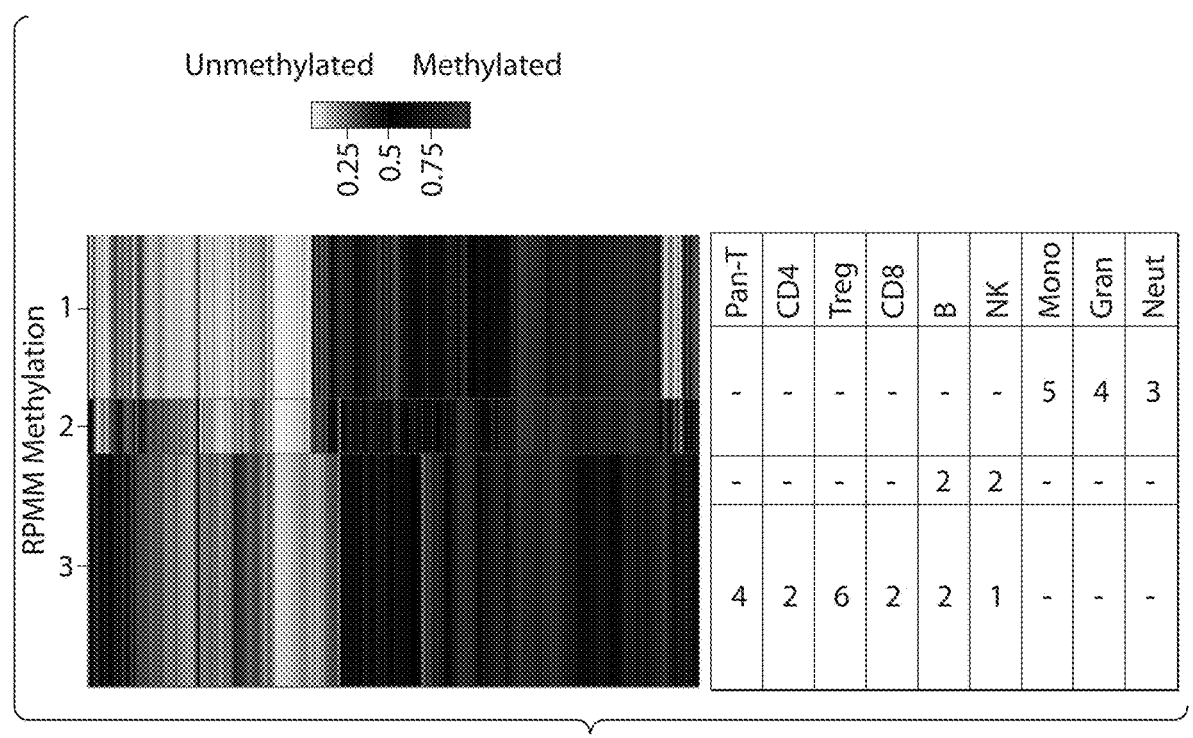
FIG. 9 is a photograph of the methylation profiles of white blood cells obtained from a DNA methylation array analysis described in Example 9. Methylation array assay was performed using Infinium HumanMethylation27 Beadchip Microarrays obtained from Illumina, Inc. (San Diego, Calif.). The number of individual leukocyte samples in each methylation class is shown in the table to the right. The DNA methylation profile distinguishes Lymphocytes from Myeloid Derived Leukocytes. The 5000 most variable CpG loci are plotted on the left. Less methylated loci are represented as grey areas and more methylated loci are represented as black areas. A partitioned mixture model (RPMM) of autosomal gene Infinium beta values from sorted human peripheral blood leukocytes was performed using an R version 2.11.1 of Illumina's software which provides convenient mechanisms for loading and analyzing of the results of methylation status, and quality control and basic visualization tasks.

A comparison of methylation in sorted normal human immune cells was observed to produce distinct profiles of methylation markers for further consideration. As shown in FIG. 9 DNA Methylation profiles distinguished lymphocytes from myeloid derived leukocytes. Recursively partitioned mixture model (RPMM) of autosomal gene Infinium beta values from sorted, human, peripheral blood leukocytes was performed in R version 2.11.1 of Illumina's software which provides convenient mechanisms for loading and analyzing the results of methylation status, and for quality control and basic visualization tasks.

Candidate DNA regions with high potential to discriminate CD3+ T cells from non-T cells were chosen based on the criteria of being differentially demethylated and differentially overexpressed in CD3+ T cells compared with other cell types (monocytes, granulocytes, NK cells, and B cells). Two quantitative methylation methods, bisulfite pyrosequencing and MS-qPCR, were used to confirm array methylation.

The highest ranking 5000 most variable CpG loci were plotted on the left (FIG. 9 left panel), such that the less methylated loci appear as grey and more methylated loci appear as black. The number of individual leukocyte samples in each methylation class is shown in FIG. 9 in the table to the right. The algorithm for prioritizing these candidates described herein yielded CD3E and CD3Z as specific DMR for identifying CD3+ T cells.

Example 14

Patient Characteristics and Biological Samples for Determining CD3+ T Cell Distribution in Glioma Cases and Controls Whole blood samples from glioma patients (N=94) and controls (N=71) were obtained from the UCSF San Francisco Adult Glioma Study (AGS) for these examples (Table 16). The patients included in this example were diagnosed between 1997 and 2011. Details of subject ascertainment through the rapid case ascertainment program of San Francisco regional population-based registry or the UCSF Neuro-oncology Clinic have been described (Wrensch M et al., 2007, Clin Cancer Res 13(1): 197-205; Felini M J et al. 2009, Cancer Causes Control 20(1): 87-96; Wrensch M et al., 2009, Nat Genet 41(8): 905-8; Christensen B C et al., 2011, J Natl Cancer Inst 103(2): 143-53). Pertinent data for this analysis included age at histological diagnosis, gender, vital status, and survival time between diagnosis date and date of death for those deceased or between diagnosis date and date of last contact for those alive, and any of cigarette smoking history and exposure to steroids, chemotherapy and radiation therapy.

A panel of 120 fresh frozen glioma tumors from the UCSF Brain Tumor Research Center tissue bank, obtained under appropriate institutional review board approval, which were previously characterized for molecular features (Christensen B C et al., 2011, J Natl Cancer Inst 103(2): 143-53; Zheng S et al., 2011, Neuro Oncol 13(3): 280-9) was chosen for tumor MS-qPCR and IHC studies (Table 16). Tumor samples were defined as secondary GBM if the patients had prior histological diagnosis of a low-grade glioma. The ages are given at the time of surgery, which occurred at UCSF between 1990 and 2003. This tumor set contained the following histological subtypes: 2 pilocytic astrocytoma (PA), 15 ependymoma grade II (EPII), 20 oligodendroglioma grade II (ODII), 16 oligoastroglioma grade II (OAII), 3 oligoastroglioma grade III (OAIII), 23 astrocytoma grade II (ASII), 4 astrocytoma grade III (ASIII) and 37 astrocytoma grade IV, also called glioblastoma multiforme grade IV (GBM), ten of which were recurrent and five of which were secondary.

Sorted, normal, human, peripheral blood leukocyte subtypes were isolated from different non-diseased individuals' whole blood by MACS using a combination of negative and positive selection with highly specific cell surface antibodies conjugated to magnetic beads. The purity of separated cells was determined with flow cytometry to be >97%.

Example 15

Bisulfite Pyrosequencing and MS-qPCR Assays for Validating CD3Z, CD3E and FOXP3 Specific DMRs The demographic characteristics of donors for samples (N=285) used in MS-qPCR analysis is as shown in Table 16. CpGenome Universal Methylated DNA (Cat. No. S7821, Millipore Corp., Temecula, Calif.), purified T cell and Treg DNA were bisulfite converted at the same time. Bisulfite pyrosequencing assays were designed using Pyromark Assay Design 2.0 (QIAGEN), and carried out using a Pyromark MD pyrosequencer running Pyromark qCpG software (QIAGEN). Custom oligonucleotide primers used in bisulfite pyrosequencing were obtained from Invitrogen (Life Technologies Co, Carlsbad Calif.). For MS-qPCR reactions, primers and TaqMan major groove binding (MGB) probes with 5' 6FAM and 3' non-fluorescent quencher (NFQ) as well as TaqMan 1000 RXN Gold with Buffer A Pack were obtained from Applied Biosystems (Part No. 4304971, 4316034 and 4304441, Applied Biosystems, Foster City, Calif.). The primer and probe sequences are shown in Table 17 and FIG. 12. Solutions for MS-qPCR: 10×TaqMan Stabilizer containing 0.1% Tween-20, 0.5% gelatin were prepared weekly. Each reaction of 20 µl contained 5 µl DNA, 11.9 µl PreMix, 3 µl OligoMix, and 0.1 µl Taq DNA polymerase. Cycling was performed using a 7900HT Fast Real-Time PCR System (Applied Biosystems, Foster City, Calif.); 50 cycles at 95° C. for 15 sec and 60° C. for 1 min after 10 min at 95° C. preheat. Samples were run in triplicate using the absolute quantification method. Copy number of the target locus in each sample was determined by reference to a four-point standard curve, which was based on known copies of bisulfite converted template.

TABLE 16

Demographic characteristics of donors for samples (N = 285) used in MS-qPCR analysis

| Characteristic | Control Blood samples (n = 94) | Case Blood samples (n = 71) | Excised Tumors (n = 120) |
|---|---|---|---|
| Age | | | |
| Median (range) | 57 (22-87) | 57 (20-86) | 41 (1-78) |
| Mean (standard deviation) | 55 (16.5) | 56 (13) | 41 (15) |
| Gender, No (%) | | | |
| Female | 43 (46%) | 26 (36%) | 42 (35%) |
| Male | 51 (54%) | 45 (64%) | 78 (65%) |
| Race, No (%) | | | |
| White, Non-Hispanic | 78 (83%) | 67 (95%) | 102 (85%) |
| Hispanic | 3 (3%) | 3 (4%) | 7 (6%) |
| Asian | 6 (7%) | 0 (0%) | 4 (3%) |
| Black | 5 (6%) | 0 (0%) | 0 (0%) |
| Other | 1 (1%) | 1 (1%) | 7 (6%) |

Quantification of total bisulfite converted DNA copies for standard and biological samples was determined by reference to the C-less qPCR assay as described previously (Weisenberger D J et al., 2008, Nucleic Acids Res 36(14): 4689-98; Campan M et al., 2009, Methods Mol Biol 507: 325-37). In this procedure one determines the relative amounts of a bisulfite converted sample through the use of a TaqMan PCR reaction using primers and probes that recognize a DNA strand that does not contain cytosines, and hence is able to amplify the total amount of DNA (bisulfite-converted or unconverted) in a PCR reaction well. The absolute copy number in DNA Standard Solution (Cambio Ltd. Cambridge, UK) was used to calibrate the C-less reaction and assuming 3.3 pg=1 genome copy. Universal methylated DNA and purified CD3+ T cell and Treg DNA (bisulfite converted) were quantified at the same time. Since C-less primers hybridize to both strands of the standard DNA (non-bisulfite converted) and bisulfite converted samples allow for only single strand hybridization during the first cycle, the resultant copy number in bisulfite samples is multiplied by two. After C-less assay, the copy number of the different standards: universal methylated, CD3+ T cell and Treg DNA was used to create standard curves for CD3Z and FOXP3. To create a calibration curve known quantities of CD3+ T cell or Treg DNA were spiked into universal methylated DNA in ratios that maintained a constant total copy number in each reaction across the dilution scheme. The latter procedure mimics the conditions of detection that exist in differentiating different relative numbers of CD3+ T cells and Tregs within a mixture of cells in a complex biological sample. For absolute quantification of CD3Z, the four-point standard curve used 10,000, 1,000, 100, and 10 bisulfite converted CD3+ T cell DNA copies; absolute quantification of FOXP3 used, 5,000, 500, 50 and 5 bisulfite converted Treg cell DNA copies.

TABLE 17

Primer and probe sequences for MS-qPCR assays

| Oligonucleotide Name | Sequence (5' to 3') |
|---|---|
| C-less Fwd | TTGTATGTATGTGAGTGTGGGAGAGA (SEQ ID NO: 97) |
| C-less Rev | TTTCTTCCACCCCTTCTCTTCC (SEQ ID NO: 98) |
| C-less Probe | (6FAM) CTCCCCCTCTAACTCTAT (MGB, NFQ) (SEQ ID NO: 99) |
| CD3Z Fwd | GGATGGTTGTGGTGAAAAGTG (SEQ ID NO: 100) |
| CD3Z Rev | CAAAAACTCCTTTTCTCCTAACCA (SEQ ID NO: 101) |
| CD3Z Probe | (6FAM) CCAACCACCACTACCTCAA (MGB, NFQ) (SEQ ID NO: 102) |
| FOXP3 Fwd | GGGTTTTGTTGTTATAGTTTTTG (SEQ ID NO: 103) |
| FOXP3 Rev | TTCTCTTCCTCCATAATATCA (SEQ ID NO: 104) |
| FOXP3 Probe | (6FAM) CAACACATCCAACCACCAT (MGB, NFQ) (SEQ ID NO: 105) |

MGB: major groove binding
FAM: 6-Carboxyfluorescein
NGQ: NFQ
C-less qPCR assay: Campan M et al., 2009, Methods Mol Biol, 507: 325-37; Weisenberger DJ et al., 2008, Nucleic Acids Res 2008; 36: 4689-98

Figure 11:
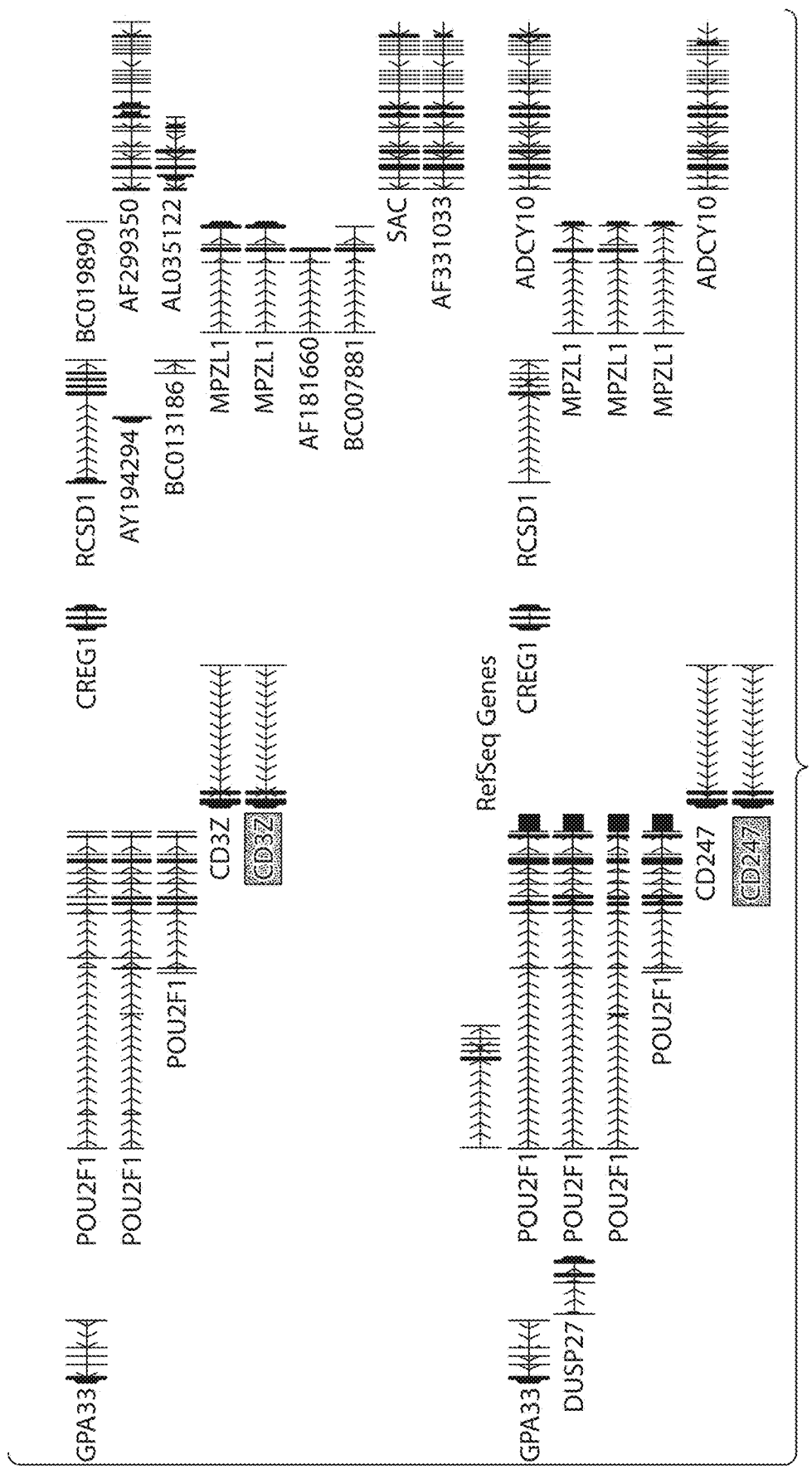
FIG. 11 is a drawing of the genomic region containing CD3Z gene, based on information available from the public databases UniProt, RefSeq and GenBank. UniProt is a freely accessible universal protein resource of protein sequence and functional information. RefSeq is a collection that provides integrated and annotated set of sequences including genomic DNA, transcripts and protein. GenBank® is the genetic sequence database of the National Institutes of Health which contains an annotated collection of publicly available DNA sequences.

The CD3E specific DMR DNA methylation status of the DMR in CD3E gene was measured by pyrosequencing bisulfite converted DNA from sorted, human, peripheral blood leukocytes. FIG. 10A. The CD3Z specific DMR, DNA methylation status of the DMR in CD3Z gene was measured by MethyLight® qPCR. of converted DNA from sorted, human, peripheral blood leukocytes (FIG. 10B). The genomic region containing the CD3Z DMR is shown in FIG. 11.

Standard calibration curves were used to determine if the newly identified CD3Z DMR was useful to quantify CD3+ T cells, Tregs (FOXP3 demethylated) and ratios of Tregs/CD3+ T cells in biological specimens such as whole or separated blood or other tissues. To obtain these curves quantitative real time methylation specific PCR was performed. DNA isolated from purified cell types was bisulfite converted and serially diluted into a background of fully methylated commercial DNA standard (Qiagen). This method is referred to herein as "CS-DM assay" or assays.

Figure 13A:
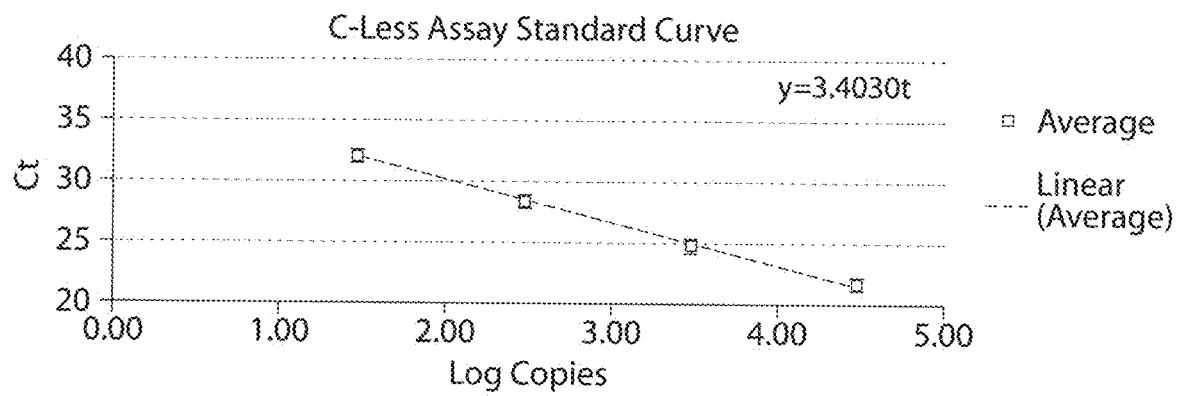
FIG. 13A shows the calibration curve for C-less total input. (N=eight replicates); errors denote standard error of the mean Ct value.
Figure 13B:
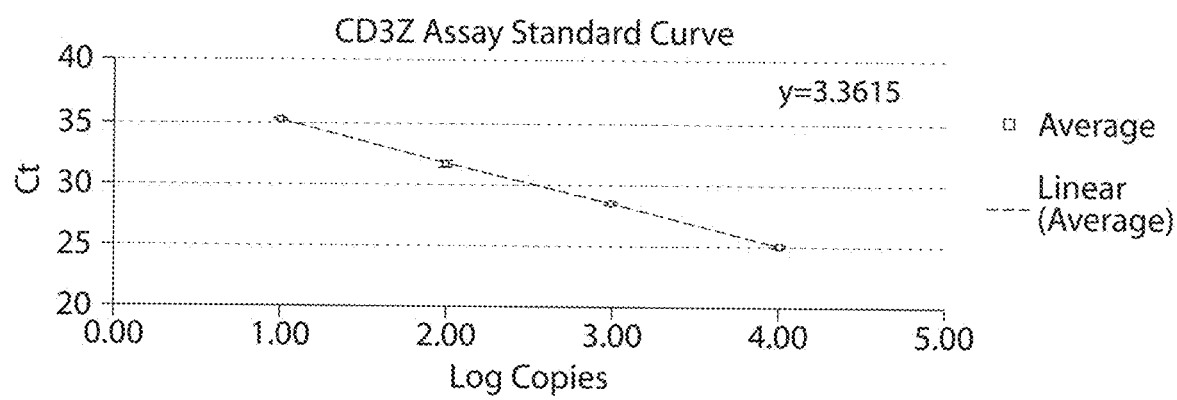
FIG. 13B and FIG. 13C are graphical representations of standard calibration curves which show the relationship between copy numbers of genomic DNA and the signal obtained from quantitative real time methylation specific PCR. The calibration curves are used for quantifying CD3+ T cells, Tregs (FOXP3 demethylated) and ratios of Tregs/CD3+ T cells. DNA isolated from purified cell types was bisulfite converted and serially diluted into a background of fully methylated commercial DNA standard (Qiagen). The total genomic copy numbers of each sample within a dilution series remained constant. Log dilutions were performed in the appropriate range of Ct values corresponding to test samples (whole blood, tumor specimens). Using cytosine-less: C-less primers genome copy numbers for each test standard were measured to ensure adequate input DNA and to normalize the CD3+ and Treg assay values.
Figure 13C:
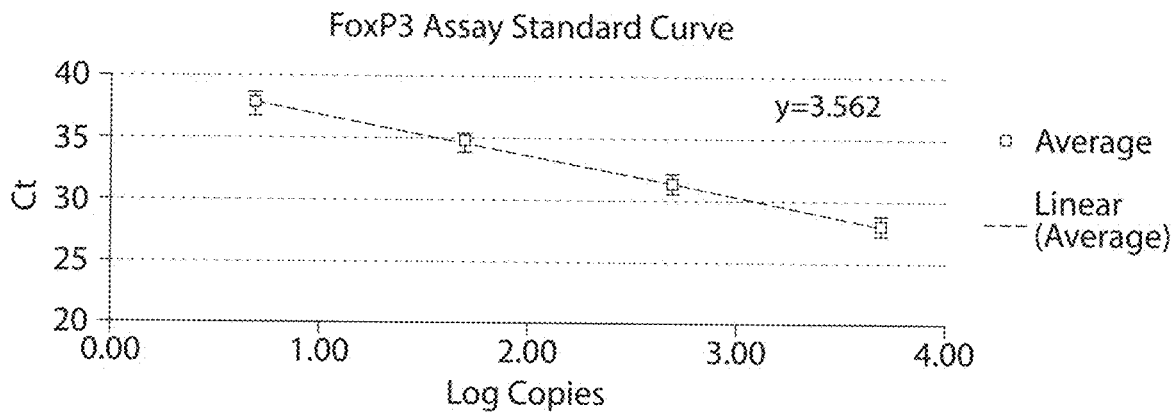

It was observed that the total genomic copy numbers of each sample within a dilution series remained constant. Log dilutions were prepared to include the appropriate range of Ct values corresponding to test samples (whole blood, tumor specimens). Using cytosine less: C-less primers genome copy numbers for each test standard were measured to ensure adequate input DNA and to normalize the CD3+ and Treg assay values. The calibration curve for C-less total input is shown in FIG. 13A (N=8 replicates); errors denote standard error of the mean Ct value. FIG. 13B shows dilution of isolated normal PanT cells (N=7 replicates) and FIG. 13C shows dilution and calibration curve for isolated CD3+CD25+ T cells (N=8 replicates). For samples to be tested these calibration curves (FIG. 13A-C) were used to estimate total input copies, CD3+ T cell, and Tregs copies, respectively.

The results show that the DNA methylation status of this region identified herein in the promoter of CD3Z gene in sorted human peripheral blood leukocytes, which was validated as an immune cell type specific differentially methylated region (FIG. 10B) was observed to be useful to quantify CD3+ T cells in biological specimens such as whole or separated blood, or other tissues.

Example 16

Figure 18A:
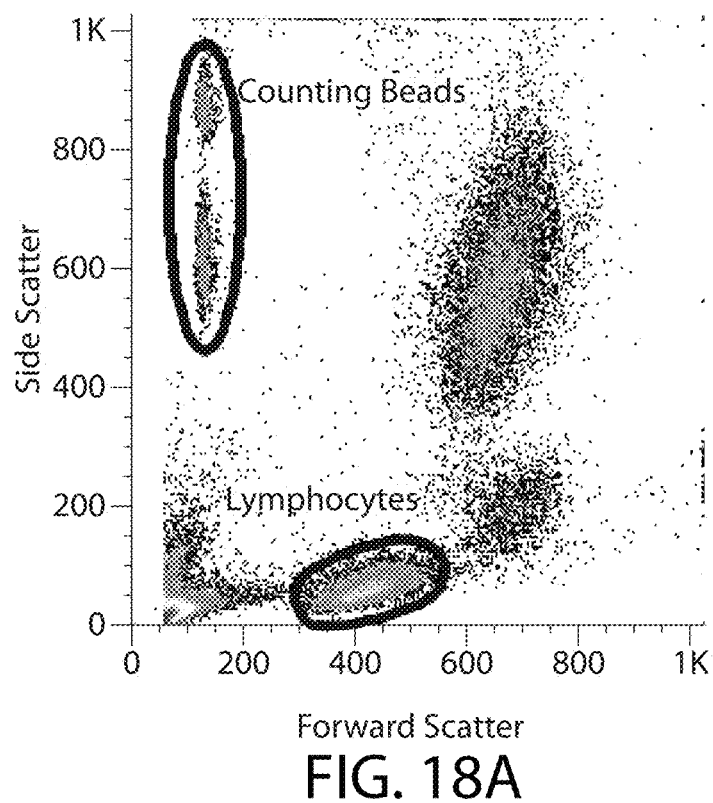
FIG. 18A, FIG. 18B and FIG. 18C (FIG. 18A-C) are graphical representations of flow cytometry analysis of CD3+ T cells and total leukocytes in whole blood from glioma cases and controls.
Figure 18B:
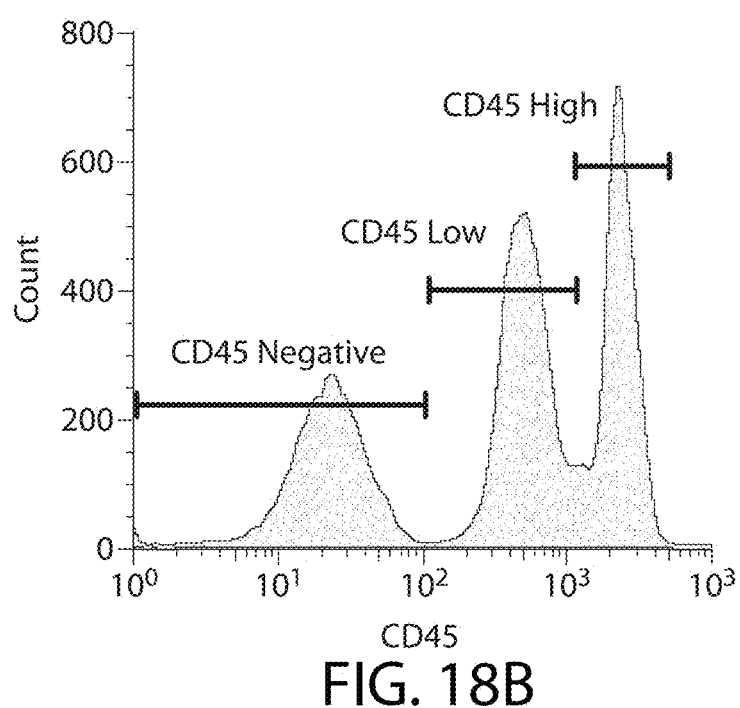
Figure 18C:
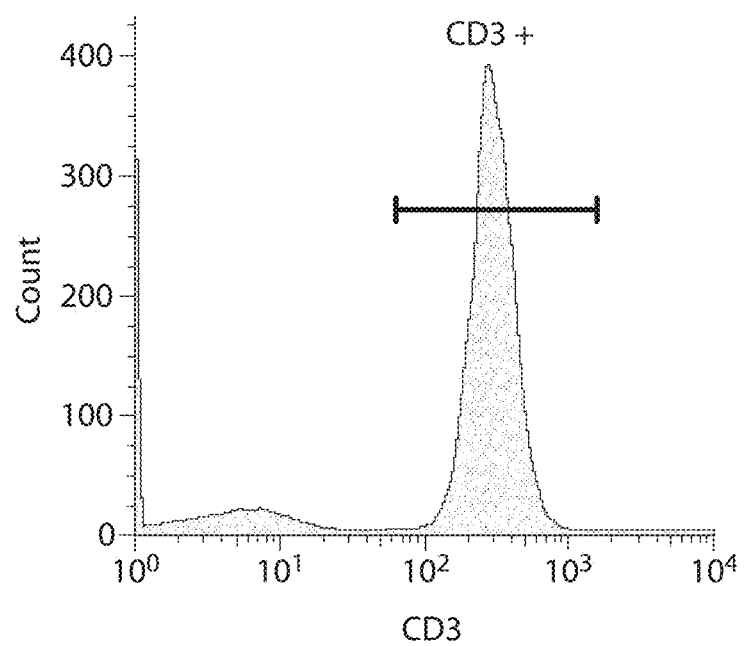

Flow Cytometry of Blood Lymphocytes in Whole Blood for Quantification of CD3+ T Cells Levels of CD3+ T cells in whole blood were quantified by flow cytometry for comparison with CD3+ T cell levels determined using CD3Z Ms-qPCR assay. Venous whole blood samples were collected in citrate EDTA and processed using a lysis no wash protocol (Invitrogen, Carlsbad, Calif. cat # GAS-010). Cells were labeled by direct staining with the appropriate fluorochrome-conjugated antibodies (eBioscience Inc, San Diego, Calif.), and were incubated for 20 minutes in the dark at 4° C.; CD3-fluorescein isothiocyanate (FITC, cat #11-0038-41), anti-CD4-allophycocyanin (APC, cat #17-0048-41), anti-CD8-phycoerythrin (PE, cat #12-0086-41), and anti-CD45-PerCP-Cy5.5 (cat #45-0459-41). Isotype control mAbs were used as negative controls. Accucheck counting beads (Invitrogen, Carlsbad Calif. cat # PCB 100) were used for quantifying leukocyte numbers. Acquisition was preformed within 48 hrs of blood draw on a FACScalibur flow cytometer using Cell-Quest Software (Becton Dickinson, Franklin Lakes, N.J.). For CD3+ cells a minimum of 10,000 events were collected on the lymphocyte gate that was set on the forward scatter vs. side scatter (FSC vs. SSC) and then gated on CD3+ cells. CD45+ counts were obtained by first gating on non-bead events using the FSC vs. SSC. A CD45+ histogram plot of the non-bead events was then created, CD45+ cells were gated. Examples are seen in FIG. 18. Absolute counts (number cells per µl) were obtained by taking the number of cells counted, divided by total number of beads counted, multiplied by the known concentration of beads. Flowjo software (TreeStar Inc, Ashland, Oreg.) was used for data analysis.

Example 17

Figure 19A:
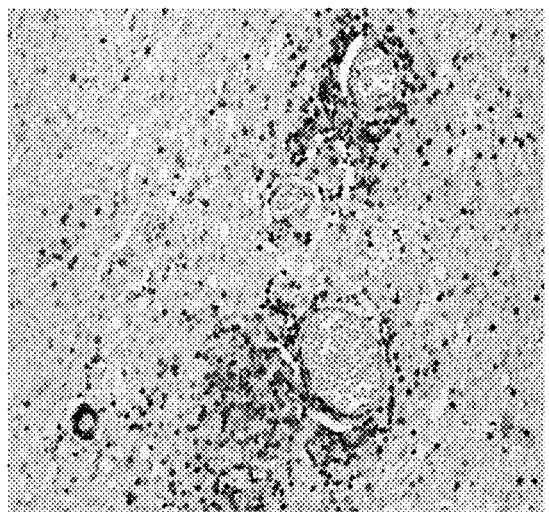
FIG. 19A-C are photographs and a lie graph that show immunohistochemical (IHC) staining of a representative GBM specimen.
Figure 19B:
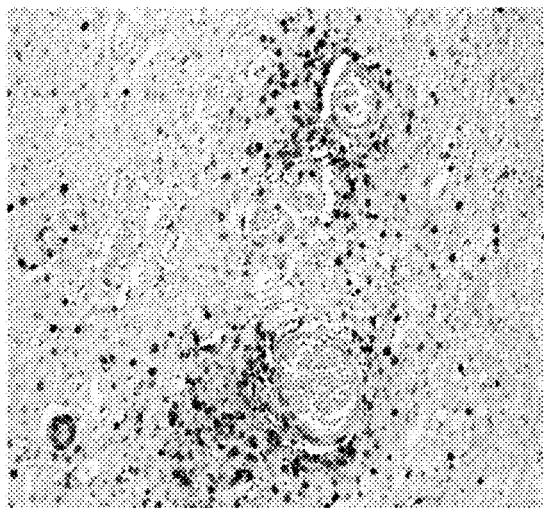
Figure 19C:
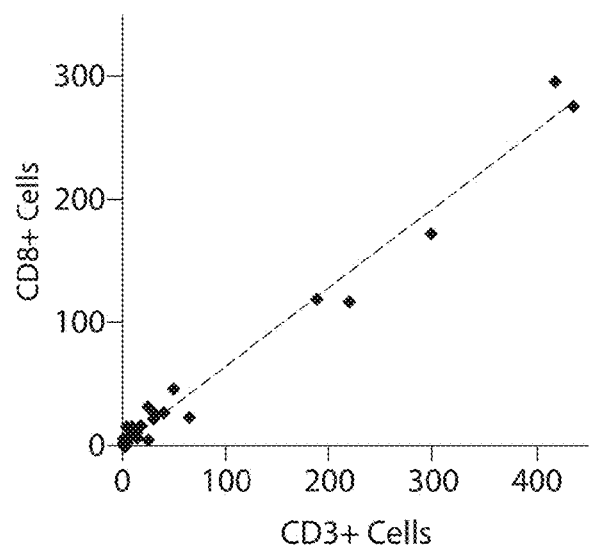

Tumor Immunohistochemistry (IHC) for Measuring Levels of Tumor Infiltrating Lymphocytes (TIL) in Glioma Tumors Slides were prepared from a 5 micron slice of each FFPE tumor block. Slides were stained using a Benchmark XT instrument per manufacturer's instructions (Ventana, Tucson, Ariz.). CD3 antibody (Dako, Carpinteria, Calif. cat # A0452) was added in a 1:600 dilution, and incubated for 30 minutes. CD8 antibody (Dako, Carpinteria, Calif. cat # M7103) was added in a 1:200 dilution and incubated for 60 minutes. CD4 antibody (Leica Microsystems, Buffalo Grove Ill., cat # NCL-L-CD4-368) was added in a 1:50 dilution, and incubated for 2 hours. Slides were counterstained with hematoxylin. Each slide was scanned at a magnification of 10× to identify four suitable fields that were then scored at 25× magnification. Examples are seen in FIG. 19A-C. The numbers of positive staining cells were recorded and the average count per four fields calculated. Photomicrographs was taken and scored for specimens with very high cell counts to increase accuracy. Samples were also examined to see if they contained predominantly perivascular and/or parenchymal infiltrates. A blind comparison of observation by two individuals was carried out to ensure uniform interpretation. Data from tumor IHC were analyzed in combination with CD3Z MS-qPCR data to determine association between the two data sets. (see Example 19)

Example 18

Statistical Analysis of Differential Methylation in CD3+ T Cells for Identification of Cell-Specific DMRs To identify putative cell specific DMRs, MACS sorted leukocyte DNA methylation data consisting of un-normalized average beta values from the Illumina HumanMethylation27 microarray were calculated from probe intensities using Illumina GenomeStudio. Locus by locus comparisons of DNA methylation between the sorted cell types were performed using a linear mixed effects model (controlling for beadchip) in SAS version 9.2, thereby generating estimates and p-values for differential methylation in CD3+ T cells compared to other cell types. Resultant p-values were adjusted for multiple comparisons using the qValue package in the software program R project for statistical computing, version 2.13 available for downloading from the internet, and q-values of less than 0.05 were considered significant. Correlations, F-tests, Wicoxon rank sum and Kruskal-Wallis one-way analysis of variance by ranks tests were carried out in R version 2.11.1 and survival analysis was performing using the survival pack in R version 2.11.1.

Example 19

Discovery and Validation of CD3Z Demethylation as a Marker of CD3+ T Cells

Figure 20A:
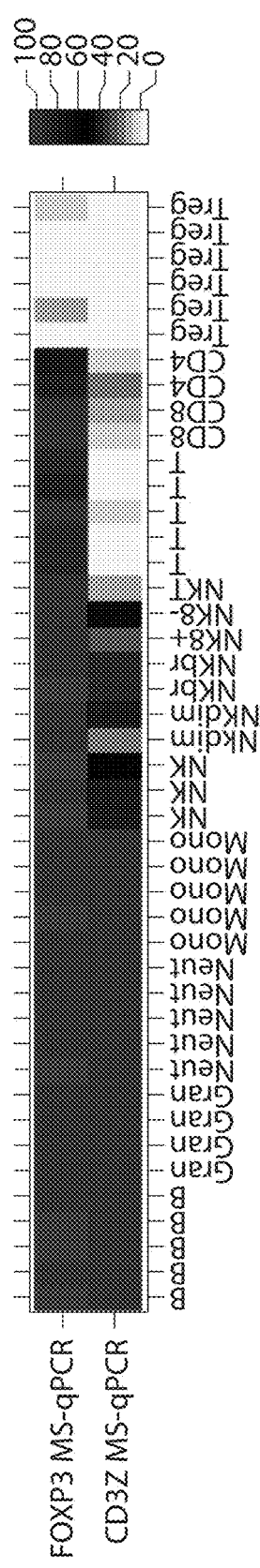
FIG. 20A-B are a set of two heatmaps showing results of MS-qPCR and bisulfite pyrosequencing of Magnetic activated cell sorting (MACS) sorted human leukocyte subsets. Abbreviations: B=B lymphocytes, Gran=Granulocytes, Neut=Neutrophils, Mono=Monocytes, NK=CD56+ Natural killer cells, Nkdim=CD16+CD56dim natural killer cells, NKbr=CD16−CD56bright natural killer cells, NK8+=CD8+CD56+ natural killer cells, NK8−=CD8-CD56+ natural killer cells, NKT=CD3+CD56+ natural killer T cells, T=CD3+ T lymphocytes, CD8=CD3+CD8+ T lymphocytes (cytotoxic T cells), CD4=CD3+CD4+ T lymphocytes (helper T cells), Treg=CD3+CD4+CD25+FOXP3+ regulatory T cells.
Figure 20B:
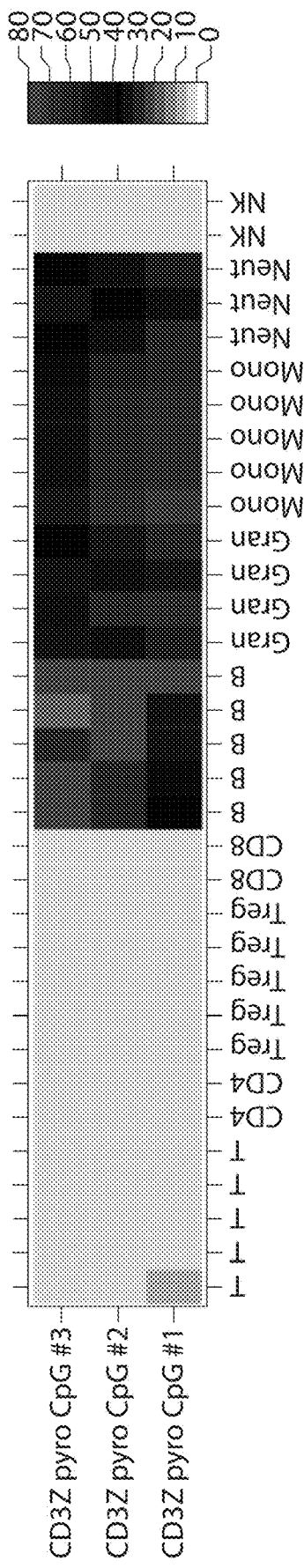

The search for genes containing DMRs specific for CD3+ T cells using methods herein revealed candidate CpG sites within the genes encoding several components of the T cell receptor (TCR) complex; namely, CD3D, CD3E, CD3G, and CD3Z. Myeloid derived blood cells (granulocytes, neutrophils, monocytes) and B-lymphocytes contained methylated CpG sites within CD3D, CD3E, CD3G and CD3Z loci compared with T cells, which were demethylated. CD3Z was also unmethylated in CD16+NK cells, but was methylated in CD16-NK cells. The promoter regions of the CD3D, CD3E and CD3G genes are CpG sparse compared with CD3Z, which contains a CpG island that is optimally suited for designing MS-qPCR assays (FIG. 1A). For these reasons the CD3Z locus was analyzed for the development of a CD3+ T cell epigenetic marker. CD3Z is significantly overexpressed (p=0.0001; Palmer, Diehn et al. 2006) and demethylated (q=0.00026) in CD3+ T cells compared with non-T cells. Pyrosequencing of CD3Z showed the extent of differences in demethylation among immune cell lineages, which approaches complete demethylation in CD3+ T cells and nearly complete methylation in other cell lineages (FIG. 20A-B).

Figure 14A:
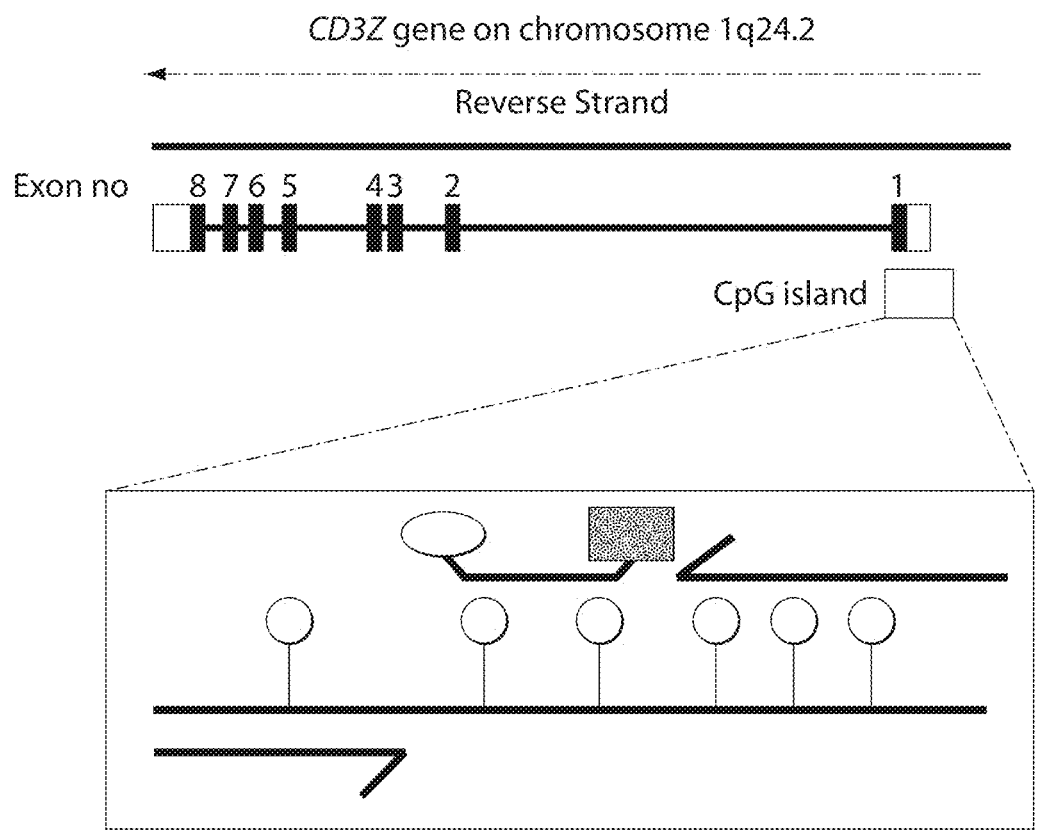
FIG. 14A-D are a drawing and a set of graphical representations showing detection of CD3+ T cell numbers by measuring differential demethylation using MS-qPCR.
Figure 14B:
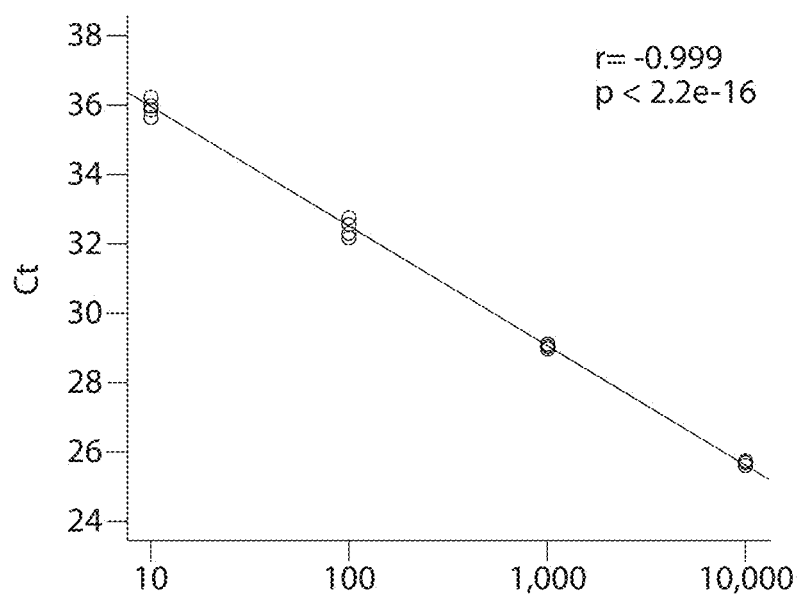

Bisulfite converted universal methylated DNA and DNA from purified CD3+ Tcells were used to prepare a four point calibration curve to estimate CD3+ T cell numbers in mixtures of cells (FIG. 14B). Total amount of DNA was held constant at four points. Log Linear PCR kinetics were demonstrated over a range of CD3+ T cell DNA inputs corresponding to 10 to 100000 genomic copies, indicating that the MS-qPCR assay was able to detect a few demethylated cells within a background of many thousands of methylated cells.

Figure 14C:
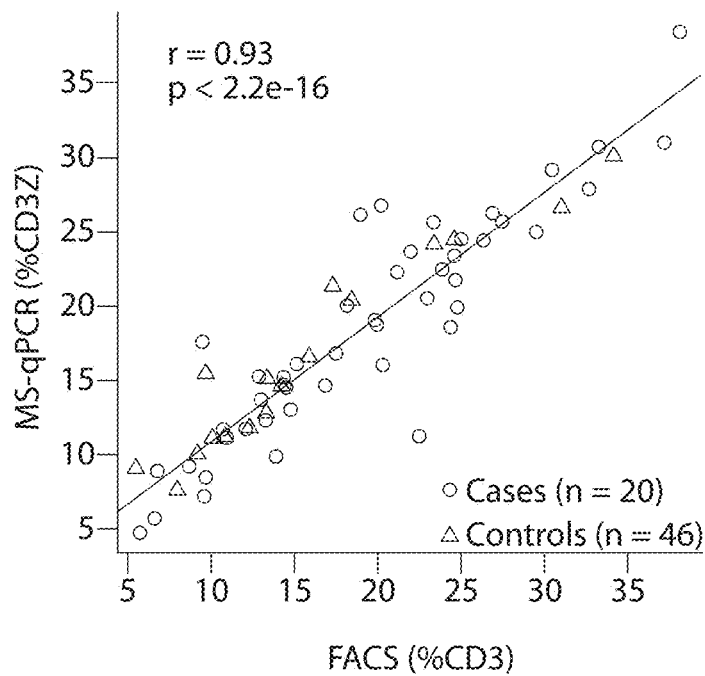

Whole blood samples from 46 healthy controls and 20 patients with glioma were then used to compare flow cytometry quantification of CD3+ T cells with the CD3Z MS-qPCR assay (FIG. 14C). The MS-qPCR measurements were observed to correlate highly with conventional flow measurement of T cells as a fraction of total blood leukocytes (Pearson R=0.93; F test p<2.2×10-16). The uniform regression and close correspondence of the two methods was true for both glioma patients (labeled "cases") and the healthy controls. These data show that the disease process itself and treatment exposures did not influence the demethylation assay.

Figure 14D:
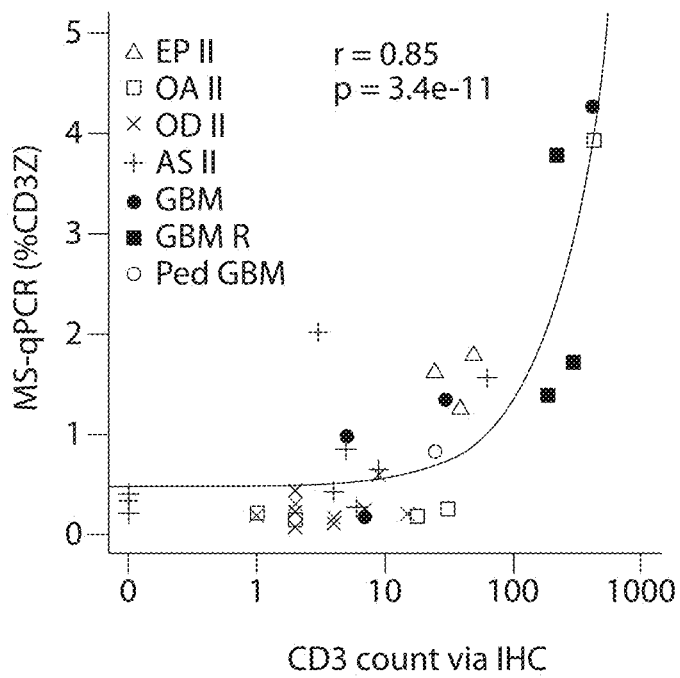

The correlation of CD3+ T cells detected by IHC and MS-qPCR was assessed in a set of FFPE samples; the results indicated a significant association of IHC score with CD3Z demethylation (Pearson R=0.85; F test p=3.4×10$^{-11}$; FIG. 14D). Most CD3+ TILs were CD8+ and only a few stained positively for CD4+ (FIG. 19). Glioma cell lines (A172, T98G) were also studied; both expressed Foxp3 copy numbers <0.06% of total input. Analysis of two autopsy brain specimens revealed Foxp3 copy numbers <0.04% of total input. These values show limits of detection of the assay which were observed to be much lower than values observed in patient blood or tumor samples. These results demonstrate the specificity of the CD3Z epigenetic assay for detecting CD3+ immune cells within a background of tumor cells.

Example 20

Figure 15A:
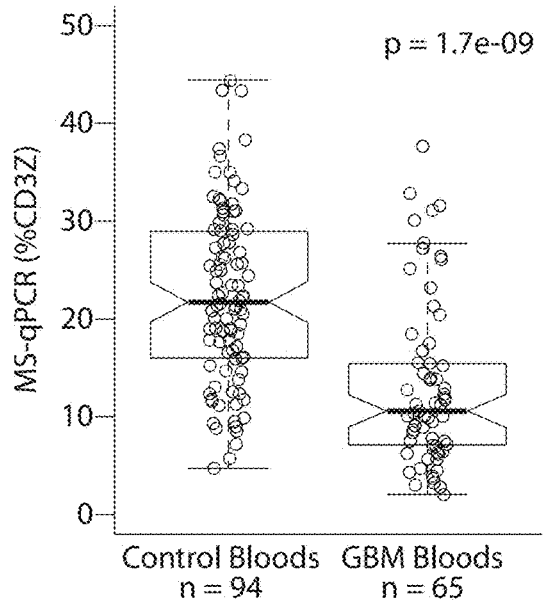
FIG. 15A shows comparison of T cell numbers in blood between GBM patients and control subjects measured using CD3Z demethylation assay.
Figure 15B:
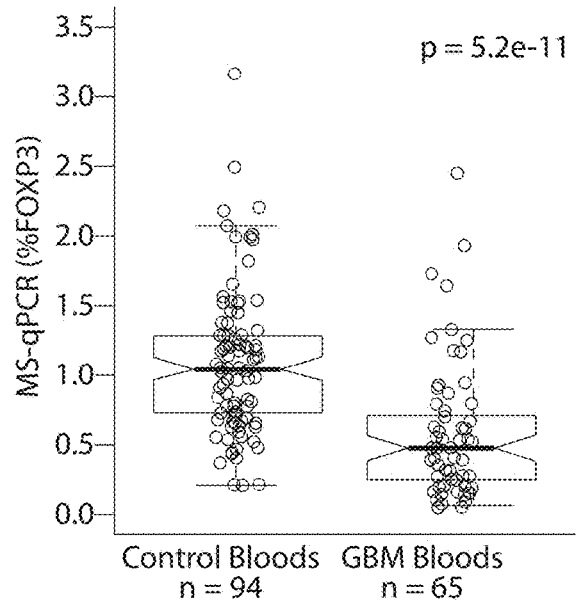
FIG. 15B shows comparison of Tregs between GBM patients and control subjects measured using FOXP3 demethylation assay.
Figure 15C:
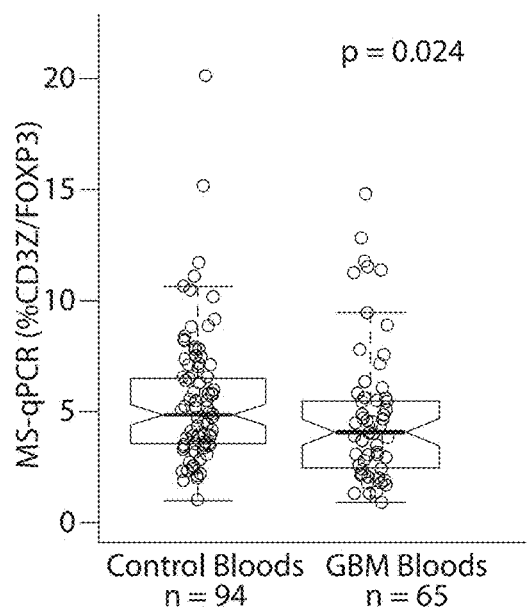
FIG. 15C is a graph showing comparison of Treg percent of T cells between GBM patients and control subjects determined by the ratio of FOXP3/CD3Z demethylation. Wilcoxon rank sum p-values are shown.
Figure 16B:
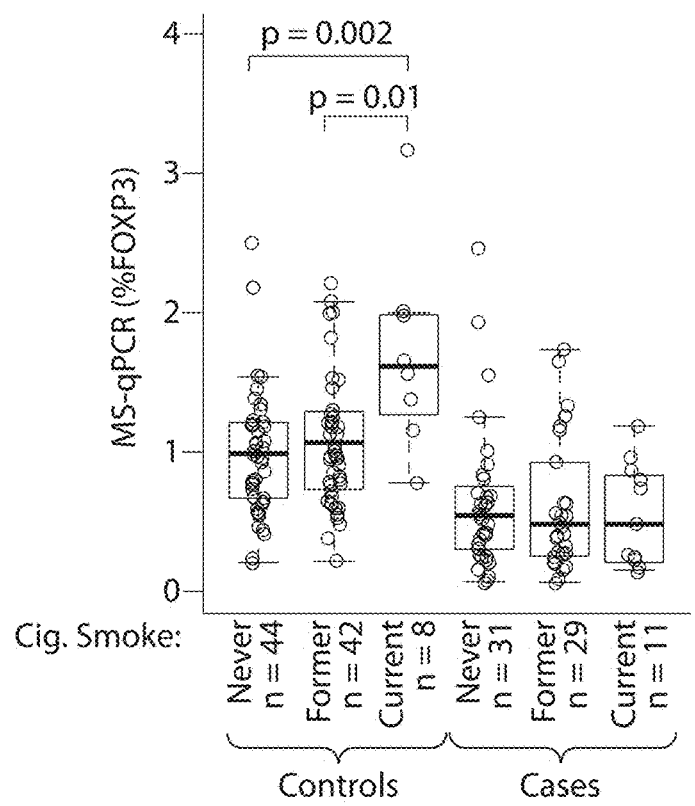
FIG. 16B shows a comparison of peripheral blood Treg levels, determined by FOXP3 demethylation, among never, former and current cigarette smokers stratified by glioma case status.
Figure 16C:
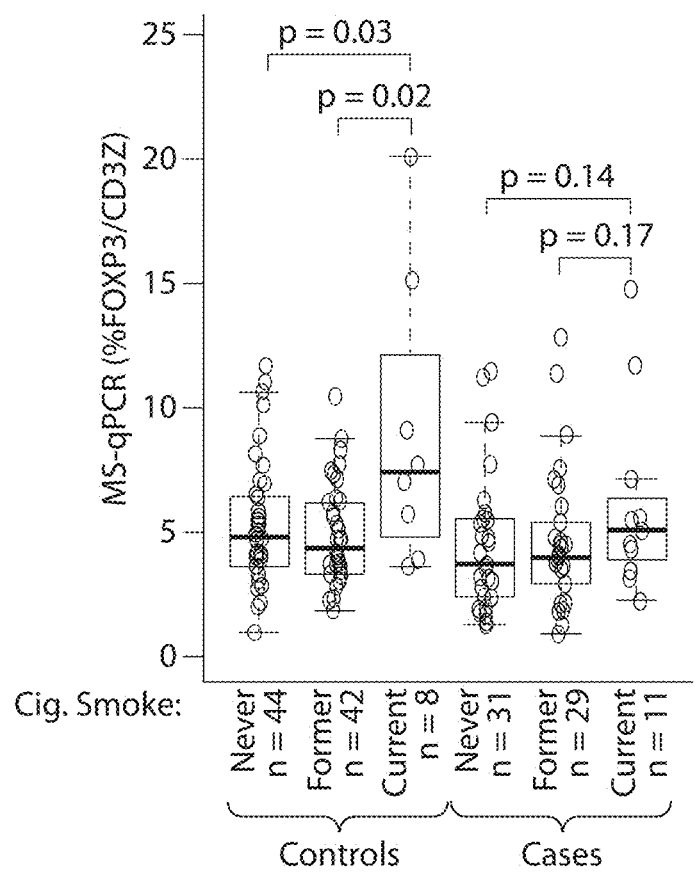
FIG. 16C shows a comparison of peripheral blood Treg percent of T cells, determined by ratio of FOXP3 to CD3Z demethylation, among never, former and current cigarette smokers stratified by glioma case status. Wilcoxon rank sum p-values are shown.

Determination of T Cells and Tregs Levels in Peripheral Blood by CD3Z and FOXP3 MS-qPCR Assays in Glioma Cases and Controls The utility of the epigenetic assays using archived frozen blood specimen samples was tested by performing a case control analysis of CD3Z and FOXP3 demethylation in glioma patients and control subjects to measure CD3+ T cell and Treg levels, respectively, in stored peripheral blood specimens from the University of San Francisco Adult Glioma Study (AGS). Results of MS-qPCR assays are summarized in Table 18. The total inputs of DNA from whole blood from the 94 controls and 71 glioma cases were not significantly different from each other. In patients with grade IV glioblastoma multiforme (GBM), peripheral blood CD3+ T cell levels were observed to be significantly lower (Wilcoxon p=1.7×10-9; FIG. 15A), peripheral blood Treg levels were observed to be significantly lower (Wilcoxon p=5.2×10-11; FIG. 15B) and peripheral blood Treg/CD3+ T cell ratios were observed to be moderately lower (Wilcoxon p=0.024; FIG. 15C) compared to healthy controls. In glioma patients and controls subjects, levels of T cells and Tregs were positively correlated (Pearson R=0.61, F test p<2.2×10-16). Use of dexamethasone or chemotherapy was not associated with T cell measures. The GBM case patients received steroid treatments prior to blood sampling. In healthy controls, but not glioma patients, people who had smoked were observed to have higher peripheral blood CD3+ T cell levels than those who had never smoked (Wilcoxon p=0.08, FIG. 16A) and current smokers had significantly higher levels of peripheral blood Tregs than former smokers (Wilcoxon p=0.01) and never smokers (Wilcoxon p=0.002; FIG. 16B). Furthermore, the ratio of Tregs/CD3+ T cells was significantly elevated in the peripheral blood of current smokers compared to former smokers (Wilcoxon p=0.01) and never smokers (Wilcoxon p=0.03) among healthy controls, and trended towards elevated levels in current smokers compared to former smokers (Wilcoxon p=0.17) and never smokers (Wilcoxon p=0.14; FIG. 16C).

TABLE 18

Summary of MS-qPCR measurements for samples (N = 285)

| Sample Description | Percent Demethylation, Median (Range) | | |
|---|---|---|---|
| | CD3Z | FOXP3 | FOXP3/CD3Z |
| Blood samples (n = 165) | 17.6 (2.1-44.4) | 0.8 (0.06-3.2) | 4.5 (0.9-20.2) |
| Controls (n = 94) | 21.7 (4.7-44.4) | 1.0 (0.2-3.2) | 4.8 (1.0-20.2) |
| Never Smokers (n = 44) | 19.3 (4.7-32.1) | 1.0 (0.2-2.5) | 4.8 (1.0-11.7) |
| Former Smokers (n = 42) | 22.4 (8.8-43.4) | 1.1 (0.2-2.2) | 4.4 (1.8-10.5) |
| Current Smokers (n = 8) | 23.4 (5.7-44.4) | 1.6 (0.8-3.2) | 7.4 (3.6-20.2) |
| Glioma Cases (n = 71) | 11.2 (2.1-37.7) | 0.5 (0.06-2.5) | 4.1 (0.9-14.8) |
| Never Smokers (n = 31) | 11.3 (2.7-37.7) | 0.5 (0.06-2.5) | 3.8 (1.3-11.5) |
| Former Smokers (n = 29) | 12.7 (3.3-32.8) | 0.5 (0.06-1.7) | 4.1 (0.9-12.8) |
| Current Smokers (n = 11) | 9.6 (2.1-27.8) | 0.5 (0.1-1.2) | 5.1 (2.3-14.8) |
| Non-GBM (n = 6) | 18.5 (3.5-26.6) | 0.9 (0.2-1.6) | 6.0 (3.8-7.1) |
| GBM (n = 65) | 10.5 (2.1-37.7) | 0.5 (0.06-2.5) | 4.1 (0.9-14.8) |
| Excised Tumors (n = 120) | 0.5 (0.03-18.7) | 0.03 (0-1.5) | 5.1 (0-100) |
| Grades I, II & III (n = 83) | 0.3 (0.03-3.9) | 0.02 (0-0.5) | 3.4 (0-100) |
| Pilocytic Astrocytoma (n = 2) | 1.4 (1.0-1.9) | 0 (0-0) | 0 (0-0) |
| Ependymoma (n = 15) | 0.5 (0.09-3.0) | 0.03 (0-0.3) | 3.4 (0-29.4) |
| Oligodendroglioma (n = 20) | 0.2 (0.04-1.6) | 0 (0-0.2) | 0 (0-57.3) |
| Oligoastrocytoma (n = 19) | 0.25 (0.04-3.9) | 0.05 (0-0.4) | 10.5 (0-100) |
| Astrocytoma (n = 27) | 0.3 (0.03-2.0) | 0 (0-0.5) | 0 (0-100) |
| Grade IV, GBM (n = 37) | 1.1 (0.17-18.7) | 0.08 (0-1.5) | 7.8 (0-47.4) |

Example 21

Figure 17A:
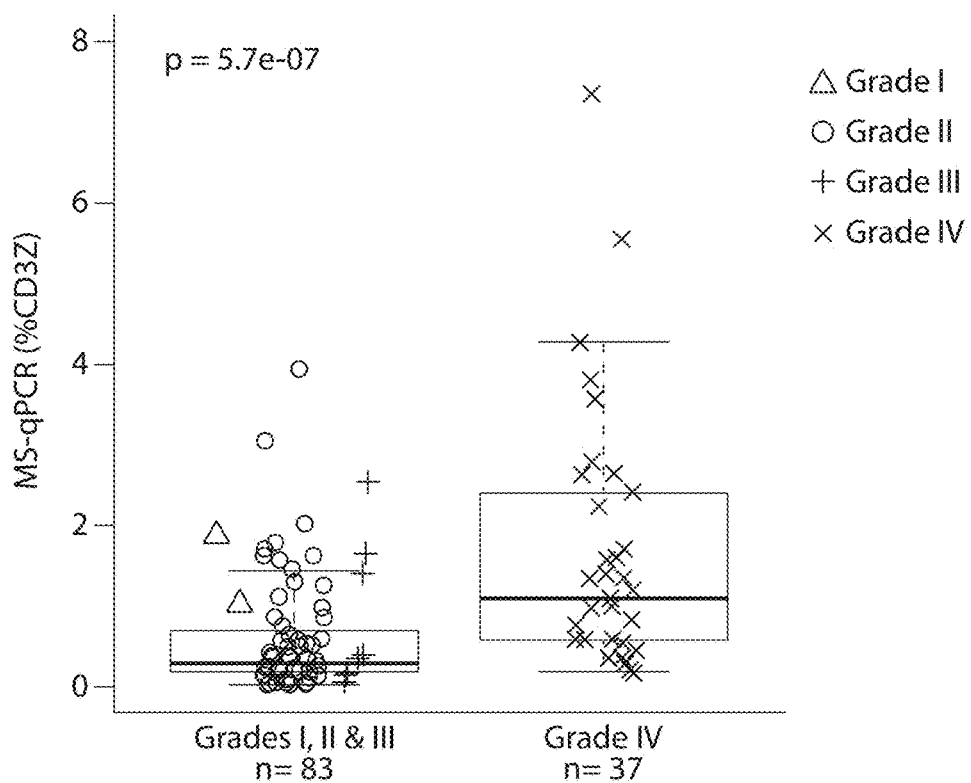
FIG. 17A, FIG. 17B and FIG. 17C (FIG. 17A-C) are graphical representations showing levels of T cell and Treg infiltrates in excised glioma tumors determined by MS-qPCR for demethylation of specific CpG loci.
Figure 17B:
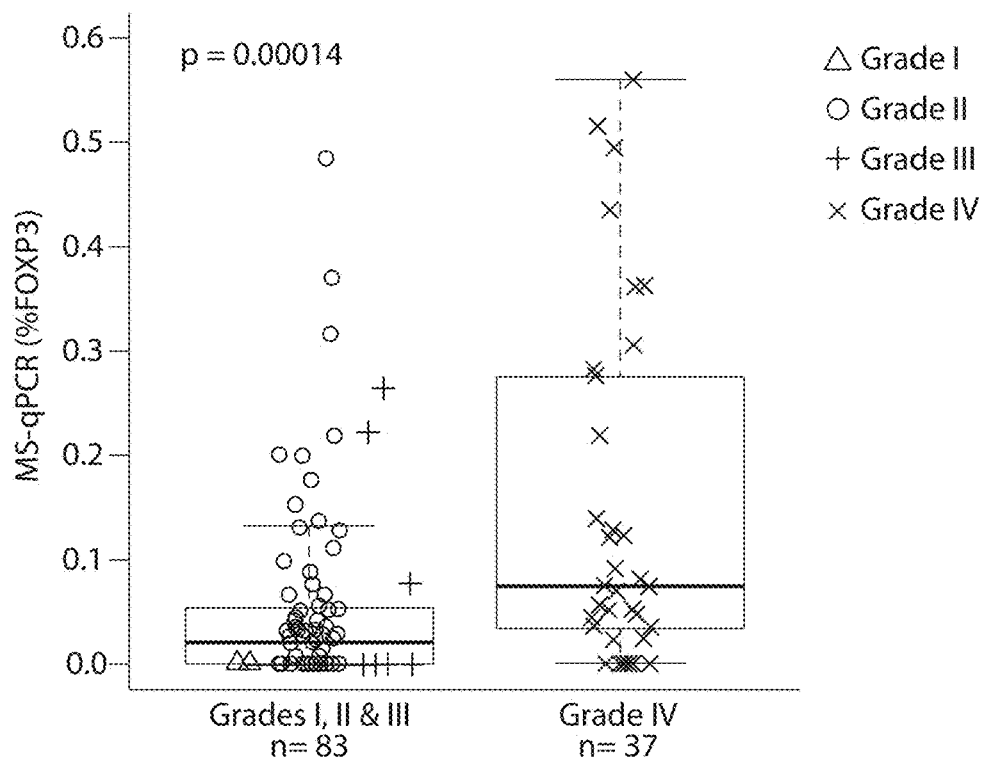
Figure 17C:
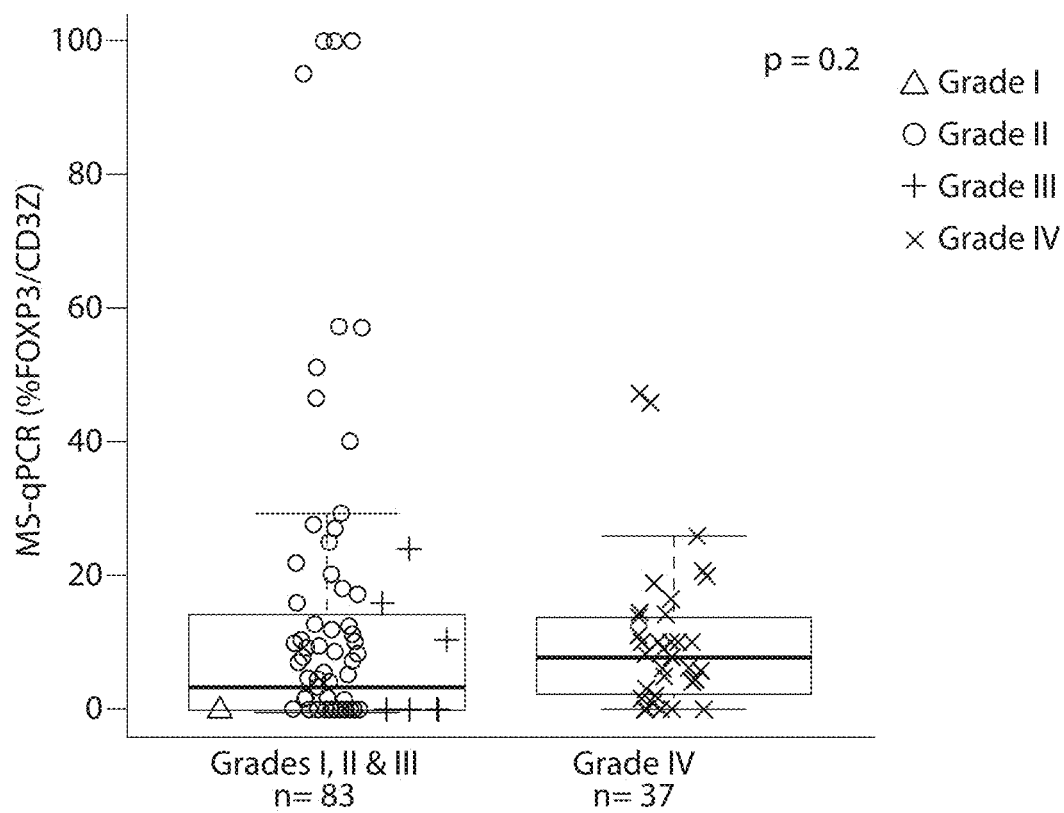
Figure 21A:
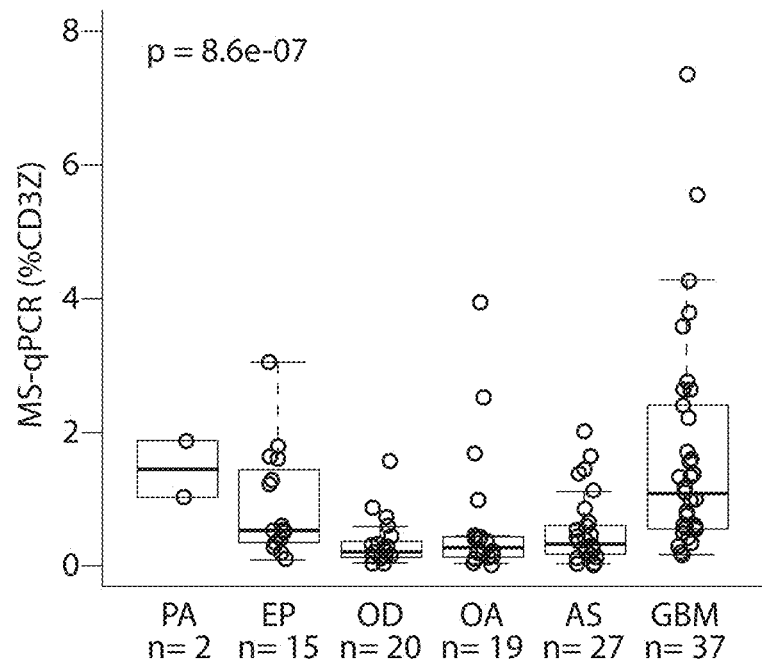
FIG. 21A-C are graphical representations showing levels of T cell and Treg infiltrates in glioma tissues stratified by histological subtype determined by MS-qPCR for demethylation of specific CpG loci. Abbreviations: PA=Pilocytic Astrocytoma, EP=Ependymoma, OD=Oligodendroglioma, OA=Oligoastrocytoma, AS=Astrocytoma, GBM=Glioblastoma multiforme. Kruskal-Wallis one-way analysis of variance by rank test p-values is shown.
Figure 21B:
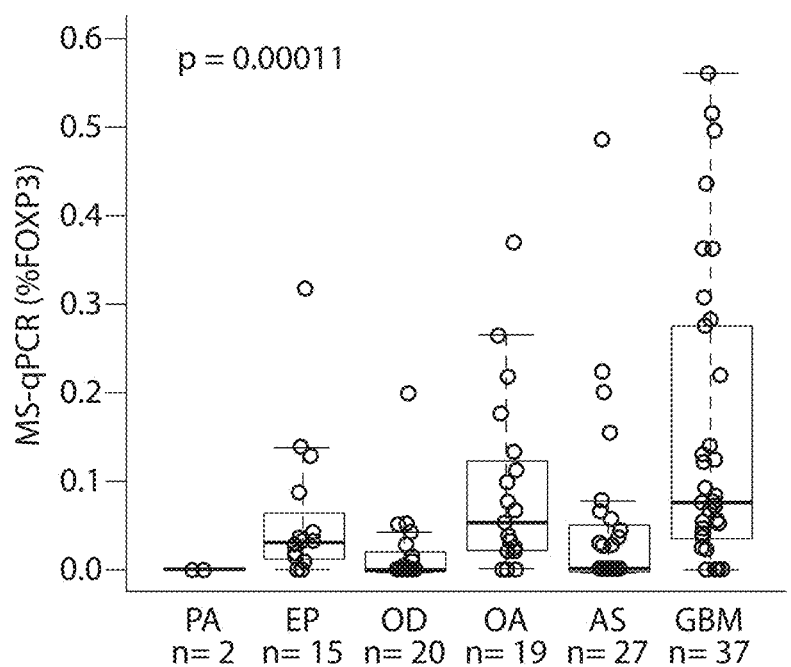
Figure 21C:
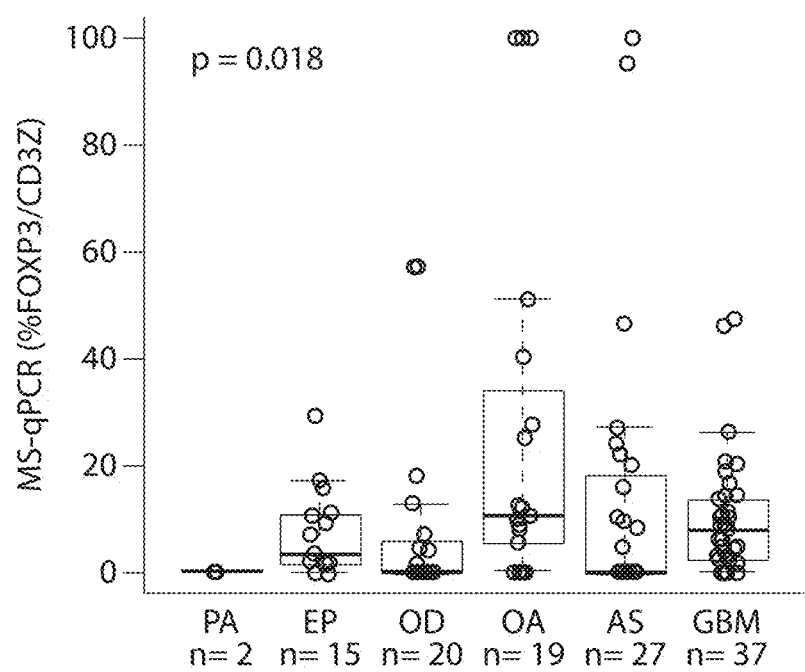
Figure 22A:
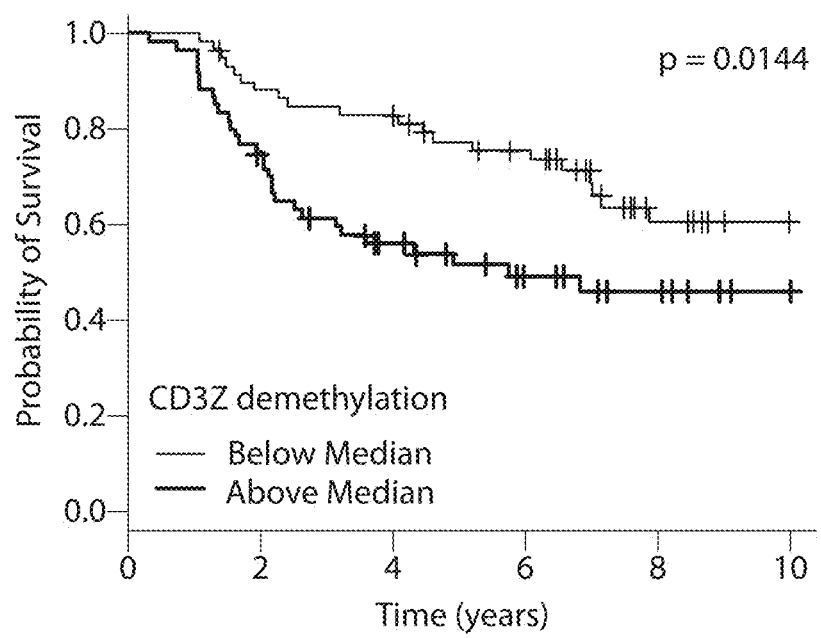
FIG. 22A-C are graphical representations showing Kaplan Meier analysis of time of survival of glioma patients stratified according to whether the level of T cells or Tregs in the tumor infiltrates of the patients are above or below the median level of T cells or Tregs, respectively. Log Rank p-values shown.
Figure 22B:
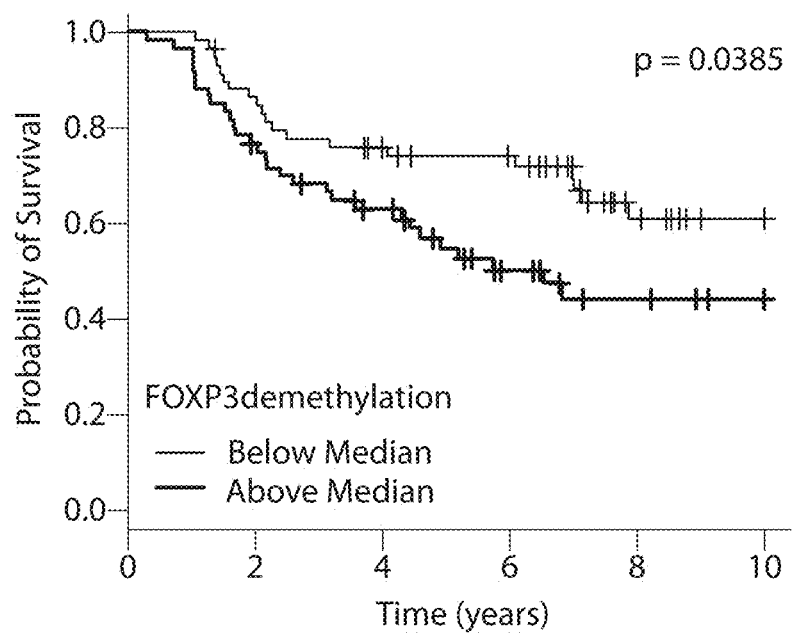

Determination of T Cells and Tregs Levels in Tumor Infiltrates by CD3Z and FOXP3 MS-qPCR Assays in Excised Glioma Tumors The demethylation assays of CD3Z and FOXP3 were used to measure levels of tumor infiltrating CD3+ T cells and Tregs, respectively, in 120 fresh frozen glioma tumors from the UCSF Brain Tumor Research Center tissue bank. Results of MS-qPCR assays are summarized in Table 18. Increased glioma tumor grade and higher levels of both CD3+ T cell (Wilcoxon p=5.7×10-7; FIG. 17A) and Treg (Wilcoxon p=0.00014; FIG. 17B) in tumor infiltrates were observed to be significantly associated. In grade IV glioma tumor tissues the median level of Treg percentage of T cells was observed to be higher than that of control blood samples (Table 18), and higher than that of lower grade tumors (FIG. 17C). Data from MS-qPCR showed significant differences among glioma tumor histologies in levels of CD3+ T cells (Kruskal-Wallis p=8.6×10-7; FIG. 21A), Tregs (Kruskal-Wallis p=0.00011; FIG. 21B) and Treg/CD3+ T cell ratios (Kruskal-Wallis p=0.018; FIG. 21C). Poorer patient survival was associated with and higher levels of tumor infiltrating CD3+ T cells (Log-Rank p-value=0.014; FIG. 22A) and Tregs (Log-Rank p-value=0.039; FIG. 22B) measured by MS-qPCR.

Example 22

Figure 22C:
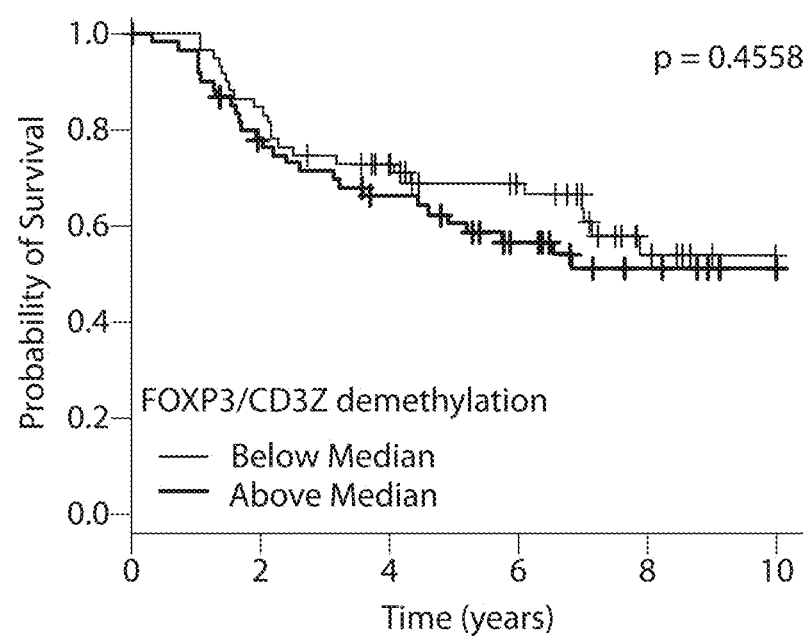
Figure 23A:
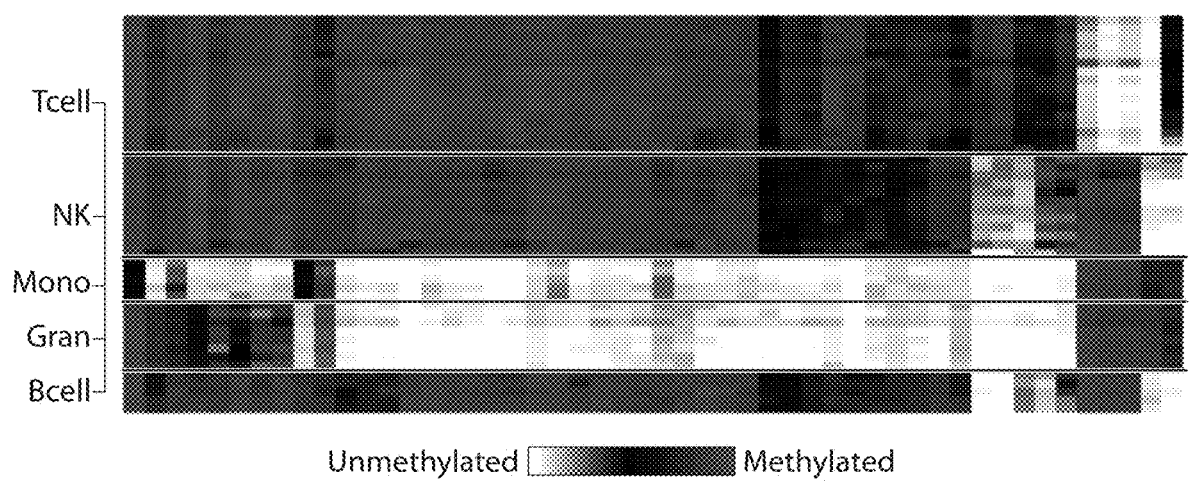
FIG. 23A-B are representations of results obtained from analysis of DMRs of leukocyte subtypes.
Figure 23B:
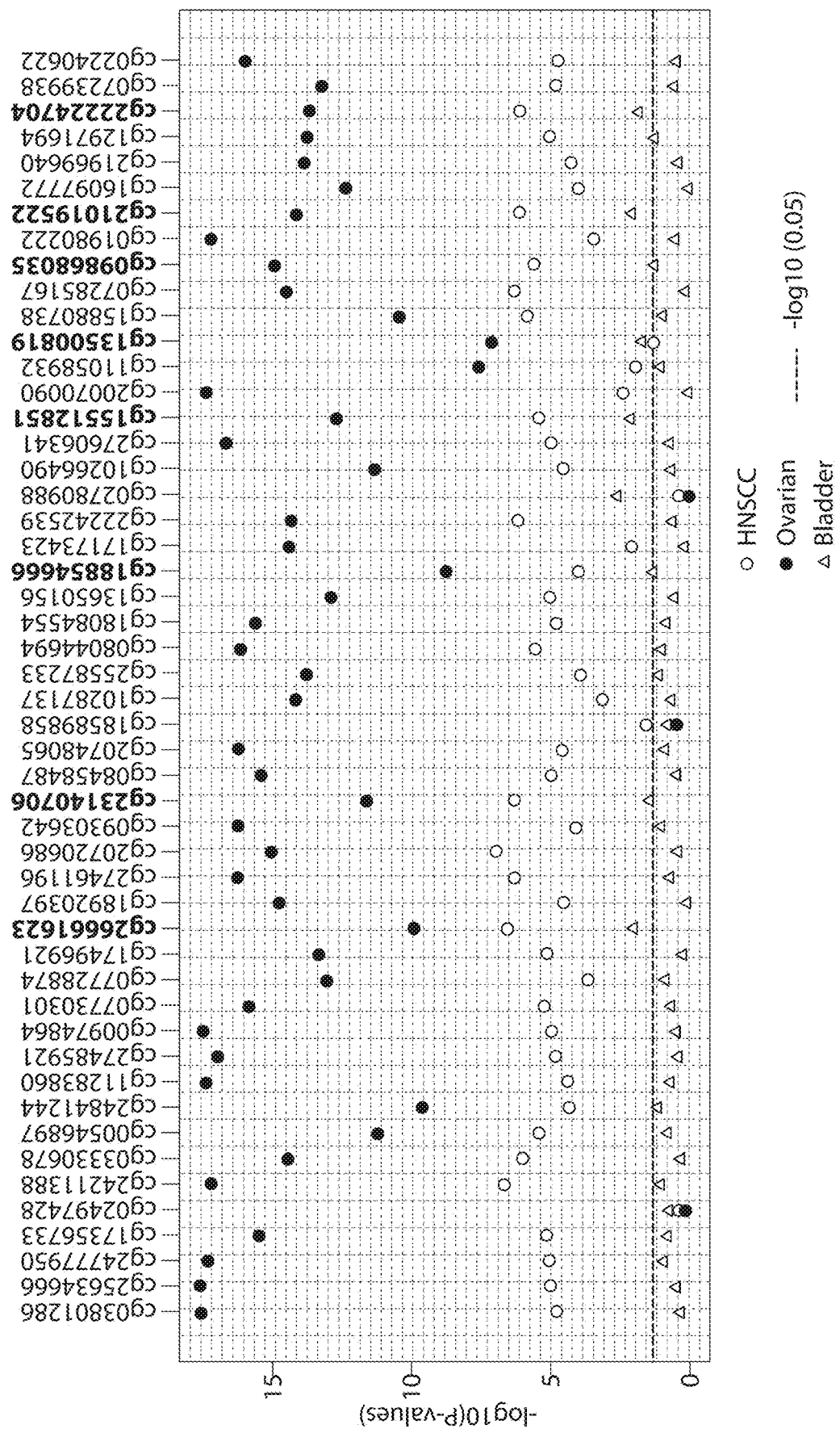

Kaplan-Meier Survival Curves for Glioma Cases Show Association of Lower Treg with Improved Survival Survival of glioma patients were correlated with the incidence of CD3+ T cells and Tregs as measured by CD3Z demethylation assays. (FIG. 22A-C). Both univariate and multivariate survival analyses were performed. Kaplan-Meier survival curves for glioma cases were stratified by median values of CD3Z demethylation assays. For depicting the survival results in FIG. 22A-C, patients were divided into two groups. In each panel the top trace represents survival data of the group of patients for whom the measured variable (methylation status of CD3+ T cells, or of Tregs, or a ratio Tregs/T cells) was below the median observed for that variable, and the bottom trace represents survival data of the group of patients for whom the measured variable was above the median observed for that variable.

The results show that after controlling for age, gender and grade the CD3Z demethylation assays for CD3+ and CD3+ Tregs in glioma tumor tissue were significantly associated (FIG. 22A-C) with poorer patient survival.

A CD3+ T cell CD3Z demethylation assay was performed which showed that lower CD3+ T cell/total input in glioma tumor tissue was significantly associated (FIG. 22A) with improved survival (Log-Rank p-value=0.0144). A Treg CS-DM CD3Z demethylation assays was performed which showed (FIG. 22B) that lower Treg/total input in glioma tumor tissue was significantly associated with improved survival (Log-Rank p-value=0.0385). A measurement of Treg/CD3+ T cell ratio was performed by CD3Z demethylation assay which showed (FIG. 22C) that lower Treg percentage of CD3+ T cells in glioma tumor tissue was significantly associated with improved survival (Log-Rank p-value=0.4558).

Example 23

Cells, and Cancer Patient and Control Datasets for Determining DNA Methylation Based Epigenetic Signatures for Differentiating Patients and Controls Sorted, normal, human peripheral blood leukocyte subtypes were isolated from whole blood by magnetic activated cell sorting (MACS) (AllCells LLC, Emeryville, Calif.). The purity of separated cells was confirmed with flow cytometry to be >97%. Genomic DNA was extracted and purified from cell pellets using a commercially available method (Qiagen, Valencia, Calif.), treated with sodium bisulfite (Zymo Research, Irvine, Calif.) and subjected to methylation profiling using the Infinium HumanMethylation27 BeadArray (Illumina, San Diego, Calif.). This same platform was used for the analysis of samples from the case-control studies described below.

The HNSCC data set consists (Table 19) of 92 incident cases from the greater Boston area and 92 cancer-free population-based control subjects from the same region (Applebaum K M et al., Int J Cancer 124:2690-2696, 2009). The clinical characteristics for this study population are contained in Table 19. The ovarian cancer data set (Teschendorff A E et al., 2009, PLoS One 4:e8274, 2009) is publicly available from Gene Expression Omnibus (GEO, http://www.ncbi.nlm.nih.gov/geo/, Accession number GSE19711), and consists of 266 postmenopausal women diagnosed with primary epithelial ovarian cancer (131 pre-treatment and 135 post-treatment cases) from the UK Ovarian Cancer Population Study (UKOPS). Controls (n=274) were cancer-free postmenopausal women for which annual serum samples were available. To avoid potential biases due to therapy, only pre-treatment ovarian cases were included in the analysis. The bladder cancer data set (Marsit C J et al., 2011, J Clin Oncol 29:1133-1139) consists of 223 incident bladder cancer cases identified from the New Hampshire state cancer registry and 237 population controls from the same region (Karagas M R et al., 1998, Environ Health Perspect 106:1047-1050; Wallace K et al., 2009, Cancer Prev Res 2:70-73). Table 20 provides a summary of the participant characteristics.

TABLE 19

Characteristics of the study population in the HNSCC data set.

| Characteristics | Cases (n = 92) | Controls (n = 92) |
|---|---|---|
| Age, median years (range) | 58 (31-84) | 59 (32-86) |
| Gender, n (%) | | |
| Male | 64 (69.6%) | 64 (69.6%) |
| Female | 28 (30.4%) | 28 (30.4%) |
| Smoking history, n (%) | | |
| Never | 17 (18.5%) | 32 (34.8%) |
| Former | 59 (64.1%) | 47 (51.1%) |
| Current | 16 (17.4%) | 13 (14.1%) |
| Pack-years*, median (range) | 40.0 (0.8-135.0) | 24.5 (0.5-85.0) |
| Alcohol history, median drinks/week (range) | 15.7 (0-307.0) | 5.6 (0-140.6) |
| HPV16 (E6, E7 or L1 seropositivity), n (%) | | |
| Negative | 66 (71.7%) | 83 (90.2%) |
| Positive | 26 (28.3%) | 9 (9.8%) |
| Tumor Site, n (%) | | |
| Oral cavity | 39 (42.4%) | — |
| Pharynx | 35 (38.0%) | — |
| Larynx | 18 (19.6%) | — |
| Stage, n (%) | | |
| I | 9 (12.5%) | — |
| II | 9 (12.5%) | — |
| III | 14 (19.4%) | — |
| IV | 40 (55.6%) | — |

*Restricted to ever-smokers (current + former)

TABLE 20

Characteristics of the study population in the Bladder cancer data set.

| Characteristics | Controls No. | % | Cases No. | % |
|---|---|---|---|---|
| Total No. | 237 | | 223 | |
| Age, years | | | | |
| Median | 65 | | 66 | |
| Range | 28-74 | | 25-74 | |
| Sex | | | | |
| Male | 158 | 48 | 171 | 52 |
| Female | 79 | 60 | 52 | 40 |
| Family history of bladder cancer* | | | | |
| No | 224 | 53 | 199 | 47 |
| Yes | 7 | 44 | 9 | 56 |
| Smoking history | | | | |
| Never | 72 | 64 | 40 | 36 |
| Former | 126 | 53 | 111 | 47 |
| Current | 39 | 35 | 72 | 66 |
| Tumor stage/grade designation | | | | |
| Carcinoma in situ | NA | | 6 | 3 |
| Noninvasive low grade (grade 1-2) | NA | | 140 | 63 |
| Noninvasive high grade (grade 3) | NA | | 17 | 7 |
| Invasive | NA | | 60 | 27 |

*Data on family history were not available for 13 subjects

Example 24

Statistical Analysis of Differences in Methylation Status in Leucocyte Subsets for Determining Signatures Based on Leukocyte DMRs The analytic strategy was aimed toward examining the extent to which peripheral blood DNA methylation of non-hematopoietic cancers is driven by the epigenetic signatures that define leukocyte subtypes. Linear mixed-effects models were used to assess differences in methylation across the leukocyte subtypes and controlled for the large number of comparisons using false discovery rate (fdr) estimation. Leukocyte DMRs were subsequently ranked based on their strength of association and the highest ranking 50 DMRs were examined across the three cancer data sets between cancer cases and cancer-free controls.

An analysis was performed that capitalized on the aggregate methylation signatures across a collection of leukocyte DMRs. Each one of the full cancer data sets was split into equally sized training and testing sets. Samples in the training sets were then clustered using leukocyte DMRs. Clustering analysis was achieved using the Recursively Partitioned Mixture Model20 (RPMM), a hierarchical model-based method for clustering used for the clustering of array-based methylation data ((Christensen B C et al., 2009, PLoS Genet 5:e1000602; Christensen B C et al., 2011, J Natl Cancer Inst 103:143-153; Hinoue T et al., 2012, Genome Res. 22(2):271-82; Koestler D C et al., 2010, Bioinformatics 26:2578-2585). Based on the RPMM fit to the training sets, methylation class membership for the observations in the respective testing sets was predicted and the association between predicted methylation class and cancer case/control status were assessed.

The detailed statistical methodologies employed in the analysis are shown in Examples 25-26. Analyses were carried out using the R statistical package, R project for statistical computing, version 2.13 R available for downloading from the internet.

Example 25

Figure 24A:
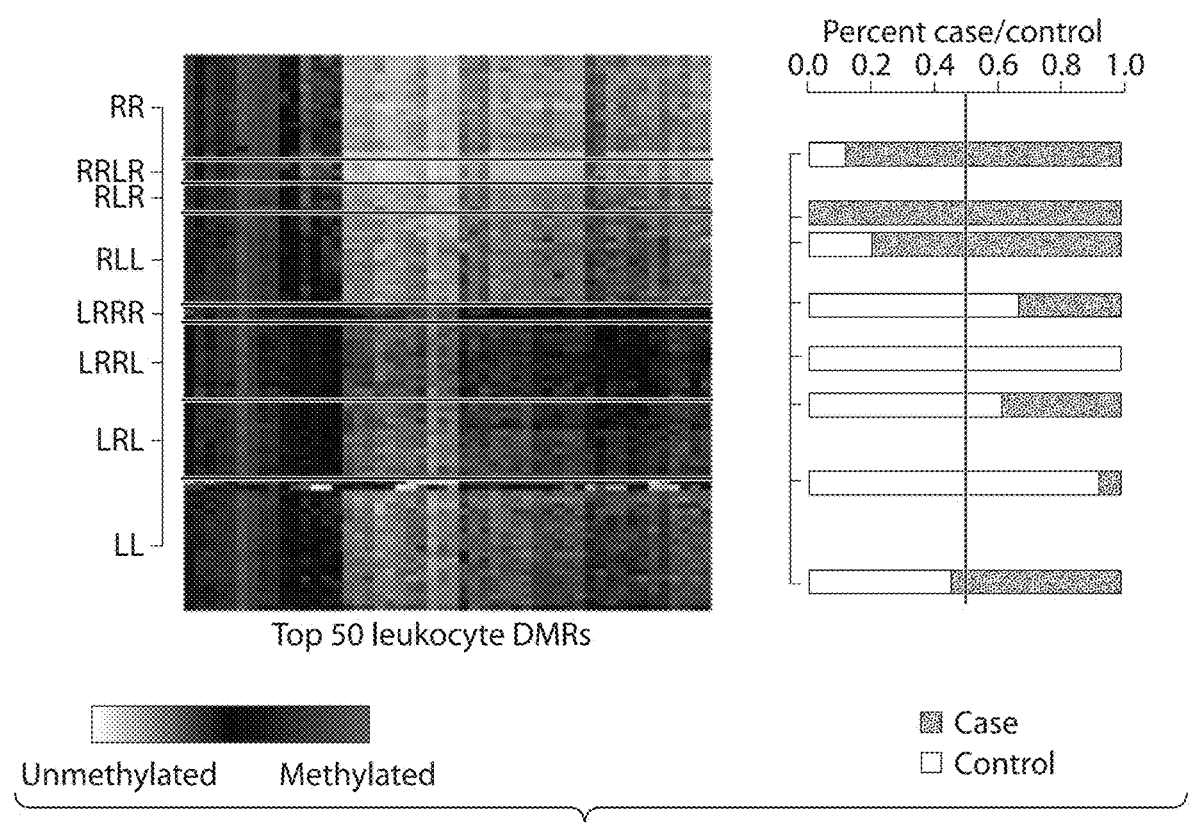
FIG. 24A-B show results obtained from the DMR profile analysis of the HNSCC data set determining methylation class membership.
Figure 24B:
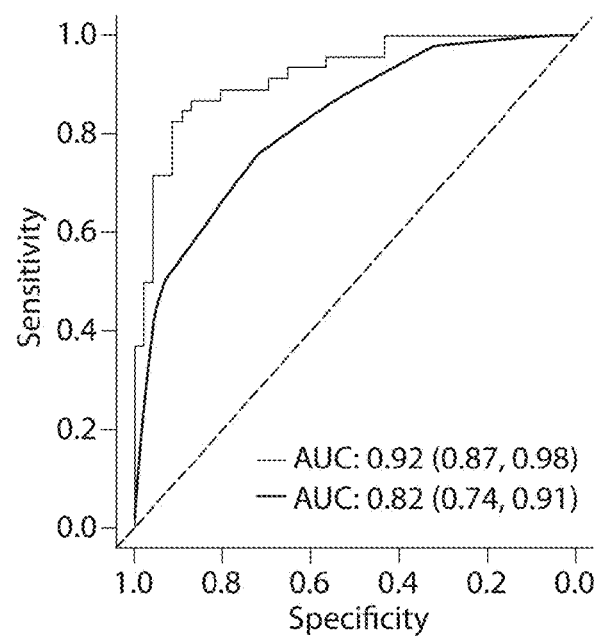
Figure 28:
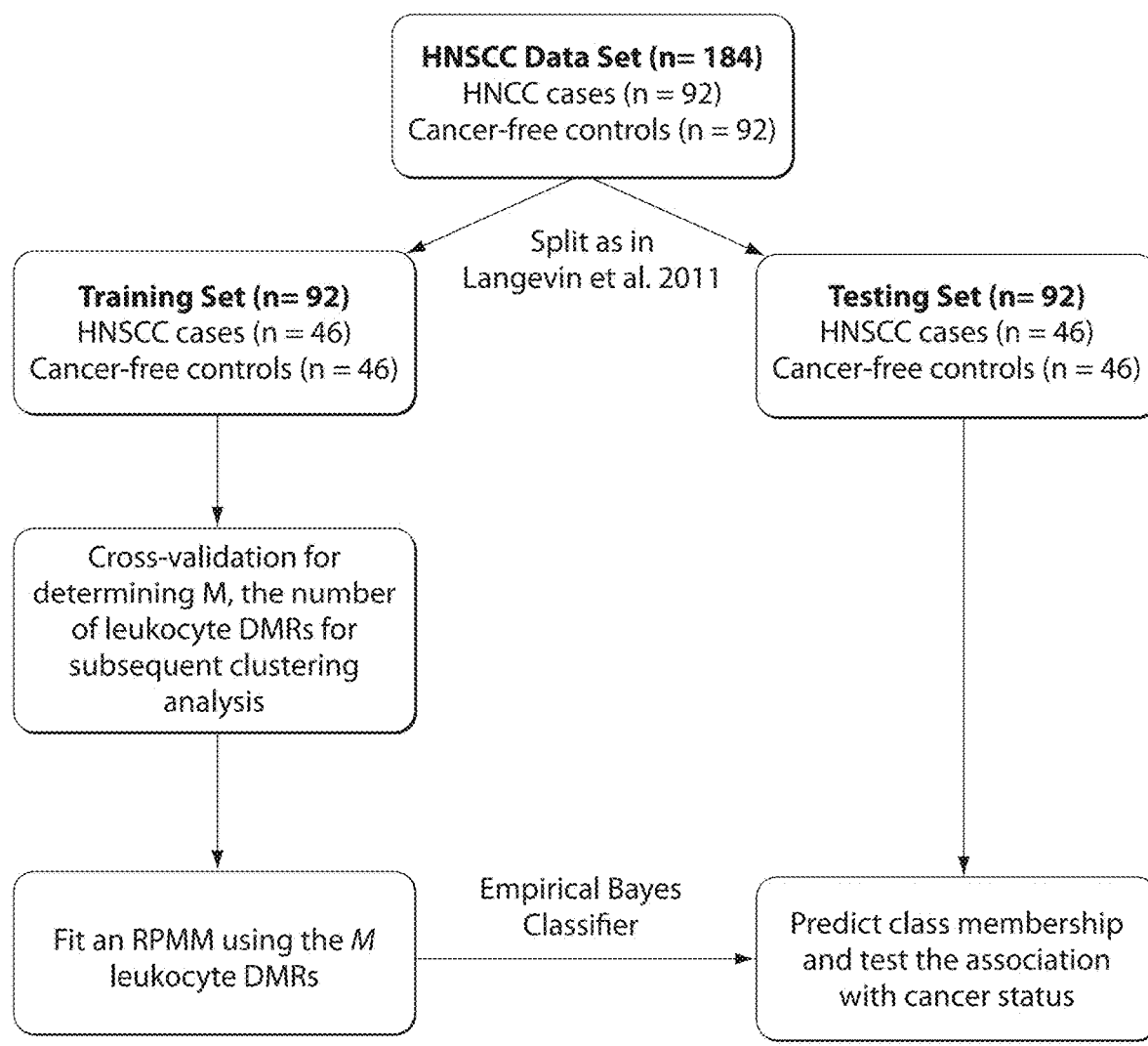
FIG. 28 is a schematic diagram showing hierarchy of leukocyte subtypes and sample sizes for each of the leukocyte subtypes used in the analysis for determination of methylation class membership.

Prediction of Methylation Class Membership Based on Epigenetic Signatures from Leukocyte Derived DMRs Genome-wide DNA methylation was profiled in 46 samples of magnetic antibody sorted, normal human peripheral blood leukocyte subtypes (including B cells, granulocytes, monocytes, NK-cells, CD4+ T cells, CD8+ T cells, and Pan-T cells; FIG. 28) using the Infinium HumanMethylation27 BeadArray. To discern leukocyte subtype DMRs, an association between methylation and leukocyte subtype for each of 26,486 autosomal CpG loci was examined. This data revealed 10,370 significantly differentially methylated CpGs among the leukocyte subtypes (fdr q-value <0.05), which were ranked by q-value (Table 22 and FIG. 24A). The highest ranking 50 DMRs (Table 21) from this ranked list were selected for use in the case-control analyses. Since the publically available ovarian cancer data set included both pre- and post-treatment cases, only pre-treatment cases (n=131) were considered in subsequent analyses to avoid potential biases resulting from therapy. Using unconditional logistic regression models, adjusted for available and relevant confounders (FIG. 24A), a substantial proportion of the 50 selected leukocyte DMRs were found to be significantly differentially methylated between cancer cases and cancer-free controls at the $\alpha$=0.05 threshold (48, 47, and 8 out of 50, permutation p-values=<0.001, <0.001, 0.085, for HNSCC, ovarian cancer, and bladder cancer, respectively; FIG. 24B).

Eight of the leukocyte DMRs that were significantly differentially methylated in cancer cases compared to controls were observed to be common to the three cancer types (FIG. 24B). In HNSCC and ovarian cancer, seven of these eight leukocyte DMRs were hypomethylated in cases relative to controls, whereas the 8 DMRs were hypermethylated in bladder cancer cases relative to controls (Table 22).

Figure 25A:
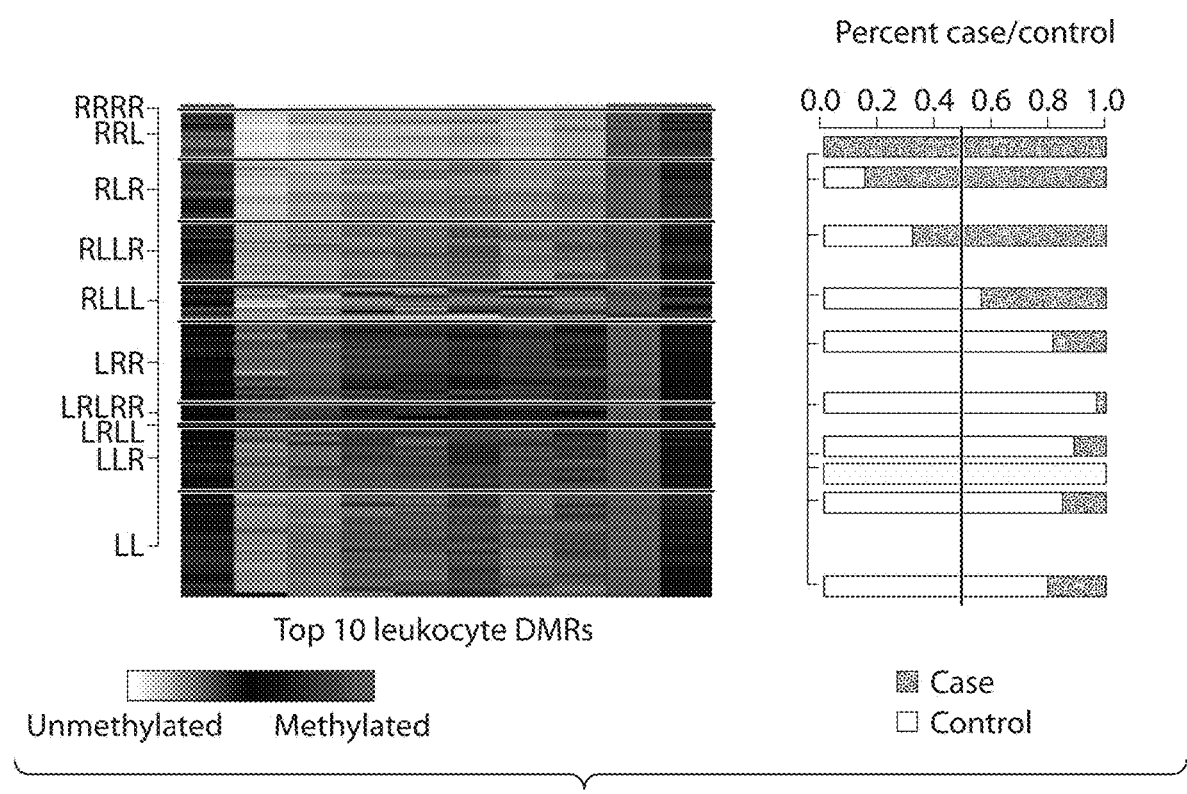
FIG. 25A-B show results obtained from the DMR profile analysis of the Ovarian data set for determining methylation class membership.
Figure 26A:
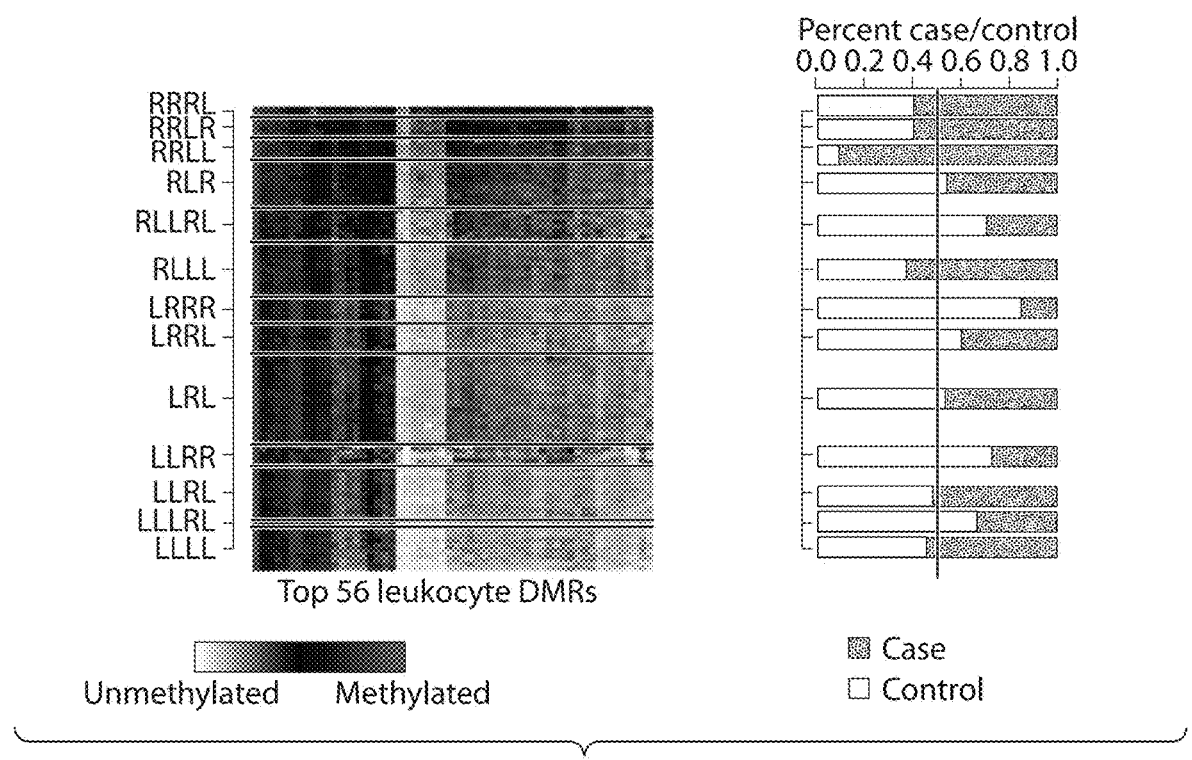
FIG. 26A-B show results obtained from the DMR profile analysis of the bladder data set for determining methylation class membership.
Figure 29:
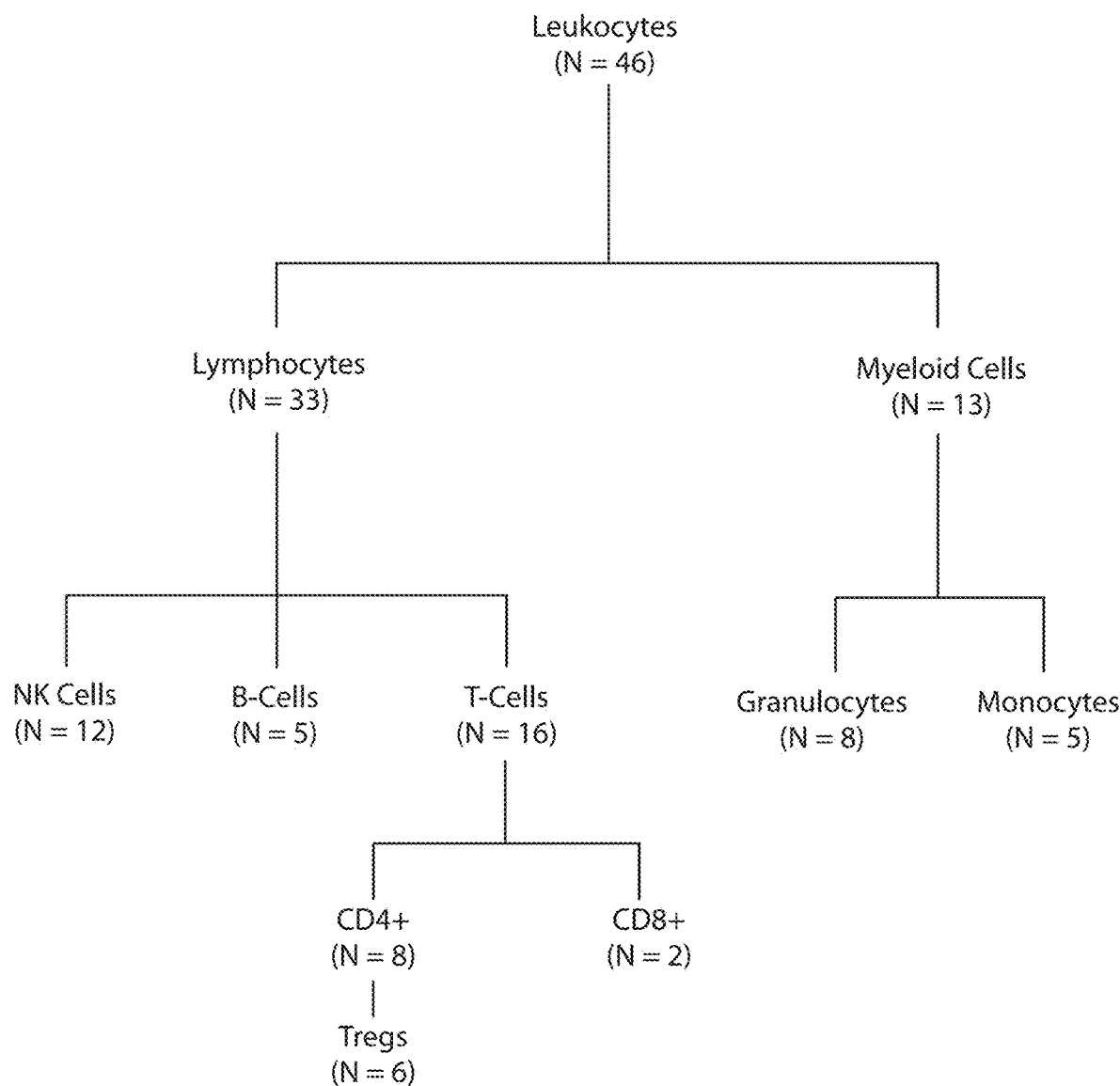
FIG. 29 is a diagram representing the analytic workflow the HNSCC data set (n=184; 92 HNSCC cases and 92 cancer-free controls). The full HNSCC data set was first divided into equally sized training and testing sets. The training sets were used in development of a classifier based on leukocyte DMRs. The resulting classifiers were then used to predict methylation class membership for the observations in the respective independent testing sets. The phenotypic importance of the predicted methylation classes in the testing data was examined subsequently.
Figure 30:
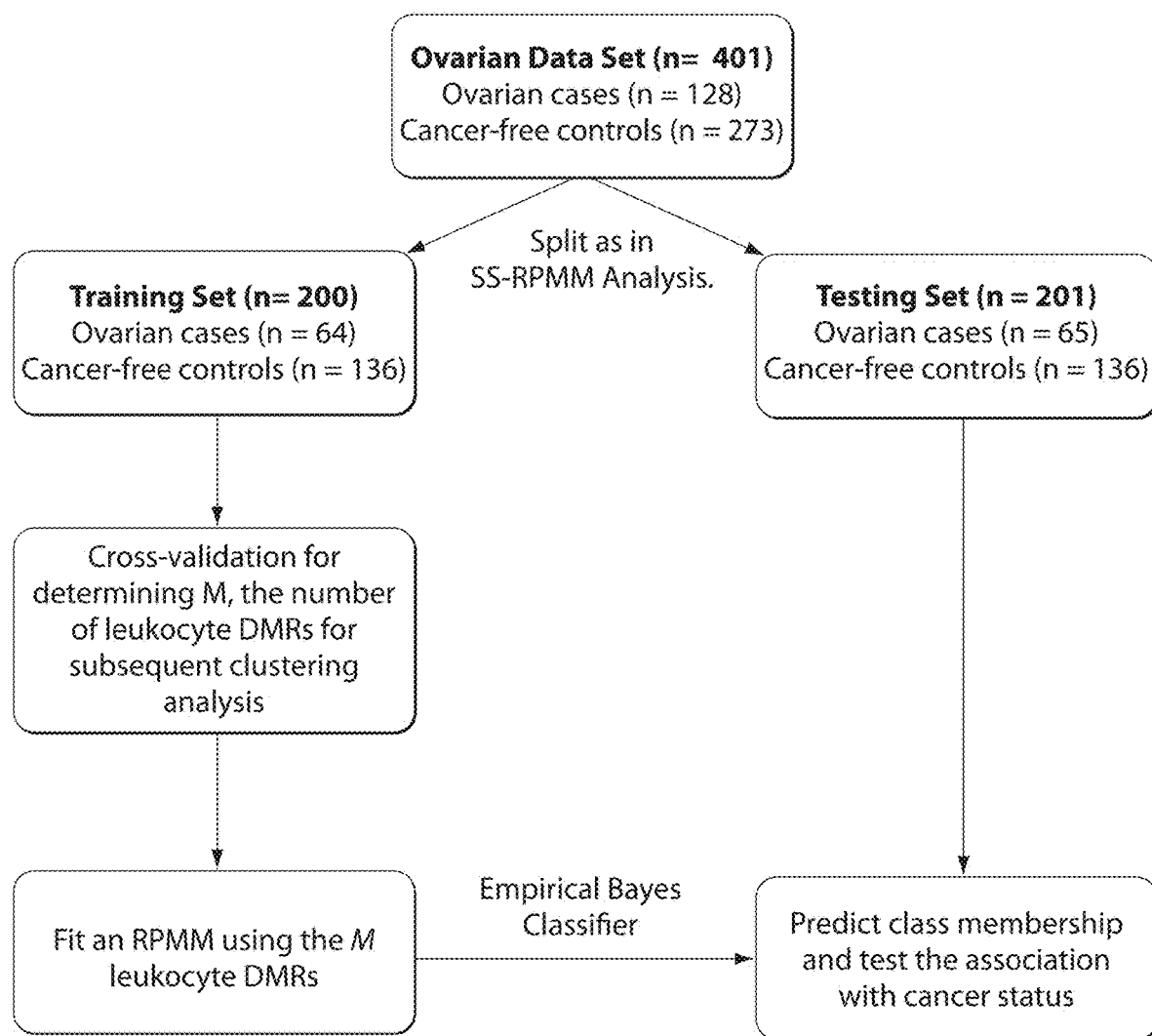
FIG. 30 is a diagram representing the analytic workflow the ovarian cancer data set (n=401; 128 ovarian cancer cases and 273 cancer-free controls). The full ovarian cancer data set was divided into equally sized training and testing sets. The training sets were used in the development of a classifier based on leukocyte DMRs. The resulting classifiers were then used to predict methylation class membership for the observations in the respective independent testing sets. The phenotypic importance of the predicted methylation classes in the testing data was then examined.
Figure 31:
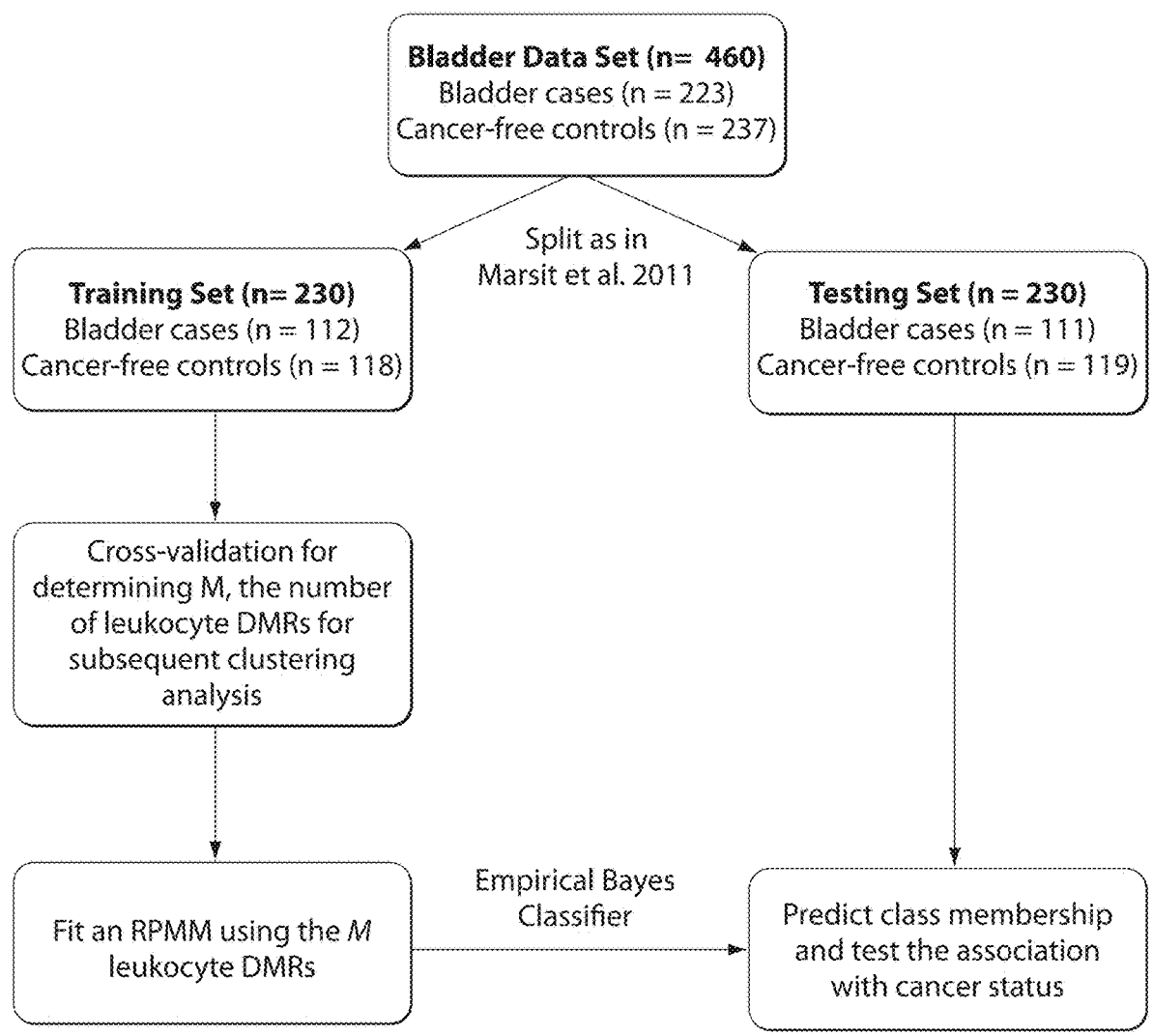
FIG. 31 is a diagram representing the analytic workflow of the bladder cancer data set (n=460; 23 Bladder cancer cases and 237 cancer-free controls). The full bladder cancer data set was divided into equally sized training and testing sets. The training sets were used in the development of a classifier based on leukocyte DMRs. The resulting classifiers were then used to predict methylation class membership for the observations in the respective independent testing sets. The phenotypic importance of the predicted methylation classes in the testing data was then examined.

To extend on the aggregate methylation signatures across a collection of leukocyte DMRs, classifiers based on profiles of leukocyte DMRs obtained from the subset analysis were developed and tested and the performance of these classifiers for successfully discriminating cancer cases from cancer-free controls was assessed. The workflow of the DMR methylation profile analysis is shown in FIGS. 29-31. For each of the three cancer data sets, a cross-validation procedure (Christensen B C et al., 2011, J Natl Cancer Inst 103:143-153) was implemented on the training sets only to determine the number of highest ranking leukocyte DMRs (M) for subsequent clustering analysis of the training sets. The highest ranking 50, 10, and 56 leukocyte DMRs from the respective cross-validation procedures using the 10,370 putative DMRs initially identified were selected to cluster the observations in the HNSCC, ovarian cancer, and bladder cancer training sets respectively. The resultant clustering solutions were used to predict methylation class membership for the subjects within the respective independent testing sets. FIG. 24A, FIG. 25A and FIG. 26A depict heat maps of the respective testing sets by predicted methylation class for each cancer data set. Methylation classes derived from leukocyte subtype DMRs were significantly associated with cancer case status within each cancer type (permutation $\chi^2$ p-values <0.0001, <0.0001, 0.03, HNSCC, ovarian cancer, and bladder cancer data sets respectively), supporting the phenotypic relevance of predicted methylation classes based on leukocyte DMRs.

For the HNSCC testing set, subjects predicted to be in the right most classes of the dendrogram (classes beginning with R) were six-fold more likely to be HNSCC cases compared to subjects in the left most classes (classes beginning with L) (OR=5.99; 95% CI [1.96, 18.36]), controlling for age, gender, smoking, alcohol consumption, and HPV serostatus. Assessing the clinical utility of the predicted methylation classes in HNSCC demonstrated that methylation classes derived from the highest ranking 50 leukocyte DMRs were highly predictive of HNSCC case/control status (area under the curve (AUC)=0.82 95% CI [0.74, 0.91]), which increased to 0.92 (0.87, 0.98 with age, gender, smoking, alcohol consumption, and HPV serostatus included in the model (FIG. 24B).

Figure 25B:
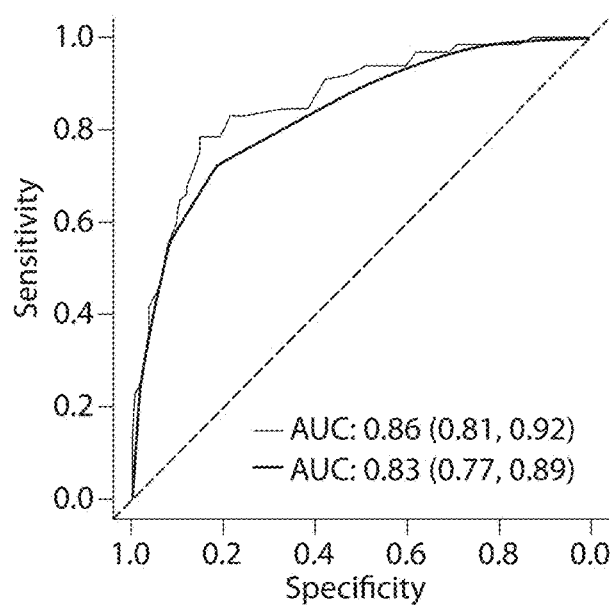

For ovarian cancer, subjects predicted to be in the right most classes were approximately ten-fold more likely to be ovarian cancer cases compared to subjects in the left most classes (OR=9.87, 95% CI [4.63, 21.10]), controlling for age. Additionally, the predicted methylation classes in the ovarian cancer data demonstrated remarkably high sensitivity and specificity for predicting ovarian cancer case/control status (AUC=0.83 95% CI [0.77, 0.89]), which increased to AUC=0.86 95% CI [0.81, 0.92] with age included in the model (FIG. 25B).

Figure 26B:
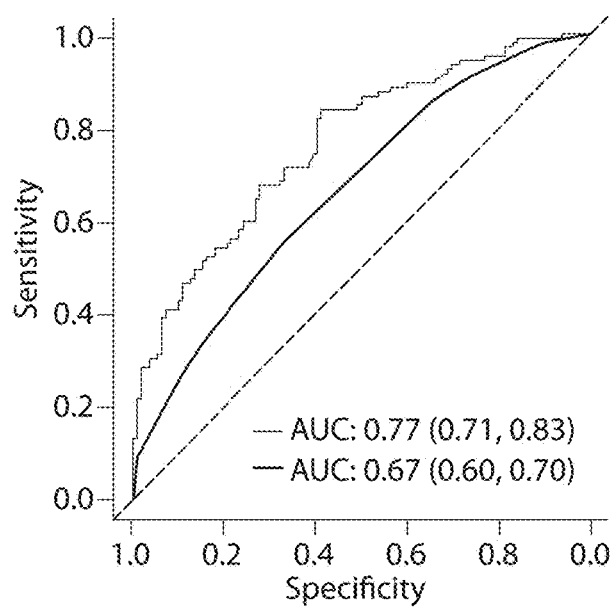

In the bladder cancer data, subjects in the right most classes were nearly twice as likely to be bladder cancer cases compared to subjects in the left most (OR=1.94 95% CI [0.95, 3.98], adjusted for age, gender, smoking and family history of bladder cancer). The clinical utility of the predicted methylation classes in the bladder cancer data was lower than that observed for HNSCC and ovarian cancer (bladder AUC=0.67 95% CI [0.60, 0.73] and adjusted AUC=0.77 95% CI [0.71, 0.83] with age, gender, smoking, and family history in the model) (FIG. 26B).

Figure 27A:
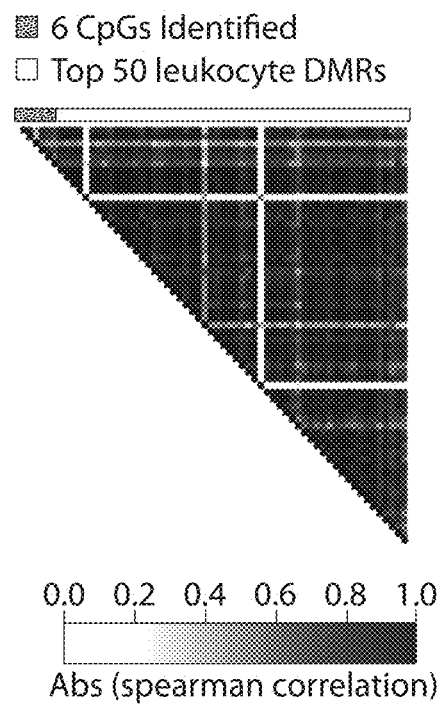
FIG. 27A-C are graphical representations showing image plots representing the pairwise spearman correlation coefficients.
Figure 27B:
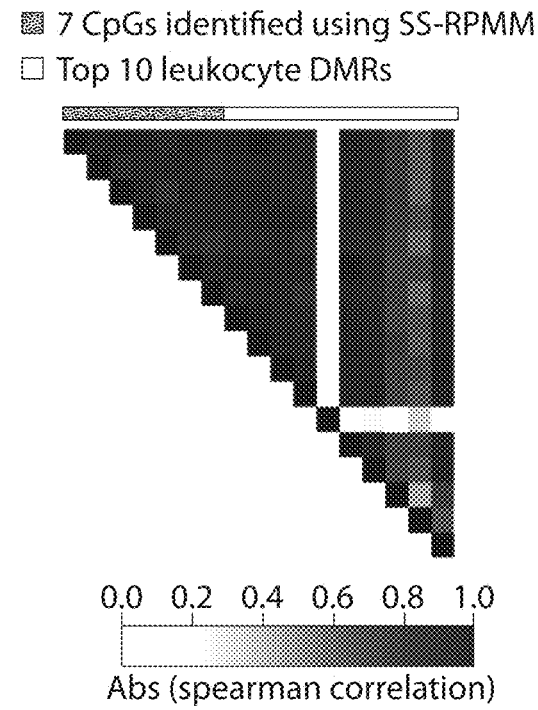
Figure 27C:
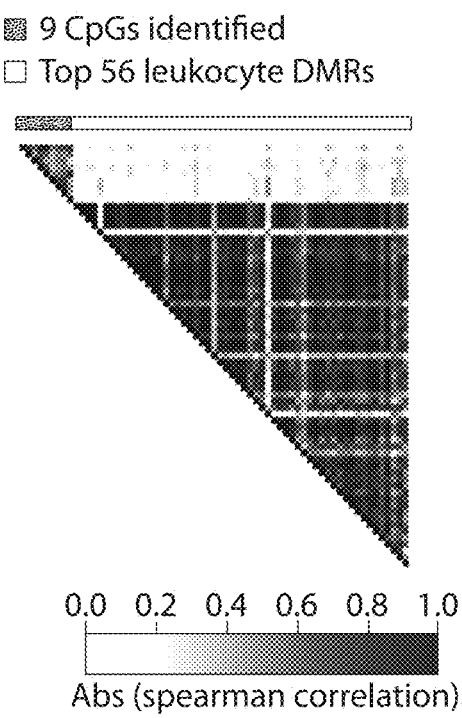

Utilizing leukocyte-derived DMRs to differentiate cases and controls resulted in methylation profiles that were consistent, and in the case of HNSCC and ovarian tumors, considerably better in terms of their prediction performance compared to previously published results using the same data sets (Teschendorff A E et al., 2009, PLoS One 4:e8274; Marsit C J et al., 2011, J Clin Oncol 29:1133-1139; Langevin S M et al., Epigenetics. 2012 March; 7(3):291-9). For the HNSCC and ovarian data sets there was a high degree of correlation in the methylation status of leukocyte DMRs and CpG loci identified by previous analytic strategies (Langevin S M et al., Epigenetics. 2012 March; 7(3):291-9; mean absolute spearman correlations=0.68 and 0.75, respectively; FIG. 27A and FIG. 27B). In contrast, the highest ranking 56 DMRs in the bladder data set were found to be less correlated with the CpG loci used to form the methylation classes in a previous study using the same data set (mean absolute spearman correlation=0.11; FIG. 27C).

TABLE 21

The highest ranking 50 differentially methylated regions (DMRs) among the leukocyte subtypes (false discovery rate q-values < 0.001 for all)

| CpG Name | Chromosome | Gene Name | F-statistic |
| --- | --- | --- | --- |
| cg03801286 | 21 | KCNE1 | 373.63 |
| cg25634666 | 11 | FOLR3 | 369.50 |
| cg24777950 | 14 | CTSG | 350.66 |
| cg17356733 | 21 | IFNGR2 | 291.97 |
| cg02497428 | 16 | IGSF6 | 291.35 |
| cg24211388 | 6 | AIF1 | 285.92 |
| cg03330678 | 17 | 9-Sep | 284.79 |
| cg00546897 | 21 | LOC284837 | 279.64 |
| cg24841244 | 11 | CD3D | 271.62 |
| cg11283860 | 1 | SLC45A1 | 271.09 |
| cg27485921 | 2 | ATP6V1E2 | 267.19 |
| cg00974864 | 1 | FCGR3B | 260.62 |
| cg07730301 | 11 | ALDH3B1 | 252.52 |
| cg07728874 | 11 | CD3D | 250.67 |
| cg17496921 | 19 | TSPAN16 | 246.58 |
| cg26661623 | 17 | ASGR2 | 242.83 |
| cg18920397 | 1 | LY9 | 238.64 |
| cg27461196 | 19 | FXYD1 | 236.64 |
| cg20720686 | 7 | POR | 232.23 |
| cg09303642 | 12 | NFE2 | 231.34 |
| cg23140706 | 12 | NFE2 | 224.95 |
| cg08458487 | 10 | SFTPD | 217.67 |
| cg20748065 | 7 | POR | 217.63 |
| cg18589858 | 11 | SLCO2B1 | 217.14 |
| cg10287137 | 11 | P2RY2 | 215.31 |
| cg25587233 | 9 | PPP2R4 | 207.25 |
| cg08044694 | 19 | BRD4 | 202.50 |
| cg18084554 | 19 | ARID3A | 198.61 |
| cg13650156 | 7 | PILRA | 197.87 |
| cg18854666 | 2 | SLC11A1 | 197.42 |
| cg17173423 | 11 | MS4A3 | 195.50 |
| cg22242539 | 17 | SERPINF1 | 194.11 |
| cg02780988 | 17 | KRTHA6 | 193.25 |
| cg10266490 | 1 | ACOT11 | 192.62 |
| cg27606341 | 5 | FYB | 191.23 |
| cg15512851 | 6 | FGD2 | 185.34 |
| cg20070090 | 1 | S100A8 | 183.43 |
| cg11058932 | 7 | TSGA13 | 183.31 |
| cg13500819 | 5 | PACAP | 182.82 |
| cg15880738 | 11 | CD3G | 182.73 |
| cg07285167 | 1 | CSF3R | 182.16 |
| cg09868035 | 20 | C20orf135 | 179.56 |
| cg01980222 | 6 | TREM2 | 178.94 |
| cg21019522 | 11 | SLC22A18 | 176.20 |
| cg16097772 | 12 | LYZ | 172.89 |
| cg21969640 | 12 | GPR84 | 172.51 |
| cg12971694 | 9 | CD72 | 172.43 |
| cg22224704 | 11 | GSTP1 | 172.40 |
| cg07239938 | 19 | ELA2 | 170.70 |
| cg02240622 | 15 | PLCB2 | 169.99 |

TABLE 22

Methylation differences between cancer cases and controls for the eight overlapping differentially methylated leukocyte DMRs. Mean delta-beta refers to the difference in mean methylation between cancer cases and controls (i.e. βcases − βcontrols).

| Gene Locus | Mean delta-beta (95% CI) | | |
|---|---|---|---|
| | HNSCC | Ovarian | Bladder |
| C20orf135 | −0.05 (−0.07, −0.03) | −0.06 (−0.08, −0.05) | 0.02 (0.0, 0.04) |
| PACAP | 0.02 (0.00, 0.04) | 0.04 (0.02, 0.05) | 0.02 (0.0, 0.04) |
| FGD2 | −0.05 (−0.07, −0.03) | −0.06 (−0.07, −0.04) | 0.02 (0.01, 0.04) |
| SLC22A18 | −0.05 (−0.07, −0.04) | −0.05 (−0.06, −0.04) | 0.02 (0.01, 0.04) |
| GSTP1 | −0.05 (−0.07, −0.04) | −0.06 (−0.07, −0.05) | 0.02 (0.01, 0.04) |
| NFE2 | −0.04 (−0.05, −0.03) | −0.04 (−0.05, −0.03) | 0.02 (0.0, 0.03) |
| ASGR2 | −0.06 (−0.08, −0.04) | −0.05 (−0.07, −0.04) | 0.02 (0.01, 0.04) |
| SLC11A1 | −0.05 (−0.07, −0.04) | −0.05 (−0.04, −0.06) | 0.02 (0.0, 0.04) |

Example 26

Statistical Analysis of Methylation Differences in Leukocyte DMRs Between Cancer Cases and Cancer-Free Controls for Determining Epigenetic Signatures Specific to Each Group Linear mixed-effects models were used to assess differences in methylation across the leukocyte subtypes, modeling arcsine square-root transformed methylation as the response1, leukocyte subtype as a fixed effect covariate, and a random effect term for plate/BeadChip. False discovery rate (fdr) estimation was used to control for the large number of comparisons and putative leukocyte DMRs were defined as those with fdr q-value <0.05. Leukocyte DMRs were then ranked based on their strength of association using the F-statistics that resulted from the respective linear mixed-effects models.

Methylation differences among the highest ranking 50 leukocyte DMRs were examined between cancer cases and cancer-free controls using a series of unconditional logistic regression models that were adjusted using available and relevant covariate information. A leukocyte DMR was considered differentially methylated if the nominal p-value from the unconditional logistic regression model was less than 0.05. Permutation tests were then applied to each of the three data sets to determine if the number of differentially methylated leukocyte DMRs was significantly greater than expected by chance. Specifically, samples were randomly permuted (same permutation across the highest ranking 50 DMRs) and an unconditional logistic regression model was fit to the resampled data. For each data set 1000 permutations were considered to generate a null distribution of the number of differentially methylated leukocyte DMRs. Permutation p-values were then obtained by comparing the observed number of differentially methylated leukocyte DMRs to the respective null distribution.

The leukocyte DMR profile analysis involved splitting the full cancer data sets into equally sized training and testing sets (FIGS. 29-32). Samples in the training set were clustered using the highest ranking M leukocyte DMRs, where M was determined from the total pool of putative DMRs using the previously described cross-validation procedure (Sincic N and Herceg Z, 2011, Curr Opin Oncol 23:69-76). Clustering analysis was achieved using the Recursively Partitioned Mixture Model3 (RPMM), a hierarchical model-based method for clustering that has been extensively used for the clustering of array-based methylation data (Cui H M, 2007, Dis Markers 23:105-112; Wilhelm-Benartzi C S et al., 2010, Carcinogenesis 31:1972-1976; Schwartzman J et al., 2011, Epigenetics 6:1248-1256, 2011). Based on the RPMM fit to the training data, a naive Bayes classifier was used to predict methylation class membership for the observations in the independent testing set. Associations between predicted methylation class and cancer case/control status were assessed using permutation $\chi^2$ tests and unconditional logistic regression models adjusted for available and relevant confounders. The clinical utility of the identified methylation classes were investigated using receiver operating characteristic (ROC) curves and the corresponding area under the curve (AUC).

Pairwise spearman correlation coefficients were computed between the highest ranking M leukocyte DMRs and the CpG loci identified from the corresponding semi-supervised RPMM2 (SS-RPMM) analysis of the HNSCC, ovarian, and bladder cancer data sets. A diagram illustrating the analytic framework for SS-RPMM is provided in FIG. 32. Briefly SS-RPMM is a statistical methodology for identifying classes of methylation that are associated with a phenotype of interest and has been successfully applied in several of settings (Christensen B C et al., 2009, Cancer Res 69:227-234; Marsit C J et al., 2006, Cancer Res 66:10621-10629, 2006).

Figure 33A:
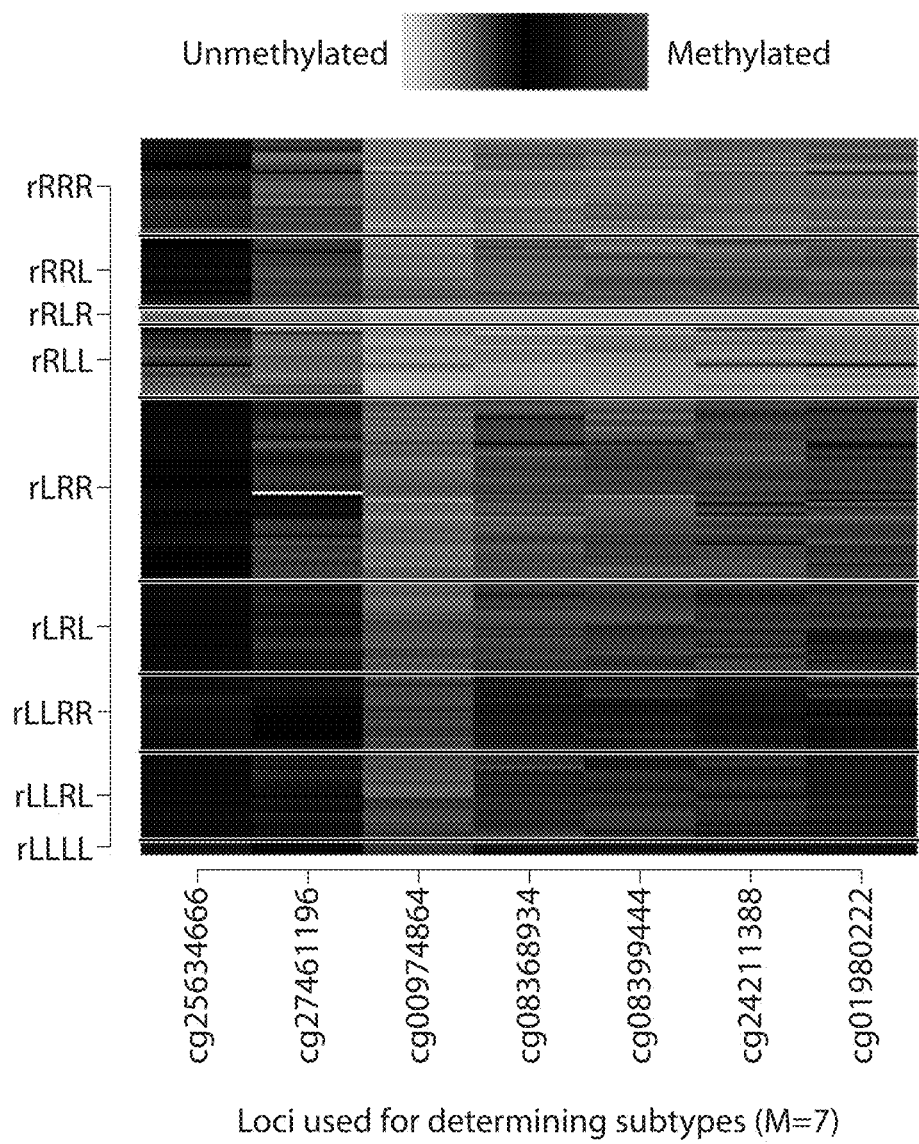
FIG. 33A-D show results obtained from SS-RPMM analysis (see FIG. 30) of the ovarian cancer data set for determination of methylation class membership.
Figure 33B:
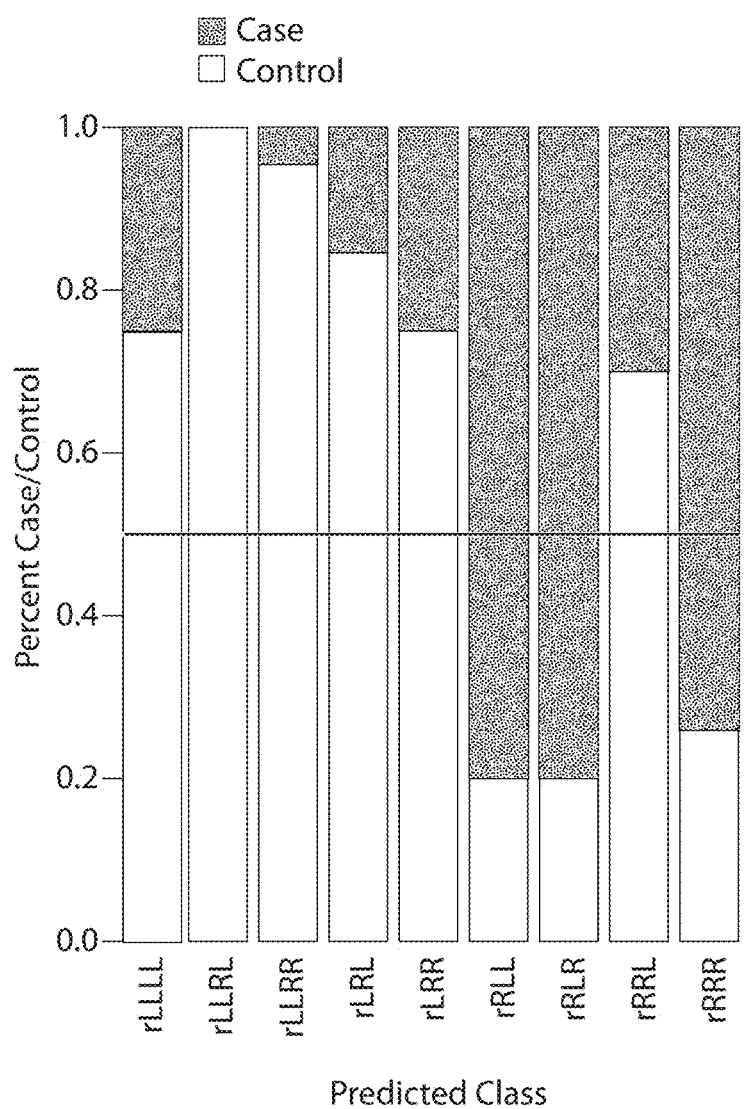
Figures 33C, 33D:
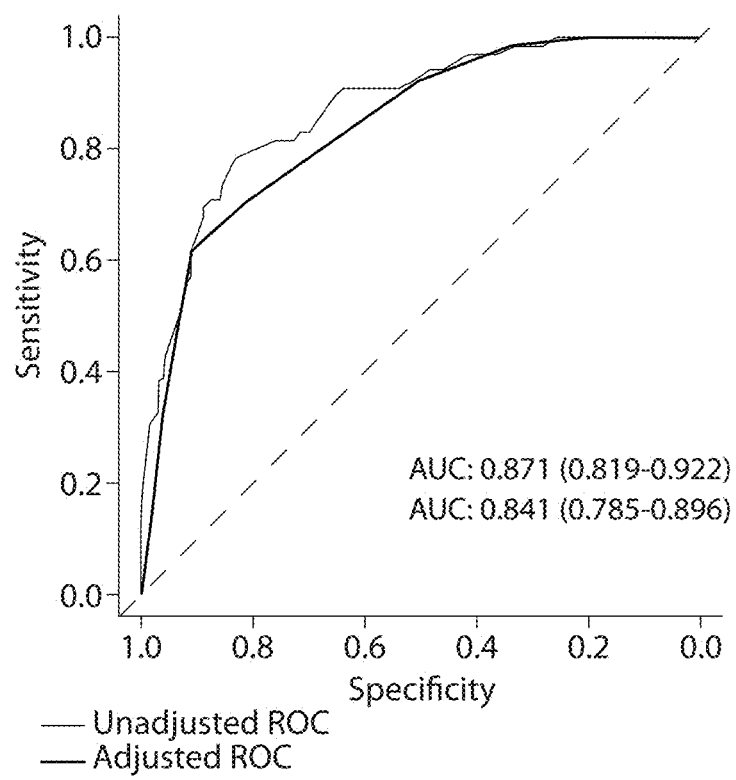

The same training and testing sets were used for the HNSCC and bladder cancer data sets as were used in the references Langevin S M et al., Epigenetics. 2012 March; 7(3):291-9 and Christensen B C et al., 2009, Cancer Res 69:227-234, to compare the results of the present analysis to previously published results, and to provide additional insight with respect to the findings of those studies. The ovarian cancer data set was also analyzed using SS-RPMM strategy described in Langevin S M et al., Epigenetics. 2012 March; 7(3):291-9 and Christensen B C et al., 2009, Cancer Res 69:227-234, and the results are shown in FIG. 33. Following the logic above, the training sets used for the SS-RPMM analysis were applied to the leukocyte DMR profile analysis of the ovarian data.

Analyses were carried out using the R statistical package, R project for statistical computing, version 2.13 R available for downloading from the internet.

Example 27

Methylation Analysis by DNA Methylation Microarray for NK Cell Specific DMR

Normal human peripheral blood leukocytes were isolated by magnetic activated cell sorting (MACS; Miltenyi Biotec Inc., Auburn, Calif.) and purity was confirmed by fluorescence activated cell sorting (FACS). The major cell types obtained included NK cells (n=9), B cells (n=5), T cells (n=16), monocytes (n=5), and granulocytes (n=8). DNA and RNA were co-extracted from MACS sorted leukocytes using AllPrep DNA/RNA mini kit (Qiagen Inc., Valencia, Calif.). DNA from archived blood was extracted with DNeasy Blood & Tissue kit (Qiagen Inc., Valencia, Calif.). DNA was treated with sodium bisulfite according to the EZ DNA Methylation Kit (Zymo Research Corporation, Irvine, Calif.).

Methylation analysis was performed using The Infinium® HumanMethylation27 Beadchip Microarray (Illumina Inc., San Diego, Calif.), which quantifies the methylation status of 27,578 CpG loci from 14,495 genes, with a redundancy of 15-18 fold. The ratio of fluorescent signals was computed from both alleles using the following equation: $\beta=(\max(M, 0))/(|U|+|M|)+100$. The resultant β-value is a continuous variable ranging from 0 (unmethylated) to 1 (completely methylated) that represents the methylation at each CpG site and is used in subsequent statistical analyses. Data were assembled with the methylation module of GenomeStudio software (Illumina, Inc., San Diego, Calif.; Bibikova M et al., 2009, Epigenomics 2009; 1:177-200)

Example 28

Validation of DNA Methylation Microarray Results for Identifying NK Cell-Specific DMRs by Pyrosequencing Pyrosequencing assays to validate microarray results were designed using Pyromark Assay Design 2.0 (Qiagen Inc., Valencia, Calif.), and carried out on a Pyromark MD pyrosequencer running Pyromark qCpG 1.1.11 software (Qiagen Inc., Valencia, Calif.). Oligonucleotide primers were obtained from Life Technologies™ (Grand Island, N.Y.).

Example 29

Protein Expression Analysis by mRNA Expression Array for Identifying NK Cell-Specific DMRs The Whole-Genome DASL HT Assay Kit (Illumina Inc., San Diego, Calif.) was used to obtain simultaneous profiles of more than 29,000 mRNA transcripts. Data were assembled with the expression module of GenomeStudio software (Illumina Inc., San Diego, Calif.). The mRNA expression array data was used in combination with DNA methylation array data to identify NK cell-specific DNA methylation.

Example 30

Methylation Specific Quantitative Polymerase Chain Reaction (MS-qPCR) Analysis for Quantification of NKp46 Demethylation Primers and TaqMan major groove binding (MGB) probes (Table 23) with 5' 6-FAM (6-Carboxyfluorescein) and 3' non-fluorescent quencher (NFQ) as well as TaqMan® 1000 RXN Gold with Buffer A Pack were obtained from Life Technologies™ (Grand Island, N.Y.). MS-qPCR was performed using solutions and conditions according to Campan M et al., 2009, Methods Mol Biol, 507:325-37 with the following modifications. A solution of 10×TaqMan® Stabilizer containing 0.1% Tween-20, 0.5% gelatin was prepared weekly. Each reaction of 20 μl contained 5 μl DNA, 11.9 μl preMix, 3 μl oligoMix, and 0.1 μl Taq DNA polymerase. Cycling was performed using a 7900HT Fast Real-Time PCR System (Applied Biosystems, Foster City, Calif.); 50 cycles at 95° C. for 15 sec and 60° C. for 1 min after 10 min at 95° C. preheat. Samples were run in triplicate using the absolute quantification method.

TABLE 23

MS-qPCR oligonucleotide sequences

| Oligonucleotide name | Sequence |
|---|---|
| NKp46 forward primer | ATTAGGTTGGTAGAATTTGAGT (SEQ ID NO: 116) |
| NKp46 reverse primer | CCCATTCCCCTTCCACA (SEQ ID NO: 117) |
| NKp46 probe | (6FAM) CTCACCAACACAAAACAA (MGB, NFQ) (SEQ ID NO: 118) |
| C-less forward primer | TTGTATGTATGTGAGTGTGGGAGAGA (SEQ ID NO: 97) |
| C-less reverse primer | TTTCTTCCACCCCTTCTCTTCC (SEQ ID NO: 98) |
| C-less probe | (6FAM) CTCCCCCTCTAACTCTAT (MGB, NFQ) (SEQ ID NO: 99) |

MGB: major groove binding
FAM: 6-Carboxyfluorescein
NGQ: NFQ
C-less qPCR assay: Campan M et al., 2009, Methods Mol Biol, 507: 325-37; Weisenberger DJ et al., 2008, Nucleic Acids Res 2008; 36: 4689-98

Quantification of total bisulfite converted DNA copies was performed by reference to the C-less qPCR assay (Campan M et al., 2009, Methods Mol Biol, 507:325-37; Weisenberger D J et al., 2008, Nucleic Acids Res 2008; 36:4689-98). C-less primers and probes recognize a DNA sequence without cytosines; hence, the assay amplifies the total amount of DNA in a PCR reaction regardless of bisulfite conversion or methylation status. A conversion factor was used for a diploid human cell, which is 6.6 picograms (pg) of DNA (3.3 pg per copy) to calculate copy number.

Normal human blood DNA quantified by UV absorption (Nanodrop, Inc) was used to generate a four point standard curve with 30,000 copies, 3,000 copies, 300 copies and 30 copies of genomic DNA. This standard curve was included on each sample plate to obtain quantification of DNA from Ct values. Since C-less primers hybridize to both strands of the standard DNA (non-bisulfite converted) and since bisulfite converted samples hybridize to a single strand during the first cycle, the resultant copy number obtained from bisulfite treated samples was multiplied by two. Bisulfite converted, universal methylated DNA standard (Zymo Research Corporation, Valencia, Calif.) and bisulfite converted, isolated NK cell DNA were quantified at the same time using the C-less assay. Resultant copy number measurements were used to prepare a calibration curve for the NKp46 demethylation assay. NK cell DNA in known copy numbers was spiked into universal methylated DNA in ratios that maintained a constant total number of DNA copies (10,000 copies) in each reaction across the dilution scheme. This mimics conditions for detecting different relative numbers of NK cells within a complex mixture of cells in a biological sample. For absolute quantification of NKp46 demethylation, the four-point standard curve used 10,000 copies, 1,000 copies, 100 copies, and 10 copies of bisulfite converted NK cell DNA.

Example 31

Statistical Modeling of the DNA Methylation Microarray Data for Estimation of Differential Methylation A linear mixed effects model was applied to the Illumina Infinium® HumanMethylation27 data using SAS (SAS Institute Inc., Cary, N.C.). Cell type was designated as the fixed effect and beadchip plate was the random effect. For this example, the fixed effect groups were NK cells and non-NK cells, which included pan T lymphocytes, CD4+ T-lymphocytes, Tregs, CD8+ T-lymphocytes, B-lymphocytes, granulocytes and monocytes. Coefficients were generated that estimated differential methylation were generated such that, for any particular locus, a negative coefficient indicated less methylation in NK cells than in the other cell types. Resultant p-values were adjusted for multiple comparisons using the "qvalue" package in the software, the R project for statistical computing available for downloading from the internet.

Example 32

Statistical Modeling of the RNA Expression Array for Estimation of Differential RNA Expression Linear models were applied to the Illumina Whole-Genome DASL HT using the "limma" package in the software, the R project for statistical computing. RNA expression for MACS isolated NK cells was compared to each of the following MACS isolated leukocytes: pan T-lymphocytes, CD4+ T-lymphocytes, Tregs, CD8+ T-lymphocytes, B lymphocytes, granulocytes and monocytes. Thus, estimates were obtained for log-fold changes in RNA expression between NK cells and each of the aforementioned cell types, in which a positive value indicated higher RNA expression in NK cells compared to a particular cell type. Resultant p values were adjusted for multiple comparisons using the "qvalue" package in R project for statistical computing. NK cell specific differential RNA expression was considered significant only if the seven q-values were each less than 0.1.

Example 33

Statistical Analysis of the (MS-qPCR) Data

Statistical analyses were carried out in R project for statistical computing. A generalized linear model analysis and F-test were performed to determine log linear PCR kinetics for the NK cell standard curve. To test for univariate associations between continuous NKp46 demethylation measurements and discrete variables, Wilcoxon rank sum tests (for dichotomous variables, such as case status) and Kruskal-Wallis one-way analysis of variance tests were employed. To test for univariate associations between continuous NKp46 demethylation and other continuous variables linear regression analysis, calculation of Pearson product-moment correlations and F-tests were performed. A chi-squared test for trends in proportions was applied to identify trends in HNSCC prevalence by control-determined demethylation tertiles. Multivariate logistic regression analyses were performed using the "glm" function with family set to binary.

Example 34

NKp46 Demethylation is a Biomarker of NK Cells

Figure 34:
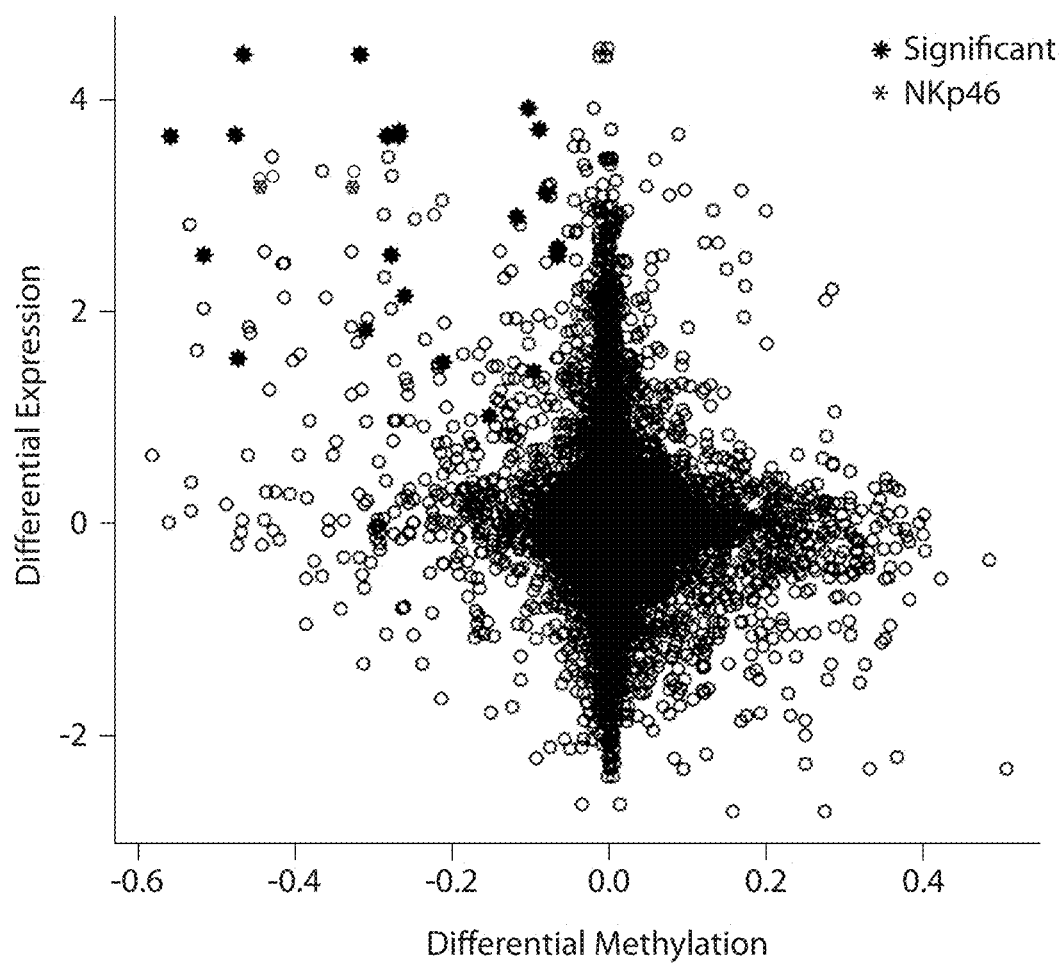
FIG. 34 is a graphical representation showing loci in the gene NKp46 chosen from candidate NK cell-specific differential DNA methylation markers, selected by DNA methylation and mRNA expression criteria.

Analysis of DNA methylation and RNA expression microarray data from MACS isolated (FACS validated) normal human leukocytes were integrated to identify putative, NK cell-specific DMRs that could potentially serve as reliable biomarkers of the cell type. The list of candidate gene regions was narrowed to CpG loci that were significantly demethylated in NK cells (q<0.1, coefficient <0) and that were located within genes whose RNA expression was significantly elevated in NK cells (q<0.1, log fold-change>1). These candidates are marked as darkened asterisks in the top left quadrant of FIG. 34. Pyrosequencing and MS-qPCR of bisulfite converted DNA from the MACS isolated leukocytes confirmed that a region near the promoter of NKp46 is demethylated in NK cells, and is methylated in T cells, B cells, granulocytes, and monocytes (FIGS. 35 and 38). Furthermore, the $CD56^{dim}$ subset of NK cells showed complete demethylation in the NKp46 region, whereas $CD56^{bright}$ NK cells exhibited only partial demethylation in the region as measured by MS-qPCR. The NKp46 MS-qPCR assay was optimized to fit a log-linear relationship between lower Ct values (more demethylated copies of NKp46) and increased NK cell DNA content (Pearson R=−0.996, $p<2.2. \times 10^{16}$; FIG. 36).

Example 35

Samples from HNSCC Patients have Diminished Circulating NK Cells

The calibrated NKp46 MS-qPCR assay was used to measure the level of circulating NK cells in the peripheral blood of patients with HNSCC and cancer free controls. The demographics of the study population are shown in Table 24.

Univariate analysis revealed that significantly fewer demethylated copies of NKp46 were detected in HNSCC blood than in control blood (p<0.0001, FIG. 39), indicative of a diminished NK cell compartment in the peripheral blood of HNSCC patients. There was no significant univariate association observed between the measured number of demethylated NKp46 copies and age, gender, HPV16 (E6 and/or E7) serology, cigarette smoking, alcohol consumption, or body mass index. There was no significant difference in the number of demethylated NKp46 copies detected in patients with oral, pharyngeal, and laryngeal tumors.

To determine whether the observed association between NK cells and case status was attributable to systemic chemotherapy or other treatments, the number of demethylated NKp46 copies detected in case blood samples drawn within one month of diagnosis was compared to those drawn more than one month after diagnosis, and no significant difference was observed.

TABLE 24

| Characteristic | Total (N = 244) | Controls (n = 122) | HNSCC (n = 122) | Oral (n = 43) | Pharyngeal (n = 53) | Laryngeal (n = 26) |
|---|---|---|---|---|---|---|
| Demographic characteristics | | | | | | |
| Age | | | | | | |
| Mean (SD) | 61 (12) | 62 (12) | 61 (12) | 60 (15) | 60 (10) | 64 (9.5) |
| Median (Range) | 60 (29-87) | 60 (31-87) | 60 (29-86) | 59 (29-86) | 60 (41-86) | 64 (50-83) |
| Gender | | | | | | |
| Male, No. (%) | 178 (73%) | 89 (73%) | 89 (73%) | 27 (63%) | 41 (77%) | 21 (81%) |
| Female, No. (%) | 66 (27%) | 33 (27%) | 33 (27%) | 16 (37%) | 12 (23%) | 5 (19%) |
| HPV 16 Serology | | | | | | |
| L1+, No.(%) | 33 (14%) | 4 (3%) | 29 (24%) | 6 (14%) | 22 (42%) | 1 (4%) |
| E6+, No.(%) | 41 (17%) | 4 (3%) | 37 (30%) | 2 (5%) | 32 (60%) | 3 (12%) |
| E7+, No.(%) | 28 (11%) | 2 (2%) | 26 (21%) | 1 (2%) | 23 (43%) | 2 (8%) |
| E6+ and E7+, No. (%) | 25 (10%) | 0 (0%) | 25 (20%) | 0 (0%) | 23 (43%) | 2 (8%) |
| E6+ or E7+, No. (%) | 44 (18%) | 6 (5%) | 38 (31%) | 3 (7%) | 32 (60%) | 3 (12%) |
| Cigarette Smoking Status | | | | | | |
| Never, No. (%) | 65 (27%) | 41 (34%) | 24 (20%) | 11 (26%) | 11 (21%) | 2 (8%) |
| Former, No. (%) | 149 (61%) | 66 (54%) | 83 (68%) | 29 (67%) | 35 (66%) | 19 (73%) |
| Current, No. (%) | 30 (12%) | 15 (12%) | 15 (12%) | 3 (7%) | 7 (13%) | 5 (19%) |
| Cigarette Pack-Years | | | | | | |
| Mean (SD) | 26 (29) | 17 (23) | 35 (32) | 26 (27) | 36 (35) | 45 (30) |
| Median (Range) | 16 (0-116) | 7 (0-114) | 31 (0-116) | 20 (0-105) | 33 (0-116) | 45 (0-96) |
| Alcohol Drinks per Week | | | | | | |
| Mean (SD) | 18 (26) | 15 (27) | 21 (24) | 18 (23) | 22 (25) | 23 (25) |
| Median (Range) | 7 (0-199) | 6 (0-199) | 14 (0-155) | 7 (0-90) | 18 (0-155) | 19 (0-113) |

The NKp46 MS-qPCR measurements from cancer-free control blood samples were used to determine suitable cutoffs for NKp46 demethylation tertiles. The proportion of total HNSCC cases decreased significantly with increasing demethylation tertile (p>0.001, FIG. 37), indicating that HNSCC patients are more likely to have depressed levels of NK cells in their peripheral blood. The trend held true independent of the case stratification by HPV16 (E6 and/or E7) serology, or time of blood drawing within a month of diagnosis or earlier. Multivariate logistic regression controlling for age, gender, cigarette smoking, alcohol consumption, BMI, and HPV16 (E6 and/or E7) serology confirmed increased HNSCC risk for individuals in the lower two normal NKp46 demethylation tertiles (Table 25), strongly indicating that lower levels of NK cells in the peripheral blood are significantly associated with HNSCC.

TABLE 25

Logistic regression of HNSCC risk

| NKp46 demethylation tertile | Crude | | Adjusted* | |
|---|---|---|---|---|
| | OR (95% CI) | p-value | OR (95% CI) | p-value |
| 1st (lowest) | 4.3 (2.2, 9.0) | $5.0 \times 10^{-5}$ | 5.6 (2.0, 17.4) | 0.002 |
| 2nd (middle) | 2.8 (1.4, 6.0) | 0.006 | 4.9 (1.8, 16.1) | 0.004 |
| 3rd (highest) | Reference | | Reference | |

*Unconditional multivariate model controlling for age, gender, smoking, drinking, BMI and HPV16 (E6 and/or E7) serology Example 36

Application of the Methodology to mRNA Data

The statistical methods described herein for determining changes the distribution of white blood cells among different subpopulations are applicable to mRNA expression profiles with the following considerations. A mathematical consideration is that mRNA is typically analyzed on a logarithmic scale, yet the assumptions of the methods herein involve linearity on an arithmetic scale, since the mixing coefficients are assumed to act linearly on absolute numbers of nucleic acid molecules; thus, the proposed methods would require analysis of untransformed fluorescence intensities, for which skewed distributions would result in numerical instabilities. A biological consideration is absence of a linear relationship between cell number and mRNA copies, since proteins may be translated as a consequence of an initial burst of mRNA transcription upon cellular development, followed by significant mRNA degradation. In contrast, one would expect the average beta value provided by Illumina bead-array products, as well as similarly constructed quantities from other platforms to scale in proportion to the actual fraction of methylated nucleic acids with a biologically reasonable assumption of two DNA molecules per cell.

An example of an application of methods herein is shown using mRNA data. The validation data set $S_0$ was obtained from Watkins N A et al., 2009, Blood 113: e1-e9, in which the Illumina Human-6 v2 Expression BeadChip was used to characterize the mRNA expression profile of eight types of blood cells: B cells, granulocytes, erythroblasts, megakaryocytes, monocytes, natural killer cells, CD4+ T cells, and CD8+ T cells. For this analysis erythroblasts (nucleated progenitors of red blood cells) and megakaryocytes (progenitors of platelets) were removed. The target data set $S_1$ was obtained from Showe M K et al., 2009, Cancer Res 69: 9202-10, in which the same mRNA expression platform was used to characterize expression differences in isolated mononuclear cells between nonsmall cell lung cancer (NSCLC) cases and controls having non-cancer lung disease, adjusting for age, sex and smoking. In addition, data was presented from 18 matched case samples, pre- and post-operative.

The same methodology was used as for the DNA methylation data sets herein, ordering the 46,693 transcripts by F statistic according to their ability to distinguish six types of leukocytes. Of the 100 transcripts having the largest F statistics it was observed that 86 overlapped with the transcripts in Showe M K et al., 2009, Cancer Res 69: 9202-10. Thus the remainder of the analysis was carried out using the 86 overlapping loci. In the analyses, untransformed data (i.e. using either the normalized fluorescence intensities or 2 raised to the power of the normalized $\log_2$ intensities) were used. Application of the constrained projection in Examples 1 and 5 resulted in an average percentage estimates consistent with mononuclear cells (i.e. a subfraction with most granulocytes removed): 3.3% B cell, 3.4% granulocyte, 18.1% monocyte, 29.5% NK cell, 11.6 CD4+ T cell, and 2.2% CD8+ T cell.

Table 26 presents results from 137 NSCLC cases and 91 controls, adjusted for age, sex, and smoking status. Table 27 presents results from 18 matched pre-operative and post-operative samples from NSCLC cases, where the analyzed outcome was the difference in untransformed expression (post-operative expression minus pre-operative expression), and coefficients displayed correspond to the intercept of $B_1$ (analogous to a paired t-test). Perturbations in T cell distribution were consistent with known immunological changes resulting from NSCLC (Ginns L C et al., 1982, Am Rev Respir Dis 23: 265-9; Mazzoccoli G et al., 1999, In Vivo 13: 205-9), as well as with age and smoking. The perturbations and coefficient signs were reasonable; the magnitudes were potentially biased. For example, the estimates corresponding to granulocyte distribution were much larger than expected given the relatively small number of granulocytes present in a mononuclear subfraction. Thus, the methods herein were determined to be suitable for application to mRNA data sets.

TABLE 26

White blood cell distribution comparing cases to controls in NSCLC mRNA data set

| | Est | $SE_2$ | p-value |
|---|---|---|---|
| Case Status | | | |
| B Cell | 0.8 | 4.15 | 0.8511 |
| Granulocyte | −34.6 | 9.48 | 0.0003 |
| Monocyte | 17.9 | 9.58 | 0.0613 |
| NK | 1.3 | 5.18 | 0.8095 |
| T Cell (CD4+) | 24.9 | 9.01 | 0.0057 |
| T Cell (CD8+) | −15.2 | 9.03 | 0.0931 |
| Age (decades) | | | |
| B Cell | −0.7 | 1.36 | 0.5824 |
| Granulocyte | −7.9 | 3.45 | 0.0218 |
| Monocyte | −6.5 | 2.76 | 0.0180 |
| NK | −4.0 | 1.80 | 0.0255 |
| T Cell (cd4+) | 13.0 | 2.89 | 0.0000 |
| T Cell (CD8+) | 8.3 | 2.96 | 0.0052 |
| Sex (male) | | | |
| B Cell | 0.1 | 2.66 | 0.9827 |
| Granulocyte | −34.8 | 6.41 | 0.0000 |
| Monocyte | 6.8 | 5.44 | 0.2091 |
| NK | −7.8 | 3.32 | 0.0193 |
| T Cell (CD4+) | 21.1 | 5.39 | 0.0001 |
| T Cell (CD8+) | 13.2 | 5.76 | 0.0223 |
| Former Smoker | | | |
| B Cell | 1.6 | 3.97 | 0.6821 |
| Granulocyte | 17.2 | 8.25 | 0.0375 |
| Monocyte | 6.1 | 7.84 | 0.4368 |
| NK | 2.7 | 5.19 | 0.6103 |
| T Cell (CD4+) | −11.3 | 8.02 | 0.1578 |
| T Cell (CD8+) | −20.3 | 8.28 | 0.0141 |
| Current Smoker | | | |
| B Cell | 3.4 | 5.21 | 0.5183 |
| Granulocyte | 31.6 | 11.26 | 0.0049 |
| Monocyte | 17.8 | 10.49 | 0.0907 |
| NK | 5.4 | 6.93 | 0.4373 |
| T Cell (CD4+) | −21.8 | 10.25 | 0.0337 |
| T Cell (CD8+) | −41.2 | 11.10 | 0.0002 |

Est = Regression coefficient estimate (×100%)
$SE_2$ = Double-bootstrap standard error (×100%).

TABLE 27

White blood cell distribution comparing matched pre-operative and post-operative cases in NSCLC mRNA data set

| | Est | $SE_2$ | p-value |
|---|---|---|---|
| B Cell | −10.7 | 5.55 | 0.0543 |
| Granulocyte | −19.4 | 11.16 | 0.0826 |
| Monocyte | −13.4 | 10.43 | 0.1987 |
| NK | 6.3 | 7.15 | 0.3794 |
| T Cell (CD4+) | −11.3 | 10.57 | 0.2859 |
| T Cell (CD8+) | 48.8 | 11.33 | 0.0000 |

Est = Regression coefficient estimate (×100%)
$SE_2$ = Double-bootstrap standard error (×100%).

Example 37

An Array for High-Throughput DNA Methylation Analysis

An array for performing DNA methylation analysis in a high-throughput manner was made using VeraCode microbeads (Illumina, San Diego, Calif. USA) and DNA sequences of regions in 96 different genes, each sequence having one CpG dinucleotide shown within square brackets (FIG. 40) and used to determine methylation status of the gene. Veracode beads are cylindrical glass microbeads 240 microns in length by 28 microns in diameter with a surface suitable for attaching DNA, RNA, protein, antibody and other ligands for performing bioassays. For performing DNA methylation analysis various CpG specific DNA oligomers were attached to these beads. Each microbead is inscribed with a high-density holographic code (24-bit), allowing development of very large numbers of bead types. When a laser is shone at the high density codes of the beads they emit a signal specific to the code and the signal is detected by a CCD camera. The fluorescence of the bead indicates whether the particular CpG site carried by the bead is demethylated. The result is compared with the fluorescence readout obtained from DNA from a purified leukocyte sample. A VeraCode array is a collection of beads, each carrying a DNA oligomer specific for either the methylated or the unmethylated form of a particular CpG locus, distributed into different wells of a micro titer plate. A user selects the entirety or a subset of nucleotide sequences containing CpG sites in a gene or genes of interest for attaching to VeraCode beads to have a custom designed VeraCode array particularly advantageous for the user's analysis.

To ascertain which 96 CpGs would give optimal precision for the white blood cell (WBC) types the following procedure was followed. The Infinium HumanMethylation 27K data corresponding to the Magnetic activated cell sorting (MACS sorted leukocyte DNA were assembled in the methylation module of GenomeStudio, and the quality of the data was assessed by calculating Mahalanobis distances. Forty-seven samples yielded acceptable data. A matrix of β-values was generated with rows defined by microarray CpG locus and columns defined by sample identification. A corresponding matrix indicating cellular phenotypes was also generated, with rows defined by sample identification (in precisely the same order as the columns in the corresponding matrix) and columns defining the cell lineage(s) to which each cell lineage belongs.

A linear mixed effects (LME) model was applied to the Illumina Infinium HumanMethylation27 WBC lineage as the fixed effect and beadchip plate as the random effect. The fixed effect groups were: Pan-T cell, CD4+ T cell, CD8+ T cell, Pan-NK cell, $CD56^{dim}$ NK cell, $CD56^{bright}$ NK cell, B cell, granulocyte, neutrophil, eosinophil, and monocyte. Across the gene loci, this model generated coefficients for each fixed effect group indicating relative estimates of DNA methylation for each of the different cell types. Collapsing categories accounted for the hierarchical relationships among cell lineages and a linear transformation was applied to convert coefficient estimates to estimated mean value per cell type, resulting in a matrix $\tilde{B}_0$ of mean values, each row corresponding to a CpG locus and each column corresponding to a cell type. The model also generated an F-statistic for each locus that indicates how significantly different DNA methylation was between the cell types.

A stochastic search algorithm was then employed to select the differentially methylated regions (DMRs) that work best in concert on a custom microarray to distinguish leukocyte lineages, and would therefore be the most effective at quantifying immune cell types in a biological sample. The objective was to ascertain which 96 CpGs would give optimal precision for the WBC types.

The stochastic search algorithm was designed to maximize precision of estimated cellular fractions, under the assumption that the variance-covariance of the fraction estimates is proportional to $(\tilde{B}_0^T \tilde{B}_0)^{-1}$. To optimize precision for a single individual cell type, the corresponding diagonal element of $(\tilde{B}_0^T \tilde{B}_0)^{-1}$ was minimized; to optimize a set of cell types, the sum of the corresponding diagonal elements was minimized.

The general strategy was as follows. The engine is a stochastic search algorithm that starts with an initial set of CpGs, which is the beginning choice for the "current" set. On each iteration a randomly chosen CpG from the current set is switched out with a randomly chosen CpG from the remaining (unselected) CpGs, and precision is compared between the current set and the "candidate" set. If the candidate set gives better precision then the switch is accepted. Otherwise it is rejected. Ideally, by the end of the algorithm, the acceptance rate should be 0%.

The algorithm was run for 50,000 iterations starting with the 500 CpGs having the best F statistics. This was repeated ten times with different random number seeds each time. Then, the algorithm was run for 50,000 iterations starting with the CpGs having the 500 largest absolute effect sizes (coefficients generated by the LME model) for the WBC types. This was also repeated ten times with different random number seeds each time. Next 20 runs were compared and the algorithm run for 50,000 iterations starting with the 500 most frequently chosen CpGs from the previous 20 runs. This was repeated five times with different random number seeds each time. Finally, a run was performed for 750,000 iterations starting with the 96 most frequently chosen CpGs from the previous five runs.

Example 38

Mediation Analysis for Estimating Effects of an Exposure or Phenotype on Measured DNA Methylation A method is described for conducting a mediation analysis to estimate the effects of an exposure or to estimate the effects of a specific phenotype on measured DNA methylation along two paths: through changes in WBC distribution, and directly, unmediated by changes in WBC distribution. Most Epigenome-wide association scans (EWAS) have attempted to estimate the marginal effect (β, depicted in FIG. 41A) on measured DNA methylation, which are effects not adjusted for WBC distribution. However, a significant portion of the effect on DNA methylation is mediated through changes in WBC distribution as shown in FIG. 41B. Of interest in EWAS studies is α, the direct effect adjusted for WBC distribution. Estimating this effect requires estimation of two other quantities, Γ, the effect of exposure or phenotype on WBC distribution, and ξ, the effect of WBC distribution on methylation. If y is the DNA methylation measured for subject i at a particular CpG site (j, subscript suppressed for clarity), $z_i$ is a p×1 matrix of covariates for subject i (including the exposure or phenotype of interest), and $\omega_i$ is the subject-specific WBC distribution estimated using constrained projection in the manner described in Example 1 then $y_i = z_i^T \alpha + \omega_i^T \xi + e_i$, where $e_i$ is a zero-mean error. Additionally, the effect of exposure/phenotype on WBC distribution can be modeled as $\omega_i = \Gamma z_i + u_i$, where $u_i$ is a zero-mean error vector. It is noted that α is a p×1 vector, and K cell types are assumed, so that $\omega_i$ is a K×1 vector, Γ is a K×p matrix, and ξ is a K×1 vector. It follows that $y = z_i^T(\alpha + \Gamma^T \xi) + u_i^T \xi + e_i$, so that the marginal effect β is the p×1 vector $\alpha + \Gamma^T \xi$. Estimation proceeds first by computing $$\hat{\Gamma} = \left(\sum_{i=1}^{n} \omega_i z_i\right)\left(\sum_{i=1}^{n} z_i^T z_i\right)^{-1},$$

then computing $\hat{u}_i = \omega_i - \hat{\Gamma} z_i$, $r_i = (z_i^T, \hat{u}_i^T)^T$, $$\hat{\zeta} = \left(\sum_{i=1}^{n} r_i^T r_i\right)^{-1}\left(\sum_{i=1}^{n} r_i y_i\right),$$

extracting $\hat{\xi}$ as the last K components of $\hat{\zeta}$ and obtaining $\hat{\alpha}$ by subtracting $\hat{\Gamma}^T \hat{\xi}$ from the first p components of $\hat{\zeta}$.

Statistical inference is achieved by permutation. Specifically, the null distributions of $\hat{\alpha}$ and $\hat{\Gamma}$ are obtained by permuting the exposure or phenotype of interest within z (only the components representing the covariate to be tested), and the null distribution of $\hat{\xi}$ is obtained by permuting the subject assignments corresponding to $\omega_i$. Adjustments for multiple comparisons are achieved by nesting within each permutation a loop that estimates $\hat{\alpha}_j$, $\hat{\Gamma}_j$, and $\hat{\xi}_j$ for each individual CpG, with adjusted p-values obtained by comparing the maximum absolute values of $\hat{\alpha}_j$, $\hat{\Gamma}_j$, and $\hat{\xi}_j$ (over the CpGs) to the corresponding statistics computed from each individual permutation. For comparison purposes, a similar permutation test can be applied for the marginal coefficient β.

This method to a data set consisting of n=205 control subjects in a bladder cancer case/control study (Karagas M R et al., 1998, Environ Health Perspect 106: 1047-1050). Four separate analyses were performed: (1) the phenotype of interest was age; (2) the exposure of interest was current smoker status; (3) the exposure of interest was toenail arsenic; and (4) the exposure of interest was reported use of hair dye. Sex was included as a covariate in analyses, and age was included in (2)-(4).

The relationship between $\hat{\alpha}$ and $\hat{\beta}$ for the covariate of interest over autosomal CpGs is shown in FIG. 42. Dots represents overall methylation as indicated by the first component of the coefficient vector $\hat{\beta}$, corresponding to the intercept (light=low, black=moderate, dark=high). The diagonal straight line represents the identity ($\hat{\alpha}=\hat{\beta}$). The curve depicts a loess fit to the scatter plot. In each of the cases there is an S-shaped relationship that shows attenuation of effect ($\hat{\alpha}$ tends to be smaller than $\hat{\beta}$). Table 28 shows the multiple-comparisons adjusted p-values for each coefficient corresponding to the covariate of interest (β, α, γ) and overall WBC distribution effect on DNA methylation (ξ), obtained by permutation test using 5000 permutations. As shown in the table, significance of α may be greater than, less than, or equal to the significance of β. Remarkably, in every case, the covariate of interest shows a strongly significant association with WBC distribution. It is noted that WBC shows significant overall association with DNA methylation.

TABLE 28

Multiple-comparisons adjusted p-values

| Exposure/Phenotype | β | α | γ | ξ |
|---|---|---|---|---|
| Age | 0.0358 | 0.0838 | <0.0002 | 0.0100 |
| Current Smoker | 0.0326 | 0.0200 | <0.0002 | 0.0134 |
| Toenail Arsenic | 0.1054 | 0.0512 | <0.0002 | 0.0148 |
| Dye Use | 0.2614 | 0.2570 | <0.0002 | 0.0102 |

Example 39

Comparison of Methods Herein for Estimating Fractions of Blood Cell Types with Non-Negative Matrix Factorization (NNMF)

The methods herein are predicated on the relationship $$E(Y_i) = \sum_{l=1}^{d_0} b_{0l}\omega_{il},$$

where $Y_i$ is a vector of DNA methylation measurements obtained for subject i, $d_0$ is the number of blood cell types to be assayed, $\omega_{il}$ are the fractions of each blood cell type corresponding to subject i, and $b_l$ is the vector of methylation fractions corresponding to blood cell type l; the methods herein provide techniques for estimating the fractions $\omega_{il}$ assuming the values of $b_l$ have been obtained from an external validation data set. In contrast, non-negative matrix factorization (NNMF) could be used to estimate $\omega_{il}$ and $b_l$ simultaneously in absence of an external validation set. In the context of NNMF, the $d_0$ vectors $\omega_{\bullet l}$ are considered "factors", and the $d_0$ vectors (assumed to represent individual methylation profiles) are considered "basis vectors" and the number of factors $d_0$ must be provided to the NNMF algorithm.

Using the 12 experimental samples described in Example 5 NNMF was compared to methods herein (Examples 1-3). Highest ranking 100 and 500 pseudo-DMRs were selected on the basis of informativeness as in Example 4; for each choice, the constrained projection described in Examples 1 and 5 was used to impute specific cell distributions, then NNMF was performed assuming four, five, and six factors (i.e. factor values assumed to represent the fractions $\omega_{il}$ for one cell type l). The nmf function in the R package NMF was used with default settings. Since NNMF requires random inputs, NNMF was applied 100 times, each with different randomly generated starting values according to the default settings of the nmf function. Six cases were considered, viz., 100 CpGs and 500 CpGs for each of four, five and six factors. For each of the 100 runs in each of the six cases, the fitted factors $\omega_{\bullet l}$ (values of which were assumed to correspond to fractions $\omega_{il}$) were correlated to expected fractions of B cells, T cells, monocytes, and granulocytes, and for each specific cell type, the factor with the maximum correlation to that type was assigned to it. Then, for each cell type in each case, the median correlation with assigned factor was tabulated. Table 29 below reports these median values, and Table 30 reports the correlation between expected fraction and the fraction observed using methods herein. A comparison of these tables demonstrates that, though NNMF can achieve high correlation with expected cell fraction if the pseudo-DMRs are known in advance, the methods described herein in Examples 1-4 still achieves higher correlation. In addition, NNMF occasionally fails to match known cell types to imputed cell types in a monomorphic manner. Table 31 reports the percentage of runs for which at least two different cell types were matched via NNMF to the same factor.

It is expected that NNMF would behave less favorably than methods described herein (Examples 1-4), since NNMF requires the estimation of (n+M) F unknown parameters (where n=# of target samples, M=# of CpGs, and F=# of factors) and methods herein require the estimation of only n K unknown parameters, where K<F and K is the number of known cell types.

TABLE 29

Median correlation for two different sets of CpG containing sequences

| | Factors = 4 | Factors = 5 | Factors = 6 |
|---|---|---|---|
| 100 CpGs | | | |
| B cells | 0.998 | 0.996 | 0.996 |
| T cells | 0.988 | 0.989 | 0.990 |
| Monocytes | 0.832 | 0.900 | 0.927 |
| Granulocytes | 0.967 | 0.954 | 0.963 |
| 500 CpGs | | | |
| B cells | 0.998 | 0.996 | 0.996 |
| T cells | 0.985 | 0.993 | 0.990 |
| Monocytes | 0.798 | 0.896 | 0.879 |
| Granulocytes | 0.943 | 0.977 | 0.970 |

TABLE 30

Correlation between expected fraction and
the fraction observed using methods herein.

|  | 100 DMRs | 500 DMRs |
|---|---|---|
| B cells | 1.000 | 1.000 |
| T cells | 0.998 | 0.997 |
| Monocytes | 1.000 | 1.000 |
| Granulocytes | 0.997 | 0.999 |

TABLE 31

Percentage of runs for which at least two different
cell types were matched to the same factor

| Factors | DMRs = 100 | DMRs = 500 |
|---|---|---|
| 4 | 4 | 2 |
| 5 | 0 | 1 |
| 6 | 0 | 0 |

Example 40

Quantitation of T Cell, Treg and CD16+CD56$^{dim}$ NK Cell Numbers by CD3Z, FoxP3 and NKp46 Methylation Assays, Respectively Using Droplet Digital PCR A droplet digital PCR technique was used to quantitate T cell, Treg and CD16+CD56$^{dim}$ NK cell numbers using CD3Z, FoxP3 and NKp46 methylation assays described in Examples 15 and 30. Digital PCR (dPCR) is a refinement of conventional PCR methods and is used to directly quantify and clonally amplify nucleic acids. dPCR and traditional PCR differ in method of measuring nucleic acid amounts, as dPCR is more precise. The two PCR methods differ in that the sample is separated into a large number of partitions in dPCR, and the reaction in each partition is carried out individually. This separation produces a more reliable collection and sensitive measurement of nucleic acid amounts.

Isolated and purified T cells and Tregs were serially diluted, and copies of each of the targets were quantified as measures of cell numbers. Bisulfite converted DNA from whole blood, isolated human T-cells and Treg cells and from NK cells was quantified using the emulsion partitioning method of BioRad QX100™ Droplet Digital™ PCR (ddPCR™) system. This system creates portioned PCR reaction using water-in-oil droplets for performing high-throughput digital PCR. The QX100 droplet generator partitions samples into 20,000 nanoliter-sized droplets. After PCR using a thermal cycler, droplets from the samples were streamed in single file on a reader (QX100 droplet reader). The PCR-positive and PCR-negative droplets were counted to obtain quantification of target DNA in digital form. Results are shown in FIGS. 43-46 as dot plots of fluorescence intensities of the droplets, with each point on the plot representing a single droplet. The horizontal lines are cutoffs between "positive" and "negative" droplets for each sample. A measure of concentration of the target sequence (demethylated CD3Z, Fox3P or NKp46) in copies per microliter was obtained as readout from the system. Dividing target sequence concentration by total DNA concentration obtained by C-less PCR yielded the percent of total DNA that was positive for the target DNA region (FIGS. 45-46).

Data in figures show that successful amplification and detection of CD3Z and Foxp3 DMRs, respectively were obtained. FIG. 43A and FIG. 44A show dot plots indicating distinguishing of positive droplets and negative droplets. FIG. 43B and FIG. 44B show the calculated absolute numbers of positive PCR droplets. Results obtained from dilution of standard purified T cells shows correspondence of quantities of CD3Z and FoxP3 genes with extent of dilution and hence validity of dPCR as a detection method for methylation based assay of immune cell identity. Other partitioning approaches have been developed that employ microfluidic manipulation and results similar to the data obtained herein are expected from the use of such other methods of partitioning. FIG. 45 shows quantitation of purified NK cells under different conditions and FIG. 46 shows quantitation of whole blood and of purified leukocyte subsets by measuring demethylated NKp46 DMR described in Example 30.

Example 41

Sample Workflow

FIG. 47 summarizes the workflow carried out for samples derived from human whole blood utilized in the following examples. FIG. 51 describes 85 venous whole blood samples that were collected from disease free human donors. Of these, 79 samples were used for isolation of target cell type by magnetic activated cell separation (MACS) and six samples were subjected to conventional immune profiling in which fresh aliquots are analyzed by protein based methods. Purity was confirmed in the 79 samples isolated by MACS by fluorescence activated cell sorting (FACS). The six samples separated by conventional immune profiling were stored under 12 specific storage conditions which differed by presence of coagulants and temperatures, and duration, which yielded 72 samples.

DNA was extracted from each of the 79 samples from FACS and the 72 samples from the 12 specific storage conditions. An aliquot of the genomic DNA from five of the FACS purified, DNA extracted 79 samples samples were combined in quantities that mimicked human blood by artificially reconstituting peripheral blood. Aliquots of each of seven of the cell DNA mixtures, the FACS purified DNA extracted 79 samples, and the 72 samples in the 12 specific storage conditions were then randomized. Aliquots of the resulting 158 samples were contacted with sodium bisulfate, which is used in the analysis of methylation status of cytosines in DNA, and 158 sodium bisulfate treated aliquots of the 58 samples were analyzed using each of a high-density methylation microarray (HDMA) and a low-density methylation microarray (LDMA).

Date for DNA methylation microarrays are available at an NCBI website entitled, "Gene Expression Omnibus" (GEO) in accordance with a protocol known as, "Minimum Information About a Microarray Experiment" (MIAME). The methods, materials and conditions described in this example and FIG. 47 are fully described in the following examples.

Example 42

Purified Leukocyte Subtypes

Venous whole blood samples were collected from 79 disease-free human donors whose demographic characteristics are shown in Table 32. A homogenous populations of one specific type of leukocyte was obtained from each sample, which were purified by MACS, a method of cell separation that utilizes antibody-conjugated magnetic microbeads, and a combination of positive and negative selection protocols (Miltenyi Biotec Inc., Auburn, Calif.). Purity of the 79 purified cell samples was determined by FACS. Representative FACS results for 15 sample types are shown in FIG. 48A-48P. The hierarchical relationship between the different populations of MACS purified leukocyte subtypes, and the number of replicate samples for each cell type, is shown in FIG. 49.

TABLE 32

Demographic characteristics of blood donor for purified cells

| | |
|---|---|
| Total number | 79 |
| Age, Mean (SD) | 30 (9) |
| Weight (lbs), Mean (SD) | 181 (38) |
| Height (inches), Mean (SD) | 69 (3.7) |
| Gender | |
| Male, No. (%) | 62 (78%) |
| Female, No. (%) | 15 (19%) |
| Unknown, No. (%) | 2 (3%) |
| Race | |
| White No. (%) | 32 (41%) |
| Hispanic, No. (%) | 12 (15%) |
| Black, No. (%) | 13 (16%) |
| Asian, No. (%) | 13 (16%) |
| Native American, No. (%) | 3 (4%) |
| Unknown/Other, No. (%) | 6 (8%) |
| Tobacco smoking | |
| Yes, No. (%) | 13 (16%) |
| No, No. (%) | 33 (42%) |
| Unknown, No. (%) | 33 (42%) |

Example 43

Conventionally Profiled Whole Bloods

Six additional venous whole blood samples were collected from different disease free human donors whose demographic characteristics are summarized in Table 32. The workflow for these samples is shown in FIG. 58. Each whole blood sample was divided into three aliquots, which contained an anticoagulant: heparin, citrate, or EDTA. A portion of the aliquot in Heparin was used to perform conventional immune profiling methods, including flow cytometry which is described below, manual 5-part white blood cell differential and CBC with automated 5-part white blood cell differential. Another portion of this aliquot for each sample was analyzed for methylation assessment using the high-density DNA methylation microarray (HDMA; described in examples below). Another portion was analyzed for methylation assessment using the low-density methylation array (LDMA; described in examples below) directly without storage. Aliquots for each of the six blood samples were each stored overnight at one of three temperatures (room temperature, 4° C., and −80° C.) prior to methylation assessment on the HDMA.

Example 44

Differential Leukocyte Counts

Manual white blood cell (WBC) counts were performed according to established standards (Koepke J A. 1977 Differential Leukocyte Counting. Stokie, Ill.: College of American Pathologists; Houwen B. 2001 The differential cell count. Laboratory Hematology 89-100). Automated WBC counts were performed using the XE-5000™ Automated Hematology System (Sysmex America, Inc., Mundelein, Ill.) according to manufacturer instructions. The following cell types were enumerated: total WBC, lymphocytes, monocytes, neutrophils, basophils and eosinophils.

Example 45

Fluorescence Activated Cell Sorting (FACS) of Leukocyte Subsets

Blood samples were directly stained for cell surface markers and were incubated for 20 minutes in the dark at 4° C. Antibodies were purchased from eBioscience Inc (San Diego, Calif.). Each blood sample was divided into two aliquots. The first aliquot cells were stained with: anti-human CD3e FITC (catalog number 11-0039-41), anti-human CD4 APC-eFluor 780 (catalog number 47-0049-41), anti-human CD8a 605NC (catalog number 93-0088-41), anti-human CD16 PE-Cy7 (catalog number 25-0168-41), anti-human CD25 APC (catalog number 17-0259-41), anti-human CD45 PerCP-Cy5.5 (catalog number 45-9459-41), antihuman CD56 PE (catalog number 12-0567-41), and anti-human CD127 eFluor 127 (catalog number 48-1278-41) to analyze T-cells, NKT cells, and NK cells. The second aliquot cells were stained with: anti-human CD14 FITC (catalog number 11-0149-41), anti-human CD15 eFluor 450 (catalog number 48-0159-41), anti-human CD16 PE-Cy-7, anti-human CD19 APC-eFluor 780 (catalog number 47-0199-41), anti-human CD45 PerCP-Cy5.5, and anti-human CD123 PE (catalog number 12-1239-41) to analyze B-cells, monocytes, and granulocytes (neutrophils, eosinophils, and basophils).

Unstained, isotype, and fluorescence-minus-one (FMO) controls were used to determine sample gating and background. Individual compensation controls were used in each sample run. CountBright counting beads (Invitrogen, catalog number C36950) was added for quantification of total leukocytes and each subset. Acquisition was performed within 12 hours of blood draw on the FACSAria III flow cytometer (Becton Dickinson) using FACSDiva Software (Becton Dickinson). An acquisition limit of 10,000 events was used on the monocyte gate, using FSC versus SSC dot plot, for each aliquot. Final data analysis and presentation of results was done using Flowjo software (TreeStar Inc).

Cell types and detection parameters were set as follows: Lymphocytes: low SSC (side scatter) and low FSC (forward scatter); B-cells: CD45+ and CD19+; T-cells: CD45+ and CD3+ antibodies; Helper T-cells (Th): CD3+ and CD4+; Regulatory T-cells (Tregs): CD3+ and CD4+ and CD25+ and FOXP3+; Cytotoxic T-cells (Tc): CD3+ and CD8+; Natural Killer T-cells (NKT): CD3+ and C56+; Natural Killer (NK) cells: CD3- and CD56+; Effector NK cells: CD3- and CD16+ and CD56 dim (i.e. lower level); Regulatory NK cells: CD3- and CD16- and CD56 bright (i.e. higher level); CD8+ NK cells: CD3- and CD8+ and CD56+ antibodies; CD8-NK cells: CD3- and CD8- and CD56+; Granulocytes: high SSC (side scatter) and high FSC (forward scatter); Eosinophils: CD44+ and high SSC and high FSC; Basophils: CD123+ and high SSC and high FSC; Neutrophils: CD15+ and CD16+ and high SSC and high FSC; Monocytes: low SSC (side scatter) and high FSC (forward scatter) and CD14+.

Example 46

DNA Extraction

Genomic DNA was extracted and purified from whole blood and from MACS purified leukocyte samples using AllPrep DNA/RNA/Protein Mini Kit (QIAGEN, catalog number 8004) or DNeasy blood and tissue kit (QIAGEN, catalog number 69506) according to manufacturer's instructions and protocol. DNA was quantified by NanoDrop ND-1000 Spectrophotometer (NanoDrop Technologies, Inc.). DNA samples for some applications were further purified using the DNA Clean and Concentrator according to manufacturer's protocol (ZYMO Research Corporation, catalog number D4004). Samples were kept at 4° C. for shortterm storage or at −20° C. for long-term storage.

Example 47

Artificial Blood Samples

Genomic DNA from five of the purified leukocyte samples was combined in quantities that mimicked human blood under seven clinical conditions (Table 33). DNA was mixed thoroughly and stored briefly at 4° C. prior to analysis.

TABLE 33

Proportions of DNA from purified cells combined into mixtures that artificially reconstruct blood under clinical conditions

| Clinical condition | T-cells | B-cells | NK cells | Granu-locytes | mono-cytes |
|---|---|---|---|---|---|
| normal | 20% | 2.5% | 1.5% | 67% | 9% |
| T-cell lymphopenia-1 | 6% | 6% | 5% | 70.5% | 12.5% |
| T-cell lymphopenia-2 | 2% | 7% | 6% | 71.5% | 13.5% |
| granulocytosis | 10% | 0% | 0% | 90% | 0% |
| granulocytopenia | 34.5% | 17% | 16% | 9% | 23.5% |
| B-cell lymphoma | 20.5% | 0.5% | 2% | 67.5% | 9.5% |
| monocytosis | 14% | 0% | 0% | 61% | 25% |

Example 48

Sodium Bisulfite Conversion

Genomic DNA from six conventionally profiled whole blood samples, genomic DNA from the 79 purified leukocyte samples, and DNA mixtures in the seven artificial blood samples were randomized and treated with sodium bisulfite using ZYMO EZ-96 DNA Methylation Kit (ZYMO Research Corp., catalog number D5004), and were stored at −80° C. until used. This method and procedure was used for assessment of DNA methylation by converting unmethylated cytosine residues to uracil.

Example 49

High-Density DNA Methylation Microarray (HDMA)

To analyze patterns of cell-lineage specific DNA methylation and examine the viability of the mathematical models herein, methods were developed. Forty-six of the purified leukocyte DNA samples, six of the artificial blood reconstruction samples (excluding T-cell lymphopenia 1), and the six conventionally profiled whole blood samples were analyzed using the Infinium® HumanMethylation27 Beadchip microarray (Illumina Inc., San Diego, Calif.). This platform was used to quantify the methylation status of 27,578 CpG loci from 14,495 genes, with a redundancy of 15-fold to 18-fold. The ratio of fluorescent signals was computed from both alleles using the following equation: $\beta=(\max(M,0))/(|U|+|M|)+100$. The resultant β-value was a continuous variable from 0 (unmethylated) to 1 (completely methylated) that represents the methylation at each CpG site and was used in subsequent statistical analyses. Data were assembled with the methylation module of GenomeStudio software, a product of Illumina, Inc. (Bibikova, M. et al. 2009 Epigenomics 1:177-200).

Following the crosscheck optimization procedure, a minimum number of 34 CpG loci were selected to establish DNA methylation signatures for the HDMA reference library. These loci were found in the following genes: CLEC9A (2 loci) (SEQ ID NO: 119), INPP5D (SEQ ID NO:120), INHBE (SEQ ID NO:28), UNQ473 (SEQ ID NO:121), SLC7A11 (SEQ ID NO:122), ZNF22 (SEQ ID NO:11), XYLB (SEQ ID NO:123), HDC (SEQ ID NO:26), RGR (SEQ ID NO:124), SLCO2B1 (SEQ ID NO:125), C1orf54 (SEQ ID NO:126), TM4SF19 (SEQ ID NO:127), IGSF6 (SEQ ID NO:28), KRTHA6 (SEQ ID NO:128), CCL21 (SEQ ID NO:129), SLC1A1 (SEQ ID NO:130), FGD2 (SEQ ID NO:2), TCL1A (SEQ ID NO:131), MGMT (SEQ ID NO:132), CD19 (SEQ ID NO:133), LILRB4 (SEQ ID NO:134), VPREB3 (SEQ ID NO:135), FLJ10379 (SEQ ID NO:136), HLA-DOB (SEQ ID NO:43), EPS8L3 (SEQ ID NO:4), SHANK1 (SEQ ID NO:137), CD3D (2 loci) (SEQ ID NO:93), CHRNA3 (SEQ ID NO:138), CD3G (2 loci) (SEQ ID NO:92), RARA (SEQ ID NO:139), GRASP (SEQ ID NO:140).

Example 50

Low-Density DNA Methylation Microarray (LDMA)

To thoroughly validate the DNA methylation-based approach to immune profiling used herein, methods in examples herein were performed to analyze the 79 purified leukocyte samples, the seven artificial blood reconstruction samples, and the 72 samples of the six conventionally profiled whole blood samples (each stored under 12 different conditions) by the VeraCode® custom GoldenGate® Methylation assay (GGMA). The assay used a four-probe design to differentiate between methylated and unmethylated sequences for a custom panel of 96 different CpG loci. The method generated DNA targets through allele-specific, amplification using universal primers, and hybridization to a bead array at sites bearing complementary address sequences. The hybridized targets contained a fluorescent label denoting a methylated or unmethylated state for a given locus.

Methylation status of each interrogated CpG site was calculated as the ratio of fluorescent signal from one allele relative to the sum of both methylated and unmethylated alleles, thereby generating a β-value ranging from 0 (unmethylated) to 1 (fully methylated). Several different control types were used to ensure data quality. Each bead type was represented with an average 30-fold redundancy. Data were assembled with the methylation module of GenomeStudio software (Illumina, Inc.).

Following the crosscheck optimization procedure, a minimum number of 20 CpG loci were selected to establish DNA methylation signatures for the LDMA reference library. The selected loci were found in the following genes: FGD2 (SEQ ID NO:2), HLA-DOB (SEQ ID NO:43), BLK (SEQ ID NO:40), IGSF6 (SEQ ID NO:28), CLDN15 (SEQ ID NO:29), SFT2D3 (SEQ ID NO:89), ZNF22 (SEQ ID NO:11), CEL (SEQ ID NO:39), HDC (SEQ ID NO:26), GSG1 (SEQ ID NO:67), FCN1 (SEQ ID NO:53), OSBPL5 (SEQ ID NO:64), LDB2 (SEQ ID NO:36), NCR1 (SEQ ID NO:91), EPS8L3 (SEQ ID NO:4), CD3D (SEQ ID NO:93), PPP6C (SEQ ID NO:7), CD3G (SEQ ID NO:92), TXK (SEQ ID NO:30), FAIM (SEQ ID NO:32).

Example 51

Statistical Methods

Statistical analyses in the examples herein were performed using the R statistical platform (www.Rproject.org)

Example 52

Identification of Cell Lineage-Specific Methylation

A linear mixed effects (LME) model was applied to the purified leukocyte HDMA data with cell type designated as the fixed effect and beadchip as the random effect (controlling for plate effects) to identify DNA methylation signatures that represent biomarkers of leukocyte subtypes. This method generated F-statistics for every CpG on the array indicating how well differential methylation at that locus distinguishes seven different leukocyte lineages: T-cells, B-cells, NK cells, monocytes, eosinophils, basophils, and neutrophils. This method and calculation also generated seven coefficients for each CpG indicating directionality and intensity of differential methylation at that locus for the cell types.

Example 53

Selection of CpG Panel for Immune Profiling

Using the LME results, a stochastic search algorithm was implemented to determine the best combination of putative DMRs to use for the simultaneous assessment of T-cells, B-cells, NK cells, monocytes, and granulocytes in a human blood sample. This algorithm was used to assess the predictive ability of a selected panel of CpG loci by analyzing the variance in methylation across cell types as designated in a contrast matrix. If substitution of randomly selected locus of one of the loci in the panel would improve the predictive ability, the substitution would be accepted and the new locus would replace the old in the panel. This search algorithm was implemented for 50,000 iterations starting from ten different random number seeds in three stages: first starting with the top 500 F-statistics, then the top 500 absolute effect sizes (based on the LME coefficients), and then the top 500 from the first two stages. The stochastic search algorithm was implemented an additional iteration, starting from the top 96 from the final stage above until the acceptance rate for substitutions definitively dropped to zero.

Example 54

DNA Methylation-Based Cell Quantification

To estimate cell mixtures by DNA methylation marks, methods herein employed a constrained projection, in which a DNA methylation profile from a target profile is projected onto mean methylation profiles for isolated cell types, subject to the constraint that the projection values (estimated mixing weights) were greater than or equal to zero and sum to less than one. The mean values were obtained from a reference library of DNA methylation signatures, and the projection was implemented via quadratic programming (Goldfarb, D. et al. 1982 Idnani A. Dual and Primal-Dual Methods for Solving Strictly Convex Quadratic Programs. In: Hennart J P, ed. Numerical Analysis. Berlin: Springer-Verlag pages 226-39; Goldfarb D et al. 1983 Mathematical Programming 27:1-33; Houseman, E. A. et al. 2012 BMC Bioinformatics 13:86).

Example 55

Cell Differential Quantification Using DNA Methylation

Methods herein used DNA methylation to detect and quantify the proportions of each of T-cells, B-cells, NK cells, monocytes, basophils, eosinophils, and neutrophils in any single human blood sample. The first step in achieving this goal was to establish a reference library of DNA methylation signatures that serve as biomarkers for those cell types. A microarray was used to identify and to assess DNA methylation in WBC subsets purified from normal (disease-free) human blood, to generate a reference data set. To generate a target data set, DNA methylation at the same CpG loci as the reference data set was assessed in the target samples using the same platform used to establish the reference library. The cell types of interest were quantified in the target samples by projecting their DNA methylation profiles onto the mean methylation profiles for the purified WBC types of interest from the reference data set using quadratic programming (Houseman, E. A. et al. 2012 BMC Bioinformatics 13 (86): pages 1-16, which is hereby incorporated by herein in its entirety). Sample workflows are illustrated in FIG. 47.

Example 56

DNA Methylation Distinguishes WBC Subsets

Venous whole blood was collected from 79 disease free human donors (Table 32) and homogenous populations of the WBC types of interest were isolated from each blood sample using magnetic activated cell separation (MACS) with the purity confirmed by FACS (FIG. 48A-48P). To account for inter-individual variation, at least four samples of each cell type were purified from each donor (FIG. 49). A subset of these purified cell samples were analyzed by a high-density methylation microarray (HDMA), the Infinium HumanMethylation (Illumina Inc., San Diego, Calif.), to identify patterns of WBC lineage-specific DNA methylation. See Houseman, E. A. et al. 2012 BMC Bioinformatics 13 (86): pages 1-16, which is hereby incorporated by herein in its entirety. The HDMA assessed DNA methylation at 27,578 CpG loci in 14,495 genes throughout the human genome. A linear mixed effects model applied to these data (with cell type as the fixed effect and beadchip as the random effect) revealed hundreds of CpG loci exhibiting lineage-specific DNA methylation patterns that distinguished the WBC types of interest.

A panel of 96 CpG loci was selected that function in concert for DNA methylation-based immune profiling, which loci could be placed on a custom low-density DNA methylation microarray (LDMA), the VeraCode GoldenGate methylation array (Illumina Inc., San Diego, Calif.), which allowed independent confirmation of the HDMA results, and would lead to more efficient use of resources for the quantification of WBC subsets in target samples. A bioinformatic search algorithm was applied that works in a stochastic manner, substituting CpG loci and assessing the predictive ability of the selected loci by analyzing the variance in methylation across WBC types as designated in a contrast matrix.

A panel of 96 CpG loci were selected from which DNA methylation clearly distinguished the WBC types of interest, B-cells, T-cells, NK cells, monocytes, neutrophils, basophils, and eosinophils, as indicated by unsupervised hierarchical clustering of HDMA data for the purified WBC subsets (FIG. 50). These 96 CpG loci were placed on the LDMA, which used different chemistry was used than for the HDMA and therefore represented an independent platform. Unsupervised hierarchical clustering of LDMA data for the purified WBC subsets identified that DNA methylation at these loci clearly and reliably distinguished the WBC types of interest (FIG. 51).

Example 57

Accurate Prediction of Purified WBC Subset Identities Using DNA Methylation

To test the performance of the method, both HDMA and LDMA derived DNA methylation data sets for the purified WBC subset samples were analyzed as if the data sets were target data sets containing unknown samples. Projection was performed using quadratic programming to quantity seven different leukocyte subtypes in each of the purified WBC subset samples using methylation signatures from the corresponding HDMA or LDMA reference library. This crosscheck procedure was used to improve efficiency by identifying any problematic purified WBC subset samples in the reference set, and to determine the minimum number of CpG loci required for accurate leukocyte subtype detection and quantification.

It was observed that only 34 and 20 CpG loci respectively, were required to accurately predict the leukocyte subtype identity of unknown purified WBC subset samples using the HDMA (FIG. 52), and LDMA (FIG. 53), respectively. These loci are listed in Examples 49-50 herein. The disparity in the minimum number of loci required with each of the two platforms resulted from the fact that fewer purified WBC subset samples were analyzed using the HDMA (due to higher costs associated with that platform) and more CpG loci were therefore needed to compensate.

These methods and arrays used herein revealed that CD16-CD56bright "regulatory" NK cells should be eliminated from subsequent reference data sets, since this cell type was frequently misclassified. These cells were not present in significant numbers in peripheral blood, and were found primarily in lymphatic tissue. The purities of the regulatory NK cell samples obtained from peripheral blood were low according to FACS analysis (FIG. 48I), providing one plausible explanation for any consistent misclassification.

Example 58

Clinically Relevant Shifts in the WBC Composition Detected Using DNA Methylation Efficacy of methods and arrays herein were analyzed by detecting specific immune modulations that occur in peripheral blood of human patients exhibiting particular clinical conditions: diminished T-cells (T-cell lymphopenia), increased granulocytes (granulocytosis), diminished granulocytes (granulocytopenia), diminished B-cells (B-cell lymphopenia), and increased monocytes (monocytosis). Genomic DNA extracted from five of the purified WBC subset samples were combined in precise quantities that represented/mimicked constitution of human blood found in patients exhibiting each of these clinical conditions, and in normal patients (Table 33).

DNA methylation was assessed in these DNA mixtures using both the HDMA and LDMA platforms and methods. Five different WBC types in each mixture were quantified by performing projections by quadratic programming using the appropriate reference data set, utilizing only the minimum numbers of (34 or 20) CpG loci established by the crosscheck procedure described in examples herein.

Five WBC quantities measured using DNA methylation methods using HDMA and LDMA were observed to have comparable results to the expected values (FIG. 54A and FIG. 55A). These data indicate that methods and compositions herein were effectively detected five specific, clinically relevant modulations in peripheral blood immune cell samples.

Example 59

DNA Methylation Analysis Provides Accurate WBC Quantification Compared to Established Methods Methods and arrays described herein were compared to gold standard methods of WBC quantification. Venous whole blood was collected from six different, disease-free, human donors (FIG. 47). Blood samples were analyzed using methods described herein and were compared to three different, well established immune profiling methods: manual 5-part differential, CBC with automated 5-part differential, and FACS.

Genomic DNA was extracted the blood samples, and DNA methylation was assessed using both the HDMA and LDMA platforms and methods described in examples herein. WBC types were quantified by quadratic programming using the corresponding reference data set, and utilizing only the minimum numbers of (34 or 20) CpG loci identified by the crosscheck procedure described in examples herein. Quantities of WBC types measured by the DNA methylation methods were comparable to the results obtained using the gold standard methods (FIG. 54B-D, FIG. 55B-D, and FIG. 56).

Agreement between methods herein and the gold standard methods was excellent, and little evidence of systematic bias was observed. The mean difference between each pair of estimates was approximately zero. Standard deviations in model prediction values was determined by calculating root mean square error (RMSE) between WBC quantities measured using DNA methylation and WBC quantities measured by each of the gold standard methods (FIG. 57A-C). It was observed that the standard deviations were low. The levels of uncertainty were similar to those levels observed among the gold standard methods (FIG. 57D-F).

Example 60

Storage Conditions do not Affect WBC Estimates Obtained Using DNA Methylation

Examples analyzed whether the stability of DNA allows methods and arrays herein to overcome many limitations of previous WBC quantification methods. The DNA methods and arrays used herein did not require fresh blood or an intact cell membrane. Thus these methods and materials are useful for analyzing samples that were previously precluded from immunological assessment, such as archived blood samples that are stored in hospitals and laboratories, or blood samples collected in an anticoagulant not compatible with a particular method.

Examples analyzed whether a blood anticoagulant and/or storage temperature variations alter WBC quantification by DNA methylation methods herein. Six venous whole blood samples were collected from disease-free human donors and were contacted with an anticoagulants: citrate, heparin, or EDTA. DNA extracted was extracted from fresh samples and also from samples stored at room temperature, 4° C. or −80° C. for at least 24 hours prior to DNA extraction (FIG. 58). DNA samples were analyzed using a LDMA platform to assess DNA methylation and to generate a target data set to consider the effects of blood storage conditions. Seven WBC types of interest were quantified in each of these target samples by performing a projection by quadratic programming using the LDMA reference set. The minimum number of 20 CpG loci established by the crosscheck procedure described above was used.

It was observed that the storage conditions examined did not alter WBC subset quantities measured in human blood by DNA methylation (FIG. 59A-59D).

What is claimed is:

1. A method of predicting a methylation class membership of a patients for assessing the disease status of the patients, wherein the methylation class membership corresponds to an epigenetic signature of a plurality of leukocyte types in a bodily fluid samples of the patients, the method comprising:

measuring in bodily fluid samples of control subjects and in samples of the patients amounts of DNA methylation in each of a plurality of leukocyte type populations to determine leukocytes differentially methylated regions (DMRs) of the plurality of leukocyte type;

ranking the resulting leukocyte DMRs for each leukocyte type in the control subjects and the patients respectively according to a statistical strength of association of the each DMR with each leukocyte type to obtain a data set for known controls for each of the leukocyte types and a patient set respectively;

randomly dividing the data set of the bodily fluid samples of the control subjects and patient samples respectively into groups having substantially the same numbers of the control subjects and the patients in each group, thereby obtaining each of a training set and a testing set;

clustering samples of the control subjects in the training set using a highest ranked leukocyte DMRs to determine clustering solutions, wherein a clustering solution corresponds to the methylation class membership;

assessing a methylation class membership for each of the control subjects within the testing set by applying the clustering solutions obtained from the training set to the highest ranked leukocyte DMRs in the testing set, wherein the methylation class membership predicts the disease status of the control subjects;

predicting the methylation class membership of each of the patients by applying the clustering solutions obtained from the training set and the testing set to the highest ranked leukocyte DMRs from the patient set for assessing the disease status of the patients;

diagnosing the disease status of the patients; and if the disease is present, then administering a therapy to the patients.

2. The method according to claim 1, wherein ranking further comprises the highest ranked leukocyte DMRs shown in Table 21, wherein each DMR is identified, by chromosomal location and gene name, and the defined number of highest ranked leukocyte DMRs is selected from: at least 10, at least 20, at least 30, at least 40 and 50.

3. The method according to claim 1, wherein the bodily fluid samples are fresh or archival samples.

4. The method according to claim 1, wherein the methylation class membership of the subject in the testing set is predicted using a naive Bayes classifier.

5. The method according to claim 1, wherein testing the association of the predicted methylation class with the disease status comprises using receiver operating chrematistic curves (ROC) and the corresponding area under each curve.

6. The method according to claim 1, further comprising at least one of: monitoring; prognosing; and measuring response in the patient to the therapy.

7. The method according to claim 1 wherein the leukocyte types are selected from the group of: Natural killer cells, B Cells, CD4+ T cells, CD8+ T cells, granulocytes, and monocytes.

8. The method according to claim 1, wherein the disease is one of: head and neck squamous cell carcinoma (HNSCC), ovarian cancer and bladder cancer.

* * * * *

SEQUENCE LISTING

```
<160> NUMBER OF SEQ ID NOS: 140

<210> SEQ ID NO 1
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 1
gccagcccca gcaaacggtt ttacttcttc tcagtcctgt agaggctgag gtgtcaagga      60
cgggaccctg ttgctgactg ctcaagagga ggcaagctgg atctctctta tagagtttcc     120
at                                                                    122

<210> SEQ ID NO 2
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 2
tctccactga acctggtctg tgtcctggag tgcagggcct gagcctcggt gctcttggta      60
cgtgaagtgc ctggaacagc ttcacgctcc agtaactgtg aaccctggg gcctcacatg      120 cc                                                                    122

<210> SEQ ID NO 3
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 3
gatcatgtgt ttgtggcaac ttcctctgtg ggcttttgcc caggtctgtc cccaagcata      60
cgatggccaa aacttctgca ccagagcagc atcctgtgta acacagtcag gtccagcagt     120
ta                                                                    122

<210> SEQ ID NO 4
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 4
agcttctctg ctagtggcca caggcagagc ctgcctttga tgaggttaca gaggcagcca      60
cgcctgtgct ctttggactc tggtgggtgg ggaggcttcc tggtcactaa ccgctcaaca     120
``` tc                                                                        122

<210> SEQ ID NO 5
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 5
cacccacggg gccaggctgg cacaacgccc caacgctgca atcctgggaa gagtcacacg      60
cgccctcccg ggacccacgt gaccatcaag ggagtgtgga ggacacatcc ctcgggggtg     120
ac                                                                        122

<210> SEQ ID NO 6
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 6
tggcttcctc tctgaggatg cagctgctgc ctccctgggc ctggctgctt gcatcctgtg      60
cgcctggctt ccacagctcc accgcagagt ctgagctcca aaagagaggc acaagggggt     120
ct                                                                        122

<210> SEQ ID NO 7
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 7
tttttgtagc tacagataga atagagatct ttgtctattt tgttcacgaa gtactgcaag      60
cgccttgagc tgtacctggc acatctttgt tgctcagcaa agagtggttg gataaacgaa     120
cg                                                                        122

<210> SEQ ID NO 8
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 8
accaaatgag agagccattt ggggatacaa atcattccca acccagagct acagaagaca      60
cgtgtccaca aacacaactg tgcacaaact cactgggcaa tcctgttcaa atatttagca     120
ag                                                                        122

<210> SEQ ID NO 9
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 9
tctctacgga cttcctcggt gatacccact cgtccatctt cgatgctaag gccggcattg      60

```
cgctcaatga caatttcgtg aagctcattt catggtaagg gggaaggagc tggagactta    120
ga                                                                    122

<210> SEQ ID NO 10
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 10
cgcgccagct gtcaggcggt ttctagcctc gcttcggtta ttttaagctg atgagcctga    60
cgcatctcat cactaatatc agcagtttca tttctcctgt tttccattcg ctgtaataaa    120
at                                                                    122

<210> SEQ ID NO 11
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 11
catttacagg aaaggaacca aggctcagag aagaaatgtg ctccgttcac cgtgtgtaag    60
cggacgaccc agaattggaa tggttctttg tggctccaaa gtctgatttc aacacacccc    120
tt                                                                    122

<210> SEQ ID NO 12
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 12
gggagacctg acctgaaagg accccttca agtgataggg cagagcacag attgcaaaaa    60
cgcatattaa gaaatcactc ttggccgggc gcggtggctc atgcctgtaa tcccagcact    120
tt                                                                    122

<210> SEQ ID NO 13
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 13
tcccaggcag ccctgctggc ccctaaggac atagagtacc tgcttctgag agggctgcca    60
cggtggccac ctgtgaagcc tgtcacccag aactggatgg tacctgactt tcttcataga    120
cc                                                                    122

<210> SEQ ID NO 14
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 14
tttaacattc ctaacagact acattttgca aaagaataac aacgaagggg acttgtccta    60
```
cgagctagca cacatggtgt aaaccggagt aattacaagg gtgtagcagg ggtgtgcaga    120
aa                                                                  122

<210> SEQ ID NO 15
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 15
ggcctcccct tgaccactcca cgctgtccga gagctcaaag gccctcacgg tatacactca    60
cgctgggcat ccagtccaca tgggacccac agccctgaat ggcccaaacc acgtgagtgt    120
gg                                                                   122

<210> SEQ ID NO 16
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 16
cctcctcccc acggaggcct aggcatcagc cccctccctc atcctttcca gagtttggga    60
cgggatgtct tcagttgcca cggccacagt atggcttccc ctacagttag gctacagttg    120
gg                                                                   122

<210> SEQ ID NO 17
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 17
agggaagata cggctattat agaagtgact cctcccagga actgtgcttc cgggattgga    60
cgcagggcct caggcatttt gcgtgtccac agtcacaact gtgtgaatat aggtgtgtca    120
ta                                                                   122

<210> SEQ ID NO 18
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 18
gtcggcatcg gtgcgtgttg gtcaggggtc tgggcgggtg tctgatgcgg cctggcctct    60
cgcccgcagt tctctcggca ctggtgactg gcgagagcct ggagcggctt cggagagggc    120
ta                                                                   122

<210> SEQ ID NO 19
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 19
tggcttggtg gttatagcag tggaagtgtt gaaagtggct tgataatgaa tatattttaa    60
cgatgaagcc gacagaattt gtggataaat cacaggtgaa ttttggatga aaaaagaag    120 ag    122

<210> SEQ ID NO 20
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 20
cccaaaggaa gattccactt ggcgcaggca tcaggagtta tccaatgtga cttccaaaga    60
cgccttgaaa aggttttctg ctaacgaaac tcttcttagt caaatgagga accaaaagca    120
ga    122

<210> SEQ ID NO 21
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 21
gcccggggag ctaggggaca tgtgtgagca tgaggcctcc attgacctct ccgcctacat    60
cgagtctggg gaagagcagc ttctctccga tctctttgcc gtgaagccag cgcctgaggc    120
ca    122

<210> SEQ ID NO 22
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 22
tgagtatgtc tgggaaacac aagagtccca gaagattgag tggcctgcag atacgcatta    60
cggggtgtac atttgtattg tggagaagaa aagattttgt gccactctct tcagcctcca    120
ct    122

<210> SEQ ID NO 23
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 23
cagctgcagt ggaggcggcg gtgggaaagc ctggcccaca cacgtggtct gtagcgacag    60
cggcttggaa gtgctctacc agagttgcgg taagcccttg cagtacaccc atgtgtgttt    120
at    122

<210> SEQ ID NO 24
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 24

```
cagccccttg cccaaaccag ttctgcagag agcccaggcc cggctgttgc aggaaccttg    60
cgccaacctc catttccagg gaaaagctcc gttccccgac aaggacgatc ctctccggct   120
tc                                                                  122

<210> SEQ ID NO 25
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 25
tttctgtgct gggaattccc ttagctccag cctccactgg gcagtttatt atcttaattc    60
cgcatgaaga gtgtcctccc tcaccctcca ccctgccctg accagacct  ccagccgcga   120 ca                                                                  122

<210> SEQ ID NO 26
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 26
gagctaaggt caaagaaaga acctttaaa taaagggccc acactggctg ccagggagtg     60
cgcaggactg gcaagaggga agccgggctg ctccacgcct ttcacgcctt ccacctcctg   120
cg                                                                  122

<210> SEQ ID NO 27
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 27
ccgtcctcgt agtaaatgat gtcttggggc tgtggcccga gctgcctcag gtagatccca    60
cgcaggcccc cgctggtgga gcaggtgatg ttgacggagg ctcccacggg gacagtcgtg   120
ca                                                                  122

<210> SEQ ID NO 28
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 28
ggagagacac aaggcctggg agccgctttc ctggcctgcc gtgcagctga ggcactggca    60
cgcagcctaa gccaggcaca cttgcccatg ccctggaatg gagagccagt gacccagagt   120
ag                                                                  122

<210> SEQ ID NO 29
<211> LENGTH: 122
<212> TYPE: DNA
<213> ORGANISM: Artificial Sequence
<220> FEATURE:
<223> OTHER INFORMATION: The sequence has been designed and synthesized.
```

<400> SEQUENCE: 29

```
gctgatgctg ggggtgactc tgccaaacag ctactggcga gtgtccactg tgcacgggaa      60
cgtcatcacc accaacacca tcttcgagaa cctctggttt agctgtgcca ccgactccct     120
gg                                                                    122
```

<210> SEQ ID NO 30
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 30

```
gaggaaagga tcatggtagc cccttctgcg gggagcacac aacagtcttc agttcttctg      60
cggtgctcta ctcacaaaaa cacatctttc aactgaaatc atagttcgct caagatgttt     120
ct                                                                    122
```

<210> SEQ ID NO 31
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 31

```
tggcccggag ggcacccggg cagagacgga agaaattgca cgtgagcgtt tgtgtgcata      60
cgtgtgcctg tccatgtgtg cacacacttg tgcttgtgag tctctgtgtg cccatgcata     120
tg                                                                    122
```

<210> SEQ ID NO 32
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 32

```
aagtgtgggt aggagccggc cgctggcccc gctctgggct agacggtggg gacatactgg      60
cgggcaaaaa cagccctgtg cctgctctgc agctatgggg aaggaatatc tgttcatggc     120
ag                                                                    122
```

<210> SEQ ID NO 33
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 33

```
ttggtggcag cctcctaacc ttagccagaa ctattcctgc taagttcttg cacgagttga      60
cgctttgctg agcacagccg atacccagcc tttgcagcaa agatccttgg tcaaagggat     120
aa                                                                    122
```

<210> SEQ ID NO 34
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 34
ccagaaagtg atcctgcaga tggtgccgat tcatgagtgc ggctagtgag tccgatggag     60
cgcctcgcct agtgaatgct ccagcaagga ggtgtgtgtc tgtgtggtga acgtgtggtt    120
cc                                                                   122

<210> SEQ ID NO 35
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 35
gacaatgcta cttcagtttg gagcacaaac atatgatcag cacatggaaa tgtggtaatt     60
cggatgcatt cgtgattgca acagattgaa gaaattagac cagacaaaga gtgttttag    120 ag                                                                   122

<210> SEQ ID NO 36
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 36
ctccagccag gacccttcac aacctgattg ctaagcttgt tagcatagag gtggtctaac     60
cgctacatga gccgctcacc cctgacaacc acactgttgt aatgtatcag aaatgttgat    120
ta                                                                   122

<210> SEQ ID NO 37
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 37
cacgcggaaa caggtaaaaa tcattttgct tttattttgc attcaacaag caagttatta     60
cggaacagca gttatgggcc aggcatacct cccagagctg ggaacacagt ggggacctcc    120
ct                                                                   122

<210> SEQ ID NO 38
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 38
accttgtgat ccgcccacgt cagcctccca aagtgctggg attacaggcg taagccacag     60
cgcccagcct cgctgttctt atcttggcag cagattccga atgtcggctg gtgcccctgt    120
ca                                                                   122

<210> SEQ ID NO 39
<211> LENGTH: 122
<212> TYPE: DNA
<213> ORGANISM: Artificial Sequence
<220> FEATURE:

<223> OTHER INFORMATION: The sequence has been designed and synthesized.

<400> SEQUENCE: 39

```
aggctggatg gtgacacttc cacacccttg agtgggactg ccttgtgctg ctctgggatt    60
cgcacccagc ttggactacc cgctccacgg gccccaggaa aagctcgtac agataaggtc   120
ag                                                                  122
```

<210> SEQ ID NO 40
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 40

```
cagagttagc aaacctccat gctgactcta caaggtaatt tgccctgccg tgtggacaaa    60
cgctgcagat ctcatggaga gggcttgggc tctgccatgt gccatctgtg tgcaccaggg   120
ca                                                                  122
```

<210> SEQ ID NO 41
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 41

```
gcccatggct gggcagagaa atgtcaactc ctgggcttgc ctgggcactg atgcagcatt    60
cgcctgaggg caggaaacat ctgcctcaga aagtcacttg gggtgggaga aggaaatga   120
tg                                                                  122
```

<210> SEQ ID NO 42
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 42

```
attgcccagg tcctcagcta caaggaagct gtgcttcgtg ctatagatgg catcaaccag    60
cggtcctcgg atgctaacct ctaccgcctc ctggacctgg accccaggcc cacgatggtg   120
ag                                                                  122
```

<210> SEQ ID NO 43
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 43

```
gagaaacaac ctgcagtagg ctgggtcaca gaggcaatct gtgatttttt ggtcaggaca    60
cggaaacaaa tctcagttgg ggtatatgtg gacaaatgaa actggaaaca aaggttgctc   120
ct                                                                  122
```

<210> SEQ ID NO 44
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 44

```
acgcccgtcc tagtcccatc tcaggtgcgc acttgctgtg tgactttggg cccctctctg    60
cgctgcagtc agactccaaa gtcaggaacg tgagggctac catctctcaa gacatttcag   120
ct                                                                  122
```

<210> SEQ ID NO 45
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 45

```
gtgactcagg tggcaagtgc agtggggagc cccagctttt cccttcttgg atgcttcatt    60
cgcttgggc caccaaatat cgactgagga ctttctgccc atgccaggct ctgctctcgg   120
tg                                                                  122
```

<210> SEQ ID NO 46
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 46

```
ctaggaaact tcttccatat atcataaaca gagaccagta ttacaatact tcacccactg    60
cgccaatttg gctttcatgt ctgtttcctg tgtcgatcac aacatcctag acagcccaaa   120
ca                                                                  122
```

<210> SEQ ID NO 47
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 47

```
gctctccagg gggctgcgag gggctcatgg gatccccatg ggccaaggcc aggtggttga    60
cgtgagtttt tgtcagtgcg aaaacccag ccctcccttt atcaccctgc agacgtctag   120
gg                                                                  122
```

<210> SEQ ID NO 48
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 48

```
tgcccccaag caggccggga ctgccaggct ttacatcaga gaactgagtt tcagttacca    60
cggtgaaggc tgacagcaca gagcacagtt ccgtgcaaat caagacacat ttcccaagtc   120
cc                                                                  122
```

<210> SEQ ID NO 49
<211> LENGTH: 122
<212> TYPE: DNA

<213> ORGANISM: Artificial Sequence
<220> FEATURE:
<223> OTHER INFORMATION: The sequence has been designed and synthesized.

<400> SEQUENCE: 49

```
ccacccttaa agtcctcaga aggtgggaac tgaactggca caggatggga accggctgtg    60
cgctggccac ttgattttgc cagctgccct gtaattcagc tggtgaggaa actgaggcac   120
ag                                                                  122
```

<210> SEQ ID NO 50
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 50

```
tgatagccaa ttaggcttgg ggacctgcat gcccagcccc tgccttcctg gagcccatga    60
cgcaggggcc atccctgacc acagcagatt tcatcgagta cttgcttgtt gagtggtgga   120
gc                                                                  122
```

<210> SEQ ID NO 51
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 51

```
ctccagaggg gatggagagg cgcgactgtg ggagctggaa ggggcaccac ccggcaattg    60
cgggataaag caaatgctgc acacagagtg tgaaacttaa cctggttgag aattttcggc   120
ac                                                                  122
```

<210> SEQ ID NO 52
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 52

```
ctgacctcac cacccaccag ggaggtgggt cttattctgg gcatcgtgcc aagttcttag    60
cggggccctc tagaatctct aaagcaaatc aggctgaaga ggggaaaacc agcagggga   120 gg                                                                  122
```

<210> SEQ ID NO 53
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 53

```
gggttgttac cagcttttag ggaccagaaa acccaggtct gtctcacctg gacatgtgtc    60
cgcagcctgg gcaggcaggt tcttgatatg caggaacaag actagcagga cagcgagccc   120
cc                                                                  122
```

<210> SEQ ID NO 54
<211> LENGTH: 122

<212> TYPE: DNA
<213> ORGANISM: Artificial Sequence
<220> FEATURE:
<223> OTHER INFORMATION: The sequence has been designed and synthesized.

<400> SEQUENCE: 54

```
tcccttgcca gcttccctgg tgaccagcca ggacccaaat cacctgggtc ccctccccta    60
cgccctcctg caaagaggaa gtgctcatga acttcggccc tgccagggcc ttatcagagc   120
cc                                                                  122
```

<210> SEQ ID NO 55
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 55

```
aggctgagaa ggagcagagc aggggcagc cacatggctc tgccttcccg gctcctcgtc    60
cgcctgatct gcaaccagtg gcaaatgcag atcccagatg cactctggaa gttctgcctg   120
ag                                                                  122
```

<210> SEQ ID NO 56
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 56

```
accaactggg aggaagctta aatagccttg tctcaattga ggtctggttt gatggccaaa    60
cgagtttgct acagaatgct cagaattgca agcaagggt gtagagctgc ctctcttctg   120
tc                                                                  122
```

<210> SEQ ID NO 57
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 57

```
agtttgtttc tcaagcacac tgggagggtg agtggtgtag tccaggcctg aagatgaaat    60
cgctgataga catcaggtga caggaaatca gtagcttctg ctaccttggg cttcgctcca   120
at                                                                  122
```

<210> SEQ ID NO 58
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 58

```
aagcccagct gctggctgat aaatatttta tcactgctca cagagcagtc cccaggaagg    60
cgcctgcatc ctccaagccc acagagcacc ccttcctgcc cggacagaag gaactggcca   120
gg                                                                  122
```

<210> SEQ ID NO 59
```

```
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 59
aaggcccttt ggagtaactg cagcaatgag tgcccgggct gtgcttggag taccagtgct    60
cgcccggggc tatactgaat gagtaagcag ccccgtctgc ttttgctgtg caaaggtaag   120
gg                                                                  122

<210> SEQ ID NO 60
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 60
gaaatctgcc taatgagggt cgaggccagc acacacaggg acctatttgc agtaaaacaa    60
cgtggggtga cgcctaagaa atagacaaca ttaacacaaa gggagcctac tacgtagcac   120
at                                                                  122

<210> SEQ ID NO 61
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 61
tggccagcag cggctacaga gccgtcacta tggggaggga caggacttga ggggttgcct    60
cggtccacct cactggagaa tgggcagagt ttatggagtc tgaaccacct ggtctccagg   120
cc                                                                  122

<210> SEQ ID NO 62
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 62
tttctgaccc cgaaggctgt ggtgttcacc tggacagcag tagcttccca gtaaggcaca    60
cgccacgacg cgcaatatta tgcggccctt taggaggacg ttgccgaatg gtgtgtatcg   120
ac                                                                  122

<210> SEQ ID NO 63
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 63
agtgggccag cagtcgggcc agagtccagc tcagcaactc cgggttacag gcagcccagg    60
cgggcctagc caccggcagc tgcactcaga ggccactgtg tcctggctga gctcatctgc   120
ct                                                                  122
```

```
<210> SEQ ID NO 64
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 64
cggcaaagcc acgctcacct tcctgaaccg agccgaggat tacaccctta ccatgcccta    60
cgcccactgc aaaggtgaga ggctcagcca cacactccga gggcagagcc aggctctgtg   120
ag                                                                   122

<210> SEQ ID NO 65
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 65
gagctgcctc ggcgcacggc cactggcccg gctccaggcg gcgcagtctg gctgatgaca    60
cgagcgctgt tctcaccagc tgcctgagcc agtcagatgg aaaagtaatc ctatttgtgc   120
tt                                                                   122

<210> SEQ ID NO 66
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 66
taaagacaac aatttcacag ctctgatgat cagaaatgat gtaatggcca caggcggctc    60
cgcctgcgtc atccatgatt tcatcacaca cctcgggagg ctcagggtga cagacagtgc   120
at                                                                   122

<210> SEQ ID NO 67
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 67
aaaccaaagg gacttggagt gcagatggca tccttcggtt cttccagaca agctgcaaga    60
cgctgaccat ggccaaggta accggcttcc cctcctattg ctcaaaggat gcagtctaca   120
gc                                                                   122

<210> SEQ ID NO 68
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 68
agaagtggac acagcaggtc ttggctctta agatctgcag ttgtgagttc cttttgcaat    60
cgctgtaggt cattgtgcaa cctgctggtc tctggactcc tgatttctag acatctataa   120
aa                                                                   122
```

<210> SEQ ID NO 69
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 69
cccttcaaag cccgccttct tgccgtgtga tgctgcctgg gccagcaggg caggtcacca      60
cgctgtctct tcaaagcagc tcgctcatgc ccacagcgct gggcacaagg gcagccacga     120
gc                                                                    122

<210> SEQ ID NO 70
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 70
tcgggtacaa gagcatgaat ttgggcctcc ccaacatctg cagtgcaaaa tatttaacaa      60
cgggtgtggc acagcctctg accaacagcc agaacacaca caagccacac acagccatgc     120
ct                                                                    122

<210> SEQ ID NO 71
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 71
ttttccggtt tttgatcttt cttctgctta gtcggcgaac tggggtctgg ttccctctct      60
cgctctctcc tctggtccct cccttctccc acagcctctc ctccgtcccc gccccagtgc     120
cc                                                                    122

<210> SEQ ID NO 72
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 72
ccaggcccag acgagcgatt ggcggaggcc ggtcccgtga ccacgaattc cctgtaattt      60
cgctggagtc ctgggtttaa tagagagagt ccccatacgc ttgtatttat cagcaatata     120
ca                                                                    122

<210> SEQ ID NO 73
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 73
ctcacatgac ctggattgga acttggctca gccactgact agccagacaa actcaaataa      60
cgtacacagc ttctcagcac ctcaccccct cattcataaa aaacagggac aatggtaccc     120
ac                                                                    122

<210> SEQ ID NO 74
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 74

```
ctgtctgcat gcactggaat tgaggtctgt ggatgtgcct ttcctgacaa tatttcttca      60
cgcttgctgc ccactggtgc tgtgagggca caataacgaa tgtttacttt gcccttgcac     120
tc                                                                    122
```

<210> SEQ ID NO 75
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 75

```
tgagctaatt aatactagta atctacctgc aacagctgca gcgaggactc tgtgaggtca      60
cgtgggaagg agcttggcac agtgtcaagg acgcctcctt gaactgagct taggactctg     120
ga                                                                    122
```

<210> SEQ ID NO 76
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 76

```
ggaagtggac cctcgggtgc caggtttgca ggaatccact tccttgatgt cagtccttgg      60
cgccaagcct cagttgggta tcagaagcct tgctccatca gagatgggt cccagccatc     120 ag                                                                    122
```

<210> SEQ ID NO 77
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 77

```
ctgccagcaa cagcagtgac cttctggggc gggtcctgcc tggctggggt tcctctttct      60
cgctcctggg tcgagccccc actcccaggc tgcgcctccc tcttttctgg agaggtatct     120
tt                                                                    122
```

<210> SEQ ID NO 78
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 78

```
tgtgggtcct ggtctgcggt ctctcttgcc cctctgagtc cacgcccTgc agggaggtta      60
cgctttgtga tgtaattcag cacctgtgtc ttgtcccagt gaggacatct cccacttgcc     120
``` ag 122

<210> SEQ ID NO 79
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 79
ctttggttac cgaaaacagc ccggctggga ctgctgggct gggaacttag ctaagcagtg    60
cggaggctga accccaccat ctctgggatc cgcagcaaat cagaagcccc cacccacgat   120
aa 122

<210> SEQ ID NO 80
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 80
tgggggtgcc tggagtttgg ctggggctgg gtgcccagtg ggcgggcaca ggccccttga    60
cgtggctgtg gcctagctgg cagcctcgtc cttcctctcc gctaggcggg cactggagct   120
tt 122

<210> SEQ ID NO 81
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 81
cttcccagct tcctctgcct ggattcttag aggcctgggg tcctagaacg agctggtgca    60
cgtggcttcc caaagatctc tcagataatg agaggaaatg cagtcatcag tttgcagaag   120
gc 122

<210> SEQ ID NO 82
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 82
aggggcggga caggggtagg gtggcgcggt ggctgggcgc aaaggtcccg cagtgggcca    60
cgcaggcacc gggctgacct ggcaaaactt tggcgtctct gaaaacctct ggtaaccagc   120
tc 122

<210> SEQ ID NO 83
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 83
tgcctgccag gactgataag gggccctcct agggctccca caaacggttt atcggtttat    60
cgctggggga cagcctgcag gcttcaggag gggacacaag catggagcgg ctttggggtc   120

```
ta                                                                    122

<210> SEQ ID NO 84
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 84
cctccgcgac tacctgagct ccttcccctt ccagatttga ccggcagcgc ccgccgtgca     60
cgcagcatta actgggatgc cgtgttattt tgttattact tgcctggaac catgtgggta    120
cc                                                                    122

<210> SEQ ID NO 85
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 85
gacacacact ataatgatcc tttctatact ccttagccat tgaacgagag atcaaataaa     60
cgcagtaaca tccctcagat gcatgatttg agcatggctt ggaaagtatt agcagttacc    120
tg                                                                    122

<210> SEQ ID NO 86
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 86
gttgaacagg ccagttactg ggatgcagtt ctgcgtttcc cttgggtctc accttaacat     60
cgctcgctga agtgtgccca gattacagag cgggcaaagg gaagcagtgg ttttgctcac    120
ag                                                                    122

<210> SEQ ID NO 87
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 87
ttggtttttt tcaagagatg agaaaagaga tgtgccagtt gtgttgccaa atcacagtga     60
cgggccctgg tccagaaaag attttcatgt tacacaattg caggcttctg attttttttt    120
ct                                                                    122

<210> SEQ ID NO 88
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 88
cctggggcaa ggcccccttcc tgttcgggtg ttggctccgg aacttggttc tggggctgac     60
```

```
cgctgctggg gccccactta gtctgagtct gcagttaact ccgtgacccc aaggcatcca    120
ag                                                                   122

<210> SEQ ID NO 89
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 89
tgcttctcta ttctgttctc agtttcggcc acaggcctgg caacatcctt gactccttcg    60
cgccccttgt ccaagactcg gtgctgctgt cccatgtgtt tggtgtcact ctcgtgctct    120
gg                                                                   122

<210> SEQ ID NO 90
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 90
attggagccg gtggccacgg ccaaggagga tgctggcctg aagggggact tcagaagcta    60
cggggcagca gaccactatg ggcctgaccc cactaaggcc cggcctgcat cctcatttgc    120
cc                                                                   122

<210> SEQ ID NO 91
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 91
tgaaggaagg actcacgctg ctgggcgctg atcctctgac tcagacacag ccctggaaga    60
cgggagtaat gagacctgtt gcctcccagg cacaccgtga tcccattccc cttccacgcc    120
ag                                                                   122

<210> SEQ ID NO 92
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 92
tggagccagt ctagctgctg cacaggctgg ctggctggct ggctgctaag ggctgctcca    60
cgcttttgcc ggaggacaga gactgacatg gaacagggga agggcctggc tgtcctcatc    120
ct                                                                   122

<210> SEQ ID NO 93
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 93
agggcagctc tcacccaggc tgatagttcg gtgacctggc tttatctact ggatgagttc    60
```

-continued cgctgggaga tggaacatag cacgtttctc tctggcctgg tactggctac ccttctctcg    120
ca    122

<210> SEQ ID NO 94
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 94
ctgcctccca gcctctttct gagggaaagg acaagatgaa gtggaaggcg cttttcaccg    60
cggccatcct gcaggcacag ttgccgatta caggtagggc cgacgtgtcg acggcaggga    120
ac    122

<210> SEQ ID NO 95
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 95
ttggattatt agaagagaga ggtctgcggc ttccacaccg tacagcgtgg ttttcttct    60 cggtataaaa gcaaagttgt ttttgatacg tgacagtttc ccacaagcca ggctgatcct    120
tt    122

<210> SEQ ID NO 96
<211> LENGTH: 122
<212> TYPE: DNA
<213> ORGANISM: Artificial Sequence
<220> FEATURE:
<223> OTHER INFORMATION: The sequence has been designed and synthesized.

<400> SEQUENCE: 96
tcgatgaagc ccggcgcatc cggccgccat gacgtcaatg gcggaaaaat ctgggcaagt    60
cgggggctgt gacaacaggg cccagatgca gaccccgata tgaaaacata atctgtgtcc    120
ca    122

<210> SEQ ID NO 97
<211> LENGTH: 26
<212> TYPE: DNA
<213> ORGANISM: Artificial Sequence
<220> FEATURE:
<223> OTHER INFORMATION: The sequence has been designed and synthesized.

<400> SEQUENCE: 97
ttgtatgtat gtgagtgtgg gagaga    26

<210> SEQ ID NO 98
<211> LENGTH: 22
<212> TYPE: DNA
<213> ORGANISM: Artificial Sequence
<220> FEATURE:
<223> OTHER INFORMATION: The sequence has been designed and synthesized.

<400> SEQUENCE: 98
tttcttccac cccttctctt cc    22

<210> SEQ ID NO 99

<211> LENGTH: 18
<212> TYPE: DNA
<213> ORGANISM: Artificial Sequence
<220> FEATURE:
<223> OTHER INFORMATION: The sequence has been designed and synthesized.

<400> SEQUENCE: 99
ctccccctct aactctat					18

<210> SEQ ID NO 100
<211> LENGTH: 21
<212> TYPE: DNA
<213> ORGANISM: Artificial Sequence
<220> FEATURE:
<223> OTHER INFORMATION: The sequence has been designed and synthesized.

<400> SEQUENCE: 100
ggatggttgt ggtgaaaagt g					21

<210> SEQ ID NO 101
<211> LENGTH: 24
<212> TYPE: DNA
<213> ORGANISM: Artificial Sequence
<220> FEATURE:
<223> OTHER INFORMATION: The sequence has been designed and synthesized.

<400> SEQUENCE: 101
caaaaactcc ttttctccta acca				24

<210> SEQ ID NO 102
<211> LENGTH: 19
<212> TYPE: DNA
<213> ORGANISM: Artificial Sequence
<220> FEATURE:
<223> OTHER INFORMATION: The sequence has been designed and synthesized.

<400> SEQUENCE: 102
ccaaccacca ctacctcaa					19

<210> SEQ ID NO 103
<211> LENGTH: 23
<212> TYPE: DNA
<213> ORGANISM: Artificial Sequence
<220> FEATURE:
<223> OTHER INFORMATION: The sequence has been designed and synthesized.

<400> SEQUENCE: 103
gggttttgtt gttatagttt ttg				23

<210> SEQ ID NO 104
<211> LENGTH: 21
<212> TYPE: DNA
<213> ORGANISM: Artificial Sequence
<220> FEATURE:
<223> OTHER INFORMATION: The sequence has been designed and synthesized.

<400> SEQUENCE: 104
ttctcttcct ccataatatc a					21

<210> SEQ ID NO 105
<211> LENGTH: 19
<212> TYPE: DNA
<213> ORGANISM: Artificial Sequence
<220> FEATURE:
<223> OTHER INFORMATION: The sequence has been designed and synthesized.

<400> SEQUENCE: 105
caacacatcc aaccaccat                                              19

<210> SEQ ID NO 106
<211> LENGTH: 26
<212> TYPE: DNA
<213> ORGANISM: Artificial Sequence
<220> FEATURE:
<223> OTHER INFORMATION: The sequence has been designed and synthesized.

<400> SEQUENCE: 106
ttgtatgtat gtgagtgtgg gagaga                                     26

<210> SEQ ID NO 107
<211> LENGTH: 22
<212> TYPE: DNA
<213> ORGANISM: Artificial Sequence
<220> FEATURE:
<223> OTHER INFORMATION: The sequence has been designed and synthesized.

<400> SEQUENCE: 107
tttcttccac cccttctctt cc                                         22

<210> SEQ ID NO 108
<211> LENGTH: 28
<212> TYPE: DNA
<213> ORGANISM: Artificial Sequence
<220> FEATURE:
<223> OTHER INFORMATION: The sequence has been designed and synthesized.

<400> SEQUENCE: 108
catctgggcc ctgttgtcac agcccccg                                   28

<210> SEQ ID NO 109
<211> LENGTH: 24
<212> TYPE: DNA
<213> ORGANISM: Artificial Sequence
<220> FEATURE:
<223> OTHER INFORMATION: The sequence has been designed and synthesized.

<400> SEQUENCE: 109
cgacaccacg gaggaagaga agag                                       24

<210> SEQ ID NO 110
<211> LENGTH: 19
<212> TYPE: DNA
<213> ORGANISM: Artificial Sequence
<220> FEATURE:
<223> OTHER INFORMATION: The sequence has been designed and synthesized.

<400> SEQUENCE: 110
atggcggccg gatgcgccg                                             19

<210> SEQ ID NO 111
<211> LENGTH: 21
<212> TYPE: DNA
<213> ORGANISM: Artificial Sequence
<220> FEATURE:
<223> OTHER INFORMATION: The sequence has been designed and synthesized.

<400> SEQUENCE: 111
ggatggccgc ggtgaaaagc g                                          21

<210> SEQ ID NO 112
<211> LENGTH: 24
<212> TYPE: DNA

```
<213> ORGANISM: Artificial Sequence
<220> FEATURE:
<223> OTHER INFORMATION: The sequence has been designed and synthesized.

<400> SEQUENCE: 112
cggttaggag aaaaggagtc tctg                                          24

<210> SEQ ID NO 113
<211> LENGTH: 19
<212> TYPE: DNA
<213> ORGANISM: Artificial Sequence
<220> FEATURE:
<223> OTHER INFORMATION: The sequence has been designed and synthesized.

<400> SEQUENCE: 113
ctgaggcagc ggtggccgg                                                19

<210> SEQ ID NO 114
<211> LENGTH: 22
<212> TYPE: DNA
<213> ORGANISM: Artificial Sequence
<220> FEATURE:
<223> OTHER INFORMATION: The sequence has been designed and synthesized.

<400> SEQUENCE: 114
ggaagagaag gggtggaaga aa                                            22

<210> SEQ ID NO 115
<211> LENGTH: 18
<212> TYPE: DNA
<213> ORGANISM: Artificial Sequence
<220> FEATURE:
<223> OTHER INFORMATION: The sequence has been designed and synthesized.

<400> SEQUENCE: 115
atagagttag agggggag                                                 18

<210> SEQ ID NO 116
<211> LENGTH: 22
<212> TYPE: DNA
<213> ORGANISM: Artificial Sequence
<220> FEATURE:
<223> OTHER INFORMATION: The sequence has been designed and synthesized.

<400> SEQUENCE: 116
attaggttgg tagaatttga gt                                            22

<210> SEQ ID NO 117
<211> LENGTH: 17
<212> TYPE: DNA
<213> ORGANISM: Artificial Sequence
<220> FEATURE:
<223> OTHER INFORMATION: The sequence has been designed and synthesized.

<400> SEQUENCE: 117
cccattcccc ttccaca                                                  17

<210> SEQ ID NO 118
<211> LENGTH: 18
<212> TYPE: DNA
<213> ORGANISM: Artificial Sequence
<220> FEATURE:
<223> OTHER INFORMATION: The sequence has been designed and synthesized.

<400> SEQUENCE: 118
ctcaccaaca caaaacaa                                                 18
```

<210> SEQ ID NO 119
<211> LENGTH: 726
<212> TYPE: DNA
<213> ORGANISM: Artificial Sequence
<220> FEATURE:
<223> OTHER INFORMATION: The sequence has been designed and synthesized.

<400> SEQUENCE: 119

```
atgcacgagg aagaaatata cacctctctt cagtgggata gcccagcacc agacacttac      60
cagaaatgtc tgtcttccaa caaatgttca ggagcatgct gtcttgtgat ggtgatttca     120
tgtgttttct gcatgggatt attaacagca tccattttct gggcgtcaa gttgttgcag     180
gtgtccacca ttgcgatgca gcagcaagaa aaactcatcc aacaagagag ggcactgcta     240
aactttacag aatggaagag aagctgtgcc cttcagatga atattgcca agccttcatg     300
caaaactcat taagttcagc ccataacagc agtccttgtc aaacaattg gattcagaac     360
agagaaagtt gttactatgt ctctgaaatt tggagcattt ggcacaccag tcaagagaat     420
tgtttaaagg aaggttccac gctgctacaa atagagagca agaagaaat ggattttatc     480
actggcagct tgaggaagat taaaggaagc tatgattact gggtgggtt gtctcaggat     540
ggacacagcg gacgctggct ttggcaagat ggctcctctc cttctcctgg cctgttgcca     600
gcagagagat cccagtcagc taaccaagtc tgtggatacg tgaaaagcaa ttcccttctt     660
tcgtctaact gcagcacgtg gaagtatttt atctgtgaga agtatgcgtt gagatcctct     720
gtctga                                                                726
```

<210> SEQ ID NO 120
<211> LENGTH: 4928
<212> TYPE: DNA
<213> ORGANISM: Artificial Sequence
<220> FEATURE:
<223> OTHER INFORMATION: The sequence has been designed and synthesized.

<400> SEQUENCE: 120

```
aaacaggaag tcagtcagtt aagctggtgg cagcagccga ggccaccaag aggcaacggg      60
cggcaggttg cagtggaggg gcctccgctc ccctcggtgg tgtgtgggtc ctggggtgc     120
ctgccggccc ggccgaggag gcccacgccc accatggtcc cctgctggaa ccatggcaac     180
atcacccgct ccaaggcgga ggagctgctt tccaggacag caaggacgg agcttcctc     240
gtgcgtgcca gcgagtccat ctcccgggca tacgcgctct gcgtgctgta tcggaattgc     300
gtttacactt acagaattct gcccaatgaa gatgataaat tcactgttca ggcatccgaa     360
ggcgtctcca tgaggttctt caccaagctg accagctca tcgagtttta caagaaggaa     420
aacatggggc tggtgaccca tctgcaatac cctgtgccgc tggaggaaga ggacacaggc     480
gacgaccctg aggaggacac agtagaaagt gtcgtgtctc cacccgagct gccccccaaga     540
aacatcccgc tgactgccag ctcctgtgag gccaaggagg ttccttttc aaacgagaat     600
ccccgagcga ccgagaccag ccggccgagc ctctccgaga cattgttcca gcgactgcaa     660
agcatggaca ccagtgggct tccagaagag catcttaagg ccatccaaga ttattaagc     720
actcagctcg cccaggactc tgaatttgtg aagacaggg ccagcagtct tcctcacctg     780
aagaaactga ccacactgct ctgcaaggag ctctatggag aagtcatccg gaccctccca     840
tccctgagt ctctgcagag gttatttgac cagcagctct cccgggcct ccgtccacgt     900
cctcaggttc ctggtgaggc caatcccatc aacatggtgt ccaagctcag ccaactgaca     960
```

```
agcctgttgt catccattga agacaaggtc aaggccttgc tgcacgaggg tcctgagtct    1020
ccgcaccggc cctcccttat ccctccagtc acctttgagg tgaaggcaga gtctctgggg    1080
attcctcaga aaatgcagct caaagtcgac gttgagtctg ggaaactgat cattaagaag    1140
tccaaggatg gttctgagga caagttctac agccacaaga aaatcctgca gctcattaag    1200
tcacagaaat ttctgaataa gttggtgatc ttggtggaaa cagagaagga gaagatcctg    1260
cggaaggaat atgttttgc tgactccaaa agagagaag gcttctgcca gctcctgcag    1320
cagatgaaga acaagcactc agagcagccg gagcccgaca tgatcaccat cttcatcggc    1380
acctggaaca tgggtaacgc ccccctccc aagaagatca cgtcctggtt tctctccaag    1440
gggcagggaa agacgcggga cgactctgcg gactacatcc cccatgacat ttacgtgatc    1500
ggcacccaag aggaccccct gagtgagaag gagtggctgg agatcctcaa acactccctg    1560
caagaaatca ccagtgtgac tttaaaaca gtcgccatcc acacgctctg gaacatccgc    1620
atcgtggtgc tggccaagcc tgagcacgag aaccggatca gccacatctg tactgacaac    1680
gtgaagacag gcattgcaaa cacactgggg aacaagggag ccgtgggggt gtcgttcatg    1740
ttcaatggaa cctccttagg gttcgtcaac agccacttga cttcaggaag tgaaagaaa    1800 ctcaggcgaa accaaaacta tatgaacatt tccggttcc tggccctggg cgacaagaag    1860
ctgagtccct ttaacatcac tcaccgcttc acgcacctct tctggtttgg ggatcttaac    1920
taccgtgtgg atctgcctac ctgggaggca gaaaccatca tccagaaaat caagcagcag    1980
cagtacgcag acctcctgtc ccacgaccag ctgctcacag agaggaggga gcagaaggtc    2040
ttcctacact tcgaggagga agaaatcacg ttgccccaa cctaccgttt tgagagactg    2100
actcgggaca atacgccta caccaagcag aaagcgacag ggatgaagta caacttgcct    2160
tcctggtgtg accgagtcct ctggaagtct tatcccctgg tgcacgtggt gtgtcagtct    2220
tatggcagta ccagcgacat catgacgagt gaccacagcc ctgtctttgc cacattgag    2280 gcaggagtca cttcccagtt tgtctccaag aacggtcccg ggactgttga cagccaagga    2340
cagattgagt ttctcaggtg ctatgccaca ttgaagacca agtcccagac caaattctac    2400
ctggagttcc actcgagctg cttggagagt tttgtcaaga gtcaggaagg agaaaatgaa    2460
gaaggaagtg agggggagct ggtggtgaag tttggtgaga ctcttccaaa gctgaagccc    2520
attatctctg accctgagta cctgctagac cagcacatcc tcatcagcat caagtcctct    2580
gacagcgacg aatcctatgg cgagggctgc attgcccttc ggttagaggc cacagaaacg    2640
cagctgccca tctacacgcc tctcacccac catgggggagt tgacaggcca cttccagggg    2700
gagatcaagc tgcagacctc tcagggcaag acgagggaga agctctatga ctttgtgaag    2760
acggagcgtg atgaatccag tgggccaaag accctgaaga gcctcaccag ccacgacccc    2820
atgaagcagt gggaagtcac tagcagggcc cctccgtgca gtggctccag catcactgaa    2880
atcatcaacc ccaactacat gggagtgggg cctttgggc caccaatgcc cctgcacgtg    2940
aagcagacct tgtcccctga ccagcagccc acagcctgga gctacgacca gccgcccaag    3000
gactccccgc tggggccctg caggggagaa agtcctccga cacctcccgg ccagccgccc    3060
atatcaccca agaagttttt accctcaaca gcaaaccggg gtctccctcc caggacacag    3120
gagtcaaggc ccagtgacct ggggaagaac gcaggggaca cgctgcctca ggaggacctg    3180
ccgctgacga agcccgagat gttgagaac cccctgtatg ggtccctgag ttccttccct    3240
aagcctgctc ccaggaagga ccaggaatcc cccaaaatgc cgcggaagga accccgcccc    3300
tgcccggaac ccggcatctt gtcgcccagc atcgtgctca ccaaagccca ggaggctgat    3360
```

```
cgcggcgagg ggcccggcaa gcaggtgccc gcgccccggc tgcgctcctt cacgtgctca    3420
tcctctgccg agggcagggc ggccggcggg gacaagagcc aagggaagcc caagaccccg    3480
gtcagctccc aggccccggt gccggccaag aggcccatca agccttccag atcggaaatc    3540
aaccagcaga ccccgcccac cccgacgccg cggccgccgc tgccagtcaa gagcccggcg    3600
gtgctgcacc tccagcactc caagggccgc gactaccgcg acaacaccga gctcccgcat    3660
cacggcaagc accggccgga ggaggggcca ccagggcctc taggcaggac tgccatgcag    3720
tgaagccctc agtgagctgc cactgagtcg ggagcccaga ggaacggcgt gaagccactg    3780
gaccctctcc cgggacctcc tgctggctcc tcctgcccag cttcctatgc aaggctttgt    3840
gttttcagga aagggcctag cttctgtgtg gcccacagag ttcactgcct gtgagactta    3900
gcaccaagtg ctgaggctgg aagaaaaacg cacaccagac gggcaacaaa cagtctgggt    3960
ccccagctcg ctcttggtac ttgggacccc agtgcctcgt tgagggcgcc attctgaaga    4020
aaggaactgc agcgccgatt tgagggtgga gatatagata ataataatat taataataat    4080
aatggccaca tggatcgaac actcatgatg tgccaagtgc tgtgctaagt gctttacgaa    4140
cattcgtcat atcaggatga cctcgagagc tgaggctcta gccacctaaa accacgtgcc    4200
caaacccacc agtttaaaac ggtgtgtgtt cggaggggtg aaagcattaa gaagcccagt    4260
gccctcctgg agtgagacaa gggctcggcc ttaaggagct gaagagtctg ggtagcttgt    4320
ttagggtaca agaagcctgt tctgtccagc ttcagtgaca caagctgctt tagctaaagt    4380
cccgcgggtt ccggcatggc taggctgaga gcagggatct acctggcttc tcagttcttt    4440
ggttggaagg agcaggaaat cagctcctat tctccagtgg agagatctgg cctcagcttg    4500
ggctagagat gccaaggcct gtgccaggtt ccctgtgccc tcctcgaggt gggcagccat    4560
caccagccac agttaagcca agccccccaa catgtattcc atcgtgctgg tagaagagtc    4620
tttgctgttg ctcccgaaag ccgtgctctc cagcctggct gccagggagg gtgggcctct    4680
tggttccagg ctcttgaaat agtgcagcct tttcttccta tctctgtggc tttcagctct    4740
gcttccttgg ttattaggag aatagatggg tgatgtcttt ccttatgttg cttttttcaac    4800 atagcagaat taatgtaggg agctaaatcc agtggtgtgt gtgaatgcag aagggaatgc    4860
accccacatt cccatgatgg aagtctgcgt aaccaataaa ttgtgccttt ctcactcaaa    4920
aaaaaaaa                                                            4928
```

<210> SEQ ID NO 121
<211> LENGTH: 870
<212> TYPE: DNA
<213> ORGANISM: Artificial Sequence
<220> FEATURE:
<223> OTHER INFORMATION: The sequence has been designed and synthesized.

<400> SEQUENCE: 121

```
ctcgccctca aatgggaacg ctggcctggg actaaagcat agaccaccag gctgagtatc      60
ctgacctgag tcatccccag ggatcaggag cctccagcag ggaaccttcc attatattct     120
tcaagcaact tacagctgca ccgacagttg cgatgaaagt tctaatctct tccctcctcc     180
tgttgctgcc actaatgctg atgtccatgg tctctagcag cctgaatcca ggggtcgcca     240
gaggccacag ggaccgaggc caggcttcta ggagatggct ccaggaaggc ggccaagaat     300
gtgagtgcaa agattggttc ctgagagccc cgagaagaaa attcatgaca gtgtctgggc     360
tgccaaagaa gcagtgcccc tgtgatcatt tcaagggcaa tgtgaagaaa acaagacacc     420
```

| | |
|---|---|
| aaaggcacca cagaaagcca acaagcatt ccagagcctg ccagcaattt ctcaaacaat | 480 |
| gtcagctaag aagctttgct ctgcctttgt aggagctctg agcgcccact cttccaatta | 540 |
| aacattctca gccaagaaga cagtgagcac acctaccaga cactcttctt ctcccacctc | 600 |
| actctcccac tgtacccacc cctaaatcat tccagtgctc tcaaaaagca tgttttcaa | 660 |
| gatcattttg tttgttgctc tctctagtgt cttcttctct cgtcagtctt agcctgtgcc | 720 |
| ctccccttac ccaggcttag gcttaattac ctgaaagatt ccaggaaact gtagcttcct | 780 |
| agctagtgtc atttaacctt aaatgcaatc aggaaagtag caaacagaag tcaataaata | 840 |
| tttttaaatg tcaaaaaaaa aaaaaaaaa | 870 |

<210> SEQ ID NO 122
<211> LENGTH: 9648
<212> TYPE: DNA
<213> ORGANISM: Artificial Sequence
<220> FEATURE:
<223> OTHER INFORMATION: The sequence has been designed and synthesized.

<400> SEQUENCE: 122

| | |
|---|---|
| ggtttgtaat gatagggcgg cagcagcagc agcagcagca gtggtggaac gaggaggtgg | 60 |
| agaattgaga gcacgatgca tacacaggtg tttctgagta gtaattagat cgctgtgaag | 120 |
| gaaaaagcac acctttgagt tttcacctgt gaacactata gcgctgagag agacagtctg | 180 |
| aaagcagagg aagacatcga tcagtaacac caagagacac caaagttgaa agttttgttt | 240 |
| tctttccctc tgttttattt ttccccgtg tgtccctact atggtcagaa agcctgttgt | 300 |
| gtccaccatc tccaaaggag gttacctgca gggaaatgtt aacgggaggc tgccttccct | 360 |
| gggcaacaag gagccacctg gcaggagaa agtgcagctg aagaggaaag tcactttact | 420 |
| gaggggagtc tccattatca ttggcaccat cattggagca ggaatcttca tctctcctaa | 480 |
| gggcgtgctc cagaacacgg gcagcgtggg catgtctctg accatctgga cggtgtgtgg | 540 |
| ggtcctgtca ctatttggag cttttgtctta tgctgaattg ggaacaacta taagaaaatc | 600 |
| tggaggtcat tacacatata ttttggaagt ctttggtcca ttaccagctt ttgtacgagt | 660 |
| ctgggtggaa ctcctcataa tacgccctgc agctactgct gtgatatccc tggcatttgg | 720 |
| acgctacatt ctgaaccat ttttttattca atgtgaaatc cctgaacttg cgatcaagct | 780 |
| cattacagct gtgggcataa ctgtagtgat ggtcctaaat agcatgagtg tcagctggag | 840 |
| cgccccggatc cagattttct taaccttttg caagctcaca gcaattctga taattatagt | 900 |
| ccctggagtt atgcagctaa ttaaaggtca acgcagaac tttaaagacg ccttttcagg | 960 |
| aagagattca agtattacgc ggttgccact ggcttttat tatggaatgt atgcatatgc | 1020 |
| tggctggttt tacctcaact ttgttactga agaagtagaa aaccctgaaa aaaccattcc | 1080 |
| ccttgcaata tgtatatcca tggccattgt caccattggc tatgtgctga caaatgtggc | 1140 |
| ctactttacg accattaatg ctgaggagct gctgctttca aatgcagtgg cagtgacctt | 1200 |
| ttctgagcgg ctactgggaa atttctcatt agcagttccg atctttgttg ccctctcctg | 1260 |
| ctttggctcc atgaacggtg gtgtgtttgc tgtctccagg ttattctatg ttgcgtctcg | 1320 |
| agagggtcac cttccagaaa tcctctccat gattcatgtc cgcaagcaca ctcctctacc | 1380 |
| agctgttatt gttttgcacc ctttgacaat gataatgctc ttctctggag acctcgacag | 1440 |
| tcttttgaat ttcctcagtt ttgccaggtg gcttttatt gggctggcag ttgctgggct | 1500 |
| gatttatctt cgatacaaat gcccagatat gcatcgtcct ttcaaggtgc cactgttcat | 1560 |
| cccagctttg ttttccttca catgcctctt catggttgcc ctttccctct attcggaccc | 1620 |

```
atttagtaca gggattggct tcgtcatcac tctgactgga gtccctgcgt attatctctt   1680
tattatatgg gacaagaaac ccaggtggtt tagaataatg tcagagaaaa taaccagaac   1740
attacaaata atactggaag ttgtaccaga agaagataag ttatgaacta atggacttga   1800
gatcttggca atctgcccaa ggggagacac aaaatatggga tttttacttc attttctgaa   1860
agtctagaga attacaactt tggtgataaa caaaaggagt cagttatttt tattcatata   1920
ttttagcata ttcgaactaa tttctaagaa atttagttat aactctatgt agttatagaa   1980
agtgaatatg cagttattct atgagtcgca caattcttga gtctctgata cctacctatt   2040
ggggttagga gaaagactag gacaattact atgtggtcat tctctacaac atatgttagc   2100
acggcaaaga accttcaaat tgaagactga gatttttctg tatatatggg ttttgtaaag   2160
atggttttac acactataga tgtctatact gtgaaaagtg ttttcaattc tgaaaaaaag   2220
catacatcat gattatggca aagaggagag aaagaaattt attttacatt gacattgcat   2280
tgcttcccct tagataccaa tttagataac aaacactcat gctttaatgg attatacccca   2340
gagcactttg aacaaaggtc agtggggatt gttgaataca ttaaagaaga gtttctaggg   2400
gctactgttt atgagacaca tccaggagtt atgtttaagt aaaaatcctt gagaatttat   2460
tatgtcagat gttttttcat tcattatcag gaagttttag ttatctgtca tttttttttt   2520
tcacatcagt ttgatcagga aagtgtataa cacatcttag agcaagagtt agtttggtat   2580
taaatcctca ttagaacaac cacctgtttc actaataact taccctgat gagtctatct   2640
aaacatatgc attttaagcc ttcaaattac attatcaaca tgagagaaat caccaacaaa   2700
gaagatgttc aaaataatag tcccatatct gtaatcatat ctacatgcaa tgttagtaat   2760
tctgaagttt tttaaatttta tggctatttt tacacgatga tgaatttga cagtttgtgc   2820
attttctttta tacattttat attcttctgt taaaatatct cttcagatga aactgtccag   2880
attaattagg aaaaggcata tattaacata aaaattgcaa agaaatgtc gctgtaaata   2940
agatttacaa ctgatgtttc tagaaaattt ccacttctat atctaggctt tgtcagtaat   3000
ttccacacct taattatcat tcaacttgca aagagacaa ctgataagaa gaaaattgaa   3060
atgagaatct gtggataagt gtttgtgttc agaagatgtt gttttgccag tattagaaaa   3120
tactgtgagc cgggcatggt ggcttacatc tgtaatccca gcactttggg aggctgaggg   3180
ggtggatcac ctgaggtcgg gagttctaga ccagcctgac caacatggag aaaccccatc   3240
tctactaaaa atacaaaatt agctgggcat ggtggcacat gctggtaatc tcagctattg   3300
aggaggctga ggcaggagaa ttgcttgaac ccgggaggcg gaggttgcag tgagccaaga   3360
ttgcaccact gtactccagc ctgggtgaca aagtcagact ccatctccaa aaaaaaaga   3420
ttatatatat atatatatgt gtgtgtatgt gtgtgtgtgt gtgtgtgtgt atatatatat   3480
atatatatat acacacacac acacacactt tttatatata tatatatata tatatagtgg   3540
aacttacaaa tgagagtaat ataatgatga aattttgaac tgttatttat aaacatctaa   3600
ggtaaaatgg ttagtcatgg ccagagtatg tttcatcctt taattttgt ccatttgaaa   3660
ataaggattt ttgaaagaat tataccaatt aaaattatta aaggcaaaca tagaattcat   3720
aaaaaattgt ccaaagtaga aatgatgacc tataatttgg agcatttcca attcagtaat   3780
ttcaattttg ctcttgaaaa catttaatat atatccaaga ctgacatttc tttagctgaa   3840
cctaacgttt gggtctctga gtgaatttat aataactcct tccttcctta gcatagggtt   3900
ttcaaaattt gatttataat tcctatttcc agtaaatatt gttcatttgt ccacatctct   3960
```

```
ccctatgata tgttgctgga ggtaagaatt tctttcatat tcctatttt ttttcccca    4020 tagactaggc tcatagaatt taaacaagca aatttctg agcttttct tgccaaatga      4080 aagaagactg gtaaattctc atagagaggt tgtgtagtt cttggctctt cctggggtta    4140
atgtgcttat attcacagtg gcaaattggt ctcagacttt aatttattta tttttgattt   4200
gaatttctct ttaaaagtat caatttaaaa ggtaactaga attattcttt ctcattttca   4260
aaagtgattt ttgcattatt aaatttccct gccattgtaa tgccatttca cgcagaaaaa   4320
aagtcagcca gtaattaaga aaaaagtga tggagattaa gtagtatttt ggcttatttt    4380
taggactcat catgagaaga cacagttcct ttaatcagga aattaatatc cataatttc    4440 actcaaaatt gcagtatgta aagcagattc tcaaaaactc tcctgaacac ttatttatat   4500
atatgttttt ataaagtaa aattttctc atattttat acgatatgca cacacacaca     4560
tacatgcaca tactacttac tacatgttct gtacttgtac tttgtaccat gcatattcaa   4620
atgtttatat acataagttt attataacat aaacagtaaa agtaatgaat actgtttaaa   4680
ataactaata tagtatttt taattttgt ggggatggat tctcaaatac ttgtgatttt     4740 aaagattct aaagctaaaa cacaacttga ttttaaaaag aatgattctc cttacacaat    4800
tataaatatt tgcagtaaat attttcctta taatactgtt ttgaccccat ttaaaaagta   4860
ttagattata ttcctttgat ccaatgaaaa ctgaaccta taaatggtta gctgaaagta    4920
gaccttattc ttgtccttct ttagaagagt aaagattgt cctagggaag atggctgact    4980
tcggttccca acatgcgtat gcatttagac tgtagctcct cagccctgtg gacacaaat    5040 ttggacagct tattaggtta cgttagcaat gcatgacgtt ttctccaaca ctaagatatt   5100
cacgttgaaa cagattcct gttcgtctta tgtgtctggt aaaattgttt ccccaattac   5160
aatttgacat atcaatagag ggttaacaag agtataata cataacagaa ttcctcatga    5220
actgtaatca gtctacagga aaatcattat tttatcttga tttgcagatg aatatactgc   5280
taagaaaggg agcaactctg acctttgtta aagttgatct tttgtaattg aggtataagg   5340
tatgaaaaga taaaaaaccg aaggccagag aatcaggaaa tgaaagatag tatggactga   5400
aggtaacaat attttaatgt tatgcaatat agtcagagaa atattaaaaa ttagttgttt   5460
gctgtgcata ggtggatctc gcaggaagct aatgaaacct aagcttcagt gcctctcact   5520
tagacatgtt ccattcgagg tcctgaacct aactttgtat taggaattct gtactaattt   5580
tgttgaagaa gaccagcaaa gttgtgtaca cttctacccc cacaaaatct gcattgtcca   5640
tgtgagtaaa gtaaataat tcctgttatt ttttctgtt agaataagt atggaggata     5700 tgtttttaaa aatttatgag ttaattgaaa tatccatata taacaagtga ctttctcaca   5760
atatatatga tgtgatatat agggagatag tttcactttc atcatattt atacgttgat    5820 tctgaactat agaaaaataa taaatgggat tttaattata gctcttagtt gggaagaaa    5880 tatagagaga tgtgggattt gaatgcccat gaaagacatt ttattttact tgaatatatt   5940
cttgcttcac tttaccctcc ataatatgtt gtacattagt gctgatcaag tttacagagt   6000
tacattttgc tttcctaacc attcagtcag gaattaaaat atggcattgt ataacaactg   6060
ggaagaagct catagtggat ataaattaga gtagataatg ggtcaccttg atagcctctg   6120
tttacattac ttgtatatgg gcaaaataat tattacctat acgtgtattt aagcttaatt   6180
ttcatataaa cagtattttt aatctatgtt aaaatagata atatctaaaa gtgtgatctc   6240
taggtagtcc ttagttttatt agtactgtac ttcaaaaaga ttttaaata ggtccggcac    6300 ggtggctcat gcctgtaatc ccagcacttt gggaggctga ggcgggcgaa tcacctgagg   6360
```

```
tcaggagttc gagatcagcc tggccaacat ggtgaaaccc tgtctcaact aaaaatataa    6420
aaattagccg ggcgtggtgg caggcgcctg taatcccagc tactcgggag gctgaggcag    6480
gagaatcact tgaacccaag gggcagaagc tgcagttagc caagatcgca tcattgcact    6540
ccagcctagg gacaagagc gcgagacttc atctcaaaaa aaaaaaaaaa aaaaaaaaaa    6600
gatttttaaa taatagctaa aggtatgctc tctaggtcat ccttagttta ttagtactgt    6660
acttaaaaat tattttttaa tagtcaattt tgggagataa ttatttcttt ccttatattt    6720
tccaattagt tggtgtctaa aaataaatgt tttgtctaat tttagatcag gtatacattc    6780
acaaaagcat aaatcatagt ctcacaggaa attccaccaat tttccatatg tcgtgagata    6840
actgtccttt ctacaacctc ataacaatga atttatataa ttacctagat tttcttagtg    6900
tgaatctacc cattagtttt atttttcttgg tagttatttt tttccctcct ctctgttact    6960
attggcctta aaatacacag aggacggtta cagtgtccta atagctgtta catgtgtgtg    7020
tttcagcgta cttgaatcaa gtgtacattt atagtaccaa taaccgcctt tacagcttta    7080
cagttaacaa ttctctcaca aaactgtaga gcattaggca tctgagagcc atagagggcc    7140
aactttgttc cagagtgaac atgcttttttt tcctcaacat atacactact gattttttttt    7200 aaaagtatga ctttcaagtg aattaatgta ttggttagga gaactgcttg ctaagtcctt    7260
attacctctt gttaaagcct cagaaggccg tgctgaaagc cagaggggaa aaaaagagta    7320
atgcacaggt atctcttttg cagtggtgac tgtattttga gtaccttgtg tgacagggta    7380
ttattacagc atcttgtggg aaaacctatt aggcctttgc atgttaaagc tgtataattt    7440
gttgggttgt gagtggtctg acttaaatgt gtattataaa atttagacat caaattttcc    7500
tactaactaa ctttattaga tgcatacttg gaagcacagt catatcacac tgggaggcaa    7560
tgcaatgtgg ttacctggtc ctaggtttga actgtcttat ttcaaaagat ttctgaatta    7620 attttttccct agaatttctc cttcattcca aagtacaaac atactttgaa gaatgaaaca    7680
gattgttccc atgaatgtat gctcatactc gactagaaac gatctatgtt aaatgactgt    7740
gtatatgaat tatttcaagt actaccccaa ataactttct tattgctctg aaagaagaaa    7800
agcaatgtaa atcactatga ttattgcaca aacaaccaga attctccaac aatttttaagt    7860 aatctgatcc tcttcttgga gaaaattgtt acctaatagt ttttccttat gaatgttatt    7920
actactggta taaatcaaat ttctataaat ttcctactta agtcttaaga actgggttct    7980
tcctttgatg ttattcatgt tcagaaagga aacaacactt tactctttta ggacaattcc    8040
tagaatctat agtagtatca ggatatattt tgctttaaaa tatattttgg ttattttgaa    8100
tacagacatt ggctccaaat tttcatcttt gcacaatagt atgacttttc actagaactt    8160
ctcaacattt gggaactttg caaatatgag catcatatgt gttaaggctg tatcatttaa    8220
tgctatgaga tacattgttt tctccctatg ccaaacaggt gaacaaacgt agttgttttt    8280
tactgatact aaatgttggc tacctgtgat tttatagtat gcacatgtca gaaaaaggca    8340
agacaaatgg cctcttgtac tgaatacttc ggcaaactta ttgggtcttc attttctgac    8400
agacaggatt tgactcaata tttgtagagc ttgcgtagaa tggattacat ggtagtgatg    8460
cactggtaga aatggttttt agttattgac tcagaattca tctcaggatg aatctttttat    8520 gtctttttat tgtaagcata tctgaattta ctttataaag atggttttag aaagctttgt    8580
ctaaaaattt ggcctaggaa tggtaacttc attttcagtt gccaagggt agaaaaataa    8640 tatgtgtgtt gttatgttta tgttaacata ttattaggta ctatctatga atgtatttaa    8700
```

-continued

| | |
|---|---|
| atatttttca tattctgtga caagcattta aatttgcaa caagtggagt ccatttagcc | 8760 |
| cagtgggaaa gtcttggaac tcaggttacc cttgaaggat atgctggcag ccatctcttt | 8820 |
| gatctgtgct taaactgtaa tttatagacc agctaaatcc ctaacttgga tctggaatgc | 8880 |
| attagttatg accttgtacc attcccagaa tttcaggggc atcgtgggtt tggtctagtg | 8940 |
| attgaaaaca caagaacaga gagatccagc tgaaaagag tgatcctcaa tatcctaact | 9000 |
| aactggtcct caactcaagc agagtttctt cactctggca ctgtgatcat gaaacttagt | 9060 |
| agagggatt gtgtgtattt tatacaaatt taatacaatg tcttacattg ataaaattct | 9120 |
| taaagagcaa aactgcattt tatttctgca tccacattcc aatcatatta gaactaagat | 9180 |
| atttatctat gaagatataa atggtgcaga gagactttca tctgtggatt gcgttgtttc | 9240 |
| ttagggttcc tagcactgat gcctgcacaa gcatgtgata tgtgaaataa aatggattct | 9300 |
| tctatagcta aatgagttcc ctctggggag agttctggta ctgcaatcac aatgccagat | 9360 |
| ggtgtttatg ggctatttgt gtaagtaagt ggtaagatgc tatgaagtaa gtgtgtttgt | 9420 |
| tttcatctta tggaaactct tgatgcatgt gcttttgtat ggaataaatt ttggtgcaat | 9480 |
| atgatgtcat tcaactttgc attgaattga attttggttg tatttatatg tattataccct | 9540 |
| gtcacgcttc tagttgcttc aaccatttta taaccatttt tgtacatatt ttacttgaaa | 9600 |
| atattttaaa tggaaattta aataaacatt tgatagttta cataataa | 9648 |

<210> SEQ ID NO 123
<211> LENGTH: 1963
<212> TYPE: DNA
<213> ORGANISM: Artificial Sequence
<220> FEATURE:
<223> OTHER INFORMATION: The sequence has been designed and synthesized.
<220> FEATURE:
<221> NAME/KEY: misc_feature
<222> LOCATION: (1676)..(1676)
<223> OTHER INFORMATION: n is a, c, g, or t

<400> SEQUENCE: 123

| | |
|---|---|
| cagtccggcc gggcggagct aggggcgggc ccctgcgtct ctgggcgctg gagcgcggcg | 60 |
| actatcacgc cgcgtggcgg acggacggac tgacggacgc gcagccttac ccgaaaggcc | 120 |
| atggcggagc acgcccctcg ccgctgctgc ctgggctggg acttcagcac gcagcaggta | 180 |
| aaggttgttg ctgttgatgc agagttgaat gtcttctatg aggaaagtgt gcattttgac | 240 |
| agagatcttc cagaatttgg gcatgtactt gatgtgcatg gtgttcatgt gcacaaggat | 300 |
| gggctgacgg tcacttctcc agtactaatg tgggtccagg cactggatat catcttggag | 360 |
| aagatgaagg cttcgggctt cgaattctct caagtcctag ccttgtccgg ggcgggccag | 420 |
| caacacggaa gtatatactg gaaggctgga gcccagcagg cactgacaag cttatcacca | 480 |
| gacctccggc tacaccagca gcttcaggac tgtttctcca tcagcgactg cccggtgtgg | 540 |
| atggactcca gcaccacagc ccagtgccgc cagctggagg ctgctgtggg tggtgctcag | 600 |
| gctctcagct gcctcacggg gtcccgtgcc tatgagcgtt tacagggaa ccaaattgca | 660 |
| aaaatttacc agcagaaccc cgaggcctac tcacatacag agagaatttc tttggtcagt | 720 |
| agctttgctg cttccctgtt ccttggctct tactccccta ttgactacag tgatggttct | 780 |
| ggaatgaatt tgttgcagat acaggataaa gtctggtccc aggcttgcct tggtgcctgt | 840 |
| gcacctcatt tagaggagaa gcttagccca ccagtaccat catgctcagt tgtgggagcc | 900 |
| atttcttcct acaacgtcca gcgctacgga tttcctccag gatgcaaagt ggtggccttc | 960 |
| actggggaca acccagcgtc gctggcaggc atgagactgg aggaaggtga cattgcggtc | 1020 |

```
agcctgggca ccagtgacac cctgtttctc tggctccaag agcccatgcc tgccctggaa    1080
ggccacatct tctgcaaccc ggttgactcc cagcactaca tggcactcct gtgctttaaa    1140
aatggctccc tcatgagaga gaagatccgc aacgagtctg tatcccgttc ctggagcgat    1200
ttctctaagg cactgcagtc cacagagatg ggcaacggtg gaaacctggg tttttatttt    1260
gatgtaatgg agatcacccc tgaaattatt ggacgtcata ggtttaacac agaaaaccac    1320
aaggttgcag cattccctgg ggatgtggag gttcgagcac taattgaagg acaattcatg    1380
gccaagagga ttcacgcaga aggcctgggc tatcgagtca tgtccaagac aaagattttg    1440
gccacaggag gagcatctca aatagagaa atcttacagg tgcttgcaga tgtgtttgat    1500
gccccggtgt atgttataga cactgccaac tcggcctgtg tgggttctgc ataccgagct    1560
tttcatggtc ttgcaggtgg aacagatgtg ccctttcag aggttgtgaa gttagctcca    1620
aatcccagac tagctgctac cccaagcccg ggagcttctc aggtgagaga ccatcngaat    1680
ttgtttgtag catttgcatt atgaaagccc gctagggttt ttttccccac caaaaggtca    1740
cctacattga acgtgatgtg ctcaactaaa ggagaaattc tgctttattg aaattatcaa    1800
gaaaatggag ctaaagggcc atgttgtcag ctgcaagtca cagatactgc tgattttaca    1860
gccagggtca gatggattgc tgggcatatt tgtattgctt cttatgcctc acggtgggcc    1920
cttccatgtc actgggctat aaaagctact gaaaggatcc atc                      1963

<210> SEQ ID NO 124
<211> LENGTH: 1475
<212> TYPE: DNA
<213> ORGANISM: Artificial Sequence
<220> FEATURE:
<223> OTHER INFORMATION: The sequence has been designed and synthesized.

<400> SEQUENCE: 124
agagacagct gggccactgg cagtgaggga gagtgaggat ggcagagacc agtgccctgc      60
ccactggctt cggggagctc gaggtgctgg ctgtggggat ggtgctactg gtggaagctc     120
tctccggtct cagcctcaat accctgacca tcttctcttt ctgcaagacc ccggagctgc     180
ggactccctg ccacctactg gtgctgagct tggctcttgc ggacagtggg atcagcctga     240
atgccctcgt tgcagccaca tccagccttc tccgtgtctc ccacaggcgc tggccctacg     300
gctcggacgg ctgccaggct cacggcttcc agggcttttgt gacagcgttg gccagcatct     360
gcagcagtgc agccatcgca tggggcgtt atcaccacta ctgcacccgt agccagctgg     420 cctgaactc agccgtctct ctggtgctct tcgtgtggct gtcttctgcc ttctgggcag     480
ctctgcccct tctgggttgg ggtcactacg actatgagcc actgggaca tgctgcaccc     540 tggactactc caaggggggac agaaacttca ccagcttcct cttcaccatg tccttcttca     600
acttcgccat gccccctcttc atcacgatca cttcctacag tctcatggag cagaaactgg     660
ggaagagtgg ccatctccag gtaaacacca ctctgccagc aaggacgctg ctgctcggct     720
ggggccccta tgccatcctg tatctatacg cagtcatcgc agacgtgact tccatctccc     780
ccaaactgca gatggtgccc gccctcattg ccaaaatggt gcccacgatc aatgccatca     840
actatgccct gggcaatgag atggtctgca ggggaatctg gcagtgcctc tcaccgcaga     900
agagggagaa ggaccgaacc aagtgagcct gccaccctgg agtgagcccc aggccaggag     960
gctgttccag gagtcctgcc cagcagcctc agtggccaag cccagacact cacccacctt    1020
ccccagtggc cccgtggatc ctggtcctag gctggacaca ggattcagaa agacaccagg    1080
```

```
ctgcacagaa agagccagat ggacctgagt gtcggtcaca gcccctaca ctcaaggctg    1140 agaggcctca ggaaagtcat tccttttaa aataataat aaatgtaagg gggtacagtg     1200
cagttttgtt acatggatag attgcctagt ggtgaagtct gggcttttag tgtaaccatc   1260
accctaataa tatacgttgt acccattaag ttatttctca tccctcaccc cctcccacct   1320 tgtcacccctt ctgagtctcc aatgtctatt attccacact ccatgtccac gtgtacacat  1380
tatttagctc ccacttacaa gtgagaacat gtggtatttg actttctgtt tttgagttat   1440
ttcacttaaa ataatgacct ccagtttcat ccatg                              1475

<210> SEQ ID NO 125
<211> LENGTH: 2327
<212> TYPE: DNA
<213> ORGANISM: Artificial Sequence
<220> FEATURE:
<223> OTHER INFORMATION: The sequence has been designed and synthesized.

<400> SEQUENCE: 125
acatttcatt gtaaacgact gggagtatct gagcaaatta tttcttacgt gactttagag     60
aaaacggcta cctatctgac cccaaaacga cttgaggaaa ctgtttccac ggtcctgctg    120 cagggggaa gcacagtcgt caagaagaga gtggggtcag gatcaaaaca catttagtgt     180
gacttaggga agaaaaacat tttccctctt tgaacctctc tggatacagt cattttgcct    240
ctacttgagg atcaactgtt caacctcaat ggcctttcag gacctcctgg gtcacgctgg    300
tgacctgtgg agattccaga tccttcagac tgttttctc tcaatctttg ctgttgctac    360
ataccttcat tttatgctgg agaacttcac tgcattcata cctggccatc gctgctgggt    420
ccacatcctg gacaatgaca ctgtctctga caatgacact ggggccctca gccaagatgc    480
actcttgaga atctccatcc cactggactc aaacatgagg ccagagaagt gtcgtcgctt    540
tgttcatcct cagtggcagc tccttcacct gaatgggacc ttccccaaca caagtgacgc    600
agacatggag ccctgtgtgg atggctgggt gtatgacaga atctccttct catccaccat    660
cgtgactgag tgggatctgg tatgtgactc tcaatcactg acttcagtgg ctaaatttgt    720
attcatggct ggaatgatgg tgggaggcat cctaggcggt catttatcag acaggtttgg    780
gagaaggttc gtgctcagat ggtgttacct ccaggttgcc attgttggca cctgtgcagc    840
cttggctccc accttcctca tttactgctc actacgcttc ttgtctggga ttgctgcaat    900
gagcctcata acaaatacta ttatgttaat agccgagtgg gcaacacaca gattccaggc    960
catgggaatt acattgggaa tgtgcccttc tggtattgca tttatgaccc tggcaggcct   1020 ggctttttgcc attcgagact ggcatatcct ccagctggtg gtgtctgtac atactttgt   1080 gatctttctg acctcaagtt ggctgctaga gtctgctcgg tggctcatta tcaacaataa   1140
accagaggaa ggcttaaagg aacttagaaa agctgcacac aggagtggaa tgaagaatgc   1200
cagagacacc ctaaccctgg agattttgaa atccaccatg aaaaagaac tggaggcagc   1260 acaaaaaaaa aaaccttctc tgtgtgaaat gctccacatg cccaacatat gtaaaaggat  1320
ctccctcctg tcctttacga gatttgcaaa ctttatggcc tattttggcc ttaatctcca   1380
tgtccagcat ctggggaaca atgttttcct gttgcagact ctcttggtg cagtcatcct   1440 cctggccaac tgtgttgcac cttgggcact gaaatacatg aaccgtcgag caagccagat  1500
gcttctcatg ttcctactgg caatctgcct tctggccatc atatttgtgc cacaagaaat  1560
gcagacgctg cgtgaggttt tggcaacact gggcttagga gcgtctgctc ttgccaatac  1620
ccttgctttt gcccatggaa atgaagtaat tcccaccata atcagggcaa gagctatggg  1680
```

```
gatcaatgca accttttgcta atatagcagg agccctggct cccctcatga tgatcctaag    1740
tgtgtattct ccaccccctgc cctggatcat ctatggagtc ttccccttca tctctggctt    1800
tgctttcctc ctccttcctg aaaccaggaa caagcctctg tttgacacca tccaggatga    1860
gaaaaatgag agaaaagacc ccagagaacc aaagcaagag gatccgagag tggaagtgac    1920
gcagttttaa ggaattccag gagctgactg ccgatcaatg agccagatga agggaacaat    1980
caggactatt cctagacact agcaaaatct agaaaataaa taacaaggct gggtgcggtg    2040
gctcacgcct gtaatcccag caccttggga ggctgaggcg ggcagatcat gaggtcagaa    2100
gataaagacc accctggcca acatggtgaa accctgtctc tactaaaaca aatacaaaac    2160
ttcgctgggc acagtggcac aggcctttaa ttccagctac ttgggaggct gaggcaggag    2220
aattacttga acccaggagg tggaaattgc aatgagccaa gattgggcca ctgcattcca    2280
gcctggtgac agagcgagac tgtctcaaaa aaaaaaaaaa aaaaaaa               2327
```

<210> SEQ ID NO 126
<211> LENGTH: 638
<212> TYPE: DNA
<213> ORGANISM: Artificial Sequence
<220> FEATURE:
<223> OTHER INFORMATION: The sequence has been designed and synthesized.

<400> SEQUENCE: 126

```
ctccagacag acagaagaaa gggattcttt tcagtctaga aaaatgctca cccccttcctc     60 agaacatttc cactgtgacg aaaagagact gatgaagcct cagagagaaa ggcaactctg    120
ggtggtgatg caatagtgca gaatccagaa tggatgtcct ctttgtagcc atctttgctg    180
tgccacttat cctgggacaa gaatatgagg atgaagaaag actgggagag gatgaatatt    240
atcaggtggt ctattattat acagtcaccc ccagttatga tgactttagt gcagatttca    300
ccattgatta ctccatattt gagtcagagg acaggctgaa caggttggat aaggacataa    360
cagaagcaat agagactacc attagtcttg aaacagcacg tgcagaccat ccgaagcctg    420
taactgtgaa accagtaaca acggaaccta gtccagatct gaacgatgcc gtgtccagtt    480
tgcgaagtcc tattcccctc ctcctgtcgt gtgcctttgt tcaggtgggg atgtatttca    540
tgtagaaggt ggaagaaggc tgctatgact ctttggatgg gagtctggca agaggaaatt    600
ggaagataaa ataaataata agtgaaataa tctggtta                            638
```

<210> SEQ ID NO 127
<211> LENGTH: 1077
<212> TYPE: DNA
<213> ORGANISM: Artificial Sequence
<220> FEATURE:
<223> OTHER INFORMATION: The sequence has been designed and synthesized.

<400> SEQUENCE: 127

```
acgtatatac agagcctccc tggccctcct ggaaagagtc ctggaaagac aaccttcagg     60
tccagccctg gagctggagg agtggagccc cactctgaag acgcagcctt tctccaggtt    120
ctgtctctcc cattctgatt cttgacacca gatgcaggat ggtgtcctct ccctgcacgc    180
aggcaagctc acggacttgc tcccgtatcc tgggactgag ccttgggact gcagccctgt    240
ttgctgctgg ggccaacgtg gcactcctcc ttcctaactg ggatgtcacc tacctgttga    300
ggggcctcct tggcaggcat gccatgctgg gaactgggct ctggggagga ggcctcatgg    360
tactcactgc agctatcctc atctccttga tgggctggag atacggctgc ttcagtaaga    420
```

```
gtgggctctg tcgaagcgtg cttactgctc tgttgtcagg tggcctggct ttacttggag      480
ccctgatttg ctttgtcact tctggagttg ctctgaaaga tggtccttt tgcatgtttg       540
atgtttcatc cttcaatcag acacaagctt ggaaatatgg ttacccattc aaagacctgc      600
atagtaggaa ttatctgtat gaccgttcgc tctggaactc cgtctgcctg gagccctctg      660
cagctgttgt ctggcacgtg tccctcttct ccgcccttct gtgcatcagc ctgctccagc      720
ttctcctggt ggtcgttcat gtcatcaaca gcctcctggg ccttttctgc agcctctgcg      780
agaagtgaca ggcagaacct tcacttgcaa gcatgggtgt tttcatcatc ggctgtcttg      840
aatcctttct acaaggagtg ggtacgaatt ataaacaaac ttcccctta ggtatccctg       900
gagtaataat gacaacaaaa ttcactgcag gtcggtggaa tgatagaatg catttaaat      960
cacattgtaa acttccaggt gatccatgga taggataaat aactaagtta ttataattgt     1020
ttaggaatt  atagtccata aaatatcctc cagccaggga aaaaaaaa aaaaaaa         1077
```

<210> SEQ ID NO 128
<211> LENGTH: 4667
<212> TYPE: DNA
<213> ORGANISM: Artificial Sequence
<220> FEATURE:
<223> OTHER INFORMATION: The sequence has been designed and synthesized.

<400> SEQUENCE: 128

```
ccctagtttc agacccaagc tctgccagtc acttcctgtt caccctgagc aagctattaa       60
accattcgga gccccagttt ccacactggt aaaaatgaag ataaaatcag ccacctccta      120
gggttgttac gaggtgtaaa tgaaataaca atgagcctgg tacatcacag gtgctccctg      180
aattttagtt cctttgctcc cttttaccat cccagtagcc caggcagggg tgagcagcta      240
tgaggcgtgg cagcagtgga tggaagtgac aagggacaga tgaggatccc caggggaagg      300
gaggtggaga aagcaggaac caaatgtcat tcgtgcagcc actcccgatt tatgggatct      360
ggtgcagaga ctctttgaag aggcaataaa actcatattc tgctaggaaa tgacaacagt      420
ggagagtcct gacttagcaa accaaattca acgatttcat ttttttttt ttttacaag       480
gcatggggtt ccggatgggt agcaaaaatc acattctaat attagctatc tggggtagga      540
acaggctttc ccaagagcaa gagatgtgta ccatgccaac acccaatggt gagtgtacat      600
aaatgctcca tagaggcctt gagagtccag aacctgagct ccttgctaag ctgcaacctt      660
cctctgctag caccatggcc acccagacct gcaccctac cttctccact gggtctatca     720
agggcctctg tggcacagca ggcggcatct ctcgggtgtc ctccatccgt tctgtgggct      780
cctgcagggt ccccagtctc gccggtgctg cagggtacat ctcttctgct aggtcgggcc      840
tctctggcct tgggagctgc ttgcctggct cctacctgtc ttctgagtgc cacacctctg      900
gctttgtggg gagcggggc tggttctgcg agggctcctt caacggcagc gagaaggaga      960
ctatgcagtt cctgaacgac cgcctggcca actacctgga aaggtgcgt cagctggagc    1020
gggagaacgc ggagctggag agccgcatcc aggagtggta cgagtttcag atcccataca    1080
tctgcccaga ctaccagtcc tacttcaaga ccatcgaaga tttccagcag aaggtgaggg    1140
agacctggcc cctttccagc tgagcagccc aactcttagg aggcgtctgt ctcattccag    1200
ggcctttcca gatgggacgg tagcttttag ggaattctcc tggtagggca aacttttctc    1260
tctagggctt tggtttcctg ggggacccag gcttctctgc tggtctcttg cttgtacctt    1320
gttgccagcc gttcctcacc cccctcccct tgctgtagga agggaaggaa catgtaccaa    1380
gcccctaccg gatacagcac tgtgcctgac actttcctat tccctggctt atttattctt    1440
```

```
catcttggag agattggtat tactggaccc atctgacaga tgtggaagtt gaattttgag    1500
gggttcagca acttgctcaa gagcacacag gctcagtgtt agatgcagaa cctgaactca    1560
ggtctgcctc accctggtgt atcttgctgt gccactctga aggctacagg cgccaggact    1620
gatggtcact gacatcctcg ggatgcccct gtggggtgga tgctccccca cacctggggt    1680
gtggctcagg gctggaaatg tgaaggggc tggtggtaca cagtggcatg gcctctgtga    1740
gctgagctat cccctacct gcccccacac tgctgggcct cctgtagctt atgggaagcc    1800
tcttgttccc cagatcctgc tgactaagtc tgagaatgcc aggctggtcc tgcagattga    1860
taatgccaag ctggctgctg acgacttccg gaccaagtga gtgggcctga tcagggaagg    1920
tttgccatgc cactcccttg cctctgtccc ctgcctttgg gagctggtga tgtgggaata    1980
aggctggatg ggaaaatgtg gcatgagccc tggacctcag gggaaggag tgtcatgctc    2040 ctgatcccgt cagccactgc agctggacag tagggcaggg gtccctgctg gtgtgtggtt    2100
tcctttgctg cagacttggc agggttctgt gtgtgcaggt atgagacaga gctgtctctg    2160
cggcagctag tggaggccga catcaacggc ctgcgtagga tcctggatga gctgaccctg    2220
tgcaaggctg acctggaggc tcaggtggag tccctgaagg aggagctgat gtgcctcaag    2280
aagaatcacg aggaggtgag gctggtgcca tgtgacttcc cagtgtttcc catccagctt    2340
aggaagccac tgctgggctt tcagtttct gtgcggcagg aactatacaa aggccttgca    2400
tttcattctc gtttcatttc atccttacaa taatcccaag aattataaac tgttacaagc    2460
tccattttac agatgagaaa acttaggcac aaagaggtta agttgcttgc ctaaggtcat    2520
agagggtcta cacttttgcc cataacacta catgtctatt tgggctctag tgtcctgata    2580
acagcaattt aatttgccta gggtttgtat catctcacaa atatcccata gaaggaggta    2640
ggtatatacg gagaaggaga ccaaggctca gagatattta agtatcctgt ctaatgctat    2700
gcagctggtg actgagggaa gagggtttga attcaggtca ttgaaacctg caatccagca    2760 tcttttttcac aacctcatgc cgtcttgcct cctctctgca ggaagtcagt gtactccgtt    2820
gccaacttgg ggaccgactg aatgtggagg tggacgctgc tccccagtg gatctcaaca    2880 agatcctgga ggatatgaga tgccagtacg aggccctggt ggagaataac cgcagagatg    2940
tggaggcctg gttcaacacc caggtggggc tggggtgccc tgggaccaca ggctcctggg    3000
ctggggttac ccttggaagt agcttggttt gaccatgctc tgggccctgg catgtgtttc    3060
agactgagga gctgaaccag caggtggtgt ccagctcgga gcagctgcag tgctgccaga    3120
cggagatcat cgagctgaga cgtacggtca acgcgctaga gattgagctg caggctcagc    3180
acagcatggt gagtggcccc tgcctgcgtc gctggccacg gcctgtggca ggtccccgac    3240
gcaccagcct cagcgtgcag gctctcatgg ggtgtgatca caggtcgtag gcagatgccc    3300
agggctgtgg gtttctgggg tcaggggatt cctccccaat aggcagctct tcctctttcc    3360
cattgcagcg gaattccttg gaatccaccc tggccgaaac cgaggcccgc tacagctccc    3420
agctggccca gatgcagtgc ctgatcagca acgtggaggc ccagctgtct gagatccgct    3480
gcgacctgga gcggcagaac caggagtacc aggtgttact ggacgtcaag gcccggctgg    3540
agggcgagat cgctacctac cgccacctgc tggaggagga ggactgcaag tgagtggccc    3600
ttgggctggg gtagggcttg actgaaccct cagtgccatg tggagggcgt caagcccaga    3660
agtggttgtc gcccagatga agggaactaa accaaagccc cttgagattc tccatttagt    3720
cccaggcttt ggtaatgcac agcgggagaa tccaacccaa cacacgccgc gtgttttccg    3780
```

```
ccatcttttc tgattggcag tttctgctct tcattcctgt agctcagtcc tctcacccttt    3840 ggggaattca gaggcactga gatgatccgg ggccaccggt ctcgcttgat cctctagatc    3900
tgtttaacac gaatctcagc ccagtgctcc gatgccaaat gcaccctgca tgattttgtt    3960
tcctcaggct tcctcccaa ccttgtgcca cggcatgcaa gcctgttatt agagttcctt    4020 ctgtccccc ggtgccctgt gtccctctg tgccctgcac cccggctccc caggttggca    4080
ctcagatccg caccatcacc gaggagatca gagatgggaa agtcatctcc tccagggagc    4140
acgtgcagtc ccgcccgctg tgacagccca cttggtccac cagggcaggg ccctgaccac    4200
aggaaggagg acacccctgt ggctcctgga ggcttaacga ccctgccctt ctctagaggg    4260 gtcccctac gcttagcagg ttttctacc aaaacactcc ccgtattgtg tttccggact    4320
taactgtgct tttacgccat gcaaaaccag gtttcctgga aatttaccca ataaagtgtg    4380
ttctcctggc atagcaaact caaccctggc tgactctgtt gatgctcatg tgctcgtgtg    4440
gttcatgggg gtgtctgaca ggggctgcag tatagttgtg gggtttccat ttaggtctat    4500
cttctcgggc tctgagtggg aggcggtggc agggtgattt gaagtattta ataacaaaga    4560
tgcctcagag gctggccaat gagaacagac actgacccag tctggatggg tgcggccata    4620
gctctcagct tggccctgcc tgtgagtaga caccttaggg cggcccc                  4667

<210> SEQ ID NO 129
<211> LENGTH: 402
<212> TYPE: DNA
<213> ORGANISM: Artificial Sequence
<220> FEATURE:
<223> OTHER INFORMATION: The sequence has been designed and synthesized.

<400> SEQUENCE: 129
atggctcagt cactggctct gagcctcctt atcctggttc tggcctttgg catccccagg      60
acccaaggca gtgatggagg ggctcaggac tgttgcctca agtacagcca aggaagatt     120 cccgccaagg ttgtccgcag ctaccggaag caggaaccaa gcttaggctg ctccatccca    180
gctatcctgt tcttgccccg caagcgctct caggcagagc tatgtgcaga cccaaaggag    240
ctctgggtgc agcagctgat gcagcatctg gacaagacac catccccaca gaaaccagcc    300
cagggctgca ggaaggacag gggggcctcc aagactggca agaaaggaaa gggctccaaa    360
ggctgcaaga ggactgagcg gtcacagacc cctaaagggc ca                       402

<210> SEQ ID NO 130
<211> LENGTH: 3865
<212> TYPE: DNA
<213> ORGANISM: Artificial Sequence
<220> FEATURE:
<223> OTHER INFORMATION: The sequence has been designed and synthesized.

<400> SEQUENCE: 130
acagaacacg gggtgcctgg aaggggaaca gatgtgttgt ggggcacagg gcaggctggg      60
aggggaacaa aggtccactc catgggtaac cagacccttc cgccagggct ggccacttct     120
gcctttggaa aatgtttcac aacgccccat gttgtgtgtg tgtgtgaatc ggccgatgtg     180
aaccgaatgt tgatgtaaga ggcagggcac tcggctgcgg atgggtaaca gggcgtgggc    240
tggcacactt acttgcacca gtgcccagag aggggggtgca ggctgaggag ctgcccagag    300
caccgctcac actcccagag tacctgaagt cggcatttca atgacaggtg acaagggtcc    360
ccaaaggcta agcgggtcca gctatggttc catctccagc ccgaccagcc cgaccagccc    420
agggccacag caagcacctc ccagagagac ctacctgagt gagaagatcc ccatcccaga    480
```

```
cacaaaaccg ggcaccttca gcctgcggaa gctatgggcc ttcacggggc ctggcttcct    540
catgagcatt gctttcctgg acccaggaaa catcgagtca gatcttcagg ctggcgccgt    600
ggcgggattc aaacttctct gggtgctgct ctgggccacc gtgttgggct tgctctgcca    660
gcgactggct gcacgtctgg gcgtggtgac aggcaaggac ttgggcgagg tctgccatct    720
ctactaccct aaggtgcccc gcaccgtcct ctggctgacc atcgagctag ccattgtggg    780
ctccgacatg caggaagtca tcggcacggc cattgcattc aatctgctct cagctggacg    840
aatcccactc tggggtggcg tcctcatcac catcgtggac accttcttct tcctcttcct    900
cgataactac gggctgcgga agctggaagc tttttttgga ctccttataa ccattatggc    960
cttgaccttt ggctatgagt atgtggtggc gcgtcctgag cagggagcgc ttcttcgggg   1020
cctgttcctg ccctcgtgcc cgggctgcgg ccaccccgag ctgctgcagg cggtgggcat   1080
tgttggcgcc atcatcatgc cccacaacat ctacctgcac tcggccctgg tcaagtctcg   1140
agagatagac cggccccgcc gagcagacat cagagaagcc aacatgtact tcctgattga   1200
ggccaccatc gccctgtccg tctcctttat catcaacctc tttgtcatgg ctgtctttgg   1260
gcaggccttc taccagaaaa ccaaccaggc tgcgttcaac atctgtgcca acagcagcct   1320
ccacgactac gccaagatct tccccatgaa caacgccacc gtggccgtgg acatttacca   1380
gggggggcgtg atcctgggct gcctgttcgg ccccgcggcc ctctacatct gggccatagg   1440
tctcctggcg gctgggcaga gctccaccat gacgggcacc tacgcgggac agttcgtgat   1500
ggagggcttc ctgaggctgc ggtggtcacg cttcgcccgt gtcctcctca cccgctcctg   1560
cgccatcctg cccaccgtgc tcgtggctgt cttccgggac ctgagggact tgtcgggcct   1620
caatgatctg ctcaacgtgc tgcagagcct gctgctcccg ttcgccgtgc tgcccatcct   1680
cacgttcacc agcatgccca ccctcatgca ggagtttgcc aatggcctgc tgaacaaggt   1740
cgtcacctct tccatcatgg tgctagtctg cgccatcaac ctctacttcg tggtcagcta   1800
tctgcccagc ctgcccccacc ctgcctactt cggccttgca gccttgctgg ccgcagccta   1860
cctgggcctc agcacctacc tggtctggac ctgttgcctt gcccacggag ccacctttct   1920
ggcccacagc tcccaccacc acttcctgta tgggctcctt gaagaggacc agaaagggga   1980
gacctctggc taggcccaca ccagggcctg gctgggagtg gcatgtatga cgtgactggc   2040
ctgctggatg tggagggggc gcgtgcaggc agcaggatag agtgggacag ttcctgagac   2100
cagccaacct gggggcttta gggacctgct gtttcctagc gcagccatgt gattaccctc   2160
tgggtctcag tgtcctcatc tgtaaaatgg agacaccacc accttgcca tggaggttaa   2220
gcactttaac acagtgtctg cacttggga caaaacaaa caaacgaaaa acatttcaaa   2280
aggtatttat tgagcacctg caggcgtgac ctgacagccc aagggtgggt ggggtgaggg   2340
cttgaggact tgggcgggac acaggctcca aactggagct tgaaatagtg tctgatgaat   2400
gttaaattat ctatctatct atttatttat ttatttgaga cagggaaagg gtctccctct   2460
gttgccaagg ctggagtgca gtggcgcaat cttaactcat gcaacctcc accttctggg   2520
ttcaagcgat tctctttatt cagccccggg agtggcgcgc gccaccacgc ccagctaatt   2580
tgtgtatttt cagcagagac gggggtttgcc atgctggcca ggctggtctc gaactgctgg   2640
attcaagtga tccgcccatc tccgtctccc aaagtgctgg gaattacagg cgtgagccac   2700
caaacccggc ctgattaaag ttaaataaat actagttccc ttctcgtcca aggagcagg    2760
gaatgggaac cgggaaggca cgaagtctct aaagcatcca gaagacccct acaccagggt   2820
```

```
ctggtccgct cctattcgcc gcagcctttc tgttccgcct gcaacccatt ttccagacag    2880
taaaacggcg gcgcacttct ttctccgtca ggcaccaggt cataaggaac ccaagagtct    2940
gtgcctctga ggcccaaatt atttgctgtt tcctcagggg agccggcggc cgcgactccc    3000
acgccgcgcc gttaccgctc cctctctgct gactgctccc cctaggggca gagacggtcc    3060
cgacgcccgc catcccgccc cggcctcacc cctccccgcc aggcggaacg acgcggggag    3120
gcgggcgctc ggggctcgcg ccaggggccc cagaatcctt cggggagagt gggtgggagg    3180
aagctgtgtg ggcggggagc cccctctgcc ttagggagcg gctgggcacc cattcgcccc    3240
attcaggggc tgcactttat agacgttccc taggctgttt ctaggctccc ccaagtccct    3300
cctccagcct cgtcgggtcc ctcagacccc agcccaggac ctgcgagggg ccgcagcgag    3360
gagaggccaa caggcctttc cctagagttg aacctgggcc gggtgttgca cctggaagaa    3420
cccccgattt cctgggggacc cagcagggca ggcggcctgg ctccgcgctc aggtccggac    3480
gcttgtttat gagaagaatt tcctctttct taaagggca acgatgcgag tgggtccctc    3540
aaggagagaa gagatgggac cggtctggtg cgacctgggc aagcgctgca gagggtacct    3600
gggcaagagg gccgcccgcc tcctctgggt ttggcactgg agaagatggg tccatgccag    3660
ctgaaggagg agatggatgg gggacgttta gcgaagaaag gcatctccca gatcctttag    3720
cctcctggaa gtgccccgt tgtaccccct acacacccct cttggcattg agtgccagtc    3780
ctctgccagg ctctgtgtta caagttgggg agggcggcaa agtcccgaat taaagatgtc    3840
agttctcaag gaaaaaaaa aaaaa                                          3865

<210> SEQ ID NO 131
<211> LENGTH: 345
<212> TYPE: DNA
<213> ORGANISM: Artificial Sequence
<220> FEATURE:
<223> OTHER INFORMATION: The sequence has been designed and synthesized.

<400> SEQUENCE: 131
atggccgagt gcccgacact cggggaggca gtcaccgacc acccggaccg cctgtgggcc      60
tgggagaagt tcgtgtattt ggacgagaag cagcacgcct ggctgcccct aaccatcgag     120
ataaaggata ggttacagtt acgggtgctc ttgcgtcggg aagacgtcgt cctggggagg     180
cctatgaccc ccacccagat aggcccaagc ctgctgccta tcatgtggca gctctaccct     240
gatggacgat accgatcctc agactccagt ttctggcgct tagtgtacca catcaagatt     300
gacggcgtgg aggacgtgct ctctcgagctg ctgccagatg attaa                    345

<210> SEQ ID NO 132
<211> LENGTH: 1265
<212> TYPE: DNA
<213> ORGANISM: Artificial Sequence
<220> FEATURE:
<223> OTHER INFORMATION: The sequence has been designed and synthesized.

<400> SEQUENCE: 132
ctcggccccg cccccgcgcc ccggatatgc tgggacagcc cgcgccccta gaacgctttg      60
cgtcccgacg cccgcaggtc ctcgcggtgc gcaccgtttg cgacttggta cttggaaaaa     120
tggacaagga ttgtgaaatg aaacgcacca cactggacag cccttttgggg aagctggagc    180 tgtctggttg tgagcagggt ctgcacgaaa taaagctcct gggcaagggg acgtctgcag     240
ctgatgccgt ggaggtccca gccccgctg cggttctcgg aggtccggag ccctgatgc       300 agtgcacagc ctggctgaat gcctatttcc accagcccga ggctatcgaa gagttccccg     360
```

| | | |
|---|---|---|
| tgccggctct tcaccatccc gttttccagc aagagtcgtt caccagacag gtgttatgga | 420 | |
| agctgctgaa ggttgtgaaa ttcggagaag tgatttctta ccagcaatta gcagccctgg | 480 | |
| caggcaaccc caaagccgcg cgagcagtgg gaggagcaat gagaggcaat cctgtcccca | 540 | |
| tcctcatccc gtgccacaga gtggtctgca gcagcggagc cgtgggcaac tactccggag | 600 | |
| gactggccgt gaaggaatgg cttctggccc atgaaggcca ccggttgggg aagccaggct | 660 | |
| tgggagggag ctcaggtctg gcaggggcct ggctcaaggg agcgggagct acctcgggct | 720 | |
| ccccgcctgc tggccgaaac tgagtatgtg cagtaggatg gatgtttgag cgacacacac | 780 | |
| gtgtaacact gcatcggatg cggggcgtgg aggcaccgct gtattaaagg aagtggcagt | 840 | |
| gtcctgggaa caagcgtgtc tgcccttcct gtttccatat tttacagcag gatgagttca | 900 | |
| gacgcccgcg gtcctgcaca catttgtttc cttctctaac gctgcccttg ctctattttt | 960 | |
| catgtccatt aaaacaggcc aagtgagtgt ggaaggcctg gctcatgttg ggccacagcc | 1020 | |
| caggatgggg cagtctggca ccctcaggcc acagacggct gccatagccg ctgtccaggg | 1080 | |
| ccagctaagg cccatcccag gccgtccaca ctagaaagct ggccctgccc catccccacc | 1140 | |
| atgcctccct tcctggctgt gtccatggct gtgatggcat tctccactca gcagttccta | 1200 | |
| gcatcccaca cccaggtctc actgaaagaa aggggaacag gccatggcag tcagtgctta | 1260 | |
| cagag | 1265 | |

<210> SEQ ID NO 133
<211> LENGTH: 1916
<212> TYPE: DNA
<213> ORGANISM: Artificial Sequence
<220> FEATURE:
<223> OTHER INFORMATION: The sequence has been designed and synthesized.
<220> FEATURE:
<221> NAME/KEY: misc_feature
<222> LOCATION: (491)..(492)
<223> OTHER INFORMATION: n is a, c, g, or t
<220> FEATURE:
<221> NAME/KEY: misc_feature
<222> LOCATION: (612)..(613)
<223> OTHER INFORMATION: n is a, c, g, or t

<400> SEQUENCE: 133

| | | |
|---|---|---|
| ctagagcact tcaattagtg gtgaacaaca cggtctctac tccaaggggc tcacatcttg | 60 | |
| tgcagaaaac agaaatgaac aaataacaca caagatcatt tccgtggtag tgagagctgg | 120 | |
| gatgaaaata aaacagcgtg gcagggagga ggcaagtgtt gtgagtctgg agggttcctg | 180 | |
| gagaatgggg cctgaggcgt gaccaccgcc ttcctctctg gggggactgc ctgccgcccc | 240 | |
| cgcagacacc catggttgag tgccctccag gcccctgcct gccccagcat cccctgcgcg | 300 | |
| aagctgggtg ccccggagag tctgaccacc atgccacctc ctcgcctcct cttcttcctc | 360 | |
| ctcttcctca cccccatgga agtcaggccc gaggaacctc tagtggtgaa ggtggaaggt | 420 | |
| ggaaggtatg tccaaagggc agaaagggaa gggattgagg ctggaaactg agttgtggct | 480 | |
| gggtgtcctt nnctgagtaa cttaccctct ctaagcctcc attttcttat ttgtaaaatt | 540 | |
| catcaaaggg ttggaaggac tctgccggct cctccactcc cagcttttgg agtcctcgct | 600 | |
| ctataacctg gnntgtcagg agcacggggg gcttggaggt ccccccacc catggtctcc | 660 | |
| acagagggag ataacgctgt gctgcagtgc ctcaagggga cctcagatgg ccccactcag | 720 | |
| cagctgacct ggtctcggga gtccccgctt aaacccttct taaaactcag cctggggctg | 780 | |
| ccaggcctgg gaatccacat gaggccctg gcatcctggc ttttcatctt caacgtctct | 840 | |

```
caacagatgg ggggcttcta cctgtgccag ccggggcccc cctctgagaa ggcctggcag    900
cctggctgga cagtcaatgt ggagggcagc ggtgagggcc gggctgggc agggcagga    960 ggagagaagg gaggccacca tggacagaag aggtccgcgg ccacaatgga gctggagaga   1020
ggggctggag ggattgaggg cgaaactcgg agctaggtgg gcagactcct ggggcttcgt   1080
ggcttcagta tgagctgctt cctgtccctc tacctctcac tgtcttctct ctctctgcgg   1140
gtctttgtct ctatttatct ctgtctttga gtctctatct ctctccctct cctgggtgtc   1200
tctgcatttg gttctgggtc tcttcccagg ggagctgttc cggtggaatg tttcggacct   1260
aggtggcctg ggctgtggcc tgaagaacag gtcctcagag ggcccagct ccccttccgg    1320 gaagctcatg agccccaagc tgtatgtgtg ggccaaagac cgccctgaga tctgggaggg   1380
agagcctccg tgtgtcccac cgagggacag cctgaaccag agcctcagcc agggtatggt   1440
gatgactggg gagatgccgg gaagctgggg tccagagaca gagaggggag ggaaactgaa   1500
gaggtgaaac cctgaggatc aggctttcct tgtcttatct ctccctgtcc cagacctcac   1560 catgcccct ggctccacac tctggctgtc ctgtggggta cccctgact ctgtgtccag     1620 gggcccctc tcctggaccc atgtgcaccc caaggggcct aagtcattgc tgagcctaga    1680
gctgaaggac gatcgcccgg ccagagatat gtgggtaatg gagacgggtc tgttgttgcc   1740
ccgggccaca gctcaagacg ctggaaagta ttattgtcac cgtggcaacc tgaccatgtc   1800
attccacctg gagatcactg ctcggccagg tagagtttct ctcaactggg aggcatctgt   1860
gtgggggtac tgggaagaag tggagccagt caatcttaga ttcccccaac ccgagg       1916

<210> SEQ ID NO 134
<211> LENGTH: 1341
<212> TYPE: DNA
<213> ORGANISM: Artificial Sequence
<220> FEATURE:
<223> OTHER INFORMATION: The sequence has been designed and synthesized.

<400> SEQUENCE: 134
atgatcccca ccttcacggc tctgctctgc ctcgggctga gtctgggccc caggacccac     60
atgcaggcag ggcccctccc caaacccacc ctctgggctg agccaggctc tgtgatcagc    120
tgggggaact ctgtgaccat ctggtgtcag gggaccctgg aggctcggga gtaccgtctg    180
gataaagagg aaagcccagc accctgggac agacagaacc cactgagcc caagaacaag    240 gccagattct ccatcccatc catgacagag gactatgcag ggagataccg ctgttactat    300
cgcagccctg taggctggtc acagcccagt gaccccctgg agctggtgat gacaggagcc    360
tacagtaaac ccaccctttc agccctgccg agtcctcttg tgacctcagg aaagagcgtg    420
accctgctgt gtcagtcacg gagcccaatg gacactttcc ttctgatcaa ggagcgggca    480
gcccatcccc tactgcatct gagatcagag cacggagctc agcagcacca ggctgaattc    540
cccatgagtc ctgtgacctc agtgcacggg gggacctaca ggtgcttcag ctcacacggc    600
ttctcccact acctgctgtc acaccccagt gaccccctgg agctcatagt ctcaggatcc    660
ttggaggatc ccaggccctc acccacaagg tccgtctcaa cagctgcagg ccctgaggac    720
cagcccctca tgcctacagg gtcagtcccc acagtggtc tgagaaggca ctgggaggta    780
ctgatcgggg tcttggtggt ctccatcctg cttctctccc tcctcctctt cctcctcctc    840
caacactggc gtcagggaaa acacaggaca ttggcccaga acaggctga tttccaacgt    900 cctccagggg ctgccgagcc agagcccaag gacggggcc tacagaggag gtccagccca    960
gctgctgacg tccagggaga aaacttctgt gctgccgtga agaacacaca gcctgaggac   1020
```

```
ggggtggaaa tggacactcg gagcccacac gatgaagacc cccaggcagt gacgtatgcc      1080
aaggtgaaac actccagacc taggagagaa atggcctctc ctccctcccc actgtctggg      1140
gaattcctgg acacaaagga cagacaggca gaagaggaca gacagatgga cactgaggct      1200
gctgcatctg aagccccca ggatgtgacc tacgcccagc tgcacagctt taccctcaga      1260
cagaaggcaa ctgagcctcc tccatcccag gaaggggcct ctccagctga gcccagtgtc      1320
tatgccactc tggccatcca c                                                1341

<210> SEQ ID NO 135
<211> LENGTH: 458
<212> TYPE: DNA
<213> ORGANISM: Artificial Sequence
<220> FEATURE:
<223> OTHER INFORMATION: The sequence has been designed and synthesized.

<400> SEQUENCE: 135
tctacttgcc tgcctccctg cctctggcca tggcctgccg gtgcctcagc ttccttctga        60
tggggacctt cctgtcagtt tcccagacag tcctggccca gctggatgca ctgctggtct       120
tcccaggcca agtggctcaa ctctcctgca cgctcagccc ccagcacgtc accatcaggg       180
actacggtgt gtcctggtac cagcagcggg caggcagtgc ccctcgatat ctcctctact       240
accgctcgga ggaggatcac caccggcctg ctgacatccc cgatcgattc tcggcagcca       300
aggatgaggc ccacaatgcc tgtgtcctca ccattagtcc cgtgcagcct aagacgacg        360 cggattacta ctgctctgtt ggctacggct ttagtcccta ggggtggggt gtgagatggg       420
tgcctcccct ctgcctccca tttctgcccc tgaccttg                               458

<210> SEQ ID NO 136
<211> LENGTH: 2692
<212> TYPE: DNA
<213> ORGANISM: Artificial Sequence
<220> FEATURE:
<223> OTHER INFORMATION: The sequence has been designed and synthesized.

<400> SEQUENCE: 136
ccacgcgtcc ggggactaaa gcccagagag caagacagtt gggcttagaa ggagcagcca        60
gggcactgct tgagaaacca ggggagctca gtctgctatc gtacattagg cctgacgtta       120
aagggctttc aacgcttcag gatattgaaa taggagtgca gcatatttta gcagatatga       180
ttgctaaaga caaagacacg cttgacttca ttcggaactt gtgccagaag agacatgttt       240
gtatccagtc atctctggca aaagtatcct caaaaaaggt aaatgagaaa gatgttgata       300
agtttctgct ctaccagcat ttttcctgca acataagaaa cattcaccat catcagattc       360
tggcaattaa ccgtggagaa aatttgaagg tactgacggt taaggtcaat atttctgatg       420
gagtgaagga tgaattctgt aggtggtgca tccaaaacag gtggagacca cgtagctttg       480
caaggccaga gttaatgaag atcttatata attcactgaa tgattccttt aaacgcctta       540
tttatcctct tctctgtaga gaattcagag ccaaactaac atcagatgca gagaaggaat       600
cagtaatgat gtttggacgg aaccttcgtc agctcctttt aacaagccct gttccagggc       660
gcaccttaat gggagtggat cctggttata acatggttg caaattagct ataatttctc       720
ctactagtca gatacttcat actgatgtgg tttacttgca ttgtggacaa ggcttccgag       780
aggcggagaa aataaagaca cttttgctga atttcaactg cagcacagta gtgattggaa       840
atggaactgc ctgcagggaa acagaagctt actttgctga cctgataatg aagaattatt       900
```

```
ttgcaccact ggatgttgtt tactgtatcg tcagtgaagc aggagcatca atctacagtg    960
tcagccctga agctaacaaa gagatgccag ggctggaccc taatttgaga agtgcagttt   1020
ccatagcaag gcgtgtacaa gatccattag ctgagctagt gaaaattgag ccaaagcaca   1080
ttggagttgg aatgtatcag catgacgtat cccagacttt actcaaggca acactggaca   1140
gtgttgtaga agaatgtgtc agctttgtgg gagtggatat taacatctgt tcagaagttt   1200
tgttaaggca tattgcagga ctcaatgcca acagggccaa aaatattatt gaatggcgag   1260
agaaaaatgg acccttatc aaccgagaac agctgaagaa agtgaaaggg ctgggcccaa    1320
aatccttcca acagtgtgct ggcttcatca gaatcaacca ggattatatc cgaacgtttt   1380
gcagtcagca aactgaaact tcaggccaaa ttcaaggagt tgctgtgaca tcttcagcag   1440
acgttgaggt cacaaatgag aagcagggca aaagaagag caaaactgca gtgaatgttt    1500
tactgaagcc aaatcctttg gaccaaactt gtattcatcc agaatcatat gacatagcaa   1560
tgaggttttt gtcatccatt ggagggacac tgtatgaggt tggaaagcct gaaatgcaac   1620
aaaaaataaa ttcattcctt gaaaaggaag gaatggagaa aattgcagaa agattgcaaa   1680
caacagtaca caccttacag gtcatcatag atggtctcag ccagcctgaa agctttgact   1740
ttcgaacaga ttttgataaa cctgatttca agagaagcat agtatgcctg gaagatctgc   1800
agattgggac agttcttaca ggcaaagttg agaatgccac tctctttgga attttttgtgg   1860 atataggagt ggggaaatct gggctgattc ccatacgaaa tgtaacagaa gcaaaacttt   1920
caaaaacaaa gaagagaaga agccttggac tgggccccgg agaaagagtg aagtccaag    1980 tactcaacat tgacatcccc cgatctagga ttactctgga cctcattcgg gtgttatgag   2040
tatcccacga aggccagacg ctgatttat tttctcattt ccacagattg acaaggataa    2100
gtcagttgtt tgtaaactct aggtagcaga tgagaaataa ttcacttaat atcagaaata   2160
ttttccaaac actttccttt attttttctt ctgaataaat agaaaccaa cagtttgatt    2220 tccttttccc ttaaaggaaa caactaatac acattcttat atggctttat gtagtaatag   2280
ttttctgact aaaattttgt tttttatttt ttgtaattta tctttaactc cttttgcatt   2340
ttgtataaca gattgcttaa cttctacttg ccaacatctg ccttgctgga cttgtatggg   2400
attgtcttct tgatttgaat tgtaccgtct ttgttgacac agtagggctg ggcagtgttt   2460
aatccttcca ttttatagat tttttttta tcaggccttt tggacttcat tcataatttt    2520
gcaataatct ctttttccctt gtcatgcaag ccaaaaatat accagtaaaa cagattctga   2580
cgtgtttgta gttatcaaat gaatggctcg aaacacttct caaaaggata tacgtattga   2640
ccccaacaat aaatgtttgt ggctagtgaa aaaaaaaaa aaaaaaaaa aa               2692
```

<210> SEQ ID NO 137
<211> LENGTH: 6643
<212> TYPE: DNA
<213> ORGANISM: Artificial Sequence
<220> FEATURE:
<223> OTHER INFORMATION: The sequence has been designed and synthesized.

<400> SEQUENCE: 137

```
gtcgccccgt ggccccacaa tgacccacag ccccgcgaca agcgaggacg aggaacgcca     60
cagtgccagc gagtgtcccg aggggggctc agagtccgac agctccccag acgggccagg    120
tcgaggcccc cggggacccc ggggccaggg cagtggggca cctggtagcc tggcctctgt    180
tagaggcctc cagggccgct caatgtccgt cccagacgac gcccacttca gcatgatggt    240
cttcaggatt ggcatcccgg acctgcacca gacaaaatgc cttcgcttca accccgatgc    300
```

```
caccatctgg acggccaagc agcaggtgct ctgtgccctg agcgagagcc tgcaggatgt    360
gctcaactat ggcctgttcc aaccggccac ctccggccgc gatgccaact tcctggagga    420
ggagaggctg ctgcgggagt accccccagtc ctttgagaag ggggtcccct acctggagtt    480
ccgatacaag acccgagttt acaaacagac caacctggat gagaagcagc tggccaagtt    540
gcacacgaag acggggttga agaagttcct ggagtatgtg cagctcggga catctgacaa    600
ggtggcgcgg ctgctggaca aggggctgga ccccaattac catgactcgg attcgggaga    660
gacccccttg acactggcgg cccagaccga aggctctgta gaggtgattc gaaccctgtg    720
cctgggcggg gcccacattg acttccgggc cgggatggc atgaccgcac tgcataaggc    780
cgcatgcgcc cgacactgcc tggcactcac ggcgctcctg gaccttgggg gttcccccaa    840
ctacaaggac cgtcggggc tgacccctct gttccacacg gccatggtgg gtggtgaccc    900
ccgatgctgc gagctgctcc tgttcaacag ggcccagctg gcatagctg atgagaacgg    960 ctggcaggaa atccaccagg cctgccacgc gggtcactct cagcacctgg agcatctgct   1020
tttctacggg gctgagcctg gagcccagaa cgcctcgggg aacacggctc tgcacatctg   1080
cgccctctac aacaaggaga cctgtgccag gatcctcctg tatcgaggtg ccgacaagga   1140
tgtgaagaac aacaacggac agaccccctt ccaggtggca gtgattgctg gaattttga   1200 gctgggggag ctgatccgaa accaccgaga acaggatgtg gtgcccttcc aggagtcccc   1260
caagtacgcg gcccggcgac ggggggcccc aggcacaggg ctgacggtgc ccccggcgct   1320
gctgcgggcc aacagtgaca ccagcatggc gctgcccgac tggatggtgt tctccgcccc   1380 ggggggccgcg tcctctgggg cccctggccc tacctcaggg tcccagggcc agtcgcagcc   1440
ctcggccccc accaccaagc tcagcagcgg gaccctccga agtgccagca gcccccgggg   1500
tgccagggcc cgctctccat cccgagggag gcaccctgag gacgccaaga gcagccccg   1560 aggccggccc agctccagcg ggacaccccg ggaagggcca gccggggca cgggggctc   1620 agggggcccc ggggctccc tgggcagccg cgggaggcgg aggaagctct actcagcggt   1680 accccggacgc tccttcatgg ctgtgaagtc ctaccaggcc caagccgagg gggagatctc   1740
cctgagcaag ggcgagaaga tcaaagtact tagcatcggg gaaggaggct ctgggaagg   1800 ccaggtcaaa ggtcgtgttg gctggttccc ctctgactgc ctggaagaag tggcgaatcg   1860
ctctcaggag agcaagcaag aaagccgcag tgacaaggca aagagactct ccggcatta   1920 taccgtgggc tcctacgaca gctttgatgc ccaagcttta atggatggga ttggcccagg   1980
gagcgattac atcattaagg agaagacagt cttgctgcag aagaaggaca gtgaggggtt   2040
tgggttcgtg ctccggggg ccaaggcgca gaccccatc gaggagttca ccccccacccc   2100 ggccttcccg gcgctgcagt acctggagtc ggtggacgag ggtggcgtgg catggcgagc   2160
tggactgcga atgggagact tcctcatcga ggtgaacggg cagaatgtgg tgaaggtcgg   2220
ccaccgacag gtggtgaaca tgatccgcca aggggcaac acgctgatgg tgaaggtggt   2280
gatggtcacc aggcacccgg acatggatga ggcagtgcac aagaaagcac cccagcaggc   2340
caagcggctg ccgcccccaa ccatctccct gcgttccaaa tctatgacct cagagctgga   2400
ggagatggag tacgagcagc agccggcgcc ggtgcccagc atggagaaaa agcggaccgt   2460
gtatcagatg gctctcaaca aactggacga atcctggcc gcagctcaac agaccatcag   2520
tgcaagcgaa agcctggtc ccggtggcct cgcgtccctg gcaaacacc gacccaaagg   2580 tttctttgcc actgagtcga gcttcgatcc ccaccaccgt gcccagccaa gttacgagcg   2640
```

```
tccttctttc ctgcctccag gacctgggtt gatgctccgg caaaaatcta tcggtgcggc    2700
agaagatgac agaccttacc tagcaccccc agccatgaaa ttcagccgca gcctgtctgt    2760
gcctggttcg gaggacattc ccccgccacc caccacgtcc ccaccggagc ctccctacag    2820
cacacctcca gtccctcct cctcaggcg cctcaccccc tccctcggg agggccctt       2880 caaccctggc tctggtggcc ccctccccgc ctcctcccct gcatcctttg acgggccctc    2940
ccctcccgac actcgcgtgg ggagccgcga aagagcctg taccacagtg ggcccctgcc    3000
cccggcccac caccacccgc cccaccacca ccaccaccac gccccgcccc ctcagcccca    3060
ccaccaccac gcccaccccc ctcatcctcc cgagatggag acaggcggct ctcccgacga    3120
ccctccaccc cgcctggctc tggggcccca gcccagcctg cgaggctgga ggggcggcgg    3180
gcccagcccg accccggggg cccgtcccc atcgcaccac ggcagcgcgg cggggcgg     3240 cggctcctcc cagggcccgg ctctacgcta tttccagctg ccccgcggg cggccagcgc    3300 agccatgtac gtgcccgccc gctcgggccg cggccgcaag ggcccgctgg tcaagcagac    3360
caaggtggaa ggcgagcccc agaagggcgg cggcctcccg ccgcgccgt cgcccacgtc    3420 cccggcctcc ccgcagccgc cgcccgccgt ggccgcgccc tcggagaaga actccatccc    3480
catccccacc atcatcatca aggccccgtc caccagtagc agcggccgca gcagccaggg    3540
cagcagcacc gaggcggagc ccccaccca gccggagccc acgggaggcg gcggcggcgg    3600
cggctcctcg cccagccccg cccggccat gtcacccgtg ccccgtccc cctgcccgt     3660 gcccaccccc gcctcgccca gcggccggc cacgctggac ttcacgagcc agttcggggc    3720
cgccctggtg ggggcggccc ggagggaggg gggctggcag aatgaggcgc gccggcgctc    3780
cacgctgttc ctgtccaccg acgcgggga cgaggacggc ggggacggcg ggctgggcac    3840
aggggcggcc ccgggcccgc ggctgcgcca ctccaaatcc atcgacgagg gcatgttctc    3900
cgccgagccc tacctccgac tggagtctgc gggcagcggc gcgggctacg gcggctacgg    3960
ggccggtagc cgagcctacg ggggtggcgg ggcagcagc gccttcacca gcttcctgcc    4020
cccgcgaccc ctggtgcacc cgctgaccgg caaggccctg gatcccgcct cccgctggg    4080 gctggccctg gccgccgcg agcgagcgct gaaggagtcc tcgagggcg gcggggcccc    4140 ccagccgcct cccaggcccc catcgccccg ctacgaggcc ccgccgccca cccgcacca    4200 ccactcgccc cacgcccacc acgagccagt gctgcgtctc tgggggggcct ccccgccgga    4260 ccctgcgcgc cgggagctgg ggtacagggc cgggctgggc agccaggaga agtcccttcc    4320
cgccagcccg cccgccgccc ggcgttccct gctacaccgc ctgccgccca ccgctcccgg    4380
ggtggggccc ctcctgctgc agctggggac ggagcccccg gccccgcacc ccggagtaag    4440
caagccctgg aggtccgcag cccccgaaga acccgagcgg ctgccgctgc acgtgcggtt    4500
ccttgaaaac tgccagcccc gggcccctgt gacgagcgga aggggtcccc cctcggagga    4560
cgggccgggg gtcccgccgc ccagcccacg ccggtccgtg ccccctccc cgacctcccc    4620 gagggccagc gaagagaacg ggctgcccct gctggtcctg ccgcctcccg cccctcggt    4680 ggatgtggaa gatggcgaat tcctttttcgt ggaaccgctg cctccgcctc tggaattctc    4740
caacagcttc gaaaagccag agtcgcccct cacgcctggg cctccccacc cgctgccga    4800 cacacctgcc cctgccaccc cgttaccccc tgtgccaccc ccggctgtgg ccgcagcccc    4860
tcccaccctg gactccaccg catccagcct gacatcctat gacagcgagg tggccaccct    4920
gacccagggg gcctccgccg ctcctgggga ccccatccc caggcccgc ctgccccagc    4980 agcaccggct cccgctgccc cacagcctgg cccggaccct ccgctggca cggattctgg    5040
```

```
catcgaggag gtggacagtc ggagcagcag tgaccaccca ctggagacca tcagcagcgc    5100
ctccacgctg agcagcctat ctgccgaagg tggtggcagc gcaggggctg ggggcgggggc   5160 tgggccggt gtggccagtg ggccggagct tctggacacc tatgtggcct acctggacgg     5220
ccaggccttt gggggcagca gtactcccgg cccgccatac cctcctcagc tcatgactcc    5280
ctctaagctc cggggccggg cgctaggagc cagcggaggc ctgcggcctg ccccagcgg    5340 gggactccga gaccctgtta ccccaccag ccccaccgtc tcggtgacag gggctggaac    5400
cgatgggctg ctgccctgc gtgcttgttc aggaccccc acggcaggcg tggcgggggg     5460
tccggtggct gtagagccag aagtcccacc ggtgcccttg ccgacggcct cctctctgcc    5520
ccggaagctg ctgccctggg aggagggccc gggcccaccg ccaccacctc tgcccgggcc    5580
cttggcccag cctcaggcct cagccttggc cacagtaaaa gccagcatca tcagtgaact    5640
cagctccaag cttcagcagt ttgggggctc ctcggcagct ggcggcgctc tgccctgggc    5700
ccgaggaggc agtgggggag gcggagacag ccaccacggg ggagccagct atgtccccga    5760
gaggacctcc tccctgcagc ggcagagact ctccgacgac tcccagtcct cactcctctc    5820
caagcctgtc agcagcctgt ttcagaactg gcccaaacca cctctgccgc cactccccac    5880
cggaacaggg gtctcccta cagccgctgc ggccccaggg gccacctcac cctcagcctc    5940
ctcctcctcc acgtccaccc gccacctcca gggcgtggag ttcgagatgc ggcccccttct   6000 gctccgccgg gccccccagcc cctcgctgct gcccgcctcg gagcacaagg tcagccctgc    6060
gcccaggccc tcgtccctgc ccatcctgcc ttccggaccc ctctacccag gcctctttga    6120
catccgtggc tccccaactg gaggggcagg aggctcggct gaccccttcg ccccagtctt    6180
tgtgccgcca caccggggga tatccgggggg gctcggggga gccttgtcag gggcctcgcg    6240
ctccctctca ccgacccgcc tgctctcgct gccccggac aagccgtttg gcgctaaacc    6300
tctggggttc tggaccaagt cgacgtggc tgattggctg gagtggctgg gtttggcgga    6360
gcaccgagcc cagttcctgg accacgagat cgatggctcc cacctgcccg ccttgaccaa    6420
ggaggactac gtcgatctag gtgtgaccag ggtgggccac cgcatgaaca tcgaccgggc    6480
tctcaaattc ttcctggaga ggtgatggct ggcctgacg gaccagcccc gtccacagaa     6540
ctcttgagcc tgctggcctc ttgacctctg accctgact gtcattctct ccccgggcca    6600
gggactctgt tcaaactgcg ccctgccctc atctcccaag gcc                      6643
```

<210> SEQ ID NO 138
<211> LENGTH: 3318
<212> TYPE: DNA
<213> ORGANISM: Artificial Sequence
<220> FEATURE:
<223> OTHER INFORMATION: The sequence has been designed and synthesized.

<400> SEQUENCE: 138

```
gtccttccca gggtgtgtta gcgtctctcc tacggcgccc gcctagcccg gtggtcccaa    60
ccccctgcgg gagctgcaca cgccccggaa acctgggaca gaaactgagt ccctctcctt    120
cctggtggtg gtgacagcac ctgctcagat ctggtcggac ccgccggcc ggagcaccca    180 gcccggcgga gaaggagctc gcccggcgct ggggactggg acctggagcc ccttccccta    240
ccgcacgtac gccccgcccc ggcacgcccc ggcccgccgc ccgcgcctgg cgcagcttca    300
ctccggatgt ttcctgtcct cccgcgggtc cgagggcgct ggaaacccag cggcggcgaa    360
gcggagagga gccccgcgcg tctccgcccg cacggctcca ggtctggggt ctgcgctgga    420
```

```
gccgcgcggg gagaggccgt ctctgcgacc gccgcgcccg ctcccgaccg tccgggtccg    480
cggccagccc ggccaccagc catgggctct ggcccgctct cgctgcccct ggcgctgtcg    540
ccgccgcggc tgctgctgct gctgctgctg tctctgctgc cagtggccag ggcctcagag    600
gctgagcacc gtctatttga gcggctgttt gaagattaca atgagatcat ccggcctgta    660
gccaacgtgt ctgacccagt catcatccat ttcgaggtgt ccatgtctca gctggtgaag    720
gtggatgaag taaaccagat catggagacc aacctgtggc tcaagcaaat ctggaatgac    780
tacaagctga aatggaaccc ctctgactat ggtggggcag agttcatgcg tgtccctgca    840
cagaagatct ggaagccaga cattgtgctg tataacaatg ctgttgggga tttccaggtg    900
gacgacaaga ccaaagcctt actcaagtac actggggagg tgacttggat acctccggcc    960
atctttaaga gctcctgtaa aatcgacgtg acctacttcc cgtttgatta ccaaaactgt   1020
accatgaagt tcggttcctg gtcctacgat aaggcgaaaa tcgatctggt cctgatcggc   1080
tcttccatga acctcaagga ctattgggag agcggcgagt gggccatcat caaagcccca   1140
ggctacaaac acgacatcaa gtacaactgc tgcgaggaga tctaccccga catcacatac   1200
tcgctgtaca tccggcgcct gcccttgttc tacaccatca acctcatcat cccctgcctg   1260
ctcatctcct tcctcactgt gctcgtcttc tacctgccct ccgactgcgg tgagaaggtg   1320
accctgtgca tttctgtcct cctctccctg acggtgtttc tcctggtgat cactgagacc   1380
atcccttcca cctcgctggt catccccctg attggagagt acctcctgtt caccatgatt   1440
tttgtaacct tgtccatcgt catcaccgtc ttcgtgctca acgtgcacta cagaaccccg   1500
acgacacaca caatgcccct catgggtgaag actgtattct tgaacctgct ccccagggtc   1560
atgttcatga ccaggccaac aagcaacgag ggcaacgctc agaagccgag gcccctctac   1620
ggtgccgagc tctcaaatct gaattgcttc agccgcgcag agtccaaagg ctgcaaggag   1680
ggctacccct gccaggacgg gatgtgtggt tactgccacc accgcaggat aaaaatctcc   1740
aatttcagtg ctaacctcac gagaagctct agttctgaat ctgttgatgc tgtgctgtcc   1800
ctctctgctt tgtcaccaga aatcaaagaa gccatccaaa gtgtcaagta tattgctgaa   1860
aatatgaaag cacaaaatga agccaaagag attcaagatg attggaagta tgttgccatg   1920
gtgattgatc gtattttttct gtgggttttc accctggtgt gcattctagg gacagcagga   1980
ttgtttctgc aaccccctgat ggccaggaa gatgcataag cactaagctg tgtgcctgcc   2040
tgggagactt ccttgtgtca gggcaggagg aggctgcttc ctagtaagaa cgtactttct   2100
gttatcaagc taccagcttt gttttttggca tttcgaggtt tacttatttt ccacttatct   2160
tggaatcatg caaaaaaaaa aatgtcaaga gtatttatta ccgataaatg aacatttaac   2220
tagccttttt ggtatggtaa agagatgtca aaatgtgatt ctatgtgatt agtatgctat   2280
gctatggaat atacatgtaa aaatgtttcc ttttagttgt tgaaacaaaa ctggatagaa   2340
aaatgctgtt cagaaatatg aaaagtcatt cagttatcac tacagatctc ccagtaattt   2400
ttcttattta gcccataatc tctttgaagg tttatactaa ttcagcaatc ccccatcgtt   2460
acccatttct taccatgcat ttctcgttct ttactgggtc taaagggcta tgcctccatt   2520
tcagagagct tcaactactt ctcttgcata cttctaaatt ataccatgag aaatcatgcc   2580
tagttattca ttgttaatat aactgtctta gtacaccata aactgggtgg attataaaca   2640
acagaaactt ctcagttttg gaggtttggga ggtccaaggt caaggcacca gcaaatttgg   2700
tgtctggtga gggtcctctt cctcaaaggg tgccttctag ctgtgtcctc acatgactga   2760
agggactagc tatctctgtg gggtctattt tataagggca ctaaccccat tcatgagagc   2820
```

```
agagccccca tggcctaatc acctttccaa ggccccacct tctatctaag acaatcacgc    2880
tgggaatagg tttcaacata tgaattgggg gaggacacat ttggaccaca gcatgaacct    2940
ttagaacagg gtttctcagc cttagcacta tggacatttt gggctggata aatatgtgtt    3000
ggtacagaat gggggtatcc tgtgcattgt aggatcttta gcagtaccct agcctcaact    3060
cactagatgc caatgacata ccttgcttct tcaccagtta tgataaccaa gaatgtctcc    3120
attgttaaat gttcccttag gagcaaaatt gcccctggtt gagaaacatt gctttagaca    3180
aattgttaag agtatcatgt actacacttc tgaaacttaa cgtgatcatc accactgaca    3240
gatgattcac agagactgtt tgaatcttgt ctcactagtt tttcctgtgc aaaaataaaa    3300
tggacagaat tgcagccc                                                  3318
```

<210> SEQ ID NO 139
<211> LENGTH: 1389
<212> TYPE: DNA
<213> ORGANISM: Artificial Sequence
<220> FEATURE:
<223> OTHER INFORMATION: The sequence has been designed and synthesized.

<400> SEQUENCE: 139

```
atggccagca acagcagctc ctgcccgaca cctgggggcg ggcacctcaa tgggtacccg      60
gtgcctccct acgccttctt cttccccct  atgctgggtg gactctcccc gccaggcgct     120
ctgaccactc tccagcacca gcttccagtt agtggatata gcacaccatc cccagccacc     180
attgagaccc agagcagcag ttctgaagag atagtgccca gccctccctc gccacccccct   240 ctaccccgca tctacaagcc ttgctttgtc tgtcaggaca agtcctcagg ctaccactat     300
ggggtcagcg cctgtgaggg ctgcaagggc ttcttccgcc gcagcatcca gaagaacatg     360
gtgtacacgt gtcaccggga caagaactgc atcatcaaca aggtgacccg gaaccgctgc     420
cagtactgcc gactgcagaa gtgctttgaa gtgggcatgt ccaaggagtc tgtgagaaac     480
gaccgaaaca agaagaagaa ggaggtgccc aagcccgagt gctctgagag ctacacgctg     540
acgccggagg tggggagct  cattgagaag gtgcgcaaag cgcaccagga aaccttccct     600
gccctctgcc agctgggcaa atacactacg aacaacagct cagaacaacg tgtctctctg     660
gacattgacc tctgggacaa gttcagtgaa ctctccacca agtgcatcat taagactgtg     720
gagttcgcca agcagctgcc cggcttcacc accctcacca tcgccgacca gatcacccctc   780 ctcaaggctg cctgcctgga catcctgatc ctgcggatct gcactcggta cacgcccgag     840
caggacacca tgaccttctc ggacgggctg accctgaacc ggacccagat gcacaacgct     900
ggcttcggcc ccctcaccga cctggtcttt gccttcgcca accagctgct gcccctggag     960
atggatgatg cggagacggg gctgctcagc gccatctgcc tcatctgcgg agaccgccag    1020
gacctggagc agccggaccg ggtggacatg ctgcaggagc gctgctggga ggcgctaaag    1080
gtctacgtgc ggaagcggag gcccagccgc ccccacatgt tccccaagat gctaatgaag    1140
attactgacc tgcgaagcat cagcgccaag ggggctgagc gggtgatcac gctgaagatg    1200
gagatcccgg gctccatgcc gcctctcatc caggaaatgt tggagaactc agagggcctg    1260
gacactctga gcggacagcc gggggtggg  ggcgggacg ggggtggcct ggccccccg      1320 ccaggcagct gtagccccag cctcagcccc agctccaaca gaagcagccc ggccacccac    1380
tccccttaa                                                             1389
```

<210> SEQ ID NO 140

```
<211> LENGTH: 1973
<212> TYPE: DNA
<213> ORGANISM: Artificial Sequence
<220> FEATURE:
<223> OTHER INFORMATION: The sequence has been designed and synthesized.

<400> SEQUENCE: 140
tggcatcccc cagccgccgc cagccccgcc gagggagcc agcgccgtct ctgaggggcg      60
tccggcgccg gagccatgac cctccgccga ctcaggaagc tgcagcagaa ggaggaggcg     120
gcggccaccc cggaccccgc cgcccggact cccgactcgg aagtcgcgcc cgccgctccg     180
gtcccgaccc cgggaccccc tgccgcagcc gccacccctg gcccccagc ggacgagctg      240
tacgcggcgc tggaggacta tcaccctgcc gagctgtacc gcgcgctcgc cgtgtccggg     300
ggcaccctgc cccgccgaaa gggctcagga ttccgctgga agaatctcag ccagagtcct     360
gaacagcagc ggaaagtgct gacgttggag aaggaggata accagacctt cggctttgag     420
atccagactt atggccttca ccaccggag gagcagcgtg tggaaatggt gacctttgtc      480
tgccgagttc atgagtctag ccctgcccag ctggctgggc tcacaccagg ggacaccatc     540
gccagcgtca atggcctgaa tgtggaaggc atccggcatc gagagattgt ggacatcatt     600
aaggcgtcag gcaatgttct cagactggaa actctatatg ggacatcaat tcggaaggca     660
gaactggagg ctcgtctgca gtacctgaag caaaccctgt atgagaagtg gggagagtac     720
aggtccctaa tggtgcagga gcagcggctg gtgcatggcc tggtggtgaa ggaccccagc     780
atctacgaca cgctggagtc ggtgcgctcc tgcctctacg gcgcgggcct gctcccgggc     840
tcgctgccct tcgggcctct gctcgccgtg cccgggcgtc cccgcggagg cgcccgacgg     900
gccaggggcg acgccgacga cgccgtctac cacacgtgct tcttcgggga ctccgagccg     960
ccggcgctgc cgcccccgcc gccccccgcc cgcgccttcg gccgggccc cgccgagacc    1020
cctgccgtgg ggccgggccc tgggccgcgg gccgcgctga gccgcagcgc cagtgtgcgg    1080
tgcgcgggcc ctggcggggg cggaggcggg ggcgcgccgg gcgcgctctg gactgaggct    1140
cgcgagcagg ccctatgcgg ccccggcctg cgcaaaacca agtaccgcag cttccgccgg    1200
cggctgctca agttcatccc cggactcaac cgctccctgg aggaggagga gagccagctg    1260
taggggcggg ggcgggcagg gaggtattta tttatttatt cgcaacagcc agcgctaaaa    1320
gagggggagg ccgagccaag aggacccag gagcccagag cagcgggaga gggtccttcc     1380
tagcctcggc ccgccgggtc ggttcctggc tggtgtctgc tgagggagtg gggggcccag    1440
cccctttctct tctcccccgc caaaccacag tgggagctgg ggcaggggga gagccaggca    1500
atcgggggcc aaagatgggg gtgctcgcct acagtctgca tctgtagtgc cttgtggggt    1560
atccaggaac accctcccag cagggatgg gaaccctgtc ccatgaagcc ctctcctcag     1620
ctttacttgc tccccgccc ttagccttgg ggagaaatgg cccgtggtgg gctgacccc      1680
caccctccac acacacagtt ccatgaccca gcgggcccc aggggcatca ggtgctggtc     1740
ctcctccctc ctggcctcga ccctaaggg cttcgcccct cccaggggcc tgtaactaag     1800
tcgggtcctg ccaggcaggg ggcctgtgtt ctgtgcccct tgggagacag gaactggcga    1860
gttcaggtgg ggtggggaca gcacagactg ttccaccgtt gtgcatattg ttgcttctga    1920
accacaaact gtataaatgg atggtttttt gcaaaaaaaa aaaaaaaaaa aaa           1973
```